(12) United States Patent
Becknell et al.

(10) Patent No.: US 10,221,135 B2
(45) Date of Patent: *Mar. 5, 2019

(54) 1,4-SUBSTITUTED PIPERIDINE DERIVATIVES

(71) Applicant: 89BIO LTD, Herzliya (IL)

(72) Inventors: Nadine C. Becknell, Coatesville, PA (US); Reddeppa Reddy Dandu, Downingtown, PA (US); Bruce D. Dorsey, Ambler, PA (US); Dimitar B. Gotchev, Hatboro, PA (US); Robert L. Hudkins, Chester Springs, PA (US); Linda Weinberg, King of Prussia, PA (US); Craig A. Zificsak, Downingtown, PA (US); Allison L. Zulli, Wayne, PA (US)

(73) Assignee: 89BIO LTD, Herzliya (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/903,150

(22) Filed: Feb. 23, 2018

(65) Prior Publication Data

US 2018/0179159 A1 Jun. 28, 2018

Related U.S. Application Data

(63) Continuation of application No. 15/185,710, filed on Jun. 17, 2016, now Pat. No. 9,902,696.

(Continued)

(51) Int. Cl.
| | |
|---|---|
| C07D 211/44 | (2006.01) |
| C07D 211/54 | (2006.01) |
| C07D 409/12 | (2006.01) |
| C07D 401/04 | (2006.01) |
| C07D 495/04 | (2006.01) |
| C07D 211/58 | (2006.01) |
| C07D 405/06 | (2006.01) |
| C07D 471/04 | (2006.01) |
| C07D 413/14 | (2006.01) |
| C07D 495/02 | (2006.01) |
| C07D 401/14 | (2006.01) |
| C07D 417/14 | (2006.01) |
| C07D 471/02 | (2006.01) |
| C07D 491/048 | (2006.01) |
| C07D 401/12 | (2006.01) |
| C07D 405/14 | (2006.01) |
| C07D 471/08 | (2006.01) |
| C07D 405/12 | (2006.01) |

(Continued)

(52) U.S. Cl.
CPC ......... *C07D 211/44* (2013.01); *C07D 211/54* (2013.01); *C07D 211/58* (2013.01); *C07D 401/04* (2013.01); *C07D 401/12* (2013.01); *C07D 401/14* (2013.01); *C07D 405/06* (2013.01); *C07D 405/12* (2013.01); *C07D 405/14* (2013.01); *C07D 409/12* (2013.01); *C07D 409/14* (2013.01); *C07D 413/14* (2013.01); *C07D 417/12* (2013.01); *C07D 417/14* (2013.01); *C07D 471/02* (2013.01); *C07D 471/04* (2013.01); *C07D 471/08* (2013.01); *C07D 491/048* (2013.01); *C07D 495/02* (2013.01); *C07D 495/04* (2013.01)

(58) Field of Classification Search
None
See application file for complete search history.

(56) References Cited

U.S. PATENT DOCUMENTS

| 6,867,200 B1 | 3/2005 | Allen et al. | |
| 9,902,696 B2 * | 2/2018 | Becknell | C07D 401/14 |

(Continued)

FOREIGN PATENT DOCUMENTS

| EP | 1719761 A1 | 11/2006 |
| KR | 10-2013-0120795 A | 11/2013 |

(Continued)

OTHER PUBLICATIONS

Wu et al., "Antidiabetic and Antisteatotic Effects of the Selective Fatty Acid Synthase (FAS) Inhibitor Platensimycin in Mouse Models of Diabetes", PNAS, vol. 108, No. 13, Mar. 2011.

(Continued)

*Primary Examiner* — Brian J Davis
(74) *Attorney, Agent, or Firm* — Baker & Hostetler LLP

(57) ABSTRACT

Described herein are 1,4-substituted piperidine compounds according to Formula I that have demonstrated activity as fatty acid synthase inhibitors. Also described herein are pharmaceutical compositions containing the described 1,4-substituted piperidine compounds, and methods of treating diseases mediated by fatty acid synthase, by administering one or more of the compounds or pharmaceutical formulations described herein. Also described herein are methods of synthesizing the compounds described, including the described 1,4-substituted piperidine compounds and synthetic intermediates useful in those syntheses.

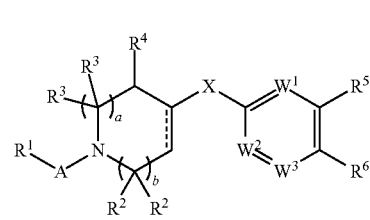

I

30 Claims, No Drawings

Related U.S. Application Data

(60) Provisional application No. 62/181,384, filed on Jun. 18, 2015.

(51) Int. Cl.
    *C07D 409/14*    (2006.01)
    *C07D 417/12*    (2006.01)

(56) References Cited

U.S. PATENT DOCUMENTS

| | | |
|---|---|---|
| 2005/0182045 A1 | 8/2005 | Nagase et al. |
| 2006/0004039 A1 | 1/2006 | Breitenbucher et al. |
| 2013/0281399 A1 | 10/2013 | McLure et al. |
| 2015/0051190 A1 | 2/2015 | Takeda et al. |

FOREIGN PATENT DOCUMENTS

| | | |
|---|---|---|
| KR | 10-2014-0127991 A | 11/2014 |
| WO | 00/35886 A2 | 6/2000 |
| WO | 2004/026883 A1 | 4/2004 |
| WO | 2005/014543 A1 | 2/2005 |
| WO | 2005/037198 A2 | 4/2005 |
| WO | 2005/049622 A1 | 6/2005 |
| WO | 2007/075629 A2 | 7/2007 |
| WO | 2007/089634 A2 | 8/2007 |
| WO | 2008/013818 A2 | 1/2008 |
| WO | 2008/013838 A2 | 1/2008 |
| WO | 2008/075070 A1 | 6/2008 |
| WO | 2008/078091 A1 | 7/2008 |
| WO | 2008/097991 A1 | 8/2008 |
| WO | 2008/138834 A1 | 11/2008 |
| WO | 2008/138889 A2 | 11/2008 |
| WO | 2009/149066 A1 | 12/2009 |
| WO | 2010/011653 A1 | 1/2010 |
| WO | 2010/106436 A2 | 9/2010 |
| WO | 2010/138758 A1 | 12/2010 |
| WO | 2011/048018 A1 | 4/2011 |
| WO | 2011/056635 A1 | 5/2011 |
| WO | 2011/062253 A1 | 5/2011 |
| WO | 2011/066211 A1 | 6/2011 |
| WO | 2011/103202 A2 | 8/2011 |
| WO | 2011/103546 A1 | 8/2011 |
| WO | 2011/138427 A2 | 11/2011 |
| WO | 2011/140190 A1 | 11/2011 |
| WO | 2011/152485 A1 | 12/2011 |
| WO | 2012/036233 A1 | 3/2012 |
| WO | 2012/064642 A1 | 5/2012 |
| WO | 2012/069917 A1 | 5/2012 |
| WO | 2012/096928 A2 | 7/2012 |
| WO | 2012/122391 A1 | 9/2012 |
| WO | 2012/175520 A1 | 12/2012 |
| WO | 2012/178125 A1 | 12/2012 |
| WO | 2013/028445 A1 | 2/2013 |
| WO | 2013/028447 A1 | 2/2013 |
| WO | 2013/052716 A1 | 4/2013 |
| WO | 2013/053051 A1 | 4/2013 |
| WO | 2013/147711 A1 | 10/2013 |
| WO | 2013/157022 A1 | 10/2013 |
| WO | 2013/175281 A1 | 11/2013 |
| WO | 2014/004863 A2 | 1/2014 |
| WO | 2014/008197 A1 | 1/2014 |
| WO | 2014/039769 A1 | 3/2014 |
| WO | 2014/044356 A1 | 3/2014 |
| WO | 2014/075754 A1 | 5/2014 |
| WO | 2014/146747 A1 | 9/2014 |
| WO | 2014/151784 A1 | 9/2014 |
| WO | 2014/160203 A1 | 10/2014 |
| WO | 2014/164749 A1 | 10/2014 |
| WO | 2015/014446 A1 | 2/2015 |
| WO | 2015/014543 A1 | 2/2015 |
| WO | 2015/084606 A1 | 6/2015 |
| WO | 2016/205633 A1 | 12/2016 |

OTHER PUBLICATIONS

Wang et al., "Novel Fatty Acid Synthase (FAS) Inhibitors: Design, Synthesis, Biological Evaluation, and Molecular Docking Studies", Bioorganic & Medicinal Chemistry 17, pp. 1898-1904, 2009.

Vazquez et al., "Discovery of GSK837149A, An Inhibitor of Human Fatty Acid Synthase Targeting the B-Ketoacyl Reductase Reductase Reaction", The FEBS Journal, pp. 1556-1567, Jan. 2008.

Turrado et al., "New Synthetic Inhibitors of Fatty Acid Synthase with Anticancer Activity", Journal of Medicinal Chemistry, 1012, 55 (11), pp. 5013-5023.

Sounni, N. et al., "Blocking Lipid Synthesis Overcomes Tumor Regrowth and Metastasis after Angiogenic Therapy Withdrawal", Cell Metabolism, 2014, 20, 1-15.

Selvendiran et al., "HO-3867, a Synthetic Compound, Inhibits the Migration and Invasion of Ovarian Carcinoma Cells through Downregulation of Fatty Acid Synthase and Focal Adhesion Kinase", Molecular Cancer Research 8(9), Sep. 2010.

Schoemaker, H.E. et al, Biomimetic a-acylimmonium cyclisations of unactivated olefin, Tetrahedron, 1978, 34, 163-172.

Rivkin et al. "3-Aryl-4-Hydroxyquinolin-2(1H) One Derivatives as Type I Fatty Acid Synthase Inhibitors", Bioorganic & Medicinal Chemistry Letters 16, pp. 4620-4623, 2006.

Richardson et al., "Novel Antagonists of the Thioesterase Domain of Human Fatty Acid Synthase" Molecular Cancer Therapeutics, 6, pp. 2120-2126, 2007.

Purohit et al., "Practical, Catalytic, Asymmetric Synthesis of B-Lactones via a Sequential Ketene Dimerization/Hydrogenation Process: Inhibitors of the Thioesterase Domain of Fatty Acid Synthase" J. Organic Chemistry, 71, pp. 4549-4558, 2006.

Puig, et al., "Novel Inhibitors of Fatty Acid Synthase with Anticancer Activity", Clinical Cancer Research, 15, pp. 7608-0615, Dec. 2009.

Pollak M, "Targeting Oxidative Phosphorylation: Why, When and How; Cancer Cell" Feb. 18, 2013, 263-63.

Pandey, "Anti-Cancer Drugs Targeting Fatty Acid Synthase" Bentham Science Publishers, 7, pp. 185-197, 2012.

Orita et al., "Selective Inhibition of Fatty Acid Synthase for Lung Cancer Treatment", Cancer Therapy: Preclinical, 13(23) pp. 7139-7145, Dec. 2007.

Oliveras et al., "Novel anti-fatty Acid Synthase Compounds with Anti-Cancer Activity in HER2+ Breast Cancer", Annals of the New York Academy of Sciences, 2010, 86-93.

Notification of Transmittal of the International Search Report and The Written Opinion dated Aug. 19, 2016.

Nasheri, N. et al., "Modulation of Fatty Acid Synthase Enzyme Activity and Expression during Hepatitis C Virus Replication" Chemistry and Biology, 2013, 20, 570-582.

Menendez et al. "Fatty acid synthase and the lipogenic phenotype in cancer pathogenesis" Nature Reviews Cancer, 2007, 7, 763-777.

McFadden J. et al., "Application of a Flexible Synthesis of (5R) Thiolactomycin to Develop New Inhibitors of Type I Fatty Acid Synthase" J. Med. Chem., 2005, 48, 946-961.

Lupu, R. et al., "Pharmacological Inhibitors of Fatty Acid Synthase (FASN)-Catalyzed Endogenous Fatty Acid Biogenesis: A New Family of Anti-Cancer Agents", Current Pharmaceutical Biotechnology, 2006, 7, 483-494.

Liu, Y. et al. "The Discovery of Orally Bioavailable Tyrosine Threonine Kinase (TTK) Inhibitors: 3-(4-(heterocyclyl)phenyl)-IH-indazole-5-carboxamides as Anticancer Agents", Journal of Medicinal Chemistry, 2015, vol. 58, No. 8, 3366-3392.

Lin, J. et al., "Antisense Technologies Targeting Fatty Acid Synthetic Enzymes", Recent Patents on Anti-Cancer Drug Discovery, 2012, 7, 198-206.

Kuhajda "Fatty Acid Synthase and Cancer: New Application of an Old Pathway" Cancer Res., 2006, 66, 5977-5980.

Hunt et al. "mRNA Stability and Overexpression of Fatty Acid Synthase in Human Breast Cancer Cell Lines" Anticancer Res. 2007, 27, 27-34.

Hardwicke et al., "A Human Fatty Acid Synthase Inhibitor Binds B-Ketoacyl Reductase in the Keto-Substrate Site", Nature Chemical Biology, 2014, vol. 10, pp. 774-781.

(56) References Cited

OTHER PUBLICATIONS

Everts, B. et al., "TLR-driven early glycolytic reprogramming via the kinases TBKI-IKKEpsilon: supports the anabolic demands of dendritic cell activation", Nature Immunology, 2014, 15, 323-332.
Database CAPLUS in STN, Acc. No. 2005:823314, Nagase et al,, US 20050182045 A1 (Aug. 18, 2005) (abstract).
Database CAPLUS in STN, Acc. No. 2000:421114, Allen et al,, WO 2000035886 A2 (Jun. 22, 2000) (abstract).
Chung et al.; "A fluorescence-based thiol quantification assay for ultra-high-throughput screening for inhibitors of coenzyme A production," Assay Drug Dev Tech 2008; 6:361-374.
Berod et al "De novo fatty acid synthesis controls the fate between regulatory T and T helper 17 ceils" Nature Medicine, Mar. 20, 2014, 1327-1333.
Angeles et al. "Recent Advances in Targeting the Fatty Acid Biosynthetic Patlhway Using Fatty Acid Synthase Inhibitors" Expert Opinion on Drug Discovery, vol. 11., No. 12, pp. 1187-1199, 2016.

\* cited by examiner

1,4-SUBSTITUTED PIPERIDINE DERIVATIVES

CROSS REFERENCE TO RELATED APPLICATIONS

This application is a continuation of U.S. patent application Ser. No. 15/185,710, filed on Jun. 17, 2016, which claims the benefit of U.S. provisional patent application No. 62/181,384, filed Jun. 18, 2015, each of which is incorporated by reference herein in its entirety.

FIELD OF THE INVENTION

The present invention relates to compounds according to Formula I, as well as to pharmaceutical compositions containing these compounds and to methods of treatment of cancer, and to methods of treatment of weight gain associated with antipsychotic drug therapy, the methods comprising administering a therapeutically effective dose of one or more of the compounds of Formula I, or a pharmaceutical composition comprising one or more of the compounds of Formula I, to a patient in need of such therapy

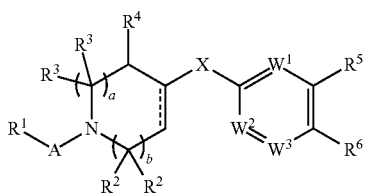

I

BACKGROUND

Fatty acid synthase (FASN) is a multi-enzyme protein complex that catalyzes the synthesis of fatty acids involved in energy production and storage, cellular structure and formation of intermediates in the biosynthesis of hormones and other biologically significant molecules (Nature Reviews Cancer, 2007, 7, 763-777). FASN is composed of two identical 272 kDa multifunctional polypeptides. As its main function, it catalyzes the synthesis of palmitate from acetyl-CoA and malonyl-CoA, in the presence of nicotinamide adenine dinucleotide phosphate (NADPH). In normal human tissues (with the exception of liver and adipose tissue), fatty acids are preferentially acquired from the diet, and expression of FASN levels are low. In contrast, FASN expression and activity is highly elevated in several pathological states including cancer, inflammatory and metabolic diseases. In particular, evidence shows that increased endogenous fatty acid synthesis is critical for tumorigenesis.

Cancer is a disease of accelerated cell growth and proliferation. Cancer cells adapt metabolically to increase levels of lipids to support their anabolic requirements. Increased synthesis of fatty acids represents a fundamental metabolic adaptation of cancer cells and is facilitated by high levels of FASN expression. Increased expression of FASN is an early event in tumorigenesis and is found in numerous tumor types, often correlating with a poor prognosis (Nature Reviews Cancer, 2007, 7, 763-777). FASN gene amplification and protein overexpression was observed in human breast, ovarian, prostate, colon, lung, bladder, stomach and kidney cancers suggesting FASN as a potential drug target and marker of poor prognosis (Nature Reviews Cancer, 2007, 7, 763-777; Anticancer Res. 2007, 27, 27-34; Cancer Res., 2006, 66, 5977-5980, Nutrition, 2000, 16, 202-208).

In addition to tumor cells, immune cells metabolically adapt, proliferate and differentiate into distinct functional classes in response to immunogenic stimuli. Studies have demonstrated that lipogenesis plays a critical role in immune responses and metabolic adaptation of activated immune cells. Inhibition of fatty acid synthesis during T-cell differentiation result in a switch from Th17 to Treg cells, suggesting a novel approach to treat autoimmune diseases, such as multiple sclerosis, and to modulate immune responses (Nature Medicine, 2014, 20, 1327-1333). Similarly, de novo fatty acid synthesis is critical for CD8+T cell expansion and dendritic cell activation (Nature Immunology, 2014, 15, 323-332). These results demonstrate that modulation of the fatty acid synthesis pathway might represent a strategy to control immune responses and to treat a wide range of autoimmune diseases.

FASN has been implicated as an important enzyme promoting a life cycle of multiple viruses and microorganisms. De novo lipid biosynthesis has been shown to be necessary for replication of the Flaviviridae family including Hepatitis C Virus, Dengue virus, yellow fever virus, West Nile virus and others (Chemistry and Biology, 2013, 570-582). Inhibition of FASN by small molecule inhibitors such as Cerulenin and Orlistat resulted in a strong inhibition of viral replication. Other viruses also depend on FASN activity including human cytomegalo virus (HCMV) influenza A, Epstein-Barr virus (EBV) and coxsackievirus B3 (CVB3). Numerous genome wide screens identified multiple host genes involved in lipid metabolism which are crucial for replication of viruses and increased expression FASN is often required for efficient viral replication (Nature Biotechnology, 2008, 26, 179-186). Taken together, these results provide a strong rationale for targeting FASN for the antiviral therapy.

Fatty acid accumulation is associated with variety of metabolic diseases and has been shown to contribute to their pathogenesis. The non-alcoholic hepatic steatosis (NASH), also called fatty liver disease, encompasses a spectrum of liver diseases (steatosis, steatosis with inflammation, cirrhosis) characterized by a fatty acid accumulation in hepatocytes. Currently, NASH is the most common liver disease in developed countries and is associated with obesity, insulin resistance and type 2 diabetes. Studies in animal models demonstrated that pharmacological inhibition of FASN improved hepatic function and decreased liver fat accumulation (PloS One, 2013, 9, 1-8).

FASN is highly expressed in tissues with high metabolic activity (liver, adipose tissue and brain), and is a critical enzyme for endogenous lipogenesis and modulation of key intermediates of lipid and carbohydrate cellular metabolism. A FASN inhibitor has been proposed for treatment of obesity, and inhibition of FASN in the hypothalamus may result in reduced food intake. The non-specific irreversible FASN inhibitors cerulenin and C-75 have been reported to decrease brain levels of orexigenic neuropeptides and decrease food intake. Therefore, FASN inhibition represents a therapeutic target in a wide spectrum of pathologies including cancer, antiviral, liver and cardiovascular diseases and treatment of obesity, diabetes and drug-induced body weight gain; e.g. antipsychotics.

Recent advances in the treatment and management of cancer show that many anticancer therapies lead to profound changes in tumor metabolism. Inhibition of BRAF signaling by vemurafenib and inhibition of BCR-ABL by imatinib led to increased oxidative phosphorylation (Pollak M, (2013)

Targeting Oxidative Phosphorylation: Why, When and How; *Cancer Cell* 18, 263-63). Such a drug-induced reprogramming of cellular metabolism from glycolysis to oxidative phosphorylation might create a dependency on lipids which could be exploited therapeutically by use of FASN inhibitors. In yet another example, it was demonstrated that cessation of the anti-angiogenic therapy by sunitinib and sorafenib resulted in a rapid regrowth of tumors and increased metastasis which were mediated by a rapid metabolic switch of tumor and stromal cells to de novo lipogenesis. Pharmacological inhibition of FASN was sufficient to reverse tumor regrowth and metastatic dissemination further confirming the role of lipid metabolism in tumor adaptation to anticancer therapies (Sounni N E, Cimino J, Blacher S, Primac I, Truong A, Mazucchelli G, Paye A, calligaris D, Debois D, mari B, de pauw E, Noel A (2014) Blocking Lipid Synthesis Overcomes Tumor Regrowth and Metastasis after Angiogenic Therapy Withdrawal; *Cell Metabolism* 20, 1-15) and providing a rationale for combinatorial treatments using FASN inhibitors.

SUMMARY

This application relates to compounds according to Formula I:

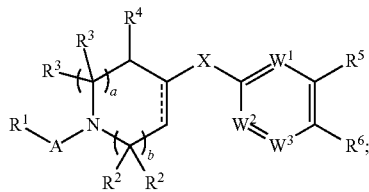

including all stereoisomeric forms, and mixtures of stereoisomeric forms of these compounds. The application further relates to salts of compounds according to Formula I, e.g., pharmaceutically acceptable salts, and to compositions, e.g., pharmaceutical compositions, that contain compounds according to Formula I, or salts thereof.

The compounds of Formula I and/or their pharmaceutically acceptable salts are useful for treating conditions, disorders and diseases that are directed or indirectly controlled, mediated, affected or influenced by FASN expression. Compounds of Formula I are FASN inhibitors and are therefore useful in the treatment of various conditions, disorders or diseases mediated by FASN expression, including conditions related to cancer, metabolic disorders, and the central nervous system (CNS).

DETAILED DESCRIPTION

The following provides additional non-limiting details of the compounds of Formula I, as well as various species and more specific embodiments of the same, intermediates, and synthesis processes.

One aspect of this application is directed to compounds of Formula I:

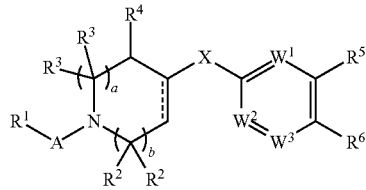

and salts thereof, e.g., pharmaceutically acceptable salts thereof, wherein:

A is selected from —C(=O)— and —SO$_2$—;

$R^1$ is selected from —H, —(C$_1$-C$_{10}$) hydrocarbyl, substituted —(C$_1$-C$_{10}$) hydrocarbyl, 3-7 membered heterocyclyl, substituted 3-7 membered heterocyclyl, —(C$_6$-C$_{10}$) aryl, substituted —(C$_6$-C$_{10}$) aryl, 5-6 membered heteroaryl, substituted 5-6 membered heteroaryl, —NR$^7$R$^8$, —OR$^7$, —SR$^7$, —N(OR$^8$)R$^7$, —N(SR$^8$)R$^7$ and —C(=O)—(C$_1$-C$_6$) alkyl;

a and b are independently selected from 0 and 1;

each $R^2$ is independently selected from —H and —(C$_1$-C$_4$) alkyl;

each $R^3$ is independently selected from —H and —(C$_1$-C$_4$) alkyl $R^4$ is selected from —H, —(C$_1$-C$_6$) alkyl, =O, —OH, —O(C$_1$-C$_6$) alkyl, halogen, and —CN; wherein one of the $R^3$ groups can optionally be structurally connected to one of the $R^2$ groups to form an alkylene bridge to produce a bicyclic ring; or one of the $R^3$ groups can optionally be structurally connected to the $R^1$ group to form a 5 to 7 membered heterocyclyl ring fused to the 1-2 face of the piperidine ring; or one of the $R^3$ groups can optionally be structurally connected to the $R^4$ group to form a 5-7 membered carbocyclic or heterocyclic ring fused to the 2-3 face of the piperidine ring;

===== indicates that the designated bond is a carbon-carbon single bond or a carbon-carbon double bond;

X is selected from —O—, —S—, —SO—, —SO$_2$—, —NH— and —NR$^9$—;

$W^1$, $W^2$ and $W^3$ are independently selected from N, CH, and C—R$^{10}$; provided that $W^2$ and $W^3$ are not both N;

$R^5$ is selected from —H, —C$_1$-C$_7$ hydrocarbyl, —C$_3$-C$_6$ heterocyclyl; halogen, —(C$_1$-C$_3$) haloalkyl, —OR$^{7a}$, —CN, —NR$^{7a}$R$^{8a}$, —O(CH$_2$)$_n$NR$^{7a}$R$^{8a}$, —O(CH$_2$)$_n$OR$^{8a}$, —NR$^{8a}$(CH$_2$)$_n$NR$^{7a}$R$^{8a}$, —NR$^{8a}$(CH$_2$)$_n$OR$^{8a}$, —C(=O)NR$^{7a}$R$^{8a}$, —C(=O)OR$^{7a}$, 5-6 membered heteroaryl, substituted 5-6 membered heteroaryl, 8-10 membered bicyclic heteroaryl, and substituted 8-10 membered bicyclic heteroaryl;

n is an integer selected from 1, 2, 3, and 4;

$R^6$ is selected from 6-membered heteroaryl, substituted 6-membered heteroaryl, 9-10 membered bicyclic heteroaryl, and substituted 9-10 membered bicyclic heteroaryl;

$R^7$ is selected from —H, —(C$_1$-C$_7$) hydrocarbyl, substituted —(C$_1$-C$_7$) hydrocarbyl, —C(=O)R$^8$, —(C$_1$-C$_6$) heteroalkyl, 6 membered aryl, 5-6 membered heteroaryl and 5-6 membered heterocyclyl;

$R^8$ is selected from —H, and —(C$_1$-C$_6$) alkyl, wherein $R^7$ can optionally be structurally connected to $R^8$ to form a 5 to 7 membered heterocyclyl ring;

$R^{7a}$ is selected from —H, —(C$_1$-C$_7$) hydrocarbyl, substituted —(C$_1$-C$_7$) hydrocarbyl, —C(=O)R$^8$, and —(C$_1$-C$_6$) heteroalkyl;

$R^{8a}$ is selected from —H, and —$(C_1-C_6)$ alkyl, wherein $R^{7a}$ can optionally be structurally connected to $R^{8a}$ to form a 5 to 7 membered heterocyclyl ring;

$R^9$ is selected from —$(C_1-C_7)$ hydrocarbyl, wherein $R^9$ can optionally be structurally connected to $R^4$ to form a 5 to 7 membered heterocyclyl ring;

each $R^{10}$ is independently selected from —$(C_1-C_7)$ hydrocarbyl, substituted —$(C_1-C_7)$ hydrocarbyl, halogen, —C(=O)$(C_1-C_7)$ hydrocarbyl, —C(=O)$NH_2$, —C(=O)NH$(C_1-C_7)$ hydrocarbyl, —C(=O)N$(C_1-C_7)$hydrocarbyl)$_2$, —OH, —O$(C_1-C_7)$ hydrocarbyl, substituted —O$(C_1-C_7)$ hydrocarbyl, —$(C_3-C_6)$ heterocyclyl, substituted —$(C_3-C_6)$ heterocyclyl —CN, —$NH_2$, —NH$(C_1-C_6)$alkyl, —N$(C_1-C_6$ alkyl)$_2$, —NH$(CH_2)_m$—$R^{11}$, —N$(C_1-C_6$ alkyl)$(CH_2)_m$—$R^{11}$, —O—$(CH_2)_m$—$R^{11}$, and —$(C_1-C_6)$ heteroalkyl;

m is an integer independently selected from 1, 2, 3, and 4; and $R^{11}$ is selected from —O$(C_1-C_6)$alkyl, —N$(C_1-C_6$ alkyl)$_2$, —$(C_3-C_6)$heterocyclyl and substituted —$(C_3-C_6)$ heterocyclyl.

According to some embodiments, A is —C(=O)—.

According to some embodiments, $R^1$ is selected from —H, —$(C_1-C_{10})$ hydrocarbyl, substituted —$(C_1-C_{10})$ hydrocarbyl, 3-7 membered heterocyclyl, substituted 3-7 membered heterocyclyl, —$(C_6-C_{10})$ aryl, substituted —$(C_6-C_{10})$ aryl, 5-6 membered heteroaryl, substituted 5-6 membered heteroaryl, —NR$^7$R$^8$, —OR$^7$, —N(OR$^8$)R$^7$ and —C(=O)—$(C_1-C_6)$ alkyl.

According to some embodiments, $R^1$ is selected from —$(C_1-C_{10})$ hydrocarbyl, substituted —$(C_1-C_{10})$ hydrocarbyl, 3-7 membered heterocyclyl, substituted 3-7 membered heterocyclyl, —$(C_6-C_{10})$ aryl, substituted —$(C_6-C_{10})$ aryl, 5-6 membered heteroaryl, substituted 5-6 membered heteroaryl, —SR$^7$, —NR$^7$R$^8$, —N(OR$^8$)R$^7$, —N(SR$^8$)R$^7$ and —C(=O)—$(C_1-C_6)$ alkyl.

According to some embodiments, $R^1$ is selected from —$(C_1-C_{10})$ hydrocarbyl, substituted —$(C_1-C_{10})$ hydrocarbyl, 3-7 membered heterocyclyl, substituted 3-7 membered heterocyclyl, —$(C_6-C_{10})$ aryl, substituted —$(C_6-C_{10})$ aryl, 5-6 membered heteroaryl, substituted 5-6 membered heteroaryl, —NR$^7$R$^8$, —N(OR$^8$)R$^7$ and —C(=O)—$(C_1-C_6)$ alkyl.

According to some embodiments, $R^1$ is selected from —$(C_1-C_6)$ alkyl, substituted —$(C_1-C_6)$ alkyl, —$(C_3-C_6)$ cycloalkyl, substituted —$(C_3-C_6)$cycloalkyl, —$(C_2-C_6)$ alkenyl, substituted —$(C_2-C_6)$alkenyl, benzyl, substituted benzyl, 3-7 membered heterocyclyl, substituted 3-7 membered heterocyclyl, —$(C_6-C_{10})$ aryl, substituted —$(C_6-C_{10})$ aryl, 5-6 membered heteroaryl, substituted 5-6 membered heteroaryl, —SR$^7$, —NR$^7$R$^8$ and —C(=O)—$(C_1-C_6)$ alkyl.

According to some embodiments, $R^1$ is selected from —$(C_1-C_6)$ alkyl, substituted —$(C_1-C_6)$ alkyl, —$(C_3-C_6)$ cycloalkyl, substituted —$(C_3-C_6)$cycloalkyl, —$(C_2-C_6)$ alkenyl, substituted —$(C_2-C_6)$alkenyl, benzyl, substituted benzyl, 3-7 membered heterocyclyl, substituted 3-7 membered heterocyclyl, —$(C_6-C_{10})$ aryl, substituted —$(C_6-C_{10})$ aryl, 5-6 membered heteroaryl, substituted 5-6 membered heteroaryl, —NR$^7$R$^8$ and —C(=O)—$(C_1-C_6)$ alkyl.

According to some embodiments, a is 1 and b is 0. According to some embodiments, a is 0 and b is 1. According to some embodiments, a and b are both 1.

According to some embodiments, $R^2$ is —H.

According to some embodiments, $R^3$ is —H.

According to some embodiments, $R^4$ is selected from —H, —$(C_1-C_6)$ alkyl and halogen.

According to some embodiments, one of the $R^3$ groups is structurally connected to one of the $R^2$ groups to form a —$CH_2$—$CH_2$— alkylene bridge to produce a bicyclic ring; e.g.:

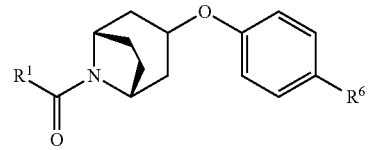

According to some embodiments, one of the $R^3$ groups may be structurally connected to the $R^1$ group to form a 5- or 6-membered heterocycle, e.g., a lactam or imidazole ring, fused to the 1-2 face of the piperidine ring; for example:

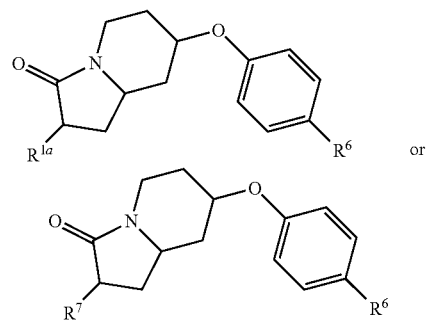

wherein the $R^{1a}$ moiety represents the residue of the $R^1$ substituent covalently bonded to the carbon atom that is alpha to the A moiety carbonyl group, e.g., —H, —$(C_1-C_9)$ hydrocarbyl, or substituted —$(C_1-C_9)$ hydrocarbyl. Examples of ring systems that may be formed by structurally connecting the $R^1$ and $R^3$ groups include indolizin-3-one, quinolizin-4-one, octahydro-1H-pyrido[1,2-c]pyrimidine and octahydroimidazo[1,5-a]pyridine rings.

According to some embodiments, one of the $R^3$ groups may be structurally connected to the $R^4$ group to form a 5- or 6-membered carbocyclic or heterocyclic ring fused to the 2-3 face of the piperidine ring; for example:

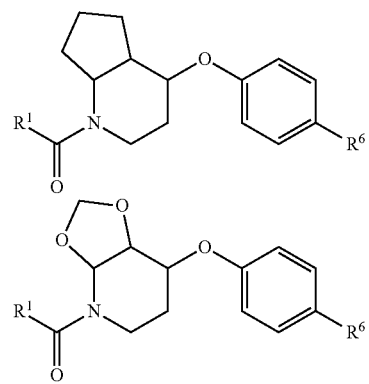

According to some embodiments, ====== is a carbon-carbon single bond.

According to some embodiments, X is —O—.

According to some embodiments, $W^1$, $W^2$ and $W^3$ are independently selected from CH, and C—$R^{10}$. According to some embodiments, $W^1$, $W^2$ and $W^3$ are CH.

According to some embodiments, $R^5$ is selected from —H, —$C_1$-$C_7$ hydrocarbyl, —$C_3$-$C_6$ heterocyclyl; halogen, —($C_1$-$C_3$) haloalkyl, —$OR^{7a}$, —CN, —$NR^{7a}R^{8a}$, —$O(CH_2)_nNR^{7a}R^{8a}$, —$O(CH_2)_nOR^{8a}$, —$NR^{8a}(CH_2)_nNR^{7a}R^{8a}$, —$NR^{8a}(CH_2)_nOR^{8a}$, —$C(=O)NR^{7a}R^{8a}$, —$C(=O)OR^{7a}$, 5-6 membered heteroaryl, and substituted 5-6 membered heteroaryl. According to some embodiments, $R^5$ is selected from —H, —$C_1$-$C_6$ alkyl, and halogen. According to some embodiments, $R^5$ is —H.

According to some embodiments, $R^6$ is selected from 9-10 membered bicyclic heteroaryl, and substituted 9-10 membered bicyclic heteroaryl. According to some embodiments, $R^6$ is selected from:

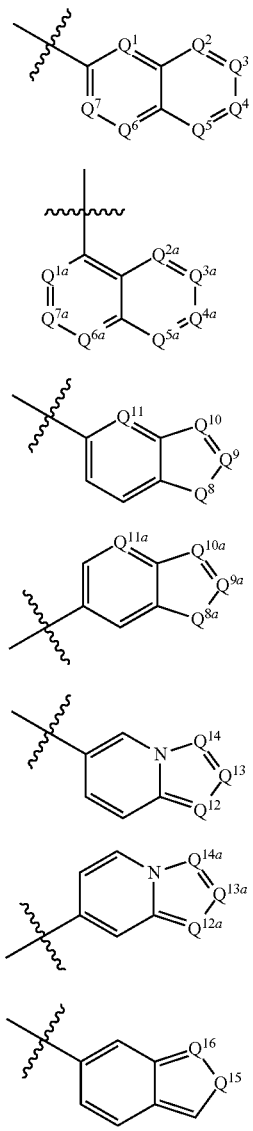

(i)
(ii)
(iii)
(iv)
(v)
(vi)
(vii)

wherein, when $R^6$ is (i), $Q^1$, $Q^2$, $Q^3$, $Q^4$, $Q^5$, $Q^6$ and $Q^7$ are independently selected from N and C—$R^{12}$, provided that 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$;

when $R^6$ is (ii), $Q^{1a}$, $Q^{2a}$, $Q^{3a}$, $Q^{4a}$, $Q^{5a}$, $Q^{6a}$ and $Q^{7a}$ are independently selected from N and C—$R^{12}$, provided that 1, 2 or 3 of $Q^{1a}$, $Q^{2a}$, $Q^{3a}$, $Q^{4a}$, $Q^{5a}$, $Q^{6a}$ and $Q^{7a}$ are N, and the remainder of $Q^{1a}$, $Q^2a$, $Q^3a$, $Q^{4a}$, $Q^{5a}$, $Q^{6a}$ and $Q^7a$ are C—$R^{12}$;

when $R^6$ is (iii), $Q^8$ is selected from O, S, and N—$R^{12n}$, $Q^9$, $Q^{10}$ and $Q^{11}$ are independently selected from N and C—$R^{12}$, provided that 1 or 2 of $Q^9$, $Q^{10}$ and $Q^{11}$ are N, and the remainder of $Q^9$, $Q^{10}$ and $Q^{11}$ are C—$R^{12}$;

when $R^6$ is (iv), $Q^{8a}$ is selected from O, S, and N—$R^{12n}$, $Q^{9a}$, $Q^{10a}$ and $Q^{11a}$ are independently selected from N and C—$R^{12}$, provided that 1 or 2 of $Q^9$, $Q^{10}$ and $Q^{11}$ are N, and the remainder of $Q^9$, $Q^{10}$ and $Q^{11}$ are C—$R^{12}$;

when $R^6$ is (v), $Q^{12}$, $Q^{13}$ and $Q^{14}$ are independently selected from N and C—$R^{12}$; and when $R^6$ is (vi), $Q^{12a}$, $Q^{13a}$ and $Q^{14a}$ are independently selected from N and C—$R^{12}$;

when $R^6$ is (vii), $Q^{15}$ is selected from N—$R^{12n}$ and C—$R^{12}$ and $Q^{16}$ is selected from N and C—$R^{12}$; provided that $Q^{15}$ and $Q^{16}$ are not both C—$R^{12}$;

and wherein each $R^{12}$ is independently selected from —H, halogen, —($C_1$-$C_6$) alkyl, —($C_3$-$C_6$) cycloalkyl, —($C_1$-$C_3$) haloalkyl, —O($C_1$-$C_3$) haloalkyl, -5-6 membered heterocyclyl, —OH, —O($C_1$-$C_6$) alkyl, —$O(CH_2)_r$-(5-6 membered heterocyclyl), —$O(CH_2)_r$—O($C_1$-$C_6$) alkyl, —$O(CH_2)_r$—NH($C_1$-$C_6$ alkyl)$_2$, —$NH_2$, —CN, —NH($C_1$-$C_6$) alkyl, —N($C_1$-$C_6$ alkyl)$_2$, —$NH(CH_2)_r$—O($C_1$-$C_6$) alkyl, —NH$(CH_2)_r$—N($C_1$-$C_6$ alkyl)$_2$, —$C(=O)NH_2$, —C(=O)NH ($C_1$-$C_6$) alkyl, and —C(=O)N($C_1$-$C_6$ alkyl)$_2$; wherein r is an integer selected independently from 1, 2, 3, and 4; and each $R^{12n}$ is independently selected from —H, —($C_1$-$C_7$) hydrocarbyl and substituted —($C_1$-$C_7$) hydrocarbyl.

It will be understood that the non-bridgehead ring carbon ring atoms in (i), (ii), (iii), (iv), (v), (vi) and (vii) above (i.e., non-bridgehead ring atoms which are not designated as Q) may optionally be substituted. According to some embodiments, none of these ring carbon ring atoms are substituted. According to some embodiments one or two of these ring carbon ring atoms is substituted. According to some embodiments one or two of these ring carbon ring atoms is substituted with a substituent selected from —OH, —($C_1$-$C_3$) alkyl, —O($C_1$-$C_3$)alkyl and halogen. According to some embodiments, one of these ring carbon ring atoms is substituted with a substituent selected from —OH, —$CH_3$, —$OCH_3$, —F and —Cl.

According to some embodiments, each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —$O(CH_2)_r$-(5-6 membered heterocyclyl), —$O(CH_2)_r$—O($C_1$-$C_6$) alkyl, —$NH_2$, —CN, —NH($C_1$-$C_6$) alkyl, —N($C_1$-$C_6$ alkyl)$_2$, —$NH(CH_2)_r$—O($C_1$-$C_6$) alkyl, —$NH(CH_2)_r$—N($C_1$-$C_6$ alkyl)$_2$, —$C(=O)NH_2$, —C(=O)NH($C_1$-$C_6$) alkyl, and —C(=O)N($C_1$-$C_6$ alkyl)$_2$.

According to some embodiments, each $R^{12}$ is independently selected from —Cl, —F, —$CH_3$, —$CH_2CH_3$, —$OCH_3$, —$OCH_2CH_3$, —$OCH(CH_3)_2$, —$CF_3$, —$OCF_3$, —$O(CH_2)_2$(pyrrolidin-1-yl), —$O(CH_2)_3$(pyrrolidin-1-yl), —$O(CH_2)_2$(morpholin-1-yl), —$O(CH_2)_3$(morpholin-1-yl), —$O(CH_2)_2$(piperidin-1-yl), —$O(CH_2)_3$(piperidin-1-yl), —$O(CH_2)_2$(N-methylpiperazin-1-yl), —$O(CH_2)_3$(N-methylpiperazin-1-yl), —$O(CH_2)_2$—$OCH_3$, —$O(CH_2)_3$—$OCH_3$, —$O(CH_2)_2$—N($CH_3$)$_2$, —$O(CH_2)_3$—N($CH_3$)$_2$, —$NH_2$, $NHCH_3$, N($CH_3$)$_2$, N-methylpiperazin-1-yl, pyrrolidin-1-yl, morpholin-1-yl, and piperidin-1-yl.

According to some embodiments, each $R^{12}$ is independently selected from —Cl, —F, —$CH_3$, —$CH_2CH_3$, —$OCH_3$, —$OCH_2CH_3$, —$OCH(CH_3)_2$, —$O(CH_2)_2$(pyrrolidin-1-yl), —$O(CH_2)_3$(pyrrolidin-1-yl), —$O(CH_2)_2$(morpholin-1-yl), —$O(CH_2)_3$(morpholin-1-yl), —$O(CH_2)_2$(piperidin-1-yl), —O(CH$_2$)$_3$(piperidin-1-yl), —O(CH$_2$)$_2$(N-methylpiperazin-1-yl), —O(CH$_2$)$_3$(N-methylpiperazin-1-yl), —O(CH$_2$)$_2$—OCH$_3$, —O(CH$_2$)$_3$—OCH$_3$, —O(CH$_2$)$_2$—N(CH$_3$)$_2$, —O(CH$_2$)$_3$—N(CH$_3$)$_2$, —NH$_2$, NHCH$_3$, N(CH$_3$)$_2$, N-methylpiperazin-1-yl, pyrrolidin-1-yl, morpholin-1-yl, and piperidin-1-yl.

According to some embodiments, each R$^{12n}$ is independently selected from —H, benzyl and —(C$_1$-C$_6$) alkyl.

According to some embodiments, R$^6$ is:

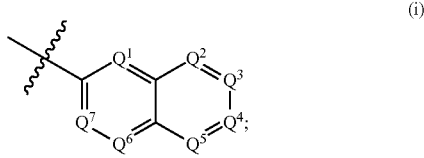

(i)

wherein 1 or 2 of Q$^1$, Q$^2$, Q$^3$, Q$^4$, Q$^5$, Q$^6$ and Q$^7$ are N, and the remainder of Q$^1$, Q$^2$, Q$^3$, Q$^4$, Q$^5$, Q$^6$ and Q$^7$ are C—R$^{12}$. According to some embodiments, when R$^6$ is (i), one of Q$^1$, Q$^2$, Q$^3$, Q$^4$, Q$^5$, Q$^6$ and Q$^7$ is N, and the remainder of Q$^1$, Q$^2$, Q$^3$, Q$^4$, Q$^5$, Q$^6$ and Q$^7$ are C—R$^{12}$. According to some embodiments, when R$^6$ is (i), Q$^2$ is N, and the remainder of Q$^1$, Q$^3$, Q$^4$, Q$^5$, Q$^6$ and Q$^7$ are C—R$^{12}$. According to some embodiments, when R$^6$ is (i), Q$^6$ is N, and Q$^1$, Q$^2$, Q$^3$, Q$^5$, Q$^5$ and Q$^7$ are C—R$^{12}$. According to some embodiments, when R$^6$ is (i), Q$^6$ is N, Q$^2$, Q$^3$, Q$^5$, Q$^5$ and Q$^7$ are CH, and Q$^1$ is C—R$^{12}$, wherein —R$^{12}$ is other than —H.

According to some embodiments, R$^6$ is selected from 9-10 membered bicyclic heteroaryl and substituted 9-10 membered bicyclic heteroaryl; provided that, when R$^6$ is a 9-membered bicyclic heteroaryl or a substituted 9-membered bicyclic heteroaryl, the point of attachment of R$^6$ to the aromatic ring containing W$^1$, W$^2$ and W$^3$ is on a 6-membered ring portion of the 9-membered bicyclic heteroaryl or substituted 9-membered bicyclic heteroaryl.

According to some embodiments, R$^6$ is:

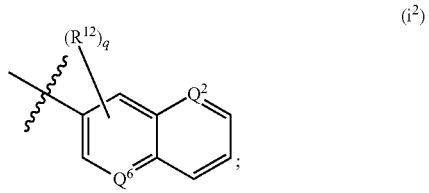

(i$^2$)

wherein one of Q$^2$ and Q$^6$ is N, and the other of Q$^2$ and Q$^6$ is C—R$^{12}$, and q is an integer selected from 0, 1, 2 and 3. According to some embodiments of i$^2$, Q$^2$ is N, and Q$^6$ is C—R$^{12}$. According to some embodiments, Q$^6$ is N, and Q$^2$ is C—R$^{12}$. According to some embodiments, q is selected from 0, 1 and 2. According to some embodiments of i$^2$, q is 0 or 1. It will be understood that a q value of 0 is the equivalent of designating all R$^{12}$ that are bonded to the i$^2$ bicyclic heteroaryl at other than Q$^2$ and Q$^6$ as being —H.

According to some embodiments of i$^2$, each R$^{12}$ is independently selected from —H, —Cl, —F, —CH$_3$, —CH$_2$CH$_3$, —OCH$_3$, —OCH$_2$CH$_3$, —OCH(CH$_3$)$_2$, —O(CH$_2$)$_2$(pyrrolidin-1-yl), —O(CH$_2$)$_3$(pyrrolidin-1-yl), —O(CH$_2$)$_2$(morpholin-1-yl), —O(CH$_2$)$_3$(morpholin-1-yl), —O(CH$_2$)$_2$(piperidin-1-yl), —O(CH$_2$)$_3$(piperidin-1-yl), —O(CH$_2$)$_2$(N-methylpiperazin-1-yl), —O(CH$_2$)$_3$(N-methylpiperazin-1-yl), —O(CH$_2$)$_2$—OCH$_3$, —O(CH$_2$)$_3$—OCH$_3$, —O(CH$_2$)$_2$—N(CH$_3$)$_2$, —O(CH$_2$)$_3$—N(CH$_3$)$_2$, —NH$_2$, NHCH$_3$, N(CH$_3$)$_2$, N-methylpiperazin-1-yl, pyrrolidin-1-yl, morpholin-1-yl, and piperidin-1-yl. According to some embodiments of i$^2$, each R$^{12}$ is independently selected from —H, —Cl, —F, —CH$_3$, —CH$_2$CH$_3$, —OCH$_3$, and —OCH$_2$CH$_3$.

According to some embodiments of i$^2$, each R$^{12n}$ is independently selected from —H, benzyl and —C$_1$-C$_6$ alkyl.

According to some embodiments, R$^6$ is:

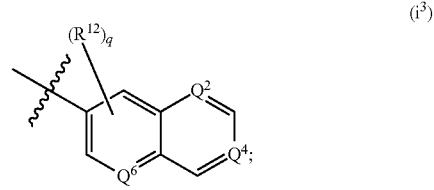

(i$^3$)

wherein one or two of Q$^2$, Q$^4$ and Q$^6$ is N, and the remainder of Q$^2$, Q$^4$ and Q$^6$ are C—R$^{12}$ and q is an integer selected from 0, 1, 2 and 3.

According to some embodiments of i$^3$, each R$^{12}$ is independently selected from —H, halogen, —(C$_1$-C$_6$) alkyl, —(C$_3$-C$_6$) cycloalkyl, 5-6 membered heterocyclyl, —OH, —O(C$_1$-C$_6$) alkyl, —O(CH$_2$)$_r$-(5-6 membered heterocyclyl), —O(CH$_2$)$_r$—O(C$_1$-C$_6$) alkyl, —NH$_2$, —CN, —NH(C$_1$-C$_6$) alkyl, —N(C$_1$-C$_6$ alkyl)$_2$, —NH(CH$_2$)$_r$—O(C$_1$-C$_6$) alkyl, —NH(CH$_2$)$_r$—N(C$_1$-C$_6$ alkyl)$_2$, —C(=O)NH$_2$, —C(=O)NH(C$_1$-C$_6$) alkyl, and —C(=O)N(C$_1$-C$_6$ alkyl)$_2$; wherein r is an integer selected from 1, 2, 3 and 4; or a salt thereof.

According to some embodiments of i$^3$, each R$^{12}$ is independently selected from —H, —Cl, —F, —CH$_3$, —CH$_2$CH$_3$, —OCH$_3$, —OCH$_2$CH$_3$, —OCH(CH$_3$)$_2$, —O(CH$_2$)$_2$(pyrrolidin-1-yl), —O(CH$_2$)$_3$(pyrrolidin-1-yl), —O(CH$_2$)$_2$(morpholin-1-yl), —O(CH$_2$)$_3$(morpholin-1-yl), —O(CH$_2$)$_2$(piperidin-1-yl), —O(CH$_2$)$_3$(piperidin-1-yl), —O(CH$_2$)$_2$(N-methylpiperazin-1-yl), —O(CH$_2$)$_3$(N-methylpiperazin-1-yl), —O(CH$_2$)$_2$—OCH$_3$, —O(CH$_2$)$_3$—OCH$_3$, —O(CH$_2$)$_2$—N(CH$_3$)$_2$, —O(CH$_2$)$_3$—N(CH$_3$)$_2$, —NH$_2$, NHCH$_3$, N(CH$_3$)$_2$, N-methylpiperazin-1-yl, pyrrolidin-1-yl, morpholin-1-yl, and piperidin-1-yl. According to some embodiments of i$^3$, each R$^{12}$ is independently selected from —H, —Cl, —F, —CH$_3$, —CH$_2$CH$_3$, —OCH$_3$, and —OCH$_2$CH$_3$.

According to some embodiments of i$^3$, q is 0, 1 or 2. According to some embodiments, q is 0 or 1. It will be understood that a q value of 0 is the equivalent of designating all R$^{12}$ that are bonded to the bicyclic heteroaryl moiety at other than Q$^2$, Q$^4$ or Q$^6$ as being —H.

According to some embodiments of i$^3$, Q$^2$ is N, and Q$^4$ and Q$^6$ are C—R$^{12}$. According to some embodiments of i$^3$, Q$^6$ is N, and Q$^2$ and Q$^4$ are C—R$^{12}$. According to some embodiments of i$^3$, Q$^4$ is N, and Q$^2$ and Q$^6$ are C—R$^{12}$. According to some embodiments of i$^3$, Q$^2$ is C—R$^{12}$, and Q$^4$ and Q$^6$ are N. According to some embodiments of i$^3$, Q$^6$ is C—R$^{12}$, and Q$^2$ and Q$^4$ are N. According to some embodiments of i$^3$, Q$^4$ is C—R$^{12}$, and Q$^2$ and Q$^6$ are N.

According to some embodiments, R$^7$ is selected from —H, —(C$_1$-C$_7$) hydrocarbyl, substituted —(C$_1$-C$_7$) hydrocarbyl, —C(=O)R$^8$, and —(C$_1$-C$_6$) heteroalkyl.

According to some embodiments, R$^7$ is selected from —H, —(C$_1$-C$_6$) alkyl, substituted —(C$_1$-C$_6$)alkyl, —(C$_3$-C$_6$) cycloalkyl, substituted —(C$_3$-C$_6$)cycloalkyl, —(C$_2$-C$_6$) alkenyl, substituted —(C$_2$-C$_6$)alkenyl, benzyl, substituted benzyl, —C(=O)R$^8$, and —(C$_1$-C$_6$) heteroalkyl. According to some embodiments, R$^7$ is selected from —H, and —(C$_1$-C$_6$) alkyl.

According to some embodiments, R$^{7a}$ is selected from —H, —(C$_1$-C$_6$) alkyl, substituted —(C$_1$-C$_6$)alkyl, —(C$_3$-C$_6$) cycloalkyl, substituted —(C$_3$-C$_6$)cycloalkyl, —(C$_2$-C$_6$) alkenyl, substituted —(C$_2$-C$_6$)alkenyl, benzyl, substituted benzyl, —C(=O)R$^8$, and —(C$_1$-C$_6$) heteroalkyl. According to some embodiments, R$^{7a}$ is selected from —H and —(C$_1$-C$_6$) alkyl.

According to some embodiments, R$^8$ is selected from —H, and —(C$_1$-C$_6$) alkyl. According to some embodiments, R$^8$ is selected from —H, —CH$_3$ and —CH$_2$CH$_3$.

According to some embodiments, R$^{8a}$ is selected from —H, and —(C$_1$-C$_6$) alkyl. According to some embodiments, R$^{8a}$ is selected from —H, —CH$_3$ and —CH$_2$CH$_3$.

Another aspect of this application is directed to compounds of Formula II:

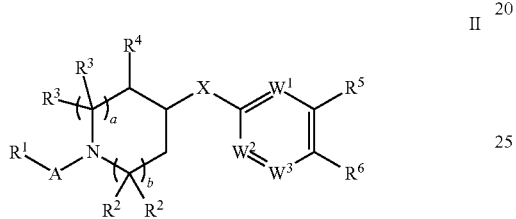

II and salts thereof, e.g., pharmaceutically acceptable salts thereof, wherein:

A is selected from —C(=O)— and —SO$_2$—;
R$^1$ is selected from —(C$_1$-C$_{10}$) hydrocarbyl, substituted —(C$_1$-C$_{10}$) hydrocarbyl, 3-7 membered heterocyclyl, substituted 3-7 membered heterocyclyl, —(C$_6$-C$_{10}$) aryl, substituted —(C$_6$-C$_{10}$) aryl, 5-6 membered heteroaryl, substituted 5-6 membered heteroaryl, —NR$^7$R$^8$, —N(OR$^8$)R$^7$, —N(SR$^8$)R$^7$, —SR$^7$, —C(=O)—(C$_1$-C$_6$) alkyl, and —(C$_1$-C$_6$) heteroalkyl;
a and b are independently selected from 0 and 1;
each R$^2$ is independently selected from —H and —(C$_1$-C$_4$) alkyl;
each R$^3$ is independently selected from —H and —(C$_1$-C$_4$) alkyl
R$^4$ is selected from —H, —(C$_1$-C$_6$) alkyl, =O, —OH, —O(C$_1$-C$_6$) alkyl, halogen and —CN; wherein one of the R$^3$ groups can optionally be structurally connected to one of the R$^2$ groups to form an alkylene bridge to produce a bicyclic ring; or
one of the R$^3$ groups can optionally be structurally connected to the R$^1$ group to form a 5 to 7-membered heterocyclyl ring fused to the 1-2 face of the piperidine ring; or
one of the R$^3$ groups can optionally be structurally connected to the R$^4$ group to form a 5 to 7-membered carbocyclic or heterocyclic ring fused to the 2-3 face of the piperidine ring;
X is selected from —O—, —S—, —SO—, —SO$_2$—, —NH— and —NR$^9$—;
W$^1$, W$^2$ and W$^3$ are independently selected from N, CH, and C—R$^{10}$; provided that W$^2$ and W$^3$ are not both N;
R$^5$ is selected from —H, —(C$_1$-C$_7$) hydrocarbyl, —(C$_3$-C$_6$) heterocyclyl; halogen, —(C$_1$-C$_3$) haloalkyl, —OR$^{7a}$, —CN, —NR$^{7a}$R$^{8a}$, —O(CH$_2$)$_n$NR$^{7a}$R$^{8a}$, —O(CH$_2$)$_n$OR$^{8a}$, —NR$^{8a}$(CH$_2$)$_n$NR$^{7a}$R$^{8a}$, —NR$^{8a}$(CH$_2$)$_n$OR$^{8a}$, —C(=O) NR$^{7a}$R$^{8a}$, and —C(=O)OR$^{7a}$, 5-6 membered heteroaryl, and substituted 5-6 membered heteroaryl;
n is an integer independently selected from 1, 2, 3, and 4;

R$^6$ is selected from:

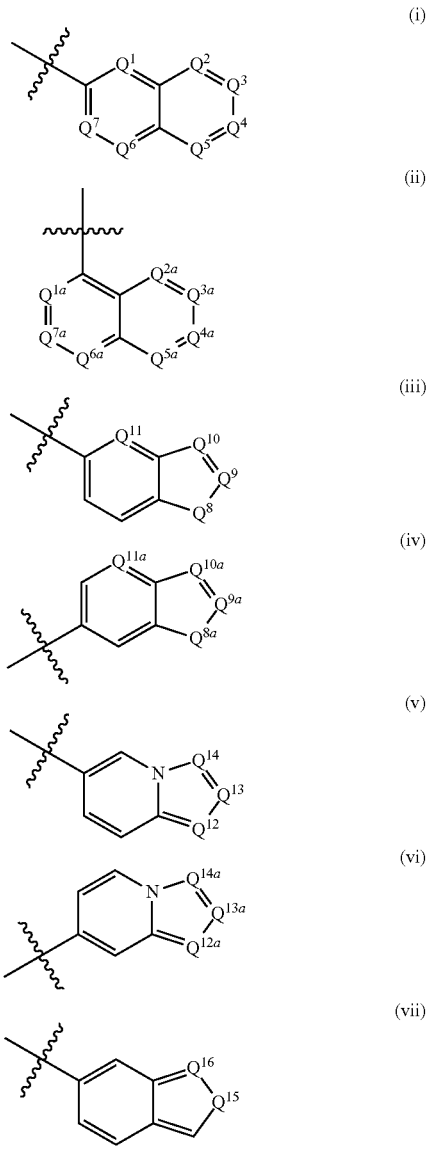

wherein, when R$^6$ is (i), Q$^1$, Q$^2$, Q$^3$, Q$^4$, Q$^5$, Q$^6$ and Q$^7$ are independently selected from N and C—R$^{12}$, provided that 1, 2 or 3 of Q$^1$, Q$^2$, Q$^3$, Q$^4$, Q$^5$, Q$^6$ and Q$^7$ are N, and the remainder of Q$^1$, Q$^2$, Q$^3$, Q$^4$, Q$^5$, Q$^6$ and Q$^7$ are C—R$^{12}$;

when R$^6$ is (ii), Q$^{1a}$, Q$^{2a}$, Q$^{3a}$, Q$^{4a}$, Q$^{5a}$, Q$^{6a}$ and Q$^7$a are independently selected from N and C—R$^{12}$, provided that 1, 2 or 3 of Q$^{1a}$, Q$^2$a, Q$^3$a, Q$^{4a}$, Q$^{5a}$, Q$^{6a}$ and Q$^7$a are N, and the remainder of Q$^{1a}$, Q$^2$a, Q$^3$a, Q$^{4a}$, Q$^{5a}$, Q$^{6a}$ and Q$^7$a are C—R$^{12}$;

when R$^6$ is (iii), Q$^8$ is selected from O, S, and N—R$^{12n}$, Q$^9$, Q$^{10}$ and Q$^{11}$ are independently selected from N and C—R$^{12}$, provided that 1 or 2 of Q$^9$, Q$^{10}$ and Q$^{11}$ are N, and the remainder of Q$^9$, Q$^{10}$ and Q$^{11}$ are C—R$^{12}$;

when R$^6$ is (iv), Q$^{8a}$ is selected from O, S, and N—R$^{12n}$, Q$^{9a}$, Q$^{10a}$ and Q$^{11a}$ are independently selected from N and C—R$^{12}$, provided that 1 or 2 of Q$^9$, Q$^{10}$ and Q$^{11}$ are N, and the remainder of Q$^9$, Q$^{10}$ and Q$^{11}$ are C—R$^{12}$;

when R$^6$ is (v), Q$^{12}$, Q$^{13}$ and Q$^{14}$ are independently selected from N and C—R$^{12}$; and when $R^6$ is (vi), $Q^{12a}$, $Q^{13a}$ and $Q^{14a}$ are independently selected from N and C—$R^{12}$;

when $R^6$ is (vii), $Q^{15}$ is selected from N—$R^{12n}$ and C—$R^{12}$ and $Q^{16}$ is selected from N and C—$R^{12}$; provided that one of $Q^{15}$ and $Q^{16}$ are not both C—$R^{12}$;

$R^7$ is selected from —H, —($C_1$-$C_7$) hydrocarbyl, substituted —($C_1$-$C_7$) hydrocarbyl, —C(=O)$R^8$, —($C_1$-$C_6$) heteroalkyl, 6 membered aryl, 5-6 membered heteroaryl and 5-6 membered heterocyclyl;

$R^8$ is selected from —H, and —($C_1$-$C_6$) alkyl, wherein $R^7$ can optionally be structurally connected to $R^8$ to form a 5 to 7 membered heterocyclyl ring;

$R^{7a}$ is selected from —H, —($C_1$-$C_7$) hydrocarbyl, substituted —($C_1$-$C_7$) hydrocarbyl, —C(=O)$R^8$, and —($C_1$-$C_6$) heteroalkyl;

$R^{8a}$ is selected from —H, and —($C_1$-$C_6$) alkyl, wherein $R^{7a}$ can optionally be structurally connected to $R^{8a}$ to form a 5 to 7 membered heterocyclyl ring;

$R^9$ is selected from —($C_1$-$C_7$) hydrocarbyl, wherein $R^9$ can optionally be structurally connected to $R^4$ to form a 5 to 7 membered heterocyclyl ring;

$R^{10}$ is selected from —($C_1$-$C_7$) hydrocarbyl, substituted —($C_1$-$C_7$) hydrocarbyl, halogen, —C(=O)—($C_1$-$C_7$) hydrocarbyl, —C(=O)$NH_2$, —C(=O)NH—($C_1$-$C_7$) hydrocarbyl, —C(=O)N($C_1$-$C_7$) hydrocarbyl)$_2$, —OH, —O($C_1$-$C_7$) hydrocarbyl, substituted —O($C_1$-$C_7$) hydrocarbyl, —($C_3$-$C_6$) heterocyclyl, substituted —($C_3$-$C_6$) heterocyclyl —CN, —$NH_2$, —NH($C_1$-$C_6$)alkyl, —N($C_1$-$C_6$ alkyl)$_2$, —NH($CH_2$)$_m$—$R^{11}$, —N($C_1$-$C_6$ alkyl)($CH_2$)$_m$—$R^{11}$, —O—($CH_2$)$_m$—$R^{11}$, and —($C_1$-$C_6$) heteroalkyl;

m is an integer selected independently from 1, 2, 3, and 4;

$R^{11}$ is selected from —O($C_1$-$C_6$)alkyl, —N(($C_1$-$C_6$) alkyl)$_2$, —($C_3$-$C_6$)heterocyclyl and substituted —($C_3$-$C_6$) heterocyclyl;

each $R^{12}$ is independently selected from —H, halogen, —($C_1$-$C_6$) alkyl, —($C_3$-$C_6$) cycloalkyl, —($C_1$-$C_3$) haloalkyl, —O($C_1$-$C_3$) haloalkyl, 5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$) alkyl, —O($CH_2$)$_r$—N($C_1$-$C_6$ alkyl)$_2$, —$NH_2$, —CN, —NH($C_1$-$C_6$) alkyl, —N($C_1$-$C_6$ alkyl)$_2$, —NH($CH_2$)$_r$—O($C_1$-$C_6$) alkyl, —NH($CH_2$)$_r$—N ($C_1$-$C_6$ alkyl)$_2$, —C(=O)$NH_2$, —C(=O)NH($C_1$-$C_6$) alkyl, and —C(=O)N($C_1$-$C_6$ alkyl)$_2$; wherein r is an integer selected independently from 1, 2, 3, and 4; and each $R^{12n}$ is independently selected from —H, —($C_1$-$C_7$) hydrocarbyl and substituted —($C_1$-$C_7$) hydrocarbyl.

According to some embodiments, A is —C(=O)—. According to other embodiments, A is —$SO_2$—.

According to some embodiments, a and b are both 0, thus making the ring containing these elements a 4-membered ring. According to other embodiments, a is 0 and b is 1, or a is 1 and b is 0, thus making the ring containing these elements a 5-membered ring. According to some embodiments, a and b are both 1, thus making the ring containing these elements a 6-membered ring.

According to some embodiments, each $R^2$ is —H or —$CH_3$. According to other embodiments each $R^2$ is —H.

According to some embodiments, each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$) alkyl, —$NH_2$, —CN, —NH($C_1$-$C_6$) alkyl, —N($C_1$-$C_6$ alkyl)$_2$, —NH($CH_2$)$_r$—O($C_1$-$C_6$) alkyl, —NH($CH_2$)$_r$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$.

According to some embodiments, $R^1$ is selected from —($C_1$-$C_{10}$) hydrocarbyl, substituted —($C_1$-$C_{10}$) hydrocarbyl, 3-7 membered heterocyclyl, substituted 3-7 membered heterocyclyl, —($C_6$-$C_{10}$) aryl, substituted —($C_6$-$C_{10}$) aryl, 5-6 membered heteroaryl, substituted 5-6 membered heteroaryl, —N$R^7R^8$, —N(O$R^8$)$R^7$, and —C(=O)—($C_1$-$C_6$) alkyl and —($C_1$-$C_6$) heteroalkyl.

According to some embodiments, $R^1$ is selected from —($C_1$-$C_6$) alkyl, substituted —($C_1$-$C_6$) alkyl, —($C_1$-$C_6$) cycloalkyl, substituted —($C_1$-$C_6$) cycloalkyl, —C(=O)—($C_1$-$C_6$) alkyl, —S($C_1$-$C_6$) alkyl, substituted —S($C_1$-$C_6$) alkyl, 5-6 membered heterocyclyl, substituted 5-6 membered heterocyclyl, $NH_2$, —NH($C_1$-$C_6$) alkyl, —N(($C_1$-$C_6$) alkyl)$_2$, —NH—O($C_1$-$C_6$) alkyl, —($CH_2$)$_n$O($C_1$-$C_6$) alkyl, —($CH_2$)$_n$OH, —($CH_2$)$_n$$SO_2$($C_1$-$C_6$)alkyl, —($C_6$-$C_{10}$) aryl, substituted —($C_6$-$C_{10}$) aryl and —($CH_2$)$_n$—CN.

According to some embodiments, $R^1$ is selected from —($C_1$-$C_6$) alkyl, substituted —($C_1$-$C_6$) alkyl, —($C_1$-$C_6$) cycloalkyl, substituted —($C_1$-$C_6$) cycloalkyl, —C(=O)—($C_1$-$C_6$) alkyl, 5-6 membered heterocyclyl, substituted 5-6 membered heterocyclyl, $NH_2$, —NH($C_1$-$C_6$) alkyl, —N(($C_1$-$C_6$) alkyl)$_2$, —NH—O($C_1$-$C_6$) alkyl, —($CH_2$)$_n$O ($C_1$-$C_6$) alkyl, —($CH_2$)$_n$OH, —($CH_2$)$_n$$SO_2$($C_1$-$C_6$)alkyl, —($C_6$-$C_{10}$) aryl, substituted —($C_6$-$C_{10}$) aryl and —($CH_2$)$_n$—CN.

According to other embodiments, $R^1$ is selected from —$CH_3$, —$CH_2CH_3$, —($CH_2$)$_2CH_3$, —($CH_2$)$_3CH_3$, —($CH_2$)$_4CH_3$, —CH($CH_3$)$_3$, —C($CH_3$)$_3$, cyclopropyl, substituted cyclopropyl, cyclobutyl, substituted cyclobutyl, cyclopentyl, —C(=O)$CH_3$, —C(=O)$CH_2CH_3$, —NH—OH, —NH—$OCH_3$, —NH—$OCH_2CH_3$, —N($CH_3$)—$OCH_3$, —$NH_2$, —$NHCH_3$, —NH—$CH_2CH_3$, —NH($CH_2$)$_2$—$CH_3$, —NH($CH_2$)$_3$—$CH_3$, —NH($CH_2$)$_4$—$CH_3$, —NH($CH_2$)$_5$—$CH_3$, —N($CH_3$)$_2$, —N(Et)$_2$, —NH—CH ($CH_3$)$_2$, —NH—$OCH_2CH_3$, —$NHSCH_3$, —$NHSCH_2CH_3$, —$SCH_3$, —$SCH_2CH_3$, —SCH($CH_3$)$_2$, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —$CH_2$—$OCH_3$, —($CH_2$)$_2$—$OCH_3$, and —($CH_2$)$_3$—$OCH_3$.

According to other embodiments, $R^1$ is selected from —$CH_3$, —$CH_2CH_3$, —($CH_2$)$_2CH_3$, —($CH_2$)$_3CH_3$, —($CH_2$)$_4CH_3$, —CH($CH_3$)$_3$, —C($CH_3$)$_3$, cyclopropyl, substituted cyclopropyl, cyclobutyl, substituted cyclobutyl, cyclopentyl, —C(=O)$CH_3$, —C(=O)$CH_2CH_3$, —NH—OH, —NH—$OCH_3$, —NH—$OCH_2CH_3$, —N($CH_3$)—$OCH_3$, —$NH_2$, —$NHCH_3$, —NH—$CH_2CH_3$, —NH($CH_2$)$_2$—$CH_3$, —NH($CH_2$)$_3$—$CH_3$, —NH($CH_2$)$_4$—$CH_3$, —NH($CH_2$)$_5$—$CH_3$, —N($CH_3$)$_2$, —N(Et)$_2$, —NH—CH ($CH_3$)$_2$, —NH—$OCH_2CH_3$, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —$CH_2$—$OCH_3$, —($CH_2$)$_2$—$OCH_3$, and —($CH_2$)$_3$—$OCH_3$.

According to some embodiments, when $R^1$ is substituted cyclopropyl, the cyclopropyl ring is substituted with 1 or two substituents selected from —OH, —$CH_2$, —OH, —C(=O)$NH_2$, —$NH_2$, —$CH_3$, —CN, and —$CF_3$.

According to some embodiments, when $R^1$ is tetrahydrofuranyl, it is tetrahydro-furan-2-yl or tetrahydrofuran-3-yl.

According to some embodiments, when $R^1$ is substituted tetrahydrofuranyl it is 2-methyltetrahydrofuran-2-yl, 5-methyltetrahydrofuran-2-yl, 2,5-dimethyltetrahydrofuran-2-yl or tetrahydrofuran-4-one-2-yl, or 4,4-difluorotetrahydrofuran-2-yl.

According to some embodiments, when $R^1$ is furanyl, it is 2-furanyl or 3-furanyl.

According to some embodiments, when $R^1$ is substituted furanyl, it is 2-methylfuran-2-yl, 5-methylfuran-2-yl, or 2,5-dimethylfuran-2-yl.

According to some embodiments, when $R^1$ is dioxolanyl, it is 1,3-dioxolan-2-yl. According to some embodiments, when $R^1$ is substituted dioxolanyl it is 2-methyl-1,3-dioxolan-2-yl.

According to some embodiments, when $R^1$ is tetrahydroisoxazolidine, it is tetra-hydroisoxazolidin-2-yl. According to some embodiments, when $R^1$ is tetrahydropyrrolyl, it is tetrahydropyrrol-1-yl. According to some embodiments, when $R^1$ is morpholinyl, it is morpholin-1-yl. According to some embodiments, when $R^1$ is piperidinyl, it is piperidin-1-yl. According to some embodiments, when $R^1$ is furanyl, it is 2-furanyl or 3-furanyl. According to some embodiments, when $R^1$ is thiophenyl, it is 2-thiophenyl or 2-thiophenyl. According to some embodiments, when $R^1$ is tetrahydrothiophenyl, it is 2-tetrahydrothiophenyl or 2-tetrahydrothiophenyl. According to some embodiments, when $R^1$ is sulfolanyl, it is sulfolan-2-yl or sulfolan-3-yl. According to some embodiments, when $R^1$ is oxazolyl, it is oxazol-1-yl, oxazol-2-one-1-yl oxazol-2-yl or oxazol-5-yl. According to some embodiments, when $R^1$ is isoxazolyl, it is isoxazol-1-yl, isoxazol-3-yl or isoxazol-5-yl. According to some embodiments, when $R^1$ is imidazolyl, it is imidazol-2-yl or imidazol-5-yl. According to some embodiments, when $R^1$ is thiazolyl, it is thiazol-2-yl or thiazol-5-yl. According to some embodiments, when $R^1$ is isothiazolyl, it is isothiazol-3-yl or isothiazol-5-yl. According to some embodiments, when $R^1$ is pyridyl, it is 2-pyridyl, 3-pyridyl, or 4-pyridyl. According to some embodiments, when $R^1$ is substituted quinolyl, it is quinolin-1-yl, quinolin-2-yl or quinolin-3-yl. According to some embodiments, when $R^1$ is substituted phenyl, it is 2-methylphenyl, 3-methylphenyl, 4-methylphenyl, or 2,5-dimethylphenyl. According to some embodiments, $R^1$ is selected from the moieties depicted in Table 1 and Table 1a below

TABLE 1

A selection of some suitable $R^1$ moieties.

| | |
|---|---|
| —CH₃ | —NHCH₂CH₃ |
| —CH(CH₃)CH₃ | —CH₂—OH |
| —CH₂CH₃ | —NHCH(CH₃)CH₃ |
| —CH₂—CN | —NHCH₃ |
| —(CH₂)₂CH₃ | —C(=O)CH₃ |
| —CH(CH₃)₂—OH | —CF₃ |
| —(CH(CH₃))₃ | —CH—SO₂—CH₃ |
| —CF₂—CH₃ | —CH₂—OCH₃ |
| —NH₂ | —NH—OH |
| —NH—OCH₂CH₃ | —N(CH₃)—OCH₃ |
| —CH₂CH(CH₃)CH₃ | —CH(CH₃)—OCH₃ |
| —NH—OCH₃ | —N(CH₃)₂ |

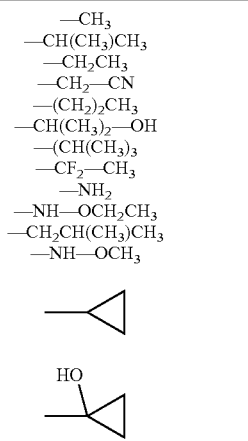

TABLE 1-continued

A selection of some suitable $R^1$ moieties.

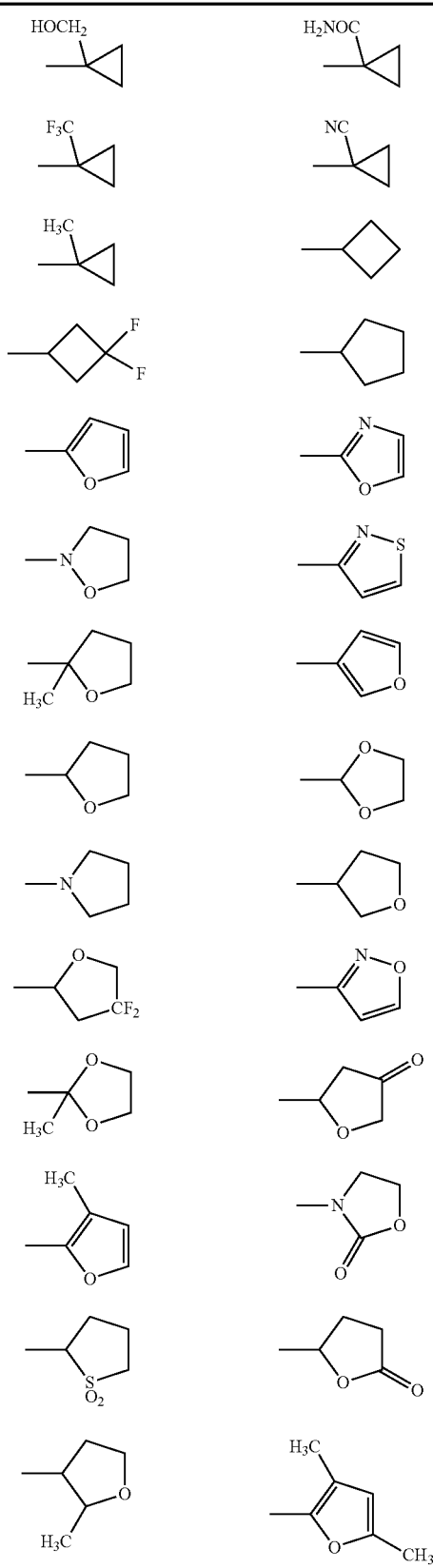

TABLE 1-continued

A selection of some suitable $R^1$ moieties.

TABLE 1a

A Selection of Some Additional Suitable $R^1$ moieties.

TABLE 1a-continued

A Selection of Some Additional Suitable $R^1$ moieties.

TABLE 1a-continued

A Selection of Some Additional Suitable R¹ moieties.

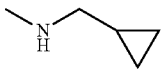 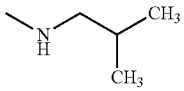

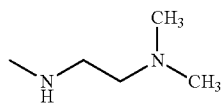 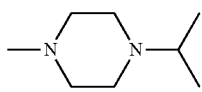

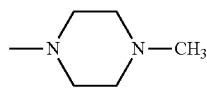 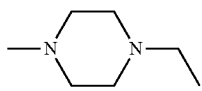

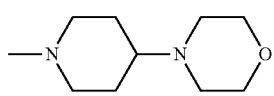 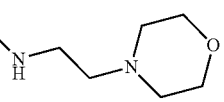

According to some embodiments each $R^3$ is —H or —$CH_3$. According to other embodiments, each $R^3$ is —H.

According to some embodiments, $R^4$ is selected from —H, —($C_1$-$C_6$)alkyl, —OH, —O($C_1$-$C_6$)alkyl, —CN and halogen According to other embodiments, $R^4$ is selected from —H, —$CH_3$, —OH, —$OCH_3$, —F, —Cl, and —CN. According to some embodiments, $R^4$ is halogen or —H. According to some embodiments, $R^4$ is —F or —H. According to some embodiments, $R^4$ is —H.

According to some embodiments, one of the $R^3$ groups can optionally be structurally connected to one of the $R^2$ groups to form a $C_2$-$C_3$ alkylene bridge to produce a bicyclic ring. According to some embodiments, one of the $R^3$ groups is structurally connected to one of the $R^2$ groups to form a —$CH_2$—$CH_2$— bridge to produce a bicyclic ring; for example:

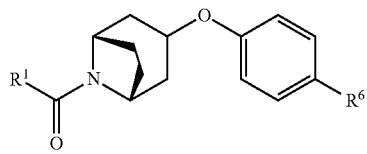

According to some embodiments, one of the $R^3$ groups, can optionally be structurally connected to the $R^1$ group to form a 5 to 7-membered heterocyclyl ring fused to the 1-2 face of the piperidine ring. According to some embodiments, one of the $R^3$ groups is structurally connected to the $R^1$ group to form a 5- or 6-membered heterocycle, e.g., a lactam or imidadole ring fused to the 1-2 face of the piperidine ring; for example:

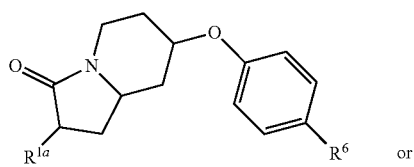

or

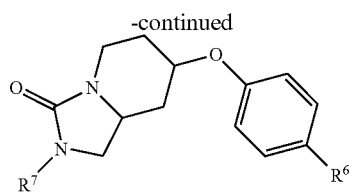

wherein the $R^{1a}$ moiety represents the residue of the $R^1$ substituent covalently bonded to the carbon atom that is alpha to the A moiety carbonyl group, e.g., —H, —($C_1$-$C_9$) hydrocarbyl, or substituted —($C_1$-$C_9$) hydrocarbyl. Examples of ring systems that may be formed by structurally connecting the $R^1$ and $R^3$ groups include indolizin-3-one, quinolizin-4-one, octahydro-1H-pyrido[1,2-c]pyrimidine and octahydroimidazo[1,5-a]pyridine rings.

According to some embodiments, one of the $R^3$ groups can optionally be structurally connected to the $R^4$ group to form a 5-7 membered carbocyclic or heterocyclic ring fused to the 2-3 face of the piperidine ring. According to some embodiments, one of the $R^3$ groups can optionally be structurally connected to the $R^4$ group to form a 5-membered carbocyclic ring, a 6-membered carbocyclic ring or a 7-membered carbocyclic ring fused to the 2-3 face of the piperidine ring. According to some embodiments, one of the $R^3$ groups can optionally be structurally connected to the $R^4$ group to form a 5-membered heterocyclic ring, a 6-membered heterocyclic ring or a 7-membered heterocyclic ring fused to the 2-3 face of the piperidine ring. According to some embodiments, one of the $R^3$ groups is structurally connected to the $R^4$ group to form a 5-membered carbocyclic or heterocyclic ring fused to the 2-3 face of the piperidine ring; for example:

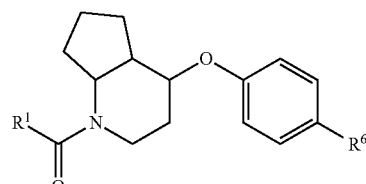

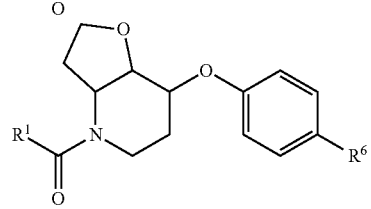

According to some embodiments, X is selected from —O—, —S—, —SO—, and —$SO_2$—. According to some embodiments, X is selected from —O—, —S— and —$SO_2$—. According to some embodiments, X is selected from —O— and —S—. According to some embodiments, X is —O—. According to some embodiments, X is —S—. According to some embodiments, X is —SO—. According to some embodiments, X is —$SO_2$—. According to some embodiments, X is —$NR^9$—. According to some embodiments, X is —NH—.

According to some embodiments, $R^9$ is —($C_1$-$C_6$) alkyl. According to some embodiments, the $R^9$ group can optionally be structurally connected to the $R^4$ group to form a 5 to 7-membered heterocyclyl ring. According to some embodiments, the $R^9$ group can optionally be structurally connected to the R⁴ group to form a 5-membered heterocyclyl ring. According to some embodiments, the $R^9$ group can optionally be structurally connected to the $R^4$ group to form a 6-membered heterocyclyl ring. According to some embodiments, the $R^9$ group can optionally be structurally connected to the $R^4$ group to form a 7-membered heterocyclyl ring.

According to some embodiments, $W^1$, $W^2$ and $W^3$ are independently selected from CH, and C—$R^{10}$. According to some embodiments, $W^1$, $W^2$ and $W^3$ are all CH. According to some embodiments, one of $W^1$ and $W^2$ is N, and $W^3$ and the other of $W^1$ and $W^2$ is CH or C—$R^{10}$. According to some embodiments, $W^1$ is N, and $W^2$ and $W^3$ are CH or C—$R^{10}$. According to some embodiments, $W^1$ is N, and $W^2$ and $W^3$ are CH. According to some embodiments, $W^1$ and $W^2$ are N and $W^3$ is CH or C—$R^{10}$. According to some embodiments, $W^1$ and $W^2$ are N and $W^3$ is CH. According to some embodiments, $W^1$ and $W^2$ are CH or C—$R^{10}$, and $W^3$ is N. According to some embodiments, $W^1$ and $W^2$ are CH, and $W^3$ is N.

According to some embodiments, each $R^{10}$ is independently selected from —F, —Cl, —CN, —($C_1$-$C_6$)alkyl, —($C_3$-$C_6$)cycloalkyl, —C(=O)—($C_1$-$C_6$) alkyl, —C(=O)—($C_3$-$C_6$) cycloalkyl, C(=O)NH₂, —C(=O)NH—$C_1$-$C_6$ alkyl, —C(=O)N($C_1$-$C_6$ alkyl)₂, —O($C_1$-$C_6$) alkyl, —($C_1$-$C_6$)alkyl, —OH, —($C_5$-$C_6$) heterocyclyl, substituted —($C_5$-$C_6$) heterocyclyl, —O—(CH₂)$_m$—O($C_1$-$C_6$) alkyl, —O(CH₂)$_n$—($C_5$-$C_6$) heterocyclyl, substituted O—(CH₂)$_m$—($C_5$-$C_6$) heterocyclyl, —NH₂, —N(($C_1$-$C_6$) alkyl)₂, —NH—(CH₂)$_m$—O—($C_1$-$C_6$)alkyl, and —NH—(CH₂)$_m$—N(($C_1$-$C_6$)alkyl)₂.

According to some embodiments, each $R^{10}$ is independently selected from —F, —Cl, —CN, —($C_1$-$C_6$)alkyl, —($C_3$-$C_6$)cycloalkyl, —OH, —O($C_1$-$C_6$)alkyl, NH₂, —NH($C_1$-$C_6$)alkyl, —N(($C_1$-$C_6$)alkyl)₂, —C(=O)($C_1$-$C_6$)alkyl, —C(=O)—($C_3$-$C_6$) cycloalkyl, —C(=O)NH₂, —CF₃, —O(CH₂)$_m$-morpholine-1-yl, —O(CH₂)$_m$-pyrrolidline-1-yl, —O(CH₂)$_m$-4-methylpiperidine-1-yl, —O(CH₂)$_m$—OCH₃, morpholine-1-yl, 4-methylpiperidine-1-yl, —NH(CH₂)$_m$—OCH₃, and —NH(CH₂)$_m$—N(CH₃)₂.

According to some embodiments, each $R^{10}$ is independently selected from —F, —Cl, —CN, —CH₃, —CH₂CH₃, —OCH₃, and —OCH₂CH₃.

According to some embodiments, $R^5$ is selected from —H, —($C_1$-$C_6$) alkyl, —($C_3$-$C_6$) cycloalkyl, and halogen. According to some embodiments, $R^5$ is —H.

According to some embodiments, $R^6$ may be selected from the bicyclic ring systems shown in Table 1b, wherein $R^{12n}$ is as defined herein, and the non-bridgehead carbon atoms in the bicyclic ring systems may optionally be substituted. According to some embodiments, 0, 1, 2 or 3 of the non-bridgehead carbon atoms in the ring systems shown in Table 1b may be substituted by $R^{12}$ substituents as $R^{12}$ is defined herein TABLE 1b A selection of some suitable $R^6$ moieties.

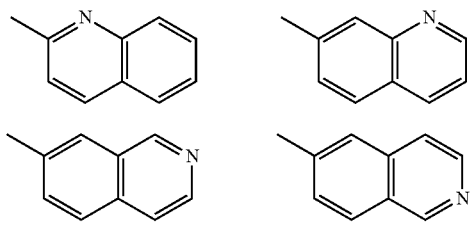

TABLE 1b-continued

A selection of some suitable $R^6$ moieties.

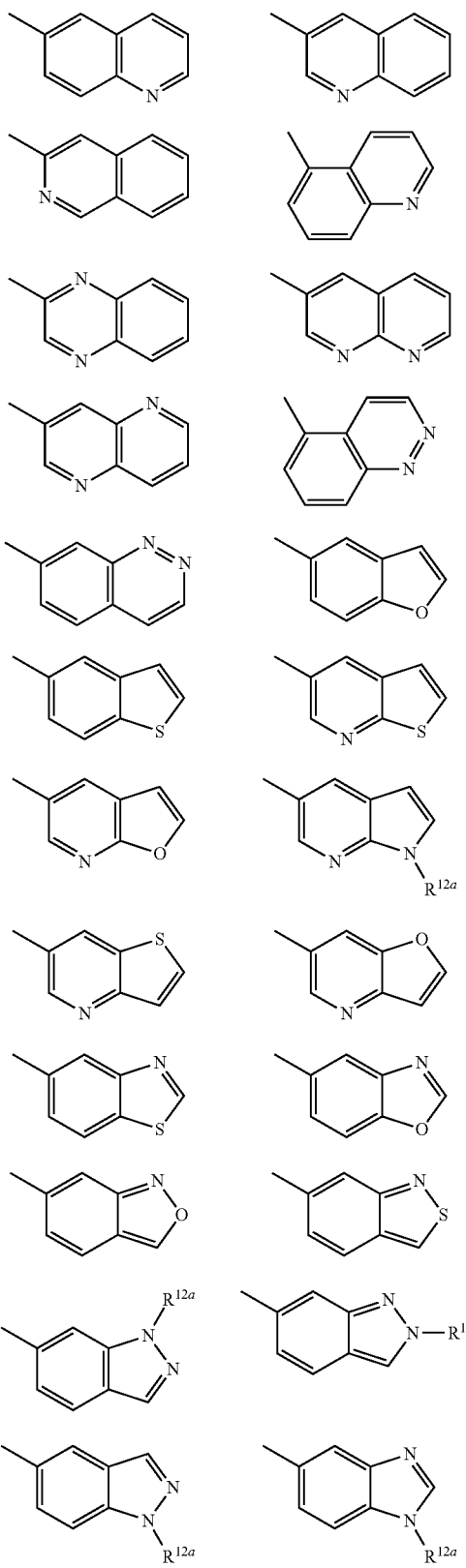

TABLE 1b-continued

A selection of some suitable R⁶ moieties.

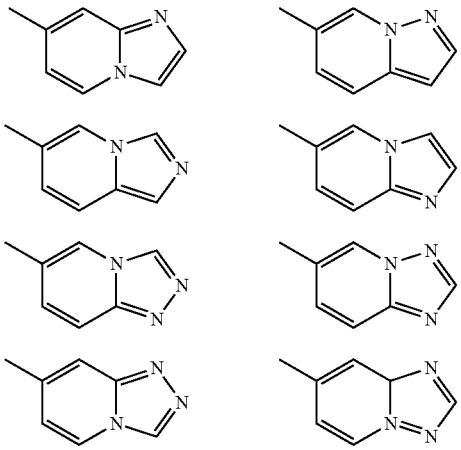

According to some embodiments, R⁶ is:

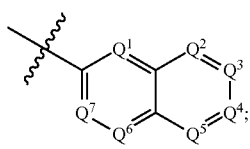

(i)

wherein 1 or 2 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$. According to some embodiments, when $R^6$ is (i), one of $Q^1$, $Q^2$, $Q^3$, $Q^4$, $Q^5$, $Q^6$ and $Q^7$ is N, and the remainder of $Q^1$, $Q^2$, $Q^3$, $Q^4$, $Q^5$, $Q^6$ and $Q^7$ are C—$R^{12}$. According to some embodiments, when $R^6$ is (i), $Q^2$ is N, and the remainder of $Q^1$, $Q^3$, $Q^4$, $Q^5$, $Q^6$ and $Q^7$ are C—$R^{12}$. According to some embodiments, when $R^6$ is (i), $Q^6$ is N, and $Q^1$, $Q^2$, $Q^3$, $Q^4$, $Q^5$ and $Q^7$ are C—$R^{12}$. According to some embodiments, when $R^6$ is (i), $Q^6$ is N, $Q^2$, $Q^3$, $Q^4$, $Q^5$ and $Q^7$ are CH, and $Q^1$ is C—$R^{12}$, wherein —$R^{12}$ is other than —H.

It will be understood that, when $R^6$ is (iii), (iv), (v), (vi) or (vii), the non-bridgehead ring carbon ring atoms (i.e., non-bridgehead ring atoms which are not designated as Q) may optionally be substituted. According to some embodiments, none of these ring carbon ring atoms are substituted. According to some embodiments, one or two of these ring carbon ring atoms may be substituted with a substituent selected from —OH, —($C_1$-$C_3$) alkyl, —O($C_1$-$C_3$)alkyl and halogen. According to some embodiments, one of these ring carbon ring atoms is substituted with a substituent selected from —OH, —$CH_3$, —$OCH_3$, —F and —Cl.

According to some embodiments, R⁶ is:

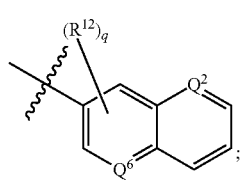

(i²)

wherein one of $Q^2$ and $Q^6$ is N, and the other of $Q^2$ and $Q^6$ is C—$R^{12}$, and q is an integer selected from 0, 1, 2 and 3. According to some embodiments of i², $Q^2$ is N, and $Q^6$ is C—$R^{12}$. According to some embodiments, $Q^6$ is N, and $Q^2$ is C—$R^{12}$. According to some embodiments, q is selected from 0, 1 and 2. According to some embodiments of i², q is 0 or 1. It will be understood that a q value of 0 is the equivalent of designating all $R^{12}$ that are bonded to the i² bicyclic heteroaryl at other than $Q^2$ and $Q^6$ as being —H.

According to some embodiments of i², each $R^{12}$ is independently selected from —H, —Cl, —F, —$CH_3$, —$CH_2CH_3$, —$OCH_3$, —$OCH_2CH_3$, —$OCH(CH_3)_2$, —$O(CH_2)_2$(pyrrolidin-1-yl), —$O(CH_2)_3$(pyrrolidin-1-yl), —$O(CH_2)_2$(morpholin-1-yl), —$O(CH_2)_3$(morpholin-1-yl), —$O(CH_2)_2$(piperidin-1-yl), —$O(CH_2)_3$(piperidin-1-yl), —$O(CH_2)_2$(N-methylpiperazin-1-yl), —$O(CH_2)_3$(N-methylpiperazin-1-yl), —$O(CH_2)_2$—$OCH_3$, —$O(CH_2)_3$—$OCH_3$, —$O(CH_2)_2$—$N(CH_3)_2$, —$O(CH_2)_3$—$N(CH_3)_2$, —$NH_2$, $NHCH_3$, $N(CH_3)_2$, N-methylpiperazin-1-yl, pyrrolidin-1-yl, morpholin-1-yl, and piperidin-1-yl. According to some embodiments of i², each $R^{12}$ is independently selected from —H, —Cl, —F, —$CH_3$, —$CH_2CH_3$, —$OCH_3$, —$OCH_2CH_3$, and —$OCH(CH_3)_2$.

According to some embodiments of i², each $R^{12n}$ is independently selected from —H, benzyl and —$C_1$-$C_6$ alkyl.

According to some embodiments, R⁶ is:

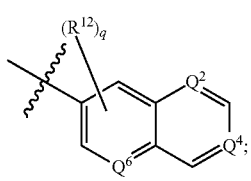

(i³)

wherein one or two of $Q^2$, $Q^4$ and $Q^6$ is N, and the remainder of $Q^2$, $Q^4$ and $Q^6$ are C—$R^{12}$, and q is an integer selected from 0, 1, 2 and 3.

According to some embodiments of i³, each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$) alkyl, —$NH_2$, —CN, —NH($C_1$-$C_6$) alkyl, —N($C_1$-$C_6$ alkyl)$_2$, —NH($CH_2$)$_r$—O($C_1$-$C_6$) alkyl, —NH($CH_2$)$_r$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$; wherein r is an integer selected from 1, 2, 3 and 4; or a salt thereof.

According to some embodiments of i³, each $R^{12}$ is independently selected from —H, —Cl, —F, —$CH_3$, —$CH_2CH_3$, —$OCH_3$, —$OCH_2CH_3$, —$OCH(CH_3)_2$, —$O(CH_2)_2$(pyrrolidin-1-yl), —$O(CH_2)_3$(pyrrolidin-1-yl), —$O(CH_2)_2$(morpholin-1-yl), —$O(CH_2)_3$(morpholin-1-yl), —$O(CH_2)_2$(piperidin-1-yl), —$O(CH_2)_3$(piperidin-1-yl), —$O(CH_2)_2$(N-methylpiperazin-1-yl), —$O(CH_2)_3$(N-methylpiperazin-1-yl), —$O(CH_2)_2$—$OCH_3$, —$O(CH_2)_3$—$OCH_3$, —$O(CH_2)_2$—$N(CH_3)_2$, —$O(CH_2)_3$—$N(CH_3)_2$, —$NH_2$, $NHCH_3$, $N(CH_3)_2$, N-methylpiperazin-1-yl, pyrrolidin-1-yl, morpholin-1-yl, and piperidin-1-yl. According to some embodiments of i³, each $R^{12}$ is independently selected from —H, —Cl, —F, —$CH_3$, —$CH_2CH_3$, —$OCH_3$, and —$OCH_2CH_3$.

According to some embodiments of i³, q is 0, 1 or 2. According to some embodiments, q is 0 or 1. It will be understood that a q value of 0 is the equivalent of designating all R$^{12}$ that are bonded to the bicyclic heteroaryl moiety at other than Q$^2$, Q$^4$ or Q$^6$ as being —H.

According to some embodiments of i$^3$, Q$^2$ is N, and Q$^4$ and Q$^6$ are C—R$^{12}$. According to some embodiments of i$^3$, Q$^6$ is N, and Q$^2$ and Q$^4$ are C—R$^{12}$. According to some embodiments of i$^3$, Q$^4$ is N, and Q$^2$ and Q$^6$ are C—R$^{12}$. According to some embodiments of i$^3$, Q$^2$ is C—R$^{12}$, and Q$^4$ and Q$^6$ are N. According to some embodiments of i$^3$, Q$^6$ is C—R$^{12}$, and Q$^2$ and Q$^4$ are N. According to some embodiments of i$^3$, Q$^4$ is C—R$^{12}$, and Q$^2$ and Q$^6$ are N.

According to some embodiments, R$^7$ is selected from —H, —(C$_1$-C$_7$) hydrocarbyl, substituted —(C$_1$-C$_7$) hydrocarbyl, —C(=O)R$^8$, and —(C$_1$-C$_6$) heteroalkyl.

According to some embodiments, each R$^{12}$ is independently selected from —H, —Cl, —F, —CH$_3$, —CH$_2$CH$_3$, —OCH$_3$, —OCH$_2$CH$_3$, —OCH(CH$_3$)$_2$, —O(CH$_2$)$_2$(pyrrolidin-1-yl), —O(CH$_2$)$_3$(pyrrolidin-1-yl), —O(CH$_2$)$_2$(morpholin-1-yl), —O(CH$_2$)$_3$(morpholin-1-yl), —O(CH$_2$)$_2$(piperidin-1-yl), —O(CH$_2$)$_3$(piperidin-1-yl), —O(CH$_2$)$_2$(N-methylpiperazin-1-yl), —O(CH$_2$)$_3$(N-methylpiperazin-1-yl), —O(CH$_2$)$_2$—OCH$_3$, —O(CH$_2$)$_3$—OCH$_3$, —O(CH$_2$)$_2$—N(CH$_3$)$_2$, —O(CH$_2$)$_3$—N(CH$_3$)$_2$, —NH$_2$, NHCH$_3$, N(CH$_3$)$_2$, N-methylpiperazin-1-yl, pyrrolidin-1-yl, morpholin-1-yl, piperidin-1-yl, —CF$_3$, —OCF$_3$, cyclopropyl, —OH, —C(=O)NH$_2$, —NH(CH$_2$)$_2$ pyrrolidin-1-yl, —NH(CH$_2$)$_2$N(CH$_3$)$_2$, —NH(CH$_2$)$_{20}$CH$_3$ and —CN.

According to some embodiments, each R$^{12}$ is independently selected from —H, —Cl, —F, —CH$_3$, —CH$_2$CH$_3$, —OCH$_3$, —OCH$_2$CH$_3$, —OCH(CH$_3$)$_2$, —O(CH$_2$)$_2$(pyrrolidin-1-yl), —O(CH$_2$)$_3$(pyrrolidin-1-yl), —O(CH$_2$)$_2$(morpholin-1-yl), —O(CH$_2$)$_3$(morpholin-1-yl), —O(CH$_2$)$_2$(piperidin-1-yl), —O(CH$_2$)$_3$(piperidin-1-yl), —O(CH$_2$)$_2$(N-methylpiperazin-1-yl), —O(CH$_2$)$_3$(N-methylpiperazin-1-yl), —O(CH$_2$)$_2$—OCH$_3$, —O(CH$_2$)$_3$—OCH$_3$, —O(CH$_2$)$_2$—N(CH$_3$)$_2$, —O(CH$_2$)$_3$—N(CH$_3$)$_2$, —NH$_2$, NHCH$_3$, N(CH$_3$)$_2$, N-methylpiperazin-1-yl, pyrrolidin-1-yl, morpholin-1-yl and piperidin-1-yl.

According to some embodiments, R$^{12}$ is selected from —F, —Cl, —CH$_3$, and —OCH$_3$.

According to some embodiments, R$^{12n}$ is selected from —H, benzyl and —(C$_1$-C$_6$) alkyl.

Another aspect of this application is directed to compounds of Formula III:

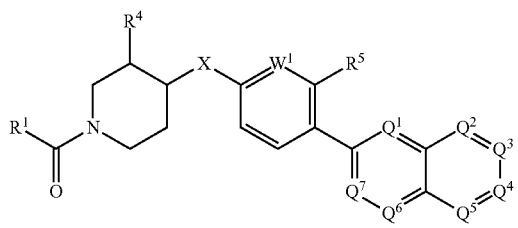

and salts thereof, e.g., pharmaceutically acceptable salts thereof, wherein:

R$^1$ is selected from —(C$_1$-C$_{10}$) hydrocarbyl, substituted —(C$_1$-C$_{10}$) hydrocarbyl, 3-7 membered heterocyclyl, substituted 3-7 membered heterocyclyl, —(C$_6$-C$_{10}$) aryl, substituted —(C$_6$-C$_{10}$) aryl, 5-6 membered heteroaryl, substituted 5-6 membered heteroaryl, —NR$^7$R$^8$, —N(OR$^8$)R$^7$, —N(SR)R$^7$, —S—R$^7$ and —C(=O)—(C$_1$-C$_6$) alkyl and —(C$_1$-C$_6$) heteroalkyl;

X is selected from —O—, —S—, —SO—, —SO$_2$—, and —NR$^9$—;

W$^1$ is CH or C—R$^{10}$;

R$^4$ is halogen or —H;

R$^5$ is selected from —H, —(C$_1$-C$_7$) hydrocarbyl, —(C$_3$-C$_6$) heterocyclyl; halogen, —(C$_1$-C$_3$) haloalkyl, —OR$^{7a}$, —CN, —NR$^{7a}$R$^{8a}$, —O(CH$_2$)$_n$NR$^{7a}$R$^{8a}$, —O(CH$_2$)$_n$OR$^{8a}$, —NR$^{8a}$(CH$_2$)$_n$NR$^{7a}$R$^{8a}$, —NR$^{8a}$(CH$_2$)$_n$OR$^{8a}$, —C(=O)NR$^{7a}$R$^{8a}$, —C(=O)OR$^{7a}$, 5-6 membered heteroaryl, and substituted 5-6 membered heteroaryl;

n is an integer selected independently from 1, 2, 3, and 4;

Q$^1$, Q$^2$, Q$^3$, Q$^4$, Q$^5$, Q$^6$ and Q$^7$ are independently selected from N and C—R$^{12}$, provided that 1 or 2 of Q$^1$, Q$^2$, Q$^3$, Q$^4$, Q$^5$, Q$^6$ and Q$^7$ are N, and the remainder of Q$^1$, Q$^2$, Q$^3$, Q$^4$, Q$^5$, Q$^6$ and Q$^7$ are C—R$^{12}$;

R$^7$ is selected from —H, —(C$_1$-C$_7$) hydrocarbyl, substituted —(C$_1$-C$_7$) hydrocarbyl, —C(=O)R$^8$, —(C$_1$-C$_6$) heteroalkyl, 6 membered aryl, 5-6 membered heteroaryl and 5-6 membered heterocyclyl;

R$^8$ is selected from —H, and —(C$_1$-C$_6$) alkyl, wherein R$^7$ can optionally be structurally connected to R$^8$ to form a 5 to 7 membered heterocyclyl ring;

R$^{7a}$ is selected from —H, —(C$_1$-C$_7$) hydrocarbyl, substituted —(C$_1$-C$_7$) hydrocarbyl, —C(=O)R$^8$, and —(C$_1$-C$_6$) heteroalkyl;

R$^{8a}$ is selected from —H, and —(C$_1$-C$_6$) alkyl, wherein R$^{7a}$ can optionally be structurally connected to R$^{8a}$ to form a 5 to 7 membered heterocyclyl ring;

R$^9$ is selected from —(C$_1$-C$_6$) alkyl, wherein R$^9$ can optionally be structurally connected to R$^4$ to form a 5 to 7 membered heterocyclyl ring;

R$^{10}$ is selected from —F, —Cl, —CN, —(C$_1$-C$_6$)alkyl, —(C$_3$-C$_6$)cycloalkyl, —OH, —O—(C$_1$-C$_6$)alkyl, NH$_2$, —NH(C$_1$-C$_6$)alkyl, —N((C$_1$-C$_6$)alkyl)$_2$, —C(=O)(C$_1$-C$_6$) alkyl, —C(=O)—(C$_3$-C$_6$) cycloalkyl, —C(=O)NH$_2$, —CF$_3$, —O(CH$_2$)$_m$-morpholine-1-yl, —O(CH$_2$)$_m$-pyrrolidine-1-yl, —O(CH$_2$)$_m$-4-methylpiperidine-1-yl, —O(CH$_2$)$_m$—OCH$_3$, morpholine-1-yl, 4-methylpiperidine-1-yl, —NH(CH$_2$)$_m$—OCH$_3$, and —NH(CH$_2$)$_m$—N(CH$_3$)$_2$;

m is an integer selected independently from 1, 2, 3, and 4;

R$^{11}$ is selected from —O(C$_1$-C$_6$)alkyl, —N((C$_1$-C$_6$) alkyl)$_2$, —(C$_3$-C$_6$)heterocyclyl and substituted —(C$_3$-C$_6$) heterocyclyl; and each R$^{12}$ is independently selected from —H, halogen, —(C$_1$-C$_6$) alkyl, —(C$_3$-C$_6$) cycloalkyl, —(C$_1$-C$_3$) haloalkyl, —O(C$_1$-C$_3$) haloalkyl, 5-6 membered heterocyclyl, —OH, —O(C$_1$-C$_6$) alkyl, —O(CH$_2$)$_p$-(5-6 membered heterocyclyl), —O(CH$_2$)$_r$—O(C$_1$-C$_6$) alkyl, —O(CH$_2$)$_r$—N(C$_1$-C$_6$ alkyl)$_2$, —NH$_2$, —CN, —NH(C$_1$-C$_6$) alkyl, —N(C$_1$-C$_6$ alkyl)$_2$, —NH(CH$_2$)$_r$—O(C$_1$-C$_6$) alkyl, —NH(CH$_2$)$_r$—N (C$_1$-C$_6$ alkyl)$_2$, —C(=O)NH$_2$, —C(=O)NH(C$_1$-C$_6$) alkyl, and —C(=O)N(C$_1$-C$_6$ alkyl)$_2$; wherein r is an integer selected independently from 1, 2, 3, and 4.

According to some embodiments, R$^1$ is selected from —(C$_1$-C$_{10}$) hydrocarbyl, substituted —(C$_1$-C$_{10}$) hydrocarbyl, 3-7 membered heterocyclyl, substituted 3-7 membered heterocyclyl, —(C$_6$-C$_{10}$) aryl, substituted —(C$_6$-C$_{10}$) aryl, 5-6 membered heteroaryl, substituted 5-6 membered heteroaryl, —NR$^7$R$^8$, —N(OR$^8$)R$^7$, and —C(=O)—(C$_1$-C$_6$) alkyl and —(C$_1$-C$_6$) heteroalkyl.

According to some embodiments, R$^1$ is selected from —(C$_1$-C$_6$) alkyl, substituted —(C$_1$-C$_6$) alkyl, —(C$_1$-C$_6$) cycloalkyl, substituted —(C$_1$-C$_6$) cycloalkyl, —C(=O)—(C$_1$-C$_6$) alkyl, 5-6 membered heterocyclyl, substituted 5-6 membered heterocyclyl, —NH$_2$, —NH(C$_1$-C$_6$) alkyl, —N((C$_1$-C$_6$) alkyl)$_2$, —NH—O(C$_1$-C$_6$) alkyl, —NH—S (C$_1$-C$_6$) alkyl, —S(C$_1$-C$_6$) alkyl, —(CH$_2$)$_n$O(C$_1$-C$_6$) alkyl, —(CH$_2$)$_n$OH, —(CH$_2$)$_n$SO$_2$(C$_1$-C$_6$)alkyl, —(C$_6$-C$_{10}$) aryl, substituted —(C$_6$-C$_{10}$) aryl, and —(CH$_2$)$_n$—CN.

According to some embodiments, $R^1$ is selected from —($C_1$-$C_6$) alkyl, substituted —($C_1$-$C_6$) alkyl, —($C_1$-$C_6$) cycloalkyl, substituted —($C_1$-$C_6$) cycloalkyl, —C(=O)—($C_1$-$C_6$) alkyl, 5-6 membered heterocyclyl, substituted 5-6 membered heterocyclyl, —$NH_2$, —NH($C_1$-$C_6$) alkyl, —N(($C_1$-$C_6$) alkyl)$_2$, —NH—O($C_1$-$C_6$) alkyl, —($CH_2$)$_n$O ($C_1$-$C_6$) alkyl, —($CH_2$)$_n$OH, —($CH_2$)$_n$$SO_2$($C_1$-$C_6$)alkyl, —($C_6$-$C_{10}$) aryl, substituted —($C_6$-$C_{10}$) aryl, and —($CH_2$)$_n$—CN.

According to other embodiments, $R^1$ is selected from —$CH_3$, —$CH_2CH_3$, —($CH_2$)$_2$$CH_3$, —($CH_2$)$_3$$CH_3$, —($CH_2$)$_4$$CH_3$, —CH($CH_3$)$_3$, —C($CH_3$)$_3$, cyclopropyl, substituted cyclopropyl, cyclobutyl, substituted cyclobutyl, cyclopentyl, —C(=O)$CH_3$, —C(=O)$CH_2CH_3$, —NH—OH, —NH—$OCH_3$, —NH—$OCH_2CH_3$, —N($CH_3$)—$OCH_3$, —$NH_2$, —$NHCH_3$, —NH—$CH_2CH_3$, —NH ($CH_2$)$_2$—$CH_3$, —NH($CH_2$)$_3$—$CH_3$, —NH($CH_2$)$_4$—$CH_3$, —NH($CH_2$)$_5$—$CH_3$, —N($CH_3$)$_2$, —N(Et)$_2$, —NH—CH($CH_3$)$_2$, —NH—$OCH_2CH_3$, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —$CH_2$—$OCH_3$, —($CH_2$)$_2$—$OCH_3$, and —($CH_2$)$_3$—$OCH_3$.

According to other embodiments, $R^1$ is selected from —$CH_3$, —$CH_2CH_3$, —($CH_2$)$_2$$CH_3$, —($CH_2$)$_3$$CH_3$, —($CH_2$)$_4$$CH_3$, —CH($CH_3$)$_3$, —C($CH_3$)$_3$, cyclopropyl, substituted cyclopropyl, cyclobutyl, substituted cyclobutyl, cyclopentyl, —C(=O)$CH_3$, —C(=O)$CH_2CH_3$, —NH—OH, —NH—$OCH_3$, —NH—$OCH_2CH_3$, —N($CH_3$)—$OCH_3$, —$NH_2$, —$NHCH_3$, —NH—$CH_2CH_3$, —NH ($CH_2$)$_2$—$CH_3$, —NH($CH_2$)$_3$—$CH_3$, —NH($CH_2$)$_4$—$CH_3$, —NH($CH_2$)$_5$—$CH_3$, —N($CH_3$)$_2$, —N(Et)$_2$, —NH—CH($CH_3$)$_2$, —NH—$OCH_2CH_3$, —NH—$SCH_2CH_3$, —NH—$SCH_3$, —$SCH_3$, —$SCH_2CH_3$, —SCH($CH_3$)$_2$, tetrahydrofuranyl, substituted tetrahydrofuranyl, furanyl, substituted furanyl, dioxolanyl, substituted dioxolanyl, tetrahydropyrrolyl, piperidinyl, morpholinyl, tetrahydropyranyl, thiophenyl, tetrahydrothiophenyl, sulfolanyl, tetrahydroisoxazolidinyl, oxazolyl, isoxazolyl, thiazolyl, isothiazolyl, imidazole, pyrydyl, substituted pyridyl, quinolyl, substituted quinolyl, phenyl, substituted phenyl, —$CH_2$—$OCH_3$, —($CH_2$)$_2$—$OCH_3$, and —($CH_2$)$_3$—$OCH_3$.

According to some embodiments, when $R^1$ is substituted cyclopropyl, the cyclopropyl ring is substituted with 1 or 2 substituents selected from —OH, —$CH_3$, —OH, —C(=O)$NH_2$, —$NH_2$, —$CH_3$, —CN, and —$CF_3$.

According to some embodiments, when $R^1$ is tetrahydrofuranyl, it is tetrahydro-furan-2-yl or tetrahydrofuran-3-yl. According to some embodiments, when $R^1$ is substituted tetrahydrofuranyl, it is 2-methyltetrahydrofuran-2-yl, 5-methyltetrahydrofuran-2-yl, 2,5-dimethyltetrahydrofuran-2-yl or tetrahydrofuran-4-one-2-yl, 4,4-difluorotetrahydrofuran-2-yl.

According to some embodiments, when $R^1$ is furanyl, it is 2-furanyl or 3-furanyl. According to some embodiments, when $R^1$ is substituted furanyl it is 2-methylfuran-2-yl, 5-methylfuran-2-yl, or 2,5-dimethylfuran-2-yl.

According to some embodiments, when $R^1$ is dioxolanyl, it is 1,3-dioxolan-2-yl. According to some embodiments, when $R^1$ is substituted dioxolanyl it is 2-methyl-1,3-dioxolan-2-yl.

According to some embodiments, when $R^1$ is tetrahydroisoxazolidine, it is tetra-hydroisoxazolidin-2-yl. According to some embodiments, when $R^1$ is tetrahydropyrrolyl, it is tetrahydropyrrol-1-yl. According to some embodiments, when $R^1$ is morpholinyl, it is morpholin-1-yl. According to some embodiments, when $R^1$ is piperidinyl, it is piperidin-1-yl. According to some embodiments, when $R^1$ is furanyl, it is 2-furanyl or 3-furanyl. According to some embodiments, when $R^1$ is thiophenyl, it is 2-thiophenyl or 2-thiophenyl. According to some embodiments, when $R^1$ is tetrahydrothiophenyl, it is 2-tetrahydrothiophenyl or 2-tetrahydrothiophenyl. According to some embodiments, when $R^1$ is sulfolanyl, it is sulfolan-2-yl or sulfolan-3-yl. According to some embodiments, when $R^1$ is oxazolyl, it is oxazol-1-yl, oxazol-2-one-1-yl, oxazol-2-yl or oxazol-5-yl. According to some embodiments, when $R^1$ is isoxazolyl, it is isoxazol-1-yl, isoxazol-3-yl or isoxazol-5-yl. According to some embodiments, when $R^1$ is imidazolyl, it is imidazol-2-yl or imidazol-5-yl. According to some embodiments, when $R^1$ is thiazolyl, it is thiazol-2-yl or thiazol-5-yl. According to some embodiments, when $R^1$ is isothiazolyl, it is isothiazol-3-yl or isothiazol-5-yl. According to some embodiments, when $R^1$ is pyridyl, it is 2-pyridyl, 3-pyridyl, or 4-pyridyl. According to some embodiments, when $R^1$ is substituted quinolyl, it is quinolin-1-yl, quinolin-2-yl or quinolin-3-yl. According to some embodiments, when $R^1$ is substituted phenyl, it is 2-methylphenyl, 3-methylphenyl, 4-methylphenyl, or 2,5-dimethylphenyl. According to some embodiments, $R^1$ is selected from the moieties depicted in Table 1 and Table 1a (infra).

According to some embodiments, X is selected from —O—, —S—, —SO—, and —$SO_2$—. According to some embodiments, X is selected from —O—, —S— and —$SO_2$—. According to some embodiments, X is selected from —O— and —S—. According to some embodiments, X is —O—. According to some embodiments, X is —S—. According to some embodiments, X is —SO—. According to some embodiments, X is —$SO_2$—. According to some embodiments, X is —$NR^9$—.

According to some embodiments, $R^9$ is —($C_1$-$C_6$) alkyl. According to some embodiments, the $R^9$ group can optionally be structurally connected to the $R^4$ group to form a 5 to 7 membered heterocyclyl ring. According to some embodiments, the $R^9$ group can optionally be structurally connected to the $R^4$ group to form a 5-membered heterocyclyl ring. According to some embodiments, the $R^9$ group can optionally be structurally connected to the $R^4$ group to form a 6-membered heterocyclyl ring. According to some embodiments, the $R^9$ group can optionally be structurally connected to the $R^4$ group to form a 7-membered heterocyclyl ring.

According to some embodiments, $R^4$ is —F or —H. According to some embodiments, $R^4$ is —H.

According to some embodiments, $R^5$ is selected from —H, —$C_1$-$C_6$ alkyl, —$C_3$-$C_6$ cycloalkyl, and halogen. According to some embodiments, $R^5$ is —H.

According to some embodiments, each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_p$-(5-6 membered heterocyclyl), —O($CH_2$)$_r$—O($C_1$-$C_6$) alkyl, —$NH_2$, —CN, —NH($C_1$-$C_6$) alkyl, —N($C_1$-$C_6$ alkyl)$_2$, —NH($CH_2$)$_r$—O($C_1$-$C_6$) alkyl, —NH($CH_2$)$_r$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$.

According to some embodiments, each $R^{12}$ is independently selected from —H, —Cl, —F, —$CH_3$, —$CH_2CH_3$, —$OCH_3$, —$OCH_2CH_3$, —OCH($CH_3$)$_2$, —O($CH_2$)$_2$(pyrrolidin-1-yl), —O($CH_2$)$_3$(pyrrolidin-1-yl), —O($CH_2$)$_2$(morpholin-1-yl), —O($CH_2$)$_3$(morpholin-1-yl), —O($CH_2$)$_2$(piperidin-1-yl), —O($CH_2$)$_3$(piperidin-1-yl), —O($CH_2$)$_2$(N-methylpiperazin-1-yl), —O($CH_2$)$_3$(N-methylpiperazin-1- yl), —O(CH$_2$)$_2$—OCH$_3$, —O(CH$_2$)$_3$—OCH$_3$, —O(CH$_2$)$_2$—N(CH$_3$)$_2$, —O(CH$_2$)$_3$—N(CH$_3$)$_2$, —NH$_2$, NHCH$_3$, N(CH$_3$)$_2$, N-methylpiperazin-1-yl, pyrrolidin-1-yl, morpholin-1-yl, piperidin-1-yl, —CF$_3$, —OCF$_3$, cyclopropyl, —OH, —C(=O)NH$_2$, —NH(CH$_2$)$_2$ pyrrolidin-1-yl, —NH(CH$_2$)$_2$N(CH$_3$)$_2$, —NH(CH$_2$)$_2$OCH$_3$ and —CN.

According to some embodiments, R$^6$ is:

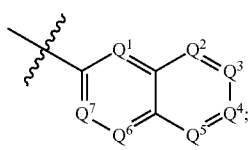

(i)

wherein 1 or 2 of Q$^1$, Q$^2$, Q$^3$, Q$^4$, Q$^5$, Q$^6$ and Q$^7$ are N, and the remainder of Q$^1$, Q$^2$, Q$^3$, Q$^4$, Q$^5$, Q$^6$ and Q$^7$ are C—R$^{12}$. According to some embodiments, one of Q$^1$, Q$^2$, Q$^3$, Q$^4$, Q$^5$, Q$^6$ and Q$^7$ is N, and the remainder of Q$^1$, Q$^2$, Q$^3$, Q$^4$, Q$^5$, Q$^6$ and Q$^7$ are C—R$^{12}$. According to some embodiments, Q$^2$ is N, and the remainder of Q$^1$, Q$^3$, Q$^4$, Q$^5$, Q$^6$ and Q$^7$ are C—R$^{12}$. According to some embodiments, Q$^6$ is N, and Q$^1$, Q$^2$, Q$^3$, Q$^4$, Q$^5$ and Q$^7$ are C—R$^{12}$. According to some embodiments, Q$^6$ is N; Q$^2$, Q$^3$, Q$^4$, Q$^5$ and Q$^7$ are CH, and Q$^1$ is C—R$^{12}$, wherein —R$^{12}$ is other than —H. According to some embodiments, Q$^6$ is N; Q$^2$, Q$^3$, Q$^4$, Q$^5$ and Q$^7$ are CH, and Q$^1$ is C—R$^{12}$, wherein each —R$^{12}$ is independently selected from halogen, —(C$_1$-C$_6$) alkyl, —(C$_3$-C$_6$) cycloalkyl, 5-6 membered heterocyclyl, —OH, —O(C$_1$-C$_6$) alkyl, —O(CH$_2$)$_r$-(5-6 membered heterocyclyl), —O(CH$_2$)$_r$—O(C$_1$-C$_6$) alkyl, —NH$_2$, —CN, —NH(C$_1$-C$_6$) alkyl, —N(C$_1$-C$_6$ alkyl)$_2$, —NH(CH$_2$)$_r$—O(C$_1$-C$_6$) alkyl, —NH(CH$_2$)$_r$—N(C$_1$-C$_6$ alkyl)$_2$, —C(=O)NH$_2$, —C(=O)NH(C$_1$-C$_6$) alkyl, and —C(=O)N(C$_1$-C$_6$ alkyl)$_2$; wherein r is an integer selected independently from 1, 2, 3, and 4.

According to some embodiments, R$^7$ is selected from —H, —(C$_1$-C$_7$) hydrocarbyl, substituted —(C$_1$-C$_7$) hydrocarbyl, —C(=O)R$^8$, and —(C$_1$-C$_6$) heteroalkyl.

Another aspect of this application is directed to compounds of Formula IV:

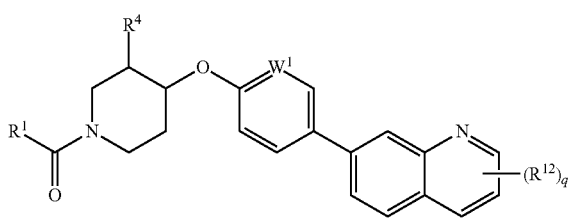

IV and salts thereof, e.g., pharmaceutically acceptable salts thereof, wherein:

R$^1$ is selected from —(C$_1$-C$_{10}$) hydrocarbyl, substituted —(C$_1$-C$_{10}$) hydrocarbyl, 3-7 membered heterocyclyl, substituted 3-7 membered heterocyclyl, —(C$_6$-C$_{10}$) aryl, substituted —(C$_6$-C$_{10}$) aryl, 5-6 membered heteroaryl, substituted 5-6 membered heteroaryl, —NR$^7$R$^8$, —N(OR$^8$)R$^7$, —N(SR$^8$)R$^7$, —SR$^7$, —C(=O)—(C$_1$-C$_6$) alkyl, and —(C$_1$-C$_6$) heteroalkyl;

W$^1$ is CH or C—R$^{10}$;

R$^7$ is selected from —H, —(C$_1$-C$_7$) hydrocarbyl, substituted —(C$_1$-C$_7$) hydrocarbyl, —C(=O)—(C$_1$-C$_7$) hydrocarbyl, —(C$_1$-C$_6$) heteroalkyl, 6 membered aryl, 5-6 membered heteroaryl and 5-6 membered heterocyclyl;

R$^8$ is selected from —H, and —(C$_1$-C$_6$) alkyl, wherein R$^7$ can optionally be structurally connected to R$^8$ to form a 5 to 7 membered heterocyclyl ring;

R$^{10}$ is selected from —F, —Cl, —CN, —(C$_1$-C$_6$)alkyl, —(C$_3$-C$_6$)cycloalkyl, —OH, —O(C$_1$-C$_6$)alkyl, NH$_2$, —NH(C$_1$-C$_6$)alkyl, —N((C$_1$-C$_6$)alkyl)$_2$, —C(=O)(C$_1$-C$_6$)alkyl, —C(=O)—(C$_3$-C$_6$) cycloalkyl, —C(=O)NH$_2$, —CF$_3$; and each R$^{12}$ is independently selected from —H, halogen, —(C$_1$-C$_6$) alkyl, —(C$_1$-C$_3$) haloalkyl, —O(C$_1$-C$_3$) haloalkyl, —(C$_3$-C$_6$) cycloalkyl, 5-6 membered heterocyclyl, —OH, —O(C$_1$-C$_6$) alkyl, —O(CH$_2$)$_r$-(5-6 membered heterocyclyl), —O(CH$_2$)$_r$—O(C$_1$-C$_6$) alkyl, —O(CH$_2$)$_r$—N(C$_1$-C$_6$ alkyl)$_2$, —NH$_2$, —CN, —NH(C$_1$-C$_6$) alkyl, —N(C$_1$-C$_6$ alkyl)$_2$, —NH(CH$_2$)$_r$O(C$_1$-C$_6$) alkyl, —NH(CH$_2$)$_r$—N(C$_1$-C$_6$ alkyl)$_2$, —C(=O)NH$_2$, —C(=O)NH(C$_1$-C$_6$) alkyl, and —C(=O)N(C$_1$-C$_6$ alkyl)$_2$; wherein R$^{12}$ may be at any position on the quinoline ring to which it is attached, and wherein r is an integer independently selected from 1, 2, 3 and 4; and q is an integer selected from 0, 1, 2 and 3. According to some embodiments, q is 0 or 1. According to some embodiments, q is 1. It will be understood that a value of 0 for q is the equivalent of all R$^{12}$ moieties being —H.

According to some embodiments, R$^1$ is selected from —(C$_1$-C$_{10}$) hydrocarbyl, substituted —(C$_1$-C$_{10}$) hydrocarbyl, 3-7 membered heterocyclyl, substituted 3-7 membered heterocyclyl, —(C$_6$-C$_{10}$) aryl, substituted —(C$_6$-C$_{10}$) aryl, 5-6 membered heteroaryl, substituted 5-6 membered heteroaryl, —NR$^7$R$^8$, —N(OR$^8$)R$^7$, —C(=O)—(C$_1$-C$_6$) alkyl, and —(C$_1$-C$_6$) heteroalkyl;

According to some embodiments, R$^1$ is selected from —NR$^7$R$^8$—SR$^7$, —N(SR$^8$)R$^7$ and —N(OR$^8$)R$^7$. According to some embodiments, R$^1$ is selected from —NR$^7$R$^8$ and —N(OR$^8$)R$^7$.

According to some embodiments, W$^1$ is CH.

According to some embodiments, R$^7$ is selected from —H, —(C$_1$-C$_7$) hydrocarbyl, substituted —(C$_1$-C$_7$) hydrocarbyl, —C(=O)—(C$_1$-C$_7$) hydrocarbyl, and —(C$_1$-C$_6$) heteroalkyl.

According to some embodiments, R$^7$ is selected from —H, —(C$_1$-C$_6$)alkyl, substituted —(C$_1$-C$_6$) alkyl, —C(=O)—(C$_1$-C$_6$) alkyl, and —(C$_1$-C$_6$) heteroalkyl;

According to some embodiments, R$^8$ is selected from —H, and —(C$_1$-C$_6$) alkyl.

According to some embodiments, each R$^{12}$ is independently selected from —H, halogen, —(C$_1$-C$_6$) alkyl, —(C$_3$-C$_6$) cycloalkyl, 5-6 membered heterocyclyl, —OH, —O(C$_1$-C$_6$) alkyl, —O(CH$_2$)$_r$-(5-6 membered heterocyclyl), —O(CH$_2$)$_r$—O(C$_1$-C$_6$) alkyl, —NH$_2$, —CN, —NH(C$_1$-C$_6$) alkyl, —N(C$_1$-C$_6$ alkyl)$_2$, —NH(CH$_2$)$_r$—O(C$_1$-C$_6$) alkyl, —NH(CH$_2$)$_r$—N(C$_1$-C$_6$ alkyl)$_2$, —C(=O)NH$_2$, —C(=O)NH(C$_1$-C$_6$) alkyl and —C(=O)N(C$_1$-C$_6$ alkyl)$_2$.

According to some embodiments, each R$^{12}$ is independently selected from —H, halogen, —(C$_1$-C$_6$) alkyl, —(C$_3$-C$_6$) cycloalkyl, 5-6 membered heterocyclyl, —OH, —O(C$_1$-C$_6$) alkyl, —CN, —NH(C$_1$-C$_6$) alkyl, —N(C$_1$-C$_6$ alkyl)$_2$, —C(=O)NH$_2$, —C(=O)NH(C$_1$-C$_6$) alkyl, and —C(=O)N(C$_1$-C$_6$ alkyl)$_2$.

Another aspect of this application is directed to compounds of Formula V:

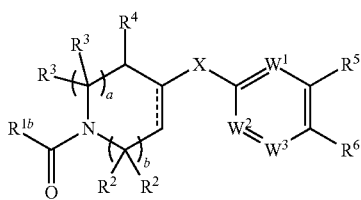

and salts thereof, e.g., pharmaceutically acceptable salts thereof, wherein:

$R^{1b}$ is selected from —$NR^7R^8$ and —$N(OR^8)R^7$;

a and b are independently selected from 0 and 1;

each $R^2$ is independently selected from —H and —($C_1$-$C_4$) alkyl;

each $R^3$ is independently selected from —H and —($C_1$-$C_4$) alkyl $R^4$ is selected from —H, —($C_1$-$C_6$) alkyl, =O, —OH, —O($C_1$-$C_6$) alkyl, halogen, and —CN; wherein one of the $R^3$ groups can optionally be structurally connected to one of the $R^2$ groups to form an alkylene bridge to produce a bicyclic ring; or one of the $R^3$ groups can optionally be structurally connected to the $R^1$ group to form a 5 to 7 membered heterocyclyl ring fused to the 1-2 face of the piperidine ring; or one of the $R^3$ groups can optionally be structurally connected to the $R^4$ group to form a 5-7 membered carbocyclic or heterocyclic ring fused to the 2-3 face of the piperidine ring;

====== signifies that the designated bond is a carbon-carbon single bond or a carbon-carbon double bond;

X is selected from —O—, —S—, —SO—, —$SO_2$—, and —$NR^9$—;

$W^1$, $W^2$ and $W^3$ are independently selected from N, CH, and C—$R^{10}$; provided that $W^2$ and $W^3$ are not both N;

$R^5$ is selected from —H, —$C_1$-$C_7$ hydrocarbyl, —$C_3$-$C_6$ heterocyclyl; halogen, —($C_1$-$C_3$) haloalkyl, —$OR^{7a}$, —CN, —$NR^{7a}R^{8a}$, —$O(CH_2)_nNR^{7a}R^{8a}$, —$O(CH_2)_nOR^{8a}$, —$NR^{8a}(CH_2)_nNR^{7a}R^{8a}$, —$NR^{8a}(CH_2)_nOR^{8a}$, —C(=O)$NR^{7a}R^{8a}$, —C(=O)$OR^{7a}$, 5-6 membered heteroaryl, and substituted 5-6 membered heteroaryl;

n is an integer selected from 1, 2, 3, and 4;

$R^6$ is selected from 6-membered heteroaryl, substituted 6-membered heteroaryl, 9-10 membered bicyclic heteroaryl, and substituted 9-10 membered bicyclic heteroaryl;

$R^7$ is selected from —H, —($C_1$-$C_7$) hydrocarbyl, substituted —($C_1$-$C_7$) hydrocarbyl, —C(=O)$R^8$, and —($C_1$-$C_6$) heteroalkyl;

$R^8$ is selected from —H, and —($C_1$-$C_6$) alkyl, wherein $R^7$ can optionally be structurally connected to $R^8$ to form a 5 to 7 membered heterocyclyl ring;

$R^{7a}$ is selected from —H, —($C_1$-$C_7$) hydrocarbyl, substituted —($C_1$-$C_7$) hydrocarbyl, —C(=O)$R^8$, and —($C_1$-$C_6$) heteroalkyl;

$R^{8a}$ is selected from —H, and —($C_1$-$C_6$) alkyl, wherein $R^{7a}$ can optionally be structurally connected to $R^{8a}$ to form a 5 to 7 membered heterocyclyl ring;

$R^9$ is selected from —($C_1$-$C_7$) hydrocarbyl, wherein $R^9$ can optionally be structurally connected to $R^4$ to form a 5 to 7 membered heterocyclyl ring;

each $R^{10}$ is independently selected from —($C_1$-$C_7$) hydrocarbyl, substituted —($C_1$-$C_7$) hydrocarbyl, halogen, —C(=O)—($C_1$-$C_7$) hydrocarbyl, —C(=O)$NH_2$, —C(=O)NH—($C_1$-$C_7$) hydrocarbyl, —C(=O)N($C_1$-$C_7$ hydrocarbyl)$_2$, —OH, —O($C_1$-$C_7$) hydrocarbyl, substituted —O($C_1$-$C_7$) hydrocarbyl, —($C_3$-$C_6$) heterocyclyl, substituted —($C_3$-$C_6$) heterocyclyl —CN, —$NH_2$, —NH($C_1$-$C_6$) alkyl, —N($C_1$-$C_6$ alkyl)$_2$, —NH($CH_2)_m$—$R^{11}$, —N($C_1$-$C_6$ alkyl)($CH_2)_m$—$R^{11}$, —O—($CH_2)_m$—$R^{11}$, and —($C_1$-$C_6$) heteroalkyl; m is an integer selected independently from 1, 2, 3, and 4; and $R^{11}$ is selected from —O—($C_1$-$C_6$)alkyl, —N($C_1$-$C_6$ alkyl)$_2$, —($C_3$-$C_6$)heterocyclyl and substituted —($C_3$-$C_6$) heterocyclyl.

According to some embodiments, a and b are both 1.
According to some embodiments, $R^2$ is —H.
According to some embodiments, $R^3$ is —H.
According to some embodiments, $R^4$ is selected from —H, —($C_1$-$C_6$) alkyl and halogen.

According to some embodiments, one of the $R^3$ groups is structurally connected to one of the $R^2$ groups to form a —$CH_2$—$CH_2$— bridge to produce a bicyclic ring; for example:

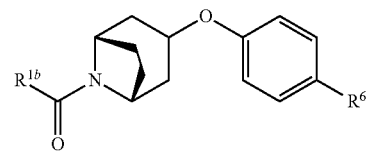

According to some embodiments, one of the $R^3$ groups is structurally connected to the $R^{1b}$ group to form a 5- or 6-membered heterocyclic ring fused to the 1-2 face of the piperidine ring; for example:

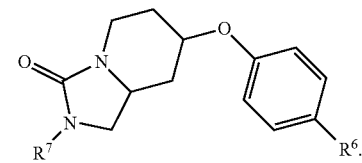

According to some embodiments, one of the $R^3$ groups is structurally connected to the $R^4$ group to form a 5-membered carbocyclic or heterocyclic ring fused to the 2-3 face of the piperidine ring; for example:

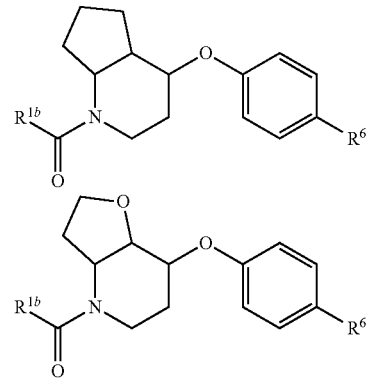

According to some embodiments, ====== is a carbon-carbon single bond.
According to some embodiments, X is —O—.
According to some embodiments, $W^1$, $W^2$ and $W^3$ are independently selected from CH, and C—$R^{10}$. According to some embodiments, $W^1$, $W^2$ and $W^3$ are CH.

According to some embodiments, $R^5$ is selected from —H, —$C_1$-$C_6$ alkyl, and halogen. According to some embodiments, $R^5$ is —H.

According to some embodiments, $R^9$ is —($C_1$-$C_6$) alkyl.

According to some embodiments, $R^6$ is selected from 9-10 membered bicyclic heteroaryl, and substituted 9-10 membered bicyclic heteroaryl; provided that, when $R^6$ is a 9-membered bicyclic heteroaryl or a substituted 9-membered bicyclic heteroaryl, the point of attachment of $R^6$ to the aromatic ring containing $W^1$, $W^2$ and $W^3$ is on a 6-membered ring portion of the 9-membered bicyclic heteroaryl or substituted 9-membered bicyclic heteroaryl. According to some embodiments, $R^6$ is selected from:

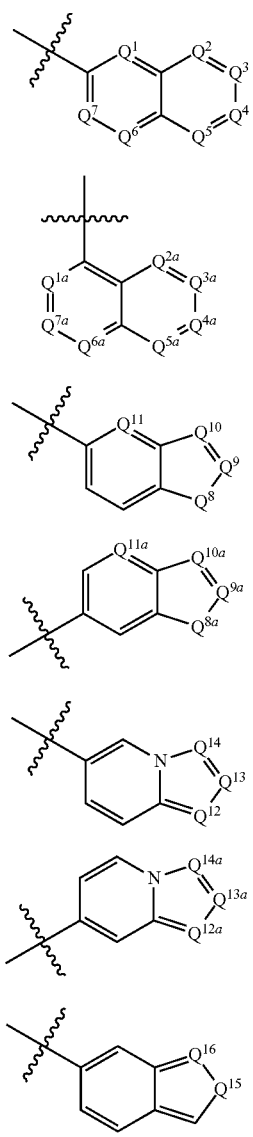

wherein, when $R^6$ is (i), $Q^1$, $Q^2$, $Q^3$, $Q^4$, $Q^5$, $Q^6$ and $Q^7$ are independently selected from N and C—$R^{12}$, provided that 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$;

when $R^6$ is (ii), $Q^{1a}$, $Q^{2a}$, $Q^{3a}$, $Q^{4a}$, $Q^{5a}$, $Q^{6a}$ and $Q^7$a are independently selected from N and C—$R^{12}$, provided that 1, 2 or 3 of $Q^{1a}$, $Q^2$a, $Q^3$a, $Q^{4a}$, $Q^{5a}$, $Q^{6a}$ and $Q^7$a are N, and the remainder of $Q^{1a}$, $Q^2$a, $Q^3$a, $Q^4$a, $Q^5$a, $Q^6$a and $Q^7$a are C—$R^{12}$;

when $R^6$ is (iii), $Q^8$ is selected from O, S, and N—$R^{12n}$, $Q^9$, $Q^{10}$ and $Q^{11}$ are independently selected from N and C—$R^{12}$, provided that 1 or 2 of $Q^9$, $Q^{10}$ and $Q^{11}$ are N, and the remainder of $Q^9$, $Q^{10}$ and $Q^{11}$ are C—$R^{12}$;

when $R^6$ is (iv), $Q^{8a}$ is selected from O, S, and N—$R^{12n}$, $Q^{9a}$, $Q^{10a}$ and $Q^{11a}$ are independently selected from N and C—$R^{12}$, provided that 1 or 2 of $Q^9$, $Q^{10}$ and $Q^{11}$ are N, and the remainder of $Q^9$, $Q^{10}$ and $Q^{11}$ are C—$R^{12}$;

when $R^6$ is (v), $Q^{12}$, $Q^{13}$ and $Q^{14}$ are independently selected from N and C—$R^{12}$; and when $R^6$ is (vi), $Q^{12a}$, $Q^{13a}$ and $Q^{14a}$ are independently selected from N and C—$R^{12}$;

when $R^6$ is (vii), $Q^{15}$ is selected from N—$R^{12n}$ and C—$R^{12}$ and $Q^{16}$ is selected from N and C—$R^{12}$; provided that one of $Q^{15}$ and $Q^{16}$ are not both C—$R^{12}$;

and wherein each $R^{12}$ is independently selected from —H, halogen, —($C_1$-$C_6$) alkyl, —($C_3$-$C_6$) cycloalkyl, —($C_1$-$C_3$) haloalkyl, —O($C_1$-$C_3$) haloalkyl, 5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$) alkyl, —O($CH_2$)$_r$—N($C_1$-$C_6$ alkyl)$_2$, —$NH_2$, —CN, —NH($C_1$-$C_6$) alkyl, —N($C_1$-$C_6$ alkyl)$_2$, —NH($CH_2$)$_r$—O($C_1$-$C_6$) alkyl, —NH($CH_2$)$_r$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$; wherein r is an integer selected independently from 1, 2, 3, and 4; and each $R^{12n}$ is selected from —H, —($C_1$-$C_7$) hydrocarbyl and substituted —($C_1$-$C_7$) hydrocarbyl.

It will be understood that the ring carbon ring atoms in (i), (ii), (iii), (iv), (v), (vi) and (vii) above (i.e., ring atoms which are not designated as N or Q) may optionally be substituted. According to some embodiments, none of these ring carbon ring atoms are substituted. According to some embodiments one or two of these ring carbon ring atoms is substituted with a substituent selected from —OH, —($C_1$-$C_3$) alkyl, —O($C_1$-$C_3$)alkyl and halogen. According to some embodiments, one of these ring carbon ring atoms is substituted with a substituent selected from —OH, —$CH_3$, —$OCH_3$, —F and —Cl.

According to some embodiments, each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$) alkyl, —$NH_2$, —CN, —NH($C_1$-$C_6$) alkyl, —N($C_1$-$C_6$ alkyl)$_2$, —NH($CH_2$)$_r$—O($C_1$-$C_6$) alkyl, —NH($CH_2$)$_r$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$.

According to some embodiments, each $R^{12}$ is independently selected from —H, —Cl, —F, —$CH_3$, —$CH_2CH_3$, —$OCH_3$, —$OCH_2CH_3$, —$OCH(CH_3)_2$, —$CF_3$, —$OCF_3$, —O($CH_2$)$_2$(pyrrolidin-1-yl), —O($CH_2$)$_3$(pyrrolidin-1-yl), —O($CH_2$)$_2$(morpholin-1-yl), —O($CH_2$)$_3$(morpholin-1-yl), —O($CH_2$)$_2$(piperidin-1-yl), —O($CH_2$)$_3$(piperidin-1-yl), —O($CH_2$)$_2$(N-methylpiperazin-1-yl), —O($CH_2$)$_3$(N-methylpiperazin-1-yl), —O($CH_2$)$_2$—$OCH_3$, —O($CH_2$)$_3$—$OCH_3$, —O($CH_2$)$_2$—N($CH_3$)$_2$, —O($CH_2$)$_3$—N($CH_3$)$_2$, —$NH_2$, $NHCH_3$, N($CH_3$)$_2$, N-methylpiperazin-1-yl, pyrrolidin-1-yl, morpholin-1-yl, and piperidin-1-yl.

According to some embodiments, each $R^{12}$ is independently selected from —H, —Cl, —F, —$CH_3$, —$CH_2CH_3$, —$OCH_3$, —$OCH_2CH_3$, —$OCH(CH_3)_2$, —O($CH_2$)$_2$(pyrrolidin-1-yl), —O($CH_2$)$_3$(pyrrolidin-1-yl), —O($CH_2$)$_2$(morpholin-1-yl), —O($CH_2$)$_3$(morpholin-1-yl), —O($CH_2$)$_2$(piperidin-1-yl), —O($CH_2$)$_3$(piperidin-1-yl), —O($CH_2$)$_2$(N-methylpiperazin-1-yl), —O($CH_2$)$_3$(N-methylpiperazin-1- yl), —O(CH₂)₂—OCH₃, —O(CH₂)₃—OCH₃, —O(CH₂)₂—N(CH₃)₂, —O(CH₂)₃—N(CH₃)₂, —NH₂, NHCH₃, N(CH₃)₂, N-methylpiperazin-1-yl, pyrrolidin-1-yl, morpholin-1-yl, and piperidin-1-yl.

According to some embodiments, $R^{12n}$ is selected from —H, benzyl and —$C_1$-$C_6$ alkyl.

According to some embodiments, $R^6$ is selected from the aromatic ring systems depicted in Table 1b (infra).

According to some embodiments, $R^6$ is:

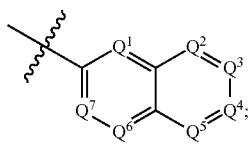

(i)

wherein 1 or 2 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$. According to some embodiments, when $R^6$ is (i), one of $Q^1$, $Q^2$, $Q^3$, $Q^4$, $Q^5$, $Q^6$ and $Q^7$ is N, and the remainder of $Q^1$, $Q^2$, $Q^3$, $Q^4$, $Q^5$, $Q^6$ and $Q^7$ are C—$R^{12}$. According to some embodiments, when $R^6$ is (i), $Q^2$ is N, and the remainder of $Q^1$, $Q^3$, $Q^4$, $Q^5$, $Q^6$ and $Q^7$ are C—$R^{12}$. According to some embodiments, when $R^6$ is (i), $Q^6$ is N, and $Q^1$, $Q^2$, $Q^3$, $Q^5$, $Q^5$ and $Q^7$ are C—$R^{12}$. According to some embodiments, when $R^6$ is (i), $Q^6$ is N, $Q^2$, $Q^3$, $Q^5$, $Q^5$ and $Q^7$ are CH, and $Q^1$ is C—$R^{12}$, wherein —$R^{12}$ is other than —H.

According to some embodiments, $R^6$ is:

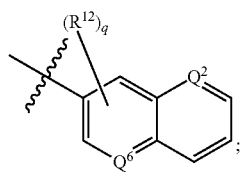

(i²)

wherein one of $Q^2$ and $Q^6$ is N, and the other of $Q^2$ and $Q^6$ is C—$R^{12}$, and q is an integer selected from 0, 1, 2 and 3. According to some embodiments of i², $Q^2$ is N, and $Q^6$ is C—$R^{12}$. According to some embodiments, $Q^6$ is N, and $Q^2$ is C—$R^{12}$. According to some embodiments, q is selected from 0, 1 and 2. According to some embodiments of i², q is 0 or 1. It will be understood that a q value of 0 is the equivalent of designating all $R^{12}$ that are bonded to the i² bicyclic heteroaryl at other than $Q^2$ and $Q^6$ as being —H.

According to some embodiments of i², each $R^{12}$ is independently selected from —H, —Cl, —F, —CH₃, —CH₂CH₃, —OCH₃, —OCH₂CH₃, —OCH(CH₃)₂, —O(CH₂)₂(pyrrolidin-1-yl), —O(CH₂)₃(pyrrolidin-1-yl), —O(CH₂)₂(morpholin-1-yl), —O(CH₂)₃(morpholin-1-yl), —O(CH₂)₂(piperidin-1-yl), —O(CH₂)₃(piperidin-1-yl), —O(CH₂)₂(N-methylpiperazin-1-yl), —O(CH₂)₃(N-methylpiperazin-1-yl), —O(CH₂)₂—OCH₃, —O(CH₂)₃—OCH₃, —O(CH₂)₂—N(CH₃)₂, —O(CH₂)₃—N(CH₃)₂, —NH₂, NHCH₃, N(CH₃)₂, N-methylpiperazin-1-yl, pyrrolidin-1-yl, morpholin-1-yl, and piperidin-1-yl.

According to some embodiments of i², each $R^{12n}$ is independently selected from —H, benzyl and —$C_1$-$C_6$ alkyl.

According to some embodiments, $R^6$ is:

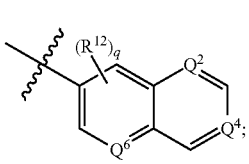

(i³)

wherein one or two of $Q^2$, $Q^4$ and $Q^6$ is N, and the remainder of $Q^2$, $Q^4$ and $Q^6$ are C—$R^{12}$, and q is an integer selected from 0, 1, 2 and 3.

According to some embodiments of i³, each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O(CH₂)ᵣ-(5-6 membered heterocyclyl), —O(CH₂)ᵣ—O($C_1$-$C_6$) alkyl, —NH₂, —CN, —NH($C_1$-$C_6$) alkyl, —N($C_1$-$C_6$ alkyl)₂, —NH(CH₂)ᵣ—O($C_1$-$C_6$) alkyl, —NH(CH₂)ᵣ—N($C_1$-$C_6$ alkyl)₂, —C(=O)NH₂, —C(=O)NH($C_1$-$C_6$) alkyl, and —C(=O)N($C_1$-$C_6$ alkyl)₂; wherein r is an integer selected from 1, 2, 3 and 4; or a salt thereof.

According to some embodiments of i³, each $R^{12}$ is independently selected from —H, —Cl, —F, —CH₃, —CH₂CH₃, —OCH₃, —OCH₂CH₃, —OCH(CH₃)₂, —O(CH₂)₂(pyrrolidin-1-yl), —O(CH₂)₃(pyrrolidin-1-yl), —O(CH₂)₂(morpholin-1-yl), —O(CH₂)₃(morpholin-1-yl), —O(CH₂)₂(piperidin-1-yl), —O(CH₂)₃(piperidin-1-yl), —O(CH₂)₂(N-methylpiperazin-1-yl), —O(CH₂)₃(N-methylpiperazin-1-yl), —O(CH₂)₂—OCH₃, —O(CH₂)₃—OCH₃, —O(CH₂)₂—N(CH₃)₂, —O(CH₂)₃—N(CH₃)₂, —NH₂, NHCH₃, N(CH₃)₂, N-methylpiperazin-1-yl, pyrrolidin-1-yl, morpholin-1-yl, and piperidin-1-yl. According to some embodiments of i³, each $R^{12}$ is independently selected from —H, —Cl, —F, —CH₃, —CH₂CH₃, —OCH₃, and —OCH₂CH₃.

According to some embodiments of i³, q is 0, 1 or 2. According to some embodiments, q is 0 or 1. It will be understood that a q value of 0 is the equivalent of designating all $R^{12}$ that are bonded to the bicyclic heteroaryl moiety at other than $Q^2$, $Q^4$ or $Q^6$ as being —H.

According to some embodiments of i³, $Q^2$ is N, and $Q^4$ and $Q^6$ are C—$R^{12}$. According to some embodiments of i³, $Q^6$ is N, and $Q^2$ and $Q^4$ are C—$R^{12}$. According to some embodiments of i³, $Q^4$ is N, and $Q^2$ and $Q^6$ are C—$R^{12}$. According to some embodiments of i³, $Q^2$ is C—$R^{12}$, and $Q^4$ and $Q^6$ are N. According to some embodiments of i³, $Q^6$ is C—$R^{12}$, and $Q^2$ and $Q^4$ are N. According to some embodiments of i³, $Q^4$ is C—$R^{12}$, and $Q^2$ and $Q^6$ are N.

According to some embodiments, $R^7$ is selected from —H, —($C_1$-$C_6$) alkyl, substituted —($C_1$-$C_6$)alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, —C(=O)$R^8$, and —($C_1$-$C_6$) heteroalkyl. According to some embodiments, $R^7$ is selected from —H, and —($C_1$-$C_6$) alkyl.

According to some embodiments, $R^{7a}$ is selected from —H, —($C_1$-$C_6$) alkyl, substituted —($C_1$-$C_6$)alkyl, —($C_3$-$C_6$) cycloalkyl, substituted —($C_3$-$C_6$)cycloalkyl, —($C_2$-$C_6$) alkenyl, substituted —($C_2$-$C_6$)alkenyl, benzyl, substituted benzyl, —C(=O)$R^8$, and —($C_1$-$C_6$) heteroalkyl. According to some embodiments, $R^{7a}$ is selected from —H and —($C_1$-$C_6$) alkyl.

According to some embodiments, $R^8$ is selected from —H, and —($C_1$-$C_6$) alkyl. According to some embodiments, $R^8$ is selected from —H, —CH₃ and —CH₂CH₃.

According to some embodiments, $R^{8a}$ is selected from —H, and —($C_1$-$C_6$) alkyl. According to some embodiments, $R^{8a}$ is selected from —H, —$CH_3$ and —$CH_2CH_3$.

Another aspect of this application is directed to compounds of Formula V(a), (which is a subset of compounds according to Formula V):

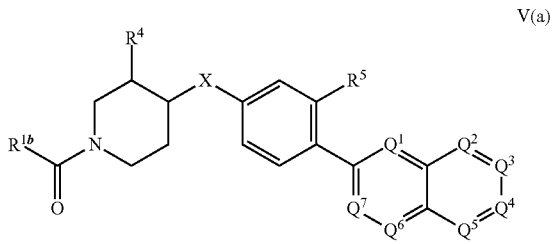

V(a)

and salts thereof, e.g., pharmaceutically acceptable salts thereof, wherein:

$R^{1b}$ is selected from —$NR^7R^8$ and —$N(OR^8)R^7$;

$R^4$ is selected from —H, —($C_1$-$C_6$) alkyl, =O, —OH, —O($C_1$-$C_6$) alkyl, halogen and —CN;

X is selected from —O— and —S—;

$R^5$ is selected from —H, —$C_1$-$C_7$ hydrocarbyl, —$C_3$-$C_6$ heterocyclyl; halogen, —($C_1$-$C_3$) haloalkyl, —$OR^{7a}$, —CN, —$NR^{7a}R^{8a}$, —O($CH_2$)$_n$$NR^{7a}R^{8a}$, —O($CH_2$)$_n$$OR^{8a}$, —$NR^{8a}$($CH_2$)$_n$$NR^{7a}R^{8a}$, —$NR^{8a}$($CH_2$)$_n$$OR^{8a}$, —C(=O) $NR^{7a}R^{8a}$, —C(=O)$OR^{7a}$, 5-6 membered heteroaryl and substituted 5-6 membered heteroaryl;

n is an integer selected from 1, 2, 3, and 4;

$R^7$ is selected from —H, —($C_1$-$C_7$) hydrocarbyl, substituted —($C_1$-$C_7$) hydrocarbyl, —C(=O)$R^8$, and —($C_1$-$C_6$) heteroalkyl;

$R^8$ is selected from —H, and —($C_1$-$C_6$) alkyl, wherein $R^7$ can optionally be structurally connected to $R^8$ to form a 5 to 7 membered heterocyclyl ring;

$R^{7a}$ is selected from —H, —($C_1$-$C_7$) hydrocarbyl, substituted —($C_1$-$C_7$) hydrocarbyl, —C(=O)$R^8$, and —($C_1$-$C_6$) heteroalkyl;

$R^{8a}$ is selected from —H, and —($C_1$-$C_6$) alkyl, wherein $R^{7a}$ can optionally be structurally connected to $R^{8a}$ to form a 5 to 7 membered heterocyclyl ring;

$Q^1$, $Q^2$, $Q^3$, $Q^4$, $Q^5$, $Q^6$ and $Q^7$ are independently selected from N and C—$R^{12}$, provided that 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$.

each $R^{12}$ is independently selected from —H, halogen, —($C_1$-$C_6$) alkyl, —($C_1$-$C_3$) haloalkyl, —O($C_1$-$C_3$) haloalkyl, —($C_3$-$C_6$) cycloalkyl, 5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$) alkyl, —$NH_2$, —O($CH_2$)$_r$—N($C_1$-$C_6$ alkyl)$_2$, —CN, —NH($C_1$-$C_6$) alkyl, —N($C_1$-$C_6$ alkyl)$_2$, —NH($CH_2$)$_r$—O($C_1$-$C_6$) alkyl, —NH ($CH_2$)$_r$—N($C_1$-$C_6$ alkyl)$_2$, —C(=O)$NH_2$, —C(=O)NH ($C_1$-$C_6$) alkyl, and —C(=O)N($C_1$-$C_6$ alkyl)$_2$; and r is an integer selected independently from 1, 2, 3, and 4.

According to some embodiments, $R^4$ is selected from —H, —($C_1$-$C_6$) alkyl and halogen.

According to some embodiments, X is —O—.

According to some embodiments, $R^5$ is selected from —H, —$C_1$-$C_6$ alkyl, and halogen. According to some embodiments, $R^5$ is —H.

According to some embodiments, each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_r$-(5-6 membered heterocyclyl), —O($CH_2$)$_r$—O($C_1$-$C_6$) alkyl, —$NH_2$, —CN, —NH($C_1$-$C_6$) alkyl, —N($C_1$-$C_6$ alkyl)$_2$, —NH($CH_2$)$_r$—O($C_1$-$C_6$) alkyl, —NH($CH_2$)$_r$—N($C_1$-$C_6$ alkyl)$_2$, —C(=O)$NH_2$, —C(=O) NH($C_1$-$C_6$) alkyl, and —C(=O)N($C_1$-$C_6$ alkyl)$_2$.

According to some embodiments, each $R^{12}$ is independently selected from —Cl, —F, —$CH_3$, —$CH_2CH_3$, —$CF_3$, —$OCF_3$, —$OCH_3$, —$OCH_2CH_3$, —$OCH(CH_3)_2$, —O($CH_2$)$_2$(pyrrolidin-1-yl), —O($CH_2$)$_3$(pyrrolidin-1-yl), —O($CH_2$)$_2$(morpholin-1-yl), —O($CH_2$)$_3$(morpholin-1-yl), —O($CH_2$)$_2$(piperidin-1-yl), —O($CH_2$)$_3$(piperidin-1-yl), —O($CH_2$)$_2$(N-methylpiperazin-1-yl), —O($CH_2$)$_3$(N-methylpiperazin-1-yl), —O($CH_2$)$_2$—$OCH_3$, —O($CH_2$)$_3$—$OCH_3$, —O($CH_2$)$_2$—N($CH_3$)$_2$, —O($CH_2$)$_3$—N($CH_3$)$_2$, —$NH_2$, $NHCH_3$, N($CH_3$)$_2$, N-methylpiperazin-1-yl, pyrrolidin-1-yl, morpholin-1-yl, and piperidin-1-yl.

According to some embodiments, each $R^{12}$ is independently selected from —Cl, —F, —$CH_3$, —$CH_2CH_3$, —$OCH_3$, —$OCH_2CH_3$, —$OCH(CH_3)_2$, —O($CH_2$)$_2$(pyrrolidin-1-yl), —O($CH_2$)$_3$(pyrrolidin-1-yl), —O($CH_2$)$_2$(morpholin-1-yl), —O($CH_2$)$_3$(morpholin-1-yl), —O($CH_2$)$_2$(piperidin-1-yl), —O($CH_2$)$_3$(piperidin-1-yl), —O($CH_2$)$_2$(N-methylpiperazin-1-yl), —O($CH_2$)$_3$(N-methylpiperazin-1-yl), —O($CH_2$)$_2$—$OCH_3$, —O($CH_2$)$_3$—$OCH_3$, —O ($CH_2$)$_2$—N($CH_3$)$_2$, —O($CH_2$)$_3$—N($CH_3$)$_2$, —$NH_2$, $NHCH_3$, N($CH_3$)$_2$, N-methylpiperazin-1-yl, pyrrolidin-1-yl, morpholin-1-yl, and piperidin-1-yl.

Compounds according to Formula I may include for example: 1-[4-(4-isoquinolin-6-yl-phenoxy)-piperidin-1-yl]-propan-1-one; 1-[4-(4-quinolin-3-yl-phenoxy)-piperidin-1-yl]-propan-1-one; 2-methyl-1-[4-(4-quinolin-7-yl-phenoxy)-piperidin-1-yl]-propan-1-one; 1-[4-(4-quinolin-7-yl-phenoxy)-piperidin-1-yl]-propan-1-one; 4-(2-fluoro-4-quinolin-3-yl-phenox)piperidine-1-carboxylic acid tert-butyl ester; 1-[4-(2-fluoro-4-quinolin-3-yl-phenoxy)-piperidin-1-yl]propan-1-one; 1-[4-(2-fluoro-4-quinolin-3-yl-phenoxy)-piperidin-1-yl]-2-methyl-propan-1-one; 1-[4-(4-benzofuran-5-yl-phenoxy)-piperidin-1-yl]-propan-1-one; 1-[4-(4-benzofuran-5-yl-phenoxy)-piperidin-1-yl]-2-methyl-propan-1-one; 1-[4-(4-naphthalen-2-yl-phenoxy)-piperidin-1-yl]-propan-1-one; 2-methyl-1-[4-(4-naphthalen-2-yl-phenoxy)-piperidin-1-yl]-propan-1-one; 1-[4-(4-1,5-naphthyridin-3-yl-phenoxy)-piperidin-1-yl]-propan-1-one; 2-methyl-1-[4-(4-1,5-naphthyridin-3-yl-phenoxy)-piperidin-1-yl]-propan-1-one; cyclopropyl-[4-(4-1,5-naphthyridin-3-yl-phenoxy)-piperidin-1-yl]-methanone; 4-(2-fluoro-4-quinolin-3-yl-phenoxy)-piperidine-1-carboxylic acid methyl ester; 1-{4-[4-(2-chloro-quinolin-3-yl)-phenoxy]-piperidin-1-yl}-propan-1-one; {4-[4-(2-chloroquinolin-3-yl)-phenoxy]-piperidin-1-yl}-cyclopropylmethanone; 1-{4-[4-(2-methoxy-quinolin-3-yl)-phenoxy]-piperidin-1-yl}-propan-1-one; cyclopropyl-{4-[4-(5,6,7,8-tetrahydroquinolin-3-yl)-phenoxy]-piperidin-1-yl}-methanone; cyclobutyl-{4-[4-(5,6,7,8-tetrahydroquinolin-3-yl)-phenoxy]-piperidin-1-yl}-methanone; 1-{4-[4-(5,6,7,8-tetrahydroquinolin-3-yl)-phenoxy]-piperidin-1-yl}-propan-1-one; 1-{4-[4-(8-fluoroquinolin-7-yl)-phenoxy]-piperidin-1-yl}-propan-1-one; cyclopropyl-{4-[4-(8-fluoro-quinolin-7-yl)-phenoxy]-piperidin-1-yl}-methanone; cyclobutyl-{4-[4-(8-fluoroquinolin-7-yl)-phenoxy]-piperidin-1-yl}-methanone; 1-{4-[4-(8-fluoro-2-methylquinolin-7-yl)-phenoxy]-piperidin-1-yl}-propan-1-one; cyclopropyl-{4-[4-(8-fluoro-2-methylquinolin-7-yl)-phenoxy]-piperidin-1-yl}-methanone; cyclobutyl-{4-[4-(8-fluoro-2-methylquinolin-7-yl)-phenoxy]-piperidin-1-yl}-methanone; {4-[4-(5-fluoroquinolin-3-yl)-phenoxy]-piperidin-1-yl}-(R)-tetrahydrofuran-2-yl-methanone; 1-{4-[4-(5-fluoroquinolin- 3-yl)-phenoxy]-piperidin-1-yl}-propan-1-one; cyclopropyl-{4-[4-(5-fluoroquinolin-3-yl)-phenoxy]-piperidin-1-yl}-methanone; cyclobutyl-{4-[4-(5-fluoroquinolin-3-yl)-phenoxy]-piperidin-1-yl}-methanone; 1-{4-[4-(1H-pyrrolo[2,3-b]pyridin-5-yl)-phenoxy]-piperidin-1-yl}-propan-1-one; cyclopropyl-{4-[4-(1H-pyrrolo[2,3-b]pyridin-5-yl)-phenoxy]-piperidin-1-yl}-methanone; cyclopropyl-{4-[4-(7-methoxy-quinolin-3-yl)-phenoxy]-piperidin-1-yl}-methanone; 1-{4-[4-(7-methoxyquinolin-3-yl)-phenoxy]-piperidin-1-yl}-propan-1-one; 1-{4-[4-(8-methylquinolin-7-yl)-phenoxy]-piperidin-1-yl}-propan-1-one; cyclopropyl-{4-[4-(8-methylquinolin-7-yl)-phenoxy]-piperidin-1-yl}-methanone; cyclobutyl-{4-[4-(8-methylquinolin-7-yl)-phenoxy]-piperidin-1-yl}-methanone; cyclopropyl-[4-(4-quinolin-2-yl-phenoxy)-piperidin-1-yl]-methanone; 1-[4-(4-quinolin-2-yl-phenoxy)-piperidin-1-yl]-propan-1-one; cyclobutyl-[4-(4-quinolin-2-yl-phenoxy)-piperidin-1-yl]-methanone; [4-(4-quinolin-2-yl-phenoxy)-piperidin-1-yl]-(R)-tetrahydrofuran-2-yl-methanone; 1-[4-(4-isoquinolin-3-yl-phenoxy)-piperidin-1-yl]-propan-1-one; cyclopropyl-[4-(4-isoquinolin-3-yl-phenoxy)-piperidin-1-yl]-methanone; cyclobutyl-[4-(4-isoquinolin-3-yl-phenoxy)-piperidin-1-yl]-methanone; [4-(4-isoquinolin-3-yl-phenoxy)-piperidin-1-yl]-(R)-tetrahydrofuran-2-yl-methanone; 1-{4-[4-(4-chloroquinolin-3-yl)-phenoxy]-piperidin-1-yl}-propan-1-one; {4-[4-(4-chloroquinolin-3-yl)-phenoxy]-piperidin-1-yl}-cyclopropyl-methanone; {4-[4-(4-chloroquinolin-3-yl)-phenoxy]-piperidin-1-yl}-cyclobutylmethanone; 1-{4-[4-(4-methoxyquinolin-3-yl)-phenoxy]-piperidin-1-yl})-propan-1-one; 1-[4-(4-furo[3,2-b]pyridin-6-yl-phenoxy)-piperidin-1-yl]-propan-1-one; cyclopropyl-[4-(4-furo[3,2-b]pyridin-6-yl-phenoxy)-piperidin-1-yl]-methanone; 1-{4-[4-(6-methoxy-quinolin-3-yl)-phenoxy]-piperidin-1-yl}-propan-1-one; cyclopropyl-{4-[4-(6-methoxy-quinolin-3-yl)-phenoxy]-piperidin-1-yl}-methanone; 1-{4-[4-(6,7-dimethoxyquinolin-3-yl)-phenoxy]-piperidin-1-yl}-propan-1-one; cyclopropyl-{4-[4-(6,7-dimethoxyquinolin-3-yl)-phenoxy]-piperidin-1-yl}-methanone; 1-{4-[4-(8-methoxyquinolin-3-yl)-phenoxy]-piperidin-1-yl}-propan-1-one; cyclopropyl-{4-[4-(8-methoxyquinolin-3-yl)-phenoxy]-piperidin-1-yl}-methanone; {4-[4-(8-chloroquinolin-7-yl)-phenoxy]-piperidin-1-yl}-cyclopropyl-methanone; 1-{4-[4-(4-methylquinolin-3-yl)-phenoxy]-piperidin-1-yl}-propan-1-one; cyclopropyl-{4-[4-(4-methylquinolin-3-yl)-phenoxy]-piperidin-1-yl}-methanone; cyclobutyl-{4-[4-(4-methylquinolin-3-yl)-phenoxy]-piperidin-1-yl}-methanone; 1-{4-[4-(7-methylquinolin-3-yl)-phenoxy]-piperidin-1-yl}-propan-1-one; cyclopropyl-{4-[4-(7-methyl-quinolin-3-yl)-phenoxy]-piperidin-1-yl}-methanone; {4-[4-(4-methylquinolin-3-yl)-phenoxy]-piperidin-1-yl}-(R)-tetrahydrofuran-2-yl-methanone; 1-[4-(4-quinoxalin-2-ylphenoxy)-piperidin-1-yl]-propan-1-one; cyclopropyl-[4-(4-quinoxalin-2-yl-phenoxy)-piperidin-1-yl]-methanone; [4-(4-quinoxalin-2-yl-phenoxy)-piperidin-1-yl]-(R)-tetrahydrofuran-2-yl-methanone; {4-[4-(8-methyl-quinolin-7-yl)-phenoxy]-piperidin-1-yl}-(R)-tetrahydrofuran-2-yl-methanone; {4-[4-(8-methylquinolin-7-yl)-phenoxy]-piperidin-1-yl}-(S)-tetrahydrofuran-2-yl-methanone; {4-[4-(4-chloroquinolin-3-yl)-phenoxy]-piperidin-1-yl}-(R)-tetrahydrofuran-2-yl-methanone; 1-{4-[4-(4-methylquinolin-3-yl)-phenoxy]-piperidin-1-yl}-propane-1,2-dione; isoxazolidin-2-yl-[4-(4-quinolin-3-yl-phenoxy)-piperidin-1-yl]-methanone; [4-(4-isoquinolin-3-yl-phenoxy)-piperidin-1-yl]-isoxazolidin-2-yl-methanone; isoxazolidin-2-yl-{4-[4-(8-methylquinolin-7-yl)-phenoxy]-piperidin-1-yl}-methanone; {4-[4-(4-chloroquinolin-3-yl)-phenoxy]-piperidin-1-yl}- isoxazolidin-2-yl-methanone; {4-[4-(8-chloroquinolin-7-yl)-phenoxy]-piperidin-1-yl}-isoxazolidin-2-yl-methanone; isoxazolidin-2-yl-{4-[4-(4-methylquinolin-3-yl)-phenoxy]-piperidin-1-yl}-methanone; isoxazolidin-2-yl-{4-[4-(8-methoxyquinolin-7-yl)-phenoxy]-piperidin-1-yl}-methanone; isoxazolidin-2-yl-{4-[4-(7-methylquinolin-3-yl)-phenoxy]-piperidin-1-yl}-methanone; isoxazolidin-2-yl-[4-(4-quinoxalin-2-yl-phenoxy)-piperidin-1-yl]-methanone; 4-[4-(4-methylquinolin-3-yl)-phenoxy]-piperidine-1-carboxylic acid methoxyamide; 4-[4-(4-methylquinolin-3-yl)-phenoxy]-piperidine-1-carboxylic acid methoxymethylamide; 4-[4-(4-methyl-quinolin-3-yl)-phenoxy]-piperidine-1-carboxylic acid ethylamide; 4-[4-(8-methoxyquinolin-7-yl)-phenoxy]-piperidine-1-carboxylic acid methylamide; 4-[4-(8-methoxyquinolin-7-yl)-phenoxy]-piperidine-1-carboxylic acid ethylamide; 4-[4-(4-methylquinolin-3-yl)-phenoxy]-piperidine-1-carboxylic acid hydroxyamide; N-ethyl-4-[4-(8-methyl-7-quinolyl)phenoxy]piperidine-1-carboxamide; N,N-dimethyl-4-[4-(8-methyl-7-quinolyl)phenoxy]piperidine-1-carboxamide; ethyl 4-[4-(8-methyl-7-quinolyl)phenoxy]piperidine-1-carboxylate; N-methoxy-4-[4-(8-methyl-7-quinolyl)phenoxy]piperidine-1-carboxamide; N-isopropyl-4-[4-(8-methyl-7-quinolyl)phenoxy]piperidine-1-carboxamide; N-ethoxy-4-[4-(8-methyl-7-quinolyl)phenoxy]piperidine-1-carboxamide; [4-[4-(8-methyl-7-quinolyl)phenoxy]-1-piperidyl]-pyrrolidin-1-yl-methanone; N-methyl-4-[4-(8-methyl-7-quinolyl)phenoxy]piperidine-1-carboxamide; 4-[4-(8-methyl-7-quinolyl)phenoxy]-N-propyl-piperidine-1-carboxamide; 4-[4-(8-methyl-7-quinolyl)phenoxy]piperidine-1-carboxamide; [4-[4-(8-methyl-7-quinolyl)phenoxy]-1-piperidyl]-(1-piperidyl)methanone; [4-[4-(8-methyl-7-quinolyl)phenoxy]-1-piperidyl]-morpholinomethanone; cyclopropyl-[4-(4-quinolin-3-yl-phenoxy)-piperidin-1-yl]-methanone; cyclobutyl-[4-(4-quinolin-3-yl-phenoxy)-piperidin-1-yl]-methanone; cyclopentyl-[4-(4-quinolin-3-yl-phenoxy)-piperidin-1-yl]-methanone; [4-(4-quinolin-3-yl-phenoxy)-piperidin-1-yl]-(R)-tetrahydrofuran-2-yl-methanone; [4-(4-quinolin-3-yl-phenoxy)-piperidin-1-yl]-(S)-tetrahydrofuran-2-yl-methanone; 2-methoxy-1-[4-(4-quinolin-3-yl-phenoxy)-piperidin-1-yl]-ethanone; [4-(4-quinolin-3-yl-phenoxy)-piperidin-1-yl]-(tetrahydropyran-2-yl)-methanone; [4-(4-quinolin-3-yl-phenoxyl)-piperidin-1-yl]-(tetrahydrofuran-3-yl)-methanone; (R)-2-methoxy-1-[4-(4-quinolin-3-yl-phenoxy)-piperidin-1-yl]-propan-1-one; (S)-2-methoxy-1-[4-(4-quinolin-3-yl-phenoxy)-piperidin-1-yl]-propan-1-one; 2-hydroxy-1-[4-(4-quinolin-3-yl-phenoxy)-piperidin-1-yl]-ethanone; [4-(4-quinolin-3-yl-phenoxy)-piperidin-1-yl]-(tetrahydropyran-2-yl)-methanone; 1-[4-(4-quinolin-3-yl-phenoxy)-piperidin-1-yl]-ethanone; 2-methyl-1-[4-(4-quinolin-3-yl-phenoxy)-piperidin-1-yl]-propan-1-one; 2,2-dimethyl-1-[4-(4-quinolin-3-yl-phenoxy)-piperidin-1-yl]-propan-1-one; (2-methyl-1,3-dioxolan-2-yl)-[4-(4-quinolin-3-yl-phenoxy)-piperidin-1-yl]-methanone; 2-methanesulfonyl-1-[4-(4-quinolin-3-yl-phenoxy)-piperidin-1-yl]-ethanone; (1,1-dioxidotetrahydrothiophen-2-yl)(4-(4-(quinolin-3-yl)phenoxy)piperidin-1-yl)methanone; (3,3-difluorocyclobutyl)-[4-(4-quinolin-3-yl-phenoxy)-piperidin-1-yl]-methanone; (R)-5-[4-(4-quinolin-3-yl-phenoxy)-piperidine-1-carbonyl]-dihydrofuran-2-one; (3-methylfuran-2-yl)-[4-(4-quinolin-3-yl-phenoxy)-piperidin-1-yl]-methanone; (3,5-dimethylfuran-2-yl)-[4-(4-quinolin-3-yl-phenoxy)-piperidin-1-yl]-methanone; oxazol-2-yl-[4-(4-quinolin-3-yl-phenoxy)-piperidin-1-yl]-methanone; isoxazol-3-yl-[4-(4-quinolin-3-yl-phenoxy)-piperidin-1-yl]-methanone; isothiazol-3-yl-[4-(4-quinolin-3-yl-phenoxy)-piperidin-1- yl]-methanone; [4-(4-quinolin-3-yl-phenoxy)-piperidin-1-yl]-(tetrahydrofuran-2-yl)-methanone; phenyl-[4-(4-quinolin-3-yl-phenoxy)-piperidin-1-yl]-methanone; (2,5-dimethyl-phenyl)-[4-(4-quinolin-3-yl-phenoxy)-piperidin-1-yl]-methanone; [3-(1H-imidazol-2-yl)-phenyl]-[4-(4-quinolin-3-yl-phenoxy)-piperidin-1-yl]-methanone; [3-(1H-benzimidazol-2-yl)-phenyl]-[4-(4-quinolin-3-yl-phenoxy)-piperidin-1-yl]-methanone; N-methoxy-4-[4-(8-methoxy-7-quinolyl)phenoxy]piperidine-1-carboxamide; 1-[4-(5-quinolin-3-yl-pyridin-2-yloxy)-piperidin-1-yl]-propan-1-one; 2-methyl-1-[4-(5-quinolin-3-yl-pyridin-2-yloxy)-piperidin-1-yl]-propan-1-one; cyclopropyl-[4-(5-quinolin-3-yl-pyridin-2-yloxy)-piperidin-1-yl]-methanone; 1-[4-(5-quinolin-7-yl-pyridin-2-yloxy)-piperidin-1-yl]-propan-1-one; 2-methyl-1-[4-(5-quinolin-7-yl-pyridin-2-yloxy)-piperidin-1-yl]-propan-1-one; cyclopropyl-[4-(5-quinolin-7-yl-pyridin-2-yloxy)-piperidin-1-yl]-methanone; 2-methyl-1-[4-(5-quinolin-3-yl-pyrimidin-2-yloxy)-piperidin-1-yl]-propan-1-one; cyclopropyl-[4-(5-quinolin-3-yl-pyrimidin-2-yloxy)-piperidin-1-yl]-methanone; 1-[4-(6-quinolin-3-yl-pyridin-3-yloxy)-piperidin-1-yl]-propan-1-one; 2-methyl-1-[4-(6-quinolin-3-yl-pyridin-3-yloxy)-piperidin-1-yl]-propan-1-one; cyclopropyl-[4-(6-quinolin-3-yl-pyridin-3-yloxy)-piperidin-1-yl]-methanone; 1-[4-(5-quinolin-3-yl-pyrimidin-2-yloxy)-piperidin-1-yl]-propan-1-one; 1-[4-(6-quinolin-7-yl-pyridin-3-yloxy)-piperidin-1-yl]-propan-1-one; 2-methyl-1-[4-(6-quinolin-7-yl-pyridin-3-yloxy)-piperidin-1-yl]-propan-1-one; cyclopropyl-[4-(6-quinolin-7-yl-pyridin-3-yloxy)-piperidin-1-yl]-methanone; 1-[4-(6-isoquinolin-6-yl-pyridin-3-yloxy)-piperidin-1-yl]-propan-1-one; 1-[4-(6-isoquinolin-6-yl-pyridin-3-yloxy)-piperidin-1-yl]-2-methyl-propan-1-one; cyclopropyl-[4-(6-isoquinolin-6-yl-pyridin-3-yloxy)-piperidin-1-yl]-methanone; 1-propionyl-piperidine-4-carboxylic acid methyl-(4-quinolin-7-yl-phenyl)-amide; 1-propionyl-piperidine-4-carboxylic acid (4-isoquinolin-6-yl-phenyl)-methyl-amide; oxo-[4-(4-quinolin-3-yl-phenoxy)-piperidin-1-yl]-acetaldehyde; 4-(4-quinolin-3-yl-phenoxy)-piperidine-1-carbaldehyde; ((2R,3S)/(2S,3R)-3-methyltetrahydrofuran-2-yl)-[4-(4-quinolin-3-yl-phenoxy)-piperidin-1-yl]-methanone; ((2R,3S,5R)/(2S,3R,5S)-3,5-dimethyl-tetrahydrofuran-2-yl)-[4-(4-quinolin-3-yl-phenoxy)-piperidin-1-yl]-methanone; ((2R,3S,5R)/(2S,3R,5S)-3,5-dimethyltetrahydrofuran-2-yl)-[4-(4-quinolin-3-yl-phenoxy)-piperidin-1-yl]-methanone; 1-propionyl-piperidine-4-carboxylic acid (4-isoquinolin-6-yl-phenyl)-methylamide; 2-fluoro-4-isoquinolin-6-yl-N-methyl-N-(1-propionyl-piperidin-4-yl)-benzamide; 1-{4-[4-(3-trifluoromethyl-1,2,4-triazolo[4,3-a]pyridin-6-yl)-phenoxy]-piperidin-1-yl}-propan-1-one; cyclopropyl-{4-[4-(3-trifluoromethyl-1,2,4-triazolo[4,3-a]pyridin-6-yl)-phenoxy]-piperidin-1-yl}-methanone; (R)-tetrahydrofuran-2-yl-{4-[4-(3-trifluoromethyl-1,2,4-triazolo[4,3-a]pyridin-6-yl)-phenoxy]-piperidin-1-yl}-methanone; 3-[4-(1-methanesulfonyl-piperidin-4-yloxy)-phenyl]-quinoline; (4,4-difluorotetrahydro-furan-2-yl)-[4-(4-quinolin-3-yl-phenoxy)-piperidin-1-yl]-methanone; (4,4-difluorotetrahydrofuran-2-yl)-{4-[4-(8-methylquinolin-7-yl)-phenoxy]-piperidin-1-yl}-methanone; (4,4-difluorotetrahydrofuran-2-yl)-{4-[4-(1-methylisoquinolin-6-yl)-phenoxy]-piperidin-1-yl}-methanone; 5-[4-(4-quinolin-3-yl-phenoxy)-piperidine-1-carbonyl]-dihydrofuran-3-one; 1-{4-[4-(8-ethoxyquinolin-7-yl)-phenoxy]-piperidin-1-yl}-propan-1-one; cyclopropyl-{4-[4-(8-ethoxyquinolin-7-yl)-phenoxy]-piperidin-1-yl}-methanone; 1-{4-[4-(8-isopropoxyquinolin-7-yl)-phenoxy]-piperidin-1-yl}-propan-1-one; cyclopropyl-{4-[4-(8-isopropoxyquinolin-7-yl)-phenoxy]-piperidin-1-yl}-methanone; 1-(4-{4-[8-(2-morpholin-4-yl-ethoxy)-quinolin-7-yl]-phenoxy}-piperidin-1-yl)-propan-1-one; cyclopropyl-(4-{4-[8-(2-morpholin-4-yl-ethoxy)-quinolin-7-yl]-phenoxy}-piperidin-1-yl)-methanone; 1-(4-{4-[8-(2-pyrrolidin-1-yl-ethoxy)-quinolin-7-yl]-phenoxy}-piperidin-1-yl)-propan-1-one; cyclopropyl-(4-{4-[8-(2-pyrrolidin-1-yl-ethoxy)-quinolin-7-yl]-phenoxy}-piperidin-1-yl)-methanone; 1-(4-{4-[8-(3-pyrrolidin-1-yl-propoxy)-quinolin-7-yl]-phenoxy}-piperidin-1-yl)-propan-1-one; cyclopropyl-(4-{4-[8-(3-pyrrolidin-1-yl-propoxy)-quinolin-7-yl]-phenoxy}-piperidin-1-yl)-methanone; 1-[4-[4-[8-[2-(4-methylpiperazin-1-yl)ethoxy]-7-quinolyl]phenoxy]-1-piperidyl]propan-1-one; 1-[4-[4-[8-(2-methoxyethoxy)-7-quinolyl]phenoxy]-1-piperidyl]propan-1-one; 1-[4-[4-[8-(3-methoxypropoxy)-7-quinolyl]phenoxy]-1-piperidyl]propan-1-one; {4-[4-(8-isopropoxyquinolin-7-yl)-phenoxy]-piperidin-1-yl}-(R)-tetrahydrofuran-2-yl-methanone; {4-[4-(8-ethoxyquinolin-7-yl)-phenoxy]-piperidin-1-yl}-(R)-tetrahydrofuran-2-yl-methanone; (4-{4-[8-(2-morpholin-4-yl-ethoxy)-quinolin-7-yl]-phenoxy}-piperidin-1-yl)-(R)-tetrahydrofuran-2-yl-methanone; (4-{4-[8-(2-pyrrolidin-1-yl-ethoxy)quinolin-7-yl]-phenoxy}-piperidin-1-yl)-(R)-tetrahydrofuran-2-yl-methanone; (4-{4-[8-(3-pyrrolidin-1-yl-propoxy)-quinolin-7-yl]-phenoxy})-piperidin-1-yl)-(R)-tetrahydrofuran-2-ylmethanone; [4-[4-[8-[2-(4-methylpiperazin-1-yl)ethoxy]-7-quinolyl]phenoxy]-1-piperidyl]-[(2R)-tetrahydrofuran-2-yl]methanone; [4-[4-[8-(2-methoxyethoxy)-7-quinolyl]phenoxy]-1-piperidyl]-[(2R)-tetrahydrofuran-2-yl]methanone; [4-[4-[8-(3-methoxypropoxy)-7-quinolyl]phenoxy]-1-piperidyl]-[(2R)-tetrahydrofuran-2-yl]methanone; 1-{4-[4-(8-hydroxyquinolin-7-yl)-phenoxy]-piperidin-1-yl}-propan-1-one; cyclopropyl-{4-[4-(8-hydroxyquinolin-7-yl)-phenoxy]-piperidin-1-yl}-methanone; {4-[4-(8-hydroxyquinolin-7-yl)-phenoxy]-piperidin-1-yl}-(R)-tetrahydrofuran-2-yl-methanone; 1-[4-(2-chloro-4-quinolin-3-yl-phenoxy)-piperidin-1-yl]-propan-1-one; 1-[4-(2-chloro-4-quinolin-3-yl-phenoxy)-piperidin-1-yl]-2-methyl-propan-1-one; [4-(2-chloro-4-quinolin-3-yl-phenoxy)-piperidin-1-yl]-cyclopropylmethanone; 1-[4-(2-chloro-4-quinolin-7-yl-phenoxy)-piperidin-1-yl]-propan-1-one; 1-[4-(2-chloro-4-quinolin-7-yl-phenoxy)-piperidin-1-yl]-2-methyl-propan-1-one; 1-[4-(2-methoxy-4-quinolin-3-yl-phenoxy)-piperidin-1-yl]-propan-1-one; 1-[4-(2-methoxy-4-quinolin-3-yl-phenoxy)-piperidin-1-yl]-2-methylpropan-1-one; cyclopropyl-[4-(2-methoxy-4-quinolin-3-yl-phenoxy)-piperidin-1-yl]-methanone; 1-[4-(2-methoxy-4-quinolin-7-yl-phenoxy)-piperidin-1-yl]-propan-1-one; 1-[4-(3-fluoro-4-quinolin-3-yl-phenoxy)-piperidin-1-yl]-propan-1-one; 1-[4-(3-fluoro-4-quinolin-3-yl-phenoxy)-piperidin-1-yl]-2-methyl-propan-1-one; cyclopropyl-[4-(3-fluoro-4-quinolin-3-yl-phenoxy)-piperidin-1-yl]-methanone; 1-[4-(3-chloro-4-quinolin-3-yl-phenoxy)-piperidin-1-yl]-propan-1-one; 1-[4-(3-chloro-4-quinolin-3-yl-phenoxy)-piperidin-1-yl]-2-methyl-propan-1-one; [4-(3-chloro-4-quinolin-3-yl-phenoxy)-piperidin-1-yl]-cyclopropylmethanone; 2-methyl-1-[4-(3-methyl-4-quinolin-3-yl-phenoxy)-piperidin-1-yl]-propan-1-one; 1-[4-(3-methyl-4-quinolin-3-yl-phenoxy)-piperidin-1-yl]-propan-1-one; 4-(3-methyl-4-quinolin-3-yl-phenoxy)-piperidine-1-carboxylic acid methyl ester; 1-[4-(3-methoxy-4-quinolin-3-yl-phenoxy)-piperidin-1-yl]-propan-1-one; 1-[4-(3-methoxy-4-quinolin-3-yl-phenoxy)-piperidin-1-yl]-2-methyl-propan-1-one; cyclopropyl-[4-(3-methoxy-4-quinolin-3-yl-phenoxy)-piperidin-1-yl]-methanone; 1-[4-(2-methyl-4-quinolin-3-yl-phenoxy)-piperidin-1-yl]-propan-1-one; 2-methyl-1-[4-(2-methyl-4-quinolin-3-yl-phenoxy)-piperidin-1-yl]-propan-1-one; cyclopropyl-[4-(2-methyl-4-quinolin-3-yl-phenoxy)-piperidin-1-yl]-methanone; 1-[4-(2,5-difluoro-4-quinolin-3-yl-phenoxy)-piperidin-1-yl]-propan-1-one; 1-[4-(2,5-difluoro-4-quinolin-3-yl-phenoxy)-piperidin-1-yl]-2-methyl-propan-1-one; cyclopropyl-[4-(2,5-difluoro-4-quinolin-3-yl-phenoxy)-piperidin-1-yl]-methanone; 3-oxo-3-[4-(4-quinolin-3-yl-phenoxy)-piperidin-1-yl]-propionitrile; 1-{4-[2-fluoro-4-(8-methoxyquinolin-7-yl)-phenoxy]-piperidin-1-yl}-propan-1-one; cyclopropyl-{4-[2-fluoro-4-(8-methoxyquinolin-7-yl)-phenoxy]-piperidin-1-yl}-methanone; {4-[2-fluoro-4-(8-methoxyquinolin-7-yl)-phenoxy]-piperidin-1-yl}-(R)-tetrahydrofuran-2-yl-methanone; {4-[4-(8-chloroquinolin-7-yl)-2-fluoro-phenoxy]-piperidin-1-yl}-cyclopropylmethanone; {4-[4-(8-chloroquinolin-7-yl)-2-fluorophenoxy]-piperidin-1-yl}-(R)-tetrahydrofuran-2-yl-methanone; 1-{4-[4-(8-chloroquinolin-7-yl)-2-fluorophenoxy]-piperidin-1-yl}-propan-1-one; 1-{4-[2-fluoro-4-(8-methylquinolin-7-yl)-phenoxy]-piperidin-1-yl}-propan-1-one; {4-[2-fluoro-4-(8-methylquinolin-7-yl)-phenoxy]piperidin-1-yl}-(R)-tetrahydrofuran-2-yl-methanone; cyclopropyl-{4-[2-fluoro-4-(8-methylquinolin-7-yl)-phenoxy]-piperidin-1-yl})-methanone; 1-{4-[2-fluoro-4-(4-methylquinolin-3-yl)-phenoxy]-piperidin-1-yl}-propan-1-one; cyclopropyl-{4-[2-fluoro-4-(4-methylquinolin-3-yl)-phenoxy]-piperidin-1-yl}-methanone; {4-[2-fluoro-4-(4-methyl-quinolin-3-yl)-phenoxy]-piperidin-1-yl}-(R)-tetrahydrofuran-2-yl-methanone; 1-{4-[4-(4-aminoquinolin-3-yl)-phenoxy]-piperidin-1-yl}-propan-1-one; 1-{4-[4-(4-dimethylamino-quinolin-3-yl)-phenoxy]-piperidin-1-yl}-propan-1-one; {4-[4-(4-dimethylaminoquinolin-3-yl)-phenoxy]-piperidin-1-yl}-(R)-tetrahydrofuran-2-yl-methanone; {4-[4-(4-amino-quinolin-3-yl)-phenoxy]-piperidin-1-yl}-(R)-tetrahydrofuran-2-yl-methanone; 1-{4-[4-(4-methylamino-quinolin-3-yl)-phenoxy]-piperidin-1-yl}-propan-1-one; {4-[4-(4-methylaminoquinolin-3-yl)-phenoxy]-piperidin-1-yl}-(R)-tetrahydrofuran-2-yl-methanone; 1-{4-[4-(4-morpholin-4-yl-quinolin-3-yl)-phenoxy]-piperidin-1-yl}-propan-1-one; {4-[4-(4-morpholin-4-yl-quinolin-3-yl)-phenoxy]-piperidin-1-yl}-(R)-tetrahydrofuran-2-yl-methanone; 1-(4-{4-[4-(4-methylpiperazin-1-yl)-quinolin-3-yl]-phenoxy}-piperidin-1-yl)-propan-1-one; (4-{4-[4-(4-methylpiperazin-1-yl)-quinolin-3-yl]-phenoxy}-piperidin-1-yl)-(R)-tetrahydrofuran-2-yl-methanone; 3-[4-(4-quinolin-3-yl-phenoxy)-piperidine-1-carbonyl]oxazolidin-2-one; 1-[4-(4-quinolin-3-yl-phenoxy)-piperidin-1-yl]-butane-1,3-dione; 1-[4-(4-quinolin-3-yl-phenoxy)-piperidine-1-carbonyl]-pyrrolidin-2-one; 4'-[1-((R)-tetrahydrofuran-2-carbonyl)-piperidin-4-yloxy]-biphenyl-4-carbonitrile; 1-[4-(4-benzofuran-2-yl-phenoxy)-piperidin-1-yl]-propan-1-one; 1-{4-[4-(1H-indol-3-yl)-phenoxy]-piperidin-1-yl}-propan-1-one; 1-[4-(4-benzo[b]thiophen-5-yl-phenoxy)-piperidin-1-yl]-propan-1-one; 1-{4-[4-(1H-indazol-3-yl)-phenoxy]-piperidin-1-yl}-propan-1-one; 1-{4-[4-(1-methyl-1H-indazol-6-yl)-phenoxy]-piperidin-1-yl}-propan-1-one; 1-[4-(4-thieno[2,3-b]pyridin-5-yl-phenoxy)-piperidin-1-yl]-propan-1-one; 1-{4-[4-(2-methyl-2H-indazol-6-yl)-phenoxy]-piperidin-1-yl}-propan-1-one; 1-[4-(4-[1,8]naphthyridin-3-yl-phenoxy)-piperidin-1-yl]-propan-1-one; 1-{4-[4-(2-methylquinolin-7-yl)-phenoxy]-piperidin-1-yl}-propan-1-one; (R)-tetrahydrofuran-2-yl-[4-(4-thieno[2,3-b]pyridin-5-yl-phenoxy)-piperidin-1-yl]-methanone; cyclopropyl-[4-(4-thieno[2,3-b]pyridin-5-yl-phenoxy)-piperidin-1-yl]-methanone; 1-[4-(4-imidazo[1,2-a]pyridin-6-yl-phenoxy)-piperidin-1-yl]-propan-1-one; {4-[4-(4-chloroquinolin-7-yl)-phenoxy]-piperidin-1-yl}-(R)-tetrahydro-furan-2-yl-methanone; {4-[4-(4-chloroquinolin-7-yl)-phenoxy]-piperidin-1-yl}-cyclopropylmethanone; 1-{4-[4-(4-chloroquinolin-7-yl)-phenoxy]-piperidin-1-yl}-propan-1-one; {4-[4-(8-chloroquinolin-7-yl)-phenoxy]-piperidin-1-yl}-(R)-tetrahydrofuran-2-yl-methanone; 1-{4-[4-(8-chloroquinolin-7-yl)-phenoxy]-piperidin-1-yl}-propan-1-one; {4-[4-(7-methoxyquinolin-3-yl)-phenoxy]-piperidin-1-yl}-(R)-tetrahydrofuran-2-yl-methanone; (R)-tetrahydrofuran-2-yl-[4-(4-thieno[3,2-b]pyridin-6-yl-phenoxy)-piperidin-1-yl]-methanone; 1-[4-(4-thieno[3,2-b]pyridin-6-yl-phenoxy)-piperidin-1-yl]-propan-1-one; {4-[4-(3-chloroquinolin-7-yl)-phenoxy]-piperidin-1-yl}-(R)-tetrahydrofuran-2-yl-methanone; 1-{4-[4-(3-chloroquinolin-7-yl)-phenoxy]-piperidin-1-yl}-propan-1-one; [4-(4-benzothiazol-5-yl-phenoxy)-piperidin-1-yl]-(R)-tetrahydrofuran-2-yl-methanone; [4-(4-benzothiazol-5-yl-phenoxy)-piperidin-1-yl]-cyclopropylmethanone; 1-[4-(4-benzothiazol-5-yl-phenoxy)-piperidin-1-yl]-propan-1-one; cyclopropyl-{4-[4-(1-methyl-1H-indazol-6-yl)-phenoxy]-piperidin-1-yl}-methanone; cyclobutyl-{4-[4-(1-methyl-1H-indazol-6-yl)-phenoxy]-piperidin-1-yl}-methanone; {4-[4-(8-methoxyquinolin-7-yl)-phenoxy]-piperidin-1-yl}-(R)-tetrahydrofuran-2-yl-methanone; 1-{4-[4-(8-methoxyquinolin-7-yl)-phenoxy]-piperidin-1-yl}-propan-1-one; cyclopropyl-{4-[4-(8-methoxyquinolin-7-yl)-phenoxy]-piperidin-1-yl}-methanone; {4-[4-(6-methylquinolin-7-yl)-phenoxy]-piperidin-1-yl}-(R)-tetrahydrofuran-2-yl-methanone; 1-{4-[4-(6-methylquinolin-7-yl)-phenoxy]-piperidin-1-yl}-propan-1-one; 7-[4-(1-propionyl-piperidin-4-yloxy)-phenyl]-quinoline-3-carbonitrile; 7-{4-[1-((R)-tetrahydrofuran-2-carbonyl)-piperidin-4-yloxy]-phenyl}-quinoline-3-carbonitrile; 7-[4-(1-cyclopropanecarbonyl-piperidin-4-yloxy)-phenyl]-quinoline-3-carbonitrile; 1-{4-[4-(3-methylquinolin-7-yl)-phenoxy]-piperidin-1-yl}-propan-1-one; {4-[4-(3-methylquinolin-7-yl)-phenoxy]-piperidin-1-yl}-(R)-tetrahydro-furan-2-yl-methanone; cyclopropyl-{4-[4-(3-methylquinolin-7-yl)-phenoxy]-piperidin-1-yl}-methanone; {4-[4-(8-methylimidazo[1,2-a]pyridin-6-yl)-phenoxy]-piperidin-1-yl}-(R)-tetrahydrofuran-2-yl-methanone; 1-{4-[4-(8-methylimidazo[1,2-a]pyridin-6-yl)-phenoxy]-piperidin-1-yl}-propan-1-one; {4-[4-(5-methylimidazo[1,2-a]pyridin-6-yl)-phenoxy]-piperidin-1-yl}-(R)-tetrahydrofuran-2-yl-methanone; 1-{4-[4-(5-methyl-imidazo[1,2-a]pyridin-6-yl)-phenoxy]-piperidin-1-yl}-propan-1-one; cyclopropyl-{4-[4-(5-methylimidazo[1,2-a]pyridin-6-yl)-phenoxy]-piperidin-1-yl}-methanone; cyclopropyl-{4-[4-(8-methyl-imidazo[1,2-a]pyridin-6-yl)-phenoxy]-piperidin-1-yl}-methanone; {4-[4-(2,3-dimethyl-imidazo[1,2-a]pyridin-6-yl)-phenoxy]-piperidin-1-yl}-(R)-tetrahydrofuran 2-yl-methanone; 1-{4-[4-(2,3-dimethylimidazo[1,2-a]pyridin-6-yl)-phenoxy]-piperidin-1-yl}-propan-1-one; cyclopropyl-{4-[4-(2,3-dimethylimidazo[1,2-a]pyridin-6-yl)-phenoxy]-piperidin-1-yl}-methanone; {4-[4-(7-methylimidazo[1,2-a]pyridin-6-yl)-phenoxy]-piperidin-1-yl}-(R)-tetrahydrofuran-2-yl-methanone; 1-{4-[4-(7-methylimidazo[1,2-a]pyridin-6-yl)-phenoxy]-piperidin-1-yl}-propan-1-one; {4-[4-(5-chloroimidazo[1,2-a]pyridin-6-yl)-phenoxy]-piperidin-1-yl}-(R)-tetrahydrofuran-2-yl-methanone; {4-[4-(5-chloroimidazo[1,2-a]pyridin-6-yl)-phenoxy]-piperidin-1-yl}-(R)-tetrahydrofuran-2-yl-methanone; 1-{4-[4-(5-chloroimidazo[1,2-a]pyridin-6-yl)-phenoxy]-piperidin-1-yl}-propan-1-one; {4-[4-(5-chloroimidazo[1,2-a]pyridin-6-yl)-phenoxy]-piperidin-1-yl}-cyclopropyl-methanone; [4-(4-imidazo[1,5-a]pyridin-6-yl-phenoxy)-piperidin-1-yl]-(R)-tetrahydrofuran-2-yl-methanone; 1-[4-(4-imidazo[1,5-a]pyridin-6-yl-phenoxy)-piperidin-1-yl]-propan-1-one; cyclopropyl-[4-(4-imidazo[1,5-a]pyridin-6-yl-phenoxy)-piperidin-1-yl]-methanone; 1-[4-

(4-imidazo[1,5-a]pyridin-6-yl-phenoxy)-piperidine-1-carbonyl]-cyclopropanecarboxylic acid amide; (1-hydroxycyclopropyl)-[4-(4-imidazo[1,5-a]pyridin-6-yl-phenoxy)-piperidin-1-yl]-methanone; (1-hydroxycyclopropyl)-{4-[4-(8-methoxy-quinolin-7-yl)-phenoxy]-piperidin-1-yl}-methanone; (1-hydroxymethylcyclopropyl)-{4-[4-(5-methylimidazo[1,2-a]pyridin-6-yl)-phenoxy]-piperidin-1-yl}-methanone; (1-amino-cyclopropyl)-{4-[4-(5-methylimidazo[1,2-a]pyridin-6-yl)-phenoxy]-piperidin-1-yl}-methanone; (1-hydroxycyclopropyl)-[4-(4-[1,2,4]triazolo[4,3-a]pyridin-7-yl-phenoxy)-piperidin-1-yl]-methanone; (R)-tetrahydrofuran-2-yl-[4-(4-[1,2,4]triazolo[4,3-a]pyridin-7-yl-phenoxy)-piperidin-1-yl]-methanone; cyclopropyl-[4-(4-[1,2,4]triazolo[4,3-a]pyridin-7-ylphenoxy)-piperidin-1-yl]-methanone; (1-hydroxycyclopropyl)-{4-[4-(5-methyl-imidazo[1,2-a]pyridin-6-yl)-phenoxy]-piperidin-1-yl}-methanone; 2-hydroxy-2-methyl-1-{4-[4-(5-methylimidazo[1,2-a]pyridin-6-yl)-phenoxy]-piperidin-1-yl}-propan-1-one; {4-[4-(5-methyl-[1,2,4]triazolo[1,5-a]pyridin-6-yl)-phenoxy]-piperidin-1-yl}-(R)-tetrahydrofuran-2-yl-methanone; (1-hydroxycyclopropyl)-{4-[4-(5-methyl-[1,2,4]triazolo[1,5-a]pyridin-6-yl)-phenoxy]-piperidin-1-yl}-methanone; 1-{4-[4-(5-methyl-[1,2,4]triazolo[1,5-a]pyridin-6-yl)-phenoxy]-piperidin-1-yl}-propan-1-one; cyclopropyl-{4-[4-(5-methyl-[1,2,4]triazolo[1,5-a]pyridin-6-yl)-phenoxy]-piperidin-1-yl}-methanone; {4-[4-(8-methyl-quinolin-7-yl)-phenoxy]-piperidin-1-yl}-(1-trifluoromethyl-cyclopropyl)-methanone; (1-aminocyclopropyl)-{4-[4-(8-methyl-quinolin-7-yl)-phenoxy]-piperidin-1-yl}-methanone; {4-[4-(1-methyl-1H-indazol-6-yl)-phenoxy]-piperidin-1-yl}-(R)-tetrahydrofuran-2-yl-methanone; [4-(4-imidazo[1,2-a]pyridin-6-yl-phenoxy)-piperidin-1-yl]-(R)-tetrahydrofuran-2-yl-methanone; 1-{4-[4-(8-methylquinolin-7-yl)-phenoxy]-piperidine-1-carbonyl}-cyclopropanecarbonitrile; (1-methylcyclopropyl)-{4-[4-(8-methylquinolin-7-yl)-phenoxy]-piperidin-1-yl}-methanone; ((S)-2,2-dimethylcyclopropyl)-{4-[4-(8-methylquinolin-7-yl)-phenoxy]-piperidin-1-yl}-methanone; (2,2-dimethylcyclopropyl)-{4-[4-(8-methylquinolin-7-yl)-phenoxy]-piperidin-1-yl}-methanone; [4-[4-[8-(4-methylpiperazin-1-yl)-7-quinolyl]phenoxy]-1-piperidyl]-[(2R)-tetrahydrofuran-2-yl]methanone; [4-[4-(8-amino-7-quinolyl)phenoxy]-1-piperidyl]-[(2R)-tetrahydrofuran-2-yl]methanone; {4-[4-(8-methylaminoquinolin-7-yl)-phenoxy]-piperidin-1-yl}-(R)-tetrahydrofuran-2-yl-methanone; 1-{4-[4-(8-methylamino-quinolin-7-yl)phenoxy]-piperidin-1-yl}-propan-1-one; (4-{4-[8-(2-methoxy-ethylamino)-quinolin-7-yl]-phenoxy}-piperidin-1-yl)-(R)-tetrahydrofuran-2-yl-methanone; 1-(4-{4-[8-(2-methoxyethylamino)-quinolin-7-yl]-phenoxy}-piperidin-1-yl)-propan-1-one; (4-{4-[8-(2-di-methylaminoethylamino)-quinolin-7-yl]-phenoxy}-piperidin-1-yl)-(R)-tetrahydrofuran-2-yl-methanone; 7-[4-(1-propionylpiperidin-4-yloxy)-phenyl]-quinoline-8-carbonitrile; [4-[4-[8-(dimethylamino)-7-quinolyl]phenoxy]-1-piperidyl]-[(2R)-tetrahydrofuran-2-yl]methanone; 1-{4-[4-(8-dimethylaminoquinolin-7-yl)-phenoxy]-piperidin-1-yl}-propan-1-one; cyclopropyl-{4-[4-(8-dimethylaminoquinolin-7-yl)-phenoxy]-piperidin-1-yl}-methanone; (4-{4-[8-(2-pyrrolidin-1-yl-ethylamino)-quinolin-7-yl]-phenoxy}-piperidin-1-yl)-(R)-tetrahydrofuran-2-yl-methanone; 1-(4-{4-[8-(2-pyrrolidin-1-yl-ethylamino)-quinolin-7-yl]-phenoxy}-piperidin-1-yl)-propan-1-one; 7-[4-[[1-[(2R)-tetrahydrofuran-2-carbonyl]-4 piperidyl]oxy]phenyl]quinoline-8-carboxamide; 7-[4-(1-propionylpiperidin-4-yloxy)-phenyl]-quinoline-8-carboxylic acid amide; 1-(3-(4-(quinolin-3-yl)phenoxy)azetidin-1-yl)propan-1-one; 2-methyl-1-(3-(4-(quinolin-3-yl)phenoxy)azetidin-1-yl)-propan-1-one; cyclopropyl(3-(4-(quinolin-3-yl)phenoxy)azetidin-1-yl)methanone; 3-methyl-1-(3-(4-(quinolin-3-yl)phenoxy)azetidin-1-yl)butan-1-one; (S)-1-(3-(4-(quinolin-7-yl)phenoxy)pyrrolidin-1-yl)propan-1-one; (S)-1-(3-(4-(quinolin-3-yl)phenoxy)pyrrolidin-1-yl)propan-1-one; (R)-1-(3-(4-(quinolin-7-yl)phenoxy)pyrrolidin-1-yl)propan-1-one; (R)-1-(3-(4-(quinolin-3-yl)phenoxy)-pyrrolidin-1-yl)propan-1-one; 1-(4-(4-(5-methylquinolin-7-yl)phenoxy)piperidin-1-yl)propan-1-one; cyclopropyl(4-(4-(5-methylquinolin-7-yl)phenoxy)piperidin-1-yl)methanone; 1-(4-(4-(7-methylquinolin-5-yl)phenoxy)piperidin-1-yl)propan-1-one; cyclopropyl-{4-[4-(7-methylquinolin-5-yl)-phenoxy]-piperidin-1-yl}-methanone; 1-(4-(4-(6-methylquinolin-5-yl)phenoxy)piperidin-1-yl)-propan-1-one; cyclopropyl(4-(4-(6-methylquinolin-5-yl)phenoxy)piperidin-1-yl)methanone; (R)-(4-(4-(5-methylquinolin-7-yl)phenoxy)piperidin-1-yl)(tetrahydrofuran-2-yl)methanone; (R)-(4-(4-(7-methylquinolin-5-yl)phenoxy)piperidin-1-yl)(tetrahydrofuran-2-yl)methanone; (R)-(4-(4-(6-methylquinolin-5-yl)phenoxy)piperidin-1-yl)(tetrahydrofuran-2-yl)methanone; (±)-(7S,8aS)-7-(4-(8-methylquinolin-7-yl)phenoxy)hexahydroindolizin-3 (2H)-one; (±)-(7R,8aS)-7-(4-(8-methylquinolin-7-yl)phenoxy)hexahydroindolizin-3 (2H)-one; 2,2,2-trifluoro-1-{4-[4-(8-methylquinolin-7-yl)-phenoxy]-piperidin-1-yl}-ethanone; 2,2-difluoro-1-{4-[4-(8-methylquinolin-7-yl)-phenoxy]-piperidin-1-yl}-propan-1-one; 2-fluoro-1-{4-[4-(8-methylquinolin-7-yl)-phenoxy]-piperidin-1-yl}-propan-1-one; {exo-3-[4-(8-methylquinolin-7-yl)-phenoxy]-8-aza-bicyclo[3.2.1]oct-8-yl}-(R)-tetrahydrofuran-2-yl-methanone; 1-{exo-3-[4-(8-methylquinolin-7-yl)-phenoxy]-8-aza-bicyclo[3.2.1]oct-8-yl}-propan-1-one; {2-methyl-4-[4-(8-methylquinolin-7-yl)-phenoxy]-piperidin-1-yl}-(R)-tetrahydrofuran-2-yl-methanone; 1-{2-methyl-4-[4-(8-methylquinolin-7-yl)-phenoxy]-piperidin-1-yl}-propan-1-one; 1-{2-methyl-4-[4-(8-methylquinolin-7-yl)-phenoxy]-piperidin-1-yl}-propan-1-one; cyclopropyl-{2-methyl-4-[4-(8-methylquinolin-7-yl)-phenoxy]-piperidin-1-yl}-methanone; {cis-3-fluoro-4-[4-(8-methylquinolin-7-yl)-phenoxy]-piperidin-1-yl}-(R)-tetrahydrofuran-2-yl-methanone; 1-{cis-3-fluoro-4-[4-(8-methylquinolin-7-yl)-phenoxy]-piperidin-1-yl}-propan-1-one; cyclopropyl-{cis-3-fluoro-4-[4-(8-methylquinolin-7-yl)-phenoxy]-piperidin-1-yl}-methanone; 1-{endo-3-[4-(8-methylquinolin-7-yl)-phenoxy]-8-aza-bicyclo[3.2.1]oct-8-yl}-propan-1-one; cyclopropyl-{endo-3-[4-(8-methylquinolin-7-yl)-phenoxy]-8-aza-bicyclo[3.2.1]oct-8-yl}-methanone; {endo-3-[4-(8-methylquinolin-7-yl)-phenoxy]-8-aza-bicyclo[3.2.1]oct-8-yl}-(R)-tetrahydrofuran-2-yl-methanone; {(trans)-3-fluoro-4-[4-(8-methylquinolin-7-yl)-phenoxy]-piperidin-1-yl}-(R)-tetrahydrofuran-2-yl-methanone; 1-{trans-3-fluoro-4-[4-(8-methylquinolin-7-yl)-phenoxy]-piperidin-1-yl}-propan-1-one; cyclopropyl-{trans-3-fluoro-4-[4-(8-methylquinolin-7-yl)-phenoxy]-piperidin-1-yl}-methanone; 1-{3-methyl-4-[4-(8-methylquinolin-7-yl)-phenoxy]-piperidin-1-yl}-propan-1-one; cyclopropyl-{3-methyl-4-[4-(8-methylquinolin-7-yl)-phenoxy]-piperidin-1-yl}-methanone; {3-methyl-4-[4-(8-methylquinolin-7-yl)-phenoxy]-piperidin-1-yl}-(R)-tetrahydrofuran-2-yl-methanone; 1-{4-[4-(6-phenylpyridin-3-yl)-phenoxy]-piperidin-1-yl}-propan-1-one; 2-methyl-1-{4-[4-(6-phenylpyridin-3-yl)-phenoxy]-piperidin-1-yl}-propan-1-one; cyclopropyl-{4-[4-(6-phenylpyridin-3-yl)-phenoxy]-piperidin-1-yl}-methanone; cyclobutyl-{4-[4-(6-phenylpyridin-3-yl)-phenoxy]-piperidin-1-yl}-methanone; {4-[4-(5-phenylpyridin-3-yl)-phenoxy]-piperidin-1-yl}-propan-1-one; 2-methyl-1-{4-[4-(5- phenylpyridin-3-yl)-phenoxy]piperidin-1-yl}-propan-1-one; cyclopropyl-{4-[4-(5-phenylpyridin-3-yl)-phenoxy]piperidin-1-yl}-methanone; cyclobutyl-{4-[4-(5-phenylpyridin-3-yl)-phenoxy]-piperidin-1-yl}-methanone; 1-{4-[4-(6-morpholin-4-yl-pyridin-3-yl)-phenoxy]-piperidin-1-yl}-propan-1-one; cyclopropyl-{4-[4-(6-morpholin-4-yl-pyridin-3-yl)-phenoxy]-piperidin-1-yl}-methanone; cyclobutyl-{4-[4-(6-morpholin-4-yl-pyridin-3-yl)-phenoxy]-piperidin-1-yl}-methanone; 1-{4-[4-(6-phenoxypyridin-3-yl)-phenoxy]-piperidin-1-yl}-propan-1-one; cyclopropyl-{4-[4-(6-phenoxy-pyridin-3-yl)-phenoxy]-piperidin-1-yl}-methanone; cyclobutyl-{4-[4-(6-phenoxypyridin-3-yl)-phenoxy]-piperidin-1-yl}-methanone; 1-{4-[4-(6-phenylaminopyridin-3-yl)phenoxy]-piperidin-1-yl}-propan-1-one; cyclopropyl-{4-[4-(6-phenylaminopyridin-3-yl)phenoxy]-piperidin-1-yl})-methanone; cyclobutyl-{4-[4-(6-phenylamino-pyridin-3-yl)-phenoxy]-piperidin-1-yl}-methanone; 1-[4-(2'-fluoro-3'-pyridin-2-yl-biphenyl-4-yloxy)-piperidin-1-yl]-propan-1-one; cyclopropyl-[4-(2'-fluoro-3'-pyridin-2-yl-biphenyl-4-yloxy)-piperidin-1-yl]-methanone; 1-{4-[4-(5-phenoxypyridin-3-yl)-phenoxy]-piperidin-1-yl}-propan-1-one; cyclobutyl-[4-(2'-fluoro-3'-pyridin-2-yl-biphenyl-4-yloxy)-piperidin-1-yl]-methanone; cyclopropyl-{4-[4-(5-phenoxypyridin-3-yl)-phenoxy]-piperidin-1-yl}-methanone; cyclobutyl-{4-[4-(5-phenoxypyridin-3-yl)-phenoxy]-piperidin-1-yl}-methanone; 1-{4-[4-(5-phenylamino-pyridin-3-yl)-phenoxy]-piperidin-1-yl}-propan-1-one; 1-{4-[4-(2-phenyl-pyridin-4-yl)-phenoxy]-piperidin-1-yl}-propan-1-one; cyclopropyl-{4-[4-(2-phenylpyridin-4-yl)-phenoxy]-piperidin-1-yl}-methanone; 1-{4-[4-(2-phenylaminopyridin-4-yl)-phenoxy]-piperidin-1-yl}-propan-1-one; cyclopropyl-{4-[4-(2-phenylaminopyridin-4-yl)-phenoxy]-piperidin-1-yl}-methanone; 1-[4-(2'-methyl-3'-pyridin-2-yl-biphenyl-4-yloxy)-piperidin-1-yl]-propan-1-one; cyclopropyl-[4-(2'-methyl-3'-pyridin-2-yl-biphenyl-4-yloxy)-piperidin-1-yl]-methanone; cyclobutyl-[4-(2'-methyl-3'-pyridin-2-yl-biphenyl-4-yloxy)-piperidin-1-yl]-methanone; 1-{4-[4-(2-phenoxypyridin-4-yl)-phenoxy]-piperidin-1-yl}-propan-1-one; 1-{4-[4-(4-methoxypyrazolo[1,5-a]pyridin-6-yl)-phenoxy]-piperidin-1-yl}-propan-1-one; cyclopropyl-{4-[4-(4-methoxypyrazolo[1,5-a]pyridin-6-yl)-phenoxy]-piperidin-1-yl}-methanone; cyclobutyl-{4-[4-(4-methoxypyrazolo[1,5-a]-pyridin-6-yl)-phenoxy]-piperidin-1-yl}-methanone; 1-{4-[4-(3-chloroisoquinolin-6-yl)-phenoxy]-piperidin-1-yl}-propan-1-one; {4-[4-(3-chloroisoquinolin-6-yl)-phenoxy]-piperidin-1-yl}-cyclopropylmethanone; 1-{4-[4-(3-methoxyisoquinolin-6-yl)-phenoxy]-piperidin-1-yl}-propan-1-one; cyclopropyl-{4-[4-(3-methoxyisoquinolin-6-yl)-phenoxy]-piperidin-1-yl}-methanone; cyclobutyl-{4-[4-(3-methoxyisoquinolin-6-yl)-phenoxy]-piperidin-1-yl}-methanone; {4-[4-(3-methoxyisoquinolin-6-yl)-phenoxy]-piperidin-1-yl}-(R)-tetrahydrofuran-2-yl-methanone; 1-{4-[4-(1-chloroisoquinolin-6-yl)-phenoxy]-piperidin-1-yl}-propan-1-one; {4-[4-(1-chloroisoquinolin-6-yl)-phenoxy]-piperidin-1-yl}-cyclopropylmethanone; 1-{4-[4-(3-dimethylaminoisoquinolin-6-yl)-phenoxy]-piperidin-1-yl}-propan-1-one; 1-{4-[4-(3-amino-isoquinolin-6-yl)-phenoxy]-piperidin-1-yl}-propan-1-one; {4-[4-(3-aminoisoquinolin-6-yl)-phenoxy]-piperidin-1-yl})-cyclopropylmethanone; {4-[4-(4-methoxypyrazolo[1,5-a]pyridin-6-yl)-phenoxy]-piperidin-1-yl})-(R)-tetrahydrofuran-2-yl-methanone; 1-{4-[4-(1-methylisoquinolin-6-yl)-phenoxy]-piperidin-1-yl})-propan-1-one; 1-{4-[4-(4-hydroxy-pyrazolo[1,5-a]pyridin-6-yl)-phenoxy]-piperidin-1-yl}-propan-1-one; cyclobutyl-{4-[4-(4-hydroxypyrazolo[1,5-a]pyridin-6-yl)-phenoxy]-piperidin-1-yl}-methanone; {4-[4-(1-chloroisoquinolin-6-yl)-phenoxy]-piperidin-1-yl-cyclobutylmethanone; {4-[4-(1-chloro-isoquinolin-6-yl)-phenoxy]-piperidin-1-yl}-(R)-tetrahydrofuran-2-yl-methanone; 1-{4-[4-(3-methylisoquinolin-6-yl)-phenoxy]-piperidin-1-yl}-propan-1-one; {4-[4-(1-methylisoquinolin-6-yl)-phenoxy]-piperidin-1-yl}-(R)-tetrahydrofuran-2-yl-methanone; {4-[4-(1-methoxyisoquinolin-6-yl)-phenoxy]-piperidin-1-yl}-(R)-tetrahydrofuran-2-yl-methanone; 1-{4-[4-(1-methoxyisoquinolin-6-yl)-phenoxy]-piperidin-1-yl}-propan-1-one; cyclobutyl-{4-[4-(1-methoxyisoquinolin-6-yl)-phenoxy]-piperidin-1-yl}-methanone; cyclopropyl-{4-[4-(1-methoxyisoquinolin-6-yl)-phenoxy]-piperidin-1-yl}-methanone; {4-[4-(3-aminoisoquinolin-6-yl)-phenoxy]-piperidin-1-yl}-(R)-tetrahydrofuran-2-yl-methanone; {4-[4-(3-methylisoquinolin-6-yl)-phenoxy]-piperidin-1-yl}-(R)-tetrahydrofuran-2-yl-methanone; {4-[4-(1-ethylisoquinolin-6-yl)-phenoxy]-piperidin-1-yl}-(R)-tetrahydrofuran-2-yl-methanone; 1-{4-[4-(1-cyclopropylisoquinolin-6-yl)-phenoxy]-piperidin-1-yl})-propan-1-one; {4-[4-(1-cyclopropylisoquinolin-6-yl)-phenoxy]-piperidin-1-yl}-(R)-tetrahydrofuran-2-yl-methanone; 1-{4-[4-(7-methoxy-6-methylquinolin-3-yl)-phenoxy]-piperidin-1-yl}-propan-1-one; cyclopropyl-{4-[4-(7-methoxy-6-methylquinolin-3-yl)-phenoxy]-piperidin-1-yl}-methanone; {4-[4-(7-methoxy-6-methylquinolin-3-yl)-phenoxy]-piperidin-1-yl}-(R)-tetrahydrofuran-2-yl-methanone; 1-{4-[4-(6-fluoro-7-methoxyquinolin-3-yl)-phenoxy]-piperidin-1-yl}-propan-1-one; cyclopropyl-{4-[4-(6-fluoro-7-methoxyquinolin-3-yl)-phenoxy]-piperidin-1-yl}-methanone; {4-[4-(6-fluoro-7-methoxyquinolin-3-yl)-phenoxy]-piperidin-1-yl}-(R)-tetrahydrofuran-2-yl-methanone; 1-{4-[4-(6-chloro-7-methoxyquinolin-3-yl)-phenoxy]-piperidin-1-yl}-propan-1-one; {4-[4-(6-chloro-7-methoxyquinolin-3-yl)-phenoxy]-piperidin-1-yl}-cyclopropylmethanone; {4-[4-(6-chloro-7-methoxyquinolin-3-yl)-phenoxy]piperidin-1-yl}-(R)-tetrahydrofuran-2-yl-methanone; {4-[4-(6-methoxyquinolin-3-yl)-phenoxy]-piperidin-1-yl}-(R)-tetrahydrofuran-2-yl-methanone; {4-[4-(3-isopropoxyisoquinolin-6-yl)-phenoxy]-piperidin-1-yl}-(R)-tetrahydrofuran-2-yl-methanone; {4-[4-(1-morpholin-4-yl-isoquinolin-6-yl)-phenoxy]-piperidin-1-yl}-(R)-tetrahydrofuran-2-yl-methanone; {4-[4-(1-dimethylaminoisoquinolin-6-yl)-phenoxy]-piperidin-1-yl}-(R)-tetrahyrofuran-2-yl methananone; {4-[4-(1-aminoisoquinolin-6-yl)-phenoxy]-piperidin-1-yl}-(R)-tetrahydrofuran-2-yl-methanone; {4-[4-(1-dimethylaminoisoquinolin-6-yl)-phenoxy]-piperidin-1-yl}-(R)-tetrahydrofuran-2-yl-methanone; {4-[4-(1-methylaminoisoquinolin-6-yl)-phenoxy]-piperidin-1-yl}-(R)-tetrahydrofuran-2-yl-methanone; 1-{4-[4-(4-methylisoquinolin-6-yl)-phenoxy]-piperidin-1-yl})-propan-1-one; cyclopropyl-{4-[4-(4-methylisoquinolin-6-yl)-phenoxy]-piperidin-1-yl}-methanone; {4-[4-(4-methylisoquinolin-6-yl)-phenoxy]-piperidin-1-yl}-(R)-tetrahydrofuran-2-yl-methanone; 1-{4-[4-(5-methylquinolin-3-yl)-phenoxy]-piperidin-1-yl}-propan-1-one; cyclopropyl-{4-[4-(5-methylquinolin-3-yl)-phenoxy]-piperidin-1-yl}-methanone; {4-[4-(5-methylquinolin-3-yl)-phenoxy]-piperidin-1-yl}-(R)-tetrahydrofuran-2-yl-methanone; 1-{4-[4-(5-methoxyquinolin-3-yl)-phenoxy]-piperidin-1-yl}-propan-1-one; cyclopropyl-{4-[4-(5-methoxyquinolin-3-yl)-phenoxy]-piperidin-1-yl}-methanone; {4-[4-(5-methoxyquinolin-3-yl)-phenoxy]-piperidin-1-yl}-(R)-tetrahydrofuran-2-yl-methanone; cyclopropyl-[4-(4-isoquinolin-6-yl-phenoxy)-piperidin-1- yl]-methanone; [4-[4-(6-isoquinolyl)phenoxy]-1-piperidyl]-[(2R)-tetrahydrofuran-2-yl]methanone; {4-[4-(5-methylisoquinolin-6-yl)-phenoxy]-piperidin-1-yl}-(R)-tetrahydrofuran-2-yl-methanone; 1-[4-[4-(1,4-dimethyl-6-isoquinolyl)phenoxy]-1-piperidyl]propan-1-one; cyclopropyl-[4-[4-(1,4-dimethyl-6-isoquinolyl)phenoxy]-1-piperidyl]methanone; [4-[4-(1,4-dimethyl-6-isoquinolyl)-phenoxy]-1-piperidyl]-[(2R)-tetrahydrofuran-2-yl]methanone; 1-[4-[4-(1,5-dimethyl-6-isoquinolyl)phenoxy]-1-piperidyl]propan-1-one; cyclopropyl-[4-[4-(1,5-dimethyl-6-isoquinolyl)-phenoxy]-1-piperidyl]methanone; [4-[4-(1,5-dimethyl-6-isoquinolyl)phenoxy]-1-piperidyl]-[(2R)-tetrahydrofuran-2-yl]methanone; [4-[4-(8-cyclopropyl-7-quinolyl)phenoxy]-1-piperidyl]-[(2R)-tetrahydrofuran-2-yl]methanone; {4-[4-(3-ethylisoquinolin-6-yl)-phenoxy]-piperidin-1-yl}-(R)-tetrahydrofuran-2-yl-methanone; cyclopropyl-{4-[4-(7-fluoroquinolin-3-yl)-phenoxy]-piperidin-1-yl}-methanone; 1-{4-[4-(7-fluoroquinolin-3-yl)-phenoxy]-piperidin-1-yl}-propan-1-one; {4-[4-(7-fluoroquinolin-3-yl)-phenoxy]-piperidin-1-yl}-(R)-tetrahydrofuran-2-yl-methanone; {4-[4-(3-cyclopropylisoquinolin-6-yl)-phenoxy]-piperidin-1-yl}-(R)-tetrahydrofuran-2-yl-methanone; cyclopropyl-{4-[4-(1-methylisoquinolin-6-yl)-phenoxy]-piperidin-1-yl}-methanone; {4-[4-(7-methylquinolin-3-yl)-phenoxy]-piperidin-1-yl}-(R)-tetrahydrofuran-2-yl-methanone; 1-{4-[4-(6-methylquinolin-3-yl)-phenoxy]-piperidin-1-yl}-propan-1-one; cyclopropyl-{4-[4-(6-methylquinolin-3-yl)-phenoxy]-piperidin-1-yl}-methanone; {4-[4-(6-methylquinolin-3-yl)-phenoxy]-piperidin-1-yl}-(R)-tetrahydrofuran-2-yl-methanone; 1-{4-[4-(8-methylquinolin-3-yl)-phenoxy]-piperidin-1-yl}-propan-1-one; cyclopropyl-{4-[4-(8-methylquinolin-3-yl)-phenoxy]-piperidin-1-yl}-methanone; {4-[4-(8-methyl-quinolin-3-yl)-phenoxy]-piperidin-1-yl}-(R)-tetrahydrofuran-2-yl-methanone; 4-(3',4'-dimethoxybiphenyl-4-yloxy)-piperidine-1-carboxylic acid tert-butyl ester; 4-(4'-cyanobiphenyl-4-yl-oxy)-piperidine-1-carboxylic acid tert-butyl ester; 1-[4-(3',4'-dimethoxy-biphenyl-4-yloxy)-piperidin-1-yl]-propan-1-one; 1-[4-(3',4'-dimethoxy-biphenyl-4-yloxy)-piperidin-1-yl]-2-methyl-propan-1-one; 4'-(1-propionylpiperidin-4-yloxy)-biphenyl-4-carbonitrile; 4'-(1-isobutyrylpiperidin-4-yloxy)-biphenyl-4-carbonitrile; 4'-(1-cyclopropanecarbonyl-piperidin-4-yloxy)-biphenyl-4-carbonitrile; 1-[4-(3-quinolin-3-yl-phenoxy)-piperidin-1-yl]-propan-1-one; cyclopropyl-[4-(3-quinolin-3-yl-phenoxy)-piperidin-1-yl]-methanone; 1-{4-[4-(5,6-dimethoxypyridin-3-yl)-phenoxy]-piperidin-1-yl}-propan-1-one; cyclopropyl-{4-[4-(5,6-dimethoxypyridin-3-yl)-phenoxy]-piperidin-1-yl}-methanone; 1-[4-(3',4'-dichlorobiphenyl-4-yloxy)-piperidin-1-yl]-propan-1-one; cyclopropyl-[4-(3',4'-dichlorobiphenyl-4-yloxy)-piperidin-1-yl]-methanone; 1-{4-[4-(2,3-dihydro-1,4-benzodioxin-6-yl)-phenoxy]-piperidin-1-yl}-propan-1-one; cyclopropyl-{4-[4-(2,3-dihydro-1,4-benzodioxin-6-yl)-phenoxy]-piperidin-1-yl}-methanone; 1-[4-(4'-benzyloxy-2'-fluorobiphenyl-4-yloxy)-piperidin-1-yl]-propan-1-one; [4-(4'-benzyloxy-2'-fluorobiphenyl-4-yloxy)-piperidin-1-yl]-cyclopropylmethanone; 1-[4-(5'-benzyloxy-3'-fluorobiphenyl-4-yloxy)-piperidin-1-yl]-propan-1-one; [4-(5'-benzyloxy-3'-fluorobiphenyl-4-yloxy)-piperidin-1-yl]-cyclopropylmethanone; 1-[4-(4'-phenoxybiphenyl-4-yloxy)-piperidin-1-yl]-propan-1-one; cyclopropyl-[4-(4'-phenoxybiphenyl-4-yloxy)-piperidin-1-yl]-methanone; 1-[4-(3'-phenoxybiphenyl-4-yloxy)-piperidin-1-yl]-propan-1-one; cyclopropyl-[4-(3'-phenoxy-biphenyl-4-yloxy)-piperidin-1-yl]-methanone; 2-methyl-1-(4-((4-(quinolin-7-yl)phenyl)sulfonyl)piperidin-1-yl)propan-1-one; 1-[4-(4-isoquinolin-7-yl-benzene-sulfonyl)-piperidin-1-yl]-2-methylpropan-1-one; 1-[4-(4-isoquinolin-6-yl-benzenesulfonyl)-piperidin-1-yl]-2-methyl-propan-1-one; 1-[4-(4-benzofuran-5-yl-benzenesulfonyl)-piperidin-1-yl]-2-methyl-propan-1-one; 1-(4-((4-(quinolin-7-yl)phenyl)thio)piperidin-1-yl)propan-1-one; 1-(4-((4-(isoquinolin-6-yl)phenyl)thio)piperidin-1-yl)propan-1-one; 1-(4-((4-(quinolin-3-yl)phenyl)thio)piperidin-1-yl)propan-1-one; 1-(4-((4-(isoquinolin-4-yl)phenyl)thio)piperidin-1-yl)propan-1-one; 1-(4-((4-(isoquinolin-6-yl)phenyl)thio)piperidin-1-yl)propan-1-one; 1-(4-((4-(isoquinolin-6-yl)phenyl)thio)piperidin-1-yl)-2-methylpropan-1-one; 2-methyl-1-(4-((4-(quinolin-3-yl)phenyl)thio)piperidin-1-yl)propan-1-one; 1-(4-((4-(isoquinolin-4-yl)phenyl)thio)piperidin-1-yl)-2-methylpropan-1-one; 1-{4-[methyl-(4-quinolin-3-yl-phenyl)-amino]-piperidin-1-yl}-propan-1-one; cyclopropyl-{4-[methyl-(4-quinolin-3-yl-phenyl)-amino]-piperidin-1-yl}-methanone; 1-[4-(4-quinolin-3-yl-phenylamino)-piperidin-1-yl]-propan-1-one; cyclopropyl-[4-(4-quinolin-3-yl-phenylamino)-piperidin-1-yl]-methanone; {4-[methyl-(4-quinolin-3-yl-phenyl)-amino]-piperidin-1-yl}-(R)-tetrahydrofuran-2-yl-methanone and salts of such compounds, e.g., pharmaceutically acceptable salts.

Additional compounds according to Formula I may include, for example: N-ethyl-4-[4-(2-hydroxy-8-methyl-7-quinolyl)phenoxy]piperidine-1-carboxamide; 4-[4-(8-methyl-7-quinolyl)phenoxy]-N-(2-pyrrolidin-1-ylethyl)piperidine-1-carboxamide; 4-[4-(8-methyl-7-quinolyl)phenoxy]-N-(2-morpholinoethyl)piperidine-1-carboxamide; (4-isopropylpiperazin-1-yl)-[4-[4-(8-methyl-7-quinolyl)phenoxy]-1-piperidyl]methanone; (4-methylpiperazin-1-yl)-[4-[4-(8-methyl-7-quinolyl)phenoxy]-1-piperidyl]methanone; [4-[4-(8-methyl-7-quinolyl)phenoxy]-1-piperidyl]-(4-morpholino-1-piperidyl)methanone; (4-ethylpiperazin-1-yl)-[4-[4-(8-methyl-7-quinolyl)phenoxy]-1-piperidyl]methanone; N-ethyl-4-[4-(7-methylpyrazolo[1,5-a]pyridin-6-yl)-phenoxy]piperidine-1-carboxamide; N-isopropoxy-4-[4-(7-methylpyrazolo[1,5-a]pyridin-6-yl)phenoxy]piperidine-1-carboxamide; N-ethoxyoxy-4-[4-(7-methylpyrazolo[1,5-a]pyridin-6-yl)phenoxy]piperidine-1-carboxamide; N-methoxyoxy-4-[4-(7-methylpyrazolo[1,5-a]pyridin-6-yl)phenoxy]piperidine-1-carboxamide; N-(cyclopropylmethyl)-4-[4-(8-methyl-7-quinolyl)phenoxy]-piperidine-1-carboxamide; N-isobutyl-4-[4-(8-methyl-7-quinolyl)phenoxy]piperidine-1-carboxamide; N-(2-methoxyethyl)-4-[4-(8-methyl-7-quinolyl)phenoxy]piperidine-1-carboxamide; N-Isopropoxy-4-[4-(8-methyl-7-quinolyl)phenoxy]piperidine-1-carboxamide; N-isobutoxy-4-[4-(8-methyl-7-quinolyl)phenoxy]piperidine-1-carboxamide; N-(2-dimethylaminoethyl)-4-[4-(8-methyl-7-quinolyl)phenoxy]piperidine-1-carboxamide; 2-morpholinoethyl 4-[4-(8-methyl-7-quinolyl)phenoxy]piperidine-1-carboxylate; 2-pyrrolidin-1-ylethyl 4-[4-(8-methyl-7-quinolyl)phenoxy]piperidine-1-carboxylate; N-[2-(1H-imidazol-4-yl)ethyl]-4-[4-(8-methyl-7-quinolyl)phenoxy]piperidine-1-carboxamide; 4-[4-(8-methyl-7-quinolyl)phenoxy]-N-tetrahydropyran-4-yl-piperidine-1-carboxamide; isobutyl 4-[4-(8-methyl-7-quinolyl)phenoxy]piperidine-1-carboxylate; allyl 4-[4-(8-methyl-7-quinolyl)phenoxy]piperidine-1-carboxylate; N-cyclobutyl-4-[4-(8-methyl-7-quinolyl)phenoxy]piperidine-1-carboxamide; cyclopropylmethyl 4-[4-(8-methyl-7-quinolyl)phenoxy]piperidine-1-carboxylate; 4-[4-(8-methyl-7-quinolyl)phenoxy]piperidine-1-carbohydroxamic acid; 2-methoxyethyl 4-[4-(8-methyl-7-quinolyl)-phenoxy]piperidine-1-carboxylate; tetrahydropyran-4-yl 4-[4-(8-methyl-7-quinolyl)phenoxy]piperidine-1-carboxylate; tetrahydropyran-3-yl 4-[4-(8- methyl-7-quinolyl)phenoxy]piperidine-1-carboxylate; [4-[4-(8-methyl-7-quinolyl)phenoxy]-1-piperidyl]-(oxazinan-2-yl)methanone; tetrahydrofuran-3-yl 4-[4-(8-methyl-7-quinolyl)phenoxy]piperidine-1-carboxylate; N-(cyclobutylmethyl)-4-[4-(8-methyl-7-quinolyl)phenoxy] piperidine-1-carboxamide; cyclobutyl 4-[4-(8-methyl-7-quinolyl)phenoxy]piperidine-1-carboxylate; azepan-1-yl-[4-[4-(8-methyl-7-quinolyl)phenoxy]-1-piperidyl]methanone; N-butyl-4-[4-(5-chloroimidazo[1,2-a]pyridin-6-yl)phenoxy]piperidine-1-carboxamide; 4-[4-(5-chloroimidazo[1,2-a]pyridin-6-yl)phenoxy]-N-ethyl-piperidine-1-carboxamide; 4-[4-(5-chloroimidazo[1,2-a]pyridin-6-yl)phenoxy]-N-isobutyl-piperidine-1-carboxamide; 4-[4-(5-chloroimidazo[1,2-a]pyridin-6-yl)phenoxy]-N-propyl-piperidine-1-carboxamide; 4-[4-(5-chloroimidazo[1,2-a]pyridin-6-yl)phenoxy]-N-(2-methoxyethyl)-piperidine-1-carboxamide; 4-[4-(5-chloroimidazo[1,2-a]pyridin-6-yl)phenoxy]-N-(cyclopropyl-methyl)-piperidine-1-carboxamide; 4-[4-(5-chloroimidazo[1,2-a]pyridin-6-yl)phenoxy]-N-isopropoxy-piperidine-1-carboxamide; 4-[4-(5-chloroimidazo[1,2-a]pyridin-6-yl)phenoxy]-N-isopropyl-piperidine-1-carboxamide; 4-[4-(5-chloroimidazo[1,2-a]pyridin-6-yl)phenoxy]-N-isobutoxy-piperidine-1-carboxamide; 4-[4-(5-chloroimidazo[1,2-a]pyridin-6-yl)phenoxy]-N-isopentyl-piperidine-1-carboxamide; 4-[4-(5-chloroimidazo[1,2-a]pyridin-6-yl)phenoxy]-N-ethoxy-piperidine-1-carboxamide; 4-[4-(8-methyl-7-quinolyl)phenoxy]-N-propoxy-piperidine-1-carboxamide; 4-[4-(5-chloroimidazo[1,2-a]pyridin-6-yl)phenoxy]piperidine-1-carbohydroxamic acid; 4-[4-(5-chloroimidazo[1,2-a]pyridin-6-yl)phenoxy]-N-propoxy-piperidine-1-carboxamide; 4-[4-(5-chloroimidazo[1,2-a]pyridin-6-yl)phenoxy]piperidine-1-carboxamide; N-ethyl-4-[4-(1-methyl-6-isoquinolyl)phenoxy]piperidine-1-carboxamide; 4-[4-(1-methyl-6-isoquinolyl)phenoxy]-N-propyl-piperidine-1-carboxamide; N-isobutyl-4-[4-(1-methyl-6-isoquinolyl)phenoxy]piperidine-1-carboxamide; 4-[4-(1-methyl-6-isoquinolyl)phenoxy]piperidine-1-carboxamide; N-(cyclopropylmethyl)-4-[4-(1-methyl-6-isoquinolyl)phenoxy]piperidine-1-carboxamide; N-isopropoxy-4-[4-(1-methyl-6-isoquinolyl)phenoxy]piperidine-1-carboxamide; 4-[4-(1-methyl-6-isoquinolyl)phenoxy]-N-propoxypiperidine-1-carboxamide; 4-[4-(1-methyl-6-isoquinolyl)phenoxy]piperidine-1-carbohydroxamic acid; N-ethoxy-4-[4-(1-methyl-6-isoquinolyl)phenoxy]piperidine-1-carboxamide; N-ethoxy-4-[4-(4-methyl-3-quinolyl)phenoxy]piperidine-1-carboxamide; N-isopropoxy-4-[4-(4-methyl-3-quinolyl)phenoxy]piperidine-1-carboxamide; 4-[4-(4-methyl-3-quinolyl)phenoxy]-N-propoxy-piperidine-1-carboxamide; N-isobutyl-4-[4-(4-methyl-3-quinolyl)phenoxy]piperidine-1-carboxamide; 4-[4-(4-methyl-3-quinolyl)phenoxy]-N-propyl-piperidine-1-carboxamide; N-ethyl-4-[4-(5-methylimidazo[1,2-a]pyridin-6-yl)phenoxy]piperidine-1-carboxamide; N-isobutyl-4-[4-(5-methylimidazo[1,2-a]pyridin-6-yl)phenoxy]piperidine-1-carboxamide; 4-[4-(5-methylimidazo[1,2-a]pyridin-6-yl)phenoxy]-N-propyl-piperidine-1-carboxamide; N-(cyclopropylmethyl)-4-[4-(5-methylimidazo[1,2-a]pyridin-6-yl)-phenoxy]piperidine-1-carboxamide; 4-[4-(5-methylimidazo[1,2-a]pyridin-6-yl)phenoxy]-N-(3-pyridyl)-piperidine-1-carboxamide; N-(2-methoxyethyl)-4-[4-(5-methylimidazo[1,2-a]pyridin-6-yl)phenoxy]piperidine-1-carboxamide; [4-[4-(5-methylimidazo[1,2-a]pyridin-6-yl)phenoxy]-1-piperidyl]-(4-methylpiperazin-1-yl)methanone; N,N-dimethyl-4-[4-(5-methylimidazo[1,2-a]pyridin-6-yl)phenoxy]piperidine-1-carboxamide; N-isopropoxy-4-[4-(5-methylimidazo[1,2-a]pyridin-6-yl)phenoxy]piperidine-1-carboxamide;

N-isobutoxy-4-[4-(5-methyl-imidazo[1,2-a]pyridin-6-yl)phenoxy]piperidine-1-carboxamide; isobutyl 4-[4-(5-methylimidazo[1,2-a]pyridin-6-yl)phenoxy]piperidine-1-carboxylate; N-isopropyl-4-[4-(5-methylimidazo[1,2-a]pyridin-6-yl)phenoxy]piperidine-1-carboxamide; 4-[4-(5-methylimidazo[1,2-a]pyridin-6-yl)phenoxy]-N-(1-methylpyrazol-4-yl)piperidine-1-carboxamide; tert-butyl 4-[4-(5-methylimidazo[1,2-a]pyridin-6-yl)phenoxy]piperidine-1-carboxylate; 4-[4-(5-methylimidazo[1,2-a]pyridin-6-yl)phenoxy]-N-(2,2,2-trifluoro-ethyl)piperidine-1-carboxamide; 4-[4-(5-methylimidazo[1,2-a]pyridin-6-yl)phenoxy]-N-propoxy-piperidine-1-carboxamide; N-ethoxy-4-[4-(5-methylimidazo[1,2-a]pyridin-6-yl)phenoxy]piperidine-1-carboxamidel 2-amino-1-[4-[4-(8-methyl-7-quinolyl)phenoxy]-1-piperidyl]ethanone 2HCl; (2R)-2-amino-1-[4-[4-(8-methyl-7-quinolyl)phenoxy]-1-piperidyl]propan-1-one 2HCl; N-methoxy-4-[4-(5-methylimidazo[1,2-a]pyridin-6-yl)phenoxy]piperidine-1-carboxamide; (2S)-2-amino-1-[4-[4-(8-methyl-7-quinolyl)phenoxy]-1-piperidyl]propan-1-one 2HCl; 4-[4-(5-methylimidazo[1,2-a]pyridin-6-yl)phenoxy]piperidine-1-carbohydroxamic acid; 2-(dimethylamino)-1-[4-[4-(8-methyl-7-quinolyl)phenoxy]-1-piperidyl]ethanone; 4-[4-(5-methylimidazo[1,2-a]pyridin-6-yl)phenoxy]piperidine-1-carboxamide; [(2R)-1-methylpyrrolidin-2-yl]-[4-[4-(8-methyl-7-quinolyl)phenoxy]-1-piperidyl]methanone; [(2S)-1-methylpyrrolidin-2-yl]-[4-[4-(8-methyl-7-quinolyl)phenoxy]-1-piperidyl]methanone; S-isopropyl 4-[4-(8-methyl-7-quinolyl)phenoxy]piperidine-1-carbothioate; 2-amino-2-methyl-1-[4-[4-(8-methyl-7-quinolyl)phenoxy]-1-piperidyl]-propan-1-one; [4-[4-(8-methyl-7-quinolyl)phenoxy]-1-piperidyl]-[(2R)-pyrrolidin-2-yl]methanone; [4-[4-(8-methyl-7-quinolyl)phenoxy]-1-piperidyl]-[(2S)-pyrrolidin-2-yl]methanone; [1-(methylamino)cyclopropyl]-[4-[4-(8-methyl-7-quinolyl)phenoxy]-1-piperidyl]methanone; 3-amino-1-[4-[4-(8-methyl-7-quinolyl)phenoxy]-1-piperidyl]propan-1-one; 2-isopropoxy-1-[4-[4-(8-methyl-7-quinolyl)phenoxy]-1-piperidyl]ethanone; [2-[4-[4-(8-methyl-7-quinolyl)phenoxy]-1-piperidyl]-2-oxo-ethyl]acetate; 2-hydroxy-1-[4-[4-(8-methyl-7-quinolyl)phenoxy]-1-piperidyl]ethanone; (1-aminocyclobutyl)-[4-[4-(8-methyl-7-quinolyl)-phenoxy]-1-piperidyl]-methanone; N-ethyl-4-(4-imidazo[1,2-a]pyridin-7-ylphenoxy)piperidine-1-carboxamide; N-ethyl-4-[4-(8-methylimidazo[1,2-a]pyridin-7-yl)phenoxy]piperidine-1-carboxamide; N-isopropoxy-4-[4-(8-methylimidazo[1,2-a]pyridin-7-yl)phenoxy]piperidine-1-carboxamide; 4-[4-(8-methylimidazo[1,2-a]pyridin-7-yl)phenoxy]-N-propyl-piperidine-1-carboxamide; N-isobutyl-4-[4-(8-methylimidazo[1,2-a]pyridin-7-yl)phenoxy]piperidine-1-carboxamide; N-isobutyl-4-[4-(7-methylpyrazolo[1,5-a]pyridin-6-yl)phenoxy]piperidine-1-carboxamide; 4-[4-(7-methylpyrazolo[1,5-a]pyridin-6-yl)phenoxy]piperidine-1-carboxamide; 4-[4-(7-methylpyrazolo[1,5-a]pyridin-6-yl)phenoxy]piperidine-1-carbohydroxamic acid; N,N-dimethyl-4-[4-(7-methylpyrazolo[1,5-a]pyridin-6-yl)phenoxy]piperidine-1-carboxamide; [4-[4-(7-methylpyrazolo[1,5-a]pyridin-6-yl)phenoxy]-1-piperidyl]-pyrrolidin-1-yl-methanone; [(3S)-3-fluoropyrrolidin-1-yl]-[4-[4-(7-methylpyrazolo[1,5-a]pyridin-6-yl)phenoxy]-1-piperidyl]methanone; [(3R)-3-fluoropyrrolidin-1-yl]-[4-[4-(7-methylpyrazolo[1,5-a]pyridin-6-yl)phenoxy]-1-piperidyl]-methanone; 4-[4-(7-methylpyrazolo[1,5-a]pyridin-6-yl)phenoxy]-N-methylsulfanyl-piperidine-1-carboxamide; N-ethylsulfanyl-4-[4-(7-methylpyrazolo[1,5-a]pyridin-6-yl)phenoxy]piperidine-1-carboxamide; 4-[4-(4-methyl-3-quinolyl)phenoxy]-N-methyl sulfanyl-piperidine-1-carboxamide;

4-[4-(4-methyl-3-quinolyl)phenoxy]-N-ethylsulfanyl-piperidine-1-carboxamide; 1-[4-[4-(7-methylpyrazolo[1,5-a]pyridin-6-yl)phenoxy]piperidine-1-carbonyl]pyrrolidin-2-one; 1-[4-[4-(4-methyl-3-quinolyl)phenoxy]piperidine-1-carbonyl]pyrrolidin-2-one; 4-[4-(7-methylpyrazolo[1,5-a]pyridin-6-yl)phenoxy]-N-propyl-piperidine-1-carboxamide; N-ethyl-4-[4-(2-fluoro-8-methyl-7-quinolyl)phenoxy]piperidine-1-carboxamide and salts of such compounds, e.g., pharmaceutically acceptable salts.

Compounds according to Formula III may include. for example: 1-[4-(4-isoquinolin-6-yl-phenoxy)-piperidin-1-yl]-propan-1-one; 1-[4-(4-quinolin-3-yl-phenoxy)-piperidin-1-yl]-propan-1-one; 2-methyl-1-[4-(4-quinolin-7-yl-phenoxy)-piperidin-1-yl]-propan-1-one; 1-[4-(4-quinolin-7-yl-phenoxy)-piperidin-1-yl]-propan-1-one; 1-[4-(2-fluoro-4-quinolin-3-yl-phenoxy)piperidin-1-yl]propan-1-one; 1-[4-(2-fluoro-4-quinolin-3-ylphenoxy)-piperidin-1-yl]-2-methylpropan-1-one; 1-[4-(4-1,5-naphthyridin-3-yl-phenoxy)piperidin-1-yl]-propan-1-one; 2-methyl-1-[4-(4-1,5-naphthyridin-3-yl-phenoxy)piperidin-1-yl]-propan-1-one; cyclopropyl-[4-(4-1,5-naphthyridin-3-yl-phenoxy)piperidin-1-yl]-methanone; 1-{4-[4-(2-chloroquinolin-3-yl)-phenoxy]-piperidin-1-yl}-propan-1-one; {4-[4-(2-chloroquinolin-3-yl)-phenoxy]-piperidin-1-yl}-cyclopropylmethanone; 1-{4-[4-(2-methoxyquinolin-3-yl)-phenoxy]-piperidin-1-yl}-propan-1-one; 1-{4-[4-(8-fluoro-quinolin-7-yl)-phenoxy]-piperidin-1-yl}-propan-1-one; cyclopropyl-{4-[4-(8-fluoro-quinolin-7-yl)-phenoxy]-piperidin-1-yl}-methanone; cyclobutyl-{4-[4-(8-fluoroquinolin-7-yl)-phenoxy]-piperidin-1-yl}-methanone; 1-{4-[4-(8-fluoro-2-methylquinolin-7-yl)-phenoxy]-piperidin-1-yl}-propan-1-one; cyclopropyl-{4-[4-(8-fluoro-2-methylquinolin-7-yl)-phenoxy]-piperidin-1-yl}-methanone; cyclobutyl-{4-[4-(8-fluoro-2-methylquinolin-7-yl)-phenoxy]-piperidin-1-yl}-methanone; {4-[4-(5-fluoroquinolin-3-yl)-phenoxy]-piperidin-1-yl}-(R)-tetrahydrofuran-2-yl-methanone; 1-{4-[4-(5-fluoroquinolin-3-yl)-phenoxy]-piperidin-1-yl}-propan-1-one; cyclopropyl-{4-[4-(5-fluoroquinolin-3-yl)-phenoxy]-piperidin-1-yl}-methanone; cyclobutyl-{4-[4-(5-fluoroquinolin-3-yl)-phenoxy]-piperidin-1-yl}-methanone; cyclopropyl-{4-[4-(7-methoxyquinolin-3-yl)-phenoxy]-piperidin-1-yl}-methanone; 1-{4-[4-(7-methoxyquinolin-3-yl)-phenoxy]-piperidin-1-yl}-propan-1-one; 1-{4-[4-(8-methylquinolin-7-yl)-phenoxy]-piperidin-1-yl}-propan-1-one; cyclopropyl-{4-[4-(8-methylquinolin-7-yl)-phenoxy]-piperidin-1-yl}-methanone; cyclobutyl-{4-[4-(8-methylquinolin-7-yl)-phenoxy]-piperidin-1-yl}-methanone; cyclopropyl-[4-(4-quinolin-2-yl-phenoxy)-piperidin-1-yl]-methanone; 1-[4-(4-quinolin-2-yl-phenoxy)-piperidin-1-yl]-propan-1-one; cyclobutyl-[4-(4-quinolin-2-yl-phenoxy)-piperidin-1-yl]-methanone; [4-(4-quinolin-2-yl-phenoxy)-piperidin-1-yl]-(R)-tetrahydrofuran-2-yl-methanone; 1-[4-(4-isoquinolin-3-yl-phenoxy)-piperidin-1-yl]-propan-1-one; cyclopropyl-[4-(4-isoquinolin-3-yl-phenoxy)-piperidin-1-yl]-methanone; cyclobutyl-[4-(4-isoquinolin-3-yl-phenoxy)-piperidin-1-yl]-methanone; [4-(4-isoquinolin-3-yl-phenoxy)-piperidin-1-yl]-(R)-tetrahydrofuran-2-yl-methanone; 1-{4-[4-(4-chloroquinolin-3-yl)-phenoxy]-piperidin-1-yl}-propan-1-one; {4-[4-(4-chloroquinolin-3-yl)-phenoxy]-piperidin-1-yl}-cyclopropylmethanone; {4-[4-(4-chloroquinolin-3-yl)-phenoxy]-piperidin-1-yl}-cyclobutylmethanone; 1-{4-[4-(4-methoxyquinolin-3-yl)-phenoxy]-piperidin-1-yl}-propan-1-one; 1-{4-[4-(6-methoxyquinolin-3-yl)-phenoxy]-piperidin-1-yl}-propan-1-one; cyclopropyl-{4-[4-(6-methoxyquinolin-3-yl)-phenoxy]-piperidin-1-yl}-methanone; 1-{4-[4-(6,7-dimethoxyquinolin-3-yl)-phenoxy]-piperidin-1-yl}-propan-1-one; cyclopropyl-{4-[4-(6,7-dimethoxyquinolin-3-yl)-phenoxy]-piperidin-1-yl}-methanone; 1-{4-[4-(8-methoxyquinolin-3-yl)-phenoxy]-piperidin-1-yl}-propan-1-one; cyclopropyl-{4-[4-(8-methoxyquinolin-3-yl)-phenoxy]-piperidin-1-yl}-methanone; {4-[4-(8-chloroquinolin-7-yl)-phenoxy]piperidin-1-yl}-cyclopropylmethanone; 1-{4-[4-(4-methylquinolin-3-yl)-phenoxy]piperidin-1-yl}-propan-1-one; cyclopropyl-{4-[4-(4-methylquinolin-3-yl)-phenoxy]piperidin-1-yl}-methanone; cyclobutyl-{4-[4-(4-methylquinolin-3-yl)-phenoxy]piperidin-1-yl}-methanone; 1-{4-[4-(7-methylquinolin-3-yl)-phenoxy]-piperidin-1-yl}-propan-1-one; cyclopropyl-{4-[4-(7-methylquinolin-3-yl)-phenoxy]-piperidin-1-yl}-methanone; {4-[4-(4-methylquinolin-3-yl)-phenoxy]-piperidin-1-yl}-(R)-tetrahydrofuran-2-yl-methanone; 1-[4-(4-quinoxalin-2-yl-phenoxy)-piperidin-1-yl]-propan-1-one; cyclopropyl-[4-(4-quinoxalin-2-yl-phenoxy)-piperidin-1-yl]-methanone; [4-(4-quinoxalin-2-yl-phenoxy)-piperidin-1-yl]-(R)-tetrahydrofuran-2-yl-methanone; {4-[4-(8-methylquinolin-7-yl)-phenoxy]-piperidin-1-yl}-(R)-tetrahydrofuran-2-yl-methanone; {4-[4-(8-methylquinolin-7-yl)-phenoxy]-piperidin-1-yl}-(S)-tetrahydrofuran-2-yl-methanone; {4-[4-(4-chloroquinolin-3-yl)-phenoxy]-piperidin-1-yl}-(R)-tetrahydrofuran-2-yl-methanone; 1-{4-[4-(4-methylquinolin-3-yl)-phenoxy]-piperidin-1-yl})-propane-1,2-dione; isoxazolidin-2-yl-[4-(4-quinolin-3-yl-phenoxy)-piperidin-1-yl]-methanone; [4-(4-isoquinolin-3-yl-phenoxy)-piperidin-1-yl-isoxazolidin-2-yl-methanone; isoxazolidin-2-yl-{4-[4-(8-methylquinolin-7-yl)-phenoxy]-piperidin-1-yl}-methanone; {4-[4-(4-chloroquinolin-3-yl)-phenoxy]piperidin-1-yl}-isoxazolidin-2-yl-methanone; {4-[4-(8-chloroquinolin-7-yl)-phenoxy]-piperidin-1-yl}-isoxazolidin-2-yl-methanone; isoxazolidin-2-yl-{4-[4-(4-methylquinolin-3-yl)-phenoxy]-piperidin-1-yl}-methanone; isoxazolidin-2-yl-{4-[4-(8-methoxyquinolin-7-yl)-phenoxy]-piperidin-1-yl}-methanone; isoxazolidin-2-yl-{4-[4-(7-methylquinolin-3-yl)-phenoxy]-piperidin-1-yl}-methanone; isoxazolidin-2-yl-[4-(4-quinoxalin-2-yl-phenoxy)-piperidin-1-yl]-methanone; 4-[4-(4-methylquinolin-3-yl)-phenoxy]-piperidine-1-carboxylic acid methoxyamide; 4-[4-(4-methyl-quinolin-3-yl)-phenoxy]-piperidine-1-carboxylic acid methoxy-methyl-amide; 4-[4-(4-methylquinolin-3-yl)-phenoxy]-piperidine-1-carboxylic acid ethylamide; 4-[4-(8-methoxyquinolin-7-yl)-phenoxy]-piperidine-1-carboxylic acid methylamide; 4-[4-(8-methoxyquinolin-7-yl)-phenoxy]-piperidine-1-carboxylic acid ethylamide; 4-[4-(4-methylquinolin-3-yl)-phenoxy]-piperidine-1-carboxylic acid hydroxyamide; N-ethyl-4-[4-(8-methyl-7-quinolyl)phenoxy]piperidine-1-carboxamide; N,N-dimethyl-4-[4-(8-methyl-7-quinolyl)phenoxy]piperidine-1-carboxamide; ethyl 4-[4-(8-methyl-7-quinolyl)phenoxy]piperidine-1-carboxylate; N-methoxy-4-[4-(8-methyl-7-quinolyl)phenoxy]piperidine-1-carboxamide; N-isopropyl-4-[4-(8-methyl-7-quinolyl)-phenoxy]piperidine-1-carboxamide; N-ethoxy-4-[4-(8-methyl-7-quinolyl)phenoxy]piperidine-1-carboxamide; [4-[4-(8-methyl-7-quinolyl)phenoxy]-1-piperidyl]-pyrrolidin-1-yl-methanone; N-methyl-4-[4-(8-methyl-7-quinolyl)phenoxy]piperidine-1-carboxamide; 4-[4-(8-methyl-7-quinolyl)-phenoxy]-N-propyl-piperidine-1-carboxamide; 4-[4-(8-methyl-7-quinolyl)phenoxy]piperidine-1-carboxamide; [4-[4-(8-methyl-7-quinolyl)phenoxy]-1-piperidyl]-(1-piperidyl)methanone; [4-[4-(8-methyl-7-quinolyl)phenoxy]-1-piperidyl]-morpholinomethanone; cyclopropyl-[4-(4-quinolin-3-yl-phenoxy)-piperidin-1-yl]-methanone; cyclobutyl-[4-(4-quinolin-3-yl-phenoxy)-piperidin-1-yl]-methanone; cyclopentyl-[4-(4-quinolin-3-yl-phenoxy)-piperidin-1-yl]-methanone; [4-(4-quinolin-3-ylphenoxy)-piperidin-1-yl]-(R)-tetrahydrofuran-2-yl-methanone; [4-(4-quinolin-3-yl-phenoxy)-piperidin-1-yl]-(S)-tetrahydrofuran-2-yl-methanone; 2-methoxy-1-[4-quinolin-3-yl-phenoxy)-piperidin-1-yl]-ethanone; [4-(4-quinolin-3-yl-phenoxy)-piperidin-1-yl]-(tetrahydropyran-2-yl)-methanone; [4-(4-quinolin-3-yl-phenoxyl)-piperidin-1-yl]-(tetrahydrofuran-3-yl)-methanone; (R)-2-methoxy-1-[4-(4-quinolin-3-yl-phenoxy)-piperidin-1-yl]-propan-1-one; (S)-2-methoxy-1-[4-(4-quinolin-3-yl-phenoxy)-piperidin-1-yl]-propan-1-one; 2-hydroxy-1-[4-(4-quinolin-3-yl-phenoxy)-piperidin-1-yl]-ethanone; [4-(4-quinolin-3-yl-phenoxy)-piperidin-1-yl]-(tetrahydropyran-2-yl)-methanone; 1-[4-(4-quinolin-3-yl-phenoxy)-piperidin-1-yl]-ethanone; 2-methyl-1-[4-(4-quinolin-3-yl-phenoxy)-piperidin-1-yl]-propan-1-one; 2,2-dimethyl-1-[4-(4-quinolin-3-yl-phenoxy)-piperidin-1-yl]-propan-1-one; (2-methyltetrahydrofuran-2-yl)-[4-(4-quinolin-3-yl-phenoxy)-piperidin-1-yl]-methanone; (2-methyl-1,3-dioxolan-2-yl)-[4-(4-quinolin-3-yl-phenoxy)-piperidin-1-yl]-methanone; 2-methanesulfonyl-1-[4-(4-quinolin-3-yl-phenoxy)piperidin-1-yl]-ethanone; (1,1-dioxidotetrahydrothiophen-2-yl)(4-(4-(quinolin-3-yl)phenoxy)piperidin-1-yl)methanone; (3,3-difluorocyclobutyl)-[4-(4-quinolin-3-yl-phenoxy)-piperidin-1-yl]-methanone; (R)-5-[4-(4-quinolin-3-yl-phenoxy)-piperidine-1-carbonyl]-dihydrofuran-2-one; (3-methylfuran-2-yl)-[4-(4-quinolin-3-yl-phenoxy)-piperidin-1-yl]-methanone; (3,5-dimethylfuran-2-yl)-[4-(4-quinolin-3-yl-phenoxy)-piperidin-1-yl]-methanone; oxazol-2-yl-[4-(4-quinolin-3-yl-phenoxy)piperidin-1-yl]-methanone; isoxazol-3-yl-[4-(4-quinolin-3-yl-phenoxy)-piperidin-1-yl]-methanone; isothiazol-3-yl-[4-(4-quinolin-3-yl-phenoxy)-piperidin-1-yl]-methanone; [4-(4-quinolin-3-yl-phenoxy)-piperidin-1-yl]-(tetrahydrofuran-2-yl)-methanone; phenyl-[4-(4-quinolin-3-yl-phenoxy)-piperidin-1-yl]-methanone; (2,5-dimethylphenyl)-[4-(4-quinolin-3-yl-phenoxy)-piperidin-1-yl]-methanone; [3-(1H-imidazol-2-yl)-phenyl]-[4-(4-quinolin-3-yl-phenoxy)-piperidin-1-yl]-methanone; [3-(1H-benzimidazol-2-yl)-phenyl]-[4-(4-quinolin-3-yl-phenoxy)-piperidin-1-yl]-methanone; N-methoxy-4-[4-(8-methoxy-7-quinolyl)phenoxy]piperidine-1-carboxamide; 1-propionylpiperidine-4-carboxylic acid methyl-(4-quinolin-7-yl-phenyl)-amide; 1-propionylpiperidine-4-carboxylic acid (4-isoquinolin-6-yl-phenyl)-methylamide; oxo-[4-(4-quinolin-3-yl-phenoxy)-piperidin-1-yl]-acetaldehyde; ((2R,3S)/(2S,3R)-3-methyltetrahydrofuran-2-yl)-[4-(4-quinolin-3-yl-phenoxy)piperidin-1-yl]-methanone; ((2R,3S,5R)/(2S,3R,5S)-3,5-dimethyltetrahydrofuran-2-yl)-[4-(4-quinolin-3-yl-phenoxy)-piperidin-1-yl]-methanone; ((2R,3S,5R)/(2S,3R,5S)-3,5-dimethyl-tetrahydrofuran-2-yl)-[4-(4-quinolin-3-yl-phenoxy)-piperidin-1-yl]-methanone; 3-[4-(1-methanesulfonyl-piperidin-4-yloxy)-phenyl]-quinoline; (4,4-difluorotetrahydrofuran-2-yl)-[4-(4-quinolin-3-yl-phenoxy)-piperidin-1-yl]-methanone; (4,4-difluorotetrahydrofuran-2-yl)-{4-[4-(8-methyl-quinolin-7-yl)-phenoxy]-piperidin-1-yl}-methanone; (4,4-difluorotetrahydrofuran-2-yl)-{4-[4-(1-methylisoquinolin-6-yl)-phenoxy]-piperidin-1-yl}-methanone; 5-[4-(4-quinolin-3-yl-phenoxy)-piperidine-1-carbonyl]-dihydrofuran-3-one; 1-{4-[4-(8-ethoxyquinolin-7-yl)-phenoxy]-piperidin-1-yl}-propan-1-one; cyclopropyl-{4-[4-(8-ethoxyquinolin-7-yl)-phenoxy]-piperidin-1-yl}-methanone; 1-{4-[4-(8-isopropoxy-quinolin-7-yl)-phenoxy]-piperidin-1-yl}-propan-1-one; cyclopropyl-{4-[4-(8-isopropoxy-quinolin-7-yl)-phenoxy]-piperidin-1-yl}-methanone; 1-(4-{4-[8-(2-morpholin-4-yl-ethoxy)quinolin-7-yl]-phenoxy}-piperidin-1-yl)-propan-1-one; cyclopropyl-(4-{4-[8-(2-morpholin-4-yl-ethoxy)-quinolin-7-yl]-phenoxyl}-piperidin-1-yl)-methanone; 1-(4-{4-[8-(2-pyrrolidin-1-yl-ethoxy)-quinolin-7-yl]-phenoxy}-piperidin-1-yl)-propan-1-one; cyclopropyl-(4-{4-[8-(2-pyrrolidin-1-yl-ethoxy)-quinolin-7-yl]-phenoxy}-piperidin-1-yl)-methanone; 1-(4-{4-[8-(3-pyrrolidin-1-yl-propoxy)-quinolin-7-yl]-phenoxy}-piperidin-1-yl)propan-1-one; cyclopropyl-(4-{4-[8-(3-pyrrolidin-1-yl-propoxy)-quinolin-7-yl]-phenoxy}-piperidin-1-yl)-methanone; 1-[4-[4-[8-[2-(4-methylpiperazin-1-yl)ethoxy]-7-quinolyl]phenoxy]-1-piperidyl]propan-1-one; 1-[4-[4-[8-(2-methoxyethoxy)-7-quinolyl]phenoxy]-1-piperidyl]propan-1-one; 1-[4-[4-[8-(3-methoxypropoxy)-7-quinolyl]phenoxy]-1-piperidyl]propan-1-one; {4-[4-(8-isopropoxyquinolin-7-yl)-phenoxy]-piperidin-1-yl}-(R)-tetrahydrofuran-2-yl-methanone; {4-[4-(8-ethoxyquinolin-7-yl)-phenoxy]-piperidin-1-yl}-(R)-tetrahydrofuran-2-yl-methanone; (4-{4-[8-(2-morpholin-4-yl-ethoxy)-quinolin-7-yl]-phenoxy}-piperidin-1-yl)-(R)-tetrahydrofuran-2-yl-methanone; (4-{4-[8-(2-pyrrolidin-1-yl-ethoxy)-quinolin-7-yl]-phenoxy}-piperidin-1-yl)-(R)-tetrahydrofuran-2-ylmethanone; (4-{4-[8-(3-pyrrolidin-1-yl-propoxy)-quinolin-7-yl]-phenoxy}-piperidin-1-yl)-(R)-tetrahydrofuran-2-ylmethanone; [4-[4-[8-[2-(4-methylpiperazin-1-yl)ethoxy]-7-quinolyl]phenoxy]-1-piperidyl]-[(2R)-tetrahydrofuran-2-yl]methanone; [4-[4-[8-(2-methoxyethoxy)-7-quinolyl]phenoxy]-1-piperidyl]-[(2R)-tetrahydrofuran-2-yl]methanone; [4-[4-[8-(3-methoxypropoxy)-7-quinolyl]phenoxy]-1-piperidyl]-[(2R)-tetrahydrofuran-2-yl]methanone; 1-{4-[4-(8-hydroxyquinolin-7-yl)-phenoxy]-piperidin-1-yl}-propan-1-one; cyclopropyl-{4-[4-(8-hydroxyquinolin-7-yl)-phenoxy]-piperidin-1-yl}-methanone; {4-[4-(8-hydroxyquinolin-7-yl)-phenoxy]-piperidin-1-yl}-(R)-tetrahydrofuran-2-yl-methanone; 1-[4-(2-chloro-4-quinolin-3-yl-phenoxy)-piperidin-1-yl]-propan-1-one; 1-[4-(2-chloro-4-quinolin-3-yl-phenoxy)-piperidin-1-yl]-2-methyl-propan-1-one; [4-(2-chloro-4-quinolin-3-yl-phenoxy)-piperidin-1-yl]-cyclopropyl-methanone; 1-[4-(2-chloro-4-quinolin-7-yl-phenoxy)-piperidin-1-yl]-propan-1-one; 1-[4-(2-chloro-4-quinolin-7-yl-phenoxy)-piperidin-1-yl]-2-methylpropan-1-one; 1-[4-(2-methoxy-4-quinolin-3-yl-phenoxy)-piperidin-1-yl]-propan-1-one; 1-[4-(2-methoxy-4-quinolin-3-yl-phenoxy)-piperidin-1-yl]-2-methyl-propan-1-one; cyclopropyl-[4-(2-methoxy-4-quinolin-3-yl-phenoxy)-piperidin-1-yl]-methanone; 1-[4-(2-methoxy-4-quinolin-7-yl-phenoxy)piperidin-1-yl]-propan-1-one; 1-[4-(3-fluoro-4-quinolin-3-yl-phenoxy)-piperidin-1-yl]-propan-1-one; 1-[4-(3-fluoro-4-quinolin-3-yl-phenoxy)-piperidin-1-yl]-2-methylpropan-1-one; cyclopropyl-[4-(3-fluoro-4-quinolin-3-ylphenoxy)-piperidin-1-yl]-methanone; 1-[4-(3-chloro-4-quinolin-3-yl-phenoxy)-piperidin-1-yl]-propan-1-one; 1-[4-(3-chloro-4-quinolin-3-yl-phenoxy)-piperidin-1-yl]-2-methylpropan-1-one; [4-(3-chloro-4-quinolin-3-yl-phenoxy)-piperidin-1-yl]-cyclopropylmethanone; 2-methyl-1-[4-(3-methyl-4-quinolin-3-yl-phenoxy)-piperidin-1-yl]-propan-1-one; 1-[4-(3-methyl-4-quinolin-3-yl-phenoxy)-piperidin-1-yl]-propan-1-one; 4-(3-methyl-4-quinolin-3-yl-phenoxy)-piperidine-1-carboxylic acid, methyl ester; 1-[4-(3-methoxy-4-quinolin-3-yl-phenoxy)-piperidin-1-yl]-propan-1-one; 1-[4-(3-methoxy-4-quinolin-3-yl-phenoxy)-piperidin-1-yl]-2-methyl-propan-1-one; cyclopropyl-[4-(3-methoxy-4-quinolin-3-yl-phenoxy)-piperidin-1-yl]-methanone; 1-[4-(2-methyl-4-quinolin-3-yl-phenoxy)-piperidin-1-yl]-propan-1-one; 2-methyl-1-[4-(2-methyl-4-quinolin-3-yl-phenoxy)-piperidin-1-yl]-propan-1-one; cyclopropyl-[4-(2-methyl-4-quinolin-3-yl-phenoxy)-piperidin-1-yl]-methanone; 3-oxo-3-[4-(4-quinolin-3-yl-phenoxy)-piperidin-1-yl]-propionitrile; 1-{4-[2-fluoro-4-(8-methoxyquinolin-7-yl)-phenoxy]-piperidin-1-yl}-propan-1- one; cyclopropyl-{4-[2-fluoro-4-(8-methoxyquinolin-7-yl)-phenoxy]-piperidin-1-yl}-methanone; {4-[2-fluoro-4-(8-methoxy-quinolin-7-yl)-phenoxy]piperidin-1-yl}-(R)-tetrahydrofuran-2-yl-methanone; {4-[4-(8-chloroquinolin-7-yl)-2-fluoro-phenoxy]-piperidin-1-yl}-cyclopropylmethanone; {4-[4-(8-chloroquinolin-7-yl)-2-fluoro-phenoxy]-piperidin-1-yl}-(R)-tetrahydrofuran-2-yl-methanone; 1-{4-[4-(8-chloroquinolin-7-yl)-2-fluorophenoxy]-piperidin-1-yl}-propan-1-one; 1-{4-[2-fluoro-4-(8-methylquinolin-7-yl)-phenoxy]-piperidin-1-yl}-propan-1-one; {4-[2-fluoro-4-(8-methylquinolin-7-yl)-phenoxy]-piperidin-1-yl}-(R)-tetrahydrofuran-2-yl-methanone; cyclopropyl-{4-[2-fluoro-4-(8-methylquinolin-7-yl)-phenoxy]-piperidin-1-yl}-methanone; 1-{4-[2-fluoro-4-(4-methylquinolin-3-yl)-phenoxy]-piperidin-1-yl}-propan-1-one; cyclopropyl-{4-[2-fluoro-4-(4-methylquinolin-3-yl)-phenoxy]-piperidin-1-yl}-methanone; {4-[2-fluoro-4-(4-methyl-quinolin-3-yl)-phenoxy]-piperidin-1-yl}-(R)-tetrahydrofuran-2-yl-methanone; 1-{4-[4-(4-aminoquinolin-3-yl)-phenoxy]-piperidin-1-yl}-propan-1-one; 1-(4-(4-(4-(dimethylamino)quinolin-3-yl)phenoxy)piperidin-1-yl)propan-1-one; {4-[4-(4-dimethylaminoquinolin-3-yl)-phenoxy]-piperidin-1-yl}-(R)-tetrahydrofuran-2-yl-methanone; {4-[4-(4-amino-quinolin-3-yl)-phenoxy]-piperidin-1-yl}-(R)-tetrahydrofuran-2-yl-methanone; 1-{4-[4-(4-methylaminoquinolin-3-yl)-phenoxy]-piperidin-1-yl}-propan-1-one; {4-[4-(4-methylaminoquinolin-3-yl)-phenoxy]-piperidin-1-yl}-(R)-tetrahydrofuran-2-yl-methanone; 1-{4-[4-(4-morpholin-4-yl-quinolin-3-yl)-phenoxy]-piperidin-1-yl}-propan-1-one; {4-[4-(4-morpholin-4-yl-quinolin-3-yl)-phenoxy]-piperidin-1-yl}-(R)-tetrahydrofuran-2-yl-methanone; 1-(4-{4-[4-(4-methylpiperazin-1-yl)-quinolin-3-yl]-phenoxy}-piperidin-1-yl)-propan-1-one; (4-{4-[4-(4-methylpiperazin-1-yl)-quinolin-3-yl]-phenoxy}-piperidin-1-yl)-(R)-tetrahydrofuran-2-yl-methanone; 3-[4-(4-quinolin-3-yl-phenoxy)-piperidine-1-carbonyl]-oxazolidin-2-one; 1-[4-(4-quinolin-3-yl-phenoxy)-piperidin-1-yl]-butane-1,3-dione; 1-[4-(4-quinolin-3-yl-phenoxy)-piperidine-1-carbonyl]-pyrrolidin-2-one; 1-[4-(4-[1,8]naphthyridin-3-yl-phenoxy)-piperidin-1-yl]-propan-1-one; 1-{4-[4-(2-methylquinolin-7-yl)-phenoxy]-piperidin-1-yl}-propan-1-one; {4-[4-(4-chloroquinolin-7-yl)-phenoxy]-piperidin-1-yl}-(R)-tetrahydrofuran-2-yl-methanone; {4-[4-(4-chloroquinolin-7-yl)-phenoxy]-piperidin-1-yl})-cyclopropylmethanone; 1-{4-[4-(4-chloroquinolin-7-yl)-phenoxy]-piperidin-1-yl}-propan-1-one; {4-[4-(8-chloroquinolin-7-yl)-phenoxy]-piperidin-1-yl}-(R)-tetrahydrofuran-2-yl-methanone; 1-{4-[4-(8-chloroquinolin-7-yl)-phenoxy]-piperidin-1-yl}-propan-1-one; {4-[4-(7-methoxyquinolin-3-yl)-phenoxy]-piperidin-1-yl}-(R)-tetrahydrofuran-2-yl-methanone; {4-[4-(3-chloroquinolin-7-yl)-phenoxy]-piperidin-1-yl}-(R)-tetrahydrofuran-2-yl-methanone; 1-{4-[4-(3-chloroquinolin-7-yl)-phenoxy]-piperidin-1-yl}-propan-1-one; {4-[4-(8-methoxyquinolin-7-yl)-phenoxy]-piperidin-1-yl})-(R)-tetrahydrofuran-2-yl-methanone; 1-{4-[4-(8-methoxyquinolin-7-yl)-phenoxy]-piperidin-1-yl}-propan-1-one; cyclopropyl-{4-[4-(8-methoxyquinolin-7-yl)-phenoxy]-piperidin-1-yl}-methanone; {4-[4-(6-methylquinolin-7-yl)-phenoxy]-piperidin-1-yl}-(R)-tetrahydrofuran-2-yl-methanone; 1-{4-[4-(6-methylquinolin-7-yl)-phenoxy]-piperidin-1-yl}-propan-1-one; 7-[4-(1-propionyl-piperidin-4-yloxy)-phenyl]-quinoline-3-carbonitrile; 7-{4-[1-((R)-tetrahydrofuran-2-carbonyl)-piperidin-4-yloxy]-phenyl}-quinoline-3-carbonitrile; 7-[4-(1-cyclopropanecarbonyl-piperidin-4-yloxy)-phenyl]-quinoline-3-carbonitrile; 1-{4-[4-(3-methylquinolin-7-yl)-phenoxy]-piperidin-1-yl}-propan-1-one; {4-[4-(3-methyl-quinolin-7-yl)-phenoxy]-piperidin-1-yl}-(R)-tetrahydrofuran-2-yl-methanone; cyclopropyl-{4-[4-(3-methylquinolin-7-yl)-phenoxy]-piperidin-1-yl}-methanone; (1-hydroxycyclopropyl)-{4-[4-(8-methoxyquinolin-7-yl)-phenoxy]-piperidin-1-yl}-methanone; {4-[4-(8-methylquinolin-7-yl)-phenoxy]-piperidin-1-yl}-(1-trifluoromethylcyclopropyl)-methanone; (1-aminocyclopropyl)-{4-[4-(8-methylquinolin-7-yl)-phenoxy]-piperidin-1-yl}-methanone; 1-{4-[4-(8-methylquinolin-7-yl)-phenoxy]-piperidine-1-carbonyl]) cyclopropanecarbonitrile; (1-methylcyclopropyl)-{4-[4-(8-methylquinolin-7-yl)-phenoxy]-piperidin-1-yl}-methanone; ((S)-2,2-dimethylcyclopropyl)-{4-[4-(8-methylquinolin-7-yl)-phenoxy]-piperidin-1-yl}-methanone; (2,2-dimethylcyclopropyl)-{4-[4-(8-methylquinolin-7-yl)-phenoxy]-piperidin-1-yl}-methanone; [4-[4-[8-(4-methylpiperazin-1-yl)-7-quinolyl]phenoxy]-1-piperidyl]-[(2R)-tetrahydrofuran-2-yl]methanone; [4-[4-[8-amino-7-quinolyl)phenoxy]-1-piperidyl]-[(2R)-tetrahydrofuran-2-yl]methanone; {4-[4-(8-methylaminoquinolin-7-yl)-phenoxy]-piperidin-1-yl}-(R)-tetrahydrofuran-2-yl-methanone; 1-{4-[4-(8-methylaminoquinolin-7-yl)-phenoxy]-piperidin-1-yl}-propan-1-one; (4-{4-[8-(2-methoxyethyl-amino)-quinolin-7-yl]-phenoxy}-piperidin-1-yl)-(R)-tetrahydrofuran-2-yl-methanone; 1-(4-{4-[8-(2-methoxyethylamino)-quinolin-7-yl]-phenoxy}-piperidin-1-yl)-propan-1-one; (4-{4-[8-(2-dimethylamino-ethylamino)-quinolin-7-yl]-phenoxy}-piperidin-1-yl)-(R)-tetrahydrofuran-2-yl-methanone; 7-[4-(1-propionyl-piperidin-4-yloxy)-phenyl]-quinoline-8-carbonitrile; [4-[4-[8-(dimethylamino)-7-quinolyl]phenoxy]-1-piperidyl]-[(2R)-tetrahydrofuran-2-yl]methanone; 1-{4-[4-(8-dimethylamino-quinolin-7-yl)-phenoxy]-piperidin-1-yl}-propan-1-one; cyclopropyl-{4-[4-(8-dimethylaminoquinolin-7-yl)-phenoxy]-piperidin-1-yl}-methanone; (4-{4-[8-(2-pyrrolidin-1-yl-ethylamino)-quinolin-7-yl]-phenoxy}-piperidin-1-yl)-(R)-tetrahydrofuran-2-yl-methanone; 1-(4-{4-[8-(2-pyrrolidin-1-yl-ethylamino)-quinolin-7-yl]-phenoxy}-piperidin-1-yl)-propan-1-one; 7-[4-[[1-[(2R)-tetrahydrofuran-2-carbonyl]-4 piperidyl]oxy]phenyl]quinoline-8-carboxamide; 7-[4-(1-propionyl-piperidin-4-yloxy)-phenyl]-quinoline-8-carboxylic acid amide; cyclopropyl(3-(4-(quinolin-3-yl)phenoxy)azetidin-1-yl)methanone; 1-(4-(4-(5-methylquinolin-7-yl)phenoxy)-piperidin-1-yl)propan-1-one; cyclopropyl(4-(4-(5-methylquinolin-7-yl)phenoxy)piperidin-1-yl)methanone; (R)-(4-(4-(5-methylquinolin-7-yl)phenoxy)piperidin-1-yl)(tetrahydrofuran-2-yl)methanone; 2,2,2-trifluoro-1-{4-[4-(8-methylquinolin-7-yl)-phenoxy]-piperidin-1-yl}-ethanone; 2,2-difluoro-1-{4-[4-(8-methylquinolin-7-yl)-phenoxy]-piperidin-1-yl}-propan-1-one; 2-fluoro-1-{4-[4-(8-methylquinolin-7-yl)-phenoxy]-piperidin-1-yl}-propan-1-one; 1-{4-[4-(3-chloroisoquinolin-6-yl)-phenoxy]-piperidin-1-yl}-propan-1-one; {4-[4-(3-chloroisoquinolin-6-yl)-phenoxy]-piperidin-1-yl}-cyclopropyl-methanone; 1-{4-[4-(3-methoxyisoquinolin-6-yl)-phenoxy]-piperidin-1-yl}-propan-1-one; cyclopropyl-{4-[4-(3-methoxyisoquinolin-6-yl)-phenoxy]-piperidin-1-yl})-methanone; cyclobutyl-{4-[4-(3-methoxyisoquinolin-6-yl)-phenoxy]-piperidin-1-yl}-methanone; {4-[4-(3-methoxyisoquinolin-6-yl)-phenoxy]-piperidin-1-yl}-(R)-tetrahydrofuran-2-yl-methanone; 1-{4-[4-(1-chloroisoquinolin-6-yl)-phenoxy]-piperidin-1-yl}-propan-1-one; {4-[4-(1-chloroisoquinolin-6-yl)-phenoxy]-piperidin-1-yl}-cyclopropylmethanone; 1-{4-[4-(3-dimethylaminoisoquinolin-6-yl)-phenoxy]-piperidin-1-yl}-propan-1-one; 1-{4-[4-(3-aminoisoquinolin-6-yl)-phenoxy]-piperidin-1-yl}-propan-1-one; {4-[4-(3-aminoisoquinolin-6-yl)-phenoxy]-piperidin-1-yl}-cyclopropyl-methanone; 1-{4-[4-(1-methylisoquinolin-6-yl)-phenoxy]-piperidin-1-yl}-propan-1-one; {4-[4-(1-chloroisoquinolin-6-yl)-phenoxy]-piperidin-1-yl}-cyclobutyl-methanone; {4-[4-(1-chloroisoquinolin-6-yl)-phenoxy]-piperidin-1-yl}-(R)-tetrahydro-furan-2-yl-methanone; 1-{4-[4-(3-methylisoquinolin-6-yl)-phenoxy]-piperidin-1-yl}-propan-1-one; {4-[4-(1-methylisoquinolin-6-yl)-phenoxy]-piperidin-1-yl}-(R)-tetrahydro-furan-2-yl-methanone; {4-[4-(1-methoxyisoquinolin-6-yl)-phenoxy]-piperidin-1-yl}-(R)-tetrahydrofuran-2-yl-methanone; 1-{4-[4-(1-methoxyisoquinolin-6-yl)-phenoxy]-piperidin-1-yl}-propan-1-one; cyclobutyl-{4-[4-(1-methoxyisoquinolin-6-yl)-phenoxy]-piperidin-1-yl}-methanone; cyclopropyl-{4-[4-(1-methoxyisoquinolin-6-yl)-phenoxy]-piperidin-1-yl}-methanone; {4-[4-(3-aminoisoquinolin-6-yl)-phenoxy]-piperidin-1-yl}-(R)-tetrahydrofuran-2-yl-methanone; {4-[4-(3-methylisoquinolin-6-yl)-phenoxy]-piperidin-1-yl}-(R)-tetrahydrofuran-2-yl-methanone; {4-[4-(1-ethylisoquinolin-6-yl)-phenoxy]-piperidin-1-yl}-(R)-tetrahydrofuran-2-yl-methanone; 1-{4-[4-(1-cyclopropylisoquinolin-6-yl)-phenoxy]-piperidin-1-yl}-propan-1-one; {4-[4-(1-cyclopropyl-isoquinolin-6-yl)-phenoxy]-piperidin-1-yl}-(R)-tetrahydrofuran-2-yl-methanone; 1-{4-[4-(7-methoxy-6-methylquinolin-3-yl)-phenoxy]-piperidin-1-yl}-propan-1-one; cyclopropyl-{4-[4-(7-methoxy-6-methylquinolin-3-yl)-phenoxy]-piperidin-1-yl}-methanone; {4-[4-(7-methoxy-6-methylquinolin-3-yl)-phenoxy]-piperidin-1-yl}-(R)-tetrahydrofuran-2-yl-methanone; 1-{4-[4-(6-fluoro-7-methoxyquinolin-3-yl)-phenoxy]-piperidin-1-yl}-propan-1-one; cyclopropyl-{4-[4-(6-fluoro-7-methoxyquinolin-3-yl)-phenoxy]-piperidin-1-yl}-methanone; {4-[4-(6-fluoro-7-methoxyquinolin-3-yl)-phenoxy]-piperidin-1-yl}-(R)-tetrahydrofuran-2-yl-methanone; 1-{4-[4-(6-chloro-7-methoxyquinolin-3-yl)-phenoxy]-piperidin-1-yl}-propan-1-one; {4-[4-(6-chloro-7-methoxyquinolin-3-yl)-phenoxy]-piperidin-1-yl}-cyclopropylmethanone; {4-[4-(6-chloro-7-methoxyquinolin-3-yl)-phenoxy]-piperidin-1-yl}-(R)-tetrahydrofuran-2-yl-methanone; {4-[4-(6-methoxyquinolin-3-yl)-phenoxy]-piperidin-1-yl}-(R)-tetrahydrofuran-2-yl-methanone; {4-[4-(3-isopropoxy-isoquinolin-6-yl)-phenoxy]-piperidin-1-yl})-(R)-tetrahydrofuran-2-yl-methanone; {4-[4-(1-morpholin-4-yl-isoquinolin-6-yl)-phenoxy]-piperidin-1-yl}-(R)-tetrahydrofuran-2-yl-methanone; {4-[4-(1-dimethylaminoisoquinolin-6-yl)-phenoxy]-piperidin-1-yl}-(R)-tetrahydrofuran-2-yl methananone; {4-[4-(1-aminoisoquinolin-6-yl)-phenoxy]-piperidin-1-yl}-(R)-tetrahydrofuran-2-yl-methanone; {4-[4-(1-dimethylaminoisoquinolin-6-yl)-phenoxy]-piperidin-1-yl}-(R)-tetrahydrofuran-2-yl-methanone; {4-[4-(1-methylaminoisoquinolin-6-yl)-phenoxy]-piperidin-1-yl}-(R)-tetrahydrofuran-2-yl-methanone; 1-{4-[4-(4-methylisoquinolin-6-yl)-phenoxy]-piperidin-1-yl}-propan-1-one; cyclopropyl-{4-[4-(4-methylisoquinolin-6-yl)-phenoxy]-piperidin-1-yl}-methanone; {4-[4-(4-methylisoquinolin-6-yl)-phenoxy]-piperidin-1-yl}-(R)-tetrahydrofuran-2-yl-methanone; 1-{4-[4-(5-methylquinolin-3-yl)-phenoxy]-piperidin-1-yl})-propan-1-one; cyclopropyl-{4-[4-(5-methylquinolin-3-yl)-phenoxy]-piperidin-1-yl}-methanone; {4-[4-(5-methylquinolin-3-yl)-phenoxy]-piperidin-1-yl}-(R)-tetrahydrofuran-2-yl-methanone; 1-{4-[4-(5-methoxyquinolin-3-yl)-phenoxy]-piperidin-1-yl}-propan-1-one; cyclopropyl-{4-[4-(5-methoxy-quinolin-3-yl)-phenoxy]-piperidin-1-yl}-methanone; {4-[4-(5-methoxyquinolin-3-yl)-phenoxy]-piperidin-1-yl}-(R)-tetrahydrofuran-2-yl-methanone; cyclopropyl-[4-(4-isoquinolin-6-yl-phenoxy)-piperidin-1-yl]-methanone; [4-[4-(6-isoquinolyl)phenoxy]-1-piperidyl]-[(2R)-tetrahydrofuran-2-yl]methanone; {4-[4-(5-methylisoquinolin-6-yl)-phenoxy]-piperidin-1-yl}-(R)-tetrahydrofuran-2-yl-methanone; 1-[4-[4-(1,4-dimethyl-6-isoquinolyl)phenoxy]-1-piperidyl]propan-1-one; cyclopropyl-[4-[4-(1,4-dimethyl-6-isoquinolyl)phenoxy]-1-piperidyl]methanone; [4-[4-(1,4-dimethyl-6-isoquin-olyl)phenoxy]-1-piperidyl]-[(2R)-tetrahydrofuran-2-yl]methanone; 1-[4-[4-(1,5-dimethyl-6-isoquinolyl)phenoxy]-1-piperidyl]propan-1-one; cyclopropyl-[4-[4-(1,5-dimethyl-6-isoquinolyl)-phenoxy]-1-piperidyl]methanone; [4-[4-(1,5-dimethyl-6-isoquinolyl)phenoxy]-1-piperidyl]-[(2R)-tetrahydrofuran-2-yl]methanone; [4-[4-(8-cyclopropyl-7-quinolyl)phenoxy]-1-piperidyl]-[(2R)-tetrahydrofuran-2-yl]methanone; {4-[4-(3-ethylisoquinolin-6-yl)-phenoxy]-piperidin-1-yl}-(R)-tetrahydrofuran-2-yl-methanone; cyclopropyl-{4-[4-(7-fluoroquinolin-3-yl)-phenoxy]-piperidin-1-yl}-methanone; 1-{4-[4-(7-fluoroquinolin-3-yl)-phenoxy]-piperidin-1-yl}-propan-1-one; {4-[4-(7-fluoroquinolin-3-yl)-phenoxy]-piperidin-1-yl}-(R)-tetrahydrofuran-2-yl-methanone; {4-[4-(3-cyclopropylisoquinolin-6-yl)-phenoxy]-piperidin-1-yl}-(R)-tetrahydrofuran-2-yl-methanone; cyclopropyl-{4-[4-(1-methylisoquinolin-6-yl)-phenoxy]-piperidin-1-yl}-methanone; {4-[4-(7-methylquinolin-3-yl)-phenoxy]-piperidin-1-yl}-(R)-tetrahydrofuran-2-yl-methanone; 1-{4-[4-(6-methyl-quinolin-3-yl)-phenoxy]-piperidin-1-yl}-propan-1-one; cyclopropyl-{4-[4-(6-methyl-quinolin-3-yl)-phenoxy]-piperidin-1-yl}-methanone; {4-[4-(6-methylquinolin-3-yl)-phenoxy]-piperidin-1-yl}-(R)-tetrahydrofuran-2-yl-methanone; 1-{4-[4-(8-methylquinolin-3-yl)-phenoxy]-piperidin-1-yl}-propan-1-one; cyclopropyl-{4-[4-(8-methylquinolin-3-yl)-phenoxy]-piperidin-1-yl}-methanone; {4-[4-(8-methylquinolin-3-yl)-phenoxy]-piperidin-1-yl}-(R)-tetrahydrofuran-2-yl-methanone; 1-[4-(3-quinolin-3-yl-phenoxy)-piperidin-1-yl]-propan-1-one; cyclopropyl-[4-(3-quinolin-3-yl-phenoxy)-piperidin-1-yl]-methanone; 1-(4-((4-(quinolin-7-yl)phenyl)thio)piperidin-1-yl)propan-1-one; 1-(4-((4-(isoquinolin-6-yl)phenyl)thio)piperidin-1-yl)propan-1-one; 1-(4-((4-(quinolin-3-yl)phenyl)thio)piperidin-1-yl)propan-1-one; 1-(4-((4-(isoquinolin-6-yl)phenyl)thio)piperidin-1-yl)propan-1-one; 1-(4-((4-(isoquinolin-6-yl)phenyl)thio)piperidin-1-yl)-2-methylpropan-1-one; and 2-methyl-1-(4-((4-(quinolin-3-yl)phenyl)thio)piperidin-1-yl)propan-1-one; and salts thereof, e.g., pharmaceutically acceptable salts thereof.

Additional compounds according to Formula III may include, for example: N-ethyl-4-[4-(2-hydroxy-8-methyl-7-quinolyl)phenoxy]piperidine-1-carboxamide; 4-[4-(8-methyl-7-quinolyl)phenoxy]-N-(2-pyrrolidin-1-ylethyl)piperidine-1-carboxamide; 4-[4-(8-methyl-7-quinolyl)phenoxy]-N-(2-morpholinoethyl)piperidine-1-carboxamide; (4-isopropylpiperazin-1-yl)-[4-[4-(8-methyl-7-quinolyl)phenoxy]-1-piperidyl]methanone; (4-methylpiperazin-1-yl)-[4-[4-(8-methyl-7-quinolyl)phenoxy]-1-piperidyl]methanone; [4-[4-(8-methyl-7-quinolyl)phenoxy]-1-piperidyl]-(4-morpholino-1-piperidyl)methanone; (4-ethylpiperazin-1-yl)-[4-[4-(8-methyl-7-quinolyl)phenoxy]-1-piperidyl]methanone; N-(cyclopropylmethyl)-4-[4-(8-methyl-7-quinolyl)phenoxy]piperidine-1-carboxamide; N-isobutyl-4-[4-(8-methyl-7-quinolyl)phenoxy]piperidine-1-carboxamide; N-(2-methoxyethyl)-4-[4-(8-methyl-7-quinolyl)phenoxy]piperidine-1-carboxamide; N-isopropoxy-4-[4-(8-methyl-7-quinolyl)phenoxy]piperidine-1- carboxamide; N-isobutoxy-4-[4-(8-methyl-7-quinolyl)phenoxy]piperidine-1-carboxamide; N-(2-dimethylaminoethyl)-4-[4-(8-methyl-7-quinolyl)phenoxy]piperidine-1-carboxamide; N-[2-(1H-imidazol-4-yl)ethyl]-4-[4-(8-methyl-7-quinolyl)phenoxy]piperidine-1-carboxamide; 4-[4-(8-methyl-7-quinolyl)phenoxy]-N-tetrahydropyran-4-yl-piperidine-1-carboxamide; N-cyclobutyl-4-[4-(8-methyl-7-quinolyl)phenoxy]-piperidine-1-carboxamide; 4-[4-(8-methyl-7-quinolyl)phenoxy]piperidine-1-carbohydroxamic acid; [4-[4-(8-methyl-7-quinolyl)phenoxy]-1-piperidyl]-(oxazinan-2-yl)methanone; N-(cyclobutylmethyl)-4-[4-(8-methyl-7-quinolyl)phenoxy]piperidine-1-carboxamide; azepan-1-yl-[4-[4-(8-methyl-7-quinolyl)phenoxy]-1-piperidyl]methanone; 4-[4-(8-methyl-7-quinolyl)phenoxy]-N-propoxy-piperidine-1-carboxamide; N-ethyl-4-[4-(1-methyl-6-isoquinolyl)phenoxy]piperidine-1-carboxamide; 4-[4-(1-methyl-6-isoquinolyl)phenoxy]-N-propyl-piperidine-1-carboxamide; N-isobutyl-4-[4-(1-methyl-6-isoquinolyl)phenoxy]piperidine-1-carboxamide; 4-[4-(1-methyl-6-iso-quinolyl)phenoxy]piperidine-1-carboxamide; N-(cyclopropylmethyl)-4-[4-(1-methyl-6-isoquinolyl)phenoxy]piperidine-1-carboxamide; N-isopropoxy-4-[4-(1-methyl-6-isoquinolyl)phenoxy]-piperidine-1-carboxamide; 4-[4-(1-methyl-6-isoquinolyl)phenoxy]-N-propoxypiperidine-1-carboxamide; 4-[4-(1-methyl-6-isoquinolyl)phenoxy]piperidine-1-carbohydroxamic acid; N-ethoxy-4-[4-(1-methyl-6-isoquinolyl)phenoxy]piperidine-1-carboxamide; N-ethoxy-4-[4-(4-methyl-3-quinolyl)phenoxy]piperidine-1-carboxamide; N-isopropoxy-4-[4-(4-methyl-3-quinolyl)-phenoxy]piperidine-1-carboxamide; 4-[4-(4-methyl-3-quinolyl)phenoxy]-N-propoxy-piperidine-1-carboxamide; N-isobutyl-4-[4-(4-methyl-3-quinolyl)phenoxy]piperidine-1-carboxamide; 4-[4-(4-methyl-3-quinolyl)phenoxy]-N-propyl-piperidine-1-carboxamide; 2-amino-1-[4-[4-(8-methyl-7-quinolyl)phenoxy]-1-piperidyl]ethanone; (2R)-2-amino-1-[4-[4-(8-methyl-7-quinolyl)phenoxy]-1-piperidyl]propan-1-one 2HCl; (2S)-2-amino-1-[4-[4-(8-methyl-7-quinolyl)phenoxy]-1-piperidyl]propan-1-one 2HCl; 2-(dimethylamino)-1-[4-[4-(8-methyl-7-quinolyl)phenoxy]-1-piperidyl]-ethanone; [(2R)-1-methylpyrrolidin-2-yl]-[4-[4-(8-methyl-7-quinolyl)phenoxy]-1-piperidyl]methanone; [(2S)-1-methylpyrrolidin-2-yl]-[4-[4-(8-methyl-7-quinolyl)phenoxy]-1-piperidyl]methanone; S-isopropyl 4-[4-(8-methyl-7-quinolyl)phenoxy]piperidine-1-carbothioate; 2-amino-2-methyl-1-[4-[4-(8-methyl-7-quinolyl)phenoxy]-1-piperidyl]-propan-1-one; [4-[4-(8-methyl-7-quinolyl)phenoxy]-1-piperidyl]-[(2R)-pyrrolidin-2-yl]methanone; [4-[4-(8-methyl-7-quinolyl)phenoxy]-1-piperidyl]-[(2S)-pyrrolidin-2-yl]methanone; [1-(methylamino)cyclopropyl]-[4-[4-(8-methyl-7-quinolyl)phenoxy]-1-piperidyl]methanone; 3-amino-1-[4-[4-(8-methyl-7-quinolyl)phenoxy]-1-piperidyl]propan-1-one; 2-isopropoxy-1-[4-[4-(8-methyl-7-quinolyl)phenoxy]-1-piperidyl]ethanone; [2-[4-[4-(8-methyl-7-quinolyl)phenoxy]-1-piperidyl]-2-oxo-ethyl]acetate; 2-hydroxy-1-[4-[4-(8-methyl-7-quinolyl)phenoxy]-1-piperidyl]ethanone; (1-aminocyclobutyl)-[4-[4-(8-methyl-7-quinolyl)phenoxy]-1-piperidyl]methanone; 4-[4-(4-methyl-3-quinolyl)phenoxy]-N-methylsulfanyl-piperidine-1-carboxamide; 4-[4-(4-methyl-3-quinolyl)phenoxy]-N-ethylsulfanyl-piperidine-1-carboxamide; 1-[4-[4-(4-methyl-3-quinolyl)phenoxy]piperidine-1-carbonyl]pyrrolidin-2-one; N-ethyl-4-[4-(2-fluoro-8-methyl-7-quinolyl)phenoxy]piperidine-1-carboxamide and salts thereof, e.g., pharmaceutically acceptable salts.

Compounds according to Formula IV may include, for example: 2-methyl-1-[4-(4-quinolin-7-yl-phenoxy)-piperidin-1-yl]-propan-1-one; 1-[4-(4-quinolin-7-yl-phenoxy)-piperidin-1-yl]-propan-1-one; 1-{4-[4-(8-fluoroquinolin-7-yl)-phenoxy]-piperidin-1-yl}-propan-1-one; cyclopropyl-{4-[4-(8-fluoroquinolin-7-yl)-phenoxy]-piperidin-1-yl}-methanone; cyclobutyl-{4-[4-(8-fluoroquinolin-7-yl)-phenoxy]-piperidin-1-yl}-methanone; 1-{4-[4-(8-fluoro-2-methyl-quinolin-7-yl)-phenoxy]-piperidin-1-yl}-propan-1-one; cyclopropyl-{4-[4-(8-fluoro-2-methylquinolin-7-yl)-phenoxy]-piperidin-1-yl}-methanone; cyclobutyl-{4-[4-(8-fluoro-2-methylquinolin-7-yl)-phenoxy]-piperidin-1-yl}-methanone; 1-{4-[4-(8-methylquinolin-7-yl)-phenoxy]-piperidin-1-yl}-propan-1-one; cyclopropyl-{4-[4-(8-methylquinolin-7-yl)-phenoxy]-piperidin-1-yl}-methanone; cyclobutyl-{4-[4-(8-methylquinolin-7-yl)-phenoxy]-piperidin-1-yl}-methanone; {4-[4-(8-chloroquinolin-7-yl)-phenoxy]-piperidin-1-yl}-cyclopropylmethanone; {4-[4-(8-methylquinolin-7-yl)-phenoxy]-piperidin-1-yl}-(R)-tetrahydrofuran-2-yl-methanone; {4-[4-(8-methylquinolin-7-yl)-phenoxy]-piperidin-1-yl}-(S)-tetrahydrofuran-2-yl-methanone; isoxazolidin-2-yl-{4-[4-(8-methylquinolin-7-yl)-phenoxy]-piperidin-1-yl}-methanone; {4-[4-(8-chloroquinolin-7-yl)-phenoxy]-piperidin-1-yl})-isoxazolidin-2-yl-methanone; isoxazolidin-2-yl-{4-[4-(8-methoxyquinolin-7-yl)-phenoxy]-piperidin-1-yl}-methanone; 4-[4-(8-methoxyquinolin-7-yl)-phenoxy]-piperidine-1-carboxylic acid methylamide; 4-[4-(8-methoxyquinolin-7-yl)-phenoxy]-piperidine-1-carboxylic acid ethylamide; N-ethyl-4-[4-(8-methyl-7-quinolyl)phenoxy]piperidine-1-carboxamide; N,N-dimethyl-4-[4-(8-methyl-7-quinolyl)phenoxy]piperidine-1-carboxamide; ethyl 4-[4-(8-methyl-7-quinolyl)phenoxy]piperidine-1-carboxylate; N-methoxy-4-[4-(8-methyl-7-quinolyl)phenoxy]piperidine-1-carboxamide; N-isopropyl-4-[4-(8-methyl-7-quinolyl)phenoxy]piperidine-1-carboxamide; N-ethoxy-4-[4-(8-methyl-7-quinolyl)phenoxy]piperidine-1-carboxamide; [4-[4-(8-methyl-7-quinolyl)phenoxy]-1-piperidyl]-pyrrolidin-1-yl-methanone; N-methyl-4-[4-(8-methyl-7-quinolyl)phenoxy]piperidine-1-carboxamide; 4-[4-(8-methyl-7-quinolyl)phenoxy]-N-propyl-piperidine-1-carboxamide; 4-[4-(8-methyl-7-quinolyl)phenoxy]piperidine-1-carboxamide; [4-[4-(8-methyl-7-quinolyl)phenoxy]-1-piperidyl]-(1-piperidyl)methanone; [4-[4-(8-methyl-7-quinolyl)phenoxy]-1-piperidyl]-morpholinomethanone; N-methoxy-4-[4-(8-methoxy-7-quinolyl)phenoxy]piperidine-1-carboxamide; (4,4-difluorotetrahydrofuran-2-yl)-{4-[4-(8-methyl-quinolin-7-yl)-phenoxy]-piperidin-1-yl}-methanone; 1-{4-[4-(8-ethoxyquinolin-7-yl)-phenoxy]-piperidin-1-yl}-propan-1-one; cyclopropyl-{4-[4-(8-ethoxyquinolin-7-yl)-phenoxy]-piperidin-1-yl}-methanone; 1-{4-[4-(8-isopropoxyquinolin-7-yl)-phenoxy]-piperidin-1-yl}-propan-1-one; cyclopropyl-{4-[4-(8-isopropoxyquinolin-7-yl)-phenoxy]-piperidin-1-yl}-methanone; 1-(4-{4-[8-(2-morpholin-4-yl-ethoxy)-quinolin-7-yl]-phenoxy}-piperidin-1-yl)-propan-1-one; cyclopropyl-(4-{4-[8-(2-morpholin-4-yl-ethoxy)-quinolin-7-yl]-phenoxyl}-piperidin-1-yl)-methanone; 1-(4-{4-[8-(2-pyrrolidin-1-yl-ethoxy)-quinolin-7-yl]-phenoxy}-piperidin-1-yl)-propan-1-one; cyclopropyl-(4-{4-[8-(2-pyrrolidin-1-yl-ethoxy)-quinolin-7-yl]-phenoxy}-piperidin-1-yl)-methanone; 1-(4-{4-[8-(3-pyrrolidin-1-yl-propoxy)-quinolin-7-yl]-phenoxy}-piperidin-1-yl)-propan-1-one; cyclopropyl-(4-{4-[8-(3-pyrrolidin-1-yl-propoxy)-quinolin-7-yl]-phenoxy}-piperidin-1-yl)-methanone; 1-[4-[4-[8-[2-(4-methylpiperazin-1-yl)ethoxy]-7-quinolyl]phenoxy]-1-piperidyl]propan-1-one; 1-[4-[4-[8-(2-methoxyethoxy)-7-quinolyl]phenoxy]-1-piperidyl]propan-1-one; 1-[4-[4-[8-(3-methoxypropoxy)-7-quinolyl]phenoxy]-1-piperidyl]propan- 1-one; {4-[4-(8-isopropoxyquinolin-7-yl)-phenoxy]-piperidin-1-yl}-(R)-tetrahydrofuran-2-yl-methanone; {4-[4-(8-ethoxy-quinolin-7-yl)-phenoxy]-piperidin-1-yl}-(R)-tetrahydrofuran-2-yl-methanone; (4-{4-[8-(2-morpholin-4-yl-ethoxy)-quinolin-7-yl]-phenoxy}-piperidin-1-yl)-(R)-tetrahydrofuran-2-yl-methanone; (4-{4-[8-(2-pyrrolidin-1-yl-ethoxy)-quinolin-7-yl]-phenoxy})-piperidin-1-yl)-(R)-tetrahydrofuran-2-yl-methanone; (4-{4-[8-(3-pyrrolidin-1-yl-propoxy)-quinolin-7-yl]-phenoxy}-piperidin-1-yl)-(R)-tetrahydrofuran-2-ylmethanone; [4-[4-[8-[2-(4-methylpiperazin-1-yl)ethoxy]-7-quinolyl]phenoxy]-1-piperidyl]-[(2R)-tetrahydrofuran-2-yl]methanone; [4-[4-[8-(2-methoxyethoxy)-7-quinolyl]phenoxy]-1-piperidyl]-[(2R)-tetrahydrofuran-2-yl]methanone; [4-[4-[8-(3-methoxypropoxy)-7-quinolyl]phenoxy]-1-piperidyl]-[(2R)-tetrahydrofuran-2-yl]methanone; 1-{4-[4-(8-hydroxyquinolin-7-yl)-phenoxy]-piperidin-1-yl}-propan-1-one; cyclopropyl-{4-[4-(8-hydroxyquinolin-7-yl)-phenoxy]-piperidin-1-yl}-methanone; {4-[4-(8-hydroxyquinolin-7-yl)-phenoxy]-piperidin-1-yl}-(R)-tetrahydrofuran-2-yl-methanone; 1-[4-(2-chloro-4-quinolin-7-yl-phenoxy)-piperidin-1-yl]-propan-1-one; 1-[4-(2-chloro-4-quinolin-7-yl-phenoxy)-piperidin-1-yl]-2-methylpropan-1-one; 1-[4-(2-methoxy-4-quinolin-7-yl-phenoxy)-piperidin-1-yl]-propan-1-one; 1-{4-[2-fluoro-4-(8-methoxyquinolin-7-yl)-phenoxy]-piperidin-1-yl}-propan-1-one; cyclopropyl-{4-[2-fluoro-4-(8-methoxyquinolin-7-yl)-phenoxy]-piperidin-1-yl}-methanone; {4-[2-fluoro-4-(8-methoxyquinolin-7-yl)-phenoxy]-piperidin-1-yl}-(R)-tetrahydrofuran-2-yl-methanone; {4-[4-(8-chloroquinolin-7-yl)-2-fluorophenoxy]-piperidin-1-yl}-cyclopropyl-methanone; {4-[4-(8-chloroquinolin-7-yl)-2-fluoro-phenoxy]-piperidin-1-yl}-(R)-tetrahydrofuran-2-yl-methanone; 1-{4-[4-(8-chloroquinolin-7-yl)-2-fluoro-phenoxy]piperidin-1-yl}-propan-1-one; 1-{4-[2-fluoro-4-(8-methylquinolin-7-yl)-phenoxy]-piperidin-1-yl}-propan-1-one; {4-[2-fluoro-4-(8-methylquinolin-7-yl)-phenoxy]piperidin-1-yl}-(R)-tetrahydrofuran-2-yl-methanone; cyclopropyl-{4-[2-fluoro-4-(8-methylquinolin-7-yl)-phenoxy]-piperidin-1-yl}-methanone; 1-{4-[4-(2-methyl-quinolin-7-yl)-phenoxy]-piperidin-1-yl}-propan-1-one; {4-[4-(4-chloroquinolin-7-yl)-phenoxy]piperidin-1-yl}-(R)-tetrahydrofuran-2-yl methanone; {4-[4-(4-chloroquinolin-7-yl)-phenoxy]-piperidin-1-yl}cyclopropylmethanone; 1-{4-[4-(4-chloroquinolin-7-yl)-phenoxy]-piperidin-1-yl}-propan-1-one; {4-[4-(8-chloroquinolin-7-yl)-phenoxy]-piperidin-1-yl}-(R)-tetrahydrofuran-2-yl-methanone; 1-{4-[4-(8-chloroquinolin-7-yl)-phenoxy]-piperidin-1-yl}-propan-1-one; {4-[4-(3-chloroquinolin-7-yl)-phenoxy]-piperidin-1-yl}-(R)-tetrahydrofuran-2-yl-methanone; 1-{4-[4-(3-chloroquinolin-7-yl)-phenoxy]-piperidin-1-yl}-propan-1-one; {4-[4-(8-methoxyquinolin-7-yl)-phenoxy]-piperidin-1-yl})-(R)-tetrahydrofuran-2-yl-methanone; 1-{4-[4-(8-methoxyquinolin-7-yl)-phenoxy]-piperidin-1-yl}-propan-1-one; cyclopropyl-{4-[4-(8-methoxyquinolin-7-yl)-phenoxy]-piperidin-1-yl}-methanone; {4-[4-(6-methylquinolin-7-yl)-phenoxy]-piperidin-1-yl}-(R)-tetrahydrofuran-2-yl-methanone; 1-{4-[4-(6-methylquinolin-7-yl)-phenoxy]-piperidin-1-yl}-propan-1-one; 7-[4-(1-propionylpiperidin-4-yloxy)-phenyl]-quinoline-3-carbonitrile; 7-{4-[1-((R)-tetrahydrofuran-2-carbonyl)-piperidin-4-yloxy]-phenyl}-quinoline-3-carbonitrile; 7-[4-(1-cyclopropanecarbonyl-piperidin-4-yloxy)-phenyl]-quinoline-3-carbonitrile; 1-{4-[4-(3-methylquinolin-7-yl)-phenoxy]-piperidin-1-yl}-propan-1-one; {4-[4-(3-methylquinolin-7-yl)-phenoxy]-piperidin-1-yl}-(R)-tetrahydrofuran-2-yl-methanone; cyclopropyl-{4-[4-(3-methylquinolin-7-yl)-phenoxy]-piperidin-1-yl}-methanone; (1-hydroxycyclopropyl)-{4-[4-(8-methoxyquinolin-7-yl)-phenoxy]-piperidin-1-yl}-methanone; {4-[4-(8-methylquinolin-7-yl)-phenoxy]-piperidin-1-yl}-(1-trifluoromethylcyclopropyl)-methanone; (1-aminocyclopropyl)-{4-[4-(8-methyl-quinolin-7-yl)-phenoxy]-piperidin-1-yl}-methanone; 1-{4-[4-(8-methylquinolin-7-yl)-phenoxy]-piperidine-1-carbonyl}-cyclopropanecarbonitrile; (1-methylcyclopropyl)-{4-[4-(8-methylquinolin-7-yl)-phenoxy]-piperidin-1-yl}-methanone; ((S)-2,2-dimethyl-cyclopropyl)-{4-[4-(8-methylquinolin-7-yl)-phenoxy]-piperidin-1-yl}-methanone; (2,2-dimethylcyclopropyl)-{4-[4-(8-methylquinolin-7-yl)-phenoxy]-piperidin-1-yl}-methanone; [4-[4-[8-(4-methylpiperazin-1-yl)-7-quinolyl]phenoxy]-1-piperidyl]-[(2R)-tetrahydrofuran-2-yl]methanone; [4-[4-(8-amino-7-quinolyl)phenoxy]-1-piperidyl]-[(2R)-tetrahydrofuran-2-yl]methanone; {4-[4-(8-methylaminoquinolin-7-yl)-phenoxy]-piperidin-1-yl}-(R)-tetrahydrofuran-2-yl-methanone; 1-{4-[4-(8-methylaminoquinolin-7-yl)-phenoxy]-piperidin-1-yl}-propan-1-one; (4-{4-[8-(2-methoxyethylamino)-quinolin-7-yl]-phenoxy}-piperidin-1-yl)-(R)-tetrahydrofuran-2-yl-methanone; 1-(4-{4-[8-(2-methoxyethylamino)-quinolin-7-yl]-phenoxy}-piperidin-1-yl)-propan-1-one; (4-{4-[8-(2-dimethylaminoethylamino)-quinolin-7-yl]-phenoxy}-piperidin-1-yl)-(R)-tetrahydrofuran-2-yl-methanone; 7-[4-(1-propionyl-piperidin-4-yloxy)-phenyl]-quinoline-8-carbonitrile; [4-[4-[8-(dimethylamino)-7-quinolyl]phenoxy]-1-piperidyl]-[(2R)-tetrahydrofuran-2-yl]methanone; 1-{4-[4-(8-dimethylaminoquinolin-7-yl)-phenoxy]-piperidin-1-yl}-propan-1-one; cyclopropyl-{4-[4-(8-dimethylaminoquinolin-7-yl)-phenoxy]-piperidin-1-yl}-methanone; (4-{4-[8-(2-pyrrolidin-1-yl-ethylamino)-quinolin-7-yl]-phenoxy}-piperidin-1-yl)-(R)-tetrahydrofuran-2-yl-methanone; 1-(4-{4-[8-(2-pyrrolidin-1-yl-ethylamino)-quinolin-7-yl]-phenoxy}-piperidin-1-yl)-propan-1-one; 7-[4-[[1-[(2R)-tetrahydrofuran-2-carbonyl]-4-piperidyl]oxy]phenyl]quinoline-8-carboxamide; 7-[4-(1-propionyl-piperidin-4-yloxy)-phenyl]-quinoline-8-carboxylic acid amide; (S)-1-(3-(4-(quinolin-7-yl)phenoxy)pyrrolidin-1-yl)propan-1-one; (R)-1-(3-(4-(quinolin-7-yl)phenoxy)pyrrolidin-1-yl)propan-1-one; 1-(4-(4-(5-methylquinolin-7-yl)phenoxy)piperidin-1-yl)propan-1-one; cyclopropyl(4-(4-(5-methylquinolin-7-yl)phenoxy)piperidin-1-yl)methanone; (R)-(4-(4-(5-methyl-quinolin-7-yl)phenoxy)piperidin-1-yl)(tetrahydrofuran-2-yl)methanone; (±)-(7S,8aS)-7-(4-(8-methylquinolin-7-yl)phenoxy)hexahydroindolizin-3 (2H)-one; (±)-(7R,8aS)-7-(4-(8-methylquinolin-7-yl)phenoxy)hexahydroindolizin-3(2H)-one; 2,2,2-trifluoro-1-{4-[4-(8-methyl-quinolin-7-yl)-phenoxy]-piperidin-1-yl}-ethanone; 2,2-difluoro-1-{4-[4-(8-methylquinolin-7-yl)-phenoxy]-piperidin-1-yl}-propan-1-one; 2-fluoro-1-{4-[4-(8-methyl-quinolin-7-yl)-phenoxy]-piperidin-1-yl}-propan-1-one; {cis-3-fluoro-4-[4-(8-methyl-quinolin-7-yl)-phenoxy]-piperidin-1-yl}-(R)-tetrahydrofuran-2-yl-methanone; 1-{cis-3-fluoro-4-[4-(8-methylquinolin-7-yl)-phenoxy]-piperidin-1-yl}-propan-1-one; cyclopropyl-{cis-3-fluoro-4-[4-(8-methylquinolin-7-yl)-phenoxy]-piperidin-1-yl}-methanone; {(trans)-3-fluoro-4-[4-(8-methylquinolin-7-yl)-phenoxy]-piperidin-1-yl}-(R)-tetrahydrofuran-2-yl-methanone; 1-{trans-3-fluoro-4-[4-(8-methylquinolin-7-yl)-phenoxy]-piperidin-1-yl}-propan-1-one; cyclopropyl-{trans-3-fluoro-4-[4-(8-methylquinolin-7-yl)-phenoxy]-piperidin-1-yl}-methanone; 1-{3-methyl-4-[4-(8-methylquinolin-7-yl)-phenoxy]-piperidin-1-yl}-propan-1-one; cyclopropyl-{3-methyl-4-[4-(8-methylquinolin-7-yl)-phenoxy]-piperidin-1-yl}-methanone; {3-methyl-4-[4-(8-methylquinolin-7-yl)-phenoxy]-piperidin-1-yl}-(R)-tetrahydrofuran-2-yl-methanone; [4-[4-(8-cyclopropyl-7-quinolyl)phenoxy]-1-piperidyl]-[(2R)-tetrahydrofuran-2-yl]methanone; 1-(4-((4-(quinolin-7-yl)phenyl)thio)piperidin-1-yl)propan-1-one; 1-(4-((4-(isoquinolin-6-yl)phenyl)thio)-piperidin-1-yl)propan-1-one; and salts thereof, e.g., pharmaceutically acceptable salts.

Additional compounds according to Formula IV may include for example: N-ethyl-4-[4-(2-hydroxy-8-methyl-7-quinolyl)phenoxy]piperidine-1-carboxamide; 4-[4-(8-methyl-7-quinolyl)phenoxy]-N-(2-pyrrolidin-1-ylethyl)piperidine-1-carboxamide; 4-[4-(8-methyl-7-quinolyl)phenoxy]-N-(2-morpholinoethyl)piperidine-1-carboxamide; (4-isopropylpiperazin-1-yl)-[4-[4-(8-methyl-7-quinolyl)phenoxy]-1-piperidyl]methanone; (4-methylpiperazin-1-yl)-[4-[4-(8-methyl-7-quinolyl)phenoxy]-1-piperidyl]methanone; [4-[4-(8-methyl-7-quinolyl)phenoxy]-1-piperidyl]-(4-morpholino-1-piperidyl)methanone; (4-ethylpiperazin-1-yl)-[4-[4-(8-methyl-7-quinolyl)phenoxy]-1-piperidyl]methanone tosylate; N-(cyclopropylmethyl)-4-[4-(8-methyl-7-quinolyl)phenoxy]piperidine-1-carboxamide; N-isobutyl-4-[4-(8-methyl-7-quinolyl)phenoxy]-piperidine-1-carboxamide; N-(2-methoxyethyl)-4-[4-(8-methyl-7-quinolyl)phenoxy]piperidine-1-carboxamide; N-isopropoxy-4-[4-(8-methyl-7-quinolyl)phenoxy]piperidine-1-carboxamide; N-isobutoxy-4-[4-(8-methyl-7-quinolyl)phenoxy]piperidine-1-carboxamide; N-(2-dimethylaminoethyl)-4-[4-(8-methyl-7-quinolyl)phenoxy]piperidine-1-carboxamide; N-[2-(1H-imidazol-4-yl)ethyl]-4-[4-(8-methyl-7-quinolyl)phenoxy]piperidine-1-carboxamide; 4-[4-(8-methyl-7-quinolyl)phenoxy]-N-tetrahydropyran-4-yl-piperidine-1-carboxamide; N-cyclobutyl-4-[4-(8-methyl-7-quinolyl)phenoxy]piperidine-1-carboxamide; 4-[4-(8-methyl-7-quinolyl)phenoxy]-piperidine-1-carbohydroxamic acid; [4-[4-(8-methyl-7-quinolyl)phenoxy]-1-piperidyl]-(oxazinan-2-yl)methanone; N-(cyclobutylmethyl)-4-[4-(8-methyl-7-quinolyl)phenoxy]piperidine-1-carboxamide; azepan-1-yl-[4-[4-(8-methyl-7-quinolyl)phenoxy]-1-piperidyl]methanone; 4-[4-(8-methyl-7-quinolyl)phenoxy]-N-propoxy-piperidine-1-carboxamide; 2-amino-1-[4-[4-(8-methyl-7-quinolyl)phenoxy]-1-piperidyl]ethanone; (2R)-2-amino-1-[4-[4-(8-methyl-7-quinolyl)phenoxy]-1-piperidyl]propan-1-one; (2S)-2-amino-1-[4-[4-(8-methyl-7-quinolyl)phenoxy]-1-piperidyl]propan-1-one; 2-(dimethylamino)-1-[4-[4-(8-methyl-7-quinolyl)phenoxy]-1-piperidyl]ethanone; [(2R)-1-methylpyrrolidin-2-yl]-[4-[4-(8-methyl-7-quinolyl)phenoxy]-1-piperidyl]methanone; [(2S)-1-methylpyrrolidin-2-yl]-[4-[4-(8-methyl-7-quinolyl)phenoxy]-1-piperidyl]methanone; S-isopropyl 4-[4-(8-methyl-7-quinolyl)phenoxy]piperidine-1-carbothioate; 2-amino-2-methyl-1-[4-[4-(8-methyl-7-quinolyl)phenoxy]-1-piperidyl]-propan-1-one; [4-[4-(8-methyl-7-quinolyl)phenoxy]-1-piperidyl]-[(2R)-pyrrolidin-2-yl]methanone; [4-[4-(8-methyl-7-quinolyl)phenoxy]-1-piperidyl]-[(2S)-pyrrolidin-2-yl]methanone; [1-(methylamino)cyclopropyl]-[4-[4-(8-methyl-7-quinolyl)phenoxy]-1-piperidyl]methanone; 3-amino-1-[4-[4-(8-methyl-7-quinolyl)phenoxy]-1-piperidyl]propan-1-one; 2-isopropoxy-1-[4-[4-(8-methyl-7-quinolyl)phenoxy]-1-piperidyl]ethanone; [2-[4-[4-(8-methyl-7-quinolyl)phenoxy]-1-piperidyl]-2-oxoethyl]acetate; 2-hydroxy-1-[4-[4-(8-methyl-7-quinolyl)phenoxy]-1-piperidyl]ethanone; (1-aminocyclobutyl)-[4-[4-(8-methyl-7-quinolyl)phenoxy]-1-piperidyl]-methanone; N-ethyl-4-[4-(2-fluoro-8-methyl-7-quinolyl)phenoxy]piperidine-1-carboxamide and salts thereof, e.g., pharmaceutically acceptable salts thereof.

Compounds according to Formula V or V(a) may include for example: isoxazolidin-2-yl-[4-(4-quinolin-3-yl-phenoxy)-piperidin-1-yl]-methanone; [4-(4-isoquinolin-3-yl-phenoxy)-piperidin-1-yl]-isoxazolidin-2-yl-methanone; isoxazolidin-2-yl-{4-[4-(8-methylquinolin-7-yl)-phenoxy]-piperidin-1-yl}-methanone; {4-[4-(4-chloro-quinolin-3-yl)-phenoxy]-piperidin-1-yl}-isoxazolidin-2-yl-methanone; {4-[4-(8-chloro-quinolin-7-yl)-phenoxy]-piperidin-1-yl}-isoxazolidin-2-yl-methanone; isoxazolidin-2-yl-{4-[4-(4-methylquinolin-3-yl)-phenoxy]-piperidin-1-yl}-methanone; isoxazolidin-2-yl-{4-[4-(8-methoxyquinolin-7-yl)-phenoxy]-piperidin-1-yl}-methanone; isoxazolidin-2-yl-{4-[4-(7-methylquinolin-3-yl)-phenoxy]-piperidin-1-yl}-methanone; isoxazolidin-2-yl-[4-(4-quinoxalin-2-yl-phenoxy)-piperidin-1-yl]-methanone; 4-[4-(4-methylquinolin-3-yl)-phenoxy]-piperidine-1-carboxylic acid methoxyamide; 4-[4-(4-methylquinolin-3-yl)-phenoxy]-piperidine-1-carboxylic acid methoxymethylamide; 4-[4-(4-methylquinolin-3-yl)-phenoxy]piperidine-1-carboxylic acid ethylamide; 4-[4-(8-methoxyquinolin-7-yl)-phenoxy]-piperidine-1-carboxylic acid methylamide; 4-[4-(8-methoxyquinolin-7-yl)-phenoxy]-piperidine-1-carboxylic acid ethylamide; 4-[4-(4-methylquinolin-3-yl)-phenoxy]piperidine-1-carboxylic acid hydroxyamide; N-ethyl-4-[4-(8-methyl-7-quinolyl)phenoxy]piperidine-1-carboxamide; N,N-dimethyl-4-[4-(8-methyl-7-quinolyl)phenoxy]piperidine-1-carboxamide; N-methoxy-4-[4-(8-methyl-7-quinolyl)phenoxy]piperidine-1-carboxamide; N-isopropyl-4-[4-(8-methyl-7-quinolyl)phenoxy]piperidine-1-carboxamide; N-ethoxy-4-[4-(8-methyl-7-quinolyl)phenoxy]piperidine-1-carboxamide; [4-[4-(8-methyl-7-quinolyl)phenoxy]-1-piperidyl]-pyrrolidin-1-yl-methanone; N-methyl-4-[4-(8-methyl-7-quinolyl)phenoxy]piperidine-1-carboxamide; 4-[4-(8-methyl-7-quinolyl)phenoxy]-N-propylpiperidine-1-carboxamide; 4-[4-(8-methyl-7-quinolyl)phenoxy]piperidine-1-carboxamide; [4-[4-(8-methyl-7-quinolyl)phenoxy]-1-piperidyl]-(1-piperidyl)methanone; [4-[4-(8-methyl-7-quinolyl)phenoxy]-1-piperidyl]-morpholinomethanone; N-methoxy-4-[4-(8-methoxy-7-quinolyl)phenoxy]piperidine-1-carboxamide; 3-[4-(4-quinolin-3-yl-phenoxy)-piperidine-1-carbonyl]-oxazolidin-2-one; 1-[4-(4-quinolin-3-yl-phenoxy)-piperidine-1-carbonyl]-pyrrolidin-2-one; and salts thereof, e.g., pharmaceutically acceptable salts thereof.

Additional compounds according to Formula V may include for example: N-ethyl-4-[4-(2-hydroxy-8-methyl-7-quinolyl)phenoxy]piperidine-1-carboxamide; 4-[4-(8-methyl-7-quinolyl)phenoxy]-N-(2-pyrrolidin-1-ylethyl)piperidine-1-carboxamide; 4-[4-(8-methyl-7-quinolyl)phenoxy]-N-(2-morpholinoethyl)piperidine-1-carboxamide; (4-isopropylpiperazin-1-yl)-[4-[4-(8-methyl-7-quinolyl)phenoxy]-1-piperidyl]methanone; (4-methylpiperazin-1-yl)-[4-[4-(8-methyl-7-quinolyl)phenoxy]-1-piperidyl]methanone; [4-[4-(8-methyl-7-quinolyl)phenoxy]-1-piperidyl]-(4-morpholino-1-piperidyl)methanone; (4-ethylpiperazin-1-yl)-[4-[4-(8-methyl-7-quinolyl)phenoxy]-1-piperidyl]methanone; N-ethyl-4-[4-(7-methylpyrazolo[1,5-a]pyridin-6-yl)phenoxy]piperidine-1-carboxamide; N-isopropoxy-4-[4-(7-methylpyrazolo[1,5-a]pyridin-6-yl)phenoxy]piperidine-1-carboxamide; N-ethoxyoxy-4-[4-(7-methylpyrazolo[1,5-a]pyridin-6-yl)phenoxy]piperidine-1-carboxamide; N-methoxyoxy-4-[4-(7-methylpyrazolo[1,5-a]pyridin-6-yl)phenoxy]piperidine-1-carboxamide; N-(cyclopropylmethyl)-4-[4-(8-methyl-7-quinolyl)phenoxy]-piperidine-1-carboxamide; N-isobutyl-4-[4-(8-methyl-7-quinolyl)phenoxy]piperidine-1-carboxamide;

N-(2-methoxyethyl)-4-[4-(8-methyl-7-quinolyl)phenoxy]piperidine-1-carboxamide; N-isopropoxy-4-[4-(8-methyl-7-quinolyl)phenoxy]piperidine-1-carboxamide; N-isobutoxy-4-[4-(8-methyl-7-quinolyl)phenoxy]piperidine-1-carboxamide; N-(2-dimethylaminoethyl)-4-[4-(8-methyl-7-quinolyl)phenoxy]piperidine-1-carboxamide; N-[2-(1H-imidazol-4-yl)ethyl]-4-[4-(8-methyl-7-quinolyl)phenoxy]-piperidine-1-carboxamide; 4-[4-(8-methyl-7-quinolyl)phenoxy]-N-tetrahydropyran-4-yl-piperidine-1-carboxamide; N-cyclobutyl-4-[4-(8-methyl-7-quinolyl)phenoxy]piperidine-1-carboxamide; 4-[4-(8-methyl-7-quinolyl)phenoxy]piperidine-1-carbohydroxamic acid; [4-[4-(8-methyl-7-quinolyl)phenoxy]-1-piperidyl]-(oxazinan-2-yl)-methanone; N-(cyclobutylmethyl)-4-[4-(8-methyl-7-quinolyl)phenoxy]piperidine-1-carboxamide; azepan-1-yl-[4-[4-(8-methyl-7-quinolyl)phenoxy]-1-piperidyl]methanone; N-butyl-4-[4-(5-chloroimidazo[1,2-a]pyridin-6-yl)phenoxy]piperidine-1-carboxamide; 4-[4-(5-chloroimidazo[1,2-a]pyridin-6-yl)phenoxy]-N-ethyl-piperidine-1-carboxamide; 4-[4-(5-chloroimidazo[1,2-a]pyridin-6-yl)phenoxy]-N-isobutyl-piperidine-1-carboxamide; 4-[4-(5-chloroimidazo[1,2-a]pyridin-6-yl)phenoxy]-N-propyl-piperidine-1-carboxamide; 4-[4-(5-chloroimidazo[1,2-a]pyridin-6-yl)phenoxy]-N-(2-methoxyethyl)-piperidine-1-carboxamide; 4-[4-(5-chloroimidazo[1,2-a]pyridin-6-yl)phenoxy]-N-(cyclopropyl-methyl)piperidine-1-carboxamide; 4-[4-(5-chloroimidazo[1,2-a]pyridin-6-yl)phenoxy]-N-isopropoxy-piperidine-1-carboxamide; 4-[4-(5-chloroimidazo[1,2-a]pyridin-6-yl)phenoxy]-N-isopropyl-piperidine-1-carboxamide; 4-[4-(5-chloroimidazo[1,2-a]pyridin-6-yl)phenoxy]-N-isobutoxy-piperidine-1-carboxamide; 4-[4-(5-chloroimidazo[1,2-a]pyridin-6-yl)phenoxy]-N-isopentyl-piperidine-1-carboxamide; 4-[4-(5-chloroimidazo[1,2-a]pyridin-6-yl)phenoxy]-N-ethoxy-piperidine-1-carboxamide; 4-[4-(8-methyl-7-quinolyl)phenoxy]-N-propoxy-piperidine-1-carboxamide; 4-[4-(5-chloroimidazo[1,2-a]pyridin-6-yl)phenoxy]piperidine-1-carbohydroxamic acid; 4-[4-(5-chloroimidazo[1,2-a]pyridin-6-yl)phenoxy]-N-propoxy-piperidine-1-carboxamide; 4-[4-(5-chloroimidazo[1,2-a]pyridin-6-yl)phenoxy]piperidine-1-carboxamide; N-ethyl-4-[4-(1-methyl-6-isoquinolyl)phenoxy]piperidine-1-carboxamide; 4-[4-(1-methyl-6-isoquinolyl)phenoxy]-N-propyl-piperidine-1-carboxamide; N-isobutyl-4-[4-(1-methyl-6-isoquinolyl)phenoxy]piperidine-1-carboxamide; 4-[4-(1-methyl-6-isoquinolyl)phenoxy]piperidine-1-carboxamide; N-(cyclopropylmethyl)-4-[4-(1-methyl-6-isoquinolyl)phenoxy]piperidine-1-carboxamide; N-isopropoxy-4-[4-(1-methyl-6-isoquinolyl)phenoxy]piperidine-1-carboxamide; 4-[4-(1-methyl-6-isoquinolyl)phenoxy]-N-propoxypiperidine-1-carboxamide; 4-[4-(1-methyl-6-isoquinolyl)phenoxy]piperidine-1-carbohydroxamic acid; N-ethoxy-4-[4-(1-methyl-6-isoquinolyl)phenoxy]piperidine-1-carboxamide; N-ethoxy-4-[4-(4-methyl-3-quinolyl)phenoxy]piperidine-1-carboxamide; N-isopropoxy-4-[4-(4-methyl-3-quinolyl)phenoxy]piperidine-1-carboxamide; 4-[4-(4-methyl-3-quinolyl)phenoxy]-N-propoxy-piperidine-1-carboxamide; N-isobutyl-4-[4-(4-methyl-3-quinolyl)phenoxy]piperidine-1-carboxamide; 4-[4-(4-methyl-3-quinolyl)phenoxy]-N-propyl-piperidine-1-carboxamide; N-ethyl-4-[4-(5-methyl-imidazo[1,2-a]pyridin-6-yl)phenoxy]piperidine-1-carboxamide; N-isobutyl-4-[4-(5-methylimidazo[1,2-a]pyridin-6-yl)phenoxy]piperidine-1-carboxamide; 4-[4-(5-methylimidazo[1,2-a]pyridin-6-yl)phenoxy]-N-propyl-piperidine-1-carboxamide; N-(cyclopropylmethyl)-4-[4-(5-methylimidazo[1,2-a]pyridin-6-yl)-phenoxy]piperidine-1-carboxamide; 4-[4-(5-methylimidazo[1,2-a]pyridin-6-yl)phenoxy]-N-(3-pyridyl)-piperidine-1-carboxamide; N-(2-methoxyethyl)-4-[4-(5-methylimidazo[1,2-a]pyridin-6-yl)phenoxy]-piperidine-1-carboxamide; [4-[4-(5-methylimidazo[1,2-a]pyridin-6-yl)phenoxy]-1-piperidyl]-(4-methylpiperazin-1-yl)methanone; N,N-dimethyl-4-[4-(5-methylimidazo[1,2-a]pyridin-6-yl)phenoxy]piperidine-1-carboxamide; N-isopropoxy-4-[4-(5-methylimidazo[1,2-a]pyridin-6-yl)phenoxy]piperidine-1-carboxamide; N-isobutoxy-4-[4-(5-methylimidazo[1,2-a]pyridin-6-yl)phenoxy]piperidine-1-carboxamide; N-isopropyl-4-[4-(5-methylimidazo[1,2-a]pyridin-6-yl)phenoxy]-piperidine-1-carboxamide; 4-[4-(5-methylimidazo[1,2-a]pyridin-6-yl)phenoxy]-N-(1-methylpyrazol-4-yl)piperidine-1-carboxamide; 4-[4-(5-methylimidazo[1,2-a]pyridin-6-yl)phenoxy]-N-(2,2,2-trifluoro-ethyl)piperidine-1-carboxamide; 4-[4-(5-methylimidazo[1,2-a]pyridin-6-yl)phenoxy]-N-propoxy-piperidine-1-carboxamide; N-ethoxy-4-[4-(5-methylimidazo[1,2-a]pyridin-6-yl)phenoxy]piperidine-1-carboxamide; N-methoxy-4-[4-(5-methylimidazo[1,2-a]pyridin-6-yl)phenoxy]piperidine-1-carboxamide; 4-[4-(5-methylimidazo[1,2-a]pyridin-6-yl)phenoxy]piperidine-1-carbohydroxamic acid; 4-[4-(5-methylimidazo[1,2-a]pyridin-6-yl)phenoxy]piperidine-1-carboxamide; N-ethyl-4-(4-imidazo[1,2-a]pyridin-7-ylphenoxy)piperidine-1-carboxamide; N-ethyl-4-[4-(8-methylimidazo[1,2-a]pyridin-7-yl)phenoxy]piperidine-1-carboxamide; N-isopropoxy-4-[4-(8-methylimidazo[1,2-a]pyridin-7-yl)phenoxy]piperidine-1-carboxamide; 4-[4-(8-methylimidazo[1,2-a]pyridin-7-yl)phenoxy]-N-propyl-piperidine-1-carboxamide; N-isobutyl-4-[4-(8-methylimidazo[1,2-a]pyridin-7-yl)phenoxy]piperidine-1-carboxamide; N-isobutyl-4-[4-(7-methylpyrazolo[1,5-a]pyridin-6-yl)phenoxy]piperidine-1-carboxamide; 4-[4-(7-methylpyrazolo[1,5-a]pyridin-6-yl)phenoxy]piperidine-1-carboxamide; 4-[4-(7-methylpyrazolo[1,5-a]pyridin-6-yl)phenoxy]piperidine-1-carbohydroxamic acid; N,N-dimethyl-4-[4-(7-methylpyrazolo[1,5-a]pyridin-6-yl)phenoxy]lpiperidine-1-carboxamide; [4-[4-(7-methylpyrazolo[1,5-a]pyridin-6-yl)phenoxy]-1-piperidyl]-pyrrolidin-1-yl-methanone; [(3S)-3-fluoropyrrolidin-1-yl]-[4-[4-(7-methylpyrazolo[1,5-a]pyridin-6-yl)phenoxy]-1-piperidyl]methanone; [(3R)-3-fluoropyrrolidin-1-yl]-[4-[4-(7-methylpyrazolo[1,5-a]pyridin-6-yl)phenoxy]-1-piperidyl]methanone; 4-[4-(7-methylpyrazolo[1,5-a]pyridin-6-yl)phenoxy]-N-methylsulfanyl-piperidine-1-carboxamide; N-ethylsulfanyl-4-[4-(7-methylpyrazolo[1,5-a]pyridin-6-yl)phenoxy]piperidine-1-carboxamide; 4-[4-(4-methyl-3-quinolyl)phenoxy]-N-methyl sulfanyl-piperidine-1-carboxamide; 4-[4-(4-methyl-3-quinolyl)phenoxy]-N-ethylsulfanyl-piperidine-1-carboxamide; 1-[4-[4-(7-methylpyrazolo[1,5-a]pyridin-6-yl)phenoxy]piperidine-1-carbonyl]pyrrolidin-2-one; 1-[4-[4-(4-methyl-3-quinolyl)phenoxy]piperidine-1-carbonyl]pyrrolidin-2-one; 4-[4-(7-methylpyrazolo[1,5-a]pyridin-6-yl)phenoxy]-N-propylpiperidine-1-carboxamide; N-ethyl-4-[4-(2-fluoro-8-methyl-7-quinolyl)phenoxy]piperidine-1-carboxamide and salts thereof, e.g., pharmaceutically acceptable salts thereof.

Additional compounds according to Formula V(a) may include, for example: N-ethyl-4-[4-(2-hydroxy-8-methyl-7-quinolyl)phenoxy]piperidine-1-carboxamide; 4-[4-(8-methyl-7-quinolyl)phenoxy]-N-(2-pyrrolidin-1-ylethyl)piperidine-1-carboxamide; 4-[4-(8-methyl-7-quinolyl)phenoxy]-N-(2-morpholinoethyl)piperidine-1-carboxamide; (4-isopropylpiperazin-1-yl)-[4-[4-(8-methyl-7-quinolyl)phenoxy]-1-piperidyl]methanone; (4-methylpiperazin-1-yl)-[4-[4-(8-methyl-7-quinolyl)phenoxy]-1-piperidyl]

methanone; [4-[4-(8-methyl-7-quinolyl)phenoxy]-1-piperidyl]-(4-morpholino-1-piperidyl)methanone; (4-ethylpiperazin-1-yl)-[4-[4-(8-methyl-7-quinolyl)phenoxy]-1-piperidyl]methanone; N-(cyclopropylmethyl)-4-[4-(8-methyl-7-quinolyl)phenoxy]piperidine-1-carboxamide; N-isobutyl-4-[4-(8-methyl-7-quinolyl)phenoxy]piperidine-1-carboxamide; N-(2-methoxyethyl)-4-[4-(8-methyl-7-quinolyl)phenoxy]piperidine-1-carboxamide; N-isopropoxy-4-[4-(8-methyl-7-quinolyl)phenoxy]piperidine-1-carboxamide; N-isobutoxy-4-[4-(8-methyl-7-quinolyl)phenoxy]piperidine-1-carboxamide; N-(2-dimethylaminoethyl)-4-[4-(8-methyl-7-quinolyl)phenoxy]piperidine-1-carboxamide; N-[2-(1H-imidazol-4-yl)ethyl]-4-[4-(8-methyl-7-quinolyl)phenoxy]-piperidine-1-carboxamide; 4-[4-(8-methyl-7-quinolyl)phenoxy]-N-tetrahydropyran-4-yl-piperidine-1-carboxamide; N-cyclobutyl-4-[4-(8-methyl-7-quinolyl)phenoxy]piperidine-1-carboxamide; 4-[4-(8-methyl-7-quinolyl)phenoxy]piperidine-1-carbohydroxamic acid; [4-[4-(8-methyl-7-quinolyl)phenoxy]-1-piperidyl]-(oxazinan-2-yl)methanone; N-(cyclobutylmethyl)-4-[4-(8-methyl-7-quinolyl)phenoxy]piperidine-1-carboxamide; azepan-1-yl-[4-[4-(8-methyl-7-quinolyl)phenoxy]-1-piperidyl]methanone; 4-[4-(8-methyl-7-quinolyl)phenoxy]-N-propoxy-piperidine-1-carboxamide; N-ethyl-4-[4-(1-methyl-6-isoquinolyl)phenoxy]piperidine-1-carboxamide; 4-[4-(1-methyl-6-isoquinolyl)phenoxy]-N-propyl-piperidine-1-carboxamide; N-isobutyl-4-[4-(1-methyl-6-isoquinolyl)phenoxy]piperidine-1-carboxamide; 4-[4-(1-methyl-6-isoquinolyl)phenoxy]piperidine-1-carboxamide; N-(cyclopropylmethyl)-4-[4-(1-methyl-6-isoquinolyl)phenoxy]piperidine-1-carboxamide; N-isopropoxy-4-[4-(1-methyl-6-isoquinolyl)phenoxy]piperidine-1-carboxamide; 4-[4-(1-methyl-6-isoquinolyl)phenoxy]-N-propoxypiperidine-1-carboxamide; 4-[4-(1-methyl-6-isoquinolyl)phenoxy]piperidine-1-carbohydroxamic acid; N-ethoxy-4-[4-(1-methyl-6-isoquinolyl)phenoxy]piperidine-1-carboxamide; N-ethoxy-4-[4-(4-methyl-3-quinolyl)phenoxy]piperidine-1-carboxamide; N-isopropoxy-4-[4-(4-methyl-3-quinolyl)phenoxy]piperidine-1-carboxamide; 4-[4-(4-methyl-3-quinolyl)phenoxy]-N-propoxy-piperidine-1-carboxamide; N-isobutyl-4-[4-(4-methyl-3-quinolyl)phenoxy]piperidine-1-carboxamide; 4-[4-(4-methyl-3-quinolyl)phenoxy]-N-propyl-piperidine-1-carboxamide; 4-[4-(4-methyl-3-quinolyl)phenoxy]-N-methylsulfanyl-piperidine-1-carboxamide; 4-[4-(4-methyl-3-quinolyl)phenoxy]-N-ethylsulfanyl-piperidine-1-carboxamide, 1-[4-[4-(4-methyl-3-quinolyl)phenoxy]piperidine-1-carbonyl]pyrrolidin-2-one; N-ethyl-4-[4-(2-fluoro-8-methyl-7-quinolyl)phenoxy]piperidine-1-carboxamide and salts thereof, e.g., pharmaceutically acceptable salts thereof.

The following terms and expressions have meanings as discussed below.

As used herein, the term "about" refers to a range of values from ±10% of a specified value. For example, the phrase "about 50" would be understood to include ±10% of 50, or from 45 to 55. The phrase "from about 10 to 100" includes ±10% of 10 and ±10% of 100, or from 9 to 110.

As used herein, a range of integer values in the form "x-y" or "x to y", or "x through y", includes the integers x and y, and includes all of the integers between x and y. For example, the expressions "1-6", or "1 to 6" or "1 through 6" are intended to include the integers 1, 2, 3, 4, 5, and 6. Preferred embodiments include each individual integer in the range, as well as any subcombination of integers. For example, preferred integers for the expression "1-6" can include 1, 2, 3, 4, 5, 6, 1-2, 1-3, 1-4, 1-5, 2-3, 2-4, 2-5, 2-6, etc.

The term "acyl" means a radical of the general formula —C(=O)—R, wherein —R is hydrogen or hydrocarbyl. Examples include, acetyl (—C(=O)CH$_3$), propionyl (—C(=O)CH$_2$CH$_3$), benzoyl (—C(=O)C$_6$H$_5$), and phenylacetyl (—C(=O)CH$_2$C$_6$H$_5$).

The term "alkyl", by itself or as part of another substituent means, a straight, branched or cyclic chain hydrocarbon radical, including di- and multi-radicals, having the number of carbon atoms designated (i.e. C$_1$-C$_6$ designates an alkyl group having from one to six carbons), and includes straight, branched chain or cyclic groups. Examples of alkyl groups include: methyl, ethyl, propyl, isopropyl, butyl, isobutyl, tert-butyl, pentyl, neopentyl, hexyl, cyclohexyl and cyclopropylmethyl.

The term "alkylene," by itself or as part of another substituent means a divalent straight, branched or cyclic chain hydrocarbon radical having the stated number of carbon atoms. For example, —(C$_1$-C$_3$)-alkylene-CO$_2$H, would include, e.g., —CH$_2$CH$_2$CH$_2$—CO$_2$H, —CH$_2$CH(CH$_3$)—CO$_2$H, —C(CH$_3$)$_2$—CO$_2$H, -cyclopropyl-CO$_2$H, and —CH(CH$_3$)—CH$_2$—CO$_2$H.

The term "alkoxy," employed alone or in combination with other terms means an alkyl group having the designated number of carbon atoms, as defined above, connected to the rest of the molecule via an oxygen atom, such as, for example, methoxy, ethoxy, 1-propoxy, 2-propoxy(isopropoxy) and the higher homologs and isomers.

The term "alkenyl," employed alone or in combination with other terms, means a stable monounsaturated or di-unsaturated hydrocarbon radical straight chain, branched chain or cyclic hydrocarbon group having the stated number of carbon atoms. Examples include vinyl, propenyl(allyl), crotyl, isopentenyl, butadienyl, 1,3-pentadienyl, 1,4-pentadienyl, cyclopentenyl, cyclopentadienyl and the higher homologs and isomers. A divalent radical derived from an alkene is exemplified by —CH=CH—CH$_2$—.

The term "amine" or "amino" refers to radicals of the general formula —NRR', wherein R and R' are independently selected from hydrogen and a hydrocarbyl radical, or wherein R and R' combined form a heterocyle. Examples of amino groups include: —NH$_2$, methylamino, diethylamino, anilino, benzylamino, piperidin-1-yl, piperazin-1-yl and indolin-1-yl.

The term "carbamyl" means the group —C(=O)NRR', wherein R and R' are independently selected from hydrogen and a hydrocarbyl radical, or wherein R and R' combined form a heterocyle. Examples of carbamyl groups include: —C(=O)NH$_2$ and —C(=O)N(CH$_3$)$_2$.

The term "cycloalkyl" refers to alkyl radicals that contain one or more rings, for example C$_3$ to C$_{10}$ cycloalkyl groups, e.g., cyclopropyl, cyclobutyl, cyclopentyl, cyclohexyl, cycloheptyl, norbornyl, and octahydro-1H-indenyl.

The term "heteroalkyl" by itself or in combination with another term, means a stable straight or branched chain radical consisting of the stated number of carbon atoms and one or two heteroatoms selected from O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$ (wherein either or both of the two consecutive heteroatoms may also be oxidized S (SO or $SO_2$) or oxidized N (NO)).

The term "heteroalkenyl," by itself or in combination with another term, means a stable straight or branched chain mono- or di-unsaturated hydrocarbon radical consisting of the stated number of carbon atoms and one or two heteroatoms selected from O, N, and S, and wherein the nitrogen and sulfur atoms may optionally be oxidized and the nitrogen heteroatom may optionally be quaternized. Up to two heteroatoms may be placed consecutively. Examples include —CH=CH—O—$CH_3$, —CH=CH—$CH_2$—OH, —$CH_2$—CH=N—$OCH_3$, —CH=CH—N($CH_3$)—$CH_3$, and —$CH_2$—CH=CH—$CH_2$—SH.

The term "hydroxyalkyl" refers to a subset of heteroalkyl groups that is an alkyl radical wherein one or more of the carbon atoms is substituted with hydroxy. Examples include —$CH_2$CH(OH)$CH_3$ and —$CH_2CH_2$OH.

The terms "halo" or "halogen" by themselves or as part of another substituent mean, a fluorine, chlorine, bromine, or iodine atom.

The term "haloalkyl" refers to a $C_1$-$C_6$ alkyl group in which one or more of the carbon atoms is substituted with one or more halogen atoms. Preferred haloalkyl groups are $C_1$-$C_4$ alkyl groups in which one or more of the carbon atoms is substituted with one or more halogen atoms. The alkyl group may be a straight, branched or cyclic alkyl group. The halogen atom is one or more of fluorine, chlorine, bromine and iodine. Examples of haloalkyl groups include, trifluoromethyl, 2,2,2-trifluoroethyl, 2,2,2-trichloroethyl and 2-chloroethyl.

The term "sulfamyl" means the group —$SO_2$NRR', wherein R and R' are independently selected from hydrogen or a hydrocarbyl radical, or wherein R and R' combined form a heterocycle. Examples of sulfamyl groups include: —$SO_2NH_2$, —$SO_2$N($CH_3$)$_2$, —$SO_2$(pyrrol-1-yl) and —$SO_2$NH($C_6H_5$).

The term "aromatic" refers to a carbocycle or heterocycle having one or more polyunsaturated rings having aromatic character (4n+2) delocalized it (pi) electrons).

The term "aryl," employed alone or in combination with other terms, means a carbocyclic aromatic system containing one or more rings (typically one, two or three rings) wherein such rings may be attached together in a pendent manner, such as a biphenyl, or may be fused, such as naphthalene. Examples include phenyl; anthracyl; and naphthyl.

The term "heterocycle" or "heterocyclyl" or "heterocyclic," by itself or as part of another substituent means, an unsubstituted or substituted, stable, mono- or multicyclic heterocyclic ring system which consists of carbon atoms and at least one heteroatom selected from N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

As used herein "stable structure" or "stable compound" refers to a compound that is sufficiently robust to survive isolation to a useful degree of purity from a reaction mixture. The compounds according to the present invention are stable compounds.

The term "heteroaryl" or "heteroaromatic" refers to a heterocycle having aromatic character.

Examples of non-aromatic heterocycles include monocyclic groups such as: Aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include: Pyridyl, pyrazinyl, pyrimidinyl, particularly 2- and 4-pyrimidyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-traizolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include: bicyclic heterocycles, such as, Indolyl, particularly 3-, 4-, 5-, 6- and 7-indolyl, indolinyl, quinolyl, tetrahydroquinolyl, isoquinolyl, particularly 1- and 5-isoquinolyl, tetrahydroisoquinolyl, cinnolinyl, quinoxalinyl, particularly 2- and 5-quinoxalinyl, quinazolinyl, 1,4-benzodioxanyl, coumarin, dihydrocoumarin, benzofuryl, particularly 3-, 4-, 5-, 6- and 7-benzofuryl, 2,3-dihydrobenzofuryl, 1,2-benzisoxazolyl, benzothienyl, particularly 3-, 4-, 5-, 6-, and 7-benzothienyl, benzoxazolyl, benzthiazolyl, particularly 2-benzothiazolyl and 5-benzothiazolyl, purinyl, benzimidazolyl, particularly 2-benzimidazolyl, benztriazolyl, thioxanthinyl, carbazolyl, carbolinyl, acridinyl, pyrrolizidinyl, and quinolizidinyl. Polycyclic heterocycles also include tricyclic and other polycyclic heterocycles such as dibenzofuran and benzofuro [2,3-b]pyridine.

The aforementioned listing of heterocyclyl and heteroaryl moieties is intended to be representative, not limiting.

The term "hydrocarbyl" refers to any moiety comprising only hydrogen and carbon atoms. For example, the term ($C_1$-$C_7$)hydrocarbyl would include hydrocarbon groups such as ($C_1$-$C_7$)alkyl groups and cycloalkyl, ($C_1$-$C_7$)alkenyl and cycloalkenyl groups, ($C_1$-$C_7$)alkynyl and cycloalkynyl groups, and aryl, e.g., benzyl and tolyl groups.

As used herein, the term "substituted" refers in general to any one or more hydrogen atoms on the indicated atom (preferably a carbon atom) being replaced with a selected group referred to herein as a "substituent", provided that the substituted atom's valency is not exceeded, and that the substitution results in a stable compound. A substituted group has from 1 to 5, preferably 1 to 3, and more preferably 1 independently selected substituents. Possible substituents include, but are not limited to halogens, —OH, —OR, —$NR_2$, —NHOH, —$NO_2$, —CN, —$CF_3$, —$CF_2CF_3$, —$C_1$-$C_7$ hydrocarbyl, —$C_1$-$C_6$ alkoxy, 3-7-membered heterocyclyl, 3-7-membered heteroaryl, =O, =S, —C(=O)R, —COOH, —$CO_2$R, —O—C(=O)R, —C(=O)NRR', —NRC(=O)R', —$NRCO_2$R', —OC(=O)NRR', —NRC(=O)NRR', —NRC(=S)NRR', and —$SO_2$NRR', wherein R and R' are each independently —H, —$C_1$-$C_7$ hydrocarbyl (e.g., —$C_1$-$C_6$ alkyl, —$C_2$-$C_6$ alkenyl —$C_3$-$C_6$ cycloalkyl, benzyl, or phenyl) or ($C_1$-$C_7$)acyl.

Where a substituent is an alkyl or alkoxy group, the carbon chain may be branched, straight or cyclic, with straight being preferred.

Accordingly, the term "substituted hydrocarbyl" refers to: a hydrocarbyl group as defined above, having 1, 2, 3, 4 or 5 substituents, independently selected from the selection provided in the definition of the term "substituent" herein. Similarly, the expressions "substituted alkyl," "substituted cycloalkyl," "substituted alkenyl," "substituted alkynyl," "substituted aryl," "substituted benzyl," etc. refer to the specified (e.g., alkyl) group as defined herein, having 1, 2, 3, 4 or 5 substituents, independently selected from the selection provided in the definition of the term "substituent" herein.

As used herein, the term "subject" refers to a warm blooded animal such as a mammal, preferably a human, which is afflicted with, or has the potential to be afflicted with one or more diseases and conditions described herein.

As used herein, a "therapeutically effective amount" refers to an amount of a compound of the present invention that is effective to treat or prevent the symptoms of a particular disorder. Such disorders include, but are not limited to; those pathological and neurological disorders associated with the aberrant activity of the receptors described herein, wherein the treatment or prevention comprises inhibiting the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable salt" refers to salts of compounds of the present invention that may be derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, trifluoroacetic, tartaric, glutamic, salicylic, oxalic, methanesulfonic, benzenesulfonic, para-toluenesulfonic, succinic, and benzoic acid, and related inorganic and organic acids.

Base addition salts include those derived from inorganic bases such as ammonium and alkali and alkaline earth metal hydroxides, carbonates, and bicarbonates, as well as salts derived from basic organic amines such as aliphatic and aromatic amines, aliphatic diamines, and hydroxy alkamines. Such bases useful in preparing the salts of this invention thus include, for example, ammonium hydroxide, potassium carbonate, sodium bicarbonate, calcium hydroxide, methylamine, diethylamine, ethylenediamine, cyclohexylamine, diisopropylethyl amine (DIPEA), ethanolamine.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and THF. Mixtures of such solvates can also be prepared. The source of such solvate can be from the solvent of crystallization, inherent in the solvent of preparation or crystallization, or adventitious to such solvent. Such solvates are within the scope of the present invention.

It will be understood that compounds of the present invention may exist in various stereoisomeric forms. As such, the compounds of the present invention include both diastereomers and enantiomers. The compounds may be prepared as racemates and can conveniently be used as such. However, individual enantiomers can be isolated by resolution or chiral separation of a racemate, or may be synthesized by conventional techniques if so desired. Such racemates and individual enantiomers and mixtures thereof form part of the present invention.

It is known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. Stereochemistry of Organic Compounds; Wiley: New York, 1994, and Jacques, J, et al. Enantiomers, Racemates, and Resolutions; Wiley: New York, 1981.

It is further recognized that functional groups present on intermediates used for the synthesis of the compounds of Formula I may contain protecting groups. For example, the amino acid side chain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenz-hydryl ("DMB"), acyl, benzyl ("Bn"), methoxybenzyl, and dimethoxy (e.g., 2-4-dimethoxy) benzyl groups. Preferred groups for protecting hydroxy groups include TBS, acyl, benzyl, benzyloxycarbonyl ("CBZ"), t-butyloxycarbonyl ("Boc"), and methoxymethyl. Many other standard protecting groups employed by one skilled in the art can be found in Greene, T. W. and Wuts, P. G. M., "Protective Groups in Organic Synthesis" 2d. Ed., Wiley & Sons, 1991.

The compounds described herein are also intended to include such compounds wherein the molecular structures include isotopes of atoms in the chemical structure, e.g., carbon, hydrogen, nitrogen sulfur, and other atoms occurring on those structures. Isotopes include those atoms having the same atomic number but different mass numbers. For example, isotopes of hydrogen include deuterium; isotopes of carbon include $^{13}C$; isotopes of nitrogen include $^{15}N$; and isotopes of sulfur include $^{33}S$.

Accordingly, within the chemical structure of any compound that is taught in this application:

any hydrogen atom or group of hydrogen atoms, e.g., in a hydrocarbyl, heteroalkyl, aryl, heteroaryl, heterocyclyl or carbocyclyl group, could suitably be replaced by an isotope of hydrogen, i.e., deuterium;

any carbon atom or group of carbon atoms, e.g., in a hydrocarbyl, heteroalkyl, aryl, heteroaryl, heterocyclyl or carbocyclyl group, could suitably be replaced by an isotope of carbon, e.g., $^{13}C$;

any nitrogen atom or group of nitrogen atoms, e.g., in a heteroalkyl, heteroaryl, or heterocyclyl group, could suitably be replaced by an isotope of nitrogen, e.g., $^{15}N$; and any sulfur atom or group of sulfur atoms, e.g., in a heteroalkyl, heteroaryl, or heterocyclyl group, could suitably be replaced by an isotope of sulfur, e.g., $^{33}S$.

As used herein, a compound that is termed "isotopically-enriched" means that the abundance, e.g., of deuterium, $^{13}C$, or $^{15}N$ or $^{33}S$ at any relevant site of the compound is substantially more than the abundance of deuterium, $^{13}C$, or $^{15}N$ or $^{33}S$ naturally occurring at that site in an amount of the compound. A relevant site in a compound as used above is a site which would be designated as "H" or "C" or "N" or "S" in a chemical structure representation of the compound when not enriched. Relevant sites in the chemical structure of compounds taught herein for isotopic replacement an atom or atoms can include any site that is synthetically accessible for such isotopic replacement. The expression, "naturally occurring," as used above refers to the abundance of the particular atom which would be present at a relevant site in a compound if the compound was prepared without any affirmative synthesis step to enrich the abundance of a different isotope.

Thus, for example in a "deuterium-enriched" compound, the abundance of deuterium at any relevant site in the chemical structure can range from an amount that is substantially more than the natural abundance of deuterium (about 0.0115%) up to 100%, for example, from about 1% to about 100%, or from about 10% to about 100%, or from about 50% to about 100%, or from about 90% to about 100%.

Similarly, for a "$^{13}C$-enriched" compound, the abundance of $^{13}C$ at any relevant site in the chemical structure of the compound can range from an amount that is substantially more than the natural abundance of $^{13}C$ (about 1.109%) all the way up to 100%, for example, from about 5% to about 100%, or from about 10% to about 100%, or from about 50% to about 100%, or from about 90% to about 100%. Similarly for a "$^{15}N$-enriched" compound, the abundance of $^{15}N$ at any relevant site in the chemical structure of the compound can range from an amount that is substantially more than the natural abundance of $^{15}N$ (about 0.364%) all the way up to 100%, for example, from about 1% to about 100%, or from about 10% to about 100%, or from about 50% to about 100%, or from about 90% to about 100%.

Isotopically-enriched compounds can generally be prepared by conventional techniques known to those skilled in the art. Such isotopically-enriched compounds can also be prepared by adapting conventional processes as described in the scientific literature for synthesis of compounds disclosed herein, and using an appropriate isotopically-substituted reagent (or reagents) in place of the corresponding non isotopically-substituted reagent(s) employed in the conventional synthesis of the non isotopically-enriched compounds. Examples of ways to obtain a deuterium-enriched compound include exchanging hydrogen with deuterium or synthesizing the compound with deuterium-enriched starting materials.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described herein.

All other terms that are used herein in the description of the present invention will be understood to have meanings such as would be understood and accepted in the art.

For therapeutic purposes, the compounds that are described herein may be administered to a subject by any means that results in the contact of the active agent with the agent's site of action in the body of the subject. The compounds may be administered by any conventional means available for use in conjunction with pharmaceuticals, either as individual therapeutic agents, or in combination with other therapeutic agents. The compounds are preferably administered in therapeutically effective amounts for the treatment of the diseases and disorders described herein to a subject in need thereof.

A therapeutically effective amount of a compound as described herein may be readily determined by an attending diagnostician, as one skilled in the art, by the use of conventional techniques. The effective dose will vary depending upon a number of factors, including the type of disease or disorder treated, the extent of progression of the disease or disorder, the overall health status of the subject to be treated, the relative biological efficacy of the compound selected, the formulation of the active agent, and the route of administration used in treatment. Typically, the compounds are initially administered at lower dosage levels, with a gradual increase until the desired therapeutic effect is obtained.

Typical dose ranges may be from about 0.01 mg/kg to about 100 mg/kg of body weight per day, or from about 0.01 mg/kg to 10 mg/kg of body weight per day. Daily doses for adult humans may include about 25, 50, 100 and 200 mg, and an equivalent dose in a human child. The compounds may be administered in one or more unit dose forms. The unit dose may range from about 1 to about 500 mg administered one to four times a day, e.g., from about 10 mg to about 300 mg, administered two times a day. In an alternate method of describing an effective dose, an oral unit dose is one that is necessary to achieve a therapeutic blood serum level, e.g., a blood serum level of about 0.05 to 20 micrograms/mL in a subject, or about 1 to 20 micrograms/mL. The compounds described herein may be administered as the pure chemicals; however it is preferable to administer the active ingredient as a pharmaceutical composition.

Generally, compounds described herein may be administered to a patient alone or in combination with a pharmaceutically acceptable carrier. Accordingly, the compounds of the invention, for example, compounds of Formulae I-V(a), are preferably combined with a pharmaceutical carrier selected on the basis of the chosen route of administration and standard pharmaceutical practice—as described, for example, in Remington's Pharmaceutical Sciences (Mack Publishing Co., Easton, Pa., 1980), the disclosures of which are hereby incorporated herein by reference, in their entireties. The carrier(s) must be acceptable in the sense of being compatible with the other ingredients of the composition and not deleterious to the subject. The relative proportions of active ingredient and carrier may be determined, for example, by the solubility and chemical nature of the compounds, the chosen route of administration and standard pharmaceutical practice.

The compounds described herein may be formulated into pharmaceutical compositions by admixture with one or more pharmaceutically acceptable excipients. The excipients may be selected on the basis of the chosen route of administration and standard pharmaceutical practice, as described, for example, in Remington: The Science and Practice of Pharmacy, 20th ed.; Gennaro, A. R., Ed.; Lippincott Williams & Wilkins: Philadelphia, Pa., 2000. The compositions may be formulated to control and/or delay the release of the active agent(s), as in fast-dissolve, modified-release, or sustained-release formulations.

According to some embodiments of the invention, a pharmaceutical composition herein may contain both an amount of a FASN inhibitor having a chemical structure as described herein, and an amount of an antipsychotic agent. Suitable antipsychotic agents for such a dual API pharmaceutical composition include, for example, clozapine, risperidone, aripiprazole, olanzapine, quetiapine and ziprasidone. Such a dual API pharmaceutical composition may contain, for example, per dosage unit, from about 5 to about 1000 mg, or more, of a FASN inhibitor having a chemical structure as described herein, and from about 5 to about 1000 mg of an antipsychoric agent. In such embodiment, it is not necessary that each single dosage unit include an effective amount so long as the total amount of drug administered to a patient is an effective amount of each. Therefore, for example, a patient may require two or more single dosage units to receive effective amounts of both agents. The dosage may be adjusted appropriately to achieve desired drug levels, locally or systemically of both drugs.

The compositions can be prepared for administration by oral means; parenteral means, including intravenous, intramuscular, and subcutaneous routes; topical or transdermal means; transmucosal means, including rectal, vaginal, sublingual and buccal routes; ophthalmic means; or inhalation means. Preferably the compositions are prepared for oral administration, particularly in the form of tablets, capsules or syrups; for parenteral administration, particularly in the form of liquid solutions, suspensions or emulsions; for intranasal administration, particularly in the form of powders, nasal drops, or aerosols; or for topical administration, such as creams, ointments, solutions, suspensions aerosols, powders.

For oral administration, e.g., tablets, pills, powders, capsules, and troches, formulations can contain one or more of the following: diluents or fillers such as starch, or cellulose; binders such as microcrystalline cellulose, gelatins, or polyvinylpyrrolidones; disintegrants such as starch or cellulose derivatives; lubricants such as talc or magnesium stearate; glidants such as colloidal silicon dioxide; sweetening agents such as sucrose or saccharin; and flavoring agents such as peppermint or cherry flavoring. Capsules may contain any of the excipients as listed above, and may additionally contain a semi-solid or liquid carrier, such as a polyethylene glycol. Solid oral dosage forms may have coatings of sugar, shellac, or enteric agents. Liquid preparations may be in the form of aqueous or oily suspensions, solutions, emulsions, syrups, elixirs, etc., or may be presented as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include, for example, mixtures of alcohols and water, and buffered media. Nonaqueous solvents include, for example, alcohols and glycols, such as ethanol, and polyethylene glycols; oils, such as vegetable oils; fatty acids and fatty acid esters. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; and antibacterial agents, such as chlorobutanol, or phenol; buffers. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be presented as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably presented as unit-dose suppositories, with a solid based carrier, such as cocoa butter, and may include a salicylate.

Pharmaceutical kits may comprise a therapeutically effective amount of a therapeutic compound as described herein, in one or more sterile containers are also within the ambit of the present invention. Sterilization of the container may be carried out using conventional sterilization methodology well known to those skilled in the art. The sterile containers of materials may comprise separate containers, or one or more multi-part containers. The compound as described herein may be separate, or may be combined into a single dosage form as described above. Such kits may further include, if desired, one or more of various conventional pharmaceutical kit components, e.g., one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in such a kit.

The compounds of the present invention may be used in methods for treating a condition or disorder associated with increased FASN expression and/or activity. Such disorders include, for example:

obesity, eating disorders drug induced body weight gain; e.g. atypical antipsychotic-induced weight gain cardiovascular diseases, gastrointestinal disorders, dermatological disorders, metabolic diseases (e.g., non-alcoholic hepatic steatosis (NASH)) and Type 2 diabetes. (NASH is a serious liver disease for which the pathogenesis and prognosis have not been clearly determined. It is generally believed that abnormal fatty acid metabolism may be involved in the pathogenesis of NASH, with triacylglycerols and their fatty acid precursors likely possibly accumulating in the hepatocyte.)

viral disorders wherein FASN inhibition correlates inhibition of viral replication, and cancers and/or cancer metastasis (e.g., human breast, ovarian, prostate, colon, lung, bladder, stomach and kidney cancers).

The methods of treatment provided herein comprise administering to a subject in need of such treatment a therapeutically effective amount of a compound of the invention, preferably a compound of Formulae I-V(a). Accordingly, the invention includes a method of treatment of a subject suffering from a disorder mediated by fatty acid synthase, comprising administering to the subject a therapeutically effective amount of a compound according to Formulae I, II, III, IV, V or V(a); or a therapeutically effective amount of a pharmaceutical composition comprising a compound according to Formulae I, II, III, IV, V or V(a). The invention also includes a method of treating a subject who is suffering from obesity, weight gain, or weight gain, or weight gain associated with drug therapy, e.g., drug therapy with an antipsychotic agent, e.g., clozapine, risperidone, aripiprazole, olanzapine, quetiapine and ziprasidone. The method comprises administering to the subject a therapeutically effective amount of a compound according to Formulae I, II, III, IV, V or V(a); or a therapeutically effective amount of a pharmaceutical composition comprising a compound according to Formulae I-V(a).

The compounds of the present invention can be synthesized using the methods as described generally herein, and by methods that are described in the working examples that are provided herein, or variations thereon. The compounds of the invention may also be prepared by using other known synthetic methods, or variations thereon. Unless otherwise stated, starting compounds in the synthetic methods described herein are commercially available, or may be readily synthesized by known methods. The reactions are generally performed in solvents that are appropriate to the reagents and reaction conditions. The materials employed in the reactions are understood to be suitable for the transformations being effected, and the materials and methods employed in product isolation understood to be suitable for the product compounds. Also, in the description of the synthetic methods herein, it is to be understood that all proposed reaction conditions, including choice of solvent, reaction atmosphere, reaction temperature, duration of experiment and workup procedures are chosen to be conditions appropriate for that reaction as would be understood by one skilled in the art of organic synthesis. It is understood that the examples and embodiments described herein are provided for illustrative purposes only, and that various modifications or changes in light thereof will be clearly understood to be included within the scope of this application and the scope of the appended claims. Specific chemical transformations are listed in the schemes and working examples provided herein, and the skilled person will readily appreciate that a variety of different reagents may be used in place of those listed. Common replacements for such reagents can be found in, for example, in texts such as "Encyclopedia of Reagents for Organic Synthesis" Leo A. Paquette, John Wiley & Son Ltd (1995) or "Comprehensive Organic Transformations: A Guide to Functional Group Preparations" Richard C. Larock. Wiley-VCH and "Strategic Applications of Named Reactions in Organic Synthesis" Kurti and Czako, Elsevier, 2005 and references therein.

Compounds according to Formula I-V(a) may be prepared by organic syntheses utilizing known organic reactions. For example, Scheme 1 below, outlines one of the general routes that was used to synthesize numerous X=O examples of the invention. In Scheme 1, starting with a compound of formula 1 (for example, the known 4-(4-iodophenoxy)piperidine-1-carboxylic acid tert-butyl ester 1, or 4-(4-bromophenoxy)piperidine-1-carboxylic acid tert-butyl ester), a transition metal (e.g., palladium) catalyzed coupling reaction with an appropriate $R^6$ boronic acid or $R^6$ organostannane reagent can be used to produce an intermediate of formula 2. The intermediate of formula 2 can then be deprotected to remove the protecting group, PG (for example, under acidic conditions if the PG is a Boc group) to give an intermediate amine of formula 3. The intermediate amine of formula 3 may then be reacted with reagents such as carboxylic acids, carboxylic acid halides, carboxylic acid anhydrides, isocyanates, or sulfonyl halides to produce compounds according to Formulae I-V(a).

Alternatively, the above order of the steps may be reversed, i.e., the starting compound of formula 1 can be deprotected to produce an intermediate amine of formula 4. The intermediate amine of formula 4 may then be reacted with reagents such as carboxylic acids, carboxylic acid halides, carboxylic acid anhydrides, isocyanates, or sulfonyl halides to produce an intermediate of formula 5. The intermediate amine of formula 5 may then be reacted with an appropriate $R^6$ boronic acid or $R^6$ organostannane reagent with transition metal (e.g., palladium) catalysis to produce compounds of Formulae I-V(a).

Scheme 1: General Synthesis method A:

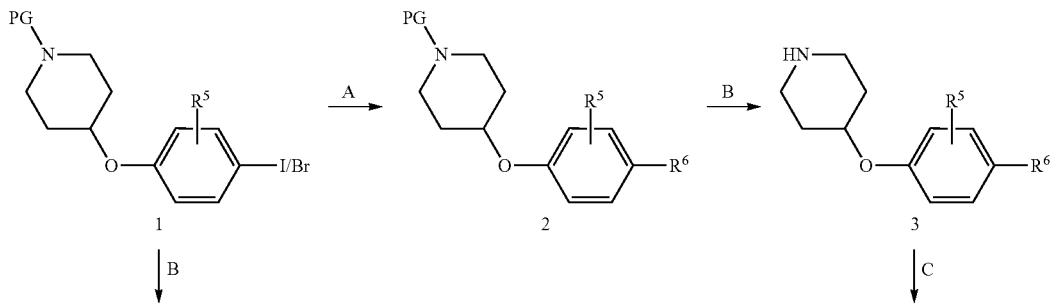

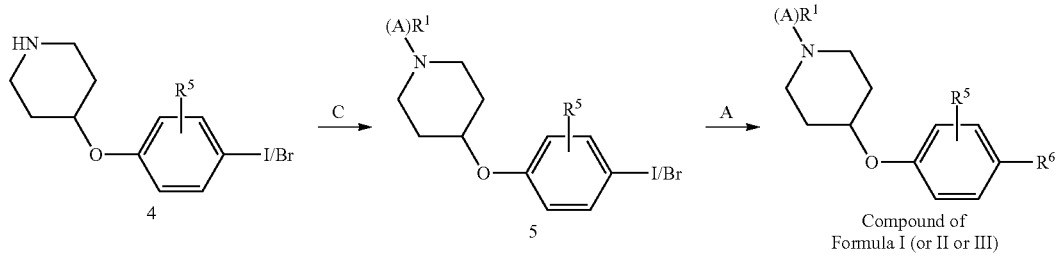

PG = Protecting Group;
A = transition metal catalyzed coupling step;
B = piperidine nitrogen deprotection step;
C = piperidine nitrogen acylation (or sulfonylation) step.

Other synthetic methodology can also be employed. For example, intermediates of formula 5 in Scheme 1 may also be synthesized using a Mitsunobu reaction between an $R^5$ substituted iodo- or bromophenol and N-substituted-hydroxypiperidine, as in Scheme 1a Scheme 1a: Mitsunobu Synthesis of Intermediate of Formula 5 Scheme 1

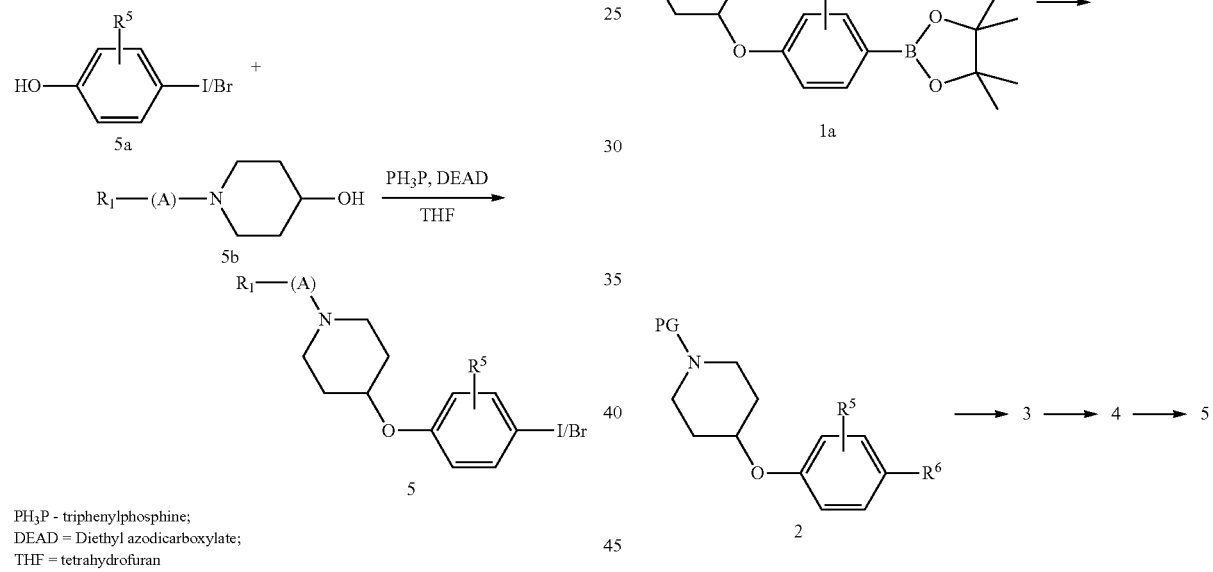

PH$_3$P - triphenylphosphine;
DEAD = Diethyl azodicarboxylate;
THF = tetrahydrofuran Compounds of Formulae I-V(a) may also be synthesized (as shown in Scheme 2 below) by reversing the functional groups on the coupling partners shown in Scheme 1, for example starting with a boronate intermediate of Formula 1a (for example, 4-[4-(4,4,5,5-tetramethyl-1,3,2-dioxaborolan-2-yl)-phenoxy]-piperidine-1-carboxylic acid tert-butyl ester). Palladium catalyzed coupling of a compound of formula 1 with bis(pinacolatato)diboron would provide such a boronate intermediate of formula 1a. The boronate intermediate 1a can be readily converted to $R^6$ substituted compounds according to Formula I (or II-V(a)) by coupling an appropriate heteroaryl-halide or triflate; followed by deprotection of the piperidine nitrogen and acylation (or sulfonation) of the piperidine nitrogen, similar to the synthesis steps described in Scheme 1

Scheme 2: Synthesis starting with Boronate Intermediates according to Formula Ia

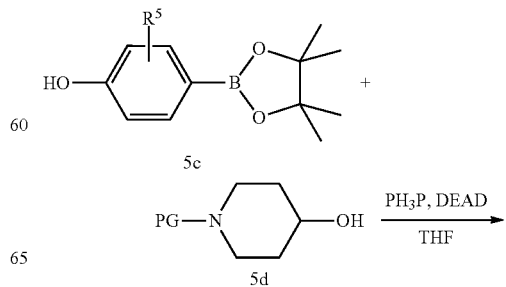

Mitsunobu chemistry could also be used to produce intermediates of formula 1a, e.g., by reaction between an $R^5$ substituted phenol boronate and an N-protected (or N-substituted) hydroxypiperidine, as in Scheme 2a, below Scheme 2a: Mitsunobu Synthesis of Intermediate of Formula 1a of Scheme 2

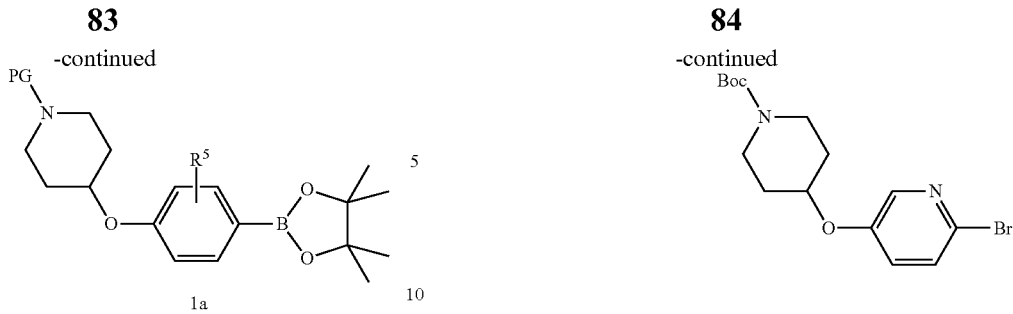

The boronate intermediate 1a could also be synthesized in other ways, for example by, employing an SNAr reaction between a 4-fluoroiodobenzene and a protected 4-hydroxy-piperidine of Formula 5d.

Compounds according to Formulae I-V(a), wherein the aromatic ring contains one or two nitrogen ring atoms (e.g., pyridinyl and pyrimidinyl ring) may be synthesized from intermediates of formula 1H (heteroaryl analogs of compounds of formula 1) as outlined in Scheme 3 below using Mitsunobu reaction conditions.

Preparation of a heteroaryl (e.g., pyridyl or pyrimidyl) intermediate of Formula 1H can of course be carried out in other ways, for example, by employing an SnAr reaction between a 2-chloropyridine or 2-chloropyrimidine intermediate and an N-protected-4-hydroxypiperidine (for example, Boc protected) as in Scheme 3b below. Completion of the synthesis of a compound of Formulae I-V(a) can be done by installation of an $R^6$ aryl or heteroaryl group (e.g., via a Suzuki reaction), followed by deprotection of the piperidine nitrogen, and acylation (or sulfonylation) of the piperidine nitrogen, as described previously.

Scheme 3: Mitsunobu Synthesis and Use of Intermediates of Formula 1H

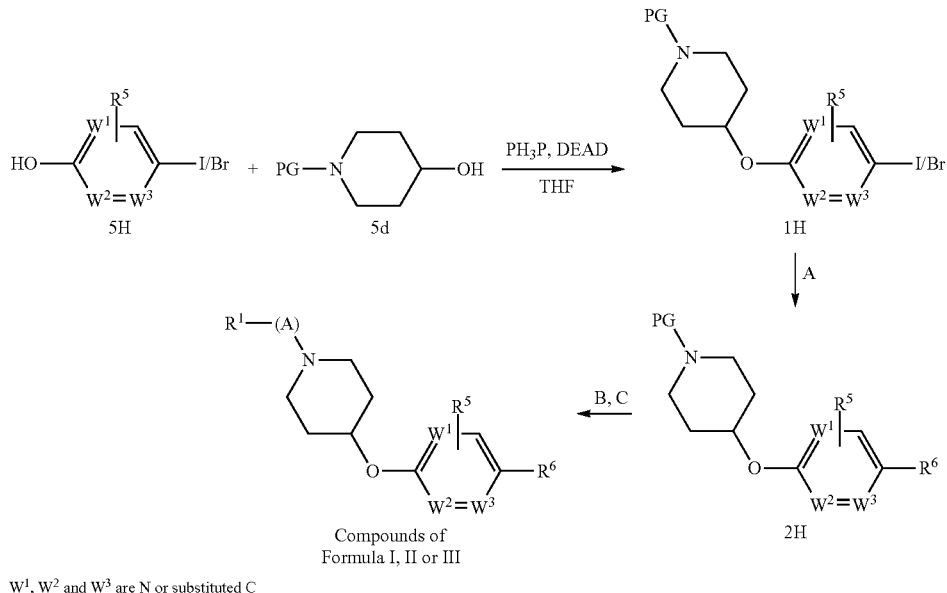

$W^1$, $W^2$ and $W^3$ are N or substituted C

For example, the Mitsunobu reaction to produce a pyridyl intermediate of Formula 1H could be carried out between a 6-bromo-pyridin-3-ol and an N-protected-4-hydroxypiperidine (for example, Boc protected) as in Scheme 3a below Scheme 3a: Mitsunobu Reaction of 6-bromopyridin-3-ol with tert-butyl 4-hydroxypiperidine-1-carboxylate

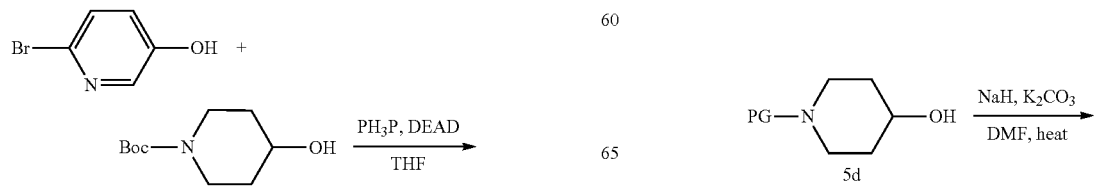

Scheme 3b: SnAR Reaction of a 2-chloropyridine or 2-chloropyrimidine with an N-protected-4-hydroxypiperidine

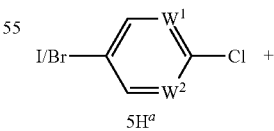

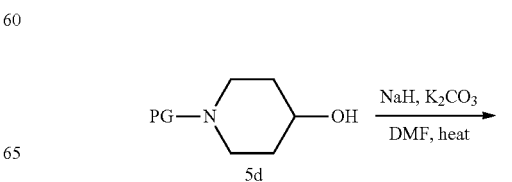

-continued

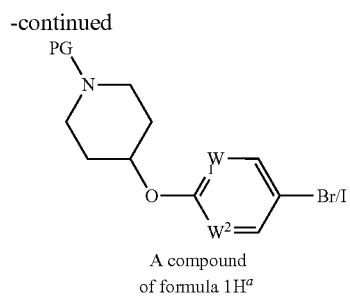

A compound
of formula 1H$^a$ $W^1$ = N, and $W^2$ = N or C (substituted or unsubstituted)

Examples of compounds of Formula I, II or III, where $X=SO_2$, $X=NR^9$ and $X=S$ may be synthesized using the same kinds of chemistry as has been described previously for:

deprotection of the piperidine nitrogen;

acylation or sulfonation of the deprotected piperidine nitrogen; and transition metal (e.g., Pd) catalyzed coupling to install the aromatic (or heteroaromatic) $R^6$ group.

For compounds of Formula I, II or III, where $X=SO_2$, a suitable starting material to use in place of the Formula 1 intermediate (in Scheme 1) would be an appropriately N-protected 4-(4-bromobenzenesulfonyl)piperidine (or 4-(4-iodobenzenesulfonyl)piperidine). Similarly, for compounds of Formula I, II or II, where $X=NR^9$, a suitable starting material to use in place of the Formula 1 intermediate (in Scheme 1) would include, for example, appropriately N-protected 4-(4-bromophenylamino)-piperidine (or 4-(4-iodophenylamino)-piperidine) compounds.

For compounds of Formula I, II or III, where X=S, a suitable starting material to use in place of the Formula 1 intermediate (in Scheme 1) would be an appropriately N-protected 4-(4-bromophenyl sulfanyl)-piperidine or 4-(4-iodophenylsulfanyl)-piperidine. Such sulfanyl intermediates could be prepared, for example, by converting the hydroxyl group of a N-protected-4-hydroxypiperidine intermediate of formula 5d to a leaving group (e.g., mesylate, tosylate, triflate, etc), and reacting with a 4-bromo- or 4-iodothiophenol, as shown in Scheme 4 below.

Scheme 4: Preparation of compounds of Formulae I, II and III via synthetic intermediates of Formula 1S

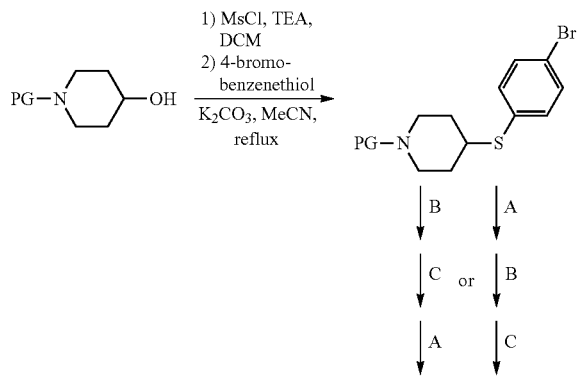

-continued

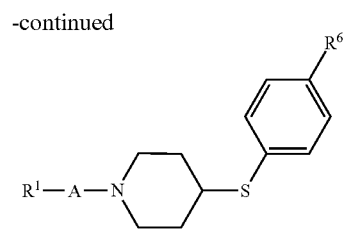

PG = Protecting Group;
A = transition metal catalyzed coupling step;
B = piperidine nitrogen deprotection step;
C = piperidine nitrogen acylation (or sulfonylation) step.

FASN Enzyme activity may be determined by detecting coenzyme A (CoA), a product of FASN-catalyzed synthesis of palmitate from acetyl-CoA and malonyl-CoA with NADPH as a cofactor. The assay is fluorescence-based and measures the interaction of free CoA with 7-diethylamino-3-(4'-malemimidylphenyl)-4-methylcoumarin (CPM; Life Technologies, CA) as described in Chung et al (2008). The coumarin derivative CPM contains a thiol-reactive maleimide that becomes fluorescent upon interaction with the sulfhydryl group of CoA.

For the example compounds described herein, the reaction was performed in 384-well low volume non-binding plates (Corning, N.Y.) using recombinant human baculovirus-expressed GST-tagged FASN. The 20-μL assay mixture contained 50 mM HEPES (pH 7.5), 5 nM FASN, 150 μM NADPH (Sigma, St. Louis, Mo.), 10 μM acetyl-CoA (Sigma), 25 μM malonyl-CoA (Sigma) and test compound [diluted in dimethyl sulfoxide (DMSO); 0.5% DMSO final in assay after 100 nL addition]. See, Chung et al.; "A fluorescence-based thiol quantification assay for ultra-high-throughput screening for inhibitors of coenzyme A production," Assay Drug Dev Tech 2008; 6:361-374.

The reaction was initiated by adding malonyl-CoA, followed by incubation for 90 minutes at 250° C. A stock solution of the CPM reagent was prepared in DMSO at 66 μM and stored at −200° C. To detect CoA produced in the FASN reaction, the CPM stock was diluted to 50 μM in 70% ethanol and added at 4 L/well to the assay plate. The reaction mixture was then incubated for 30 minutes. Fluorescence was measured using the EnVision™ 2102 multi-label plate reader (PerkinElmer, Waltham, Mass.) utilizing a general dual mirror, a 390 nM excitation filter and a 530 nM emission filter. Data analysis was performed using ActivityBase (IDBS, Guilford, UK). $IC_{50}$ values were calculated by plotting the percent inhibition versus log 10 of the concentration of the compound, and fitting to the nonlinear regression sigmoidal dose-response (variable slope) equation in XLFit (IDBS). The $IC_{50}$ data for the Examples described herein is provided in Tables 2 and 2a below (A=1 to 99 nM; B=100 to 999 nM; C=1000-10,000 nM)

TABLE 2

$IC_{50}$ data for Compounds of Formulae I-V/V(a)

| Ex # | Activity |
|---|---|
| 1 | A |
| 2 | A |
| 3 | B |
| 4 | A |
| 5 | C |
| 6 | A |
| 7 | A |
| 8 | B |

TABLE 2-continued

IC$_{50}$ data for Compounds of Formulae I-V/V(a)

| Ex # | Activity |
|---|---|
| 9 | C |
| 10 | A |
| 11 | C |
| 12 | C |
| 13 | C |
| 14 | C |
| 15 | C |
| 16 | C |
| 17 | C |
| 18 | B |
| 19 | C |
| 20 | C |
| 21 | C |
| 22 | A |
| 23 | A |
| 24 | A |
| 25 | C |
| 26 | C |
| 27 | C |
| 28 | A |
| 29 | A |
| 30 | A |
| 31 | A |
| 32 | B |
| 33 | B |
| 34 | A |
| 35 | A |
| 36 | A |
| 37 | A |
| 38 | A |
| 39 | B |
| 40 | B |
| 41 | B |
| 42 | A |
| 43 | A |
| 44 | A |
| 45 | A |
| 46 | A |
| 47 | A |
| 48 | A |
| 49 | A |
| 50 | B |
| 51 | C |
| 52 | C |
| 53 | C |
| 54 | B |
| 55 | C |
| 56 | C |
| 57 | B |
| 58 | B |
| 59 | A |
| 60 | A |
| 61 | A |
| 62 | A |
| 63 | B |
| 64 | B |
| 65 | A |
| 66 | B |
| 67 | B |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | B |
| 86 | A |
| 87 | C |
| 88 | A |
| 89 | A |
| 90 | B |
| 91 | A |
| 92 | C |
| 93 | A |
| 94 | A |
| 95 | A |
| 96 | A |
| 97 | B |
| 98 | A |
| 99 | B |
| 100 | A |
| 101 | A |
| 102 | B |
| 103 | A |
| 104 | A |
| 105 | A |
| 106 | B |
| 107 | C |
| 108 | B |
| 109 | C |
| 110 | C |
| 111 | C |
| 112 | B |
| 113 | B |
| 114 | B |
| 115 | B |
| 116 | A |
| 117 | C |
| 118 | C |
| 119 | C |
| 120 | A |
| 121 | C |
| 122 | C |
| 123 | C |
| 124 | C |
| 125 | C |
| 126 | A |
| 127 | C |
| 128 | C |
| 129 | C |
| 130 | C |
| 131 | A |
| 132 | C |
| 133 | C |
| 134 | C |
| 135 | B |
| 136 | C |
| 137 | B |
| 138 | C |
| 139 | C |
| 140 | C |
| 141 | C |
| 142 | C |
| 143 | C |
| 144 | C |
| 145 | C |
| 146 | C |
| 147 | C |
| 148 | C |
| 149 | C |
| 150 | B |
| 151 | B |
| 152 | A |
| 153 | C |
| 154 | A |
| 155 | C |
| 156 | B |
| 157 | C |
| 158 | C |
| 159 | C |
| 160 | C |

TABLE 2-continued

IC$_{50}$ data for Compounds of Formulae I-V/V(a)

| Ex # | Activity |
|---|---|
| 161 | C |
| 162 | C |
| 163 | B |
| 164 | B |
| 165 | B |
| 166 | C |
| 167 | A |
| 168 | B |
| 169 | B |
| 170 | B |
| 171 | C |
| 172 | C |
| 173 | C |
| 174 | C |
| 175 | C |
| 176 | C |
| 177 | C |
| 178 | B |
| 179 | B |
| 180 | A |
| 181 | A |
| 182 | B |
| 183 | C |
| 184 | B |
| 185 | B |
| 186 | A |
| 187 | A |
| 188 | B |
| 189 | B |
| 190 | A |
| 191 | C |
| 192 | C |
| 193 | C |
| 194 | C |
| 195 | C |
| 196 | C |
| 197 | C |
| 198 | C |
| 199 | C |
| 200 | A |
| 201 | NT |
| 202 | A |
| 203 | A |
| 204 | B |
| 205 | A |
| 206 | C |
| 207 | B |
| 208 | C |
| 209 | C |
| 210 | C |
| 211 | C |
| 212 | C |
| 213 | C |
| 214 | C |
| 215 | B |
| 216 | C |
| 217 | B |
| 218 | C |
| 219 | A |
| 220 | A |
| 221 | A |
| 222 | A |
| 223 | A |
| 224 | A |
| 225 | A |
| 226 | A |
| 227 | A |
| 228 | B |
| 229 | B |
| 230 | A |
| 231 | C |
| 232 | C |
| 233 | C |
| 234 | B |
| 235 | C |
| 236 | B |
| 237 | C |
| 238 | B |
| 239 | C |
| 240 | C |
| 241 | C |
| 242 | C |
| 243 | C |
| 244 | A |
| 245 | B |
| 246 | C |
| 247 | B |
| 248 | B |
| 249 | B |
| 250 | A |
| 251 | B |
| 252 | B |
| 253 | C |
| 254 | A |
| 255 | A |
| 256 | B |
| 257 | A |
| 258 | B |
| 259 | B |
| 260 | A |
| 261 | A |
| 262 | A |
| 263 | A |
| 264 | C |
| 265 | A |
| 266 | B |
| 267 | A |
| 268 | C |
| 269 | B |
| 270 | B |
| 271 | B |
| 272 | A |
| 273 | A |
| 274 | A |
| 275 | B |
| 276 | C |
| 277 | B |
| 278 | A |
| 279 | B |
| 280 | A |
| 281 | C |
| 282 | C |
| 283 | A |
| 284 | C |
| 285 | A |
| 286 | C |
| 287 | B |
| 288 | B |
| 289 | C |
| 290 | C |
| 291 | C |
| 292 | B |
| 293 | C |
| 294 | C |
| 295 | A |
| 296 | B |
| 297 | B |
| 298 | A |
| 299 | C |
| 300 | C |
| 301 | C |
| 302 | A |
| 303 | A |
| 304 | C |
| 305 | B |
| 306 | C |
| 307 | B |
| 308 | C |
| 309 | A |
| 310 | C |
| 311 | A |
| 312 | B |

TABLE 2-continued

IC$_{50}$ data for Compounds of Formulae I-V/V(a)

| Ex # | Activity |
|---|---|
| 313 | C |
| 314 | C |
| 315 | C |
| 316 | A |
| 317 | A |
| 318 | A |
| 319 | C |
| 320 | A |
| 321 | B |
| 322 | A |
| 323 | C |
| 324 | A |
| 325 | A |
| 326 | B |
| 327 | A |
| 328 | B |
| 329 | A |
| 330 | B |
| 331 | A |
| 332 | C |
| 333 | C |
| 334 | B |
| 335 | C |
| 336 | B |
| 337 | C |
| 338 | B |
| 339 | C |
| 340 | C |
| 341 | C |
| 342 | C |
| 343 | C |
| 344 | B |
| 345 | C |
| 346 | B |
| 347 | B |
| 348 | A |
| 349 | A |
| 350 | B |
| 351 | B |
| 352 | A |
| 353 | A |
| 354 | A |
| 355 | C |
| 356 | C |
| 357 | C |
| 358 | B |
| 359 | A |
| 360 | B |
| 361 | C |
| 362 | A |
| 363 | B |
| 364 | B |
| 365 | C |
| 366 | A |
| 367 | C |
| 368 | C |
| 369 | B |
| 370 | B |
| 371 | A |
| 372 | A |
| 373 | B |
| 374 | B |
| 375 | A |
| 376 | A |
| 377 | A |
| 378 | C |
| 379 | C |
| 380 | C |
| 381 | B |
| 382 | C |
| 383 | C |
| 384 | C |
| 385 | C |
| 386 | C |
| 387 | C |
| 388 | C |

TABLE 2-continued

IC$_{50}$ data for Compounds of Formulae I-V/V(a)

| Ex # | Activity |
|---|---|
| 389 | C |
| 390 | C |
| 391 | C |
| 392 | C |
| 393 | C |
| 394 | C |
| 395 | C |
| 396 | C |
| 397 | C |
| 398 | C |
| 399 | C |
| 400 | C |
| 401 | C |
| 402 | C |
| 403 | C |
| 404 | C |
| 405 | C |
| 406 | C |
| 407 | C |
| 408 | C |
| 409 | C |
| 410 | B |
| 411 | B |
| 412 | A |
| 413 | C |
| 414 | C |
| 415 | C |
| 416 | B |
| 417 | B |
| 418 | A |
| 419 | B |
| 420 | B |
| 421 | C |
| 422 | B |
| 423 | B |
| 424 | A |
| 425 | A |
| 426 | C |
| 427 | C |
| 428 | B |
| 429 | A |
| 430 | C |
| 431 | A |
| 432 | A |
| 433 | B |
| 434 | B |
| 435 | B |
| 436 | A |
| 437 | A |
| 438 | A |
| 439 | C |
| 440 | A |
| 441 | C |
| 442 | C |
| 443 | C |
| 444 | C |
| 445 | C |
| 446 | C |
| 447 | C |
| 448 | C |
| 449 | C |
| 450 | A |
| 451 | A |
| 452 | A |
| 453 | B |
| 454 | A |
| 455 | C |
| 456 | A |
| 457 | A |
| 458 | A |
| 459 | A |
| 460 | B |
| 461 | B |
| 462 | A |
| 463 | C |
| 464 | C |

TABLE 2-continued

IC$_{50}$ data for Compounds of Formulae I-V/V(a)

| Ex # | Activity |
|---|---|
| 465 | B |
| 466 | A |
| 467 | A |
| 468 | A |
| 469 | B |
| 470 | B |
| 471 | A |
| 472 | B |
| 473 | B |
| 474 | A |
| 475 | A |
| 476 | A |
| 477 | A |
| 478 | A |
| 479 | A |
| 480 | A |
| 481 | A |
| 482 | A |
| 483 | A |
| 484 | B |
| 485 | A |
| 486 | A |
| 487 | A |
| 488 | A |
| 489 | C |
| 490 | C |
| 491 | B |
| 492 | C |
| 493 | C |
| 494 | C |
| 495 | B |
| 496 | C |
| 497 | C |
| 498 | C |
| 499 | C |
| 500 | C |
| 501 | C |
| 502 | C |
| 503 | C |
| 504 | C |
| 505 | C |
| 506 | C |
| 507 | C |
| 508 | C |
| 509 | C |
| 510 | C |
| 511 | C |
| 512 | C |
| 513 | C |
| 514 | C |
| 515 | C |
| 516 | A |
| 517 | A |
| 518 | A |
| 519 | C |
| 520 | A |
| 521 | B |
| 522 | C |
| 523 | C |
| 524 | B |
| 525 | B |
| 526 | C |
| 527 | C |
| 528 | B |

TABLE 2a

IC$_{50}$ data for Additional Compounds of Formulae I-V(a)

| Ex # | Activity |
|---|---|
| 529 | C |
| 530 | A |
| 531 | C |
| 532 | C |
| 533 | C |
| 534 | C |
| 535 | C |
| 536 | C |
| 537 | A |
| 538 | A |
| 539 | A |
| 540 | A |
| 541 | A |
| 542 | A |
| 543 | C |
| 544 | A |
| 545 | A |
| 546 | C |
| 547 | C |
| 548 | C |
| 549 | C |
| 550 | C |
| 551 | C |
| 552 | C |
| 553 | C |
| 554 | C |
| 555 | C |
| 556 | C |
| 557 | C |
| 558 | C |
| 559 | A |
| 560 | B |
| 561 | C |
| 562 | C |
| 563 | A |
| 564 | C |
| 565 | B |
| 566 | A |
| 567 | B |
| 568 | C |
| 569 | B |
| 570 | A |
| 571 | C |
| 572 | C |
| 573 | C |
| 574 | A |
| 575 | A |
| 576 | C |
| 577 | B |
| 578 | C |
| 579 | B |
| 580 | A |
| 581 | A |
| 582 | C |
| 583 | A |
| 584 | A |
| 585 | B |
| 586 | C |
| 587 | A |
| 588 | A |
| 589 | A |
| 590 | A |
| 591 | A |
| 592 | A |
| 593 | C |
| 594 | A |
| 595 | B |
| 596 | A |
| 597 | C |
| 598 | B |
| 599 | C |
| 600 | B |
| 601 | A |
| 602 | C |
| 603 | C |
| 604 | C |
| 605 | C |
| 606 | C |

TABLE 2a-continued

IC$_{50}$ data for Additional Compounds of Formulae I-V(a)

| Ex # | Activity |
|---|---|
| 607 | C |
| 608 | B |
| 609 | A |
| 610 | C |
| 611 | C |
| 612 | A |
| 613 | C |
| 614 | C |
| 615 | C |
| 616 | C |
| 617 | C |
| 618 | C |
| 619 | C |
| 620 | C |
| 621 | C |
| 622 | C |
| 623 | C |
| 624 | C |
| 625 | A |
| 626 | A |
| 627 | C |
| 628 | A |
| 629 | C |
| 630 | B |
| 631 | A |
| 632 | A |
| 633 | A |
| 634 | NT |
| 635 | NT |
| 636 | NT |
| 637 | NT |
| 638 | NT |
| 639 | NT |
| 640 | NT |
| 641 | NT |
| 642 | NT |
| 643 | NT |
| 644 | NT |
| 645 | NT |
| 646 | NT |
| 647 | NT |

EXAMPLES

Example 1. 1-[4-(4-Isoquinolin-6-yl-phenoxy)-piperidin-1-yl]-propan-1-one

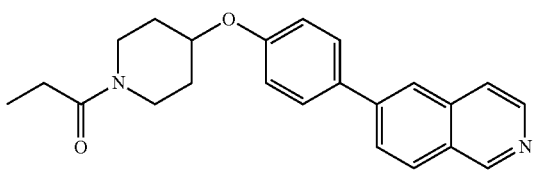 [SMILES: CCC(=O)N1CCC(Oc2ccc(-c3ccc4cnccc4c3)cc2)CC1]

Step 1. 1-[4-(4-Bromophenoxy)-piperidin-1-yl]-propan-1-one 4-(4-Bromophenoxy)piperidine (1.0 g, 3.9 mmol) and N,N-diisopropylethylamine (DIPEA) (2.72 mL, 15.6 mmol) in tetrahydrofuran (THF) (10 mL) was added propanoyl chloride (0.679 mL, 7.81 mmol). After 2 h stirring at rt, the mixture was concentrated, the product suspended in EtOAc, and washed with 1N Na$_2$CO$_3$, water and brine and then dried (MgSO$_4$). The product was chromatographed on ISCO (80 g silica gel column, 30-90% EtOAc/hexanes) to give a viscous oil. LCMS m/z=313 (M+1); $^1$H NMR (CDCl$_3$) δ: 7.37 (d, 2H, J=7 Hz), 6.79 (d, 2H, J=7 Hz), 4.49 (q, 1H, J=3 Hz), 3.74-3.80 (m, 1H), 3.59-3.71 (m, 2H), 3.36-3.42 (m, 1H), 2.36 (q, 2H, J=7.5 Hz), 1.87-1.94 (m, 2H), 1.73-1.84 (m, 2H), 1.16 (t, 3H, J=7.5 Hz).

Step 2. 1-[4-(4-Isoquinolin-6-yl-phenoxy)-piperidin-1-yl]-propan-1-one

Palladium acetate (0.00719 g, 0.0320 mmol) and triphenylphosphine (0.0336 g, 0.128 mmol) in dioxane (5 mL) were stirred 15 min under an atmosphere of nitrogen. 1-[4-(4-bromophenoxy)piperidin-1-yl]propan-1-one (0.20 g, 0.646 mmol), isoquinoline-6-boronic acid (0.122 g, 0.705 mmol), N,N-dimethylformamide (DMF) (3 mL) and 1M sodium carbonate (2.56 mL) were added and heated at 80° C. for 17 h. The mixture was concentrated, was dissolved in EtOAc, washed with 1N Na$_2$CO$_3$, water and brine, then dried over MgSO$_4$. The product was purified by ISCO (12 g silica gel column, 5% MeOH/EtOAc) to give an oil. The HCl salt was synthesized by adding 0.25 mL of 1M HCl-ether solution to a dichloromethane (DCM) solution of base. The salt was recrystallized from DCM-ether and dried to give a light yellow solid (125 mg, 54%). Analysis: LCMS m/z=361 (M+1); $^1$H NMR (DMSO-d$_6$ (deuterated dimethylsulfoxide)) δ: 9.72 (s, 1H), 8.63 (d, 1H, J=6.5 Hz), 8.56 (s, 1H), 8.52 (d, 1H, J=8 Hz), 8.39 (d, 1H, J=6.5 Hz), 8.33 (dd, 1H, J=2, 8 Hz), 7.92 (d, 2H, J=8 Hz), 7.21 (d, 2H, J=8 Hz), 4.76 (q, 1H, J=4 Hz), 3.89 (m, 1H), 3.72 (m, 1H), 3.34-3.40 (m, 1H), 3.25-3.31 (m, 1H), 2.35 (q, 2H, J=7.5 Hz), 1.99 (b, 2H), 1.63-1.67 (m, 1H), 1.54 (m, 1H), 1.00 (t, 3H, J=7.5 Hz).

Example 2. 1-[4-(4-Quinolin-3-yl-phenoxy)-piperidin-1-yl]-propan-1-one

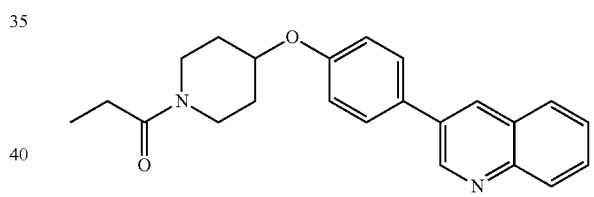

This compound was synthesized using the previous method with 1-[4-(4-bromo-phenoxy)-piperidin-1-yl]propan-1-one (0.150 g, 0.480 mmol), and 3-quinolineboronic acid (0.1247 g, 0.7207 mmol) (120 mg, 69%). Analysis: LCMS m/z=361 (m+1); $^1$H NMR (CDCl$_3$) δ: 9.16 (s, 1H), 8.24 (d, 1H, J=2 Hz), 8.10 (d, 1H, J=8 Hz), 7.86 (d, 1H, J=8 Hz), 7.68-7.73 (m, 1H), 7.66 (d, 2H, J=8 Hz), 7.55-7.59 (m, 1H), 7.07 (d, 2H, J=8 Hz), 4.63 (q, 1H, J=4 Hz), 3.79-3.85 (m, 1H), 3.65-3.76 (m, 2H), 3.41-3.47 (m, 1H), 2.38 (q, 2H, J=7.5 Hz), 1.95-1.98 (b, 2H), 1.84-1.90 (b, 2H), 1.17 (t, 3H, J=7.5 Hz).

Example 3. 2-Methyl-1-[4-(4-quinolin-7-yl-phenoxy)-piperidin-1-yl]-propan-1-one

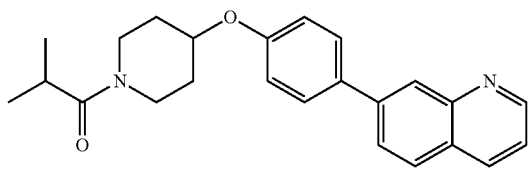 [SMILES: CC(C)C(=O)N1CCC(Oc2ccc(-c3ccc4cccnc4c3)cc2)CC1]

Step 1. 7-[4-(Piperidin-4-yloxy)-phenyl]-quinoline dihydrochloride

Palladium acetate (0.0278 g, 0.124 mmol) and triphenylphosphine (0.130 g, 0.496 mmol) in dioxane (10 mL) were stirred 15 min under an atmosphere of nitrogen. 4-(4-iodophenoxy)-piperidine-1-carboxylic acid tert-butyl ester (1.00 g, 2.48 mmol), quinoline-7-boronic acid (0.5147 g, 2.976 mmol), DMF (10 mL) and 1 M sodium carbonate (9.92 mL) were added and heated at 80° C. for 18 h. The mixture was concentrated, dissolved in EtOAc, washed with 1N Na$_2$CO$_3$, water and brine, and then dried (MgSO$_4$). The Boc intermediate was purified by ISCO (silica gel, 80 g; 40-80% EtOAc/hex) to give a white solid. This material was added 6 M HCl (10 mL) and heated at 65° C. for 4 h, then concentrated. The HCl salt was triturated with ether, dried and collected to give a yellow solid. LCMS m/z=305 (M+1).

Step 2. 2-Methyl-1-[4-(4-quinolin-7-yl-phenoxy)-piperidin-1-yl]-propan-1-one 7-[4-(Piperidin-4-yloxy)-phenyl]-quinoline dihydrochloride (0.042 g, 0.14 mmol) and DIPEA (0.097 mL, 0.55 mmol) in THF (2 mL) was added isobutyryl chloride (0.029 mL, 0.28 mmol). After 4 h stirring at rt, the mixture was concentrated, diluted with EtOAc and washed with 1N Na$_2$CO$_3$, water and brine, then dried (MgSO$_4$). The product was purified by ISCO (4 g silica gel, 0-5% MeOH/DCM). The HCl salt was made from 2N HCl ether and was recrystallized from DCM-ether to give a white solid (40 mg, 77%). Analysis: LCMS m/z=375 (M+1); $^1$H NMR (DMSO-d6, HCl salt) δ: 9.21 (d, 1H, J=4 Hz), 8.96 (d, 1H, J=8 Hz), 8.45 (s, 1H), 8.32 (d, 1H, J=8.3 Hz), 8.21 (d, 1H, J=8.3 Hz), 7.89-7.92 (m, 1H), 7.83 (d, 2H, J=8 Hz), 7.20 (d, 2H, J=8 Hz), 4.75 (m, 1H), 3.89 (b, 1H), 3.78 (b, 1H), 3.39 (b, 1H), 3.27 (b, 1H), 3.90 (q, 1H, J=7 Hz), 1.95-2.01 (b, 2H), 1.63 (b, 1H), 1.55 (b, 1H), 1.01 (d, 6H, J=7 Hz).

Example 4. 1-[4-(4-Quinolin-7-yl-phenoxy)-piperidin-1-yl]-propan-1-one

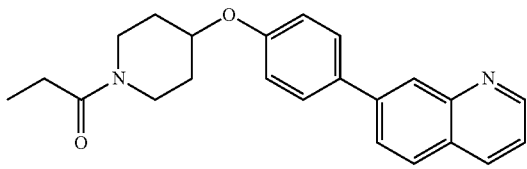 [SMILES: CCC(=O)N1CCC(Oc2ccc(-c3ccc4cccnc4c3)cc2)CC1]

This compound was synthesized using the method for Example 3. Analysis: LCMS m/z=361 (M+1); $^1$H NMR (DMSO-d6, HCl salt) δ: 9.17 (m, 1H), 8.92 (d, 1H, J=8 Hz), 8.40 (s, 1H), 8.30 (d, 1H, J=9 Hz), 8.20 (dd, 1H, J=2, 8.5 Hz), 8.86-8.90 (m, 1H), 8.63 (d, 1H, J=8.5 Hz), 7.20 (d, 2H, J=8.5 Hz), 4.74 (q, 1H, J=4 Hz), 3.89 (m, 1H), 3.73 (m, 1H), 3.33-3.39 (m, 1H), 3.24-3.29 (m, 2H), 2.34 (q, 2H, J=7.5 Hz), 1.90-2.03 (b, 2H), 1.61-1.65 (m, 1H), 1.53-1.57 (m, 1H), 1.00 (t, 3H, J=7.5 Hz).

Example 5. 4-(2-Fluoro-4-quinolin-3-yl-phenox)piperidine-1-carboxylic acid t-butyl ester

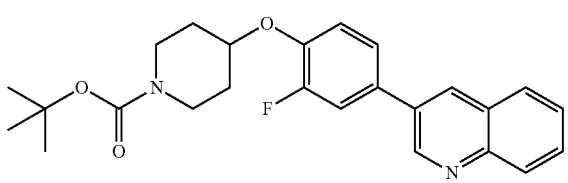 [SMILES: CC(C)(C)OC(=O)N1CCC(Oc2ccc(-c3cnc4ccccc4c3)cc2F)CC1]

Step a. 4-(4-Bromo-2-fluorophenoxy)piperidine-1-carboxylic acid tert-butyl ester Triphenylphosphine (4.12 g, 15.71 mmol) in THF was added 6 M of diethyl azodicarboxylate (DEAD) in toluene (2.62 mL, 15.71 mmol) at 0° C. After 0.5 h, 4-bromo-2-fluoro-phenol (1.13 mL, 10.5 mmol) and 4-hydroxypiperidine-1-carboxylic acid tert-butyl ester (2.63 g, 13.09 mmol) in THF (10 mL) was added dropwise and stirred for 18 h at rt. The mixture was filtered and concentrated. The product was dissolved in Et$_2$O (ca. 100 mL) and hexane (ca. 25 mL) and filtered. The ether was concentrated and the product purified by ISCO silica gel chromatography (120 g column; 15-20% EtOAc/hexanes) to give a solid (11 g, 82%). Analysis: LCMS m/z=375 (M+1); $^1$H NMR (CDCl$_3$) δ 7.23-7.26 (m, 1H), 7.11-7.21 (m, 1H), 6.84-6.92 (m, 1H), 4.41 (tt, J=7.0, 3.5 Hz, 1H), 3.65-3.75 (m, 2H), 3.33 (ddd, J=13.5, 7.6, 4.0 Hz, 2H), 1.86-1.95 (m, 2H), 1.69-1.82 (m, 3H), 1.44-1.48 (m, 9H).

Step b. 4-(2-Fluoro-4-quinolin-3-yl-phenox)piperidine-1-carboxylic acid tert-butyl ester This compound was synthesized by the method for Example 3 using 4-(4-bromo-2-fluoro-phenoxy)piperidine-1-carboxylic acid tert-butyl ester (0.50 g, 1.34 mmol), and 3-quinolineboronic acid (0.28 g, 1.60 mmol). Analysis: LCMS m/z=423 (M+1); $^1$H NMR (CDCl$_3$) 9.13 (d, 1H, J=2 Hz), 8.12 (d, 1H, J=8.4 Hz), 7.87 (d, 1H, J=8.4 Hz), 7.64-7.74 (m, 2H), 7.56-7.60 (m, 1H), 7.44-7.48 (m, 2H), 7.40-7.43 (m, 1H), 7.14 (t, 1H, J=8 Hz), 4.54 (q, 1H, J=4.5 Hz), 3.72-3.79 (m, 2H), 3.33-3.40 (m, 2H), 1.94-2.00 (m, 2H), 1.79-1.87 (m, 2H), 1.48 (s, 9H).

Example 6. 1-[4-(2-Fluoro-4-quinolin-3-yl-phenoxy)piperidin-1-yl]propan-1-one

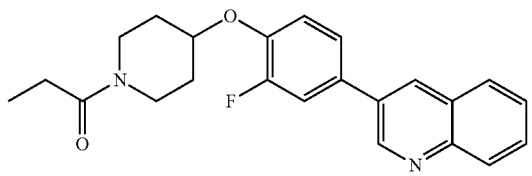 [SMILES: CCC(=O)N1CCC(Oc2ccc(-c3cnc4ccccc4c3)cc2F)CC1]

Step 1. 3-[3-Fluoro-4-(piperidin-4-yloxy)-phenyl]-quinoline 4-(2-Fluoro-4-quinolin-3-yl-phenox)piperidine-1-carboxylic acid tert-butyl ester (0.5 g) was added 6M HCl (10 mL)

and heated at 65° C., then concentrated and the residue triturated with ether to give a light yellow solid (350 mg, 82%). Analysis: LCMS m/z=323 (M+1); $^1$H NMR (DMSO-d$_6$ HCl salt) δ: 9.49 (s, 1H), 9.11 (b, 3H), 8.25 (d, 1H, J=8 Hz), 8.20 (d, 1H, J=8 Hz), 7.94-7.98 (m, 2H), 7.79-7.84 (m, 2H), 7.50 (t, 1H, J=8.5 Hz), 4.81 (b, 1H), 3.23 (b, 2H), 3.11 (b, 2H), 2.16 (b, 2H), 1.92 (b, 2H).

Step 2. 1-[4-(2-Fluoro-4-quinolin-3-yl-phenoxy) piperidin-1-yl]propan-1-one

3-[3-Fluoro-4-(piperidin-4-yloxy)phenyl]quinoline (0.070 g, 0.22 mmol) and DIPEA (0.113 mL, 0.651 mmol) in DCM (3 mL) was added propanoyl chloride (0.0377 mL, 0.434 mmol). After 2 h stirring at rt the mixture was concentrated, dissolved in EtOAc and washed with 1N Na$_2$CO$_3$ and brine then dried over MgSO$_4$. The product was purified by ISCO (4 g silica gel column, 0-5% MeOH/DCM) to give an oil. The HCl salt was made by adding 0.25 mL 1N HCl-ether to a DCM solution of the base to give a yellow solid (60 mg, 73%). Analysis: LCMS m/z=379 (M+1); $^1$H NMR (DMSO-d$_6$ HCl salt) δ: 9.45 (s, 1H), 9.03 (s, 1H), 8.18 (t, 2H, J=7 Hz), 7.91-7.94 (m, 2H), 7.75-7.81 (m, 2H), 7.48 (t, 1H, J=8 Hz), 4.77 (q, 1H, J=4 Hz), 3.78 (b, 1H), 3.70 (b, 1H), 3.27-3.39 (m, 2H), 2.34 (q, 2H, J=7 Hz), 1.93-1.99 (b, 2H), 1.66 (b, 1H), 1.57 (b, 1H), 1.00 (t, 3H, J=7 Hz).

Example 7. 1-[4-(2-Fluoro-4-quinolin-3-yl-phenoxy)-piperidin-1-yl]-2-methyl-propan-1-one

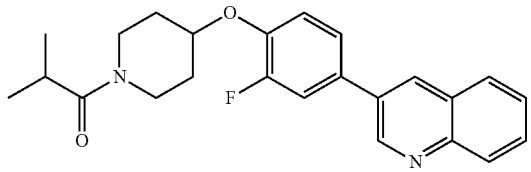 [SMILES: CC(C)C(=O)N1CCC(Oc2ccc(-c3cnc4ccccc4c3)cc2F)CC1]

Analysis: LCMS m/z=393 (M+1); $^1$H NMR (DMSO HCl salt) δ: 9.49 (s, 1H), 9.09 (s, 1H), 9.19-9.24 (m, 2H), 7.92-7.97 (m, 2H), 7.77-7.84 (m, 2H), 7.49 (t, 1H, J=8 Hz), 4.79 (q, 1H, J=4 Hz), 3.87 (b, 1H), 3.78 (b, 1H), 3.40 (b, 1H), 3.29 (b, 1H), 2.91 (q, 1H, J=7 Hz), 2.00 (b, 1H), 1.96 (b, 1H), 1.66 (b, 1H), 1.58 (b, 1H), 1.00 (d, 6H, J=7 Hz).

The following examples were synthesized starting with 4-(4-bromophenoxy)-piperidine-1-carboxylic acid t-butyl ester or 4-(4-iodophenoxy)piperidine-1-carboxylic acid t-butyl ester and an appropriate boronic acid using methods described for previous examples.

Example 8. 1-[4-(4-Benzofuran-5-yl-phenoxy)-piperidin-1-yl]-propan-1-one

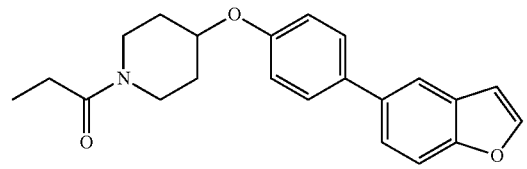 [SMILES: CCC(=O)N1CCC(Oc2ccc(-c3ccc4occc4c3)cc2)CC1]

Analysis: LCMS m/z=350 (M+1); $^1$H NMR (CDCl$_3$) δ: 7.70 (d, 1H, J=2 Hz), 7.64 (d, 1H, J=2 Hz), 7.51-7.54 (m, 3H), 7.46 (dd, 1H, J=2, 8 Hz), 7.00 (d, 2H, J=8.5 Hz), 6.80 (d, 1H, J=2 Hz), 4.58 (q, 1H, J=4 Hz), 3.79-3.85 (m, 1H), 3.63-3.74 (m, 2H), 3.39-3.46 (m, 1H), 2.38 (q, 2H, J=7.5 Hz), 1.94 (b, 2H), 1.84 (b, 2H), 1.17 (t, 3H, J=7.5 Hz).

Example 9. 1-[4-(4-Benzofuran-5-yl-phenoxy)-piperidin-1-yl]-2-methyl-propan-1-one

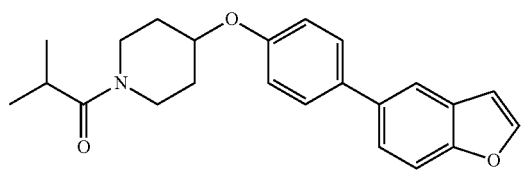 [SMILES: CC(C)C(=O)N1CCC(Oc2ccc(-c3ccc4occc4c3)cc2)CC1]

Analysis: LCMS m/z=364 (M+1); $^1$H NMR (CDCl$_3$) δ: 7.73 (d, 1H, J=2 Hz), 7.64 (d, 1H, J=2 Hz), 7.52-7.54 (m, 3H), 7.48 (d, 1H, J=2, 8 Hz), 7.00 (d, 2H, J=8.5 Hz), 6.80 (m, 1H), 4.59 (q, 1H, J=4 Hz), 3.75-3.85 (m, 2H), 3.64-3.68 (m, 1H), 3.47 (b, 1H), 2.84 (q, 1H, J=7 Hz), 1.96 (b, 2H), 1.86 (b, 2H), 1.15 (d, 6H, J=7 Hz).

Example 10. 1-[4-(4-Naphthalen-2-yl-phenoxy)-piperidin-1-yl]-propan-1-one

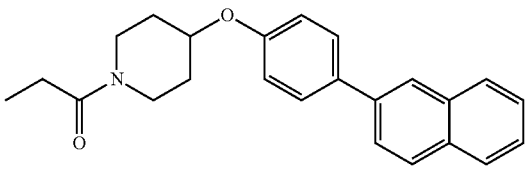 [SMILES: CCC(=O)N1CCC(Oc2ccc(-c3ccc4ccccc4c3)cc2)CC1]

Analysis: LCMS m/z=360 (M+1); $^1$H NMR (CDCl$_3$) δ: 7.98 (s, 1H), 7.83-7.98 (m, 3H), 7.70 (dd, 1H, J=2, 8.5 Hz), 7.64-7.67 (m, 2H), 7.44-7.51 (m, 2H), 7.02-7.04 (m, 2H), 4.61 (q, 1H, J=4 Hz), 3.79-3.85 (m, 1H), 3.64-3.76 (m, 2H), 3.40-3.46 (m, 1H), 2.37 (q, 2H, J=7 Hz), 1.92-1.97 (m, 2H), 1.82-1.91 (m, 2H), 1.17 (t, 3H, J=7 Hz).

Example 11. 2-Methyl-1-[4-(4-naphthalen-2-yl-phenoxy)-piperidin-1-yl]-propan-1-one

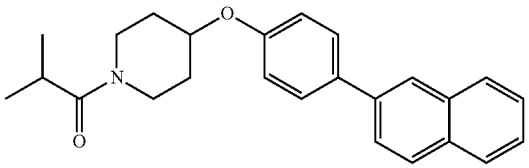 [SMILES: CC(C)C(=O)N1CCC(Oc2ccc(-c3ccc4ccccc4c3)cc2)CC1]

Analysis: LCMS m/z=374 (M+1); $^1$H NMR (CDCl$_3$) 7.98 (s, 1H), 7.84-7.90 (m, 3H), 7.70 (dd, 1H, J=2, 8 Hz), 7.64-7.67 (m, 2H), 7.44-7.51 (m, 2H), 7.02-7.05 (m, 2H), 4.61 (q, 1H, J=4 Hz), 3.75-3.85 (m, 2H), 1.65-1.72 (m, 1H), 3.48 (b, 1H), 2.84 (q, 1H, J=7 Hz), 1.96 (b, 2H), 1.87 (b, 2H), 1.15 (d, 6H, J=7 Hz).

Example 12. 1-[4-(4-1,5-Naphthyridin-3-yl-phenoxy)-piperidin-1-yl]-propan-1-one

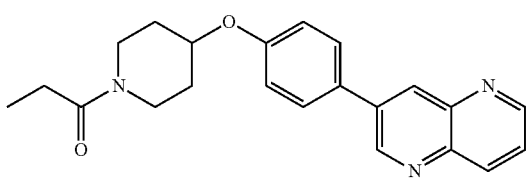 [SMILES: CCC(=O)N1CCC(Oc2ccc(-c3cnc4cccnc4c3)cc2)CC1]

Analysis: LCMS m/z=362 (M+1); ¹H NMR (DMSO-d6 HCl salt) δ: 9.42 (d, 1H, J=2 Hz), 9.10 (dd, 1H, J=2, 4 Hz), 8.67 (d, 1H, J=2 Hz), 8.57 (d, 1H, J=8.6 Hz), 7.91 (d, 2H, J=8.5 Hz), 7.85 (dd, 1H, J=2, 8 Hz), 7.20 (d, 2H, J=8.5 Hz), 4.75 (q, 1H, J=4 Hz), 3.89 (m, 1H), 3.71 (m, 1H), 3.33-3.39 (m, 1H), 3.24-3.30 (m, 1H), 2.34 (q, 2H, J=7 Hz), 1.98 (b, 2H), 1.61-1.65 (m, 1H), 1.53-1.58 (m, 1H), 1.00 (t, 3H, J=7 Hz).

Example 13. 2-Methyl-1-[4-(4-1,5-naphthyridin-3-yl-phenoxy)-piperidin-1-yl]-propan-1-one

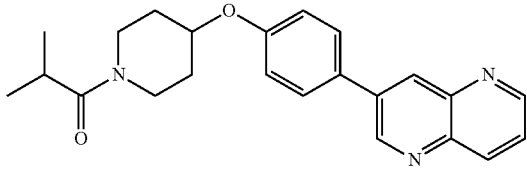 [SMILES: CC(C)C(=O)N1CCC(Oc2ccc(-c3cnc4cccnc4c3)cc2)CC1]

Analysis: LCMS m/z=376 (M+1); ¹H NMR (DMSO-d6 HCl salt) δ: 9.47 (d, 1H, J=2 Hz), 9.10 (dd, 1H, J=2, 4 Hz), 8.73 (d, 1H, J=2 Hz), 8.64 (d, 1H, J=8.5 Hz), 7.94 (d, 2H, J=8 Hz), 7.89-7.93 (m, 1H), 7.20 (d, 2H, J=8 Hz), 4.76 (q, 1H, J=4 Hz), 3.89 (b, 1H), 3.78 (b, 1H), 3.35-3.44 (m, 1H), 3.25-3.33 (m, 1H), 2.90 (q, 1H, J=6 Hz), 1.98 (b, 2H), 1.63 (b, 1H), 1.55 (b, 1H), 1.00 (d, 6H, J=6 Hz).

Example 14. Cyclopropyl-[4-(4-1,5-naphthyridin-3-yl-phenoxy)-piperidin-1-yl]-methanone

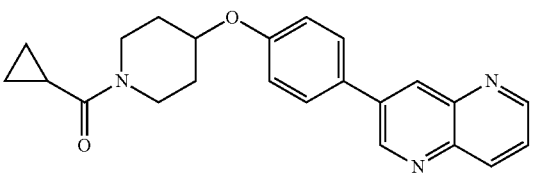 [SMILES: O=C(C1CC1)N1CCC(Oc2ccc(-c3cnc4cccnc4c3)cc2)CC1]

Analysis: LCMS m/z=374 (M+1); ¹H NMR (DMSO-d6 HCl salt) δ:9.40 (d, 1H, J=2 Hz), 9.06 (m, 1H), 9.63 (d, 1H, J=2 Hz), 8.51 (d, 1H, J=8.5 Hz), 7.91 9d, 2H, J=8 Hz), 7.80-7.84 (dd, 1H, J=2, 4 Hz), 7.19 (d, 2H, J=8 Hz), 4.77 (q, 1H, J=4 Hz), 4.00 (b, 1H), 3.90 (b, 1H), 3.57 (b, 1H), 3.29 (b, 1H), 1.91-2.10 (m, 3H), 1.66 (b, 1H), 1.56 (b, 1H), 0.69-0.74 (m, 4H).

Example 15. 4-(2-Fluoro-4-quinolin-3-yl-phenoxy)-piperidine-1-carboxylic acid methyl ester

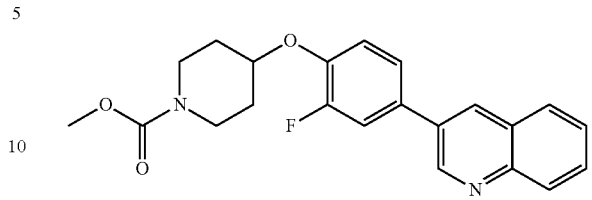

Analysis: LCMS m/z=381 (M+1); ¹H NMR (DMSO-d6 HCl salt) δ: 9.36 (s, 1H), 8.86 (s, 1H), 8.10 (d, 2H, J=8 Hz), 7.83-7.90 (m, 2H), 7.71 (m, 2H), 7.45 (t, 1H, J=9 Hz), 4.73 (m, 1H), 3.69-3.73 (m, 2H), 3.61 (s, 3H), 3.27-3.32 (m, 2H), 1.96 (m, 2H), 1.59-1.65 (m, 2H).

Example 16. 1-{4-[4-(2-Chloroquinolin-3-yl)-phenoxy]-piperidin-1-yl}-propan-1-one

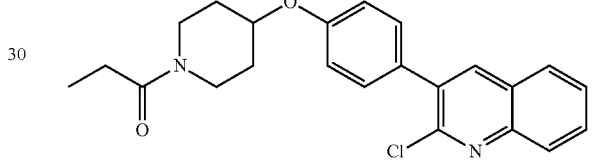

Analysis: LCMS m/z=395 (M+1); ¹H NMR (CDCl₃) δ: 8.09 (s, 1H), 8.05 (d, 1H, J=8 Hz), 7.82 (d, 1H, J=8 Hz), 7.74 (t, 1H, J=7.5 Hz), 7.58 (t, 1H, J=7.5 Hz), 7.46 (d, 2H, J=8 Hz), 7.02 (d, 2H, J=8 Hz), 4.63 (m, 1H), 3.81-3.85 (m, 1H), 3.67-3.76 (m, 2H), 3.43-3.47 (m, 1H), 2.40 (d, 2H, J=7.5 Hz), 1.97 (b, 2H), 1.88 (b, 2H), 1.18 (t, 3H, J=7.5 Hz).

Example 17. {4-[4-(2-Chloroquinolin-3-yl)-phenoxy]-piperidin-1-yl}-cyclopropyl-methanone

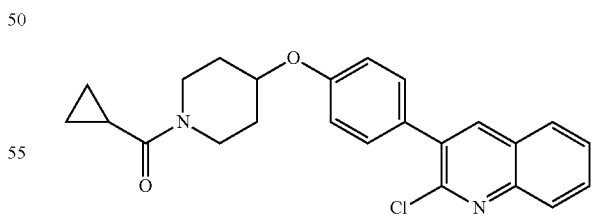

Analysis: LCMS m/z=407 (M+1); ¹H NMR (CDCl₃) δ: 8.09 (s, 1H), 8.05 (d, 1H, J=8 Hz), 7.82 (d, 1H, J=8 Hz), 7.74 (t, 1H, J=7.5 Hz), 7.58 (t, 1H, J=7.5 Hz), 7.47 (d, 2H, J=8 Hz), 7.02 (d, 2H, J=8 Hz), 4.64 (q, 1H, J=4 Hz), 3.95 (b, 1H), 3.82 (b, 1H), 3.65-3.71 (m, 2H), 1.88-2.00 (b, 4H), 1.76-1.82 (m, 1H), 0.99-1.02 (m, 2H), 0.76-0.79 (m, 2H).

Example 18. 1-{4-[4-(2-Methoxyquinolin-3-yl)-phenoxy]-piperidin-1-yl}-propan-1-one

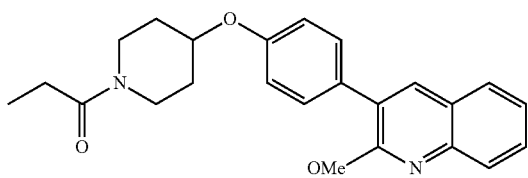 [SMILES: CCC(=O)N1CCC(Oc2ccc(-c3cc4ccccc4nc3OC)cc2)CC1]

Analysis: LCMS m/z=391 (M+1); ¹H NMR (CDCl₃) δ: 7.95 (s, 1H), 7.86 (d, 1H, J=8 Hz), 7.73 (d, 1H, J=8 Hz), 7.57-7.63 (m, 3H), 7.38 (t, 1H, J=7.5 Hz), 7.00 (d, 2H, J=8 Hz), 4.61 (q, 1H, J=4 Hz), 4.10 (s, 3H), 3.78-3.83 (m, 1H), 3.65-3.75 (m, 2H), 3.40-3.46 (m, 1H), 2.37 (q, 2H, J=7.5 Hz), 1.95 (b, 2H), 1.87 (b, 2H), 1.17 (t, 3H, J=7.5 Hz).

Example 19. Cyclopropyl-{4-[4-(5,6,7,8-tetrahydro-quinolin-3-yl)-phenoxy]-piperidin-1-yl}-methanone

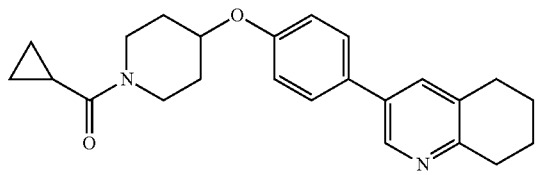 [SMILES: O=C(C1CC1)N1CCC(Oc2ccc(-c3cnc4c(c3)CCCC4)cc2)CC1]

Analysis: LCMS m/z=377 (M+1); ¹H NMR (DMSO-d6-HCl salt) δ: 8.88 (s, 1H), 8.47 (s, 1H), 7.78 (d, 2H, J=8 Hz), 7.16 (d, 1H, J=8 Hz), 4.76 (q, 1H, J=4 Hz), 3.97 (b, 1H), 3.87 (b, 1H), 3.29 (b, 2H), 3.02 (m, 2H), 2.93 (m, 2H), 1.97-2.03 (m, 2H), 1.89 (m, 3H), 1.81 (m, 2H), 1.64 (b, 1H), 1.53 (b, 1H), 0.70-0.74 (m, 4H).

Example 20. Cyclobutyl-{4-[4-(5,6,7,8-tetrahydro-quinolin-3-yl)-phenoxy]-piperidin-1-yl}-methanone

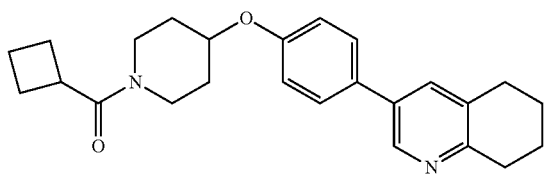 [SMILES: O=C(C1CCC1)N1CCC(Oc2ccc(-c3cnc4c(c3)CCCC4)cc2)CC1]

Analysis: LCMS m/z=391 (M+1): ¹H NMR (DMSO-d6-HCl salt) δ: 8.89 (s, 1H), 8.53 (s, 1H), 7.79 (d, 2H, J=8 Hz), 7.14 (d, 2H, J=8 Hz), 4.73 (m, 1H), 3.84 (m, 1H), 3.36 (m, 2H), 3.26 (m, 2H), 3.05 (m, 2H), 2.94 (m, 2H), 2.09-2.19 (m, 4H), 3.17-3.92 (m, 8H), 1.53 (m, 2H).

Example 21. 1-{4-[4-(5,6,7,8-Tetrahydroquinolin-3-yl)-phenoxy]-piperidin-1-yl}-propan-1-one

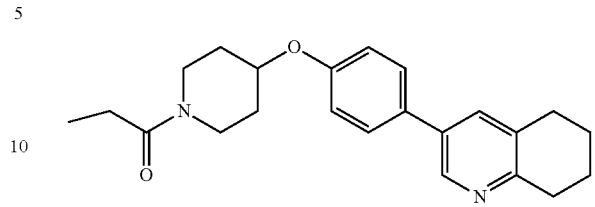

Analysis: LCMS m/z=365 (M+1); ¹H NMR (DMSO-d6-HCl salt) δ: 8.90 (s, 1H), 8.54 (s, 1H), 7.79 (d, 2H, J=8 Hz), 7.15 (d, 2H, J=8 Hz), 4.74 (m, 1H), 3.87 (m, 1H), 3.68 (m, 1H), 3.24-3.37 (m, 2H), 3.05 (m, 2H), 2.94 (m, 2H), 2.33 (q, 2H, J=7 Hz), 1.81-1.90 (m, 6H), 1.61 (m, 1H), 1.52 (m, 1H), 0.98 (t, 3H, J=7 Hz).

Example 22. 1-{4-[4-(8-Fluoroquinolin-7-yl)-phenoxy]-piperidin-1-yl}-propan-1-one

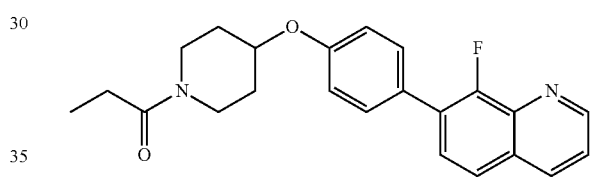

Analysis: LCMS m/z=379 (M+1); ¹H NMR (DMSO-d6) δ: 8.97 (d, 1H, J=4 Hz), 8.44 (d, 1H, J=8 Hz), 7.87 (d, 1H, J=8 Hz), 7.74 (t, 1H, J=7.5 Hz), 7.61-7.66 (m, 3H), 7.15 (d, 2H, J=8 Hz), 4.72 (q, 1H, j=4 Hz), 3.89 (b, 1H), 3.70 (b, 1H), 3.38 (m, 1H), 3.26 (m, 1H), 2.34 (q, 2H, J=7.5 Hz), 1.98 (b, 2H), 1.63 (m, 1H), 1.54 (m, 1H), 1.00 (t, 3H, J=7.5 Hz).

Example 23. Cyclopropyl-{4-[4-(8-fluoroquinolin-7-yl)-phenoxy]-piperidin-1-yl}-methanone

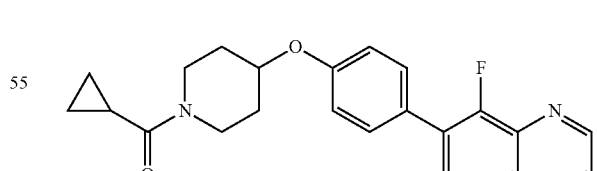

Analysis: LCMS m/z=391 (M+1); ¹H NMR (DMSO-d6) δ: 8.97 (m, 1H), 8.44 (d, 1H, J=8 Hz), 7.87 (d, 1H, J=8 Hz), 7.75 (t, 1H, J=7.5 Hz), 7.61-7.67 (m, 3H), 7.16 (d, 2H, J=8 Hz), 4.75 (q, 1H, J=4 Hz), 4.00 (b, 1H), 3.91 (b, 1H), 3.56 (b, 1H), 3.26-3.34 (m, 2H), 1.98-2.04 (m, 3H), 1.67 (b, 1H), 1.56 (b, 1H), 0.70-0.74 (m, 4H).

Example 24. Cyclobutyl-{4-[4-(8-fluoroquinolin-7-yl)-phenoxy]-piperidin-1-yl}-methanone

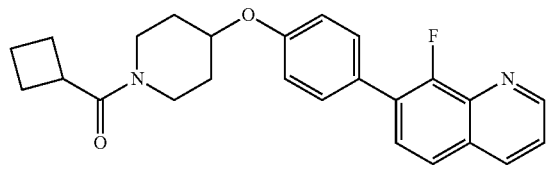 [SMILES: O=C(C1CCC1)N1CCC(Oc2ccc(-c3ccc4cccnc4c3F)cc2)CC1]

Analysis: LCMS m/z=405 (M+1); $^1$H NMR (DMSO-d6) δ: 8.97 (m, 1H), 8.44 (d, 1H, J=8 Hz), 7.87 (d, 2H, J=8 Hz), 7.73 (m, 1H), 7.61-7.66 (m, 3H), 7.14 (d, 2H, J=8 Hz), 4.70 (q, 1H, J=4 Hz), 3.85-3.90 (m, 1H), 3.57-3.60 (m, 1H), 3.34-3.39 (m, 1H), 3.22-3.29 (m, 2H), 2.06-2.20 (m, 4H), 1.86-1.95 (m, 3H), 1.72-1.77 (m, 1H), 1.52-1.60 (m, 2H).

Example 25. 1-{4-[4-(8-Fluoro-2-methylquinolin-7-yl)-phenoxy]-piperidin-1-yl}-propan-1-one

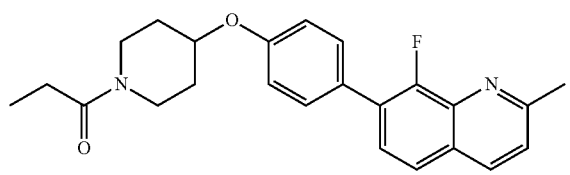 [SMILES: CCC(=O)N1CCC(Oc2ccc(-c3ccc4ccc(C)nc4c3F)cc2)CC1]

Analysis: LCMS m/z=393 (M+1); $^1$H NMR (DMSO-d6) δ: 8.57 (d, 1H, J=7 Hz), 7.92 (d, 1H, J=8 Hz), 7.78 (m, 1H), 7.65-7.69 (m, 3H), 7.18 (d, 2H, J=8 Hz), 4.8 (m, 1H), 3.95 (b, 1H), 3.70 (b, 1H), 3.33-3.39 (m, 1H), 3.24-3.29 (m, 1H), 2.80 (s, 3H), 2.34 (q, 2H, J=7 Hz), 1.94 (b, 2H), 1.63 (b, 1H), 1.53 (b, 1H), 1.00 (t, 3H, J=7 Hz).

Example 26. Cyclopropyl-{4-[4-(8-fluoro-2-methylquinolin-7-yl)-phenoxy]-piperidin-1-yl}-methanone

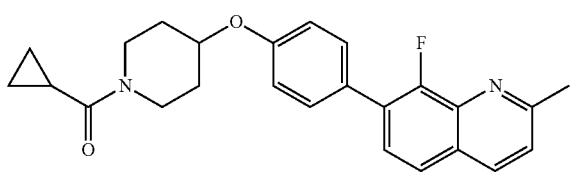 [SMILES: Cc1ccc2ccc(-c3ccc(OC4CCN(C(=O)C5CC5)CC4)cc3)c(F)c2n1]

Analysis: LCMS m/z=405 (M+1); $^1$H NMR (DMSO-d6) δ: 8.45 (d, 1H, J=7 Hz), 7.87 (d, 1H, J=7 Hz), 7.72 (m, 1H), 7.65 (d, 1H, J=8 Hz), 7.60 (d, 1H, J=8.5 Hz), 7.16 (d, 2H, J=8 Hz), 4.74 (m, 1H), 4.00 (b, 1H), 3.90 (b, 1H), 3.56 (b, 1H), 3.28 (b, 1H), 2.76 (s, 3H), 1.98-2.04 (m, 3H), 1.66 (b, 1H), 1.56 (b, 1H), 0.70-0.74 (m, 4H).

Example 27. Cyclobutyl-{4-[4-(8-fluoro-2-methylquinolin-7-yl)-phenoxy]-piperidin-1-yl}-methanone

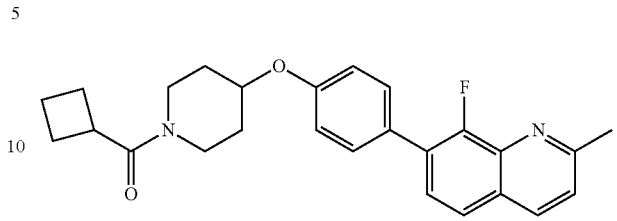

Analysis: LCMS m/z=419 (M+1); $^1$H NMR (DMSO-d6 HCl salt) δ: 8.36 (d, 1H, J=7 Hz), 7.82 (d, 1H, J=7 Hz), 7.62-7.68 (m, 3H), 7.53 (d, 1H, J=7.5 Hz), 7.14 (d, 2H, J=8 Hz), 4.70 (m, 1H), 3.8 (b, 1H), 3.57 (m, 1H), 3.35 (m, 1H), 3.22 (m, 2H), 2.72 (s, 3H), 2.09-2.20 (m, 4H), 1.86-1.95 (m, 3H), 1.75 (m, 1H), 1.52-1.57 (m, 2H).

Example 28. {4-[4-(5-Fluoroquinolin-3-yl)-phenoxy]-piperidin-1-yl}-(R)-tetrahydrofuran-2-yl-methanone

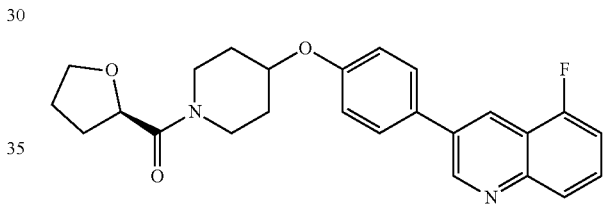

Analysis: LCMS m/z=421 (M+1); $^1$H NMR (DMSO-d6) δ: 9.19 (s, 1H), 8.72 (d, 0.5H, J=5 Hz), 8.46 (d, 0.5H, J=2, 5 Hz), 8.28 (b, 1H), 7.64 (d, 2H, J=8 Hz), 7.48-7.53 (m, 1H), 7.36-7.41 (m, 1H), 7.06 (d, 2H, J=8 Hz), 4.65 (m, 2H), 3.84-3.98 (m, 3H), 2.31 (m, 1H), 1.89-2.10 (m, 8H), 1.44-1.55 (m, 4H).

Example 29. 1-{4-[4-(5-Fluoroquinolin-3-yl)-phenoxy]-piperidin-1-yl}-propan-1-one

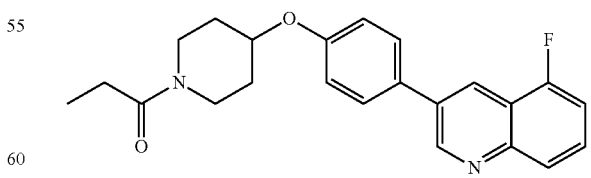

Analysis: LCMS m/z=379 (M+1); $^1$H NMR (DMSO-d6) δ: 9.28 (s, 1H), 8.66 (s, 1H), 7.84 (m, 3H), 7.55-7.62 (m, 2H), 7.17 (d, 2H, J=8 Hz), 4.72 (m, 1H), 3.88 (m, 1H), 3.70 (m, 1H), 3.28-3.38 (m, 2H), 2.34 (q, 2H, J=7 Hz), 1.93-1.99 (m, 2H), 1.53-1.64 (m, 2H), 1.00 (t, 3H, J=7 Hz).

Example 30. Cyclopropyl-{4-[4-(5-fluoroquinolin-3-yl)-phenoxy]-piperidin-1-yl}-methanone

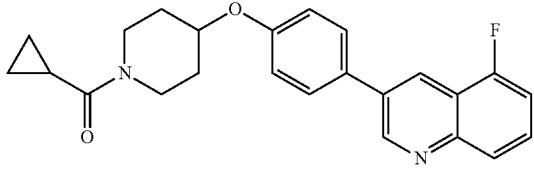 [SMILES: O=C(C1CC1)N1CCC(Oc2ccc(-c3cnc4cccc(F)c4c3)cc2)CC1]

Analysis: LCMS m/z=391 (M+1); $^1$H NMR (DMSO HCl salt) δ: 9.29 (s, 1H), 8.68 (s, 1H), 7.86 (m, 3H), 7.54-7.64 (m, 2H), 7.18 (d, 2H, J=8 Hz), 4.75 (m, 1H), 3.99 (b, 1H), 3.90 (b, 1H), 3.56 (b, 1H), 3.29 (b, 1H), 1.98-2.03 (m, 3H), 1.66 (b, 1H), 1.56 (b, 1H), 0.70-0.74 (m, 4H).

Example 31. Cyclobutyl-{4-[4-(5-fluoroquinolin-3-yl)-phenoxy]-piperidin-1-yl}-methanone

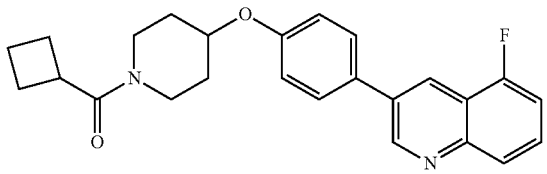 [SMILES: O=C(C1CCC1)N1CCC(Oc2ccc(-c3cnc4cccc(F)c4c3)cc2)CC1]

Analysis: LCMS m/z=405 (M+1); $^1$H NMR (DMSO-d6) δ: 9.28 (s, 1H), 8.66 (s, 1H), 7.85 (m, 3H), 7.53-7.64 (m, 2H), 7.16 (d, 2H, J=8 Hz), 4.72 (q, 1H, J=4 Hz), 3.85-3.89 (m, 1H), 3.57-3.60 (m, 1H), 3.34-3.39 (m, 1H), 3.23-3.29 (m, 2H), 2.05-2.20 (m, 4H), 1.86-1.95 (m, 3H), 1.72-1.77 (m, 1H), 1.52-1.60 (m, 2H).

Example 32. 1-{4-[4-(1H-Pyrrolo[2,3-b]pyridin-5-yl)-phenoxy]-piperidin-1-yl}-propan-1-one

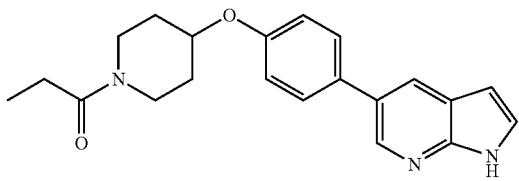 [SMILES: CCC(=O)N1CCC(Oc2ccc(-c3cnc4[nH]ccc4c3)cc2)CC1]

Step 1. 4-[4-(4,4,5,5-tetramethyl-1,3,2-dioxaborolan-2-yl)-phenoxy]-piperidine-1-carboxylic acid tert-butyl ester Triphenylphosphine (9.53 g, 36.4 mmol), and DEAD (40% w/w DEAD in toluene, 16.1 mL, 40.9 mmol) in THF (80 mL) was cooled at 0° C. and stirred under nitrogen atmosphere. A mixture of 4-(4,4,5,5-tetramethyl-1,3,2-dioxaborolan-2-yl)phenol (5.0 g, 22.7 mmol) and 4-hydroxypiperidine-1-carboxylic acid tert-butyl ester (5.72 g, 28.4 mmol) in THF (10 mL) was added dropwise to the reaction. The cooling bath was removed and furthered stirred at rt for 20 h. The reaction was evaporated under vacuum, stirred with ether, and the white solid filtered off. The filtrate was evaporated under vacuum and purified by ISCO silica gel chromatography (0-20% EtOAc/hexanes) to obtain 4-[4-(4,4,5,5-tetramethyl-1,3,2-dioxaborolan-2-yl)-phenoxy]-piperidine-1-carboxylic acid tert-butyl ester (6.3 g, 69%). LCMS m/z=404 (M+1).

Step 2. 4-[4-(1H-pyrrolo[2,3-b]pyridin-5-yl)-phenoxy]-piperidine-1-carboxylic acid t-butyl ester Palladium acetate (0.0111 g, 0.0496 mmol) and triphenylphosphine (0.0520 g, 0.198 mmol) were stirred 15 min under an atmosphere of nitrogen. 4-[4-(4,4,5,5-tetramethyl-1,3,2-dioxaborolan-2-yl)-phenoxy]-piperidine-1-carboxylic acid tert-butyl ester (0.40 g, 0.99 mmol), 5-bromo-1H-pyrrolo[2,3-b]pyridine (0.235 g, 1.19 mmol), DMF (4 mL) and 1 M Na$_2$CO$_3$ (4 mL) were added and heated at 80° C. for 18 h. The mixture was concentrated, dissolved in EtOAc, washed with 1N Na$_2$CO$_3$, water and brine, then dried (MgSO$_4$). The product was purified by ISCO (silica get, 80 g column; 40-80% EtOAc/hexanes) to give a white solid (0.25 g, 64%). Analysis: LCMS m/z=394 (M+1): $^1$H NMR (CDCl$_3$) δ 9.16 (br. s., 1H), 8.51 (d, J=2.0 Hz, 1H), 8.07 (d, J=2.0 Hz, 1H), 7.47-7.61 (m, 2H), 7.30-7.38 (m, 1H), 6.99-7.10 (m, 2H), 6.55 (dd, J=3.4, 1.9 Hz, 1H), 4.52 (dt, J=7.1, 3.6 Hz, 1H), 3.69-3.80 (m, 2H), 3.31-3.46 (m, 2H), 1.93-2.00 (m, 2H), 1.76-1.84 (m, 2H), 1.48 (s, 9H).

Step 3. 5-[4-(Piperidin-4-yloxy)-phenyl]-1H-pyrrolo[2,3-b]pyridine

4-[4-(1H-Pyrrolo[2,3-b]pyridin-5-yl)-phenoxy]-piperidine-1-carboxylic acid tert-butyl ester (200 mg, 0.51 mmol) was added 6M HCl in dioxane (4 mL, 20 mmol) and stirred at rt for 6 h. The mixture was concentrated, and triturated with ether to give a light yellow solid (150 mg, 98%). Analysis: LCMS m/z=294 (M+1); $^1$H NMR (DMSO-d$_6$) δ 12.25 (br. s., 1H), 9.19 (br. s., 2H), 8.43-8.65 (m, 2H), 7.59-7.73 (m, 3H), 7.15 (d, J=8.5 Hz, 2H), 6.64 (d, J=1.3 Hz, 1H), 4.74 (br. s., 1H), 3.23 (br. s., 2H), 3.09 (d, J=4.3 Hz, 2H), 2.14 (d, J=3.5 Hz, 2H), 1.90 (d, J=9.3 Hz, 2H)

Step 4. 1-{4-[4-(1H-Pyrrolo[2,3-b]pyridin-5-yl)-phenoxy]-piperidin-1-yl}-propan-1-one 5-[4-(Piperidin-4-yloxy)phenyl]-1H-pyrrolo[2,3-b]pyridine (0.043 g, 0.15 mmol) and DIPEA (0.0771 mL, 0.443 mmol) in DCM (2 mL) was added propanoyl chloride (0.026 mL, 0.295 mmol). After 2 h stirring at rt the mixture was concentrated, dissolved in EtOAc and washed with 1N Na$_2$CO$_3$ and brine, then dried over MgSO$_4$. The product was purified by ISCO (4 g silica gel column, 0-5% MeOH/DCM) to give an oil. The HCl salt synthesized from by adding 1N HCl ether to a dCM solution of base give a white solid (32 mg, 62%). Analysis: LCMS m/z=350 (M+1): $^1$H NMR (DMSO, HCl salt) δ: 11.89 (s, 1H), 8.51 (s, 1H), 8.29 (s, 1H), 7.63 (d, 2H, J=8 Hz), 7.54 (m, 1H), 7.09 (d, 2H, J=8 Hz), 6.55 (s, 1H), 4.67 (m, 1H), 3.87 (b, 1H), 3.69 (b, 1H), 3.34 (m, 1H), 3.26 (m, 1H), 2.33 (q, 2H, J=7 Hz), 1.91-1.97 (b, 2H), 1.61 (m, 1H), 1.51 (m, 1H), 0.99 (t, 3H J=7 Hz).

The following examples were synthesized from 4-[4-(4,4,5,5-tetramethyl-1,3,2-dioxaborolan-2-yl)-phenoxy]-piperidine-1-carboxylic acid tert-butyl ester using the general procedure.

Example 33. Cyclopropyl-{4-[4-(1H-pyrrolo[2,3-b]pyridin-5-yl)-phenoxy]-piperidin-1-yl}-methanone

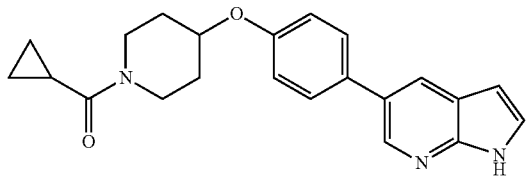 [SMILES: O=C(C1CC1)N1CCC(Oc2ccc(-c3cnc4[nH]ccc4c3)cc2)CC1]

Analysis: LCMS m/z=362 (M+1); $^1$H NMR (DMSO-$d_6$ HCl salt) δ: 11.92 (s, 1H), 8.51 (s, 1H), 8.30 (s, 1H), 7.65 (d, 2H, J=8 Hz), 7.56 (m, 1H), 7.10 (d, 2H, J=8 Hz), 6.55 (m, 1H), 4.70 (m, 1H), 3.98 (b, 1H), 3.89 (b, 1H), 3.56 (b, 1H), 3.28 (b, 1H), 1.93-2.03 (m, 3H), 1.64 (b, 1H), 1.54 (b, 1H), 0.69-0.74 (m, 4H).

Example 34. Cyclopropyl-{4-[4-(7-methoxyquinolin-3-yl)-phenoxy]-piperidin-1-yl}-methanone

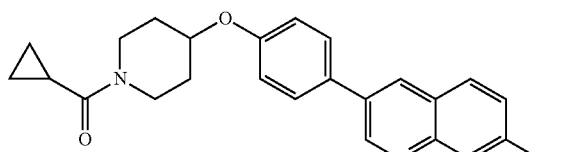

Analysis: LCMS m/z=403 (M+1): $^1$H NMR (CDCl$_3$) δ: 9.07 (s, 1H), 8.18 (s, 1H), 7.73 (s, 1H, J=8 Hz), 7.62 (d, 2H, J=8 Hz), 7.44 (s, 1H), 7.22 (dd, 1H, J=2, 8 Hz), 7.05 (d, 2H, J=8 Hz), 4.64 (m, 1H), 3.97 (s, 3H), 3.83 (b, 2H), 3.64-3.70 (m, 2H), 1.87-2.00 (b, 4H), 1.75-1.81 (m, 1H), 1.00 (m, 2H), 0.77-0.79 (m, 2H).

Example 35. 1-{4-[4-(7-Methoxyquinolin-3-yl)-phenoxy]-piperidin-1-yl}-propan-1-one

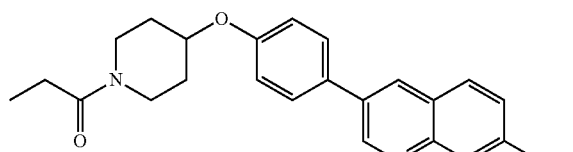

Analysis: LCMS m/z=391 (M+1); $^1$H NMR (CDCl$_3$) δ: 9.06 (d, 1H, J=2 Hz), 8.17 (d, 1H, J=2 Hz), 7.73 (d, 1H, J=9 Hz), 7.61 (d, 2H, J=8 Hz), 7.44 (d, 1H, J=2 Hz), 7.22 (dd, 1H, J=2, 8 Hz), 7.04 (d, 2H, J=8 Hz), 4.62 (q, 1H, J=4 Hz), 3.97 (s, 3H), 3.80-3.84 (m, 1H), 3.67-3.75 (m, 2H), 3.42-3.48 (m, 1H), 2.38 (q, 2H, J=7.5 Hz), 1.96 (b, 2H), 1.87 (b, 2H), 1.17 (t, 3H, J=7.5 Hz).

Example 36. 1-{4-[4-(8-Methylquinolin-7-yl)-phenoxy]-piperidin-1-yl}-propan-1-one

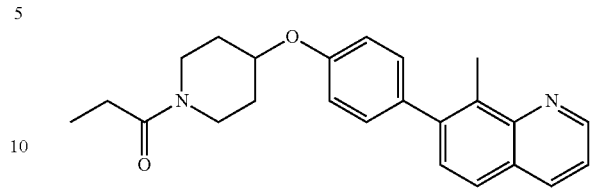

Analysis: LCMS m/z=375 (M+1); $^1$H NMR (DMSO-d6 HCl salt) δ: 9.13 (m, 1H), 8.83 (s, 1H), 8.07 (d, 1H, J=8 Hz), 7.86 (m, 1H), 7.67 (d, 1H, J=8 Hz), 7.40 (d, 2H, J=8 Hz), 7.13 (d, 2H, J=8 Hz), 4.70 (q, 1H, J=4 Hz), 3.90-393 (m, 1H), 3.71-3.74 (m, 1H), 3.33-3.39 (m, 1H), 3.24-3.28 (m, 1H), 2.72 (s, 3H), 2.34 (q, 2H, J=7 Hz), 1.95 (b, 2H), 1.64 (b, 1H), 1.53 (b, 1H), 1.00 (t, 3H, J=7 Hz).

Example 37. Cyclopropyl-{4-[4-(8-methylquinolin-7-yl)-phenoxy]-piperidin-1-yl}-methanone

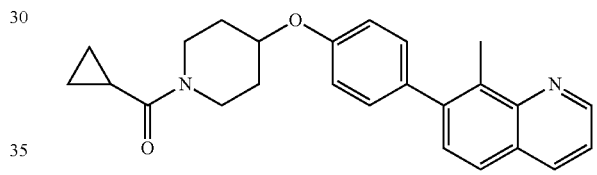

Analysis: LCMS m/z=387 (M+1); $^1$H NMR (DMSO-d6 HCl salt) δ: 9.06 (s, 1H), 8.63 (s, 1H), 7.97 (m, 1H), 7.72 (m, 1H), 7.59 (m, 1H), 7.40 (d, 2H, J=7 Hz), 7.14 (d, 2H, J=7 Hz), 4.73 (m, 1H), 4.12 (b, 1H), 3.91 (b, 1H), 3.71 (b, 1H), 3.28 (b, 1H), 2.70 (s, 3H), 1.98-2.04 (m, 3H), 1.67 (b, 1H), 1.56 (b, 1H), 0.70-0.74 (m, 4H).

Example 38. Cyclobutyl-{4-[4-(8-methylquinolin-7-yl)-phenoxy]-piperidin-1-yl}-methanone

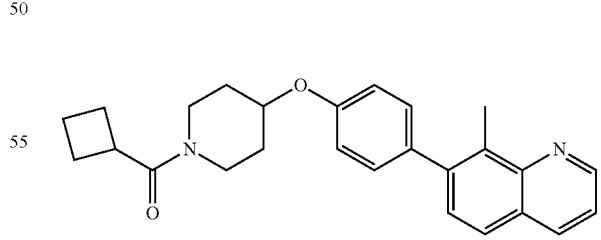

Analysis: LCMS m/z=401 (M+1); $^1$H NMR (DMSO-d6 HCL salt) δ: 9.08 (m, 1H), 8.73 (s, 1H), 8.01 (d, 1H, J=8 Hz), 7.79 (s, 1H), 7.62 (d, 1H, J=8 Hz), 7.39 (d, 2H, J=7 Hz), 7.12 (d, 2H, J=7 Hz), 4.68 (m, 1H), 3.88-3.91 (m, 1H), 3.58-3.61 (m, 1H), 3.35-3.39 (m, 1H), 3.23-3.28 (m, 2H), 2.70 (s, 3H), 2.08-2.23 (m, 4H), 1.86-1.95 (m, 3H), 1.72-1.77 (m, 1H), 1.53-1.59 (m, 2H).

Example 39. Cyclopropyl-[4-(4-quinolin-2-yl-phenoxy)-piperidin-1-yl]-methanone

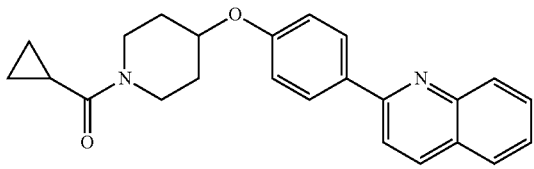 [SMILES: O=C(C1CC1)N1CCC(Oc2ccc(-c3ccc4ccccc4n3)cc2)CC1]

Analysis: LCMS m/z=373 (M+1); $^1$H NMR (DMSO-d6 HCl salt) δ: 8.66 (s, 1H), 8.18-8.26 (m, 4H), 8.08 (d, 1H, J=8 Hz), 7.88 (t, 1H, J=7 Hz), 7.68 (t, 1H, J=7 Hz), 7.22 (d, 2H, J=7 Hz), 4.81 (q, 1H, J=4 Hz), 4.01 (b, 1H), 3.90 (b, 1H), 3.58 (b, 1H), 3.30 (b, 1H), 1.98-2.04 (m, 3H), 1.66 (b, 1H), 1.57 (b, 1H), 0.70-0.74 (m, 4H).

Example 40. 1-[4-(4-Quinolin-2-yl-phenoxy)-piperidin-1-yl]-propan-1-one

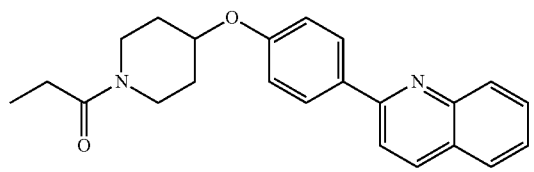 [SMILES: CCC(=O)N1CCC(Oc2ccc(-c3ccc4ccccc4n3)cc2)CC1]

Analysis: LCMS m/z=361 (M+1); $^1$H NMR (DMSO-d6 HCl salt) δ: 8.74 (s, 1H), 8.25 (m, 4H), 8.14 (d, 1H, J=8 Hz), 7.93 (m, 1H), 7.72 (m, 1H), 7.23 (d, 2H, J=8 Hz), 4.80 (m, 1H), 3.90 (m, 1H), 3.74 (m, 1H), 3.34-3.39 (m, 1H), 3.25-3.30 (m, 1H), 2.34 (q, 2H, J=7 Hz), 1.95-2.01 (b, 2H), 1.65 (b, 1H), 1.54 (b, 1H), 1.00 (t, 3H, J=7 Hz).

Example 41. Cyclobutyl-[4-(4-quinolin-2-yl-phenoxy)-piperidin-1-yl]-methanone

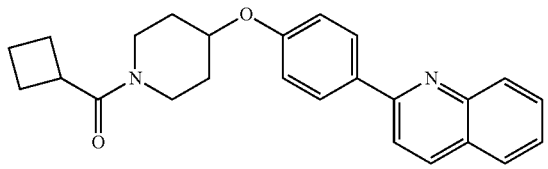 [SMILES: O=C(C1CCC1)N1CCC(Oc2ccc(-c3ccc4ccccc4n3)cc2)CC1]

Analysis: LCMS m/z=387 (M+1); $^1$H NMR (DMSO-d6 HCl salt) δ: 8.73 (s, 1H), 8.26 (m, 4H), 8.12 (d, 1H, J=8 Hz), 7.92 (m, 1H), 7.72 (m, 1H), 7.22 (d, 2H, J=8 Hz), 4.79 (m, 1H), 3.87-3.90 (m, 1H), 3.57-3.61 (m, 1H), 3.35-3.39 (m, 1H), 3.23-3.30 (m, 2H), 2.05-2.22 (m, 4H), 1.86-1.96 (m, 3H), 1.70-1.78 (m, 1H), 1.50-1.63 (m, 2H).

Example 42. [4-(4-Quinolin-2-yl-phenoxy)-piperidin-1-yl]-(R)-tetrahydrofuran-2-yl-methanone

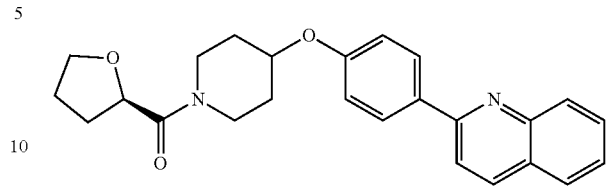

Analysis: LCMS m/z=403 (M+1); $^1$H NMR (DMSO-d6 HCl salt) δ: 8.65 (s, 1H), 8.17-8.25 (m, 4H), 8.08 (d, 1H, J=8 Hz), 7.89 (m, 1H), 7.68 (m, 1H), 7.21 (d, 2H, J=8 Hz), 4.80 (m, 1H), 4.69 (m, 1H), 3.71-3.92 (m, 3H), 3.23-3.49 (m, 2H), 1.98-2.08 (m, 3H), 1.79-1.89 (m, 2H), 1.53-1.67 (m, 2H), 1.24-1.28 (m, 2H).

Example 43. 1-[4-(4-Isoquinolin-3-yl-phenoxy)-piperidin-1-yl]-propan-1-one

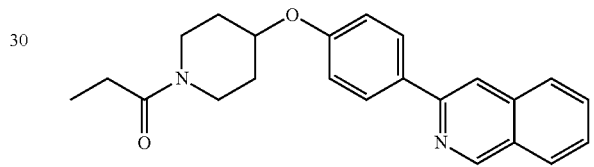

Analysis: LCMS m/z=361 (M+1); $^1$H NMR (DMSO-d6) δ: 9.36 (s, 1H), 8.32 (s, 1H), 8.15 (d, 2H, J=8 Hz), 8.10 (d, 1H, J=7.5 Hz), 7.98 (d, 1H, J=7.5 Hz), 7.77 (m, 1H), 7.63 (m, 1H), 7.11 (d, 2H, J=8 Hz), 4.71 (q, 1H, J=4 Hz), 3.24-3.35 (m, 3H), 3.19 (b, 1H), 3.70 (b, 1H), 2.34 (q, 2H, J=7 Hz), 1.93-1.98 (b, 2H), 1.63 (b, 1H), 1.53 (b, 1H), 1.00 (t, 3H, J=7 Hz).

Example 44. Cyclopropyl-[4-(4-isoquinolin-3-yl-phenoxy)-piperidin-1-yl]-methanone

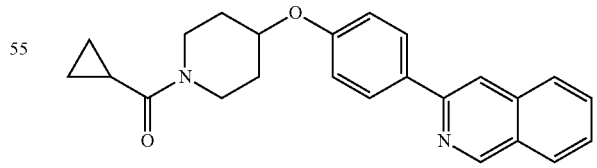

Analysis: LCMS m/z=373 (M+1); $^1$H NMR (DMSO-d6) δ: 9.36 (s, 1H), 8.32 (s, 1H), 8.16 (d, 2H, J=8.8 Hz), 8.10 (d, 1H, J=8 Hz), 7.98 (d, 1H, J=8 Hz), 7.77 (m, 1H), 7.63 (m, 1H), 7.12 (d, 2H, J=8.8 Hz), 4.74 (q, 1H, J=4 Hz), 3.99 (b, 1H), 3.90 (b, 1H), 3.56 (b, 1H), 3.29 (m, 1H), 1.92-2.10 (m, 3H), 1.66 (b, 1H), 1.55 (b, 1H), 0.69-0.75 (m, 4H).

Example 45. Cyclobutyl-[4-(4-isoquinolin-3-yl-phenoxy)-piperidin-1-yl]-methanone

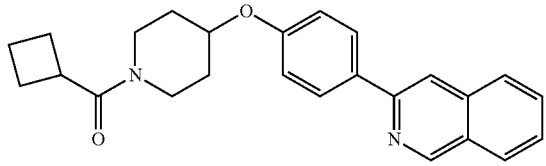 [SMILES: O=C(C1CCC1)N1CCC(Oc2ccc(-c3cc4ccccc4cn3)cc2)CC1]

Analysis: LCMS m/z=387 (M+1); $^1$H NMR (DMSO-d6) δ: 9.36 (s, 1H), 8.32 (s, 1H), 8.15 (d, 2H, J=9 Hz), 8.09 (d, 1H, J=8 Hz), 7.98 (d, 1H, J=8 Hz), 7.77 (m, 1H), 7.63 (m, 1H), 7.14 (d, 2H, J=9 Hz), 4.70 (m, 1H), 3.86-3.89 (m, 1H), 3.56-3.60 (m, 1H), 3.23-3.38 (m, 3H), 2.07-2.22 (m, 4H), 1.85-1.94 (m, 3H), 1.70-1.77 (m, 1H), 1.52-1.56 (m, 2H).

Example 46. [4-(4-Isoquinolin-3-yl-phenoxy)-piperidin-1-yl]-(R)-tetrahydrofuran-2-yl-methanone

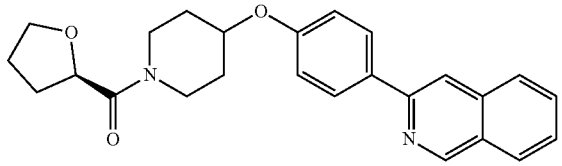 [SMILES: O=C([C@H]1CCCO1)N1CCC(Oc2ccc(-c3cc4ccccc4cn3)cc2)CC1]

Analysis: LCMS m/z=403 (M+1); $^1$H NMR (DMSO-d6 HCl salt) δ: 9.51 (s, 1H), 8.47 (s, 1H), 8.23 (d, 1H, J=8 Hz), 8.12 (d, 2H, J=9 Hz), 8.08 (d, 1H, J=8 Hz), 7.89 (m, 1H), 7.73 (m, 1H), 7.16 (d, 2H, J=9 Hz), 4.75 (m, 1H), 4.70 (m, 1H), 3.70-3.90 (m, 2H), 3.57-3.64 (m, 1H), 3.10-3.16 (m, 1H), 1.94-2.08 (m, 2H), 1.77-1.89 (m, 2H), 1.52-1.66 (b, 2H), 1.23-1.28 (m, 4H).

Example 47. 1-{4-[4-(4-Chloroquinolin-3-yl)-phenoxy]-piperidin-1-yl}-propan-1-one

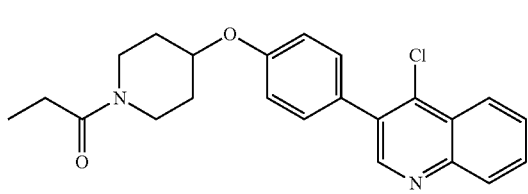 [SMILES: CCC(=O)N1CCC(Oc2ccc(-c3cnc4ccccc4c3Cl)cc2)CC1]

Analysis: LCMS m/z=395 (M+1); $^1$H NMR (DMSO HCl) δ: 8.91 (s, 1H), 8.32 (d, 1H, J=8 Hz), 8.14 (d, 1H, J=8 Hz), 7.89-7.93 (m, 1H), 7.81-7.88 (m, 1H), 7.56 (d, 2H, J=8 Hz), 7.16 (d, 2H, J=8 Hz), 4.73 (q, 1H, J=4 Hz), 3.91 (b, 1H), 3.71 (b, 1H), 3.33-3.39 (m, 1H), 3.24-3.28 (m, 1H), 2.34 (q, 2H, J=7 Hz), 1.94-2.00 (b, 2H), 1.63 (b, 1H), 1.55 (b, 1H), 1.00 (t, 3H, J=7 Hz).

Example 48. {4-[4-(4-Chloroquinolin-3-yl)-phenoxy]-piperidin-1-yl}-cyclopropyl-methanone

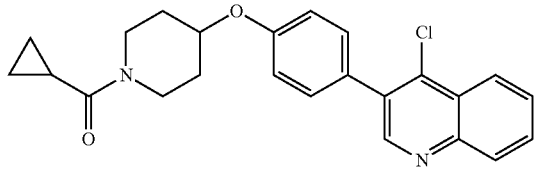 [SMILES: O=C(C1CC1)N1CCC(Oc2ccc(-c3cnc4ccccc4c3Cl)cc2)CC1]

Analysis: LCMS m/z=407 (M+1); $^1$H NMR (DMSO HCl) δ: 8.90 (s, 1H), 8.32 (d, 1H, J=8 Hz), 8.13 (m, 1H), 7.90 (t, 1H, J=8 Hz), 7.83 (m, 1H), 7.56 (d, 2H, J=8 Hz), 7.17 (d, 2H, J=8 Hz), 4.75 (q, 1H, J=4 Hz), 3.93 (b, 2H), 3.56 (b, 1H), 3.28 (b, 1H), 1.96-2.04 (m, 3H), 1.67 (b, 1H), 1.56 (b, 1H), 0.70-0.74 (m, 4H).

Example 49. {4-[4-(4-Chloroquinolin-3-yl)-phenoxy]-piperidin-1-yl}-cyclobutyl-methanone

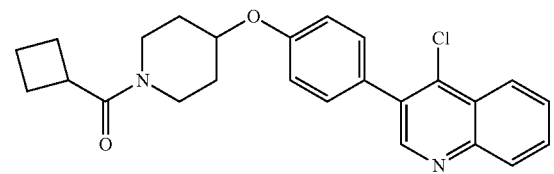

Analysis: LCMS m/z=421 (M+1); $^1$H NMR (DMSO-d6 HCl salt) δ: 8.92 (s, 1H), 8.32 (d, 1H, J=8 Hz), 8.14 (d, 1H), 7.91 (m, 1H), 7.84 (m, 1H), 7.56 (d, 2H, J=8 Hz), 7.15 (d, 2H, J=8 Hz), 4.72 (m, 1H), 3.89 (b, 1H), 3.60 (b, 1H), 3.33-3.39 (m, 1H), 3.22-3.29 (m, 2H), 2.08-2.20 (m, 4H), 1.86-1.96 (m, 3H), 1.72-1.77 (m, 1H), 1.53-1.60 (m, 2H).

Example 50. 1-{4-[4-(4-Methoxyquinolin-3-yl)-phenoxy]-piperidin-1-yl}-propan-1-one

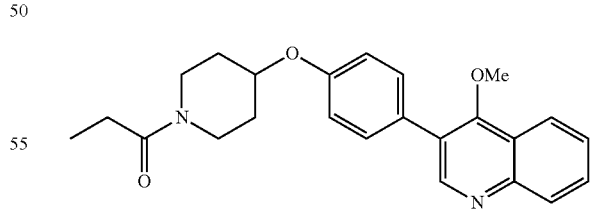

Analysis: LCMS m/z=391 (M+1); $^1$H NMR (CDCl$_3$) δ: 8.84 (s, 1H), 8.20 (d, 1H, J=8 Hz), 8.03 (d, 1H, J=8 Hz), 7.78 (t, 1H, J=8.5 Hz), 7.60-7.68 (m, 3H), 7.14 (d, 2H, J=8 Hz), 4.70 (q, 1H, J=4 Hz), 3.90 (b, 1H), 3.70 (b, 1H), 3.68 (s, 3H), 3.43-3.48 (m, 2H), 2.34 (q, 2H, J=7 Hz), 1.97 (b, 2H), 1.65 (b, 1H), 155 (b, 1H), 1.00 (t, 3H, J=7 Hz).

Example 51. 1-[4-(4-Furo[3,2-b]pyridin-6-yl-phenoxy)-piperidin-1-yl]-propan-1-one

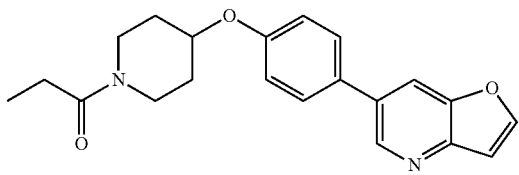 [SMILES: CCC(=O)N1CCC(Oc2ccc(-c3cnc4ccoc4c3)cc2)CC1]

Analysis: LCMS m/z=351 (M+1); 1H NMR (DMSO-d6) δ: 8.81 (d, 1H, J=2 Hz), 8.31 (d, 1H, J=2.3 Hz), 8.27 (m, 1H), 7.71 (d, 2H, J=8 Hz), 7.15 (m, 1H), 7.13 (d, 2H, J=8 Hz), 4.70 (q, 1H, J=4 Hz), 3.88 (m, 1H), 3.70 (m, 1H), 3.37 (m, 1H), 3.26 (m, 1H), 2.33 (q, 2H, J=7 Hz), 1.97 (b, 2H), 1.62 (m, 1H), 1.52 (m, 1H), 0.99 (t, 3H, J=7 Hz).

Example 52. Cyclopropyl-[4-(4-furo[3,2-b]pyridin-6-yl-phenoxy)-piperidin-1-yl]-methanone

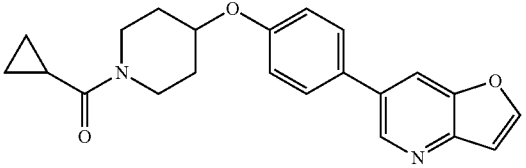 [SMILES: O=C(C1CC1)N1CCC(Oc2ccc(-c3cnc4ccoc4c3)cc2)CC1]

Analysis: LCMS m/z=363 (M+1); ¹H NMR (DMSO-d6) δ: 8.82 (s, 1H), 8.31 (d, 1H, J=2 Hz), 8.27 (s, 1H), 7.72 (d, 2H, J=8 Hz), 7.15 (s, 1H), 7.12 (d, 2H, J=8 Hz), 4.72 (q, 1H, J=4 Hz), 3.98 (b, 1H), 3.88 (b, 1H), 3.55 (b, 1H), 3.28 (m, 1H), 1.93-2.01 (m, 3H), 1.64 (b, 1H), 1.51 (b, 1H), 0.69-0.73 (m, 4H).

Example 53. 1-{4-[4-(6-Methoxyquinolin-3-yl)-phenoxy]-piperidin-1-yl}-propan-1-one

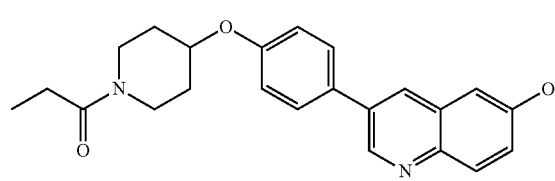

Analysis: LCMS m/z=391 (M+1); ¹H NMR (DMSO-d6 HCl salt) δ: 9.36 (s, 1H), 9.08 (s, 1H), 8.22 (d, 1H, J=9 Hz), 7.89 (d, 2H, J=8 Hz), 7.66 (m, 2H), 7.20 (d, 2H, J=8 Hz), 4.76 (q, 1H, J=4 Hz), 3.97 (s, 3H), 3.89 (m, 1H), 3.71 (m, 1H), 3.34-3.39 (m, 1H), 3.25-3.30 (m, 1H), 2.34 (q, 2H, J=7 Hz), 1.97 (b, 2H), 1.64 (m, 1H), 1.54 (m, 1H), 1.00 (t, 3H, J=7 Hz).

Example 54. Cyclopropyl-{4-[4-(6-methoxyquinolin-3-yl)-phenoxy]-piperidin-1-yl}-methanone

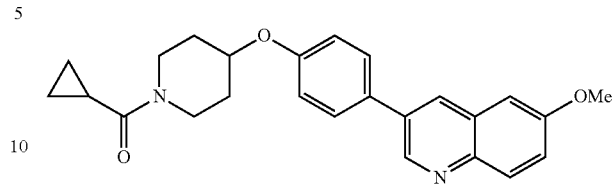

Analysis: LCMS m/z=403 (M+1); ¹H NMR (DMSO-d6 HCl salt) δ: 9.23 (s, 1H), 9.04 (s, 1H), 8.19 (d, 1H, J=9 Hz), 7.89 (d, 2H, J=8 Hz), 7.46 (m, 2H), 7.21 (d, 2H, J=8 Hz), 4.78 (q, 1H, J=4 Hz), 4.05 (b, 1H), 3.97 (s, 3H), 3.91 (b, 1H), 3.57 (b, 1H), 3.29 (b, 1H), 1.96-2.04 (m, 3H), 1.65 (b, 1H), 1.56 (b, 1H), 0.69-0.75 (m, 4H).

Example 55. 1-{4-[4-(6,7-Dimethoxyquinolin-3-yl)-phenoxy]-piperidin-1-yl}-propan-1-one

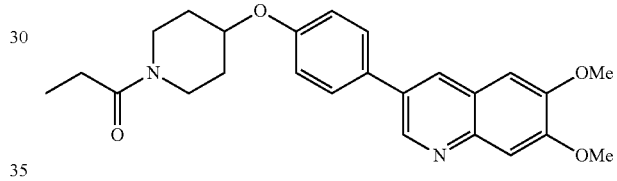

Analysis: LCMS m/z=421 (M+1); ¹H NMR (DMSO HCl salt) δ: 9.30 (s, 1H), 9.10 (s, 1H), 7.86 (d, 2H, J=8 Hz), 7.66 (d, 2H, J=7 Hz), 7.20 (d, 2H, J=8 Hz), 4.75 (q, 1H, J=4 Hz), 4.03 (s, 3H), 3.99 (s, 3H), 3.89 (m, 1H), 3.71 (m, 1H), 3.37 (m, 1H), 3.27 (m, 1H), 2.34 (q, 2H, J=7 Hz), 1.99 (b, 2H), 1.63 (m, 1H), 1.53 (m, 1H), 1.00 (t, 3H, J=7 Hz).

Example 56. Cyclopropyl-{4-[4-(6,7-dimethoxyquinolin-3-yl)-phenoxy]-piperidin-1-yl}-methanone

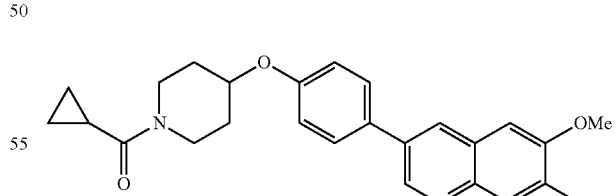

Analysis: LCMS m/z=433 (M+1); ¹H NMR (DMSO-d6 HCl salt) δ: 9.26 (s, 1H), 9.01 (s, 1H), 7.86 (d, 2H, J=8 Hz), 7.64 (s, 1H), 7.56 (s, 1H), 7.20 (d, 2H, J=8 Hz), 4.77 (q, 1H, J=4 Hz), 4.02 (s, 3H), 3.98 (s, 3H), 3.90 (b, 1H), 2.57 (b, 2H), 3.29 (m, 1H), 1.96-2.03 (m, 3H), 1.66 (b, 1H), 1.53 (br, 1H), 0.70-0.75 (m, 4H).

Example 57. 1-{4-[4-(8-Methoxyquinolin-3-yl)-phenoxy]-piperidin-1-yl}-propan-1-one

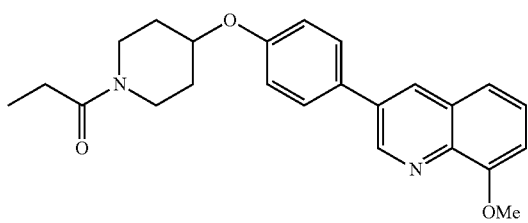 [SMILES: CCC(=O)N1CCC(Oc2ccc(-c3cnc4c(OC)cccc4c3)cc2)CC1]

Analysis: LCMS m/z=391 (M+1); ¹H NMR (DMSO-d6 base) δ: 9.14 (d, 1H, J=2 Hz), 8.51 (d, 1H, J=2 Hz), 7.08 (d, 2H, J=8 Hz), 7.54 (m, 2H), 7.16 (m, 3H), 4.72 (q, 1H, J=4 Hz), 3.98 (s, 3H), 3.99 (m, 1H), 3.70 (m, 1H), 3.38 (m, 1H), 3.25 (m, 1H), 2.34 (q, 2H, J=7 Hz), 1.98 (b, 2H), 1.62 (b, 1H), 1.53 (b, 1H), 1.00 (t, 3H, J=7 Hz).

Example 58. Cyclopropyl-{4-[4-(8-methoxyquinolin-3-yl)-phenoxy]-piperidin-1-yl}-methanone

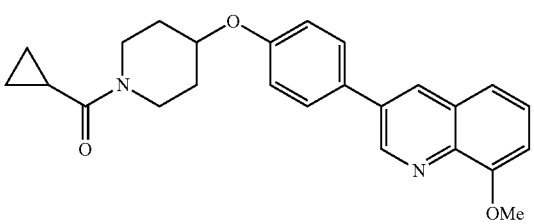 [SMILES: COc1cccc2cc(-c3ccc(OC4CCN(C(=O)C5CC5)CC4)cc3)cnc12]

Analysis: LCMS m/z=403 (M+1); ¹H NMR (DMSO-d6 base) δ: 9.14 (d, 1H, J=2 Hz), 8.51 (d, 1H, J=2 Hz), 7.81 (d, 2H, J=8 Hz), 7.54 (m, 2H), 7.16 (m, 3H), 4.74 (q, 1H, J=4 Hz), 4.02 (b, 1H), 3.98 (s, 3H), 3.89 (b, 1H), 3.57 (b, 1H), 3.29 (m, 1H), 1.94-2.04 (m, 3H), 1.66 (b, 1H), 1.55 (b, 1H), 0.69-0.74 (m, 4H).

Example 59. {4-[4-(8-Chloroquinolin-7-yl)-phenoxy]-piperidin-1-yl}-cyclopropyl-methanone

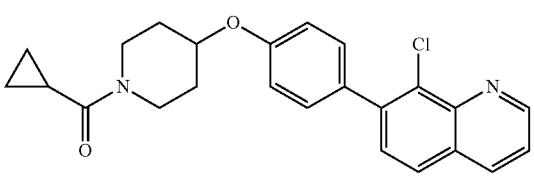

Analysis: LCMS m/z=407 (M+1); ¹H NMR (DMSO-d₆) δ: 9.05 (d, 1H, J=4 Hz), 8.48 (d, 1H, J=8 Hz), 8.01 (d, 1H, J=8 Hz), 7.62-7.68 (m, 2H), 7.50 (d, 2H, J=8 Hz), 7.1 (d, 2H, J=8 Hz), 4.73 (q, 1H, J=4 Hz), 4.01 (b, 1H), 3.92 (b, 1H), 3.56 (b, 1H), 3.22 (b, 1H), 1.98-2.04 (m, 3H), 1.68 (b, 1H), 1.56 (b, 1H), 0.70-0.74 (m, 4H).

Example 60. 1-{4-[4-(4-Methylquinolin-3-yl)-phenoxy]-piperidin-1-yl}-propan-1-one

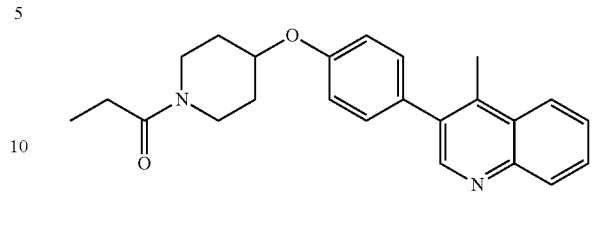

Analysis: LCMS m/z=375 (M+1); ¹H NMR (DMSO-d₆) δ: 9.13 (s, 1H), 8.47 (d, 1H, J=8.5 Hz), 8.33 (d, 1H, J=9 Hz), 8.09 (t, 1H, J=7.5 Hz), 7.95 (t, 1H, J=7.5 Hz), 7.49 (d, 2H, J=8 Hz), 7.20 (d, 2H, J=8 Hz), 4.74 (q, 1H, J=4 Hz), 3.91 (b, 1H), 3.71 (b, 1H), 3.34-3.39 (m, 1H), 3.24-3.29 (m, 1H), 2.83 (s, 3H), 2.34 (q, 2H, J=7 Hz), 1.94 (b, 2H), 1.65 (b, 1H), 1.55 (b, 1H), 1.00 (t, 3H, J=7 Hz).

Example 61. Cyclopropyl-{4-[4-(4-methylquinolin-3-yl)-phenoxy]-piperidin-1-yl}-methanone


Analysis: LCMS m/z=387 (M+1); ¹H NMR (DMSO-d₆ HCl salt) δ: 1H NMR 9.06 (s, 1H), 8.42 (d, J=8.3 Hz, 1H), 8.24 (d, J=8.3 Hz, 1H), 8.02 (t, J=7.7 Hz, 1H), 7.83-7.96 (m, 1H), 7.41-7.58 (m, 2H), 7.20 (d, J=8.5 Hz, 2H), 4.76 (dt, J=7.8, 3.9 Hz, 1H), 4.01-4.09 (m, 1H), 3.89-3.96 (m, 1H), 3.58 (br. s., 1H), 3.25-3.33 (m, 1H), 1.94-2.13 (m, 3H), 1.68 (br. s., 1H), 1.57 (br. s., 1H), 0.67-0.81 (m, 4H).

Example 62. Cyclobutyl-{4-[4-(4-methylquinolin-3-yl)-phenoxy]-piperidin-1-yl}-methanone


Analysis: LCMS m/z=401 (M+1); ¹H NMR (DMSO-d₆ HCl salt) δ: 9.09 (s, 1H), 8.45 (d, J=8.5 Hz, 1H), 8.31 (d, J=8.3 Hz, 1H), 7.86-8.13 (m, 2H), 7.49 (d, J=8.5 Hz, 2H), 7.19 (d, J=8.8 Hz, 2H), 4.61-4.81 (m, 1H), 3.84-3.97 (m, 1H), 3.60 (d, J=13.8 Hz, 1H), 3.32-3.43 (m, 1H), 3.18-3.32 (m, 2H), 2.81 (s, 3H), 2.04-2.23 (m, 4H), 1.92 (dd, J=19.4, 8.9 Hz, 4H), 1.70-1.82 (m, 1H), 1.50-1.68 (m, 3H).

Example 63. 1-{4-[4-(7-Methylquinolin-3-yl)-phenoxy]-piperidin-1-yl}-propan-1-one

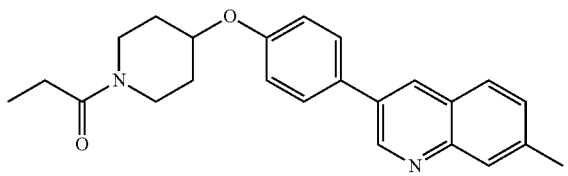 [SMILES: CCC(=O)N1CCC(Oc2ccc(-c3cnc4cc(C)ccc4c3)cc2)CC1]

Analysis: LCMS m/z=375 (M+1): $^1$H NMR (DMSO-d$_6$) δ: 9.29 (d, J=2.3 Hz, 1H), 8.79 (br. s., 1H), 7.95 (d, J=8.0 Hz, 1H), 7.87 (d, J=8.8 Hz, 2H), 7.69 (d, J=7.0 Hz, 1H), 7.56-7.65 (m, 1H), 7.19 (d, J=8.8 Hz, 2H), 4.74 (dt, J=7.7, 4.0 Hz, 1H), 3.83-4.00 (m, 1H), 3.64-3.80 (m, 1H), 3.19-3.52 (m, 2H), 2.78 (s, 3H), 2.31-2.42 (m, 2H), 2.35 (q, J=7.5 Hz, 2H), 1.86-2.10 (m, 2H), 1.64 (d, J=8.5 Hz, 1H), 1.54 (d, J=8.3 Hz, 1H), 1.00 (t, J=7.4 Hz, 3H).

Example 64. Cyclopropyl-{4-[4-(7-methylquinolin-3-yl)-phenoxy]-piperidin-1-yl}-methanone

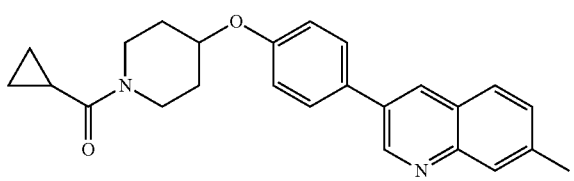 [SMILES: Cc1ccc2cc(-c3ccc(OC4CCN(C(=O)C5CC5)CC4)cc3)cnc2c1]

Analysis: LCMS m/z=387 (M+1); $^1$H NMR (DMSO-d$_6$) δ: 9.27 (d, J=2.3 Hz, 1H), 8.67 (br. s., 1H), 7.81-8.01 (m, 3H), 7.65 (d, J=6.8 Hz, 1H), 7.49-7.61 (m, 1H), 7.19 (d, J=8.5 Hz, 2H), 4.76 (br. s., 1H), 4.01 (br. s., 1H), 3.90 (br. s., 1H), 3.57 (br. s., 1H), 3.30 (br. s., 1H), 2.73-2.82 (m, 3H), 2.01 (d, J=5.3 Hz, 3H), 1.68 (br. s., 1H), 1.57 (br. s., 1H), 0.48-0.81 (m, 4H).

Example 65. {4-[4-(4-Methylquinolin-3-yl)-phenoxy]-piperidin-1-yl}-(R)-tetrahydro-furan-2-yl-methanone

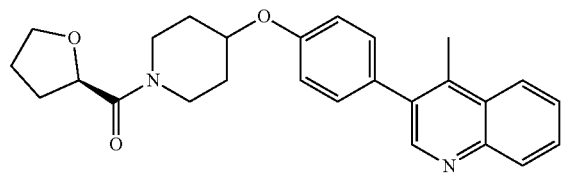 [SMILES: Cc1c(-c2ccc(OC3CCN(C(=O)[C@H]4CCCO4)CC3)cc2)cnc2ccccc12]

Analysis: LCMS m/z=417 (M+1); $^1$H NMR (DMSO-d$_6$) δ: 9.13 (1H, s), 8.47 (1H, d, J=8.3 Hz), 8.32 (1H, d, J=8.3 Hz), 8.08 (1H, t, J=7.7 Hz), 7.90-8.00 (1H, m), 7.50 (2H, d, J=8.8 Hz), 7.20 (2H, d, J=8.5 Hz), 4.76 (1H, d, J=3.5 Hz), 4.70 (1H, t, J=6.1 Hz), 3.69-4.00 (4H, m), 3.20-3.52 (2H, m), 2.82 (3H, s), 1.93-2.12 (4H, m), 1.78-1.91 (2H, m), 1.49-1.73 (2H, m).

Example 66. 1-[4-(4-Quinoxalin-2-yl-phenoxy)-piperidin-1-yl]-propan-1-one

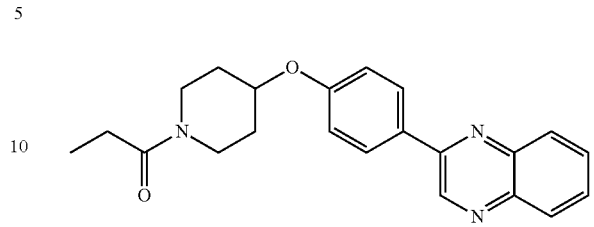

Analysis: LCMS m/z=362 (M+1); $^1$H NMR (DMSO-d$_6$ HCl salt) δ: 9.55 (s, 1H), 8.31 (d, 1H, J=8 Hz), 8.08 (d, 1H, J=8 Hz), 7.79-7.87 (m, 2H), 7.19 (d, 2H, J=8 Hz), 4.79 (m, 1H), 3.89 (m, 1H), 3.70 (m, 1H), 3.37 (m, 1H), 3.25 (m, 1H), 2.34 (q, 2H, J=7 Hz), 1.99 (b, 2H), 1.63 (b, 1H), 1.53 (b, 1H), 1.00 (t, 3H, J=7 Hz).

Example 67. Cyclopropyl-[4-(4-quinoxalin-2-yl-phenoxy)-piperidin-1-yl]-methanone

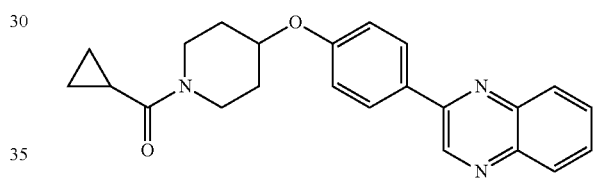

Analysis: LCMS m/z=374 (M+1); $^1$H NMR (DMSO-d6 HCl salt) δ:9.55 (s, 1H), 8.31 (d, 2H, J=9 Hz), 8.08-8.11 (m, 2H), 7.79-7.88 (m, 2H), 7.20 (d, 2H, J=8 Hz), 4.80 (q, 1H, J=4 Hz), 3.99 (b, 1H), 3.91 (b, 1H), 3.56 (b, 1H), 3.28 (b, 1H), 1.98-2.08 (m, 3H), 1.67 (b, 1H), 1.57 (b, 1H), 0.70-0.74 (m, 4H).

Example 68. [4-(4-Quinoxalin-2-yl-phenoxy)-piperidin-1-yl]-(R)-tetrahydrofuran-2-yl-methanone

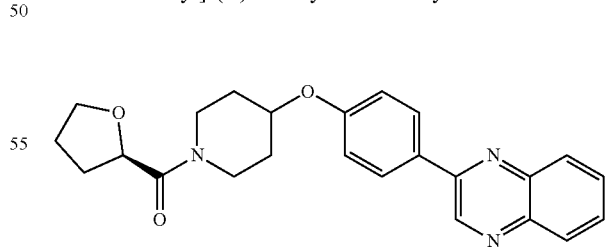

Analysis: LCMS m/z=404 (M+1); $^1$H NMR (DMSO-d$_6$ HCl salt) δ: 9.55 (s, 1H), 8.30 (d, 2H, J=8 Hz), 8.08-8.11 (m, 2H), 7.80-7.88 (m, 2H), 7.20 (d, 2H, J=8 Hz), 4.79 (m, 1H), 4.69 (m, 1H), 3.71-3.81 (m, 4H), 3.26-3.46 (m, 2H), 1.95-2.01 (m, 4H), 1.78-1.89 (m, 2H), 1.54-1.68 (m, 2H).

Example 69. {4-[4-(8-Methylquinolin-7-yl)-phenoxy]-piperidin-1-yl}-(R)-tetrahydro-furan-2-yl-methanone

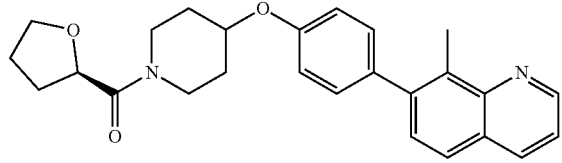 [SMILES: Cc1c(-c2ccc(OC3CCN(C(=O)[C@H]4CCCO4)CC3)cc2)ccc2cccnc12]

Analysis: LCMS m/z=417 (M+1); ¹H NMR (DMSO-d₆) δ 9.05-9.21 (m, 1H), 8.75 (br. s., 1H), 8.05 (d, J=8.5 Hz, 1H), 7.76-7.89 (m, 1H), 7.66 (d, J=8.3 Hz, 1H), 7.35-7.49 (m, 2H), 7.14 (d, J=8.5 Hz, 2H), 4.65-4.81 (m, 3H), 3.70-3.98 (m, 5H), 3.15-3.50 (m, 3H), 2.71 (s, 3H), 1.91-2.19 (m, 4H), 1.75-1.91 (m, 2H), 1.45-1.73 (m, 2H).

Example 70. {4-[4-(8-Methylquinolin-7-yl)-phenoxy]-piperidin-1-yl}-(S)-tetrahydro-furan-2-yl-methanone

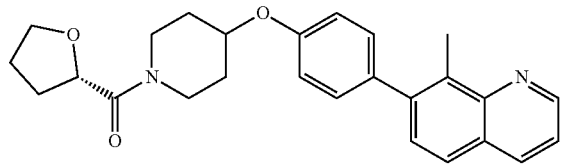

Analysis: LCMS m/z=417 (M+1); ¹H NMR (DMSO-d₆) δ: 8.97 (d, J=2.5 Hz, 1H), 8.37 (d, J=8.0 Hz, 1H), 7.85 (d, J=8.5 Hz, 1H), 7.55 (dd, J=8.3, 4.3 Hz, 1H), 7.48 (d, J=8.5 Hz, 1H), 7.38 (d, J=8.3 Hz, 2H), 7.11 (d, J=8.5 Hz, 2H), 4.70 (d, J=5.3 Hz, 2H), 3.69-4.03 (m, 4H), 3.38-3.58 (m, 1H), 3.25 (br. s., 1H), 2.68 (s, 3H), 1.91-2.13 (m, 4H), 1.85 (dt, J=13.9, 6.7 Hz, 2H), 1.53-1.73 (m, 2H)

Example 71. {4-[4-(4-Chloroquinolin-3-yl)-phenoxy]-piperidin-1-yl}-(R)-tetrahydro-furan-2-yl-methanone

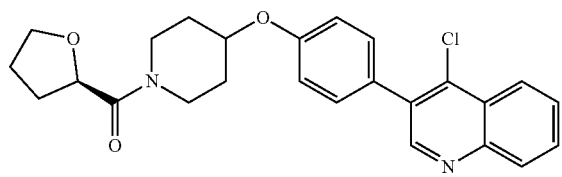 [SMILES: O=C([C@H]1CCCO1)N1CCC(Oc2ccc(-c3cnc4ccccc4c3Cl)cc2)CC1]

Analysis: LCMS m/z=437 (M+1); ¹H NMR (DMSO-d₆) δ: 8.88 (s, 1H), 8.31 (d, 1H, J=8 Hz), 8.12 (d, 1H, J=8 Hz), 7.89 (t, 1H, J=7 Hz), 7.82 (t, 1H, J=7 Hz), 7.55 (d, 2H, J=8 Hz), 7.16 (d, 2H, J=8 Hz), 4.68-4.74 (m, 2H), 3.72-3.93 (m, 4H), 3.39-3.48 (m, 1H), 3.23-3.28 (m, 1H), 1.96-2.08 (m, 4H), 1.80-1.87 (m, 2H), 1.66 (b, 1H), 1.56 (b, 1H).

Example 72. 1-{4-[4-(4-Methylquinolin-3-yl)-phenoxy]-piperidin-1-yl}-propane-1,2-dione

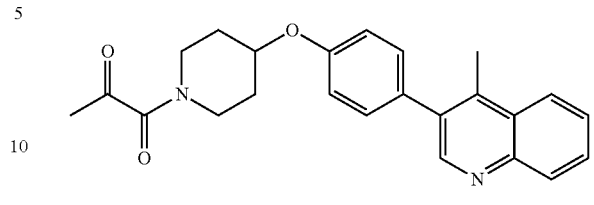

Analysis: LCMS m/z=389 (M+1); ¹H NMR (DMSO-d₆ HCl salt) δ: 9.09 (1H, s), 8.45 (1H, d, J=8.5 Hz), 8.29 (1H, d, J=8.5 Hz), 8.05 (1H, t, J=7.7 Hz), 7.86-7.98 (1H, m), 7.50 (2H, d, J=8.5 Hz), 7.21 (2H, d, J=8.5 Hz), 4.73-4.87 (1H, m), 3.77-3.90 (2H, m), 3.53-3.65 (2H, m), 3.29-3.47 (3H, m), 2.40 (3H, s), 1.95-2.10 (2H, m), 1.55-1.78 (2H, m).

Example 73. Isoxazolidin-2-yl-[4-(4-quinolin-3-yl-phenoxy)-piperidin-1-yl]-methanone

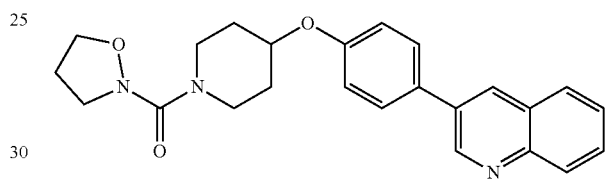

Method A: 3-[4-(Piperidin-4-yloxy)-phenyl]-quinoline.2 HCl (0.180 g, 0.477 mmol) in DCM (3 mL) was added triphosgene (0.0708 g, 0.238 mmol) on an ice bath. The mixture was warmed to rt, stirred 4 h, and then was concentrated. This material in DCM (4 mL) was added DIPEA (0.166 mL, 0.954 mmol) and isoxazolidine.HCl (0.0627 g, 0.572 mmol) and stirred at rt for 2 h. The reaction was concentrated, dissolved in EtOAc and washed with 1N Na₂CO₃ and brine and then dried (MgSO₄). The product was chromatographed on Isco (12 g silica gel, 0-5% MeOH/DCM) to give an oil. The HCl salt was prepared by adding 0.5 mL 1N HCl-ether to a DCM solution of base, was recrystallized from DCM-ether and dried to give a yellow solid (140 mg, 72%). Analysis: LCMS m/z=404 (M+1); ¹H NMR (DMSO-d6 HCl salt) δ: 9.48 (s, 1H), 9.09 (s, 1H), 8.23 (d, 2H, J=7 Hz), 7.90-7.97 (m, 3H), 7.82 (t, 1H, J=7.8 Hz), 7.20 (d, 2H, J=8 Hz), 4.75 (q, 1H, J=4 Hz), 3.76-3.83 (m, 4H), 3.43 (t, 2H, J=7.5 Hz), 3.30-3.37 (m, 2H), 2.13 (q, 2H, J=7 Hz), 1.98-2.02 (m, 2H), 1.58-1.66 (m, 2H).

The following examples were synthesized using the previous procedure.

Example 74. [4-(4-Isoquinolin-3-yl-phenoxy)-piperidin-1-yl]-isoxazolidin-2-yl-methanone

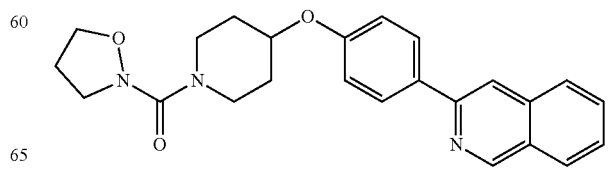

Analysis: LCMS m/z=404 (M+1); ¹H NMR (DMSO-d₆ HCl salt) δ: 9.61 (s, 1H), 8.56 (s, 1H), 8.31 (d, 1H, J=8.5 Hz), 8.11 (m, 3H), 7.97 (7, 1H, J=7 Hz), 7.79 (t, 1H, J=7 Hz), 7.20 (d, 2H, J=8 Hz), 4.75 (q, 1H, J=4 Hz), 3.81 (m, 4H), 4.43 (t, 2H, J=7 Hz), 3.31-3.36 (m, 2H), 2.13 (q, 2H, J=7 Hz), 2.00 (b, 2H), 1.61-1.65 (m, 2H).

Example 75. Isoxazolidin-2-yl-{4-[4-(8-methyl-quinolin-7-yl)-phenoxy]-piperidin-1-yl}-methanone

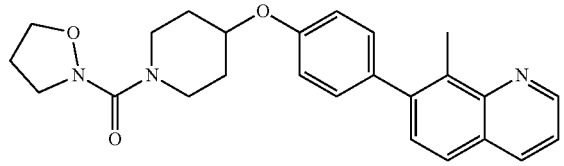 [SMILES: Cc1c(-c2ccc(OC3CCN(C(=O)N4CCCO4)CC3)cc2)ccc2cccnc12]

Analysis: LCMS m/z=418 (M+1); 1H NMR (DMSO-d₆ HCl salt) δ: 8.98 (s, 1H), 8.35 (d, 1H, J=7.7 Hz), 7.84 (d, 1H, J=8 Hz), 7.53-7.56 (m, 1H), 7.46 (d, 1H, J=8.5 Hz), 7.36 (d, 2H, J=8 Hz), 7.09 (d, 2H, J=8 Hz), 4.68 (b, 1H), 3.81 (m, 4H), 3.43 (t, 2H, J=7 Hz), 3.3 (m, 2H), 2.67 (s, 3H), 2.09-2.17 (m, 2H), 1.99 (b, 2H), 1.58-1.70 (m, 2H).

Example 76. {4-[4-(4-Chloroquinolin-3-yl)-phenoxy]-piperidin-1-yl}-isoxazolidin-2-yl-methanone

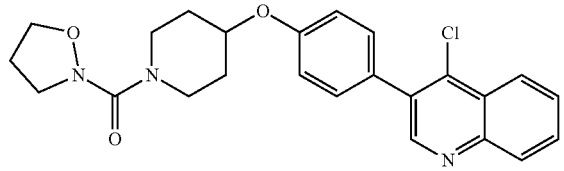 [SMILES: O=C(N1CCC(Oc2ccc(-c3cnc4ccccc4c3Cl)cc2)CC1)N1CCCO1]

Analysis: LCMS m/z=438 (M+1); 1H NMR (DMSO-d₆ HCl salt) δ: 9.13 (d, 1H, J=4 Hz), 8.85 (d, 1H, J=7 Hz), 8.08 (d, 1H, J=8 Hz), 7.85-7.89 (m, 1H), 7.68 (d, 1H, J=8 Hz), 7.42 (d, 2H, J=8 Hz), 7.16 (d, 2H, J=8 Hz), 4.69-4.73 (m, 2H), 3.78-3.83 (m, 4H), 3.43 (t, 2H, J=7 Hz), 3.29-3.36 (m, 2H), 2.13 (q, 2H, J=7.2 Hz), 1.98-2.03 (m, 2H), 1.58-1.66 (m, 2H), Example 77. {4-[4-(8-Chloroquinolin-7-yl)-phenoxy]-piperidin-1-yl}-isoxazolidin-2-yl-methanone

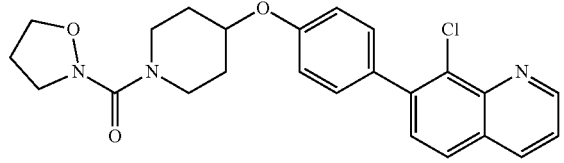 [SMILES: O=C(N1CCC(Oc2ccc(-c3ccc4cccnc4c3Cl)cc2)CC1)N1CCCO1]

Analysis: LCMS m/z=438 (M+1); 1H NMR (DMSO-d6) δ: 9.05 (d, 1H, J=5 Hz), 8.48 (d, 1H, J=8 Hz), 8.01 (d, 1H, J=8.5 Hz), 7.64-7.67 (m, 1H), 7.61 (d, 1H, J=8 Hz), 7.49 (d, 2H, J=8 Hz), 7.12 (d, 2H, J=8 Hz), 4.70 (q, 1H, J=4 Hz), 3.78-3.83 (m, 4H), 3.43 (t, 2H, J=7.5 Hz), 3.30-3.35 (m, 2H), 2.13 (q, 2H, J=7.3 Hz), 1.98.2.03 (m, 2H), 1.58-1.66 (m, 2H).

Example 78. Isoxazolidin-2-yl-{4-[4-(4-methylquinolin-3-yl)-phenoxy]-piperidin-1-yl}-methanone

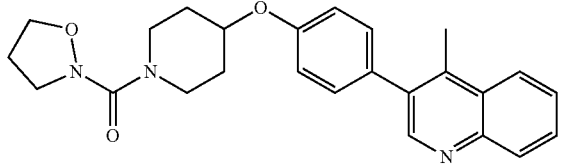 [SMILES: Cc1c(-c2ccc(OC3CCN(C(=O)N4CCCO4)CC3)cc2)cnc2ccccc12]

Analysis: LCMS m/z=418 (M+1); ¹H NMR (DMSO-d₆) δ: 8.74 (s, 1H), 8.20 (d, 1H, J=8 Hz), 8.03 (d, 1H, J=8 Hz), 7.78 (t, 1H, J=7.2 Hz), 7.68 (t, 1H, J=7.2 Hz), 7.42 (d, 2H, J=8 Hz), 7.14 (d, 2H, J=8 Hz), 4.70 (q, 1H, J=4 Hz), 3.79-3.83 (m, 4H), 3.43 (t, 2H, J=7.2 Hz), 3.29-3.36 (m, 4H), 2.63 (s, 3H), 2.13 (q, 2H, J=8 Hz), 1.99-2.02 (m, 2H).

Example 79. Isoxazolidin-2-yl-{4-[4-(8-methoxy-quinolin-7-yl)-phenoxy]-piperidin-1-yl}-methanone

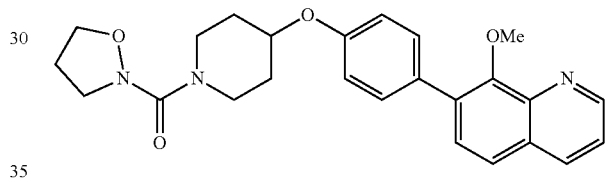

Analysis: LCMS m/z=434 (M+1); ¹H NMR (DMSO-d₆) δ: 8.94 (m, 1H), 8.38 (d, 1H, J=8 Hz), 7.75 (d, 1H, J=8.5 Hz), 7.53-7.60 (m, 4H), 7.10 (d, 2H, J=8 Hz), 4.68 (q, 1H, J=4 Hz), 3.91 (s, 3H), 3.81 (m, 4H), 3.3 (m, 2H), 3.43 (t, 2H, J=7 Hz), 2.14 (q, 2H, J=7 Hz), 2.10 (m, 2H), 1.57-1.66 (m, 2H).

Example 80. Isoxazolidin-2-yl-{4-[4-(7-methylquinolin-3-yl)-phenoxy]-piperidin-1-yl}-methanone

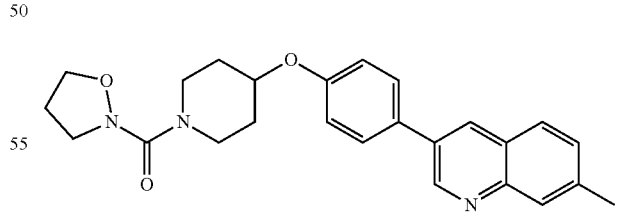

Analysis: LCMS m/z=418 (M+1); ¹H NMR (DMSO-d₆) δ: 9.24 (d, 1H, J=2 Hz), 8.52 (d, 1H, J=2 Hz), 7.81-7.86 (m, 3H), 7.58 (d, 1H, J=7 Hz), 7.51 (t, 1H, J=7 Hz), 7.15 (d, 2H, J=8 Hz), 4.70 (q, 1H, J=4 Hz), 3.77-3.83 (m, 4H), 3.43 (t, 2H, J=7.5 Hz), 3.30-3.36 (m, 2H), 2.75 (s, 3H), 2.13 (q, 2H, J=7 Hz), 1.99 (m, 2H), 1.59-1.65 (m, 2H).

Example 81. Isoxazolidin-2-yl-[4-(4-quinoxalin-2-yl-phenoxy)-piperidin-1-yl]-methanone

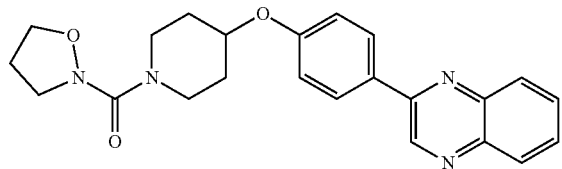 [SMILES: O=C(N1CCC(Oc2ccc(-c3cnc4ccccc4n3)cc2)CC1)N1CCCO1]

Analysis: LCMS m/z=405 (M+1); $^1$H NMR (DMSO-d$_6$) δ: 9.55 (s, 1H), 8.30 (d, 2H, J=8 Hz), 8.09 (m, 2H), 7.78-7.88 (m, 2H), 7.20 (d, 2H, J=8 Hz), 4.77 (q, 1H, J=4 Hz), 3.77-3.83 (m, 4H), 3.43 (t, 2H, J=7 Hz), 3.34 (m, 2H), 2.14 (q, 2H, J=7 Hz), 2.00 (m, 2H), 1.58-1.67 (m, 2H).

Example 82. 4-[4-(4-Methylquinolin-3-yl)-phenoxy]-piperidine-1-carboxylic acid methoxyamide

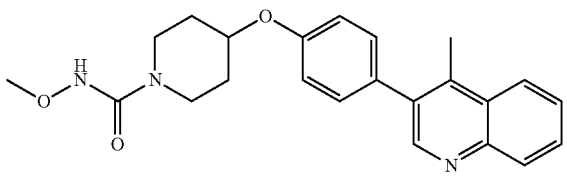 [SMILES: CONC(=O)N1CCC(Oc2ccc(-c3cnc4ccccc4c3C)cc2)CC1]

Analysis: LCMS m/z=392 (M+1); $^1$H NMR (DMSO-d$_6$ HCl salt) δ: 9.8 (s, 1H, D$_2$O exch), 8.99 (1H, br. s.), 8.43 (1H, d, J=8.3 Hz), 8.20 (1H, d, J=8.3 Hz), 8.05 (1H, t, J=7.4 Hz), 7.88-7.99 (1H, m), 7.49 (2H, d, J=8.0 Hz), 7.19 (2H, d, J=8.0 Hz), 4.70 (1H, br. s.), 3.63 (2H, d, J=12.8 Hz), 3.56 (2H, s), 3.19 (2H, t, J=9.9 Hz), 2.80 (3H, s), 1.98 (2H, br. s.), 1.60 (2H, d, J=8.3 Hz).

Example 83. 4-[4-(4-Methylquinolin-3-yl)-phenoxy]-piperidine-1-carboxylic acid methoxymethylamide

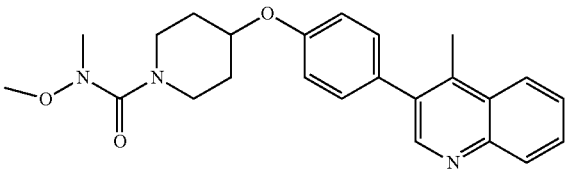 [SMILES: CON(C)C(=O)N1CCC(Oc2ccc(-c3cnc4ccccc4c3C)cc2)CC1]

Analysis: LCMS m/z=406 (M+1); 1H NMR (DMSO-d$_6$ HCl) δ: 9.05 (1H, s), 8.40 (1H, d, J=8.5 Hz), 8.17-8.27 (1H, m), 7.95-8.03 (1H, m), 7.83-7.94 (1H, m), 7.42-7.55 (2H, m), 7.13-7.26 (2H, m), 4.65-4.83 (1H, m), 3.68-3.77 (2H, m), 3.55 (3H, s), 3.23-3.34 (2H, m), 2.84 (3H, s), 2.78 (3H, s), 1.98-2.08 (2H, m), 1.59-1.71 (2H, m).

Example 84. 4-[4-(4-Methylquinolin-3-yl)-phenoxy]-piperidine-1-carboxylic acid ethylamide

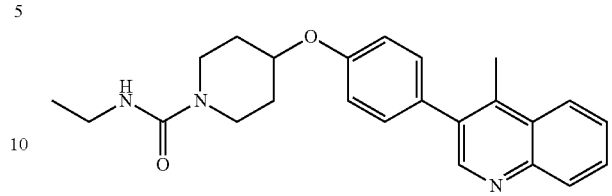

Method A Example 73 using ethyl amine. Analysis: LCMS m/z=390 (M+1); $^1$H NMR (DMSO-d$_6$) δ: 10.26 (1H, m; D$_2$O exch), 8.73 (1H, s), 8.19 (1H, d, J=8.3 Hz), 8.04 (1H, d, J=8.3 Hz), 7.77 (1H, td, J=7.5, 1.3 Hz), 7.63-7.71 (1H, m), 7.40 (2H, d, J=8.8 Hz), 7.13 (2H, d, J=8.8 Hz), 6.51 (1H, t, J=5.3 Hz), 4.63 (1H, dt, J=8.0, 4.2 Hz), 3.65-3.79 (2H, m), 2.99-3.18 (4H, m), 2.63 (3H, s), 1.88-2.02 (2H, m), 1.45-1.62 (2H, m), 1.02 (3H, t, J=7.2 Hz).

Example 85. 4-[4-(8-Methoxyquinolin-7-yl)-phenoxy]-piperidine-1-carboxylic acid methylamide

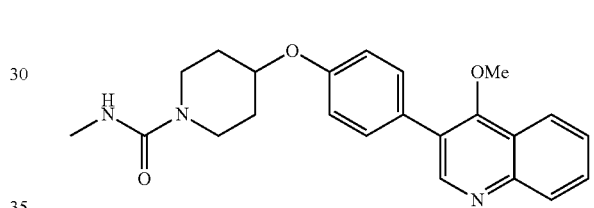

Method A Example 73 using methyl amine in methanol. Analysis: LCMS m/z=392 (M+1); $^1$H NMR (DMSO-d6 HCl salt) δ: 9.14 (1H, d, J=3.8 Hz), 8.96 (1H, br. s.), 8.05 (1H, d, J=8.5 Hz), 7.92 (1H, d, J=7.8 Hz), 7.87 (1H, d, J=8.5 Hz), 7.69 (2H, d, J=8.8 Hz), 7.16 (2H, d, J=8.8 Hz), 4.61-4.70 (1H, m), 3.74 (3H, s), 3.70 (2H, d, J=4.8 Hz), 3.13 (2H, ddd, J=13.2, 9.7, 3.0 Hz), 2.58 (3H, s), 1.90-2.00 (2H, m), 1.47-1.59 (2H, m).

Example 86. 4-[4-(8-Methoxyquinolin-7-yl)-phenoxy]-piperidine-1-carboxylic acid ethylamide

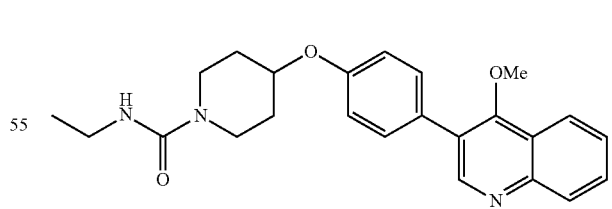

Method A Example 73 using ethyl amine HCl. Analysis: LCMS m/z=406 9M+1): $^1$H NMR (DMSO-d$_6$ HCl salt) δ: 9.17 (1H, d, J=4.0 Hz), 9.02 (1H, d, J=7.8 Hz), 8.09 (1H, d, J=8.5 Hz), 7.94-8.03 (1H, m), 7.91 (1H, d, J=8.3 Hz), 7.70 (2H, d, J=8.8 Hz), 7.17 (2H, d, J=8.8 Hz), 4.66 (1H, dt, J=8.2, 4.2 Hz), 3.72 (5H, s), 3.01-3.21 (4H, m), 1.86-2.04 (2H, m), 1.45-1.61 (2H, m), 0.98-1.05 (3H, m).

Example 87. 4-[4-(4-Methylquinolin-3-yl)-phenoxy]-piperidine-1-carboxylic acid hydroxyamide

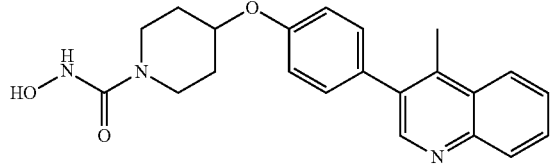 [SMILES: Cc1c(-c2ccc(OC3CCN(C(=O)NO)CC3)cc2)cnc2ccccc12]

Analysis: LCMS m/z=378 (M+1); $^1$H NMR (DMSO-d$_6$; HCl salt) δ: 8.71 (1H, s), 8.21 (1H, d, J=8.3 Hz), 8.05 (1H, d, J=8.5 Hz), 7.81 (1H, t, J=7.5 Hz), 7.66-7.76 (1H, m), 7.41 (2H, d, J=8.3 Hz), 7.10-7.21 (2H, m), 4.66 (1H, br. s.), 3.66 (2H, d, J=13.8 Hz), 3.17 (2H, t, J=9.9 Hz), 2.64 (3H, s), 1.89-2.05 (2H, m), 1.49-1.69 (2H, m).

Example 88. N-ethyl-4-[4-(8-methyl-7-quinolyl)phenoxy]piperidine-1-carboxamide

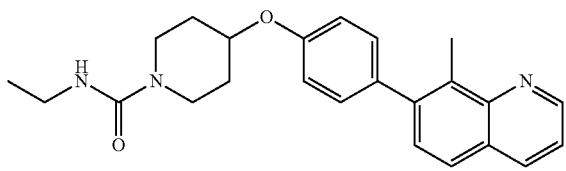

Method A Example 73 using ethyl amine HCl. Analysis: LCMS m/z=390 (M+1); $^1$H NMR (DMSO-d$_6$; HCl salt) δ: 9.13 (d, J=3.8 Hz, 1H), 8.83 (br. s., 1H), 8.07 (d, J=8.3 Hz, 1H), 7.85 (br. s., 1H), 7.68 (d, J=8.3 Hz, 1H), 7.40 (d, J=8.3 Hz, 2H), 7.13 (d, J=8.5 Hz, 2H), 4.64 (d, J=3.8 Hz, 1H), 3.72 (d, J=13.6 Hz, 2H), 3.02-3.20 (m, 4H), 2.72 (s, 3H), 1.95 (d, J=9.5 Hz, 2H), 1.47-1.65 (m, 2H), 1.02 (t, J=7.2 Hz, 3H).

Method B. B 8-Methyl-7-[4-(piperidin-4-yloxy)-phenyl]-quinoline dihydrochloride (0.1 g, 0.31 mmol) and DIEA (0.16 mL, 0.94 mmol) in DCM (2 mL) was added isocyanatoethane (0.27 g, 0.30 mL, 3.8 mmol) then stirred at 70° C. for 2 h. The reaction was concentrated, dissolved in EtOAc and washed with 1N Na$_2$CO$_3$ and brine and dried (MgSO$_4$). The product was chromatographed on ISCO (24 g silica gel, 50-100% EtOAC-hexanes) to give an oil. The HCl salt (synthesized from 1N HCl-ether and DCM) was crystallized from DCM-ether to give a yellow solid (69%).

Example 89 N,N-dimethyl-4-[4-(8-methyl-7-quinolyl)phenoxy]piperidine-1-carboxamide

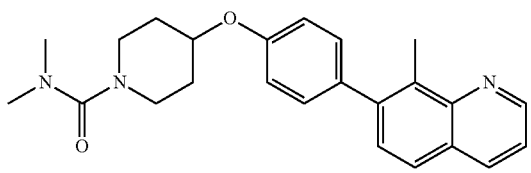 [SMILES: Cc1c(-c2ccc(OC3CCN(C(=O)N(C)C)CC3)cc2)ccc2cccnc12]

To 8-methyl-7-[4-(piperidin-4-yloxy)-phenyl]-quinoline dihydrochloride (0.150 g, 0.383 mmol) in DCM (4 mL) was added TEA (0.214 mL, 1.53 mmol) and N,N-dimethylcarbamoyl chloride (0.0824 g, 0.767 mmol). After stirring at rt for 2 h, the mixture was concentrated, washed with 1N Na$_2$CO$_3$ and brine then dried over MgSO$_4$. The product was purified by ISCO (12 g silica gel, EtOAc/hexanes 40-80%) to give an oil. The HCl salt was synthesized by adding 0.5 mL of a 2M HCl ether solution to a DCM solution of base. The salt was crystallized from DCM-ether to give a yellow solid (87%). Analysis: LCMS m/z=390 (M+1); $^1$H NMR (DMSO-d6) δ: 9.15 (d, J=3.5 Hz, 1H), 8.89 (d, J=7.3 Hz, 1H), 8.11 (d, J=8.5 Hz, 1H), 7.90 (dd, J=7.8, 4.5 Hz, 1H), 7.71 (d, J=8.3 Hz, 1H), 7.41 (d, J=8.5 Hz, 2H), 7.14 (d, J=8.5 Hz, 2H), 4.66 (dt, J=8.0, 4.2 Hz, 1H), 3.30-3.62 (m, 2H), 3.04 (ddd, J=12.9, 9.5, 2.9 Hz, 2H), 2.75 (s, 6H), 2.73 (s, 3H), 1.91-2.07 (m, 2H), 1.52-1.78 (m, 2H).

Example 90. Ethyl 4-[4-(8-methyl-7-quinolyl)phenoxy]piperidine-1-carboxylate

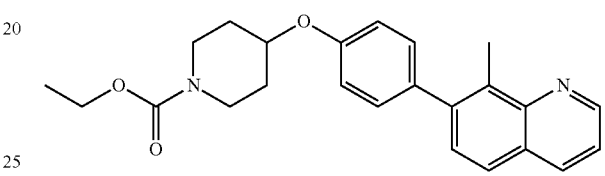

To 8-methyl-7-[4-(piperidin-4-yloxy)-phenyl]-quinoline 2HCl (0.150 g, 0.383 mmol) in DCM (4 mL) was added TEA (0.214 mL, 1.53 mmol) and ethyl chloroformate (0.0832 g, 0.767 mmol). After stirring at rt for 2 h, the mixture was concentrated, washed with 1N Na$_2$CO$_3$ and brine then dried over MgSO$_4$. The product was purified by ISCO (12 g silica gel, EtOAc/hexanes 40-80%) to give oil. The HCl salt (synthesized from 2N HCl-ether and DCM) was crystallized from DCM-ether-hexanes to give a light yellow solid (73%). Analysis: LCMS m/z=391 (M+1); $^1$H NMR (DMSO-d$_6$) δ: 9.14 (d, J=4.3 Hz, 1H), 8.87 (br. s., 1H), 8.09 (d, J=8.3 Hz, 1H), 7.88 (d, J=4.8 Hz, 1H), 7.70 (d, J=8.5 Hz, 1H), 7.41 (d, J=8.8 Hz, 2H), 7.14 (d, J=8.5 Hz, 2H), 4.64-4.78 (m, 1H), 4.06 (q, J=7.1 Hz, 2H), 3.68-3.84 (m, 2H), 3.28 (t, J=9.5 Hz, 2H), 2.67-2.80 (m, 3H), 1.98 (d, J=7.3 Hz, 2H), 1.60 (dtd, J=12.7, 8.6, 3.9 Hz, 2H), 1.20 (t, J=7.0 Hz, 3H).

Example 91. N-methoxy-4-[4-(8-methyl-7-quinolyl)phenoxy]piperidine-1-carboxamide

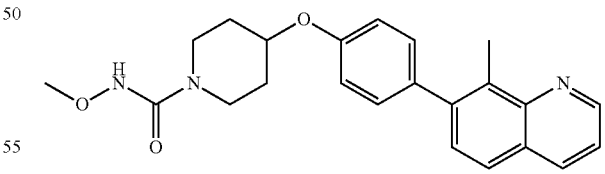

To 8-methyl-7-[4-(4-piperidyloxy)phenyl]quinoline 2HCl (0.15 g, 0.3833 mmol) in DCM (4 mL) was added TEA (0.214 mL, 1.533 mmol) and triphosgene (0.1138 g, 0.3833 mmol) on an ice bath, stirred for 1 h then concentrated. The residue in DCM (4 mL) was added TEA (0.214 mL, 1.533 mmol) and O-methylhydroxylamine HCl (0.06403 g, 0.7667 mmol) then heated at 70° C. for 2 h. The mixture was concentrated, washed with 1N Na$_2$CO$_3$ and brine then dried over MgSO$_4$. The product was purified by ISCO (12 g silica gel, EtOAc/hexanes 40-90% over 5 min) to give and oil. The HCl salt (0.5 mL 2N HCl-ether added to DCM solution of base) was crystallized from DCM-ether to give a light yellow solid (67%). Analysis: LCMS m/z=392 (M+1); $^1$H NMR (DMSO-d$_6$) δ: 9.75 (br. s., 1H), 9.08 (d, J=3.8 Hz, 1H), 8.70 (br. s., 1H), 8.02 (d, J=8.0 Hz, 1H), 7.77 (br. s., 1H), 7.63 (d, J=8.5 Hz, 1H), 7.40 (d, J=8.8 Hz, 2H), 7.12 (d, J=8.8 Hz, 2H), 4.60-4.71 (m, 1H), 3.59-3.72 (m, 2H), 3.54 (s, 3H), 3.06-3.21 (m, 2H), 2.67-2.76 (m, 3H), 1.96 (d, J=10.3 Hz, 2H), 1.47-1.64 (m, 2H)

Example 92. N-Isopropyl-4-[4-(8-methyl-7-quinolyl)phenoxy]piperidine-1-carboxamide

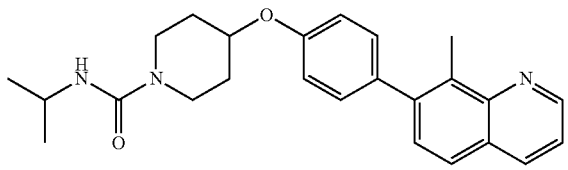 [SMILES: Cc1c(-c2ccc(OC3CCN(C(=O)NC(C)C)CC3)cc2)ccc2cccnc12]

This example was synthesized using isopropyl amine by the procedure for Example 91. Analysis: LCMS m/z=404 (M+1); $^1$H NMR (DMSO-d$_6$; HCl salt) δ: 9.08 (d, J=3.3 Hz, 1H), 8.70 (br. s., 1H), 8.01 (d, J=8.3 Hz, 1H), 7.77 (br. s., 1H), 7.63 (d, J=8.3 Hz, 1H), 7.39 (d, J=8.8 Hz, 2H), 7.12 (d, J=8.5 Hz, 2H), 6.20 (br. s., 1H), 4.63 (dt, J=7.7, 4.0 Hz, 2H), 3.69-3.81 (m, 3H), 3.11 (t, J=9.8 Hz, 2H), 2.70 (s, 3H), 1.95 (d, J=10.3 Hz, 2H), 1.46-1.59 (m, 2H), 1.07 (d, J=6.5 Hz, 6H).

Example 93. N-ethoxy-4-[4-(8-methyl-7-quinolyl)phenoxy]piperidine-1-carboxamide

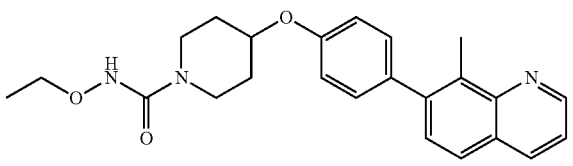 [SMILES: CCONC(=O)N1CCC(Oc2ccc(-c3ccc4cccnc4c3C)cc2)CC1]

This example was synthesized using O-ethylhydroxylamine HCl. Analysis: LCMS m/z=406 (M+1); $^1$H NMR (DMSO-d$_6$; HCl salt) δ: 9.66 (br. s., 1H), 9.07 (d, J=3.3 Hz, 1H), 8.67 (br. s., 1H), 8.00 (d, J=8.3 Hz, 1H), 7.76 (br. s., 1H), 7.61 (d, J=8.5 Hz, 1H), 7.39 (d, J=8.5 Hz, 2H), 7.12 (d, J=8.5 Hz, 2H), 4.65 (dt, J=8.0, 3.9 Hz, 1H), 3.75 (q, J=7.0 Hz, 2H), 3.69-3.58 (m, 2H), 3.22-3.06 (m, 2H), 2.72-2.68 (m, 3H), 1.96 (d, J=12.5 Hz, 2H), 1.62-1.50 (m, 2H), 1.13 (t, J=7.0 Hz, 3H).

Example 94. [4-[4-(8-methyl-7-quinolyl)phenoxy]-1-piperidyl]-pyrrolidin-1-yl-methanone

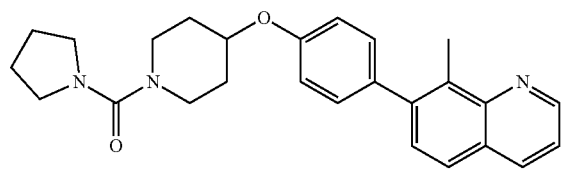 [SMILES: Cc1c(-c2ccc(OC3CCN(C(=O)N4CCCC4)CC3)cc2)ccc2cccnc12]

This example was synthesized using pyrrolidine-1-carbonyl chloride. Analysis: LCMS m/z=390 (M+1); $^1$H NMR (DMSO-d$_6$; HCl salt) δ: 9.15 (d, J=3.5 Hz, 1H), 8.89 (d, J=7.3 Hz, 1H), 8.11 (d, J=8.5 Hz, 1H), 7.90 (dd, J=7.8, 4.5 Hz, 1H), 7.71 (d, J=8.3 Hz, 1H), 7.41 (d, J=8.5 Hz, 2H), 7.14 (d, J=8.5 Hz, 2H), 4.66 (dt, J=8.0, 4.2 Hz, 1H), 3.30-3.62 (m, 2H), 3.04 (ddd, J=12.9, 9.5, 2.9 Hz, 2H), 2.75 (s, 6H), 2.73 (s, 3H), 1.91-2.07 (m, 2H), 1.52-1.78 (m, 2H).

Example 95. N-methyl-4-[4-(8-methyl-7-quinolyl)phenoxy]piperidine-1-carboxamide

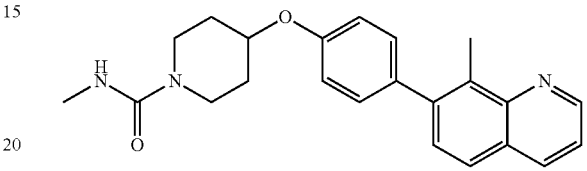

This example was synthesized using aqueous methylamine and triphosgene. Analysis: LCMS m/z=376 (M+1); $^1$H NMR (DMSO-d$_6$; HCl salt) δ: 9.10 (d, J=3.3 Hz, 1H), 8.74 (br. s., 1H), 8.03 (d, J=8.8 Hz, 1H), 7.79 (br. s., 1H), 7.64 (d, J=8.5 Hz, 1H), 7.40 (d, J=8.8 Hz, 2H), 7.12 (d, J=8.5 Hz, 2H), 4.63 (dd, J=7.8, 4.3 Hz, 2H), 3.71 (d, J=13.6 Hz, 2H), 3.20-3.04 (m, 2H), 2.71 (s, 3H), 2.58 (s, 3H), 2.04-1.88 (m, 2H), 1.61-1.48 (m, 2H).

Example 96. 4-[4-(8-methyl-7-quinolyl)phenoxy]-N-propyl-piperidine-1-carboxamide

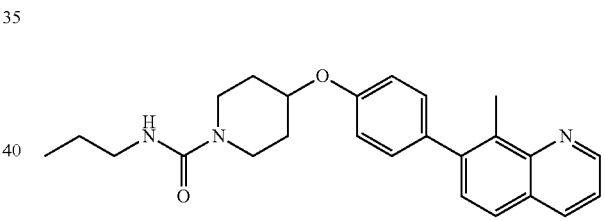

This example was synthesized using n-propylamine and triphosgene. Analysis: LCMS m/z=404 (M+1); $^1$H NMR (DMSO-d6; HCl salt) δ: 9.13 (d, J=3.5 Hz, 1H), 8.85 (br. s., 1H), 8.08 (d, J=8.3 Hz, 1H), 7.87 (br. s., 1H), 7.69 (d, J=8.5 Hz, 1H), 7.41 (d, J=8.8 Hz, 2H), 7.13 (d, J=8.5 Hz, 2H), 4.64 (dt, J=8.3, 4.1 Hz, 1H), 3.80-3.66 (m, 2H), 3.23-3.07 (m, 2H), 2.99 (t, J=7.2 Hz, 2H), 2.72 (s, 3H), 1.95 (d, J=9.8 Hz, 2H), 1.60-1.49 (m, 2H), 1.46-1.37 (m, 2H), 0.84 (t, J=7.4 Hz, 3H).

Example 97. 4-[4-(8-methyl-7-quinolyl)phenoxy]piperidine-1-carboxamide

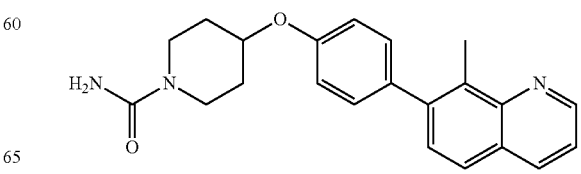

This example was synthesized using ammonia in methanol and triphosgene. Analysis: LCMS m/z=362 (M+1); $^1$H NMR (DMSO-d$_6$; HCl salt) δ: 8.97 (dd, J=4.1, 1.9 Hz, 1H), 8.36 (dd, J=8.2, 1.6 Hz, 1H), 7.85 (d, J=8.3 Hz, 1H), 7.55 (dd, J=8.3, 4.3 Hz, 1H), 7.48 (d, J=8.5 Hz, 1H), 7.37 (d, J=8.3 Hz, 2H), 7.10 (d, J=8.8 Hz, 2H), 5.96 (s, 2H, D$_2$O exch), 4.67-4.59 (m, 1H), 3.71 (d, J=14.3 Hz, 2H), 3.29 (s, 1H), 3.18-3.07 (m, 2H), 2.68 (s, 3H), 1.95 (d, J=9.0 Hz, 2H).

Example 98. [4-[4-(8-methyl-7-quinolyl)phenoxy]-1-piperidyl]-(1-piperidyl)methanone

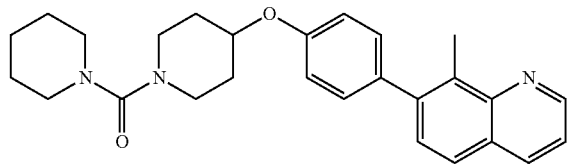 [SMILES: Cc1c(-c2ccc(OC3CCN(C(=O)N4CCCCC4)CC3)cc2)ccc2cccnc12]

This example was synthesized using piperidine-1-carbonyl chloride. Analysis: LCMS m/z=430 (M+1); $^1$H NMR (DMSO-d$_6$; HCl salt) δ: 9.08 (d, J=3.3 Hz, 1H), 8.69 (br. s., 1H), 8.01 (d, J=8.5 Hz, 1H), 7.77 (br. s., 1H), 7.62 (d, J=8.5 Hz, 1H), 7.39 (d, J=8.5 Hz, 2H), 7.19-7.08 (m, 2H), 4.64 (dt, J=8.1, 4.1 Hz, 1H), 3.49-3.40 (m, 2H), 3.15-3.10 (m, 4H), 3.05 (ddd, J=12.9, 9.5, 3.1 Hz, 2H), 2.70 (s, 3H), 2.06-1.93 (m, 2H), 1.70-1.58 (m, 2H), 1.57-1.46 (m, 6H).

Example 99. [4-[4-(8-methyl-7-quinolyl)phenoxy]-1-piperidyl]-morpholinomethanone

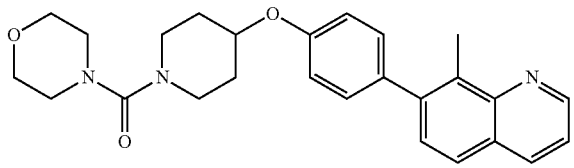 [SMILES: Cc1c(-c2ccc(OC3CCN(C(=O)N4CCOCC4)CC3)cc2)ccc2cccnc12]

This example was synthesized using morpholine-4-carbonyl chloride. Analysis: LCMS m/z=432 (M+1); $^1$H NMR (DMSO-d$_6$; HCl salt) δ: 9.13 (d, J=3.5 Hz, 1H), 8.82 (d, J=5.8 Hz, 1H), 8.07 (d, J=8.3 Hz, 1H), 7.92-7.79 (m, 1H), 7.68 (d, J=8.5 Hz, 1H), 7.41 (d, J=8.5 Hz, 2H), 7.14 (d, J=8.8 Hz, 2H), 4.67 (dt, J=7.9, 4.1 Hz, 1H), 3.61-3.54 (m, 4H), 3.53-3.45 (m, 2H), 3.20-3.04 (m, 6H), 2.72 (s, 3H), 2.00 (d, J=12.0 Hz, 2H), 1.73-1.57 (m, 2H).

The following examples were synthesized using representative procedures described above for example 3 or example 33.

Example 100. Cyclopropyl-[4-(4-quinolin-3-yl-phenoxy)-piperidin-1-yl]-methanone,HCl

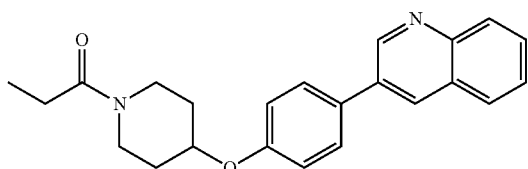

The product was isolated as a yellow solid. Analysis: mp: 170-173° C.; LCMS m/z=373 (M+1); $^1$HNMR (DMSO-d$_6$) δ: 9.51 (d, J=2 Hz, 1H), 9.15 (s, 1H), 8.29-8.24 (m, 2H), 8.00-7.95 (m, 3H), 7.87-7.83 (m, 1H), 7.23 (m, 2H), 4.79 (m, 1H), 4.08-3.82 (m, 2H), 3.66-3.49 (m, 1H), 3.39-3.22 (m, 1H), 2.13-1.87 (m, 3H), 1.75-1.46 (m, 2H), 0.79-0.65 (m, 4H).

Example 101. Cyclobutyl-[4-(4-quinolin-3-yl-phenoxy)-piperidin-1-yl]-methanone,HCl

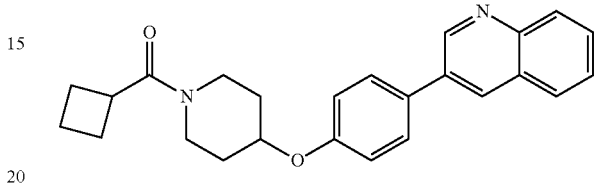

The product was isolated as a yellow solid. Analysis: mp: 164-166° C.; LCMS m/z=387 (M+1); $^1$HNMR (DMSO-d$_6$) δ: 9.53 (d, J=2 Hz, 1H), 9.17 (s, 1H), 8.31-8.24 (m, 2H), 8.01-7.84 (m, 4H), 7.21 (m, 2H), 4.75 (m, 1H), 3.94-3.82 (m, 1H), 3.66-3.53 (m, 1H), 3.44-3.21 (m, 3H), 2.25-2.03 (m, 4H), 2.02-1.83 (m, 3H), 1.80-1.68 (m, 1H), 1.64-1.47 (m, 2H).

Example 102. Cyclopentyl-[4-(4-quinolin-3-yl-phenoxy)-piperidin-1-yl]-methanone, 2HCl

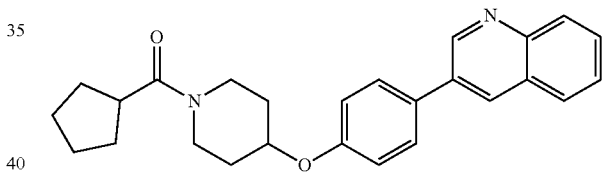

The product was isolated as an off-white solid. Analysis: mp: 145-147° C.; LCMS m/z=401 (M+1); $^1$HNMR (400 MHz, DMSO-d$_6$) δ: 9.52 (m, 1H), 9.16 (s, 1H), 8.27 (m, 2H), 8.02-7.82 (m, 4H), 7.22 (m, 2H), 4.77 (m, 1H), 3.97-3.74 (m, 2H), 3.48-3.21 (m, 2H), 3.02 (m, 1H), 2.08-1.88 (m, 2H), 1.84-1.45 (m, 10H).

Example 103. [4-(4-Quinolin-3-yl-phenoxy)-piperidin-1-yl]-(R)-tetrahydrofuran-2-yl-methanone, HCl

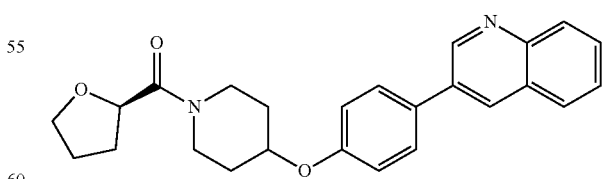

The product was isolated as a light-brown solid. Analysis: LCMS m/z=403 (M+1); $^1$HNMR (400 MHz, DMSO-d$_6$) δ: 9.52 (m, 1H), 9.16 (s, 1H), 8.26 (m, 2H), 7.99 (m, 1H), 7.93 (m, 2H), 7.85 (m, 1H), 7.22 (m, 2H), 4.78 (m, 1H), 4.70 (m, 1H), 3.95-3.70 (m, 4H), 3.66-3.07 (m, 2H), 2.12-1.75 (m, 4H), 1.73-1.45 (m, 2H), 1.33-1.21 (m, 2H).

Example 104. [4-(4-Quinolin-3-yl-phenoxy)-piperidin-1-yl]-(S)-tetrahydrofuran-2-yl-methanone, HCl

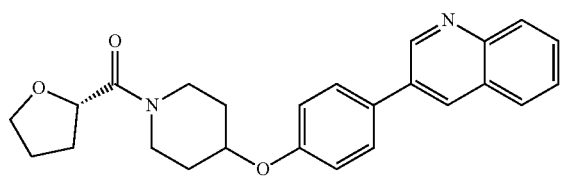

The product was isolated as a light-brown solid. Analysis: LCMS m/z=403 (M+1); ¹HNMR (400 MHz, DMSO-d$_6$) δ: 9.53 (m, 1H), 9.19 (s, 1H), 8.28 (m, 2H), 8.00 (m, 1H), 7.94 (m, 2H), 7.86 (m, 1H), 7.22 (m, 2H), 4.78 (m, 1H), 4.70 (m, 1H), 3.95-3.70 (m, 4H), 3.53-3.22 (m, 2H), 2.12-1.74 (m, 4H), 1.72-1.48 (m, 2H), 1.33-1.15 (m, 2H).

Example 105. 2-Methoxy-1-[4-quinolin-3-yl-phenoxy)-piperidin-1-yl]-ethanone, 2HCl

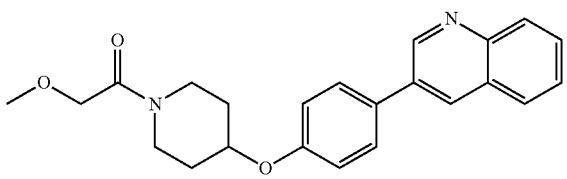 [SMILES: COCC(=O)N1CCC(Oc2ccc(-c3cnc4ccccc4c3)cc2)CC1]

The product was isolated as a tan solid. Analysis: LCMS m/z=377 (M+1); ¹HNMR (400 MHz, DMSO-d$_6$) δ: 9.53 (m, 1H), 9.20 (s, 1H), 8.29 (m, 2H), 8.00 (m, 1H), 7.94 (m, 2H), 7.87 (m, 1H), 7.22 (m, 2H), 4.78 (m, 1H), 4.11 (m, 2H), 3.87 (m, 1H), 3.66 (m, 1H), 3.32 (m, 2H), 3.30 (s, 3H), 1.99 (m, 2H), 1.62 (m, 2H).

Example 106. [4-(4-Quinolin-3-yl-phenoxy)-piperidin-1-yl]-(tetrahydropyran-2-yl)-methanone, 2HCl

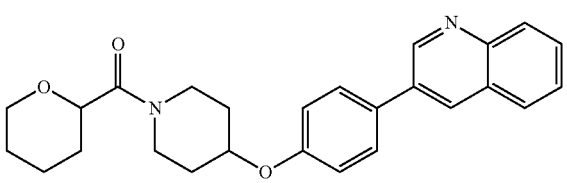 [SMILES: O=C(C1CCCCO1)N1CCC(Oc2ccc(-c3cnc4ccccc4c3)cc2)CC1]

The product was isolated as a tan solid. Analysis: LCMS m/z=417 (M+1); ¹H NMR (400 MHz, DMSO-d$_6$) δ: 9.54-9.58 (1H, m), 9.22-9.26 (1H, m), 8.25-8.33 (2H, m), 7.99-8.06 (1H, m), 7.93-7.97 (2H, m), 7.85-7.91 (1H, m), 7.20-7.25 (2H, m), 4.74-4.83 (1H, m), 4.12-4.19 (1H, m), 3.76-3.92 (3H, m), 3.56-3.65 (1H, m), 3.42-3.53 (2H, m), 3.08-3.16 (1H, m), 1.88-2.08 (2H, m), 1.79-1.86 (1H, m), 1.43-1.66 (7H, m), 1.24-1.32 (12H, m).

Example 107. [4-(4-Quinolin-3-yl-phenoxyl)-piperidin-1-yl]-(tetrahydrofuran-3-yl)-methanone, 2HCl

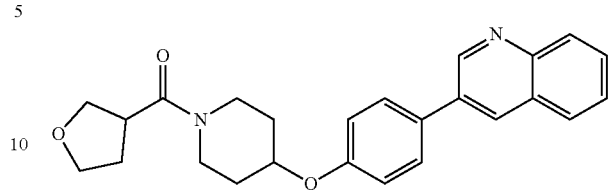

Analysis: LCMS m/z=403 (M+1); ¹HNMR (400 MHz, DMSO-d$_6$) δ: 9.53 (m, 1H), 9.19 (s, 1H), 8.28 (m, 2H), 8.00 (m, 1H), 7.94 (m, 2H), 7.86 (m, 1H), 7.22 (m, 2H), 4.78 (m, 1H), 3.96-3.55 (m, 4H), 3.50-3.27 (m, 3H), 2.10-1.89 (m, 4H), 1.70-1.50 (m, 2H), 1.33-1.22 (m, 2H).

Example 108. (R)-2-Methoxy-1-[4-(4-quinolin-3-yl-phenoxy)-piperidin-1-yl]-propan-1-one, 2HCl

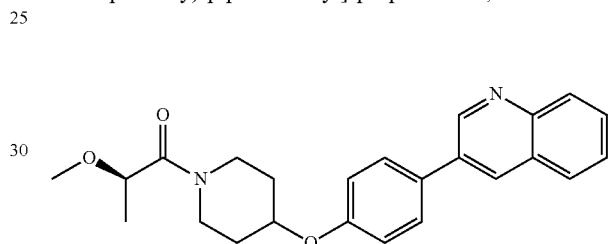

Analysis: LCMS m/z=391 (M+1); ¹H NMR (400 MHz, DMSO-d$_6$) δ: 9.22-9.25 (1H, m), 8.57-8.59 (1H, m), 8.01-8.06 (2H, m), 7.81-7.86 (2H, m), 7.72-7.78 (1H, m), 7.60-7.67 (1H, m), 7.15-7.20 (2H, m), 4.70-4.79 (1H, m), 4.20-4.29 (1H, m), 3.80-3.98 (2H, m), 3.38-3.50 (1H, m), 3.33-3.38 (1H, m), 3.22 (3H, s), 1.92-2.07 (2H, m), 1.51-1.73 (2H, m), 1.23 (3H, d, J=6.8 Hz).

Example 109. (S)-2-Methoxy-1-[4-(4-quinolin-3-yl-phenoxy)-piperidin-1-yl]-propan-1-one, 2HCl

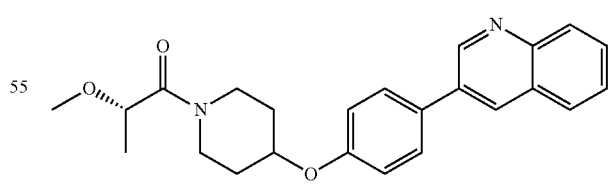

Analysis: LCMS m/z=391 (M+1); ¹H NMR (400 MHz, DMSO-d$_6$) δ: 9.22-9.25 (1H, m), 8.57-8.60 (1H, m), 8.01-8.06 (2H, m), 7.81-7.86 (2H, m), 7.72-7.78 (1H, m), 7.60-7.66 (1H, m), 7.15-7.20 (2H, m), 4.71-4.79 (1H, m), 4.20-4.28 (1H, m), 3.81-3.97 (2H, m), 3.39-3.50 (1H, m), 3.33-3.38 (1H, m), 3.22 (3H, s), 1.93-2.08 (2H, m), 1.51-1.71 (2H, m), 1.23 (3H, d, J=6.5 Hz).

Example 110. 2-Hydroxy-1-[4-(4-quinolin-3-yl-phenoxy)-piperidin-1-yl]-ethanone, 2HCl

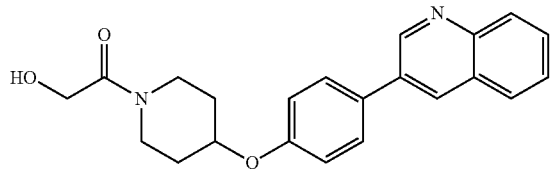 [SMILES: O=C(CO)N1CCC(Oc2ccc(-c3cnc4ccccc4c3)cc2)CC1]

The product was isolated as a light-brown solid. Analysis: LCMS m/z=363 (M+1); $^1$H NMR (400 MHz, DMSO-d$_6$) δ: 9.23 (1H, d, J=2.5 Hz), 8.58 (1H, d, J=2.3 Hz), 8.03 (2H, d, J=8.1 Hz), 7.84 (2H, d, J=8.8 Hz), 7.70-7.78 (1H, m), 7.60-7.67 (1H, m), 7.17 (2H, d, J=7.9 Hz), 4.70-4.79 (1H, m), 4.53 (1H, t, J=5.4 Hz), 4.12 (2H, d, J=5.5 Hz), 3.83-3.94 (1H, m), 3.55-3.67 (1H, m), 3.34-3.39 (1H, m), 3.24-3.31 (1H, m), 1.92-2.07 (2H, m), 1.52-1.72 (2H, m).

Example 111. [4-(4-Quinolin-3-yl-phenoxy)-piperidin-1-yl]-(tetrahydropyran-2-yl)-methanone, HCl

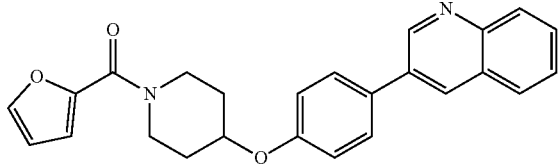 [SMILES: O=C(c1ccco1)N1CCC(Oc2ccc(-c3cnc4ccccc4c3)cc2)CC1]

The product was isolated as a yellow solid. Analysis: LCMS m/z=399 (M+1); $^1$HNMR (400 MHz, DMSO-d$_6$) δ: 9.53 (s, 1H), 9.18 (s, 1H), 8.27 (m, 2H), 8.06-7.81 (m, 5H), 7.23 (m, 2H), 7.01 (m, 1H), 6.64 (m, 1H), 4.84 (m, 1H), 3.99 (m, 2H), 3.58 (m, 2H), 2.06 (m, 2H), 1.70 (m, 2H).

Example 112. 1-[4-(4-Quinolin-3-yl-phenoxy)-piperidin-1-yl]-ethanone, HCl

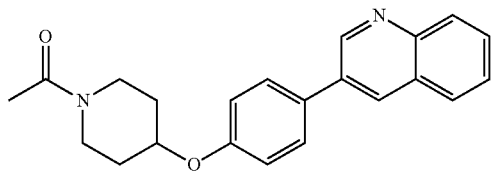 [SMILES: CC(=O)N1CCC(Oc2ccc(-c3cnc4ccccc4c3)cc2)CC1]

The product was isolated as a yellow solid. Analysis: LCMS m/z=347 (M+1); $^1$HNMR (400 MHz, DMSO-d$_6$) δ: 9.57 (m, 1H), 9.26 (s, 1H), 8.32 (m, 2H), 8.03 (m, 1H), 7.95 (m, 2H), 7.89 (m, 1H), 7.23 (m, 2H), 4.77 (m, 1H), 3.92-3.82 (m, 1H), 3.76-3.66 (m, 1H), 3.44-3.34 (m, 1H), 3.32-3.23 (1H, m), 2.03 (s, 3H), 2.07-1.87 (m, 2H), 1.72-1.48 (m, 2H).

Example 113. 2-Methyl-1-[4-(4-quinolin-3-yl-phenoxy)-piperidin-1-yl]-propan-1-one, HCl

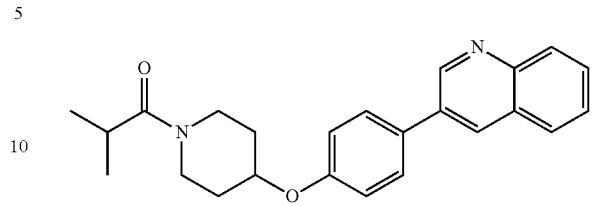

The product was isolated as a yellow solid. Analysis: LCMS m/z=375 (M+1); $^1$HNMR (400 MHz, DMSO-d$_6$) δ: 9.51 (m, 1H), 9.14 (s, 1H), 8.26 (m, 2H), 8.02-7.80 (m, 4H), 7.21 (m, 2H), 4.77 (m, 1H), 3.97-3.73 (m, 2H), 3.49-3.21 (m, 2H), 2.91 (m, 1H), 2.09-1.89 (m, 2H), 1.71-1.46 (m, 2H), 1.01 (d, J=6.7 Hz, 6H).

Example 114. 2,2-Dimethyl-1-[4-(4-quinolin-3-yl-phenoxy)-piperidin-1-yl]-propan-1-one, HCl

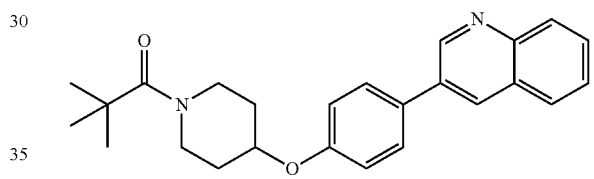

The product was isolated as a yellow solid. Analysis: LCMS m/z=389 (M+1); $^1$HNMR (400 MHz, DMSO-d$_6$) δ: 9.55 (m, 1H), 9.15 (s, 1H), 8.26 (m, 2H), 7.98 (m, 1H), 7.94 (m, 2H), 7.85 (m, 1H), 7.21 (m, 2H), 4.78 (m, 1H), 3.98-3.86 (m, 2H), 3.45-3.34 (m, 2H), 2.05-1.94 (m, 2H), 1.65-1.53 (m, 2H), 1.22 (s, 9H).

Example 115. (2-Methyltetrahydrofuran-2-yl)-[4-(4-quinolin-3-yl-phenoxy)-piperidin-1-yl]-methanone, HCl

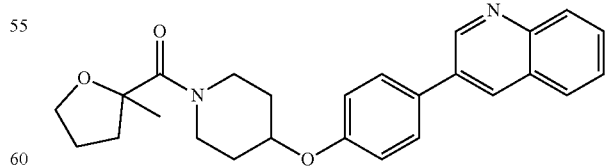

The product was isolated as a yellow solid. Analysis: LCMS m/z=417 (M+1); $^1$HNMR (400 MHz, DMSO-d$_6$) δ: 9.52 (m, 1H), 9.17 (s, 1H), 8.26 (m, 2H), 7.99 (m, 1H), 7.94 (m, 2H), 7.85 (m, 1H), 7.21 (m, 2H), 4.77 (m, 1H), 4.41-3.11 (m, 6H), 2.72-2.61 (m, 1H), 2.08-1.47 (m, 7H), 1.40 (s, 3H).

Example 116. (2-Methyl-1,3-dioxolan-2-yl)-[4-(4-quinolin-3-yl-phenoxy)-piperidin-1-yl]-methanone, HCl

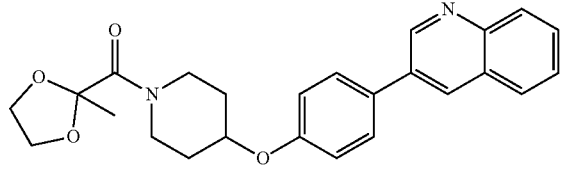 [SMILES: CC1(C(=O)N2CCC(Oc3ccc(-c4cnc5ccccc5c4)cc3)CC2)OCCO1]

The product was isolated as a tan solid. Analysis: LCMS m/z=419 (M+1); $^1$H NMR (400 MHz, DMSO-d$_6$) δ: 9.22-9.26 (1H, m), 8.56-8.60 (1H, m), 8.01-8.07 (2H, m), 7.80-7.88 (2H, m), 7.72-7.79 (1H, m), 7.60-7.67 (1H, m), 7.14-7.22 (2H, m), 4.70-4.84 (1H, m), 3.98-4.04 (1H, m), 3.92-3.98 (2H, m), 3.77-3.86 (2H, m), 3.48-3.65 (1H, m), 3.35-3.48 (2H, m), 3.33 (3H, s), 1.95-2.08 (2H, m), 1.55-1.76 (2H, m).

Example 117. 2-Methanesulfonyl-1-[4-(4-quinolin-3-yl-phenoxy)-piperidin-1-yl]-ethanone, HCl

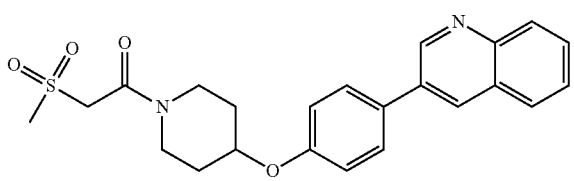 [SMILES: CS(=O)(=O)CC(=O)N1CCC(Oc2ccc(-c3cnc4ccccc4c3)cc2)CC1]

The product was isolated as a tan solid. Analysis: LCMS m/z=425 (M+1); $^1$HNMR (400 MHz, DMSO-d$_6$) δ: 9.51 (m, 1H), 9.15 (s, 1H), 8.26 (m, 2H), 7.98 (m, 1H), 7.94 (m, 2H), 7.85 (m, 1H), 7.23 (m, 2H), 4.80 (m, 1H), 4.51 (s, 2H), 3.96-3.77 (m, 2H), 3.57-3.34 (m, 2H), 3.12 (s, 3H), 2.11-1.92 (m, 2H), 1.79-1.52 (m, 2H).

Example 118. (1,1-Dioxidotetrahydrothiophen-2-yl)(4-(4-(quinolin-3-yl)phenoxy)piperidin-1-yl)methanone, HCl

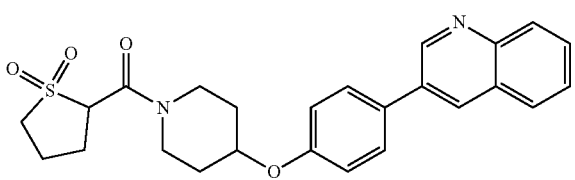 [SMILES: O=C(C1CCCS1(=O)=O)N1CCC(Oc2ccc(-c3cnc4ccccc4c3)cc2)CC1]

The product was isolated as a yellow solid. Analysis: LCMS m/z=451 (M+1); $^1$HNMR (400 MHz, DMSO-d$_6$) δ: 9.51 (s, 1H), 9.15 (s, 1H), 8.26 (m, 2H), 7.98 (m, 1H), 7.94 (m, 2H), 7.85 (m, 1H), 7.23 (m, 2H), 4.82 (m, 1H), 4.67 (m, 1H), 4.08-3.79 (m, 2H), 3.64-3.44 (m, 2H), 3.39-3.19 (m, 2H), 3.14-3.00 (m, 1H), 2.26-1.46 (m, 7H).

Example 119. (3,3-Difluorocyclobutyl)-[4-(4-quinolin-3-yl-phenoxy)-piperidin-1-yl]-methanone

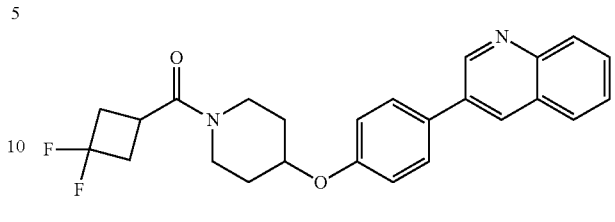

The product was isolated as an off-white solid. Analysis: LCMS m/z=423 (M+1); $^1$H NMR (400 MHz, DMSO-d$_6$) δ: 9.21-9.25 (1H, m), 8.56-8.60 (1H, m), 8.01-8.06 (2H, m), 7.81-7.86 (2H, m), 7.72-7.78 (1H, m), 7.60-7.67 (1H, m), 7.14-7.20 (2H, m), 4.69-4.78 (1H, m), 3.84-3.93 (1H, m), 3.60-3.70 (1H, m), 3.33-3.39 (2H, m), 3.23-3.31 (1H, m), 2.73-2.86 (4H, m), 1.91-2.04 (2H, m), 1.53-1.69 (2H, m).

Example 120. (R)-5-[4-(4-Quinolin-3-yl-phenoxy)-piperidine-1-carbonyl]-dihydrofuran-2-one, HCl

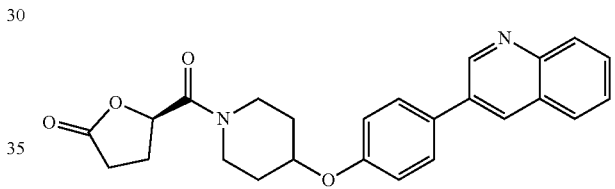

LCMS m/z=tan solid. Analysis: LCMS m/z=417 (M+1); $^1$H NMR (400 MHz, DMSO-d$_6$) δ: 9.48-9.51 (1H, m), 9.08-9.13 (1H, m), 8.20-8.28 (2H, m), 7.90-8.00 (3H, m), 7.80-7.86 (1H, m), 7.20-7.26 (2H, m), 5.51-5.57 (1H, m), 4.75-4.86 (1H, m), 3.68-3.97 (2H, m), 3.28-3.52 (2H, m), 2.39-2.49 (3H, m), 2.14-2.26 (1H, m), 1.92-2.11 (2H, m), 1.56-1.78 (2H, m).

Example 121. (3-Methylfuran-2-yl)-[4-(4-quinolin-3-yl-phenoxy)-piperidin-1-yl]-methanone, HCl

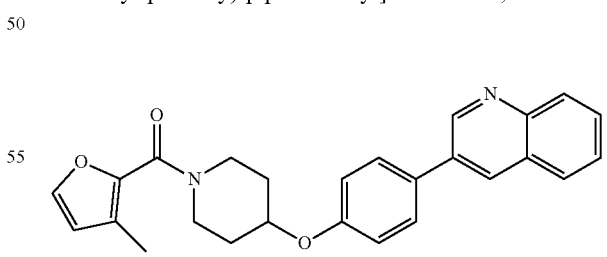

The product was isolated as a yellow solid. Analysis: LCMS m/z=413 (M+1); $^1$H NMR (400 MHz, DMSO-d$_6$) δ: 9.51-9.55 (1H, m), 9.14-9.20 (1H, m), 8.23-8.32 (2H, m), 7.92-8.04 (3H, m), 7.82-7.89 (1H, m), 7.67-7.72 (1H, m), 7.20-7.27 (2H, m), 6.48-6.53 (1H, m), 4.78-4.88 (1H, m), 3.83-3.96 (2H, m), 3.43-3.55 (2H, m), 2.16 (3H, s), 2.00-2.11 (2H, m), 1.62-1.75 (2H, m).

Example 122. (3,5-Dimethylfuran-2-yl)-[4-(4-quinolin-3-yl-phenoxy)-piperidin-1-yl]-methanone, HCl

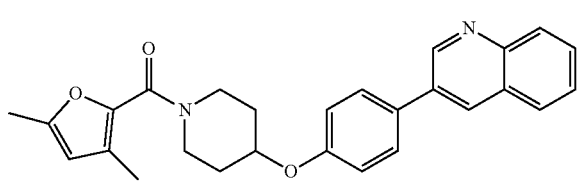 [SMILES: Cc1cc(C)c(C(=O)N2CCC(Oc3ccc(-c4cnc5ccccc5c4)cc3)CC2)o1]

The product was isolated as a yellow solid. Analysis: LCMS m/z=427 (M+1); ¹H NMR (400 MHz, DMSO-$d_6$) δ: 9.51-9.56 (1H, m), 9.15-9.21 (1H, m), 8.22-8.34 (2H, m), 7.92-8.04 (3H, m), 7.82-7.90 (1H, m), 7.20-7.27 (2H, m), 6.10-6.14 (1H, m), 4.78-4.87 (1H, m), 3.86-3.96 (2H, m), 3.42-3.53 (2H, m), 2.27 (3H, s), 2.11 (3H, s), 2.00-2.09 (2H, m), 1.61-1.73 (2H, m).

Example 123. Oxazol-2-yl-[4-(4-quinolin-3-yl-phenoxy)-piperidin-1-yl]-methanone; HCl

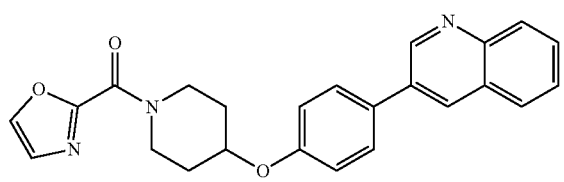 [SMILES: O=C(c1ncco1)N1CCC(Oc2ccc(-c3cnc4ccccc4c3)cc2)CC1]

The product was isolated as a yellow solid. Analysis: LCMS m/z=400 (M+1); ¹H NMR (400 MHz, DMSO-$d_6$) δ: 9.50-9.56 (1H, m), 9.14-9.21 (1H, m), 8.22-8.35 (3H, m), 7.91-8.03 (3H, m), 7.82-7.89 (1H, m), 7.44-7.49 (1H, m), 7.20-7.28 (2H, m), 4.81-4.90 (1H, m), 4.21-4.32 (1H, m), 3.94-4.04 (1H, m), 3.81-3.91 (1H, m), 3.54-3.63 (1H, m), 2.03-2.13 (2H, m), 1.67-1.81 (2H, m).

Example 124. Isoxazol-3-yl-[4-(4-quinolin-3-yl-phenoxy)-piperidin-1-yl]-methanone, HCl

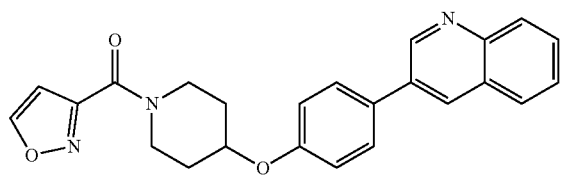 [SMILES: O=C(c1ccsn1)N1CCC(Oc2ccc(-c3cnc4ccccc4c3)cc2)CC1]

The product was isolated as a yellow solid. Analysis: LCMS m/z=400 (M+1); ¹H NMR (400 MHz, DMSO-$d_6$) δ: 9.51-9.55 (1H, m), 9.16-9.20 (1H, m), 9.09-9.12 (1H, m), 8.23-8.33 (2H, m), 7.92-8.03 (3H, m), 7.83-7.89 (1H, m), 7.21-7.27 (2H, m), 6.85-6.88 (1H, m), 4.82-4.90 (1H, m), 3.96-4.06 (1H, m), 3.74-3.83 (1H, m), 3.47-3.63 (2H, m), 1.99-2.13 (2H, m), 1.65-1.79 (2H, m).

Example 125. Isothiazol-3-yl-[4-(4-quinolin-3-yl-phenoxy)-piperidin-1-yl]-methanone, HCl

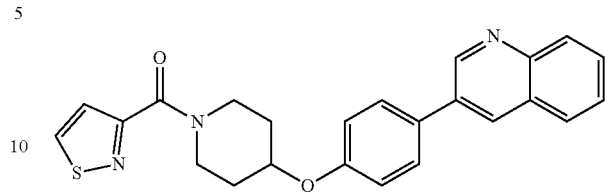

The product was isolated as a yellow solid. Analysis: LCMS m/z=416 (M+1); ¹H NMR (400 MHz, DMSO-$d_6$) δ: 9.51-9.55 (1H, m), 9.14-9.20 (2H, m), 8.23-8.32 (2H, m), 7.91-8.03 (3H, m), 7.82-7.89 (1H, m), 7.60-7.64 (1H, m), 7.21-7.27 (2H, m), 4.80-4.89 (1H, m), 3.98-4.07 (1H, m), 3.80-3.89 (1H, m), 3.48-3.61 (2H, m), 1.99-2.14 (2H, m), 1.64-1.78 (2H, m).

Example 126. [4-(4-Quinolin-3-yl-phenoxy)-piperidin-1-yl]-(tetrahydrofuran-2-yl)-methanone, HCl

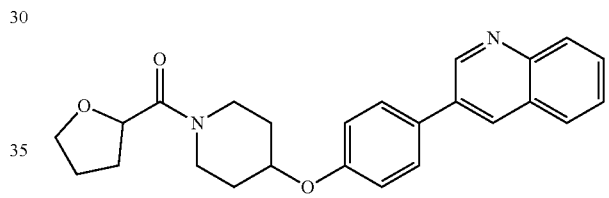

The product was isolated as a yellow solid. Analysis: LCMS m/z=403 (M+1); ¹H NMR (400 MHz, DMSO-$d_6$) δ: 9.47-9.51 (1H, m), 9.08-9.12 (1H, m), 8.20-8.27 (2H, m), 7.89-8.00 (3H, m), 7.80-7.86 (1H, m), 7.19-7.25 (2H, m), 4.73-4.82 (1H, m), 4.66-4.73 (1H, m), 4.27-4.32 (1H, m), 3.75-3.82 (4H, m), 1.96-2.06 (3H, m), 1.80-1.87 (4H, m), 1.53-1.68 (2H, m).

Example 127. Phenyl-[4-(4-quinolin-3-yl-phenoxy)-piperidin-1-yl]-methanone, HCl

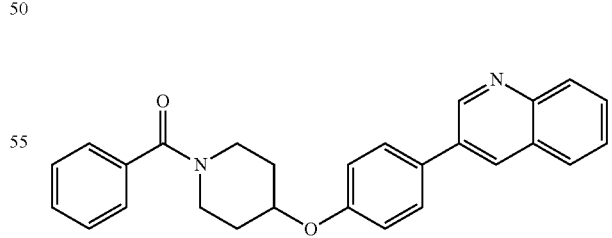

The product was isolated as a yellow solid. Analysis: LCMS m/z=409 (M+1); ¹H NMR (400 MHz, DMSO-$d_6$) δ: 9.46-9.51 (1H, m), 9.05-9.10 (1H, m), 8.18-8.27 (2H, m), 7.89-7.99 (3H, m), 7.78-7.85 (1H, m), 7.40-7.49 (5H, m), 7.19-7.25 (2H, m), 4.77-4.85 (1H, m), 3.91-4.11 (1H, m), 3.43-3.64 (2H, m), 3.26-3.43 (1H, m), 1.90-2.14 (2H, m), 1.60-1.78 (2H, m).

Example 128. (2,5-Dimethylphenyl)-[4-(4-quinolin-3-yl-phenoxy)-piperidin-1-yl]-methanone, HCl

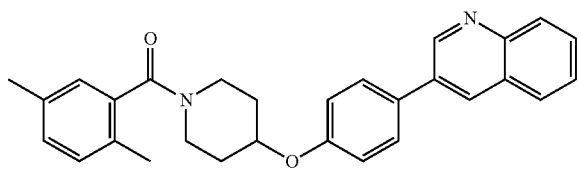 [SMILES: Cc1ccc(C)c(C(=O)N2CCC(Oc3ccc(-c4cnc5ccccc5c4)cc3)CC2)c1]

The product was isolated as a yellow solid. Analysis: LCMS m/z=437 (M+1); $^1$H NMR (400 MHz, DMSO-d$_6$) δ: 9.46-9.51 (1H, m), 9.07-9.12 (1H, m), 8.20-8.28 (2H, m), 7.89-8.00 (3H, m), 7.80-7.86 (1H, m), 7.18-7.24 (2H, m), 7.03-7.12 (3H, m), 4.75-4.84 (1H, m), 3.95-4.16 (1H, m), 3.32-3.62 (2H, m), 3.13-3.24 (1H, m), 2.29 (3H, s), 2.20 (3H, s), 2.02-2.13 (1H, m), 1.85-1.97 (1H, m), 1.64-1.77 (1H, m), 1.48-1.62 (1H, m).

Example 129. [3-(1H-Imidazol-2-yl)-phenyl]-[4-(4-quinolin-3-yl-phenoxy)-piperidin-1-yl]-methanone, HCl

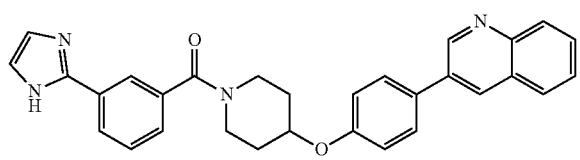 [SMILES: O=C(c1cccc(-c2ncc[nH]2)c1)N1CCC(Oc2ccc(-c3cnc4ccccc4c3)cc2)CC1]

The product was isolated as a yellow solid. Analysis: LCMS m/z=475 (M+1); $^1$H NMR (400 MHz, DMSO-d$_6$) δ: 15.02-15.51 (1H, m), 9.44-9.48 (1H, m), 9.01-9.06 (1H, m), 8.18-8.31 (4H, m), 7.89-7.97 (3H, m), 7.84 (3H, s), 7.68-7.76 (2H, m), 7.20-7.26 (2H, m), 4.80-4.89 (1H, m), 3.96-4.13 (1H, m), 3.48-3.66 (2H, m), 3.31-3.48 (1H, m), 2.00-2.18 (2H, m), 1.66-1.81 (2H, m).

Example 130. [3-(1H-Benzimidazol-2-yl)-phenyl]-[4-(4-quinolin-3-yl-phenoxy)-piperidin-1-yl]-methanone, HCl

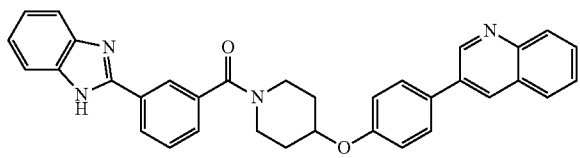 [SMILES: O=C(c1cccc(-c2nc3ccccc3[nH]2)c1)N1CCC(Oc2ccc(-c3cnc4ccccc4c3)cc2)CC1]

The product was isolated as a yellow solid. Analysis: LCMS m/z=525 (M+1); $^1$H NMR (400 MHz, DMSO-d$_6$) δ: 9.48-9.51 (1H, m), 9.09-9.13 (1H, m), 8.44-8.51 (2H, m), 8.21-8.30 (2H, m), 7.91-8.00 (3H, m), 7.78-7.89 (5H, m), 7.54-7.61 (2H, m), 7.21-7.27 (2H, m), 4.83-4.91 (1H, m), 4.00-4.14 (2H, m), 3.51-3.69 (2H, m), 3.34-3.50 (1H, m), 2.00-2.18 (2H, m), 1.70-1.83 (2H, m).

Example 131. N-Methoxy-4-[4-(8-methoxy-7-quinolyl)phenoxy]piperidine-1-carboxamide, HCl

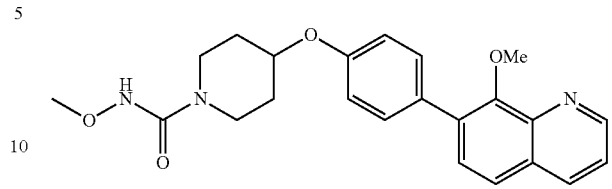

This example was synthesized using the procedure for example 91 starting with 8-methoxy-7-[4-(4-piperidyloxy) phenyl]quinoline 2HCl to give a yellow solid. Analysis: LCMS m/z=408 (M+1); 1H NMR (400 MHz, DMSO-d6) δ: 9.68-9.86 (1H, m), 9.11-9.18 (1H, m), 8.90-9.02 (1H, m), 8.02-8.12 (1H, m), 7.83-7.98 (2H, m), 7.69 (2H, d, J=8.5 Hz), 7.17 (2H, d, J=8.8 Hz), 4.61-4.73 (1H, m), 3.74 (3H, s), 3.59-3.70 (2H, m), 3.55 (3H, s), 3.08-3.22 (2H, m), 1.92-1.99 (2H, m), 1.49-1.64 (2H, m).

Example 132. 1-[4-(5-Quinolin-3-yl-pyridin-2-yloxy)-piperidin-1-yl]-propan-1-one, HCl

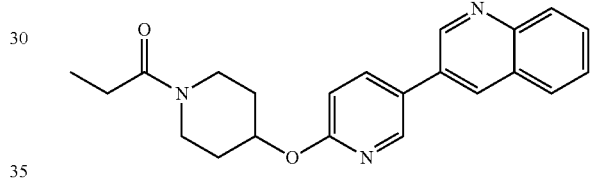

Step 1. 4-(5-Bromopyridin-2-yloxy)-piperidine-1-carboxylic acid tert-butyl ester To a solution of 4-hydroxy-piperidine-1-carboxylic acid tert-butyl ester (5.75 g, 28.6 mmol) in DMF (50 mL) was sodium hydride, 60% disp. in mineral oil (1.35 g, 33.8 mmol) in portion. After stirred for 10 min, to the reaction was added 5-bromo-2-chloro-pyridine (5.00 g, 26.0 mmol) followed by K$_2$CO$_3$ (3.59 g, 26.0 mmol). The reaction was heated at 105° C. for 16 h and cooled to room temp. It was carefully quenched with H$_2$O (100 mL), extracted with EtOAc (3×300 mL). The combined organic layers were washed with H$_2$O, brine, dried (Na$_2$SO$_4$) and concentrated. The residue was chromatography on silica gel (0-20% EtOAc/Hexanes) to give a white solid 8.30 g (89%).

Step 2. 4-(5-Quinolin-3-yl-pyridin-2-yloxy)-piperidine-1-carboxylic acid tert-butyl ester A flask charged with 4-(5-bromopyridin-2-yloxy)-piperidine-1-carboxylic acid tert-butyl ester (750 mg, 2.1 mmol), 3-quinolineboronic acid (540 mg, 3.1 mmol), palladium acetate (47 mg, 0.21 mmol), triphenylphosphine (110 mg, 0.42 mmol), 1.0 M of sodium carbonate in water (8.4 mL, 8.4 mmol), 1,4-dioxane (5 mL) and DMF (10 mL) was flashed with N$_2$ for 15 min. After stirred at 85° C. for 16 h, the reaction was cooled to room temp and added EtOAc (100 mL), washed with 1M Na$_2$CO$_3$ solution (30 mL), H$_2$O, brine, dried (Na$_2$SO$_4$), and concentrated. The residue was chromatography on silica gel (0-70% EtOAc/Hexanes) to give a grayish solid 723 mg (85%).

Step 3. 3-[6-(Piperidin-4-yloxy)-pyridin-3-yl]-quinoline, 2HCl

To a solution of 4-(5-quinolin-3-yl-pyridin-2-yloxy)-piperidine-1-carboxylic acid tert-butyl ester (701 mg, 1.73 mmol) in DCM (25 mL) was added 4.0 M of HCl in 1,4-dioxane (4.32 mL, 17.3 mmol) and stirred at room temperature for 24 h. The resulted white precipitate was collected by filtration, washed with DCM, dried to give a white solid 626 mg (96%).

Step 4

To a solution of 3-[6-(piperidin-4-yloxy)-pyridin-3-yl]-quinoline, 2HCl (100 mg, 0.3 mmol) and Et₃N in DCM (8 mL) was added propanoyl chloride (50 µL, 0.6 mmol). After 15 min, the reaction was diluted with DCM (50 mL), washed with H₂O (2×20 mL), sat. NaHCO₃, brine, dried (Na₂SO₄), and concentrated. The residue was purified by chromatography on silica gel (0-100 EtOAc/Hexanes) and the isolated product was dissolved in a mixed solvent MeOH-DCM (1:1), treated with 1.2 eq. of 2 M HCl Et₂O solution, and concentrated. It was stripped with small amount of MeOH-DCM (1:1) several times, dried to give a tan solid 88 mg (80%). Analysis: LCMS m/z=362 (M+1); ¹H NMR (400 MHz, DMSO-d₆) δ: 9.63 (1H, d, J=2.3 Hz), 9.35 (1H, s), 8.81 (1H, d, J=2.8 Hz), 8.27-8.45 (3H, m), 8.07 (1H, ddd, J=8.5, 7.1, 1.3 Hz), 7.87-7.96 (1H, m), 7.05 (1H, d, J=8.8 Hz), 5.33 (1H, tt, J=8.2, 3.9 Hz), 3.89-4.01 (1H, m), 3.69-3.81 (1H, m), 3.32-3.44 (1H, m), 3.20-3.32 (1H, m), 2.36 (2H, q, J=7.4 Hz), 1.94-2.12 (2H, m), 1.52-1.76 (2H, m), 1.01 (3H, t, J=7.4 Hz).

The following compounds were synthesized using the procedures employed in Example 132 above.

Example 133. 2-Methyl-1-[4-(5-quinolin-3-yl-pyridin-2-yloxy)-piperidin-1-yl]-propan-1-one, HCl

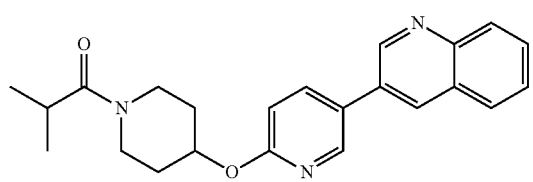 [SMILES: CC(C)C(=O)N1CCC(Oc2ccc(-c3cnc4ccccc4c3)cn2)CC1]

The product was isolated as an off-white solid. Analysis: LCMS m/z=376 (M+1); ¹H NMR (400 MHz, DMSO-d₆) δ: 9.62 (1H, d, J=2.0 Hz), 9.33 (1H, s), 8.81 (1H, d, J=2.3 Hz), 8.26-8.42 (3H, m), 8.09-8.10 (1H, m), 7.89-7.95 (1H, m), 7.05 (1H, d, J=8.5 Hz), 5.34 (1 H, tt, J=8.2, 3.9 Hz), 3.91-4.02 (1H, m), 3.78-3.88 (1H, m), 3.37-3.50 (1H, m), 3.20-3.32 (1H, m), 2.92 (1H, quin, J=6.8 Hz), 1.94-2.15 (2H, m), 1.52-1.76 (2H, m), 0.97-1.06 (6H, m).

Example 134. Cyclopropyl-[4-(5-quinolin-3-yl-pyridin-2-yloxy)-piperidin-1-yl]-methanone, HCl

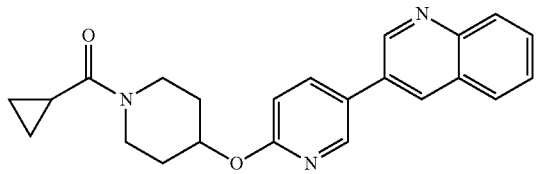 [SMILES: O=C(C1CC1)N1CCC(Oc2ccc(-c3cnc4ccccc4c3)cn2)CC1]

The product was isolated as a tan solid. Analysis: LCMS m/z=374 (M+1); ¹H NMR (400 MHz, DMSO-d₆) δ: 9.57 (1H, d, J=2.3 Hz), 9.22 (1H, s), 8.80 (1H, d, J=2.0 Hz), 8.31-8.36 (2H, m), 8.25 (1H, d, J=7.8 Hz), 8.02 (1H, t, J=7.7 Hz), 7.87 (1H, t, J=7.5 Hz), 7.05 (1H, d, J=8.5 Hz), 5.35 (1H, tt, J=8.2, 3.9 Hz), 3.90-4.12 (2H, m), 3.50-3.65 (1H, m), 3.20-3.35 (1H, m), 1.93-2.16 (3H, m), 1.52-1.79 (2H, m), 0.67-0.80 (4H, m).

Example 135. 1-[4-(5-Quinolin-7-yl-pyridin-2-yloxy)-piperidin-1-yl]-propan-1-one, HCl

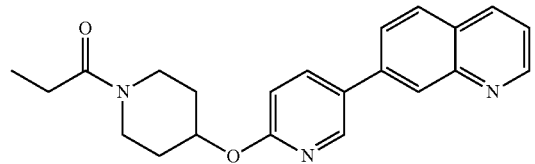 [SMILES: CCC(=O)N1CCC(Oc2ccc(-c3ccc4cccnc4c3)cn2)CC1]

The product was isolated as an off-white solid. Analysis: LCMS m/z=362 (M+1); ¹H NMR (400 MHz, DMSO-d₆) δ: 9.30 (1H, dd, J=5.1, 1.4 Hz), 9.14 (1H, d, J=8.0 Hz), 8.72 (1H, d, J=2.3 Hz), 8.62 (1H, s), 8.44 (1H, d, J=8.8 Hz), 8.31 (1H, d, J=8.7 Hz), 8.24 (1H, dd, J=8.7, 2.6 Hz), 8.04 (1H, dd, J=8.3, 5.3 Hz), 7.05 (1H, d, J=8.5 Hz), 5.29-5.37 (1H, m), 3.91-4.00 (1H, m), 3.70-3.81 (1H, m), 3.30-3.42 (1H, m), 3.19-3.30 (1H, m), 2.36 (2H, q, J=7.4 Hz), 1.95-2.12 (2H, m), 1.52-1.75 (2H, m), 1.01 (3H, t, J=7.4 Hz).

Example 136. 2-Methyl-1-[4-(5-quinolin-7-yl-pyridin-2-yloxy)-piperidin-1-yl]-propan-1-one, HCl

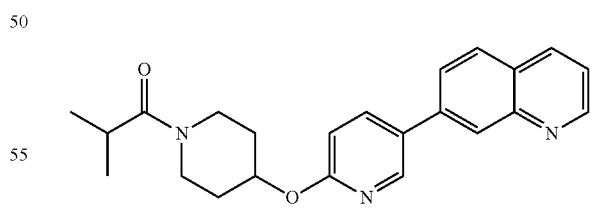

The product was isolated as a tan solid. Analysis: LCMS m/z=376 (M+1); ¹H NMR (400 MHz, DMSO-d₆) δ: 9.30 (1H, dd, J=5.3, 1.3 Hz), 9.15 (1H, d, J=8.3 Hz), 8.73 (1H, d, J=2.3 Hz), 8.63 (1H, s), 8.45 (1H, d, J=8.8 Hz), 8.31 (1H, dd, J=8.7, 1.6 Hz), 8.24 (1H, dd, J=8.7, 2.6 Hz), 8.05 (1H, dd, J=8.3, 5.3 Hz), 7.05 (1H, d, J=8.5 Hz), 5.31-5.38 (1H, m), 3.92-4.01 (1 H, m), 3.78-3.89 (1H, m), 3.36-3.48 (1H, m), 3.19-3.31 (1H, m), 2.92 (1H, quin, J=6.7 Hz), 1.95-2.15 (2H, m), 1.52-1.77 (2H, m), 1.02 (6H, d, J=6.8 Hz).

Example 137. Cyclopropyl-[4-(5-quinolin-7-yl-pyridin-2-yloxy)piperidin-1-yl]-methanone, HCl

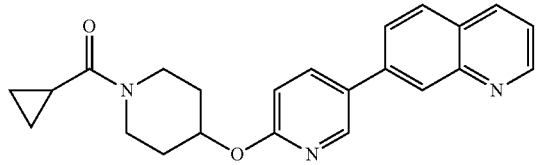 [SMILES: O=C(C1CC1)N1CCC(Oc2ccc(-c3ccc4cccnc4c3)cn2)CC1]

The product was isolated as a tan solid. Analysis: LCMS m/z=374 (M+1); $^1$H NMR (400 MHz, DMSO-d$_6$) δ: 9.29 (1H, dd, J=5.3, 1.5 Hz), 9.12 (1H, d, J=8.3 Hz), 8.73 (1H, d, J=2.3 Hz), 8.60 (1H, s), 8.44 (1H, d, J=8.8 Hz), 8.23-8.32 (2H, m), 8.03 (1H, t, J=6.4 Hz), 7.05 (1H, d, J=8.8 Hz), 5.32-5.40 (1H, m), 3.91-4.12 (2H, m), 3.57-3.62 (1H, m), 3.20-3.34 (1H, m), 1.95-2.16 (3H, m), 1.53-1.79 (2H, m), 0.67-0.79 (4H, m).

Example 138. 2-Methyl-1-[4-(5-quinolin-3-yl-pyrimidin-2-yloxy)-piperidin-1-yl]-propan-1-one, 2HCl

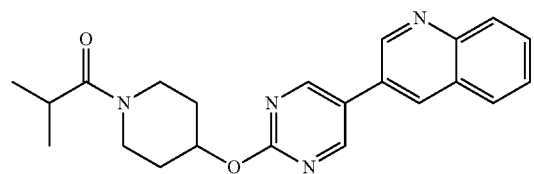 [SMILES: CC(C)C(=O)N1CCC(Oc2ncc(-c3cnc4ccccc4c3)cn2)CC1]

The product was isolated as an off-white solid. Analysis: mp: 124-130° C.; LCMS m/z=377 (M+1); $^1$HNMR (DMSO-d$_6$) δ: 9.62 (m, 1H), 9.29 (m, 1H), 9.23 (s, 2H), 8.36 (d, J=8 Hz, 2H), 8.25 (d, J=8 Hz, 1H), 8.08-8.01 (m, 1H), 7.93-7.85 (m, 1H), 5.31 (m, 1H), 4.01-3.77 (m, 2H), 3.52-3.38 (m, 1H), 3.36-3.23 (m, 1H), 2.92 (m, 1H), 2.17-1.97 (m, 2H), 1.81-1.56 (m, 2H), 1.02 (d, J=7 Hz, 6H).

Example 139. Cyclopropyl-[4-(5-quinolin-3-yl-pyrimidin-2-yloxy)-piperidin-1-yl]-methanone, 2HCl

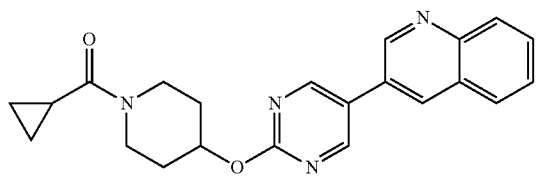 [SMILES: O=C(C1CC1)N1CCC(Oc2ncc(-c3cnc4ccccc4c3)cn2)CC1]

The product was isolated as an off-white solid. Analysis: mp: 150-153° C.; LCMS m/z 375 (M+1); $^1$HNMR (DMSO-d$_6$) δ: 9.65 (m, 1H), 9.35 (m, 1H), 9.24 (s, 2H), 8.39 (m, 1H), 8.27 (m, 1H), 8.10-8.04 (m, 1H), 7.95-7.88 (m, 1H), 5.33 (m, 1H), 4.15-3.85 (m, 2H), 3.71-3.51 (m, 1H), 3.39-3.23 (m, 1H), 2.22-1.92 (m, 3H), 1.86-1.54 (m, 2H), 0.83-0.62 (m, 4H).

Example 140. 1-[4-(6-Quinolin-3-yl-pyridin-3-yloxy)-piperidin-1-yl]-propan-1-one, 2HCl


The product was isolated as an off-white solid. Analysis: mp: 207-212° C.; LCMS m/z=362 (M+1); $^1$HNMR (DMSO-d$_6$) δ: 9.82 (m, 1H), 9.59 (m, 1H), 8.54 (m, 1H), 8.41-8.30 (m, 3H), 8.11-8.03 (m, 1H), 7.95-7.88 (m, 1H), 7.80-7.74 (m, 1H), 4.87 (m, 1H), 3.97-3.86 (m, 1H), 3.80-3.68 (m, 1H), 3.44-3.21 (m, 2H), 2.36 (q, J=7 Hz, 2H), 2.09-1.91 (m, 2H), 1.74-1.48 (m, 2H), 1.00 (t, J=7 Hz, 3H).

Example 141. 2-Methyl-1-[4-(6-quinolin-3-yl-pyridin-3-yloxy)-piperidin-1-yl]-propan-1-one, 2HCl

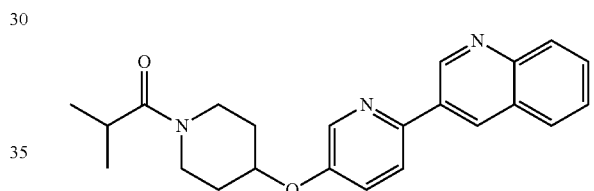

The product was isolated as an off-white solid. Analysis: mp: 99-102° C.; LCMS m/z=376 (M+1); $^1$HNMR (DMSO-d$_6$) δ: 9.84 (m, 1H), 9.68 (m, 1H), 8.55 (m, 1H), 8.44-8.33 (m, 3H), 8.15-8.07 (m, 1H), 7.99-7.91 (m, 1H), 7.83-7.75 (m, 1H), 4.89 (m, 1H), 3.99-3.75 (m, 2H), 3.49-3.21 (m, 2H), 2.98-2.85 (m, 1H), 2.12-1.91 (m, 2H), 1.72-1.49 (m, 2H), 1.02 (d, J=7 Hz, 6H).

Example 142. Cyclopropyl-[4-(6-quinolin-3-yl-pyridin-3-yloxy)-piperidin-1-yl]-methanone, 2HCl

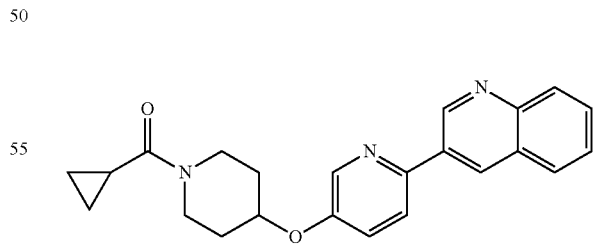

The product was isolated as an off-white solid. Analysis: mp: 230-234° C.; LCMS m/z=374 (M+1); $^1$HNMR (DMSO-d$_6$) δ: 9.84 (d, J=2 Hz, 1H), 9.67 (m, 1H), 8.55 (d, J=3 Hz, 1H), 8.42-8.35 (m, 3H), 8.12-8.08 (m, 1H), 7.96-7.92 (m, 1H), 7.81-7.78 (m, 1H), 4.90 (m, 1H), 4.12-3.85 (m, 2H), 3.66-3.50 (m, 1H), 3.38-3.23 (m, 1H), 2.16-1.92 (m, 3H), 1.77-1.51 (m, 2H), 0.79-0.66 (m, 4H).

Example 143. 1-[4-(5-Quinolin-3-yl-pyrimidin-2-yloxy)-piperidin-1-yl]-propan-1-one

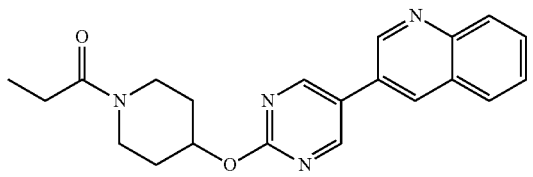 [SMILES: CCC(=O)N1CCC(Oc2ncc(-c3cnc4ccccc4c3)cn2)CC1]

The product was isolated as a white solid. Analysis: mp: 162-166° C.; LCMS m/z=363 (M+1); ¹HNMR (DMSO-d$_6$) δ: 9.29 (d, J=2 Hz, 1H), 9.15 (s, 2H), 8.75 (d, J=2 Hz, 1H), 8.06-8.03 (m, 2H), 7.83-7.79 (m, 1H), 7.70-7.66 (m, 1H), 5.28 (m, 1H), 4.00-3.88 (m, 1H), 3.81-3.70 (m, 1H), 3.44-3.20 (m, 2H), 2.37 (q, J=8 Hz, 2H), 2.14-1.95 (m, 2H), 1.80-1.55 (m, 2H), 1.01 (t, J=8 Hz, 3H).

Example 144. 1-[4-(6-Quinolin-7-yl-pyridin-3-yloxy)-piperidin-1-yl]-propan-1-one, 2HCl

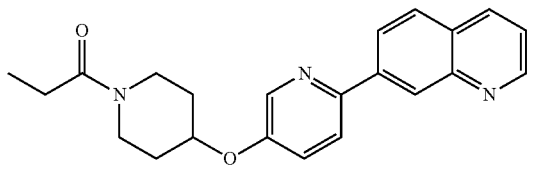 [SMILES: CCC(=O)N1CCC(Oc2ccc(-c3ccc4cccnc4c3)nc2)CC1]

The product was isolated as an off-white solid. Analysis: mp: 90-96° C.; LCMS m/z=362 (M+1); ¹HNMR (DMSO-d$_6$) δ: 9.31 (m, 1H), 9.18 (m, 1H), 9.05 (s, 1H), 8.63 (m, 1H), 8.57 (m, 1H), 8.45 (d, J=9 Hz, 1H), 8.22 (d, J=9 Hz, 1H), 8.10-8.04 (m, 1H), 7.76-7.70 (m, 1H), 4.86 (m, 1H), 3.99-3.87 (m, 1H), 3.80-3.68 (m, 1H), 3.43-3.32 (m, 1H), 3.32-3.21 (m, 1H), 2.36 (q, J=7, 7 Hz, 2H), 2.11-1.92 (m, 2H), 1.73-1.51 (m, 2H), 1.00 (t, J=7 Hz, 3H).

Example 145. 2-Methyl-1-[4-(6-quinolin-7-yl-pyridin-3-yloxy)-piperidin-1-yl]-propan-1-one, 2HCl

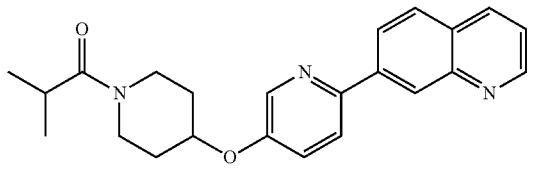 [SMILES: CC(C)C(=O)N1CCC(Oc2ccc(-c3ccc4cccnc4c3)nc2)CC1]

The product was isolated as an off-white solid. Analysis: mp: 170-179° C.; LCMS m/z=376 (M+1); ¹HNMR (DMSO-d$_6$) δ: 9.30 (m, 1H), 9.17 (m, 1H), 9.02 (s, 1H), 8.63-8.57 (m, 2H), 8.44 (d, J=9 Hz, 1H), 8.22 (d, J=9 Hz, 1H), 8.07-8.04 (m, 1H), 7.74-7.71 (m, 1H), 4.87 (m, 1H), 3.98-3.88 (m, 1H), 3.88-3.76 (m, 1H), 3.49-3.36 (m, 1H), 3.34-3.20 (m, 1H), 2.92 (m, 1H), 2.14-1.91 (m, 2H), 1.74-1.46 (m, 2H), 1.02 (d, J=7 Hz, 6H).

Example 146. Cyclopropyl-[4-(6-quinolin-7-yl-pyridin-3-yloxy)-piperidin-1-yl]-methanone, 2HCl

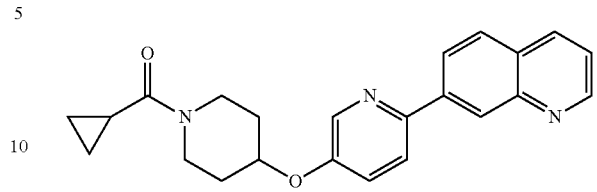

The product was isolated as an off-white solid. Analysis: mp: 170-175° C.; LCMS m/z=374 (M+1); ¹HNMR (DMSO-d$_6$) δ: 9.31 (m, 1H), 9.19 (m, 1H), 9.05 (s, 1H), 8.64-8.58 (m, 2H), 8.46 (d, J=9 Hz, 1H), 8.23 (d, J=9 Hz, 1H), 8.09-8.05 (m, 1H), 7.76-7.73 (m, 1H), 4.89 (m, 1H), 4.11-3.98 (m, 1H), 3.98-3.85 (m, 1H), 3.65-3.48 (m, 1H), 3.37-3.19 (m, 1H), 2.16-1.92 (m, 3H), 1.77-1.50 (m, 2H), 0.77-0.66 (m, 4H).

Example 147. 1-[4-(6-Isoquinolin-6-yl-pyridin-3-yloxy)-piperidin-1-yl]-propan-1-one, 2HCl

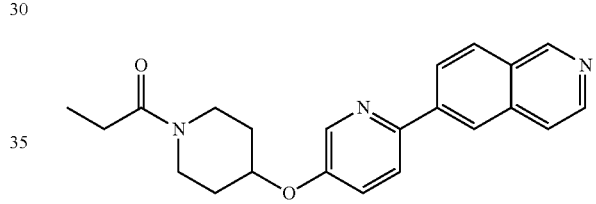

The product was isolated as an off-white solid. Analysis: mp: 236-245° C.; LCMS m/z=362 (M+1); ¹HNMR (DMSO-d$_6$) δ: 9.92 (s, 1H), 9.00 (s, 1H), 8.74-8.68 (m, 2H), 8.64-8.55 (m, 3H), 8.30 (d, J=9 Hz, 1H), 7.76-7.73 (m, 1H), 4.88 (m, 1H), 3.98-3.86 (m, 1H), 3.80-3.68 (m, 1H), 3.44-3.21 (m, 2H), 2.36 (q, J=8 Hz, 2H), 2.11-1.92 (m, 2H), 1.74-1.50 (m, 2H), 1.00 (t, J=7 Hz, 3H).

Example 148. 1-[4-(6-Isoquinolin-6-yl-pyridin-3-yloxy)-piperidin-1-yl]-2-methyl-propan-1-one, 2HCl

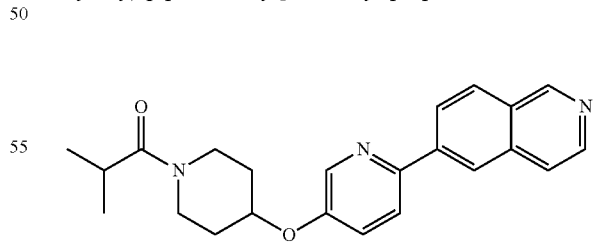

The product was isolated as an off-white solid. Analysis: mp: 236-241° C.; LCMS m/z=376 (M+1); ¹HNMR (DMSO-d$_6$) δ: 9.92 (s, 1H), 9.00 (s, 1H), 8.74-8.55 (m, 5H), 8.31 (d, J=9 Hz, 1H), 7.76-7.73 (m, 1H), 4.89 (m, 1H), 3.98-3.88 (m, 1H), 3.88-3.76 (m, 1H), 3.49-3.37 (m, 1H), 3.33-3.22 (m, 1H), 2.92 (m, 1H), 2.11-1.93 (m, 2H), 1.72-1.50 (m, 2H), 1.02 (d, J=7 Hz, 6H).

Example 149. Cyclopropyl-[4-(6-isoquinolin-6-yl-pyridin-3-yloxy)-piperidin-1-yl]-methanone, 2HCl

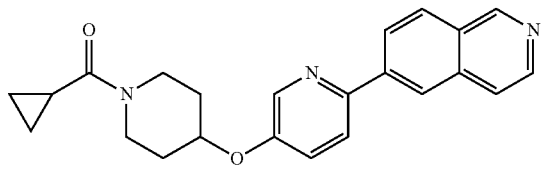 [SMILES: O=C(C1CC1)N1CCC(Oc2ccc(-c3ccc4cnccc4c3)nc2)CC1]

The product was isolated as an off-white solid. Analysis: mp: 136-146° C.; LCMS m/z=374 (M+1); $^1$HNMR (DMSO-$d_6$) δ: 9.91 (s, 1H), 9.00 (s, 1H), 8.75-8.56 (m, 5H), 8.31 (d, J=9 Hz, 1H), 7.77-7.74 (m, 1H), 4.90 (m, 1H), 4.11-3.98 (m, 1H), 3.98-3.86 (m, 1H), 3.66-3.50 (m, 1H), 3.38-3.22 (m, 1H), 2.16-1.93 (m, 3H), 1.77-1.52 (m, 2H), 0.78-0.68 (m, 4H).

Example 150 1-Propionyl-piperidine-4-carboxylic acid methyl-(4-quinolin-7-yl-phenyl)-amide

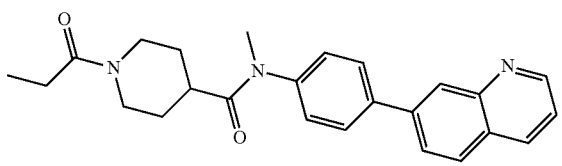 [SMILES: CCC(=O)N1CCC(C(=O)N(C)c2ccc(-c3ccc4cccnc4c3)cc2)CC1]

Step. 1-(2,2,2-Trifluoroacetyl)-piperidine-4-carboxylic acid (4-bromophenyl)-methyl-amide 1-(2,2,2-Trifluoroacetyl)-piperidine-4-carbonyl chloride (0.400 g, 1.64 mmol) and DIPEA (0.858 mL, 4.92 mmol) in DCM (6 mL) was added (4-bromophenyl)-methylamine (0.413 mL, 3.29 mmol). After stirring 4 h at rt the mixture was concentrated, dissolved in EtOAc and washed with 1N $Na_2CO_3$, water and brine then dried over $MgSO_4$. The product was purified by silica gel chromatography (15% EtOAc/hexanes) to give a viscous oil. Analysis: LCMS m/z=394 (M+1).

Step 2. Piperidine-4-carboxylic acid methyl-(4-quinolin-7-yl-phenyl)amide

Palladium acetate (0.00571 g, 0.0254 mmol) and triphenylphosphine (0.0267 g, 0.102 mmol) in dioxane were stirred 15 min under an atmosphere of nitrogen. 1-(2,2,2-trifluoro-acetyl)-piperidine-4-carboxylic acid (4-bromophenyl)-methyl-amide (0.200 g, 0.509 mmol), quinoline-7-boronic acid (0.0968 g, 0.560 mmol), DMF (2 mL) and 1 M of sodium carbonate (2.03 mL, 2.03 mmol) were added, purged under an atmosphere of nitrogen and heated at 80° C. for 17 h. The mixture was concentrated, was dissolved in EtOAc was washed with 1N $Na_2CO_3$, water and brine, then dried over $MgSO_4$. The product was purified by ISCO (silica gel, 0-25% MeOH/1% iPrNH$_2$, DCM) to give the compound as an oil. Analysis: LCMS m/z=346 (M+1).

Step 3. 1-Propionyl-piperidine-4-carboxylic acid methyl-(4-quinolin-7-yl-phenyl)-amide Piperidine-4-carboxylic acid methyl-(4-quinolin-7-yl-phenyl)amide (0.070 g, 0.20 mmol) and DIPEA (0.14 mL, 0.81 mmol) in THF (3 mL) was added propanoyl chloride (0.035 mL, 0.40 mmol). After stirring 4 h at rt, the mixture was concentrated, diluted with EtOAc and washed with 1N $Na_2CO_3$, water and brine then dried ($MgSO_4$). The product was purified by ISCO silica gel (0-5% MOH/DCM). The HCl salt was prepared by adding 2 M HCl-ether to a DCM solution of base and crystallizing from DCM-ether give a light yellow solid (60 mg, 73%). Analysis: LCMS m/z=402 (M+1); $^1$H NMR (DMSO-$d_6$ HCl salt) δ: 9.20 (d, 1H, J=4 Hz), 8.91 (d, 1H, J=8 Hz), 8.523 (s, 1H), 8.34 (d, 1H, J=8 Hz), 8.23 (d, 1H, J=8 Hz), 7.99 (d, 2H, J=8 Hz), 8.88-8.92 (m, 1H), 7.57 (d, 2H, J=8 Hz), 4.31 (d, 1H, J=12 Hz), 3.78 (d, 1H, J=12 Hz), 3.37 (q, 1H, J=7.8 Hz), 3.22 (s, 3H), 2.8 (b, 1H), 2.23-2.32 (m, 2H), 1.53-1.65 (m, 3H), 1.42 (m, 1H), 1.09 (t, 2H, J=7.3 Hz), 0.95 (t, 3H, J=7.3 Hz).

Example 151. 1-Propionyl-piperidine-4-carboxylic acid (4-isoquinolin-6-yl-phenyl)-methylamide

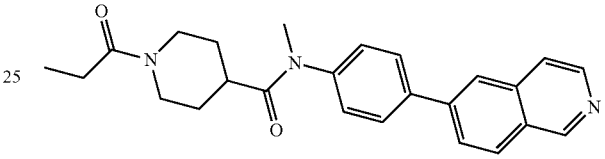

This example was synthesized using the procedure for example 150. Piperidine-4-carboxylic acid (4-isoquinolin-6-yl-phenyl)-methylamide (0.048 g, 0.14 mmol) and DIPEA (0.097 mL, 0.55 mmol) in THF (2 mL) was added propanoyl chloride (0.024 mL, 0.28 mmol). After 4 h stirring at rt, the mixture was concentrated, diluted with EtOAc and washed with 1N $Na_2CO_3$, water and brine then dried ($MgSO_4$). The product was purified by ISCO silica gel 0-5% MeOH/DCM. The HCl salt was made from 2N HCl ether and crystallized from DCM-ether to give a white solid (33 mg, 59%). Analysis: LCMS m/z=402 (M+1); $^1$H NMR (DMSO) δ: 9.82 s, 1H), 8.67 (m, 2H), 8.57 (d, 1H, J=8 Hz), 8.37-8.42 (m, 2H), 8.06 d, 2H, J=8 Hz), 7.59 (d, 2H, J=8 Hz), 4.32 (d, 1H, J=12 Hz), 3.78 (d, 2H, J=12 Hz), 3.23 (s, 3H), 2.77 (b, 1H), 2.23-2.32 (m, 3H), 1.53-1.65 (m, 3H), 1.37-1.45 (m, 1H), 0.95 (t, 3H, J=7 Hz).

Example 152- and Example 153 (as a Mixture)

A mixture of 3-[4-(piperidin-4-yloxy)-phenyl]-quinoline; 2HCl (100 mg, 0.27 mmol), glyoxalic acid hydrate (25.6 mg, 0.28 mmol), N,N,N',N'-tetramethyl-O-(7-azabenzotriazol-1-yl)uronium hexafluorophosphate (HATU), 121 mg, 0.32 mmol), and DIPEA (462 µL, 2.65 mmol) in THF (7 mL) was stirred at room temp for 1 h. To the reaction was added 2-bromoethanol (150 mL, 2.10 mmol) followed by $K_2CO_3$ (73.3 mg, 0.53 mmol). After stirred at 60° C. for 24 h, to the reaction was added additional 8 eq. of $K_2CO_3$ and continued heating for additional 3 h. After cooled to room temp, it was diluted with DCM (50 mL), washed with $H_2O$, dried ($Na_2SO_4$), and concentrated. The mixtures of two products were separated by pre-HPLC and each product fractions were combined, neutralized with sat. $NaHCO_3$ (25 mL), extracted with DCM (3×25 mL), and the combined organic layers were dried ($Na_2SO_4$), and concentrated. Both products were dissolved in DCM (~5 mL) and mixed with 1.2 eq. of 2 M HCl in $Et_2O$ and concentrated. Both residues were dissolved in a small amount of DCM and concentrated— repeated this procedure several times, dried to give to give Example 152 (43 mg, 37%) and Example 153 (35 mg, 35%).

Example 152. Oxo-[4-(4-quinolin-3-yl-phenoxy)-piperidin-1-yl]-acetaldehyde, HCl

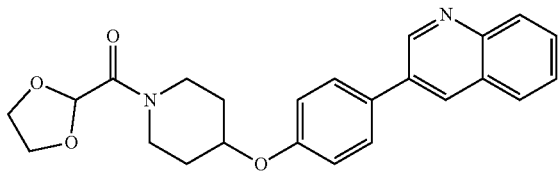

The product was isolated as a yellow solid. Analysis: LCMS m/z=405 (M+1); $^1$H NMR (400 MHz, DMSO-d$_6$) δ: 9.49-9.55 (1H, m), 9.13-9.19 (1H, m), 8.22-8.33 (2H, m), 7.90-8.03 (3H, m), 7.82-7.89 (1H, m), 7.19-7.26 (2H, m), 5.68-5.72 (1H, m), 4.75-4.84 (1H, m), 3.88-4.02 (4H, m), 3.77-3.88 (2H, m), 3.41-3.52 (1H, m), 3.27-3.38 (1H, m), 1.91-2.08 (2H, m), 1.51-1.74 (2H, m).

Example 153. 4-(4-Quinolin-3-yl-phenoxy)-piperidine-1-carbaldehyde, HCl

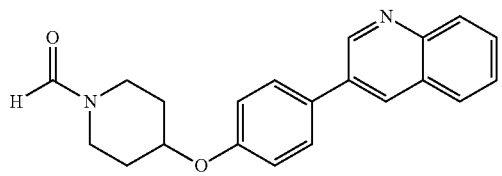 [SMILES: O=CN1CCC(Oc2ccc(-c3cnc4ccccc4c3)cc2)CC1]

The product was isolated as a yellow solid. Analysis: LCMS m/z=333 (M+1); $^1$H NMR (400 MHz, DMSO-d$_6$) δ: 9.50-9.57 (1H, m), 9.15-9.23 (1H, m), 8.23-8.35 (2H, m), 7.91-8.06 (4H, m), 7.82-7.90 (1H, m), 7.19-7.28 (2H, m), 4.76-4.85 (1H, m), 3.72-3.83 (1H, m), 3.58-3.69 (1H, m), 3.21-3.40 (2H, m), 1.90-2.08 (2H, m), 1.50-1.71 (2H, m).

Example 154. ((2R,3S)/(2S,3R)-3-Methyl-tetrahydrofuran-2-yl)-[4-(4-quinolin-3-yl-phenoxy)-piperidin-1-yl]-methanone, HCl

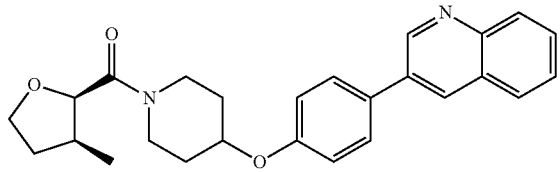 [SMILES: C[C@H]1CCO[C@H]1C(=O)N1CCC(Oc2ccc(-c3cnc4ccccc4c3)cc2)CC1]

Step 1. (2R,3S)/(2S,3R)-3-Methyl-tetrahydrofuran-2-carboxylic acid

A Parr bottle charged with 3-methyl-2-furoic acid (0.50 g, 4.0 mmol) and 5% Rh/C (5:95, Rhodium:carbon black) (50 mg, 0.02 mmol) in methanol (25 mL) was hydrogenated at 50 psi for 79 h. The reaction was filtered through a pad of Celite, eluted with MeOH, and the filtrate was concentrated to give light-brown oil crude product as racemic mixture. This material was used for next step without purification. Analysis: $^1$H NMR (400 MHz, DMSO-d$_6$) δ: 12.18-12.80 (1H, m), 4.24 (1H, d, J=7.5 Hz), 3.92-4.00 (1H, m), 3.68-3.76 (1H, m), 2.42-2.49 (1H, m), 1.99-2.09 (1H, m), 1.51-1.63 (1H, m), 0.93 (3H, d, J=7.0 Hz).

Step 2

A vial charged with 3-[4-(piperidin-4-yloxy)-phenyl]-quinoline; 2HCl (110 mg, 0.29 mmol), (2R,3S)/(2S,3R)-3-methyl-tetrahydrofuran-2-carboxylic acid (47 mg, 0.36 mmol), N,N,N',N'-tetramethyl-O-(7-azabenzotriazol-1-yl) uronium hexafluorophosphate (HATU, 122 mg, 0.32 mmol), and DIPEA (305 µL, 1.75 mmol) in THF (10 mL) was stirred at rt 16 h. The reaction was concentrated and the residue was purified by pre-HPLC and the product fractions were combined, neutralized with sat. NaHCO$_3$ (25 mL), extracted with DCM (3×25 mL), and the combined organic layers were dried (Na$_2$SO$_4$), and concentrated. The product was dissolved in DCM (~5 mL) and mixed with 1.2 eq. of 2 M HCl in Et$_2$O and concentrated. The residue was dissolved in a small amount of DCM and concentrated—repeated this procedure several times, dried to give a yellow solid 93 mg (71%). Analysis: LCMS m/z=417 (M+1); $^1$H NMR (400 MHz, DMSO-d$_6$) δ: 9.50-9.56 (1H, m), 9.15-9.21 (1H, m), 8.23-8.34 (2H, m), 7.91-8.03 (3H, m), 7.82-7.90 (1H, m), 7.18-7.27 (2H, m), 4.72-4.85 (2H, m), 3.92-4.01 (2H, m), 3.79-3.91 (1H, m), 3.66-3.77 (1H, m), 3.18-3.52 (2H, m), 2.52-2.61 (1H, m), 1.91-2.10 (3H, m), 1.49-1.73 (3H, m), 0.84-0.94 (3H, m).

The following compounds were synthesized using the procedure for Example 154.

Example 155. ((2R,3S,5R)/(2S,3R,5S)-3,5-Dimethyl-tetrahydrofuran-2-yl)-[4-(4-quinolin-3-yl-phenoxy)-piperidin-1-yl]-methanone, HCl

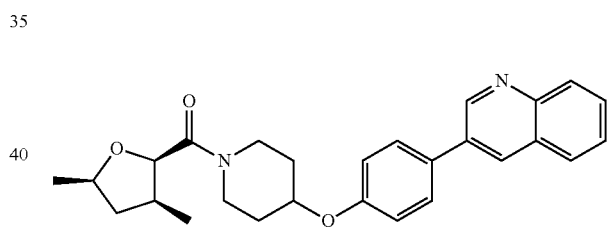

The product was isolated as a yellow solid. Analysis: LCMS m/z=431 (M+1); $^1$H NMR (400 MHz, DMSO-d$_6$) δ: 9.50-9.54 (1H, m), 9.14-9.18 (1H, m), 8.22-8.32 (2H, m), 7.91-8.02 (3H, m), 7.82-7.89 (1H, m), 7.19-7.26 (2H, m), 4.71-4.84 (2H, m), 3.89-4.04 (1H, m), 3.79-3.89 (1H, m), 3.70-3.79 (1H, m), 3.30-3.53 (1H, m), 3.17-3.27 (1H, m), 2.53-2.61 (1H, m), 2.08-2.19 (1H, m), 1.91-2.08 (2H, m), 1.49-1.70 (2H, m), 1.22-1.27 (4H, m), 0.86-0.93 (3H, m).

Example 156. ((2R,3S,5R)/(2S,3R,5S)-3,5-Dimethyl-tetrahydrofuran-2-yl)-[4-(4-quinolin-3-yl-phenoxy)-piperidin-1-yl]-methanone, HCl

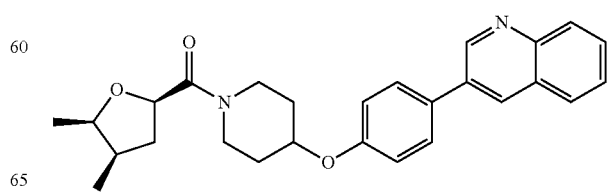

((2R,4R,5R)/(2S,4S,5S)-4, 5-Dimethyl-tetrahydrofuran-2-yl)-[4-(4-quinolin-3-yl-phenoxy)-piperidin-1-yl]-methanone, HCL. The product was isolated as a yellow solid. Analysis: LCMS m/z=431 (M+1); $^1$H NMR (400 MHz, DMSO-d$_6$) δ: 9.48-9.51 (1H, m), 9.10-9.14 (1H, m), 8.21-8.28 (2H, m), 7.90-8.00 (3H, m), 7.81-7.87 (1H, m), 7.19-7.25 (2H, m), 4.74-4.82 (1H, m), 4.53-4.59 (1H, m), 3.98-4.05 (1H, m), 3.79-3.91 (2H, m), 3.38-3.51 (1H, m), 3.25-3.37 (1H, m), 2.21-2.29 (1H, m), 2.09-2.18 (1H, m), 1.86-2.05 (3H, m), 1.51-1.69 (2H, m), 0.98-1.02 (3H, m), 0.87-0.90 (3H, m).

Example 157. 1-Propionylpiperidine-4-carboxylic acid (4-isoquinolin-6-yl-phenyl)-methylamide

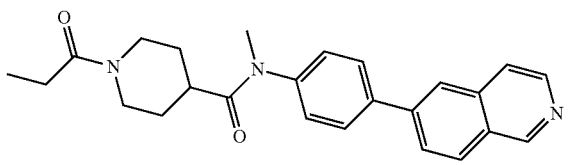 [SMILES: CCC(=O)N1CCC(C(=O)N(C)c2ccc(-c3ccc4cnccc4c3)cc2)CC1]

Step 1. 4-[(4-Bromo-2-fluorobenzoyl)-methyl-amino]-piperidine-1-carboxylic acid tert-butyl ester 4-Methylamino-piperidine-1-carboxylic acid tert-butyl ester (0.40 g, 1.87 mmol) and DIPEA (1.30 mL, 7.47 mmol) in DCM (5 mL) was added 4-bromo-2-fluoro-benzoyl chloride (0.488 g, 2.05 mmol). After 2 h stirring at rt the mixture was concentrated, dissolved in EtOAc and washed with 1N Na$_2$CO$_3$, water and brine. The product was purified by silica gel chromatography (20% EtOAc/hexanes) to give an oil (0.6 g, 77%). Analysis: LCMS m/z=416 (M+1).

Step 2. 2-Fluoro-4-isoquinolin-6-yl-N-methyl-N-piperidin-4-yl-benzamide

Palladium acetate (0.007568 g, 0.03371 mmol) and triphenylphosphine (0.03537 g, 0.1348 mmol) in dioxane were stirred 15 min under an atmosphere of nitrogen. 4-[(4-bromo-2-fluoro-benzoyl)-methyl-amino]-piperidine-1-carboxylic acid tert-butyl ester (0.3500 g, 0.8428 mmol), iso-quinoline-6-boronic acid (0.2187 g, 1.264 mmol), DMF (6 mL) and 1 M of sodium carbonate (2.56 mL) was added and heated at 80° C. for 17 h. The mixture was concentrated, was dissolved in EtOAc, washed with 1N Na$_2$CO$_3$, water and brine then dried (MgSO$_4$). The product was purified by ISCO (silica get, 12 g, 0-5% MeOH/DCM) to give a white solid. This material was dissolved in 4 M HCl in 1,4-dioxane (6 mL, 20 mmol) and was heated at 65° C. for 4 h. The material was concentrated, partitioned between EOAc and 1N Na$_2$CO$_3$, washed with water and brine then dried over MgSO$_4$ to give an oil. The amine was purified by ISCO (4 g silica gel, 0-10% MeOH with 1% IPA/DCM) to give an oil (0.25 g, 81%). Analysis: LCMS m/z=364 (M+1).

Step 3. 1-Propionylpiperidine-4-carboxylic acid (4-isoquinolin-6-yl-phenyl)-methylamide Piperidine-4-carboxylic acid (4-isoquinolin-6-yl-phenyl)-methylamide (0.048 g, 0.14 mmol) and DIPEA (0.097 mL, 0.55 mmol) in THF (2 mL) was added propanoyl chloride (0.024 mL, 0.28 mmol). After 4 h stirring at rt, the mixture was concentrated, diluted with EtOAc and washed with 1N Na$_2$CO$_3$, water and brine then dried (MgSO$_4$). The product was purified by ISCO silica gel 0-5% MeOH/DCM. The HCl salt was prepared from 2N HCl ether and crystallized from DCM-ether to give a white solid (33 mg, 59%). Analysis: LCMS m/z=402 (M+1); $^1$H NMR (DMSO; HCl salt) δ: 9.82 (s, 1H), 8.67 (m, 2H), 8.57 (d, 1H, J=8 Hz), 8.37-8.42 (m, 2H), 8.06 d, 2H, J=8 Hz), 7.59 (d, 2H, J=8 Hz), 4.32 (d, 1H, J=12 Hz), 3.78 (d, 2H, J=12 Hz), 3.23 (s, 3H), 2.77 (b, 1H), 2.23-2.32 (m, 3H), 1.53-1.65 (m, 3H), 1.37-1.45 (m, 1H), 0.95 (t, 3H, J=7 Hz).

Example 158. 2-Fluoro-4-isoquinolin-6-yl-N-methyl-N-(1-propionyl-piperidin-4-yl)-benzamide

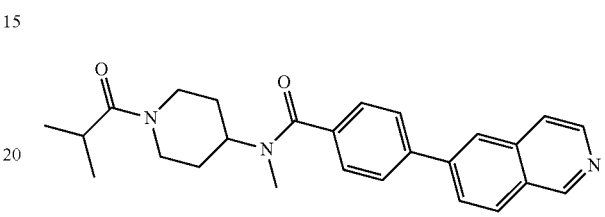

This example was synthesized using the procedure for example 157. Analysis: LCMS m/z=420 (M+1); $^1$H NMR (DMSO; HCl salt) δ: 9.84 (s, 1H), 8.70 (m, 2H), 8.58 (d, 2H, J=8.5 Hz), 8.38-8.42 (m, 2H), 7.96 (t, 1H, J=10 Hz), 7.88 (m, 1H), 7.95-7.69 (m, 1H), (rotomers 2:1) 4.58/4.44 (m, 2H), 3.98/3.86 (bd, 1H), 3.54/3.12 (1:1, m, 1H), 2.91/2.75 (1:2, s, 3H), 2.80/2.62 (1:1, m, 1H), 2.77-2.83 (m, 3H), 1.61-1.80 (m, 4H), 0.93-1.02 (m, 3H).

Example 159. 1-{4-[4-(3-Trifluoromethyl-1,2,4-triazolo[4,3-a]pyridin-6-yl)-phenoxy]-piperidin-1-yl}-propan-1-one, HCl

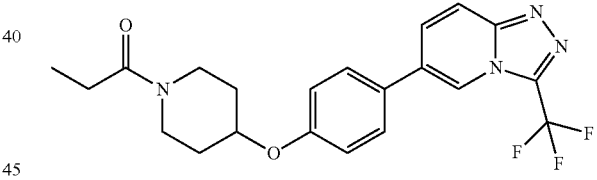

Step 1. 4-[4-(3-Trifluoromethyl-1,2,4-triazolo[4,3-a]pyridin-6-yl)-phenoxy]-piperidine-1-carboxylic acid tert-butyl ester A flask charged with 4-(4-iodo-phenoxy)-piperidine-1-carboxylic acid tert-butyl (368 mg, 0.91 mmol), 6-(4,4,5,5-tetramethyl-1,3, 2-dioxaborolan-2-yl)-3-trifluoromethyl-1,2,4-triazolo[4,3-a]pyridine (0.30 g, 0.96 mmol), palladium acetate (20.5 mg, 0.91 mmol), triphenylphosphine (47.9 mg, 0.18 mmol), 1.0 M of Na$_2$CO$_3$ in water (5 mL, 5 mmol), 1,4-dioxane (5 mL), and DMF (5 mL) was flashed with N$_2$ for 15 min. The reaction was stirred at 90° C. for 16 h then cooled to rt and concentrated. The residue was participated in EtOAc (80 mL) and sat. NaHCO$_3$ solution (30 mL), the organic layer was separated and the water layer was extracted with EtOAc (50 mL). The combined organic layers were washed with H$_2$O, brine, dried (Na$_2$SO$_4$), and concentrated. The residue was chromatography on silica gel (10-70% EtOAc/Hexanes) to give an off-white solid (404 mg, 96%). Analysis: $^1$H NMR (400 MHz, DMSO-d$_6$) δ: 8.59-

8.61 (1H, m), 8.09-8.14 (1H, m), 7.95-8.00 (1H, m), 7.71-7.76 (2H, m), 7.11-7.16 (2H, m), 4.63-4.72 (1H, m), 3.63-3.72 (2H, m), 3.16-3.28 (2H, m), 1.90-1.98 (2H, m), 1.50-1.61 (2H, m), 1.41 (9H, s).

Step 2. 6-[4-(Piperidin-4-yloxy)-phenyl]-3-trifluoromethyl-1,2,4-triazolo[4,3-a]pyridine, 2HCl To a solution of 4-[4-(3-trifluoromethyl-1,2,4-triazolo[4,3-a]pyridin-6-yl)-phenoxy]piperidine-1-carboxylic acid tert-butyl ester (396 mg, 0.86 mmol) in DCM (15 mL) was added 4.0 M of hydrogen chloride in 1,4-dioxane (2.14 mL, 8.56 mmol) and stirred at RT for 18 h. The resulted white precipitation was collected by filtration, washed with DCM, dried to give a white solid 370 mg (99%). Analysis: LCMS m/z=363 (M+1); $^1$H NMR (400 MHz, DMSO-d$_6$) δ: 9.15 (1H, br. s.), 8.59-8.63 (1H, m), 8.10-8.16 (1H, m), 7.96-8.02 (1H, m), 7.74-7.79 (2H, m), 7.14-7.20 (2H, m), 4.73-4.82 (1H, m), 3.18-3.30 (2H, m), 3.03-3.15 (2H, m), 2.10-2.21 (2H, m), 1.83-1.95 (2H, m).

Step 3

To a solution of 6-[4-(piperidin-4-yloxy)-phenyl]-3-trifluoromethyl-1,2,4-triazolo[4,3-a]pyridine; 2HCl (85 mg, 0.20 mmol), DIPEA (170 μL, 0.98 mmol) in THF (6 mL) was added propanoyl chloride (19 μL, 0.22 mmol). After 25 min, the reaction was concentrated and the residue was chromatography on silica gel (0-10% MeOH/DCM) and the isolated product was dissolved in DCM (~5 mL) and mixed with 1.2 eq. of 2 M HCl in Et$_2$O and concentrated. The residue was dissolved in a small amount of DCM and concentrated—repeated this procedure several times, dried to give to give a light-brown solid 63 mg (71%). Analysis: LCMS m/z=419 (M+1); $^1$H NMR (400 MHz, DMSO-d$_6$) δ: 8.58-8.63 (1H, m), 8.09-8.15 (1H, m), 7.96-8.01 (1H, m), 7.71-7.78 (2H, m), 7.12-7.18 (2H, m), 4.68-4.78 (1H, m), 3.82-3.93 (1H, m), 3.66-3.76 (1H, m), 3.22-3.41 (2H, m), 2.35 (2H, q, J=7.5 Hz), 1.87-2.04 (2H, m), 1.47-1.69 (2H, m), 1.00 (3H, t, J=7.4 Hz).

The following compounds were synthesized using the procedure for Example 159.

Example 160. Cyclopropyl-{4-[4-(3-trifluoromethyl-1,2,4-triazolo[4,3-a]pyridin-6-yl)-phenoxy]-piperidin-1-yl}-methanone, HCl

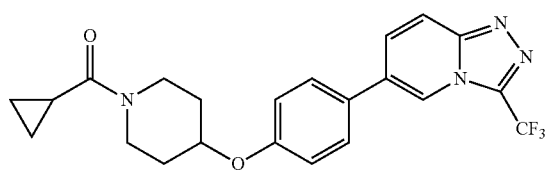 [SMILES: O=C(C1CC1)N1CCC(Oc2ccc(-c3ccc4nnc(C(F)(F)F)n4c3)cc2)CC1]

The product was isolated as an off-white solid. Analysis: LCMS m/z=431 (M+1); $^1$H NMR (400 MHz, DMSO-d$_6$) δ: 8.59-8.63 (1H, m), 8.10-8.15 (1H, m), 7.96-8.01 (1H, m), 7.72-7.78 (2H, m), 7.13-7.18 (2H, m), 4.71-4.79 (1H, m), 3.83-4.04 (2H, m), 3.50-3.63 (1H, m), 3.24-3.35 (1H, m), 1.88-2.09 (3H, m), 1.48-1.71 (2H, m), 0.67-0.75 (4H, m).

Example 161. (R)-Tetrahydrofuran-2-yl-{4-[4-(3-trifluoromethyl-1,2,4-triazolo[4,3-a]pyridin-6-yl)-phenoxy]-piperidin-1-yl}-methanone

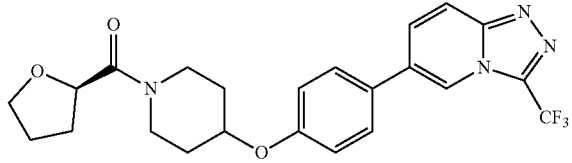 [SMILES: O=C([C@H]1CCCO1)N1CCC(Oc2ccc(-c3ccc4nnc(C(F)(F)F)n4c3)cc2)CC1]

To a solution of 6-[4-(piperidin-4-yloxy)-phenyl]-3-trifluoromethyl-1,2,4-triazolo-[4, 3-a]pyridine; 2HCl (85 mg, 0.20 mmol), HATU (81.7 mg. 0.22 mmol), DIPEA (170 mL, 0.98 mmol) in THF (6 mL) was added (R)-tetrahydrofuran-2-carboxylic acid (20 μL, 0.21 mmol) and stirred at rt for 1 h. The reaction was concentrated and the residue was purified by chromatography on silica gel (0-10% MeOH/DCM) to give a white solid 71 mg (79%). Analysis: LCMS m/z=461 (M+1); $^1$H NMR (400 MHz, DMSO-d$_6$) δ: 8.59-8.62 (1H, m), 8.10-8.15 (1H, m), 7.96-8.01 (1H, m), 7.72-7.77 (2H, m), 7.12-7.18 (2H, m), 4.66-4.78 (2H, m), 3.70-3.87 (4H, m), 2.68-2.70 (2H, m), 1.92-2.10 (4H, m), 1.79-1.88 (2H, m), 1.49-1.69 (2H, m).

Example 162. 3-[4-(1-Methanesulfonyl-piperidin-4-yloxy)-phenyl]-quinoline

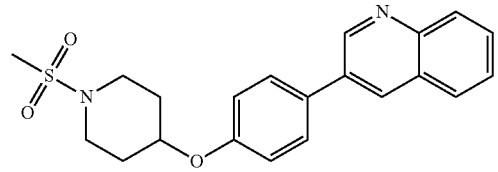 [SMILES: CS(=O)(=O)N1CCC(Oc2ccc(-c3cnc4ccccc4c3)cc2)CC1]

Step 1. Methanesulfonic acid (R)-1-(tetrahydrofuran-2-yl)methyl ester

To a solution of (R)-1-(tetrahydrofuran-2-yl)-methanol (0.50 g, 4.9 mmol), and DIPEA (2.56 mL, 14.7 mmol) in methylene chloride (20 mL) at 0° C. was added methanesulfonyl chloride (398 μL, 5.14 mmol). After 1 h at 0° C., the reaction was stirred at room temp over night (16 h) then quenched with H$_2$O (20 mL), extracted with DCM (3×30 mL). The combined organic layers were washed with H$_2$O, dried (Na$_2$SO$_4$) and concentrated to give 551 mg (62%) of crude product. This material was used for next step without purification.

Step 2

A vial charged with 3-[4-(piperidin-4-yloxy)-phenyl]-quinoline; 2HCl (85 mg, 0.22 mmol), methanesulfonic acid (R)-1-(tetrahydrofuran-2-yl)methyl ester (61 mg, 0.34 mmol), potassium carbonate (160 mg, 1.1 mmol), and acetonitrile (6 mL) was stirred at 90° C. for 1.5 h. After cooled to RT, it was diluted with DCM (50 mL), washed with H$_2$O, dried (Na$_2$SO$_4$), and concentrated. The residue was chromatography on silica gel (0-10% MeOH/DCM) to give a white solid 76 mg (88%). Analysis: LCMS m/z=373

(M+1); ¹H NMR (400 MHz, DMSO-d₆) δ: 9.22-9.25 (1H, m), 8.57-8.59 (1H, m), 8.01-8.06 (2H, m), 7.82-7.87 (2H, m), 7.72-7.78 (1H, m), 7.61-7.67 (1H, m), 7.15-7.20 (2H, m), 4.64-4.72 (1H, m), 3.34-3.43 (2H, m), 3.14-3.20 (2H, m), 2.92 (3H, s), 2.01-2.10 (2H, m), 1.74-1.85 (2H, m).

Example 163. (4,4-Difluorotetrahydrofuran-2-yl)-[4-(4-quinolin-3-yl-phenoxy)-piperidin-1-yl]-methanone, HCl

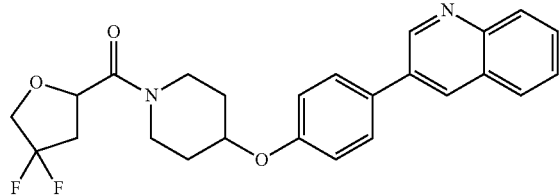 [SMILES: O=C(C1CC(F)(F)CO1)N1CCC(Oc2ccc(-c3cnc4ccccc4c3)cc2)CC1]

Step 1. 4-oxo-tetrahydrofuran-2-carboxylic acid

To a suspension of sodium hydride, 60% disp. in mineral oil (830 mg, 20.7 mmol) in THF (35 mL) was added a solution of ethyl glycolate (2.0 mL, 20.7 mmol) in THF (5 mL×2) dropwise at rt (water-bath). After the evolution of H₂ had ceased (~5 min), to the reaction was added (Z)-2-butenedioic acid, diethyl ester (2.75 mL, 17.0 mmol). The reaction was stirred at 65° C. for 1 h then rt for 5 days. The solvent was removed and to the residue was carefully added ice-water (50 mL) and 1N HCl solution (50 mL), extracted with EtOAc (2×50 mL), the combined organic layers were concentrated. This residue was heated at reflux (100° C.) with 10% H₂OS₄ water solution for 5 h and cooled to rt. The reaction was extracted with EtOAc (3×50 mL) and the combined organic layers were washed with brine, dried (Na₂SO₄), and concentrated. This material was use for next step without purification.

Step 2. 4-oxo-Tetrahydrofuran-2-carboxylic acid 4-nitro-benzyl ester

To a mixture of 4-oxo-tetrahydrofuran-2-carboxylic acid (2.21 g, 17.0 mmol), DIPEA (2.95 mL, 16.9 mmol), 4-dimethylaminopyridine (156 mg, 1.27 mmol), potassium carbonate (3.52 g, 25.5 mmol) in THF (35 mL) was added a solution of 4-nitrobenzyl chloroformate (2.75 g, 12.7 mmol) in THF (5 mL) at rt (water-bath). After 5 min, the solvent was removed and the residue was added H₂O (30 mL), extracted with EtOAc (2×50 mL). The combined organic layers were washed with brine, dried (Na₂SO₄), and concentrated. The residue was chromatography on silica gel (0-50% EtOAc/Hexanes) to give a white solid (934 mg, 28%, 3 steps). Analysis: ¹H NMR (400 MHz, CDCl₃) δ: 8.22-8.28 (2H, m), 7.50-7.57 (2H, m), 5.29-5.33 (2H, m), 4.96-5.03 (1H, m), 4.15-4.23 (1H, m), 4.00-4.07 (1H, m), 2.81-2.91 (1H, m), 2.60-2.69 (1H, m).

Step 3. 4,4-Difluorotetrahydrofuran-2-carboxylic acid 4-nitrobenzyl ester

A Teflon bottle charged with 4-oxo-tetrahydrofuran-2-carboxylic acid 4-nitro-benzyl ester (538 mg, 2.03 mmol) in DCM (10 mL) was added bis(2-methoxyethyl)aminosulfur trifluoride (1.12 mL, 6.08 mmol) and stirred at rt for 18 h. The reaction was carefully added sat. NH₄Cl solution (15 mL) cooling with water-bath, extracted with DCM (3×10 mL). The combined organic layers was dried (Na₂SO₄) and concentrated. The residue was chromatography on silica gel (0-30% EtOAc/Hexanes) to give colorless oil (496 mg, 85%). Analysis: ¹H NMR (400 MHz, CDCl₃) δ: 8.22-8.27 (2H, m), 7.51-7.56 (2H, m), 5.31 (2H, s), 4.75-4.81 (1H, m), 4.00-4.24 (2H, m), 2.70-2.84 (1H, m), 2.54-2.68 (1H, m).

Step 4. 4,4-Difluorotetrahydrofuran-2-carboxylic acid

To a solution of 4,4-difluorotetrahydrofuran-2-carboxylic acid 4-nitro-benzyl ester (270 mg, 0.94 mmol) in THF (6 mL) was added 1.0 M of tetra-n-butylammonium fluoride in THF (2.35 mL, 2.35 mmol) and stirred for 30 min. The reaction was added H₂O (10 mL) and EtOAc (10 mL) then extracted with 5% NaHCO₃ solution (3×15 mL). The combined water layers were acidified to pH-1 with HCl, extracted with EtOAc (3×20 mL). The combined organic layers were washed with brine, dried (Na₂SO₄), and concentrated to give a brown oil 140 mg. This material was used for next step without purification.

Step 5

A mixture of 3-[4-(piperidin-4-yloxy)-phenyl]-quinoline; 2HCl (106 mg, 0.28 mmol), 4,4-difluorotetrahydrofuran-2-carboxylic acid (51 mg, 0.34 mmol), HATU (107 mg, 0.28 mmol), DIPEA (245 μL, 1.40 mmol) in THF (8 mL) was stirred at rt for 1 h and concentrated. The residue was purified by pre-HPLC and the product fractions were combined and concentrated. The residue was added EtOAc (25 mL), washed with sat. NaHCO₃ solution (10 mL), brine, dried (Na₂SO₄), and concentrated. The product was dissolved in DCM (~5 mL) and mixed with 1.2 eq. of 2 M HCl in Et₂O and concentrated. The residue was dissolved in a small amount of DCM and concentrated—repeated this procedure several times, dried to give a yellow solid 117 mg (88%). Analysis: LCMS m/z=439 (M+1); ¹H NMR (400 MHz, DMSO-d₆) δ: 9.50-9.55 (1H, m), 9.14-9.19 (1H, m), 8.23-8.32 (2H, m), 7.96-8.02 (1H, m), 7.91-7.96 (2H, m), 7.83-7.89 (1H, m), 7.19-7.25 (2H, m), 5.08-5.16 (1H, m), 4.75-4.84 (1H, m), 3.88-4.09 (3H, m), 3.75-3.85 (1H, m), 3.27-3.53 (2H, m), 2.71-2.88 (1H, m), 2.54-2.71 (1H, m), 1.99 (2H, s), 1.54-1.70 (2H, m).

The following compounds were synthesized using the procedure for Example 163.

Example 164. (4,4-Difluorotetrahydrofuran-2-yl)-{4-[4-(8-methylquinolin-7-yl)-phenoxy]-piperidin-1-yl}-methanone, HCl

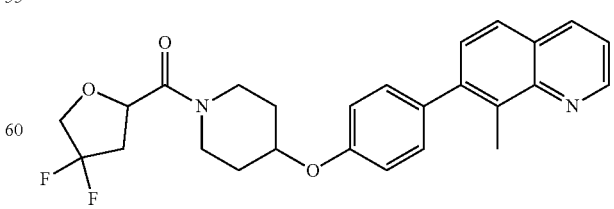

The product was isolated as a brown solid. Analysis: LCMS m/z=453 (M+1); ¹H NMR (400 MHz, DMSO-d₆) δ: 9.10-9.15 (1H, m), 8.76-8.87 (1H, m), 8.03-8.11 (1H, m), 7.79-7.89 (1H, m), 7.64-7.71 (1H, m), 7.37-7.45 (2H, m), 7.11-7.19 (2H, m), 5.08-5.17 (1H, m), 4.69-4.79 (1H, m), 3.99-4.05 (2H, m), 3.73-3.90 (2H, m), 3.25-3.53 (2H, m), 2.75-2.89 (1H, m), 2.72 (3H, s), 2.54-2.70 (1H, m), 1.99 (2H, s), 1.55-1.73 (2H, m).

Example 165. (4,4-Difluorotetrahydrofuran-2-yl)-{4-[4-(1-methylisoquinolin-6-yl)-phenoxy]-piperidin-1-yl}-methanone, HCl

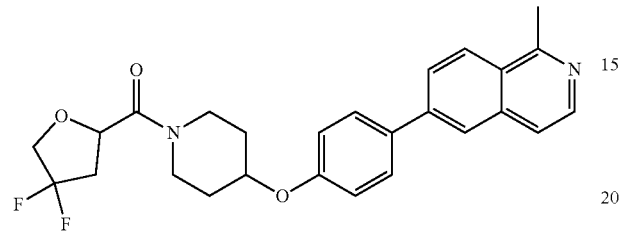

The product was isolated as an off-white solid. Analysis: LCMS m/z=453 (M+1); $^1$H NMR (400 MHz, DMSO-d$_6$) δ: 8.55-8.63 (2H, m), 8.45-8.49 (1H, m), 8.32-8.37 (1H, m), 8.26-8.30 (1H, m), 7.92-7.98 (2H, m), 7.19-7.25 (2H, m), 5.09-5.16 (1H, m), 4.76-4.85 (1H, m), 3.97-4.07 (2H, m), 3.73-3.96 (2H, m), 3.41-3.50 (2H, m), 3.21 (3H, s), 2.71-2.88 (1H, m), 2.55-2.70 (1H, m), 1.94-2.05 (2H, m), 1.52-1.75 (2H, m).

Example 166. 5-[4-(4-Quinolin-3-yl-phenoxy)-piperidine-1-carbonyl]dihydrofuran-3-one

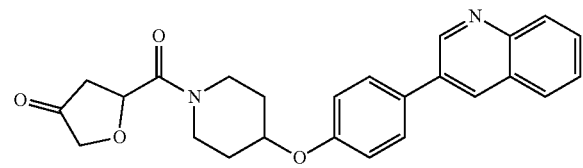 [SMILES: O=C1COC(C(=O)N2CCC(Oc3ccc(-c4cnc5ccccc5c4)cc3)CC2)C1]

A mixture of 3-[4-(piperidin-4-yloxy)-phenyl]-quinoline; 2HCl (105 mg, 0.278 mmol), 4-oxo-tetrahydrofuran-2-carboxylic acid (38 mg, 0.29 mmol), HATU (116 mg, 0.31 mmol), DIPEA (242 μL, 1.39 mmol) in THF (8 mL) was stirred at rt for 1 h and concentrated. The residue was purified by pre-HPLC and the product fractions were combined and concentrated. The residue was added EtOAc (25 mL), washed with sat. NaHCO$_3$ solution (10 mL), brine, dried (Na$_2$SO$_4$), concentrated to give a white solid 17 mg (15%). Analysis: LCMS m/z=417 (M+1); $^1$H NMR (400 MHz, DMSO-d$_6$) δ: 8.57-8.60 (1H, m), 8.01-8.06 (2H, m), 7.82-7.86 (2H, m), 7.72-7.78 (1H, m), 7.61-7.66 (1H, m), 7.16-7.20 (2H, m), 5.33-5.39 (1H, m), 4.72-4.81 (1H, m), 3.98 (2H, s), 3.77-3.94 (2H, m), 3.38-3.58 (2H, m), 3.26-3.31 (1H, m), 2.66-2.72 (2H, m), 1.91-2.12 (2H, m), 1.51-1.79 (2H, m).

Example 167. 1-{4-[4-(8-Ethoxyquinolin-7-yl)-phenoxy]-piperidin-1-yl}-propan-1-one, HCl

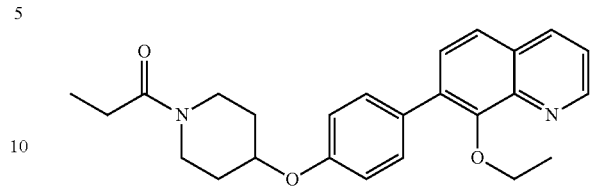

Step 1. 7-Bromo-8-ethoxyquinoline

A flask charged with 7-bromoquinolin-8-ol (1.0 g, 4.46 mmol), iodoethane (375 μL, 4.69 mmol), and K$_2$CO$_3$ (1.23 g, 8.93 mmol) in dimethyl sulfoxide (25 mL) was stirred at rt for 24 h. The reaction was diluted with DCM, washed with H$_2$O (2×30 mL), brine, dried (Na$_2$SO$_4$), and concentrated. The residue was chromatography on silica gel (0-50% EtOAc/Hexanes) to give 1.03 g (92%) as yellowish oil.

Step 2. 4-[4-(8-ethoxyquinolin-7-yl)-phenoxy]-piperidine-1-carboxylic acid t-butyl ester A flask charged with 4-[4-(4,4,5,5-tetramethyl-1,3,2-dioxaborolan-2-yl)-phenoxy]-piperidine-1-carboxylic acid tert-butyl ester (1.62 g, 4.01 mmol), 7-bromo-8-ethoxyquinoline (1.01 g, 4.01 mmol), palladium acetate (91 mg, 0.40 mmol), triphenylphosphine (0.21 g, 0.80 mmol), 1.0 M of Na$_2$CO$_3$ in water (20 mL, 20 mmol), 1,4-dioxane (20 mL), and DMF (20 mL) was flashed with N$_2$ for 15 min. After stirred at 85° C. for 17 h, the reaction was cooled to rt, and added EtOAc (100 mL), washed with sat. NaHCO$_3$ solution (35 mL), the water layer was back extracted with EtOAc (50 mL). The combined organic layers were washed with H$_2$O (35 mL), brine, dried (Na$_2$SO$_4$), and concentrated. The residue was chromatography on silica gel (0-70% EtOAc/Hexanes) to give 1.21 g (67%) as yellowish gum. Analysis: $^1$H NMR (400 MHz, DMSO-d$_6$) δ: 8.91-8.95 (1H, m), 8.35-8.40 (1H, m), 7.73-7.78 (1H, m), 7.56-7.62 (3H, m), 7.51-7.56 (1H, m), 7.07-7.13 (2H, m), 4.59-4.69 (1H, m), 4.14-4.24 (2H, m), 3.66-3.76 (2H, m), 3.13-3.28 (2H, m), 1.91-2.02 (2H, m), 1.50-1.63 (2H, m), 1.42 (9H, s), 1.14-1.21 (3H, m).

Step 3. 8-Ethoxy-7-[4-(piperidin-4-yloxy)-phenyl]-quinoline, 2HCl

To a solution of 4-[4-(8-ethoxyquinolin-7-yl)-phenoxy]-piperidine-1-carboxylic acid tert-butyl ester (1.20 g, 2.68 mmol) in DCM (30 mL) was added 4.0 M of HCl in 1,4-dioxane (6.69 mL, 26.8 mmol) slowly. The reaction was stirred at rt for 2 h and then concentrated. The solid residue was washed with mixed solvent (DCM-EtOAc ~1:1) and dried to give 976 mg (87%) as yellow solid.

Step 4

To a solution of 8-ethoxy-7-[4-(piperidin-4-yloxy)-phenyl]-quinoline; 2HCl (150 mg, 0.36 mmol) and DIPEA (310 μL, 1.78 mmol) in THF (10 mL) was added propanoyl chloride (34 μL, 0.39 mmol) and stirred for 25 min. The solvent was removed and the residue was purified by pre-HPLC. The product fractions were combined and neutralized with sat. NaHCO₃ solution (25 mL), extracted with DCM (3×25 mL), dried (Na₂SO₄), and concentrated. The product was dissolved in DCM (~5 mL) and mixed with 1.2 eq. of 2 M HCl in Et₂O and concentrated. The residue was dissolved in a small amount of DCM and concentrated—repeated this procedure several times, dried to give 97 mg (62%) yellow solid. Analysis: LCMS m/z=405 (M+1); ¹H NMR (400 MHz, DMSO-d₆) δ: 9.13-9.20 (1H, m), 8.94-9.05 (1H, m), 8.04-8.11 (1H, m), 7.86-8.01 (2H, m), 7.67-7.75 (2H, m), 7.14-7.22 (2H, m), 4.68-4.78 (1H, m), 3.93 (3H, q, J=6.8 Hz), 3.67-3.79 (1H, m), 3.20-3.43 (2H, m), 2.36 (2H, q, J=7.4 Hz), 1.90-2.09 (2H, m), 1.48-1.71 (2H, m), 1.21 (3H, t, J=7.0 Hz), 1.00 (3H, t, J=7.4 Hz).

The following compounds were synthesized using the procedure for Example 167.

Example 168. Cyclopropyl-{4-[4-(8-ethoxyquinolin-7-yl)-phenoxy]-piperidin-1-yl}-methanone, HCl

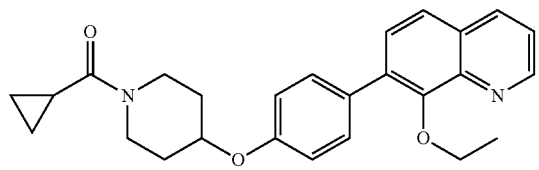 [SMILES: CCOc1c(-c2ccc(OC3CCN(C(=O)C4CC4)CC3)cc2)ccc2cccnc12]

The product was isolated as a yellow solid. Analysis: LCMS m/z=417 (M+1); ¹H NMR (400 MHz, DMSO-d₆) δ: 9.14-9.20 (1H, m), 8.97-9.06 (1H, m), 8.05-8.12 (1H, m), 7.86-8.02 (2H, m), 7.68-7.75 (2H, m), 7.16-7.22 (2H, m), 4.71-4.81 (1H, m), 3.87-3.97 (3H, m), 3.50-3.62 (1H, m), 3.22-3.35 (1H, m), 1.99 (4H, s), 1.49-1.73 (2H, m), 1.22 (3H, t, J=7.0 Hz), 0.62-0.85 (4H, m).

Example 169. 1-{4-[4-(8-Isopropoxyquinolin-7-yl)-phenoxy]-piperidin-1-yl}-propan-1-one, HCl

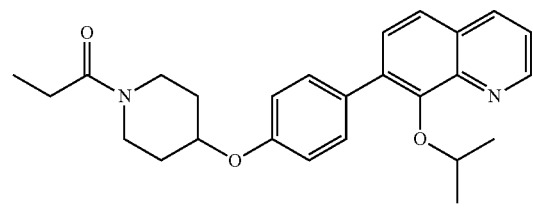 [SMILES: CCC(=O)N1CCC(Oc2ccc(-c3ccc4cccnc4c3OC(C)C)cc2)CC1]

The product was isolated as a yellow solid. Analysis: LCMS m/z=419 (M+1); ¹H NMR (400 MHz, DMSO-d₆) δ: 9.16-9.21 (1H, m), 9.01-9.11 (1H, m), 8.06-8.14 (1H, m), 7.96-8.04 (1H, m), 7.89-7.95 (1H, m), 7.68-7.75 (2H, m), 7.15-7.22 (2H, m), 4.68-4.78 (1H, m), 4.14-4.27 (1H, m), 3.90-3.97 (1H, m), 3.71-3.77 (1H, m), 3.21-3.41 (2H, m), 2.36 (2H, q, J=7.3 Hz), 1.91-2.07 (2H, m), 1.48-1.70 (2H, m), 1.11 (6H, d, J=6.0 Hz), 1.00 (3H, t, J=7.4 Hz).

Example 170. Cyclopropyl-{4-[4-(8-isopropoxyquinolin-7-yl)-phenoxy]-piperidin-1-yl}-methanone, HCl

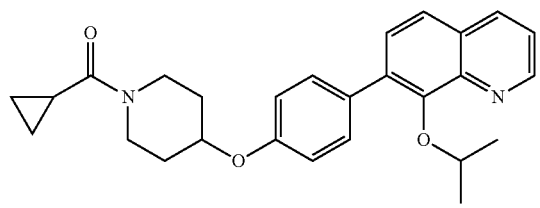 [SMILES: CC(C)Oc1c(-c2ccc(OC3CCN(C(=O)C4CC4)CC3)cc2)ccc2cccnc12]

The product was isolated as a yellow solid. Analysis: LCMS m/z=431 (M+1); ¹H NMR (400 MHz, DMSO-d₆) δ: 9.16-9.22 (1H, m), 9.03-9.12 (1H, m), 8.07-8.14 (1H, m), 7.97-8.05 (1H, m), 7.90-7.96 (1H, m), 7.69-7.76 (2H, m), 7.16-7.23 (2H, m), 4.71-4.81 (1H, m), 4.15-4.27 (1H, m), 4.00-4.05 (1H, m), 3.90-3.97 (1H, m), 3.53-3.60 (1H, m), 3.23-3.32 (1H, m), 1.92-2.11 (3H, m), 1.50-1.71 (2H, m), 1.12 (6H, d, J=6.0 Hz), 0.67-0.78 (4H, m).

Example 171. 1-(4-{4-[8-(2-Morpholin-4-yl-ethoxy)-quinolin-7-yl]-phenoxy}-piperidin-1-yl)-propan-1-one, 2HCl

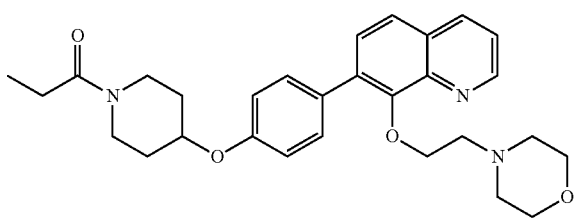 [SMILES: CCC(=O)N1CCC(Oc2ccc(-c3ccc4cccnc4c3OCCN3CCOCC3)cc2)CC1]

The product was isolated as a yellow solid. Analysis: LCMS m/z=490 (M+1); ¹H NMR (400 MHz, DMSO-d₆) δ: 9.06-9.17 (1H, m), 8.70-8.87 (1H, m), 7.96-8.06 (1H, m), 7.72-7.91 (2H, m), 7.61-7.71 (2H, m), 7.11-7.20 (2H, m), 4.69-4.76 (1H, m), 4.24-4.37 (2H, m), 3.87-3.99 (5H, m), 3.69-3.77 (1H, m), 3.51-3.56 (2H, m), 3.22-3.43 (4H, m), 2.36 (2H, q, J=7.5 Hz), 1.89-2.08 (2H, m), 1.48-1.72 (2H, m), 1.15-1.32 (2H, m), 1.01 (3H, t, J=7.4 Hz).

Example 172. Cyclopropyl-(4-{4-[8-(2-morpholin-4-yl-ethoxy)-quinolin-7-yl]-phenoxyl}-piperidin-1-yl)-methanone, 2HCl

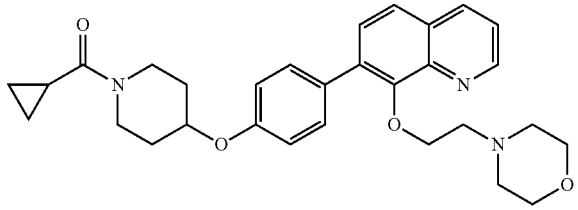 [SMILES: O=C(C1CC1)N1CCC(Oc2ccc(-c3ccc4cccnc4c3OCCN3CCOCC3)cc2)CC1]

The product was isolated as a yellow solid. Analysis: LCMS m/z=502 (M+1); ¹H NMR (400 MHz, DMSO-d₆) δ: 9.08-9.14 (1H, m), 8.68-8.84 (1H, m), 7.96-8.04 (1H, m), 7.74-7.88 (2H, m), 7.67 (2H, d, J=8.8 Hz), 7.17 (2H, d, J=8.8 Hz), 4.72-4.78 (1H, m), 4.26-4.36 (2H, m), 3.89-4.05 (6H, m), 3.49-3.64 (4H, m), 3.22-3.48 (4H, m), 1.91-2.14 (3H, m), 1.49-1.76 (2H, m), 0.68-0.79 (4H, m).

Example 173. 1-(4-{4-[8-(2-Pyrrolidin-1-yl-ethoxy)-quinolin-7-yl]-phenoxy}-piperidin-1-yl)-propan-1-one, HCl

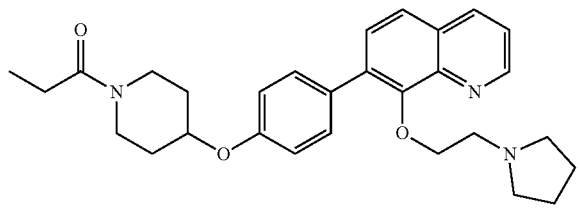 [SMILES: CCC(=O)N1CCC(Oc2ccc(-c3ccc4cccnc4c3OCCN3CCCC3)cc2)CC1]

The product was isolated as a yellow solid. Analysis: LCMS m/z=474 (M+1); $^1$H NMR (400 MHz, DMSO-$d_6$) δ: 9.16-9.25 (1H, m), 8.95-9.10 (1H, m), 8.08-8.18 (1H, m), 7.95-8.05 (1H, m), 7.86-7.94 (1H, m), 7.71 (2H, d, J=8.5 Hz), 7.20 (2H, d, J=8.8 Hz), 4.70-4.79 (1H, m), 4.08-4.19 (2H, m), 3.86-3.97 (1H, m), 3.53-3.79 (5H, m), 3.23-3.43 (2H, m), 3.00-3.16 (2H, m), 2.36 (2H, q, J=7.3 Hz), 1.90-2.09 (6H, m), 1.48-1.72 (2H, m), 1.01 (3H, t, J=7.4 Hz).

Example 174. Cyclopropyl-(4-{4-[8-(2-pyrrolidin-1-yl-ethoxy)-quinolin-7-yl]-phenoxy}-piperidin-1-yl)-methanone, HCl

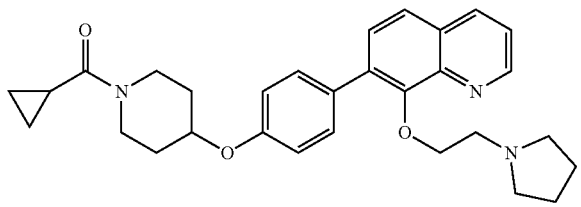 [SMILES: O=C(C1CC1)N1CCC(Oc2ccc(-c3ccc4cccnc4c3OCCN3CCCC3)cc2)CC1]

The product was isolated as a yellow solid. Analysis: LCMS m/z=486 (M+1); $^1$H NMR (400 MHz, DMSO-$d_6$) δ: 9.08-9.17 (1H, m), 8.72-8.92 (1H, m), 7.98-8.09 (1H, m), 7.77-7.94 (2H, m), 7.69 (2H, d, J=8.5 Hz), 7.18 (2H, d, J=8.5 Hz), 4.71-4.80 (1H, m), 4.16-4.26 (2H, m), 3.87-4.08 (2H, m), 3.49-3.72 (5H, m), 3.23-3.37 (1H, m), 3.00-3.20 (2H, m), 1.92-2.10 (7H, m), 1.49-1.75 (2H, m), 0.66-0.79 (4H, m).

Example 175. 1-(4-{4-[8-(3-Pyrrolidin-1-yl-propoxy)-quinolin-7-yl]-phenoxy}-piperidin-1-yl)-propan-1-one, HCl

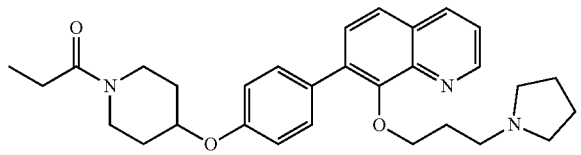 [SMILES: CCC(=O)N1CCC(Oc2ccc(-c3ccc4cccnc4c3OCCCN3CCCC3)cc2)CC1]

The product was isolated as a yellow solid. Analysis: LCMS m/z=488 (M+1); $^1$H NMR (400 MHz, DMSO-$d_6$) δ: 9.07-9.13 (1H, m), 8.71-8.82 (1H, m), 7.95-8.02 (1H, m), 7.74-7.85 (2H, m), 7.67 (2H, d, J=7.9 Hz), 7.18 (2H, d, J=8.8 Hz), 4.68-4.77 (1H, m), 3.89-3.99 (3H, m), 3.69-3.79 (1H, m), 3.58-3.69 (2H, m), 3.32-3.42 (1H, m), 3.20-3.31 (3H, m), 2.93-3.06 (2H, m), 2.36 (2H, q, J=7.4 Hz), 2.00-2.12 (5H, m), 1.86-1.98 (3H, m), 1.49-1.70 (2H, m), 1.01 (3H, t, J=7.4 Hz).

Example 176. Cyclopropyl-(4-{4-[8-(3-pyrrolidin-1-yl-propoxy)-quinolin-7-yl]-phenoxy})-piperidin-1-yl)-methanone, HCl

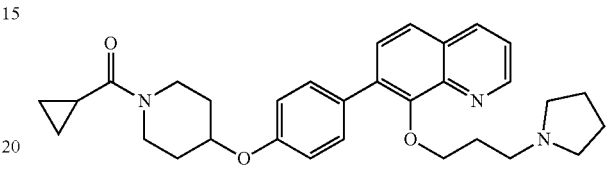

The product was isolated as a yellow solid. Analysis: LCMS m/z=500 (M+1); $^1$H NMR (400 MHz, DMSO-$d_6$) δ: 9.08-9.15 (1H, m), 8.72-8.83 (1H, m), 7.96-8.03 (1H, m), 7.75-7.88 (2H, m), 7.68 (2H, d, J=8.8 Hz), 7.19 (2H, d, J=8.8 Hz), 4.71-4.80 (1H, m), 4.01-4.07 (1H, m), 3.88-3.99 (3H, m), 3.52-3.68 (3H, m), 3.19-3.33 (3H, m), 2.93-3.07 (2H, m), 2.00-2.13 (6H, m), 1.87-1.98 (3H, m), 1.51-1.74 (2H, m), 0.67-0.79 (4H, m).

Example 177. 1-[4-[4-[8-[2-(4-Methylpiperazin-1-yl)ethoxy]-7-quinolyl]phenoxy]-1-piperidyl]propan-1-one, HCl

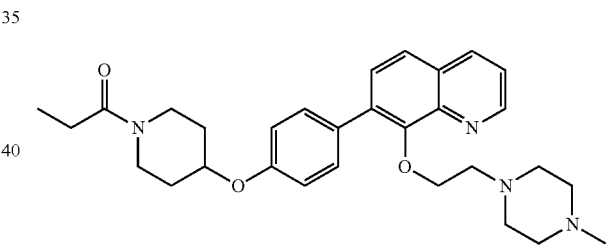

The product was isolated as a yellow solid. Analysis: LCMS m/z=503 (M+1); $^1$H NMR (400 MHz, DMSO-$d_6$) δ: 9.10 (1H, d, J=3.3 Hz), 8.60-8.78 (1H, m), 7.97 (1H, d, J=8.5 Hz), 7.71-7.83 (2H, m), 7.67 (2H, d, J=8.5 Hz), 7.16 (2H, d, J=8.8 Hz), 4.73 (1H, dt, J=7.8, 4.0 Hz), 4.31 (2H, br. s.), 3.87-4.05 (3H, m), 3.67-3.80 (3H, m), 3.43-3.67 (6H, m), 3.22-3.42 (2H, m), 2.87 (3H, s), 2.36 (2H, q, J=7.3 Hz), 1.93-2.04 (2H, m), 1.49-1.71 (2H, m), 1.01 (3H, t, J=7.4 Hz).

Example 178. 1-[4-[4-[8-(2-Methoxyethoxy)-7-quinolyl]phenoxy]-1-piperidyl]propan-1-one, HCl

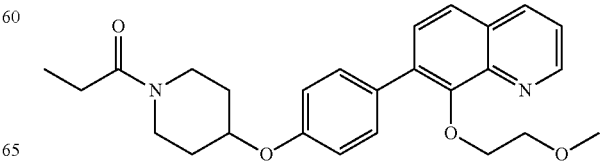

The product was isolated as a yellow solid. Analysis: LCMS m/z=435 (M+1); $^1$H NMR (400 MHz, DMSO-$d_6$) δ: 9.13-9.19 (1H, m), 8.93-9.02 (1H, m), 8.03-8.08 (1H, m), 7.91-7.98 (1H, m), 7.85-7.90 (1H, m), 7.69 (2H, d, J=7.9 Hz), 7.17 (2H, d, J=9.0 Hz), 4.73 (1H, dt, J=7.8, 4.1 Hz), 4.02-4.08 (2H, m), 3.87-3.97 (1H, m), 3.69-3.78 (1H, m), 3.54-3.59 (2H, m), 3.21-3.41 (2H, m), 3.05 (3H, s), 2.36 (2H, q, J=7.5 Hz), 1.91-2.07 (2H, m), 1.48-1.70 (2H, m), 1.00 (3H, t, J=7.4 Hz).

Example 179. 1-[4-[4-[8-(3-Methoxypropoxy)-7-quinolyl]phenoxy]-1-piperidyl]propan-1-one, HCl

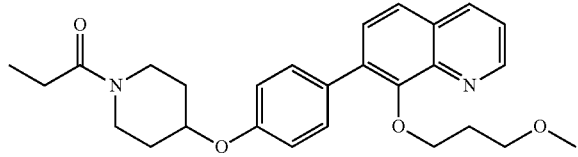 [SMILES: CCC(=O)N1CCC(Oc2ccc(-c3ccc4cccnc4c3OCCCOC)cc2)CC1]

The product was isolated as a yellow solid. Analysis: LCMS m/z=449 (M+1); $^1$H NMR (400 MHz, DMSO-$d_6$) δ: 9.15 (1H, d, J=3.8 Hz), 8.93 (1H, br. s.), 8.04 (1H, d, J=8.5 Hz), 7.89-7.96 (1H, m), 7.85 (1H, d, J=8.8 Hz), 7.66 (2H, d, J=8.8 Hz), 7.17 (2H, d, J=8.8 Hz), 4.69-4.78 (1H, m), 3.87-3.98 (3H, m), 3.69-3.78 (1H, m), 3.28-3.42 (1H, m), 3.25 (3H, t, J=6.4 Hz), 3.10 (3H, s), 2.36 (2H, q, J=7.5 Hz), 1.92-2.06 (2H, m), 1.88 (2H, quin, J=6.5 Hz), 1.49-1.70 (2H, m), 1.00 (3H, t, J=7.4 Hz).

Example 180. {4-[4-(8-Isopropoxyquinolin-7-yl)-phenoxy]-piperidin-1-yl}-(R)-tetrahydrofuran-2-yl-methanone, HCl

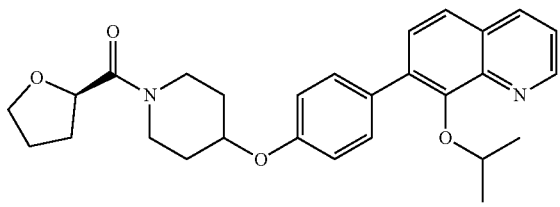 [SMILES: CC(C)Oc1c(-c2ccc(OC3CCN(C(=O)[C@H]4CCCO4)CC3)cc2)ccc2cccnc12]

A mixture of 8-isopropoxy-7-[4-(piperidin-4-yloxy)-phenyl]-quinoline; 2HCl (151 mg, 0.35 mmol), (R)-tetrahydrofuran-2-carboxylic acid (35 μL, 0.36 mmol), HATU (145 mg, 0.38 mmol), and DIPEA (300 μL, 1.73 mmol) in THF (10 mL) was stirred at rt for 1 h. The solvent was removed and the residue was purified by pre-HPLC. The product fractions were combined and concentrated to give yellowish oil. This oil was diluted in EtOAc (25 mL), washed with sat. NaHCO$_3$ solution (10 mL), brine, dried (Na$_2$SO$_4$), and concentrated. The product was dissolved in DCM (~5 mL) and mixed with 1.2 eq. of 2 M HCl in Et$_2$O and concentrated. The residue was dissolved in a small amount of DCM and concentrated—repeated this procedure several times, dried to give 129 mg (75%) of yellow solid. Analysis: LCMS m/z=461 (M+1); $^1$H NMR (400 MHz, DMSO-$d_6$) δ: 9.15-9.20 (1H, m), 8.99-9.09 (1H, m), 8.05-8.12 (1H, m), 7.95-8.03 (1H, m), 7.88-7.95 (1H, m), 7.69-7.75 (2H, m), 7.15-7.22 (2H, m), 4.67-4.80 (2H, m), 4.17-4.27 (1H, m), 3.72-3.87 (5H, m), 3.24-3.48 (2H, m), 2.00-2.09 (3H, m), 1.77-1.89 (2H, m), 1.48-1.71 (2H, m), 1.11 (6H, d, J=6.0 Hz).

The following compounds were synthesized using the procedure for Example 180.

Example 181. {4-[4-(8-Ethoxyquinolin-7-yl)-phenoxy]-piperidin-1-yl}-(R)-tetrahydro-furan-2-yl-methanone, HCl

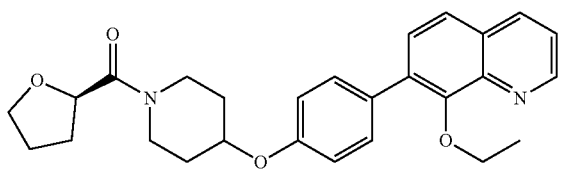 [SMILES: CCOc1c(-c2ccc(OC3CCN(C(=O)[C@H]4CCCO4)CC3)cc2)ccc2cccnc12]

The product was isolated as a brown solid. Analysis: LCMS m/z=447 (M+1); $^1$H NMR (400 MHz, DMSO-$d_6$) δ: 9.11-9.19 (1H, m), 8.91-9.04 (1H, m), 8.03-8.11 (1H, m), 7.85-7.99 (2H, m), 7.67-7.75 (2H, m), 7.13-7.22 (2H, m), 4.65-4.82 (2H, m), 4.03 (1H, q, J=7.1 Hz), 3.92-3.97 (2H, m), 3.82-3.89 (1H, m), 3.73-3.81 (2H, m), 3.18-3.52 (2H, m), 2.00-2.08 (2H, m), 1.84 (2H, d, J=7.3 Hz), 1.48-1.73 (2H, m), 1.12-1.28 (5H, m).

Example 182. (4-{4-[8-(2-Morpholin-4-yl-ethoxy)-quinolin-7-yl]-phenoxy}-piperidin-1-yl)-(R)-tetrahydrofuran-2-yl-methanone, 2HCl

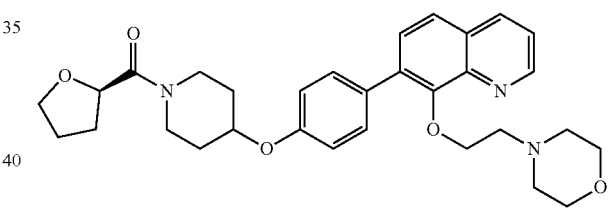

The product was isolated as a yellow solid. Analysis: LCMS m/z=532 (M+1); $^1$H NMR (400 MHz, DMSO-$d_6$) δ: 9.09-9.16 (1H, m), 8.72-8.86 (1H, m), 7.98-8.06 (1H, m), 7.74-7.89 (2H, m), 7.67 (2H, d, J=8.8 Hz), 7.17 (2H, d, J=8.5 Hz), 4.67-4.78 (3H, m), 4.25-4.35 (2H, m), 3.91-3.98 (4H, m), 3.71-3.89 (4H, m), 3.51-3.55 (2H, m), 3.22-3.50 (5H, m), 1.93-2.13 (4H, m), 1.75-1.92 (2H, m), 1.50-1.73 (2H, m).

Example 183. (4-{4-[8-(2-Pyrrolidin-1-yl-ethoxy)-quinolin-7-yl]-phenoxy}-piperidin-1-yl)-(R)-tetrahydrofuran-2-yl-methanone, HCl

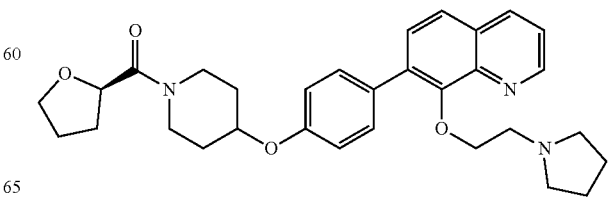

The product was isolated as a yellow solid. Analysis: LCMS m/z=516 (M+1); ¹H NMR (400 MHz, DMSO-d₆) δ: 10.67-10.91 (1H, m), 9.08-9.17 (1H, m), 8.72-8.93 (1H, m), 7.98-8.09 (1H, m), 7.77-7.92 (2H, m), 7.68 (2H, d, J=8.5 Hz), 7.18 (2H, d, J=8.5 Hz), 4.67-4.78 (2H, m), 4.15-4.24 (2H, m), 3.81-3.96 (2H, m), 3.73-3.81 (2H, m), 3.59-3.72 (2H, m), 3.49-3.57 (2H, m), 3.22-3.47 (2H, m), 3.01-3.20 (2H, m), 1.96-2.11 (8H, m), 1.78-1.90 (2H, m), 1.49-1.73 (2H, m).

Example 184. (4-{4-[8-(3-Pyrrolidin-1-yl-propoxy)-quinolin-7-yl]-phenoxy}-piperidin-1-yl)-(R)-tetrahydrofuran-2-yl-methanone, HCl

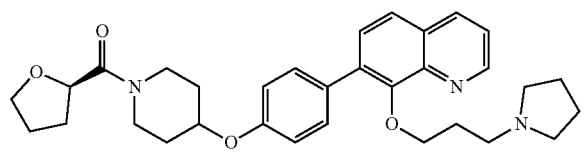 [SMILES: O=C([C@H]1CCCO1)N1CCC(Oc2ccc(-c3ccc4cccnc4c3OCCCN3CCCC3)cc2)CC1]

The product was isolated as a yellow solid. Analysis: LCMS m/z=530 (M+1); ¹H NMR (400 MHz, DMSO-d₆) δ: 9.07-9.14 (1H, m), 8.72-8.83 (1H, m), 7.95-8.02 (1H, m), 7.75-7.86 (2H, m), 7.67 (2H, d, J=8.8 Hz), 7.18 (2H, d, J=8.5 Hz), 4.67-4.77 (2H, m), 3.93-3.98 (2H, m), 3.83-3.90 (1H, m), 3.73-3.80 (2H, m), 3.59-3.67 (2H, m), 3.33-3.50 (1H, m), 3.21-3.27 (2H, m), 2.94-3.06 (2H, m), 1.97-2.10 (8H, m), 1.89-1.96 (2H, m), 1.78-1.89 (2H, m), 1.51-1.71 (2H, m).

Example 185. [4-[4-[8-[2-(4-Methylpiperazin-1-yl)ethoxy]-7-quinolyl]phenoxy]-1-piperidyl]-[(2R)-tetrahydrofuran-2-yl]methanone, HCl

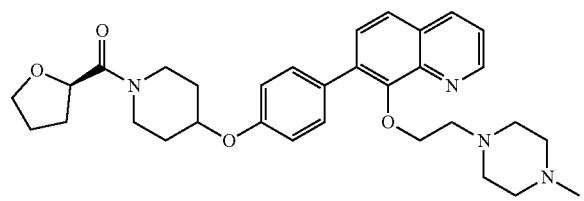 [SMILES: CN1CCN(CCOc2c(-c3ccc(OC4CCN(C(=O)[C@H]5CCCO5)CC4)cc3)ccc3cccnc23)CC1]

The product was isolated as a yellow solid. Analysis: LCMS m/z=545 (M+1); ¹H NMR (400 MHz, DMSO-d₆) δ: 9.09 (1H, d, J=3.5 Hz), 8.58-8.71 (1H, m), 7.92-7.99 (1H, m), 7.70-7.80 (2H, m), 7.67 (2H, d, J=8.5 Hz), 7.16 (2H, d, J=8.5 Hz), 4.67-4.79 (2H, m), 4.32 (2H, br. s.), 3.84-4.01 (3H, m), 3.69-3.82 (4H, m), 3.20-3.66 (9H, m), 2.86 (3H, s), 1.94-2.11 (4H, m), 1.78-1.91 (2H, m), 1.53-1.72 (2H, m).

Example 186. [4-[4-[8-(2-Methoxyethoxy)-7-quinolyl]phenoxy]-1-piperidyl]-[(2R)-tetrahydrofuran-2-yl]methanone, HCl

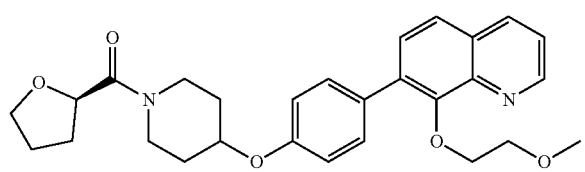 [SMILES: COCCOc1c(-c2ccc(OC3CCN(C(=O)[C@H]4CCCO4)CC3)cc2)ccc2cccnc12]

The product was isolated as a yellow solid. Analysis: LCMS m/z=477 (M+1); ¹H NMR (400 MHz, DMSO-d₆) δ: 9.13-9.18 (1H, m), 8.92-9.00 (1H, m), 8.05 (1H, d, J=8.8 Hz), 7.90-7.97 (1H, m), 7.87 (1H, d, J=8.5 Hz), 7.70 (2H, d, J=8.8 Hz), 7.17 (2H, d, J=8.5 Hz), 4.67-4.80 (2H, m), 4.03-4.09 (2H, m), 3.72-3.89 (5H, m), 3.53-3.58 (2H, m), 3.27-3.40 (1H, m), 3.05 (3H, s), 1.95-2.09 (4H, m), 1.79-1.91 (2H, m), 1.50-1.72 (2H, m).

Example 187. [4-[4-[8-(3-Methoxypropoxy)-7-quinolyl]phenoxy]-1-piperidyl]-[(2R)-tetrahydrofuran-2-yl]methanone, HCl

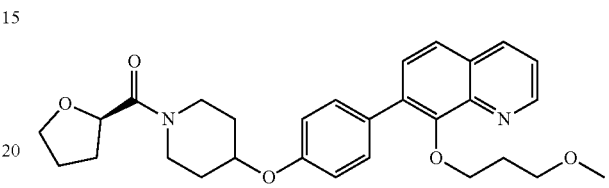

The product was isolated as a yellow solid. Analysis: LCMS m/z=491 (M+1); ¹H NMR (400 MHz, DMSO-d₆) δ: 9.16 (1H, d, J=4.8 Hz), 8.98 (1H, d, J=7.8 Hz), 8.06 (1H, d, J=8.8 Hz), 7.95 (1H, dd, J=8.0, 5.0 Hz), 7.87 (1H, d, J=8.5 Hz), 7.66 (2H, d, J=8.8 Hz), 7.18 (2H, d, J=8.8 Hz), 4.67-4.80 (2H, m), 3.93 (2H, t, J=6.5 Hz), 3.80-3.89 (2H, m), 3.71-3.80 (2H, m), 3.28-3.50 (2H, m), 3.25 (2H, t, J=6.3 Hz), 3.10 (3H, s), 1.94-2.10 (4H, m), 1.79-1.94 (4H, m), 1.51-1.71 (2H, m).

Example 188. 1-{4-[4-(8-Hydroxyquinolin-7-yl)-phenoxy]-piperidin-1-yl}-propan-1-one, HCl

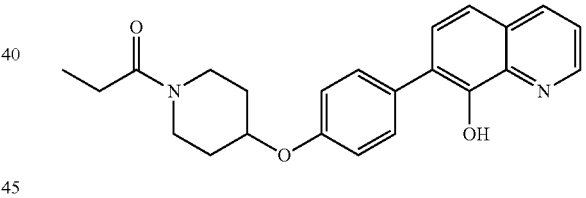

Step 1. 7-Bromo-8-(tert-butyl-dimethyl-silanyloxy)-quinoline

A mixture of 7-bromoquinolin-8-ol (5.00 g, 22.3 mmol), tert-butyldimethylsilyl chloride (3.70 g, 24.5 mmol), DIPEA (9.72 mL, 55.8 mmol), and DCM (100 mL) was stirred at rt for 3 days. The reaction was partition in DCM (100) and H₂O (50 mL), the organic layer was separated then washed with brine, dried (Na₂SO₄), and concentrated. The residue was chromatography on silica gel (DCM) to give 7.37 g of white solid.

Step 2. tert-butyl 4-[4-(8-hydroxy-7-quinolyl)phenoxy]piperidine-1-carboxylate

A flask charged with 4-[4-(4,4,5,5-tetramethyl-1,3,2-dioxaborolan-2-yl)-phenoxy]-piperidine-1-carboxylic acid tert-butyl ester (3.0 g, 7.44 mmol), 7-bromo-8-(tert-butyl-dimethyl-silanyloxy)-quinoline (2.77 g, 8.18 mmol), palladium acetate (170 mg, 0.75 mmol), triphenylphosphine (0.39 g, 1.49 mmol), 1.0 M of sodium carbonate in water (40 mL, 4.88 mmol), 1,4-dioxane (40 mL), and DMF (40 mL) was flashed with N₂ for 25 min. The reaction was stirred at 90° C. for 18 h and cooled to RT. The reaction mixture was portioned between EtOAc (150 mL), washed with saturated NaHCO₃ solution (100 mL), the organic layer was separated and the water layer was extracted with EtOAc (100 mL). The combined organic layers were washed with H₂O, brine, dried (Na₂SO₄), and concentrated. The residue was stirred in DCM (35 mL) at 0° C. and added 1.0 M of tetra-n-butylammonium fluoride in THF (4.88 mL, 4.88 mmol). After 1 h at rt, the reaction was washed with H₂O (20 mL), brine, dried (Na₂SO₄) and concentrated. The residue was chromatography on silica gel (0-70% EtOAc/Hexanes) to give (1.03 g, 33%).

Step 3. 7-[4-(Piperidin-4-yloxy)-phenyl]-quinolin-8-ol, HCl

To a solution of tert-butyl 4-[4-(8-hydroxy-7-quinolyl)phenoxy]piperidine-1-carboxylate (638 mg, 1.52 mmol) in DCM (20 mL) was added 4.0 M of HCl in 1,4-dioxane (1.90 mL, 7.59 mmol). After 22 h, the resulted precipitate was collected by filtration, washed with DCM and dried to give 418 mg (77%) of light-brown solid.

Step 4

A mixture of 7-[4-(piperidin-4-yloxy)-phenyl]-quinolin-8-ol; HCl (110 mg, 0.31 mmol), propanoic acid (27 µL, 0.36 mmol), HATU (117 mg, 0.31 mmol), DIPEA (244 µL, 1.40 mmol), and THF (8 mL) was stirred at rt for 1 h. The reaction mixture was concentrated and the residue was purified by pre-HPLC. The product fractions were combined and neutralized with sat. NaHCO₃ solution (25 mL), extracted with DCM (3×25 mL), dried (Na₂SO₄), and concentrated. The product was dissolved in DCM (~5 mL) and mixed with 1.2 eq. of 2 M HCl in Et₂O and concentrated. The residue was dissolved in a small amount of DCM and concentrated—repeated this procedure several times, dried to give 82 mg (64%) of off-white solid. Analysis: LCMS m/z=377 (M+1); ¹H NMR (400 MHz, DMSO-d₆) δ: 9.76-10.69 (1H, m), 8.98-9.03 (1H, m), 8.70-8.78 (1H, m), 7.77-7.84 (1H, m), 7.65-7.77 (4H, m), 7.10-7.17 (2H, m), 4.68-4.73 (1H, m), 3.84-3.95 (1H, m), 3.67-3.78 (1H, m), 3.21-3.43 (2H, m), 2.35 (2H, q, J=7.4 Hz), 1.89-2.06 (2H, m), 1.49-1.72 (2H, m), 1.00 (3H, t, J=7.4 Hz).

The following compounds were synthesized using the procedure for Example 188.

Example 189. Cyclopropyl-{4-[4-(8-hydroxyquinolin-7-yl)-phenoxy]-piperidin-1-yl}-methanone, HCl

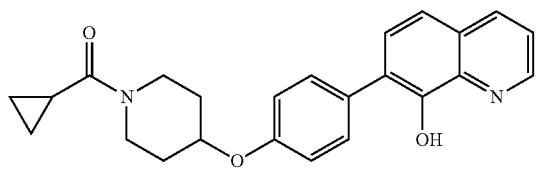 [SMILES: O=C(C1CC1)N1CCC(Oc2ccc(-c3ccc4cccnc4c3O)cc2)CC1]

The product was isolated as an off-white solid. Analysis: LCMS m/z=389 (M+1); ¹H NMR (400 MHz, DMSO-d₆) δ: 9.74-10.73 (1H, m), 9.01-9.06 (1H, m), 8.77-8.84 (1H, m), 7.81-7.88 (1H, m), 7.66-7.79 (4H, m), 7.12-7.18 (2H, m), 4.69-4.78 (1H, m), 3.85-4.07 (2H, m), 3.51-3.64 (1H, m), 3.24-3.37 (1H, m), 1.90-2.11 (3H, m), 1.49-1.74 (2H, m), 0.67-0.79 (4H, m).

Example 190. {4-[4-(8-Hydroxyquinolin-7-yl)-phenoxy]-piperidin-1-yl}-(R)-tetrahydro-furan-2-yl-methanone, HCl

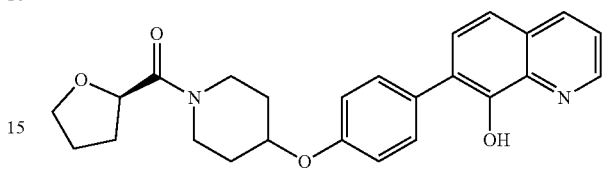

The product was isolated as an orange solid. Analysis: LCMS m/z=419 (M+1); ¹H NMR (400 MHz, DMSO-d₆) δ: 9.63-10.98 (1H, m), 9.01-9.06 (1H, m), 8.78-8.84 (1H, m), 7.81-7.89 (1H, m), 7.65-7.79 (4H, m), 7.11-7.18 (2H, m), 4.69-4.73 (1H, m), 3.71-3.96 (4H, m), 3.22-3.51 (2H, m), 1.90-2.12 (5H, m), 1.76-1.90 (2H, m), 1.49-1.72 (2H, m).

Example 191. 1-[4-(2-Chloro-4-quinolin-3-yl-phenoxy)-piperidin-1-yl]-propan-1-one

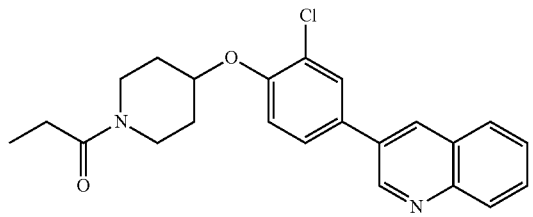 [SMILES: CCC(=O)N1CCC(Oc2ccc(-c3cnc4ccccc4c3)cc2Cl)CC1]

Step 1. 4-(4-Bromo-2-chloro-phenoxy)-piperidine-1-carboxylic acid tert-butyl ester To a 0-5° C. stirred solution of triphenylphosphine (3.1 g, 11.7 mmol) and 40% w/w DEAD in toluene (5.12 mL, 13.0 mmol) in THF (25 mL) was added a mixture of 4-bromo-2-chloro-phenol (1.5 g, 7.2 mmol) and 4-hydroxypiperidine-1-carboxylic acid tert-butyl ester (1.89 g, 9.39 mmol) in THF (5 mL) under argon. The cooling bath was removed and the reaction stirred at rt for 20 h, concentrated, then stirred with ether and filtered. The filtrate was concentrated in vacuo and the product purified by silica gel column chromatography (0-20% EtOAC in hexanes) to give 2.30 g (81%). Analysis: LCMS=291 (M-100-BOC).

Step 2. 4-(2-Chloro-4-quinolin-3-yl-phenoxy)-piperidine-1-carboxylic acid tert-butyl ester A 50 mL R. B. flask charged with 1,4-dioxane (2.5 mL), triphenylphosphine (0.119 g, 0.454 mmol), and palladium acetate (0.026 g, 0.12 mmol) was stirred at rt for 15 min. 4-(4-bromo-2-chloro-phenoxy)-piperidine-1-carboxylic acid tert-butyl ester (0.89 g, 2.3 mmol), 3-quinolineboronic acid (0.59 g, 3.4 mmol), DMF (3.00 mL) and 1M aqueous sodium carbonate (5 mL) were added and flushed with argon five times. The reaction mixture was heated at 80° C. for 7 h and concentrated. The residue was suspended in a mixture of 1M Na$_2$CO$_3$ and EtOAc and then filtered through a pad of celite/silica gel. The filtrate was separated and the aqueous layer was extracted twice with EtOAc. The combined organics was washed with brine, dried, filtered, and evaporated to give a crude product. The product was purified by silica gel chromatography using 0-5% MeOH in DCM to give 0.90 g (90%). Analysis: LCMS m/z 439 (M+H).

Step 3. 3-[3-Chloro-4-(piperidin-4-yloxy)-phenyl]-quinoline

To a stirred solution of 4-(2-chloro-4-quinolin-3-yl-phenoxy)-piperidine-1-carboxylic acid tert-butyl ester (0.90 g, 2.0 mmol) in DCM (15.00 mL) was added 4M HCl in dioxane (2 mL, 23.1 mmol) at rt. The reaction mixture was stirred at rt for 17 h and evaporated. The crude product was treated twice with EtOAc and evaporated, then crystallized from a mixture of DCM, MeOH, and ether to produce 3-[3-chloro-4-(piperidin-4-yloxy)-phenyl]-quinoline, 0.67 g (96%) as a yellow solid. Analysis: mp: 274-276° C. (DCM, ether, and MeOH); $^1$H NMR (DMSO-d$_6$) δ: 9.54 (d, 1H, J=2 Hz), 9.2-9.35 (brs, 2H), 9.19 (s, 1H), 8.30 (d, 1H, J=8 Hz), 8.23 (d, 1H, J=8 Hz), 8.15 (d, 1H, J=2 Hz), 7.93-8.03 (m, 2H), 7.85 (t, 1H, J=7 Hz), 7.50 (d, 1H, J=9 Hz), 4.88-4.99 (m, 1H), 3.05-3.30 (m, 4H), 2.12-2.27 (m, 2H), 1.89-2.03 (m, 2H).

Step 4. 1-[4-(2-Chloro-4-quinolin-3-yl-phenoxy)-piperidin-1-yl]-propan-1-one

To a stirred solution of 3-[3-chloro-4-(piperidin-4-yloxy)-phenyl]-quinoline (0.125 g, 0.369 mmol) 2HCl and DIPEA (0.450 mL, 2.58 mmol) in DCM (3.00 mL) was added propanoyl chloride (0.0641 mL, 0.738 mmol) at rt. The reaction mixture was stirred for 2 h and evaporated. The crude product was purified by Gilson. The product was stirred with 4M HCl in dioxane (1 mL) for 15 min and crystallized from a mixture of DCM, MeOH, and ether and dried at 60° C. for 16 h to give a yellow solid (0.1 g, 68%). Analysis: mp: 183-185° C.; LCMS m/z 395 (M+1); $^1$H NMR (DMSO-d$_6$) δ: 9.46 (d, 1H, J=2 Hz), 9.04 (s, 1H), 8.14-8.23 (m, 2H), 8.10 (d, 1H, J=2 Hz), 7.88-7.98 (m, 2H), 7.79 (t, 1H, J=7 Hz), 7.47 (d, 1H, 9 Hz), 4.84-4.93 (m, 1H), 3.63-3.77 (m, 2H), 3.38-3.53 (m, 2H), 2.37 (q, 2H, J=7 Hz), 1.85-2.04 (m, 2H), 1.57-1.80 (m, 2H), 1.00 (t, 3H, J=7 Hz).

The following examples were synthesized using the method for Example 191.

Example 192. 1-[4-(2-Chloro-4-quinolin-3-yl-phenoxy)-piperidin-1-yl]-2-methyl-propan-1-one

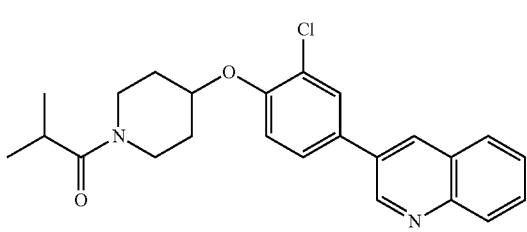 [SMILES: CC(C)C(=O)N1CCC(Oc2ccc(-c3cnc4ccccc4c3)cc2Cl)CC1]

Analysis: LCMS m/z 409 (M+1); $^1$H NMR (DMSO-d$_6$) δ: 9.56 (d, 1H, J=2 Hz), 9.23 (s, 1H), 8.31 (d, 1H, J=8 Hz), 8.25 (d, 1H, J=8 Hz), 8.14 (d, 1H, J=2 Hz), 7.96-8.07 (m, 1H), 7.93-7.96 (m, 1H), 7.86 (t, 1H, J=8 Hz), 7.49 (d, 1H, J=9 Hz), 4.85-4.96 (m, 1H), 3.68-3.80 (m, 2H), 3.40-3.58 (m, 2H), 2.83-2.99 (m, 1H), 1.82-2.05 (m, 2H), 1.52-1.78 (m, 2H), 1.01 (d, 6H, J=7 Hz).

Example 193. [4-(2-Chloro-4-quinolin-3-yl-phenoxy)-piperidin-1-yl]-cyclopropyl-methanone

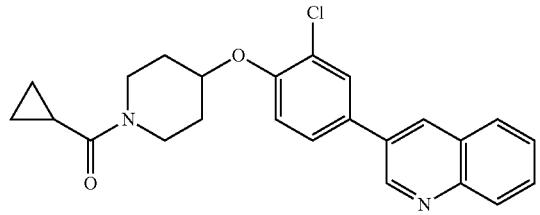 [SMILES: O=C(C1CC1)N1CCC(Oc2ccc(-c3cnc4ccccc4c3)cc2Cl)CC1]

Analysis: LCMS m/z 407 (M+1); $^1$H NMR (DMSO-d$_6$) δ: 9.58 (s, 1H), 9.20 (s, 1H), 8.29 (d, 1H, J=8 Hz), 8.24 (d, 1H, J=8 Hz), 8.15 (s, 1H), 7.90-8.09 (m, 2H), 7.85 (t, 1H, J=8 Hz), 7.50 (d, 1H, J=8 Hz), 4.87-4.96 (m, 1H), 3.34-4.06 (m, 4H), 1.81-2.07 (m, 3H), 1.53-1.81 (m, 2H), 0.65-0.82 (m, 4H).

Example 194. 1-[4-(2-Chloro-4-quinolin-7-yl-phenoxy)-piperidin-1-yl]-propan-1-one

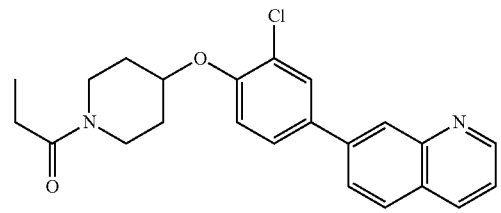 [SMILES: CCC(=O)N1CCC(Oc2ccc(-c3ccc4cccnc4c3)cc2Cl)CC1]

Analysis: LCMS m/z 395 (M+1); $^1$H NMR (DMSO-d$_6$) δ: 9.19 (d, 1H, J=3 Hz), 8.90 (d, 1H, J=8 Hz), 8.44 (s, 1H), 8.31 (d, 1H, J=8 Hz), 8.21 (d, 1H, J=1H), 8.00 (d, 1H, J=2 Hz), 7.79-7.93 (m, 2H), 7.47 (d, 1H, J=9 Hz), 4.82-4.92 (m, 1H), 3.62-3.78 (m, 2H), 3.37-3.51 (m, 2H), 2.36, (q, 2H, J=7 Hz), 1.85-2.41 (m, 2H), 1.55-1.80 (m, 2H), 1.00 (t, 3H, J=7 Hz).

Example 195. 1-[4-(2-Chloro-4-quinolin-7-yl-phenoxy)-piperidin-1-yl]-2-methyl-propan-1-one

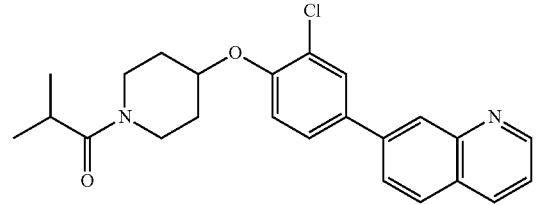 [SMILES: CC(C)C(=O)N1CCC(Oc2ccc(-c3ccc4cccnc4c3)cc2Cl)CC1]

Analysis: LCMS m/z 409 (M+1); $^1$H NMR (DMSO-d$_6$) δ: 9.15-9.24 (m, 1H), 8.85-8.97 (m, 1H), 8.40-8.49 (m, 1H), 8.27-8.37 (m, 1H), 8.16-8.25 (m, 1H), 7.99 (d, 1H, J=2 Hz), 7.70-7.83 (m, 2H), 7.47 (d, 1H, J=8 Hz), 4.83-4.92 (m, 1H), 3.34-3.83 (m, 4H), 2.87-2.98 (m, 1H), 1.83-2.08 (m, 2H), 1.56-1.80 (m, 2H), 1.01 (d, 6H, J=7 Hz).

Example 196. 1-[4-(2-Methoxy-4-quinolin-3-yl-phenoxy)-piperidin-1-yl]-propan-1-one

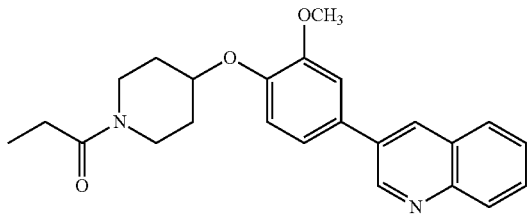 [SMILES: CCC(=O)N1CCC(Oc2ccc(-c3cnc4ccccc4c3)cc2OC)CC1]

Analysis: LCMS m/z=391 (M+1); $^1$H NMR (DMSO-d$_6$) δ: 9.51 (d, 1H, J=2 Hz), 9.11 (s, 1H), 7.95 (t, 1H, J=8 Hz), 7.82 (t, 1H, J=8 Hz), 7.57 (d, 1H, J=2 Hz), 7.50 (d, 1H, J=8 Hz), 7.26 (d, 1H, J=8 Hz), 4.60-4.69 (m, 1H), 3.81-4.00 (m, 4H), 3.63-3.79 (m, 1H), 3.21-3.42 (m, 2H), 2.34 (q, 2H, J=7 Hz), 1.82 (m, 2H, 1.45-1.69 (m, 2H) 1.00 (t, 3H, J=7 Hz).

Example 197. 1-[4-(2-Methoxy-4-quinolin-3-yl-phenoxy)-piperidin-1-yl]-2-methyl-propan-1-one

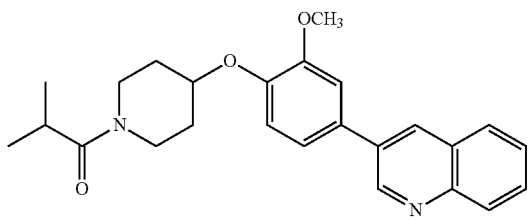 [SMILES: COc1cc(-c2cnc3ccccc3c2)ccc1OC1CCN(C(=O)C(C)C)CC1]

Analysis: LCMS m/z=405 (M+1); $^1$H NMR (DMSO-d$_6$) δ: 9.46 (d, 1H, J=2 Hz), 9.01 (s, 1H), 8.18 (d, 1H, J=8 Hz), 7.91 (t, 1H, J=7 Hz), 7.79 (t, 1H, J=7 Hz), 7.56 (d, 1H, J=2 Hz), 7.47 (d, 1H, J=8 Hz), 7.26 (d, 1H, J=8 Hz), 4.61-4.68 (m, 1H), 3.75-3.97 (m, 5H), 3.20-3.48 (m, 2H), 2.84-2.96 (m, 1H), 1.82-2.05 (m, 2H), 1.45-1.68 (m, 2H), 1.01 (d, 6H, J=7 Hz).

Example 198. Cyclopropyl-[4-(2-methoxy-4-quinolin-3-yl-phenoxy)-piperidin-1-yl]-methanone

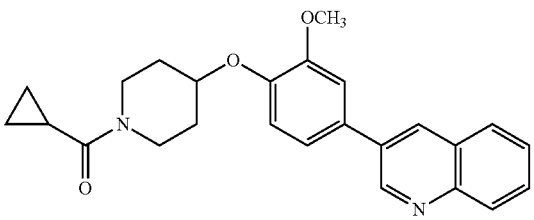 [SMILES: COc1cc(-c2cnc3ccccc3c2)ccc1OC1CCN(C(=O)C2CC2)CC1]

Analysis: LCMS m/z=403 (M+1); $^1$H NMR (DMSO-d$_6$) δ: 9.55 (d, 1H, J=2 Hz), 9.15 (s, 1H), 8.20-8.32 (m, 2H), 7.98 (t, 1H, J=8 Hz), 7.85 (t, 1H, J=8 Hz), 7.60 (d, 1H, J=2 Hz), 7.52 (d, 1H, J=8 Hz), 7.29 (d, 1H, J=8 Hz), 4.64-4.75 (m, 1H), 3.80-4.10 (m, 5H), 3.48-3.63 (m, 1H), 3.21-3.39 (m, 1H), 1.84-2.15 (m, 3H), 1.43-1.78 (m, 2H), 0.67-0.82 (4H).

Example 199. 1-[4-(2-Methoxy-4-quinolin-7-yl-phenoxy)-piperidin-1-yl]-propan-1-one

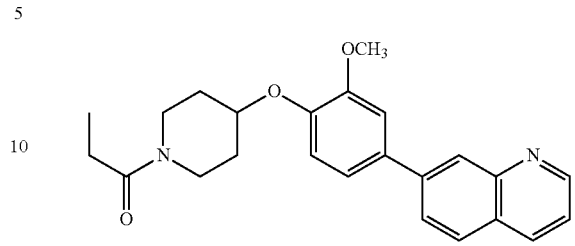

Analysis: LCMS m/z=391 (M+1); $^1$H NMR (DMSO-d$_6$) δ: 9.15 (d, 1H, J=5 Hz), 8.90 (d, 1H, J=8 Hz), 8.43 (s, 1H), 8.29 (d, 1H, J=9 Hz), 8.22 (d, 1H, J=9 Hz), 7.82-7.91 (m, 1H), 7.47 (d, 1H, J=2 Hz), 7.42 (d, 1H, J=8 Hz), 7.25 (d, 1H, J=8 Hz), 4.60-4.70 (m, 1H), 3.84-3.95 (m, 5H), 3.64-3.84 (m, 2H), 3.20-3.30 (m, 2H), 2.35 (q, 2H, J=7 Hz), 1.83-2.04 (m, 2H), 1.45-1.71 (m, 2H), 1.00 (t, 3H, J=7 Hz).

Example 200. 1-[4-(3-Fluoro-4-quinolin-3-yl-phenoxy)-piperidin-1-yl]-propan-1-one

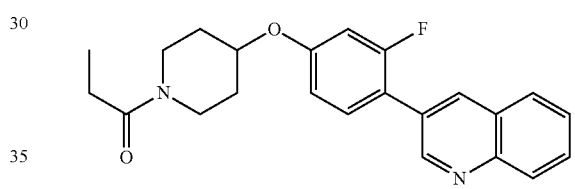

Analysis: LCMS m/z 379 (M+1); $^1$H NMR (DMSO-d$_6$) δ: 9.24 (s, 1H), 8.85 (s, 1H), 8.20 (d, 1H, J=9 Hz), 7.94 (t, 1H, J=7 Hz), 7.79 (t, 1H, J=7 Hz), 7.71 (t, 1H, J=9 Hz), 7.16 (dd, 1H, J=2 Hz, J=13 Hz), 7.06 (dd, 1H, J=2 Hz, J=9 Hz), 4.73-4.82 (m, 1H), 3.84-3.97 (m, 2H), 3.65-3.79 (m, 2H), 3.18-3.42 (m, 2H), 2.35 (q, 2H, J=7 Hz), 1.89-2.07 (m, 2H), 1.46-1.70 (m, 2H), 1.00 (t, 3H, 7 Hz).

Example 201. 1-[4-(3-Fluoro-4-quinolin-3-yl-phenoxy)-piperidin-1-yl]-2-methylpropan-1-one

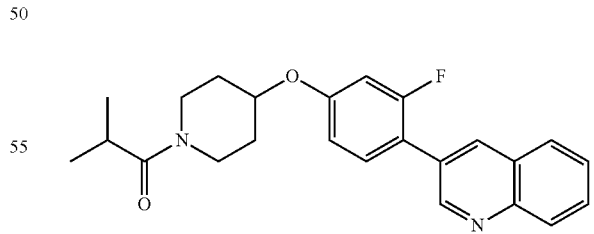

Analysis: LCMS m/z=393 (M+1). $^1$H NMR (DMSO-d$_6$) δ: 9.23 (s, 1H), 8.81 (s, 1H), 8.18 (d, 2H, J=8 Hz), 7.94 (t, 1H, J=7 Hz), 7.78 (t, 1H, J=8 Hz), 7.73 (t, 1H, J=9 Hz), 7.16 (dd, 1H, J=2 Hz, J=9 Hz), 7.06 (dd, 1H, J=2 Hz, J=8 Hz), 4.74-4.83 (m, 1H), 3.86-3.97 (m, 1H), 3.74-3.85 (m, 1H), 3.35-3.47 (m, 1H), 3.19-3.31 (m, 1H), 2.84-2.97 (m, 1H), 1.89-2.09 (m, 2H), 1.47-1.70 (m, 2H), 1.01 (d, 6H, J=7 Hz).

Example 202. Cyclopropyl-[4-(3-fluoro-4-quinolin-3-yl-phenoxy)-piperidin-1-yl]-methanone

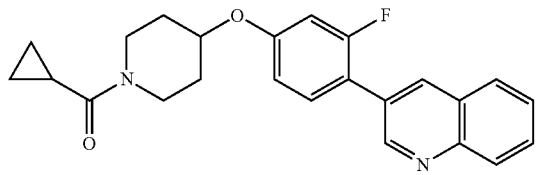

Analysis: LCMs m/z=391 (M+1); $^1$H NMR (DMSO-d$_6$) δ: 9.23 (s, 1H), 8.81 (s, 1H), 8.13-8.23 (m, 2H), 7.93 (t, 1H, J=8 Hz), 7.67-7.82 (m, 2H), 7.17 (dd, 1H, J=2 Hz), J=13 Hz), 7.07 (dd, 1H, J=2 Hz), J=9 Hz), 4.73-4.87 (m, 1H), 3.82-4.10 (m, 2H), 3.47-3.65 (m, 1H), 3.19-3.36 (m, 1H), 1.87-2.14 (m, 3H), 1.45-1.75 (m, 2H), 0.64-0.79 (m, 4H).

Example 203. 1-[4-(3-Chloro-4-quinolin-3-yl-phenoxy)-piperidin-1-yl]-propan-1-one

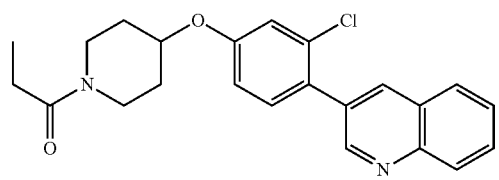 [SMILES: CCC(=O)N1CCC(Oc2ccc(-c3cnc4ccccc4c3)c(F)c2)CC1]

Analysis: LCMS m/z=395 (M+1); $^1$H NMR (DMSO-d$_6$) δ: 9.16 (s, 1H), 8.75 (s, 1H), 8.15-8.25 (m, 2H), 7.96 (t, 1H, J=7 Hz), 7.79 (t, 1H, J=7 Hz), 7.58 (d, 1H, J=8 Hz), 7.34 (d, 1H, J=2 Hz), 7.19 (dd, 1H, J=2 Hz, J=9 Hz), 4.74-4.84 (m, 1H), 3.83-3.96 (m, 2H), 3.21-3.42 (m, 2H), 2.35 (q, 2H, J=7 Hz), 1.88-2.07 (m, 2H), 1.46-1.70 (m, 2H, 1.00 (t, 3H, J=7 Hz).

Example 204. 1-[4-(3-Chloro-4-quinolin-3-yl-phenoxy)-piperidin-1-yl]-2-methyl-propan-1-one

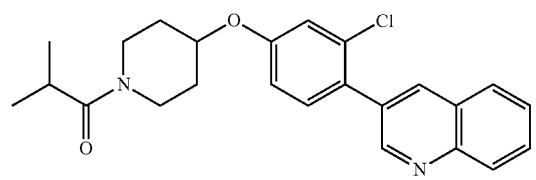 [SMILES: CC(C)C(=O)N1CCC(Oc2ccc(-c3cnc4ccccc4c3)c(Cl)c2)CC1]

Analysis: LCMS m/z=409 (M+1); $^1$H NMR (DMSO-d$_6$) δ: 9.16 (d, 1H, J=2 Hz), 8.76 (s, 1H), 8.20 (t, 1H, J=8 Hz), 7.96 (t, 1H, J=8 Hz), 7.80 (t, 1H, J=8 Hz), 7.59 (d, 1H, J=8 Hz), 7.35 (d, 1H, J=2 Hz), 7.19 (dd, 1H, J=2 Hz, J=9 Hz), 4.75-4.85 (m, 1H), 3.74-3.97 (m, 2H), 3.35-3.48 (m, 1H), 3.20-3.33 (m, 1H), 2.84-2.97 (m, 1H), 1.88-2.09 (m, 2H), 1.46-1.70 (m, 2H), 1.00 (d, 6H, J=7 Hz).

Example 205. [4-(3-Chloro-4-quinolin-3-yl-phenoxy)-piperidin-1-yl]-cyclopropyl-methanone

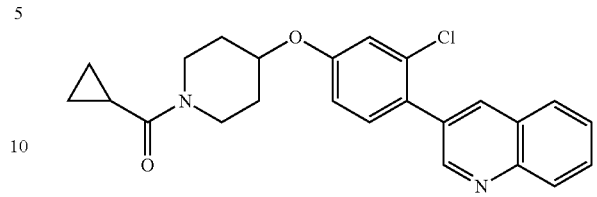

Analysis: LCMS m/z 407 (M+1); $^1$H NMR (DMSO-d$_6$) δ: 9.12 (s, 1H), 8.70 (s, 1H), 8.17 (t, 2H, J=7 Hz), 7.93 (t, 1H, J=7 Hz), 7.77 (t, 1H, J=7 Hz), 7.58 (d, 1H, J=8 Hz), 7.34 (s, 1H), 7.19 (d, 1H, J=7 Hz), 4.75-4.88 (m, 1H), some peaks merged with Water peak, 3.19-3.37 (m, 1H), 1.87-2.13 (m, 3H), 1.44-1.75 (m, 2H), 0.63-0.80 (m, 4H).

Example 206. 2-Methyl-1-[4-(3-methyl-4-quinolin-3-yl-phenoxy)-piperidin-1-yl]-propan-1-one

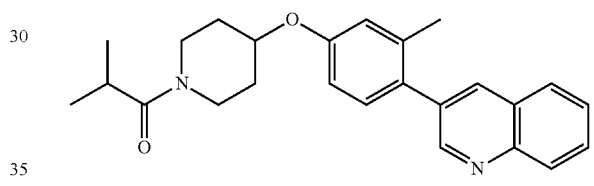

Analysis: LCMS m/z=389 (M+1); $^1$H NMR (DMSO-d$_6$) δ: 9.17 (d, 1H, J=2 Hz), 8.80 (s, 1H), 8.17-8.30 (m, 2H), 7.99 (t, 1H, J=8 Hz), 7.83 (t, 1H, J=7 Hz), 7.37 (d, 1H, J=8 Hz), 6.97-7.09 (m, 2H), 4.67-4.78 (m, 1H), 3.72-3.96 (m, 2H), 3.21-3.48 (m, 2H), 2.83-2.98 (m, 1H), 2.32 (s, 3H), 1.87-2.08 (m, 2H), 1.44-1.71 (m, 2H), 1.01 (d, 6H, J=7 Hz).

Example 207. 1-[4-(3-Methyl-4-quinolin-3-yl-phenoxy)-piperidin-1-yl]-propan-1-one

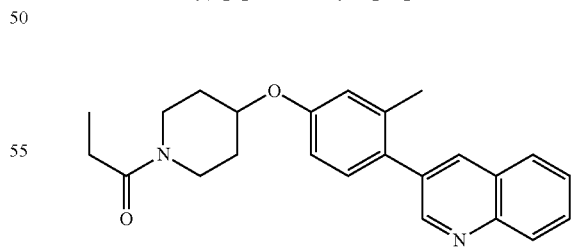

Analysis: LCMS m/z=375 (M+1); $^1$H NMR (DMSO-d$_6$) δ: 9.14 (d, 1H, J=2 Hz), 8.74 (s, 1H), 8.20 (t, 2H, J=8 Hz), 7.96 (t, 1H, J=7 Hz), 7.81 (t, 1H, J=7 Hz), 7.36 (d, 1H, J=9 Hz), 6.96-7.08 (m, 2H), 4.65-4.75 (m, 1H), 3.82-3.94 (m, 2H), 3.65-3.77 (m, 2H), 3.21-3.42 (m, 2H), 2.35 (q, 2H, J=7 Hz), 2.31 (s, 3H), 1.87-2.05 (m, 2H), 1.46-1.70 (m, 2H), 1.00 (t, 3H, J=7 Hz).

Example 208. 4-(3-Methyl-4-quinolin-3-yl-phenoxy)-piperidine-1-carboxylic acid methyl ester

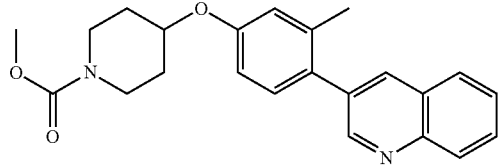 [SMILES: COC(=O)N1CCC(Oc2ccc(-c3cnc4ccccc4c3)c(C)c2)CC1]

Analysis: LCMS m/z=377 (M+1); $^1$H NMR (DMSO-d$_6$) δ: 9.15 (d, 1H, J=2H), 8.79 (s, 1H), 8.22 (t, 2H, J=8 Hz), 7.98 (t, 1H, J=8 Hz), 7.83 (t, 2H, J=8 Hz), 7.36 (d, 1H, J=8 Hz), 6.96-7.07 (m, 2H), 4.62-4.73 (m, 1H), 3.65-3.79 (m, 2H), 3.22-3.36 (m, 2H), 2.31 (s, 3H), 1.90-2.10 (m, 2H), 1.52-1.66 (m, 2H).

Example 209. 1-[4-(3-Methoxy-4-quinolin-3-yl-phenoxy)-piperidin-1-yl]-propan-1-one

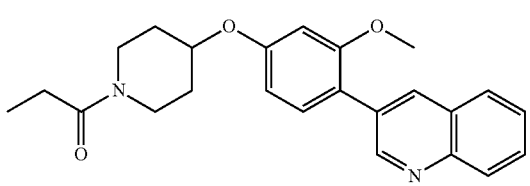 [SMILES: CCC(=O)N1CCC(Oc2ccc(-c3cnc4ccccc4c3)c(OC)c2)CC1]

Analysis: LCMS m/z=391 (M+1); $^1$H NMR (DMSO-d$_6$) δ: 9.22 (d, 1H, J=2 Hz), 8.79 (s, 1H), 8.18 (d, 2H, J=8 Hz), 7.93 (t, 1H, J=8 Hz), 7.78 (t, 1H, J=8 Hz), 7.50 (d, 1H, J=8 Hz), 6.75-6.85 (m, 2H), 4.70-4.82 (m, 1H), 3.80-3.96 (m, 2H), 3.84 (s, 3H), 3.22-3.44 (m, 2H), 2.35 (d, 2H, J=8 Hz), 1.87-2.08 (m, 2H), 1.46-1.73 (m, 2H), 1.00 (t, 3H, J=7 Hz).

Example 210. 1-[4-(3-Methoxy-4-quinolin-3-yl-phenoxy)-piperidin-1-yl]-2-methyl-propan-1-one

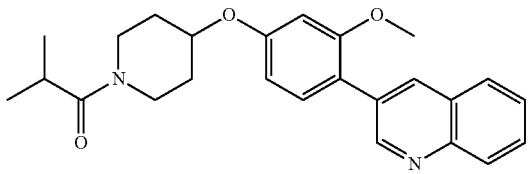 [SMILES: COc1cc(OC2CCN(C(=O)C(C)C)CC2)ccc1-c1cnc2ccccc2c1]

Analysis: LCMS m/z=405 (M+1); $^1$H NMR (DMSO-d$_6$) δ: 9.23 (d, 1H, J=2 Hz), 8.81 (s, 1H), 8.13-8.23 (m, 2H), 7.93 (t, 1H, J=8 Hz), 7.78 (t, 1H, J=8 Hz), 7.50 (d, 1H, J=8 Hz), 6.77-6.85 (m 2H), 4.73-4.84 (m, 1H), 3.73-3.95 (m, 2H), 3.84 (s, 3H), 3.23-3.49 (m, 2H), 2.85-2.97 (m, 1H), 1.88-2.09 (m, 2H), 1.46-1.71 (m, 2H), 1.01 (d, 6H, J=6 Hz).

Example 211. Cyclopropyl-[4-(3-methoxy-4-quinolin-3-yl-phenoxy)-piperidin-1-yl]-methanone

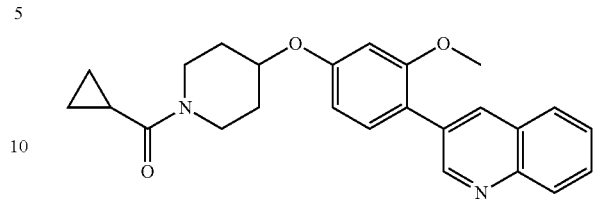

Analysis: LCMS m/z=403 (M+1); $^1$H NMR (DMSO-d$_6$) δ: 9.19 (d, 1H, J=2 Hz), 8.73 (s, 1H), 8.15 (d, 2H, J=8 Hz), 7.90 (t, 1H, J=8 Hz), 7.76 (t, 1H, J=8 Hz), 7.49 (d, 1H, J=8 Hz), 6.77-6.86 (m, 2H), 4.73-4.84 (m, 1H), 3.80-4.07 (m, 2H), 3.84 (s, 3H), 3.49-3.66 (m, 1H), 3.23-3.39 (m, 1H), 1.87-2.13 (m, 3H), 1.46-1.76 (m, 2H), 0.63-0.79 (m, 4H).

Example 212. 1-[4-(2-Methyl-4-quinolin-3-yl-phenoxy)-piperidin-1-yl]-propan-1-one

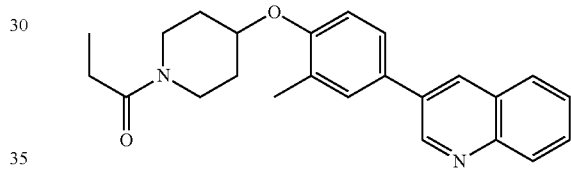

Analysis: LCMS m/z=375 (M+1); $^1$H NMR (DMDSO-d$_6$) δ: 9.47 (s, 1H, J=2 Hz), 9.06 (s, 1H), 8.22 (d, 2H, J=8 Hz), 7.94 (t, 1H, J=7 Hz), 7.86-7.73 (m, 3H), 7.24 (d, 1H, J=8 Hz), 4.83-4.73 (m, 1H), 3.80-3.59 (m, 2H), 3.50-3.37 (m, 2H), 2.36 (q, 2H, J=7 Hz), 2.29 (s, 3H), 2.04-1.84 (m, 2H), 1.76-1.54 (m, 2H), 1.01 (t, 3H, J=7 Hz).

Example 213. 2-Methyl-1-[4-(2-methyl-4-quinolin-3-yl-phenoxy)-piperidin-1-yl]-propan-1-one

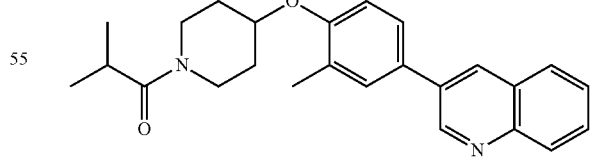

Analysis: LCMS m/z=389 (M+1); $^1$H NMR (DMSO-d$_6$) δ: 9.37 (d, 1H, J=2 Hz), 8.86 (s, 1H), 8.13 (t, 2H, J=7 Hz), 7.86 (t, 1H, 7 Hz), 7.68-7.81 (m, 3H), 7.22 (d, 1H, J=8 Hz), 4.72-4.83 (m, 1H), 2.84-2.97 (m, 1H), 2.29 (s, 3H), 1.84-2.06 (m, 2H), 1.51-1.77 (m, 2H), 1.01 (d, 6H, J=7 Hz).

Example 214. Cyclopropyl-[4-(2-methyl-4-quinolin-3-yl-phenoxy)-piperidin-1-yl]-methanone

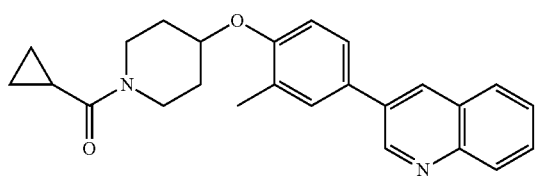 [SMILES: Cc1cc(-c2cnc3ccccc3c2)ccc1OC1CCN(C(=O)C2CC2)CC1]

Analysis: LCMS m/z=386 (M+1); $^1$H NMR (DMSO-d$_6$) δ: 9.43 (d, 1H, J=2 Hz), 8.98 (s, 1H), 8.18 (d, 2H, J=9 Hz), 7.91 (t, 1H, J=7 Hz), 7.71-7.84 (m, 3H), 7.23 (d, 1H, J=8 Hz), 4.74-4.85 (m, 1H), some peaks merged with H$_2$O, 2.29 (s, 3H), 1.82-2.10 (m, 3H), 1.52-1.81 (m, 2H).

Example 215. 1-[4-(2,5-Difluoro-4-quinolin-3-yl-phenoxy)-piperidin-1-yl]-propan-1-one

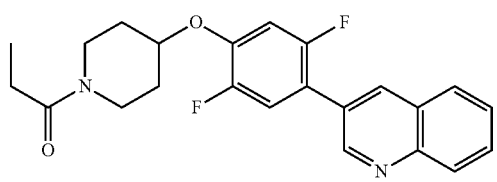 [SMILES: CCC(=O)N1CCC(Oc2cc(F)c(-c3cnc4ccccc4c3)cc2F)CC1]

Analysis: LCMS m/z=397 (M+1); $^1$H NMR (DMSO-d$_6$) δ: 9.17 (s, 1H), 8.72 (s, 1H), 8.12 (d, 2H, J=9 Hz), 7.84-7.91 (m, 1H), 7.69-7.81 (m, 2H), 7.47-7.56 (m, 1H), 4.75-4.85 (m, 1H), 3.66-3.77 (m, 2H), 3.20-3.41 (m, 2H), 2.35 (q, 2H, J=7 Hz), 1.90-2.09 (m, 2H), 1.49-1.74 (m, 2H), 1.00 (t, 3H, J=7 Hz).

Example 216. 1-[4-(2,5-Difluoro-4-quinolin-3-yl-phenoxy)-piperidin-1-yl]-2-methyl-propan-1-one

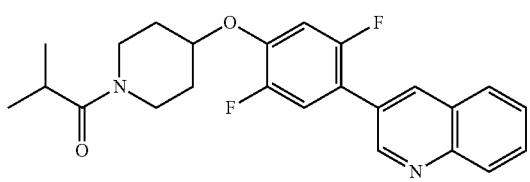 [SMILES: CC(C)C(=O)N1CCC(Oc2cc(F)c(-c3cnc4ccccc4c3)cc2F)CC1]

Analysis: LCMS m/z=411 (M+1); $^1$H NMR (DMSO-d$_6$) δ: 9.20 (d, 1H, J=2 Hz), 8.77 (s, 1H), 8.14 (d, 2H, J=9 Hz), 7.90 (t, 1H, J=7 Hz), 7.72-7.82 (m, 2H), 7.48-7.57 (m, 1H), 4.76-4.86 (m, 1H), 3.77-4.00 (m, 2H), 3.41 (t, 1H, J=10 Hz), 3.25 (t, 1H, J=9 Hz), 2.83-2.98 (m, 1H), 1.91-2.12 (m, 2H), 1.49-1.74 (m, 2H), 1.01 (d, 6H, J=7 Hz).

Example 217. Cyclopropyl-[4-(2,5-difluoro-4-quinolin-3-yl-phenoxy)-piperidin-1-yl]-methanone

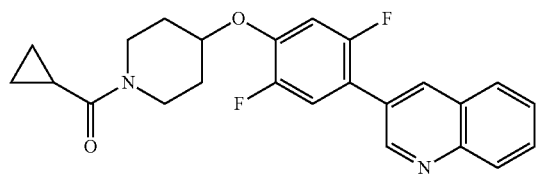 [SMILES: O=C(C1CC1)N1CCC(Oc2cc(F)c(-c3cnc4ccccc4c3)cc2F)CC1]

Analysis: LCMS m/z=409 (M+1); $^1$H NMR (DMSO-d$_6$) δ: 9.15 (t, 1H, 2H), 8.69 (s, 1H), 8.10 (d, 2H, J=9 Hz), 7.86 (t, 1H, J=7 Hz), 7.68-7.80 (m, 2H), 7.47-7.57 (m, 1H), 4.77-4.87 (m, 1H), 3.84-4.09 (m, 2H), 3.20-3.36 (m, 1H), 1.90-2.15 (m, 3H), 1.49-1.77 (m, 2H), 0.65-0.79 (m, 4H).

Example 218. 3-Oxo-3-[4-(4-quinolin-3-yl-phenoxy)-piperidin-1-yl]-propionitrile

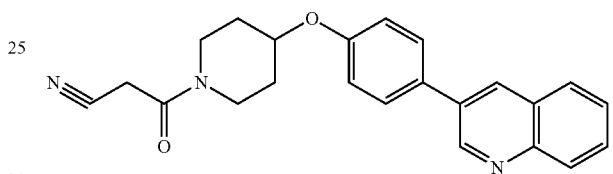

To a 25 mL R. B. flask was charged with cyanoacetic acid (0.04 g, 0.47 mmol), 3-[4-(piperidin-4-yloxy)-phenyl]-quinoline (0.11 g, 0.36 mmol), acetonitrile (2 mL), DIPEA (0.504 mL, 2.89 mmol), and HATU (0.302 g, 0.795 mmol). The reaction mixture was stirred at rt and monitored by HPLC and LCMS methods. After completion, the reaction mixture was evaporated in vacuo. to obtain a crude product. The crude product was purified by Gilson and then lyophilized to produce 3-Oxo-3-[4-(4-quinolin-3-yl-phenoxy)-piperidin-1-yl]-propionitrile, 0.102 g (60%). Analysis: LCMS m/z=372 (M+1); $^1$H NMR (DMSO-d$_6$) δ: 9.34 (d, 1H, J=2 Hz), 8.80 (s, 1H), 8.10 (t, 2H, J=9 Hz), 7.80-7.92 (m, 3H), 7.71 (t, 1H, J=8 Hz), 7.19 (d, 2H, J=8 Hz), 4.70-4.80 (m, 1H), 4.08 (s, 2H), 3.78-3.89 (m, 1H), 3.54-3.65 (m, 1H), 3.27-3.40 (m, 2H), 1.90-2.08 (m, 2H), 1.65-1.77 (m, 1H), 1.53-1.65 (m, 1H).

Example 219. 1-{4-[2-Fluoro-4-(8-methoxy-quinolin-7-yl)-phenoxy]-piperidin-1-yl}-propan-1-one

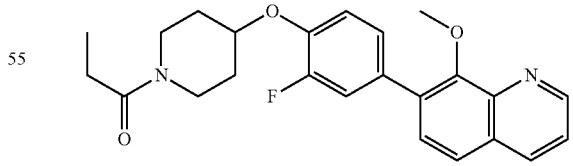

Analysis: LCMS m/z=409 (M+1); $^1$H NMR (DMSO-d$_6$) δ: 9.04-9.11 (m, 1H) 8.72 (d, J=8.28 Hz, 1H) 7.95 (d, J=8.53 Hz, 1H) 7.75-7.83 (m, 2H) 7.60 (dd, J=12.55, 2.01 Hz, 1H) 7.38-7.53 (m, 2H) 4.74 (dt, J=7.84, 3.98 Hz, 1H) 3.86-3.97 (m, 1H) 3.85 (s, 3H) 3.66-3.78 (m, 1H) 3.22-3.42 (m, 2H) 2.36 (q, J=7.45 Hz, 2H) 1.91-2.09 (m, 2H) 1.51-1.75 (m, 2H) 1.01 (t, J=7.40 Hz, 3H).

Example 220. Cyclopropyl-{4-[2-fluoro-4-(8-methoxyquinolin-7-yl)-phenoxy]-piperidin-1-yl}-methanone

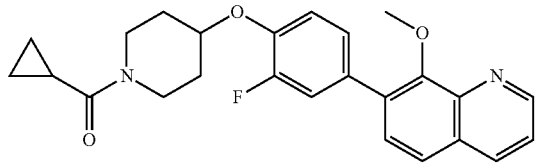 [SMILES: COc1c(-c2ccc(OC3CCN(C(=O)C4CC4)CC3)c(F)c2)ccc2cccnc12]

Analysis: LCMS m/z=421 (M+1); $^1$H NMR (DMSO-d$_6$) δ: 9.05 (dd, J=4.52, 1.51 Hz, 1H) 8.67 (d, J=8.03 Hz, 1H) 7.92 (d, J=8.53 Hz, 1H) 7.71-7.80 (m, 2H) 7.59 (dd, J=12.80, 2.01 Hz, 1H) 7.38-7.52 (m, 2H) 4.76 (dt, J=7.72, 4.05 Hz, 1H) 3.81-4.09 (m, 5H) 3.57 (br. s., 1H) 3.30 (br. s., 1H) 1.90-2.14 (m, 3H) 1.49-1.79 (m, 2H) 0.63-0.82 (m, 4H).

Example 221. {4-[2-Fluoro-4-(8-methoxyquinolin-7-yl)-phenoxy]-piperidin-1-yl}-(R)-tetrahydrofuran-2-yl-methanone

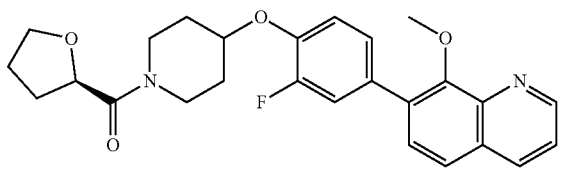 [SMILES: COc1c(-c2ccc(OC3CCN(C(=O)[C@H]4CCCO4)CC3)c(F)c2)ccc2cccnc12]

A 50 mL R.B flask charged with 7-[3-fluoro-4-(piperidin-4-yloxy)-phenyl]-8-methoxyquinoline (0.237 g, 0.673 mmol), (R)-tetrahydrofuran-2-carboxylic acid (0.091 g, 0.79 mmol), HATU (0.30 g, 0.79 mmol), Et$_3$N (0.55 mL, 3.9 mmol) and DCM (3 mL) was stirred at rt 1.5 h. The reaction mixture was concentrated, and partitioned between EtOAc and saturated aqueous NaHCO$_3$. The aqueous layer was extracted twice with EtOAc and the combined organics was washed with brine, dried, filtered, and concentrated to give a crude product that was purified by Gilson to produce {4-[2-fluoro-4-(8-methoxyquinolin-7-yl)-phenoxy]piperidin-1-yl}-(R)-tetrahydrofuran-2-yl-methanone, 85 mg (28%). Analysis: LCMS m/z=451 (M+1); $^1$H NMR (400 MHz, DMSO-d$_6$) δ: 9.06 (dd, J=4.52, 1.51 Hz, 1H) 8.68 (d, J=8.03 Hz, 1H) 7.93 (d, J=8.53 Hz, 1H) 7.72-7.80 (m, 2H) 7.59 (dd, J=12.55, 2.01 Hz, 1H) 7.38-7.52 (m, 2H) 5.76 (s, 2H) 4.65-4.81 (m, 4H) 3.70-3.96 (m, 8H) 3.20-3.52 (m, 2H) 1.92-2.13 (m, 4H) 1.77-1.91 (m, 2H) 1.51-1.75 (m, 2H).

Example 222. {4-[4-(8-Chloroquinolin-7-yl)-2-fluorophenoxy]-piperidin-1-yl}-cyclopropyl-methanone

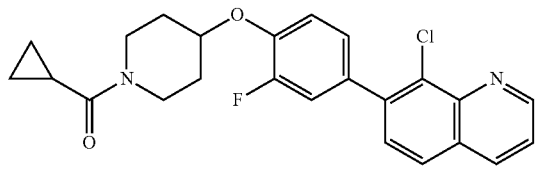 [SMILES: O=C(C1CC1)N1CCC(Oc2ccc(-c3ccc4cccnc4c3Cl)cc2F)CC1]

Analysis: LCMS m/z=425 (M+1); $^1$H NMR (400 MHz, DMSO-d$_6$) δ: 9.08 (dd, J=4.14, 1.63 Hz, 1H) 8.51 (dd, J=8.28, 1.76 Hz, 1H) 8.05 (d, J=8.53 Hz, 1H) 7.63-7.73 (m, 2H) 7.49 (dd, J=12.30, 2.26 Hz, 1H) 7.39-7.46 (m, 1H) 7.31-7.38 (m, 1H) 4.76 (tt, J=7.81, 3.73 Hz, 1H) 3.83-4.10 (m, 2H) 3.57 (br. s., 1H) 3.29 (br. s., 1H) 1.90-2.15 (m, 3H) 1.50-1.80 (m, 2H) 0.65-0.81 (m, 4H).

Example 223. {4-[4-(8-Chloroquinolin-7-yl)-2-fluorophenoxy]-piperidin-1-yl}-(R)-tetrahydrofuran-2-yl-methanone

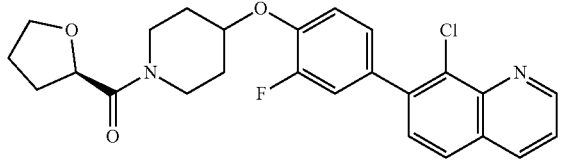 [SMILES: O=C([C@H]1CCCO1)N1CCC(Oc2ccc(-c3ccc4cccnc4c3Cl)cc2F)CC1]

Analysis: LCMS m/z=455 (M+1); $^1$H NMR (400 MHz, DMSO-d$_6$) δ: 9.07 (dd, J=4.27, 1.76 Hz, 1H) 8.51 (dd, J=8.28, 1.76 Hz, 1H) 8.05 (d, J=8.53 Hz, 1H) 7.62-7.73 (m, 2H) 7.49 (dd, J=12.17, 2.13 Hz, 1H) 7.38-7.45 (m, 1H) 7.31-7.37 (m, 1H) 4.66-4.81 (m, 2H) 3.69-3.97 (m, 4H) 3.20-3.52 (m, 2H) 1.92-2.14 (m, 4H) 1.77-1.91 (m, 2H) 1.50-1.77 (m, 2H).

Example 224. 1-{4-[4-(8-Chloroquinolin-7-yl)-2-fluorophenoxy]-piperidin-1-yl}-propan-1-one

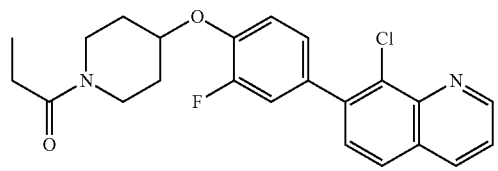 [SMILES: CCC(=O)N1CCC(Oc2ccc(-c3ccc4cccnc4c3Cl)cc2F)CC1]

Analysis: LCMS m/z=413 (M+1); $^1$H NMR (400 MHz, DMSO-d$_6$) δ: 9.03-9.11 (m, 1H) 8.51 (dd, J=8.28, 1.76 Hz, 1H) 8.05 (d, J=8.53 Hz, 1H) 7.62-7.72 (m, 2H) 7.48 (dd, J=12.17, 2.13 Hz, 1H) 7.41 (d, J=8.78 Hz, 1H) 7.35 (d, J=1.25 Hz, 1H) 4.74 (dt, J=7.91, 4.08 Hz, 2H) 3.84-3.97 (m, 1H) 3.66-3.79 (m, 1H) 3.21-3.43 (m, 2H) 2.36 (q, J=7.53 Hz, 2H) 1.98 (d, J=18.57 Hz, 2H) 1.51-1.75 (m, 2H) 1.01 (t, J=7.40 Hz, 3H).

Example 225. 1-{4-[2-Fluoro-4-(8-methylquinolin-7-yl)-phenoxy]-piperidin-1-yl}-propan-1-one

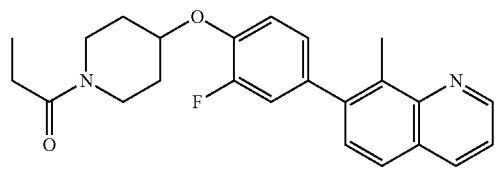 [SMILES: CCC(=O)N1CCC(Oc2ccc(-c3ccc4cccnc4c3C)cc2F)CC1]

Analysis: LCMS m/z=393 (M+1); $^1$H NMR (400 MHz, DMSO-d$_6$) δ: 9.04 (dd, J=4.52, 1.76 Hz, 1H) 8.55 (dd, J=8.16, 1.38 Hz, 1H) 7.95 (d, J=8.28 Hz, 1H) 7.68 (dd, J=8.28, 4.52 Hz, 1H) 7.57 (d, J=8.53 Hz, 1H) 7.33-7.44 (m, 2H) 7.22 (dt, J=8.47, 1.04 Hz, 1H) 4.72 (dt, J=7.78, 4.14 Hz, 1H) 3.84-3.96 (m, 1H) 3.67-3.78 (m, 1H) 3.21-3.43 (m, 2H) 2.69 (s, 3H) 2.30-2.42 (m, 2H) 1.90-2.08 (m, 2H) 1.51-1.75 (m, 2H) 1.01 (t, J=7.40 Hz, 3H).

Example 226. {4-[2-Fluoro-4-(8-methylquinolin-7-yl)-phenoxy]-piperidin-1-yl}-(R)-tetrahydrofuran-2-yl-methanone

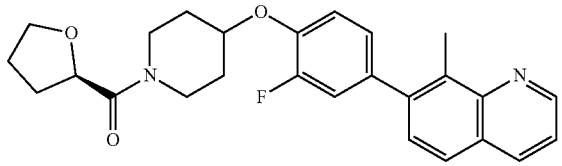

Analysis: LCMS m/z=435 (M+1); $^1$H NMR (400 MHz, DMSO-d$_6$) δ: 9.03 (dd, J=4.27, 1.76 Hz, 1H) 8.53 (d, J=8.28 Hz, 1H) 7.94 (d, J=8.28 Hz, 1H) 7.67 (dd, J=8.28, 4.27 Hz, 1H) 7.56 (d, J=8.53 Hz, 1H) 7.33-7.44 (m, 2H) 7.22 (dd, J=8.41, 1.13 Hz, 1H) 4.66-4.78 (m, 2H) 3.70-3.98 (m, 4H) 3.20-3.53 (m, 2H) 2.69 (s, 3H) 1.92-2.14 (m, 4H) 1.77-1.91 (m, 2H) 1.51-1.76 (m, 2H).

Example 227. Cyclopropyl-{4-[2-fluoro-4-(8-methylquinolin-7-yl)-phenoxy]-piperidin-1-yl}-methanone

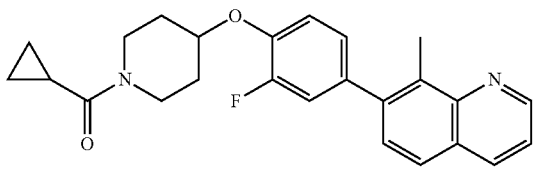 [SMILES: Cc1c(-c2ccc(OC3CCN(C(=O)C4CC4)CC3)c(F)c2)ccc2cccnc12]

Analysis: LCMS m/z=405 (M+1); $^1$H NMR (400 MHz, DMSO-d$_6$) δ: 9.04 (dd, J=4.27, 1.76 Hz, 1H) 8.54 (dd, J=8.28, 1.51 Hz, 1H) 7.95 (d, J=8.28 Hz, 1H) 7.67 (dd, J=8.28, 4.52 Hz, 1H) 7.57 (d, J=8.53 Hz, 1H) 7.33-7.45 (m, 2H) 7.23 (dt, J=8.41, 1.07 Hz, 1H) 4.74 (dt, J=7.84, 3.98 Hz, 1H) 3.82-4.09 (m, 2H) 3.57 (br. s., 1H) 3.29 (br. s., 1H) 2.70 (s, 3H) 1.88-2.14 (m, 3H) 1.50-1.78 (m, 2H) 0.62-0.81 (m, 4H).

Example 228. 1-{4-[2-Fluoro-4-(4-methylquinolin-3-yl)-phenoxy]-piperidin-1-yl}-propan-1-one

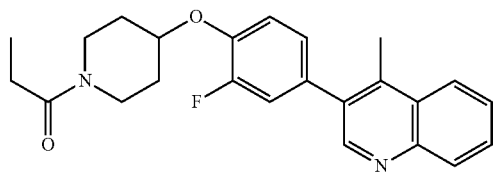 [SMILES: CCC(=O)N1CCC(Oc2ccc(-c3cnc4ccccc4c3C)cc2F)CC1]

Analysis: LCMS m/z=393 (M+1); $^1$H NMR (400 MHz, DMSO-d$_6$) δ: 9.04 (dd, J=4.27, 1.76 Hz, 1H) 8.54 (dd, J=8.28, 1.51 Hz, 1H) 7.95 (d, J=8.28 Hz, 1H) 7.67 (dd, J=8.28, 4.52 Hz, 1H) 7.57 (d, J=8.53 Hz, 1H) 7.33-7.45 (m, 2H) 7.23 (dt, J=8.41, 1.07 Hz, 1H) 4.74 (dt, J=7.84, 3.98 Hz, 1H) 3.82-4.09 (m, 2H) 3.57 (br. s., 1H) 3.29 (br. s., 1H) 2.70 (s, 3H) 1.88-2.14 (m, 3H) 1.50-1.78 (m, 2H) 0.62-0.81 (m, 4H).

Example 229. Cyclopropyl-{4-[2-fluoro-4-(4-methylquinolin-3-yl)-phenoxy]-piperidin-1-yl}-methanone

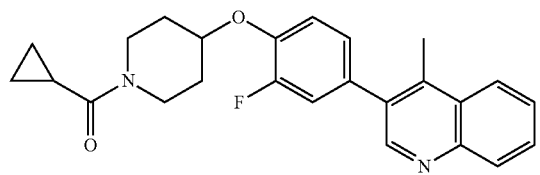 [SMILES: Cc1c(-c2ccc(OC3CCN(C(=O)C4CC4)CC3)c(F)c2)cnc2ccccc12]

Analysis: LCMS m/z=405 (M+1); $^1$H NMR (400 MHz, DMSO-d$_6$) δ: 8.95 (s, 1H) 8.34 (d, J=7.78 Hz, 1H) 8.14 (d, J=7.78 Hz, 1H) 7.90-7.98 (m, 1H) 7.78-7.86 (m, 1H) 7.42-7.52 (m, 2H) 7.30 (dd, J=8.41, 1.13 Hz, 1H) 4.73-4.82 (m, 1H) 3.83-4.09 (m, 2H) 3.58 (br. s., 1H) 3.30 (br. s., 1H) 2.73 (s, 3H) 1.90-2.15 (m, 3H) 1.50-1.79 (m, 2H) 0.65-0.80 (m, 4H).

Example 230. {4-[2-Fluoro-4-(4-methylquinolin-3-yl)-phenoxy]-piperidin-1-yl}-(R)-tetrahydrofuran-2-yl-methanone

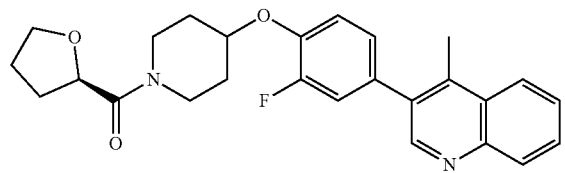 [SMILES: Cc1c(-c2ccc(OC3CCN(C(=O)[C@H]4CCCO4)CC3)c(F)c2)cnc2ccccc12]

Analysis: LCMS m/z=435 (M+1); $^1$H NMR (400 MHz, DMSO-d$_6$) δ: 8.92 (s, 1H) 8.32 (d, J=8.03 Hz, 1H) 8.12 (d, J=8.28 Hz, 1H) 7.91 (t, J=7.65 Hz, 1H) 7.75-7.85 (m, 1H) 7.39-7.52 (m, 2H) 7.29 (d, J=8.28 Hz, 1H) 4.66-4.82 (m, 3H) 3.68-3.97 (m, 6H) 3.20-3.53 (m, 3H) 2.72 (s, 3H) 1.92-2.12 (m, 4H) 1.77-1.92 (m, 2H) 1.52-1.77 (m, 2H).

Example 231. 1-{4-[4-(4-Aminoquinolin-3-yl)-phenoxy]-piperidin-1-yl}-propan-1-one

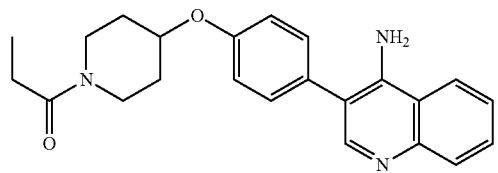 [SMILES: CCC(=O)N1CCC(Oc2ccc(-c3cnc4ccccc4c3N)cc2)CC1]

Step 1. 4-[4-(4-Aminoquinolin-3-yl)-phenoxy]-piperidine-1-carboxylic acid t-butyl ester A 50 mL R. B. flask charged with 1,4-dioxane (5.00 mL), triphenylphosphine (0.0941 g, 0.359 mmol) and palladium acetate (0.0201 g, 0.0896 mmol) was stirred at rt for 15 min under an argon atmosphere. 4-[4-(4,4,5,5-Tetramethyl-1,3,2-dioxaborolan-2-yl)-phenoxy]-piperidine-1-carboxylic acid tert-butyl ester (0.796 g, 1.97 mmol), 3-bromo-quinolin-4-ylamine (0.4 g, 2 mmol), DMF (5.00 mL) and aqueous 1M sodium carbonate (7 mL) were added and flushed with argon five times. The reaction mixture was heated at 80° C. for 7 h and concentrated. The crude residue was suspended in a mixture of aqueous 1M $Na_2CO_3$ and EtOAc and then filtered through a pad of celite/silica gel, washed with EtOAc. The filtrate was separated and the aqueous layer was extracted twice with EtOAc. The combined organics was washed with brine, dried ($Na_2SO_4$), filtered, and evaporated to give a product that was used for the next reaction without further purification. Analysis: LCMS m/z=420 (M+1).

Step 2. 4-{4-[4-(2,2,2-Trifluoroacetylamino)-quinolin-3-yl]-phenoxy}-piperidine-1-carboxylic acid tert-butyl ester To an ice cold (0° C.) stirred solution of 4-[4-(4-aminoquinolin-3-yl)-phenoxy]-piperidine-1-carboxylic acid tert-butyl ester (1.2 g, 2.9 mmol) and triethylamine (1.2 mL, 8.6 mmol) in DCM (10 mL) was added trifluoroacetic anhydride (0.52 mL, 3.7 mmol). The reaction mixture was stirred at rt for 1.5 h and then evaporated. The residue was partitioned between the saturated aqueous $NaHCO_3$ and EtOAc and the aqueous layer was extracted twice with EtOAc. The combined organics was washed with brine, dried, filtered, and evaporated to produce a crude product. The product was crystallized from a mixture of DCM, MeOH, ether and hexane to produce 4-{4-[4-(2,2,2-trifluoroacetylamino)-quinolin-3-yl]-phenoxy}-piperidine-1-carboxylic acid tert-butyl ester, (0.7 g, 76%). Analysis: LCMS m/z=516 (M+1); $^1$H NMR (400 MHz, $CDCl_3$) δ: 8.95 (s, 1H) 8.15-8.23 (m, 1H) 7.93-8.07 (m, 1H) 7.75-7.83 (m, 2H) 7.63-7.71 (m, 1H) 7.33 (d, J=8.78 Hz, 2H) 7.04 (d, J=8.78 Hz, 2H) 4.51-4.59 (m, 1H) 3.66-3.77 (m, 2H) 3.31-3.42 (m, 2H) 1.89-2.02 (m, 2H) 1.73-1.85 (m, 2H) 1.57 (br. s., 2H) 1.47 (s, 9H).

Step 3. 1-{4-[4-(4-Aminoquinolin-3-yl)-phenoxy]-piperidin-1-yl}-propan-1-one

To a solution of 4-{4-[4-(2,2,2-Trifluoroacetylamino)-quinolin-3-yl]-phenoxy}-piperidine-1-carboxylic acid tert-butyl ester (0.34 g, 0.66 mmol) in DCM (5 mL) was added trifluoroacetic Acid (1.5 mL, 19 mmol) dropwise at rt. After completion, the reaction was evaporated and concentrated twice with EtOAc. To a solution of the above product and DIPEA (0.80 mL, 4.6 mmol) in DCM (5 mL, 80 mmol) was added propanoyl chloride (0.07 mL, 0.8 mmol) at rt. After 2 h the reaction was concentrated and was used in the next step without further purification.

Step 4. 1-{4-[4-(4-Aminoquinolin-3-yl)-phenoxy]-piperidin-1-yl}-propan-1-one

A solution of the above material and $K_2CO_3$ (1.5 g, 11 mmol) in methanol (8 mL) and water (2 mL) was heated at 65° C. for 2 days. After completion, the reaction mixture was concentrated and partitioned between EtOAc and water. The aqueous layer was extracted twice EtOAc and the combined organics was washed with brine, dried, filtered, and evaporated to give a crude product. The product was purified by Gilson and then lyophilized to produce 1-{4-[4-(4-aminoquinolin-3-yl)-phenoxy]-piperidin-1-yl}-propan-1-one, 0.268 g (83%). Analysis: LCMS m/z=376 (M+1); $^1$H NMR (400 MHz, DMSO-$d_6$) δ: 13.99 (br. s., 1H) 9.00 (br. s., 1H) 8.62 (d, J=8.28 Hz, 1H) 8.46 (br. s., 1H) 7.83-8.03 (m, 3H) 7.71 (ddd, J=8.34, 6.84, 1.38 Hz, 1H) 7.40-7.49 (m, 2H) 7.19 (d, J=8.78 Hz, 2H) 4.72 (dt, J=7.72, 4.05 Hz, 1H) 3.85-3.96 (m, 1H) 3.73 (d, J=14.31 Hz, 1H) 3.22-3.43 (m, 2H) 2.36 (q, J=7.53 Hz, 2H) 1.89-2.08 (m, 2H) 1.47-1.72 (m, 2H) 1.01 (t, J=7.40 Hz, 3H).

Example 232. 1-{4-[4-(4-Dimethylaminoquinolin-3-yl)-phenoxy]-piperidin-1-yl}-propan-1-one

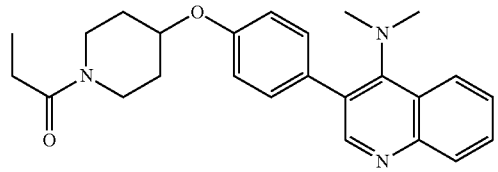 [SMILES: CCC(=O)N1CCC(Oc2ccc(-c3cnc4ccccc4c3N(C)C)cc2)CC1]

Step 1. 3-Bromoquinolin-4-yl)-dimethylamine

A 50 mL pressure reaction vessel charged with 3-bromo-4-chloroquinoline (0.545 g, 2.25 mmol), dimethylamine (9 mL, 200 mmol, 2M solution in THF), $K_2CO_3$ (1.5 g, 11 mmol), and acetonitrile (5 mL, 100 mmol) was heated at 135° C. and monitored by HPLC and LCMS. After 24 h, the reaction mixture was concentrated and then partitioned between EtOAc and saturated aqueous $NaHCO_3$. The aqueous layer was extracted twice EtOAc and the combined organics was washed with brine, dried, filtered, and evaporated to give a crude product. The product was purified by Gilson and then lyophilized to produce (3-bromoquinolin-4-yl)-dimethylamine, 0.4 g (70%). Analysis: LCMS m/z=251 (M+1); $^1$H NMR (400 MHz, $CDCl_3$) δ: 8.80 (s, 1H) 8.12 (dd, J=8.53, 0.75 Hz, 1H) 8.00-8.06 (m, 1H) 7.63-7.71 (m, 1H) 7.49-7.57 (m, 1H) 3.14 (s, 7H).

Step 2. 1-{4-[4-(4-Dimethylaminoquinolin-3-yl)-phenoxy]-piperidin-1-yl}-propan-1-one This example was synthesized using 3-bromoquinolin-4-yl)-dimethylamine using the methods described for Example 231. Analysis: LCMS m/z=404 (M+1); $^1$H NMR (400 MHz, DMSO-$d_6$) δ: 8.66 (s, 1H) 8.42 (d, J=8.28 Hz, 1H) 7.95-8.07 (m, 2H) 7.76 (dd, J=8.53, 1.51 Hz, 1H) 7.33-7.41 (m, 2H) 7.12-7.19 (m, 2H) 4.72 (dt, J=7.84, 3.98 Hz, 1H) 3.85-3.96 (m, 3H) 3.71 (br. s., 2H) 3.20-3.41 (m, 2H) 3.04 (s, 6H) 2.35 (q, J=7.53 Hz, 2H) 1.89-2.07 (m, 2H) 1.55 (br. s., 2H) 1.00 (t, J=7.40 Hz, 3H).

The following examples were prepared using the methods described for Examples 231 and 232.

Example 233. {4-[4-(4-Dimethylaminoquinolin-3-yl)-phenoxy]-piperidin-1-yl}-(R)-tetrahydrofuran-2-yl-methanone

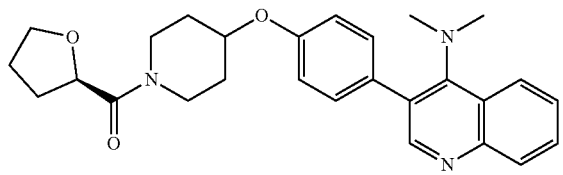 [SMILES: CN(C)c1c(-c2ccc(OC3CCN(C(=O)[C@H]4CCCO4)CC3)cc2)cnc2ccccc12]

Analysis: LCMS m/z=446 (M+1); $^1$H NMR (400 MHz, DMSO-d$_6$) δ: 8.66 (s, 1H) 8.42 (d, J=8.53 Hz, 1H) 7.94-8.07 (m, 2H) 7.76 (ddd, J=8.66, 6.90, 1.51 Hz, 1H) 7.37 (d, J=8.78 Hz, 2H) 7.16 (d, J=8.53 Hz, 2H) 4.65-4.78 (m, 3H) 3.70-3.98 (m, 4H) 3.19-3.52 (m, 2H) 3.04 (s, 6H) 1.75-2.13 (m, 6H) 1.46-1.72 (m, 2H).

Example 234. {4-[4-(4-Aminoquinolin-3-yl)-phenoxy]-piperidin-1-yl}-(R)-tetrahydro-furan-2-yl-methanone

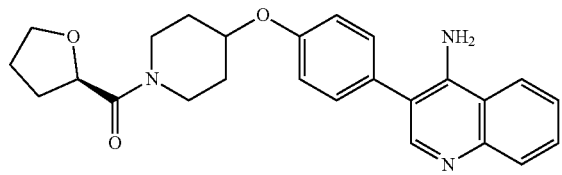 [SMILES: Nc1c(-c2ccc(OC3CCN(C(=O)[C@H]4CCCO4)CC3)cc2)cnc2ccccc12]

Analysis: LCMS m/z=418 (M+1); $^1$H NMR (400 MHz, DMSO-d$_6$) δ: 13.98 (br. s., 1H) 8.92-9.08 (m, 1H) 8.62 (d, J=8.53 Hz, 1H) 8.46 (br. s., 1H) 7.94 (td, J=8.28, 7.03 Hz, 3H) 7.71 (ddd, J=8.34, 6.84, 1.38 Hz, 1H) 7.45 (d, J=8.53 Hz, 2H) 7.19 (d, J=8.53 Hz, 2H) 4.71 (d, J=7.78 Hz, 2H) 3.69-3.98 (m, 6H) 3.21-3.53 (m, 3H) 1.90-2.13 (m, 4H) 1.77-1.90 (m, 2H) 1.47-1.74 (m, 2H).

Example 235. 1-{4-[4-(4-Methylaminoquinolin-3-yl)-phenoxy]-piperidin-1-yl}-propan-1-one

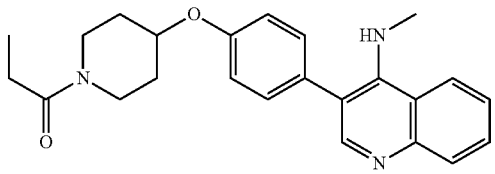 [SMILES: CCC(=O)N1CCC(Oc2ccc(-c3cnc4ccccc4c3NC)cc2)CC1]

A dried 50 mL R. B. flask under an atmosphere of argon was charged with 1-{4-[4-(4-chloroquinolin-3-yl)-phenoxy]-piperidin-1-yl}-propan-1-one (0.15 g, 0.38 mmol), methylamine (0.253 mL, 5.70 mmol), palladium acetate (9.9 mg, 0.044 mmol), bis(2-diphenyl-phosphinophenyl)ether (0.047 g, 0.088 mmol), sodium tert-butoxide (0.0730 g, 0.760 mmol), and 1,4-dioxane (2 mL). The reaction mixture was purged with argon and stirred at 85° C. overnight. The reaction mixture was cooled to RT and the solvent was evaporated in vacuo. The residue was dissolved in EtOAc and washed with brine, dried, filtered, and concentrated. The crude product was purified by Gilson and then lyophilized to produce 1-{4-[4-(4-Methylaminoquinolin-3-yl)-phenoxy]-piperidin-1-yl}-propan-1-one.TFA, 130 mg (68%). Analysis: LCMS m/z=390 (M+1); $^1$H NMR (400 MHz, DMSO-d$_6$) δ: 13.98 (br. s., 1H) 8.80 (br. s., 1H) 8.52 (d, J=8.53 Hz, 1H) 8.45 (s, 1H) 7.89-8.00 (m, 2H) 7.74 (ddd, J=8.41, 6.53, 1.63 Hz, 1H) 7.37-7.45 (m, 2H) 7.11 (d, J=8.78 Hz, 2H) 4.71 (dt, J=7.84, 3.98 Hz, 1H) 3.85-3.96 (m, 2H) 3.66-3.78 (m, 1H) 3.30-3.41 (m, 1H) 3.20-3.30 (m, 2H) 2.65 (br. s., 3H) 2.35 (q, J=7.28 Hz, 2H) 1.99 (br. s., 2H) 1.46-1.70 (m, 2H) 1.00 (t, J=7.40 Hz, 3H).

Example 236. {4-[4-(4-Methylaminoquinolin-3-yl)-phenoxy]-piperidin-1-yl}-(R)-tetrahydrofuran-2-yl-methanone

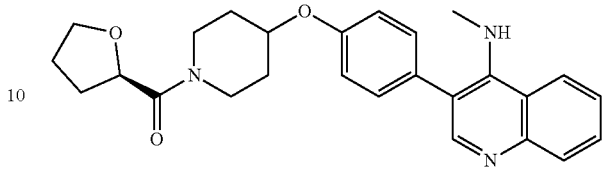

A dried 50 mL R. B. flask under an atmosphere of argon was added {4-[4-(4-chloroquinolin-3-yl)-phenoxy]-piperidin-1-yl}-(R)-tetrahydrofuran-2-yl-methanone (0.16 g, 0.38 mmol), methylamine (0.253 mL, 5.70 mmol), palladium acetate (9.9 mg, 0.044 mmol), bis(2-diphenylphosphinophenyl)ether (0.047 g, 0.088 mmol), sodium t-butoxide (0.0730 g, 0.760 mmol) and 1,4-dioxane (2 mL). The reaction mixture was purged with argon and stirred at 85° C. overnight, cooled to RT and concentrated. The crude product was dissolved in EtOAc, washed with brine and dried to obtain a crude product. The product was purified by Gilson and then lyophilized to produce {4-[4-(4-methylamino-quinolin-3-yl)-phenoxy]-piperidin-1-yl}-(R)-tetrahydrofuran-2-yl-methanone.TFA, 47 mg (24%). Analysis: LCMS m/z=432 (M+1); $^1$H NMR (400 MHz, DMSO-d$_6$) δ: 13.92 (br. s., 1H) 8.79 (br. s., 1H) 8.52 (d, J=8.53 Hz, 1H) 8.45 (br. s., 1H) 7.88-8.00 (m, 2H) 7.71-7.78 (m, 1H) 7.41 (d, J=8.53 Hz, 2H) 7.11 (d, J=8.78 Hz, 2H) 4.65-4.77 (m, 2H) 3.70-3.81 (m, 6H) 3.19-3.51 (m, 4H) 2.58-2.73 (m, 3H) 1.90-2.12 (m, 5H) 1.77-1.89 (m, 2H) 1.46-1.72 (m, 2H).

The following compounds were synthesized using the procedure as described in Examples 235 and 236.

Example 237. 1-{4-[4-(4-Morpholin-4-yl-quinolin-3-yl)-phenoxy]-piperidin-1-yl}-propan-1-one

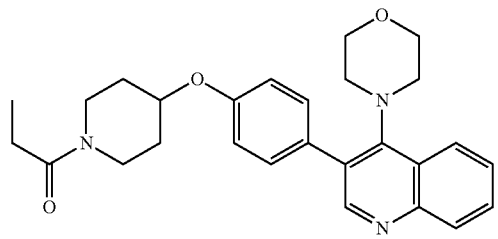 [SMILES: CCC(=O)N1CCC(Oc2ccc(-c3cnc4ccccc4c3N3CCOCC3)cc2)CC1]

Analysis: LCMS m/z=446 (M+1); $^1$H NMR (400 MHz, DMSO-d$_6$) δ: 8.77 (s, 1H) 8.30 (d, J=8.03 Hz, 1H) 8.05-8.13 (m, 1H) 7.99 (t, J=7.28 Hz, 1H) 7.80 (t, J=7.78 Hz, 1H) 7.39 (d, J=8.53 Hz, 2H) 7.18 (d, J=8.78 Hz, 2H) 4.68-4.78 (m, 1H) 3.86-3.98 (m, 2H) 3.67-3.79 (m, 6H) 3.14-3.41 (m, 7H) 2.36 (q, J=7.36 Hz, 2H) 1.90-2.08 (m, 2H) 1.47-1.71 (m, 2H) 1.00 (t, J=7.40 Hz, 3H).

Example 238. {4-[4-(4-Morpholin-4-yl-quinolin-3-yl)-phenoxy]-piperidin-1-yl}-(R)-tetrahydrofuran-2-yl-methanone

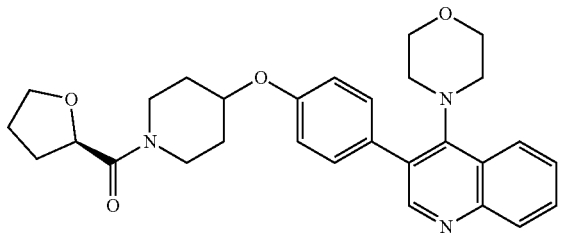 [SMILES: O=C([C@H]1CCCO1)N1CCC(Oc2ccc(-c3cnc4ccccc4c3N3CCOCC3)cc2)CC1]

Analysis: LCMS m/z=488 (M+1); $^1$H NMR (400 MHz, DMSO-$d_6$) δ: 8.76 (s, 1H) 8.30 (d, J=8.28 Hz, 1H) 8.09 (d, J=7.78 Hz, 1H) 7.99 (t, J=7.65 Hz, 1H) 7.77-7.83 (m, 1H) 7.40 (d, J=8.53 Hz, 2H) 7.18 (d, J=8.53 Hz, 2H) 4.66-4.80 (m, 2H) 3.70-3.97 (m, 12H) 3.17-3.24 (m, 6H) 1.91-2.12 (m, 5H) 1.77-1.91 (m, 2H) 1.47-1.72 (m, 2H).

Example 239. 1-(4-{4-[4-(4-Methylpiperazin-1-yl)-quinolin-3-yl]-phenoxy}-piperidin-1-yl)-propan-1-one

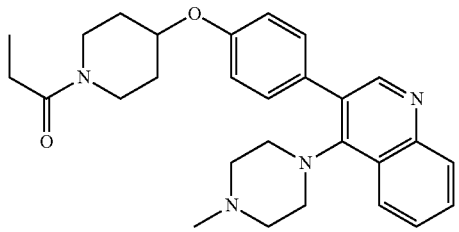 [SMILES: CCC(=O)N1CCC(Oc2ccc(-c3cnc4ccccc4c3N3CCN(C)CC3)cc2)CC1]

Analysis: LCMS m/z=459 (M+1); $^1$H NMR (400 MHz, DMSO-$d_6$) δ: 10.03 (br. s., 1H) 8.77 (s, 1H) 8.23 (d, J=8.28 Hz, 1H) 8.11 (d, J=8.03 Hz, 1H) 7.93 (t, J=7.28 Hz, 1H) 7.74-7.83 (m, 1H) 7.36 (d, J=8.53 Hz, 2H) 7.16 (d, J=8.53 Hz, 2H) 4.63-4.77 (m, 1H) 3.84 (br. s., 28H) 3.20-3.49 (m, 10H) 2.95-3.12 (m, 2H) 2.85 (s, 3H) 2.36 (q, J=7.28 Hz, 2H) 1.90-2.08 (m, 2H) 1.48-1.72 (m, 2H) 1.01 (t, J=7.40 Hz, 3H).

Example 240. (4-{4-[4-(4-Methylpiperazin-1-yl)-quinolin-3-yl]-phenoxy}-piperidin-1-yl)-(R)-tetrahydrofuran-2-yl-methanone

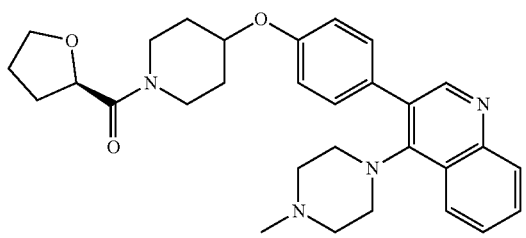 [SMILES: CN1CCN(c2c(-c3ccc(OC4CCN(C(=O)[C@H]5CCCO5)CC4)cc3)cnc3ccccc23)CC1]

Analysis: LCMS m/z=501 (M+1); $^1$H NMR (400 MHz, DMSO-$d_6$) δ: 9.59 (br. s., 1H) 8.73 (s, 1H) 8.21 (d, J=8.28 Hz, 1H) 8.09 (d, J=8.53 Hz, 1H) 7.88 (t, J=7.53 Hz, 1H) 7.75 (t, J=7.28 Hz, 1H) 7.36 (d, J=8.78 Hz, 2H) 7.17 (d, J=8.53 Hz, 2H) 4.64-4.78 (m, 2H) 3.69-3.91 (m, 22H) 3.26-3.51 (m, 11H) 2.90-3.04 (m, 3H) 2.84 (br. s., 3H) 1.91-2.13 (m, 5H) 1.85 (s, 3H) 1.48-1.73 (m, 3H).

Example 241. 3-[4-(4-Quinolin-3-yl-phenoxy)-piperidine-1-carbonyl]-oxazolidin-2-one

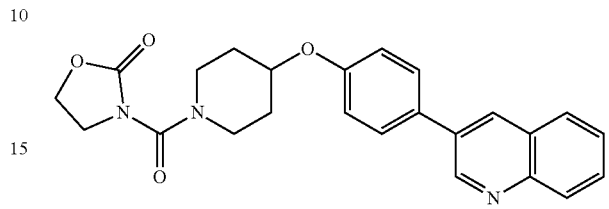

To a stirred solution of oxazolidin-2-one (0.2 g, 2 mmol) in toluene (5 mL) was added sodium hydride (0.11 g, 4.6 mmol) under argon and then heated at 60° C. for 15 h. Triphosgene (0.34 g, 1.1 mmol) was added to the reaction mixture at −20° C. and slowly warmed to rt. Triethylamine (1 mL, 7 mmol) and 3-[4-(piperidin-4-yloxy)-phenyl]-quinoline (0.15 g, 0.49 mmol) were added at 0° C., then warmed to rt and the reaction monitored by HPLC and LCMS. After 2 h, the reaction mixture was quenched with saturated aqueous NaHCO$_3$, extracted twice with EtOAc and the combined organics washed with brine, dried, filtered, and evaporated to give a crude product. The product was purified by Gilson and then lyophilized to produce 3-[4-(4-quinolin-3-yl-phenoxy)-piperidine-1-carbonyl]-oxazolidin-2-one.TFA, 0.103 g (39%). Analysis: LCMS m/z=418 (M+1); $^1$H NMR (400 MHz, DMSO-$d_6$) δ: 9.34 (d, J=2.26 Hz, 1H) 8.75-8.85 (m, 1H) 8.10 (t, J=8.91 Hz, 2H) 7.79-7.92 (m, 3H) 7.66-7.76 (m, 1H) 7.20 (d, J=8.78 Hz, 2H) 4.73-4.83 (m, 1H) 4.39 (t, J=7.65 Hz, 2H) 3.85 (t, J=7.78 Hz, 2H) 3.66-3.78 (m, 2H) 3.32-3.45 (m, 2H) 1.97-2.09 (m, 2H) 1.63-1.78 (m, 2H).

Example 242. 1-[4-(4-Quinolin-3-yl-phenoxy)-piperidin-1-yl]-butane-1,3-dione

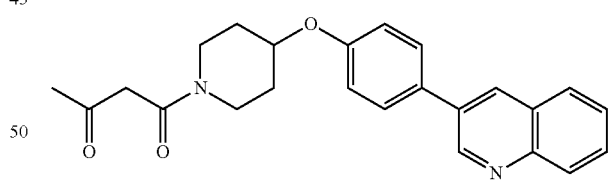

A 50 mL R. B. flask was charged with 3-[4-(piperidin-4-yloxy)-phenyl]-quinoline (0.175 g, 0.575 mmol), acetonitrile (3 mL), 3-oxobutanoic acid ethyl ester (0.523 mL, 4.11 mmol), and potassium carbonate (0.284 g, 2.05 mmol) and then heated at 97° C. under an argon atmosphere for 8 h. The reaction mixture was evaporated in vacuo, and partitioned between water and EtOAc. The aqueous layer was acidified with citric acid to pH 5 then extracted twice with EtOAc and the combined organics washed with brine, dried, filtered, and evaporated to give a crude product. The product was purified by Gilson and then lyophilized to produce 1-[4-(4-quinolin-3-yl-phenoxy)-piperidin-1-yl]-butane-1,3-dione, TFA, 0.180 g (62%). Analysis: LCMS m/z=389 (M+1); $^1$H NMR (400 MHz, DMSO-$d_6$) δ: 9.37 (d, J=2.26 Hz, 1H)

8.80-8.89 (m, 1H) 8.12 (dd, J=11.80, 8.28 Hz, 2H) 7.82-7.93 (m, 3H) 7.70-7.78 (m, 1H) 7.15-7.25 (m, 2H) 4.70-4.82 (m, 1H) 3.81-3.94 (m, 1H) 3.69 (s, 2H) 3.55-3.65 (m, 1H) 3.25-3.38 (m, 2H) 2.17 (s, 3H) 1.88-2.05 (m, 3H) 1.50-1.72 (m, 2H).

Example 243. 1-[4-(4-Quinolin-3-yl-phenoxy)-piperidine-1-carbonyl]-pyrrolidin-2-one

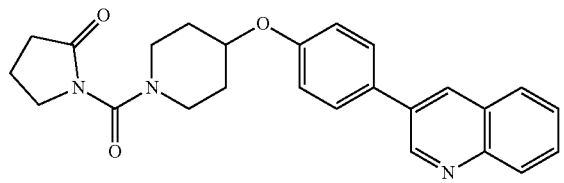 [SMILES: O=C1CCCN1C(=O)N1CCC(Oc2ccc(-c3cnc4ccccc4c3)cc2)CC1]

To a cold (0° C.) stirred solution of 2-pyrrolidinone (0.2 g, 2 mmol) and triethylamine (2 mL, 20 mmol) in 1,2-dichloroethane (5 mL) was added triphosgene (0.3 g, 1 mmol) and stirred at rt for 1.5 h. 3-[4-(piperidin-4-yloxy)-phenyl]-quinoline (0.12 g, 0.39 mmol) and $K_2CO_3$ were added to the reaction mixture at 0° C. and then stirred at rt for 4 h. The reaction mixture was evaporated and partitioned between saturated aqueous $NaHCO_3$ and EtOAc. The aqueous layer was extracted twice with EtOAc and the combined organics was washed with brine, dried, filtered, and evaporated to give a crude product. The product was purified by Gilson and then lyophilized to produce 1-[4-(4-quinolin-3-yl-phenoxy)-piperidine-1-carbonyl]-pyrrolidin-2-one.TFA, 0.125 g (61%). Analysis: LCMS m/z=416 (M+1); $^1$H NMR (400 MHz, DMSO-$d_6$) δ: 9.34 (d, J=2.26 Hz, 1H) 8.80 (s, 1H) 8.10 (t, J=8.91 Hz, 2H) 7.80-7.93 (m, 3H) 7.68-7.76 (m, 1H) 7.20 (d, J=8.78 Hz, 2H) 4.71-4.82 (m, 1H) 3.61 (t, J=7.03 Hz, 4H) 3.54-3.80 (m, 4H) 3.26-3.42 (m, 2H) 2.40 (t, J=7.91 Hz, 2H) 1.92-2.09 (m, 4H) 1.60-1.78 (m, 2H).

Example 244. 4'-[1-((R)-Tetrahydrofuran-2-carbonyl)-piperidin-4-yloxy]-biphenyl-4-carbonitrile

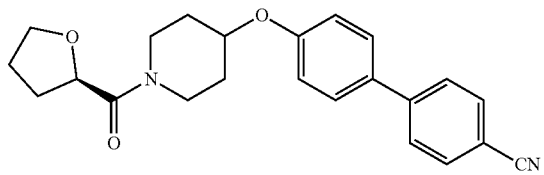 [SMILES: N#Cc1ccc(-c2ccc(OC3CCN(C(=O)[C@H]4CCCO4)CC3)cc2)cc1]

Step 1. 4-(4'-Cyanobiphenyl-4-yloxy)-piperidine-1-carboxylic acid tert-butyl ester A 50 mL R. B. flask charged with 1,4-dioxane (4.00 mL), triphenylphosphine (0.0607 g, 0.231 mmol), and palladium acetate (0.0130 g, 0.0578 mmol) was stirred at rt for 15 min under an argon atmosphere. 4-[4-(4,4,5,5-Tetramethyl-1,3,2-dioxaborolan-2-yl)-phenoxy]-piperidine-1-carboxylic acid t-butyl ester (0.6 g, 1 mmol), 4-bromobenzonitrile (0.210 g, 1.16 mmol), DMF (4.00 mL), and 1M aqueous $Na_2CO_3$ (4 mL) were added and flushed with argon five times. The reaction mixture was heated at 80° C. for 7 h and concentrated. The residue was suspended in a mixture of aqueous 1M $Na_2CO_3$ and EtOAc and then filtered through a pad of celite/silica gel. The filtrate was separated into two layers and the aqueous layer was extracted twice with EtOAc. The combined organics was washed with brine, dried, filtered, and evaporated to give a crude product that was purified by silica gel column chromatography (80 g ISCO column, using 0 to 40% EtOAc in hexane) to give 0.5 g (90%). Analysis: LCMS m/z=379 (M+1); $^1$H NMR (400 MHz, CHLOROFORM-d) δ: 7.60-7.74 (m, 4H), 7.53 (d, J=8.8 Hz, 2H), 6.98-7.04 (m, 2H), 4.50-4.58 (m, 1H), 3.65-3.77 (m, 2H), 3.32-3.42 (m, 2H), 1.89-2.01 (m, 2H), 1.73-1.84 (m, 2H), 1.44-1.51 (m, 11H).

Step 2. 4'-(Piperidin-4-yloxy)-biphenyl-4-carbonitrile

To a solution of 4-(4'-cyan-biphenyl-4-yloxy)-piperidine-1-carboxylic acid tert-butyl ester (0.5 g, 1 mmol) in DCM (7 mL) was added TFA (0.51 mL, 6.6 mmol) at RT. The reaction mixture was stirred 3 h and was then concentrated. This material was used directly in the next step. Analysis: LCMS m/z=279 (M+1).

Step 3. 4'-[1-((R)-Tetrahydrofuran-2-carbonyl)-piperidin-4-yloxy]-biphenyl-4-carbonitrile To a cold (5° C.) stirred solution of (R)-tetrahydrofuran-2-carboxylic acid (0.250 g, 2.16 mmol) and triethylamine (2.00 mL, 14.4 mmol) in DCM (5 mL) was added HATU (0.765 g, 2.01 mmol). After 15 min 4'-(piperidin-4-yloxy)-biphenyl-4-carbonitrile (0.4 g, 1 mmol) was added and further stirred at rt for 2 h. The reaction mixture was concentrated and then partitioned between EtOAc and saturated aqueous $NaHCO_3$. The aqueous layer was extracted twice with EtOAc and the combined organics was washed with brine, dried, filtered, and concentrated. The product was purified by Gilson and then lyophilized to produce 4'-[1-((R)-tetrahydrofuran-2-carbonyl)-piperidin-4-yloxy]-biphenyl-4-carbonitrile, 0.313 g (overall 58%). Analysis: LCMS m/z=377 (M+1); $^1$H NMR (400 MHz, DMSO-$d_6$) δ: 7.81-7.91 (m, 2H) 7.71 (d, J=8.78 Hz, 1H) 7.12 (d, J=8.53 Hz, 1 H) 4.65-4.77 (m, 1H) 3.76 (d, J=6.78 Hz, 2H) 3.18-3.51 (m, 2H) 1.74-2.11 (m, 3H) 1.44-1.70 (m, 1H).

The following compounds were synthesized using the procedures of Examples 1-7.

Example 245. 1-[4-(4-Benzofuran-2-yl-phenoxy)-piperidin-1-yl]-propan-1-one

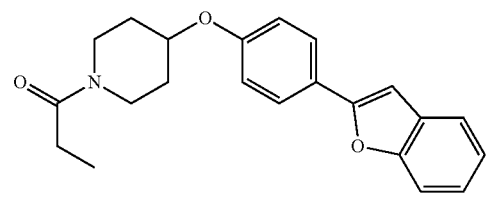 [SMILES: CCC(=O)N1CCC(Oc2ccc(-c3cc4ccccc4o3)cc2)CC1]

Analysis: LCMS m/z=350 (M+1); $^1$H NMR (400 MHz, CDCl$_3$) δ: 7.76-7.83 (m, 2H), 7.47-7.58 (m, 2H), 7.18-7.26 (m, 2H), 6.96-7.02 (m, 2H), 6.90 (s, 1H), 4.61 (tt, J=6.59, 3.33 Hz, 1H), 3.76-3.86 (m, 1H), 3.61-3.75 (m, 2H), 3.38-3.49 (m, 1H), 2.38 (q, J=7.36 Hz, 2H), 1.77-2.02 (m, 4H), 1.17 (t, J=7.40 Hz, 3H).

Example 246. 1-{4-[4-(1H-Indol-3-yl)-phenoxy]-piperidin-1-yl}-propan-1-one

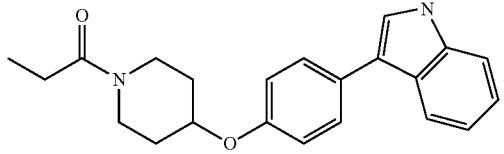 [SMILES: CCC(=O)N1CCC(Oc2ccc(-c3c[nH]c4ccccc34)cc2)CC1]

Analysis: LCMS m/z=349 (M+1); $^1$H NMR (400 MHz, CD$_3$OD): δ:7.81 (d, J=7.78 Hz, 1H), 7.58 (d, J=8.28 Hz, 2H), 7.34-7.43 (m, 2H), 7.11-7.18 (m, 1H), 7.02-7.09 (m, 3H), 4.65 (tt, J=6.93, 3.48 Hz, 1H), 3.75-3.92 (m, 2H), 3.46-3.63 (m, 2H), 2.42-2.51 (m, 2H), 1.96-2.09 (m, 2H), 1.73-1.89 (m, 2H), 1.13-1.18 (m, 3H).

Example 247. 1-[4-(4-Benzo[b]thiophen-5-yl-phenoxy)-piperidin-1-yl]-propan-1-one

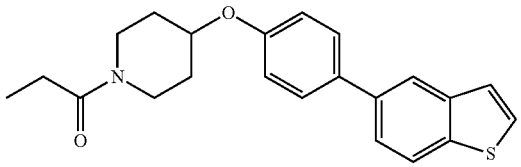

Analysis: LCMS m/z=366 (M+1); $^1$H NMR (400 MHz, CDCl$_3$) δ: 7.97 (d, J=1.51 Hz, 1H), 7.91 (d, J=8.53 Hz, 1H), 7.51-7.62 (m, 3H), 7.45-7.50 (m, 1H), 7.37 (d, J=5.52 Hz, 1H), 6.97-7.07 (m, 2H), 4.60 (tt, J=6.65, 3.26 Hz, 1H), 3.79-3.87 (m, 1H), 3.63-3.77 (m, 2H), 3.39-3.49 (m, 1H), 2.34-2.45 (m, 2H), 1.80-2.03 (m, 4H), 1.17 (t, J=7.53 Hz, 3H).

Example 248. 1-{4-[4-(1H-Indazol-3-yl)-phenoxy]-piperidin-1-yl}-propan-1-one

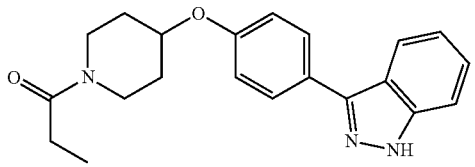 [SMILES: CCC(=O)N1CCC(Oc2ccc(-c3n[nH]c4ccccc34)cc2)CC1]

Analysis: LCMS m/z=350 (M+1); $^1$H NMR (400 MHz, CDCl$_3$) δ: 10.07 (br. s., 1H), 8.01 (d, J=8.28 Hz, 1H), 7.91 (d, J=8.78 Hz, 1H), 7.39-7.57 (m, 2H), 7.19-7.34 (m, 4H), 7.06 (d, J=8.78 Hz, 2H), 4.63 (tt, J=6.59, 3.45 Hz, 1H), 3.58-3.94 (m, 3H), 3.32-3.55 (m, 1H), 2.39 (q, J=7.53 Hz, 2H), 1.74-2.12 (m, 4H), 1.18 (t, J=7.53 Hz, 3H).

Example 249. 1-{4-[4-(1-Methyl-1H-indazol-6-yl)-phenoxy]-piperidin-1-yl}-propan-1-one, TFA salt

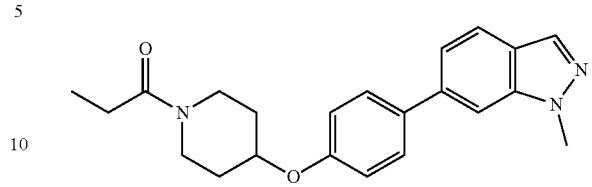

Analysis: LCMS m/z=364 (M+1); $^1$H NMR (400 MHz, CDCl$_3$) δ: 8.01 (d, J=0.75 Hz, 1H), 7.74-7.81 (m, 1H), 7.61 (d, J=8.78 Hz, 2H), 7.50 (s, 1H), 7.38 (dd, J=8.53, 1.25 Hz, 1H), 6.99-7.06 (m, 2H), 4.60-4.69 (m, 1H), 4.12 (s, 3H), 3.67-3.83 (m, 3H), 3.43-3.57 (m, 1H), 2.42-2.47 (m, 2H), 1.87-2.04 (m, 4H), 1.19 (t, J=7.53 Hz, 3H).

Example 250. 1-[4-(4-Thieno[2,3-b]pyridin-5-yl-phenoxy)-piperidin-1-yl]-propan-1-one, TFA salt

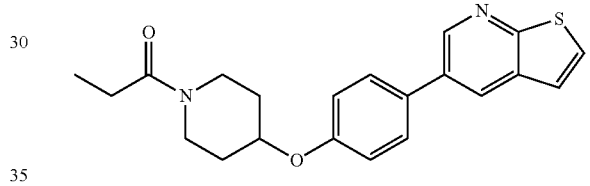

Analysis: LCMS m/z=367 (M+1); $^1$H NMR (400 MHz, CDCl$_3$) δ: 8.85 (d, J=1.76 Hz, 1H), 8.31 (d, J=2.01 Hz, 1H), 7.63 (d, J=5.77 Hz, 1H), 7.55-7.60 (m, 2H), 7.36 (d, J=6.02 Hz, 1H), 7.01-7.10 (m, 2H), 4.63-4.69 (m, 1H), 3.76 (br. s., 3H), 3.50 (br. s., 1H), 2.43 (q, J=7.36 Hz, 2H), 1.82-2.05 (m, 4H), 1.19 (t, J=7.53 Hz, 3H).

Example 251. 1-{4-[4-(2-Methyl-2H-indazol-6-yl)-phenoxy]-piperidin-1-yl}-propan-1-one

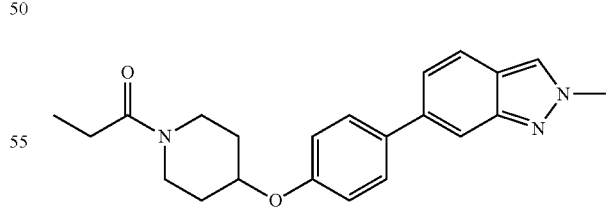

Analysis: LCMS m/z=364 (M+1); $^1$H NMR (400 MHz, CDCl$_3$) δ: 7.97 (s, 1H), 7.89 (d, J=1.25 Hz, 1H), 7.74 (dd, J=8.78, 1.00 Hz, 1H), 7.56-7.66 (m, 2H), 7.45 (dd, J=8.78, 1.51 Hz, 1H), 6.98-7.05 (m, 2H), 4.60-4.71 (m, 1H), 4.33 (s, 3H), 3.69-3.89 (m, 3H), 3.46-3.59 (m, 1H), 2.46 (q, J=7.53 Hz, 2H), 1.86-1.98 (m, 4H), 1.20 (t, J=7.53 Hz, 3H).

Example 252. 1-[4-(4-[1,8]Naphthyridin-3-yl-phenoxy)-piperidin-1-yl]-propan-1-one, TFA salt

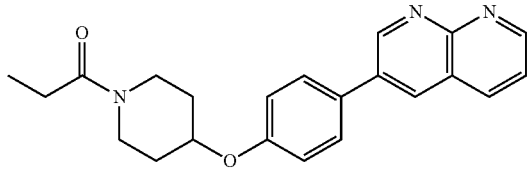 [SMILES: CCC(=O)N1CCC(Oc2ccc(-c3cnc4ncccc4c3)cc2)CC1]

Analysis: LCMS m/z=362 (M+1); $^1$H NMR (400 MHz, CDCl$_3$) δ: 9.57 (d, J=2.26 Hz, 1H), 9.32 (dd, J=4.52, 1.51 Hz, 1H), 8.48-8.59 (m, 2H), 7.78 (dd, J=8.28, 4.52 Hz, 1H), 7.66-7.73 (m, 2H), 7.07-7.16 (m, 2H), 4.62-4.76 (m, 1H), 3.77 (br. s., 3H), 3.43-3.62 (m, 1H), 2.44 (q, J=7.53 Hz, 2H), 1.84-2.09 (m, 4H), 1.19 (t, J=7.53 Hz, 3H).

Example 253. 1-{4-[4-(2-Methylquinolin-7-yl)-phenoxy]-piperidin-1-yl}-propan-1-one, TFA salt

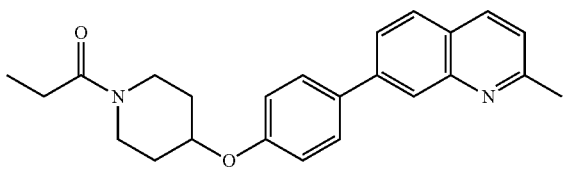 [SMILES: CCC(=O)N1CCC(Oc2ccc(-c3ccc4ccc(C)nc4c3)cc2)CC1]

Analysis: LCMS m/z=375 (M+1); $^1$H NMR (400 MHz, CDCl$_3$) δ: 8.74 (d, J=1.00 Hz, 1H), 8.57 (d, J=8.53 Hz, 1H), 8.03 (d, J=1.00 Hz, 2H), 7.73-7.81 (m, 2H), 7.54 (d, J=8.53 Hz, 1H), 7.06-7.14 (m, 2H), 4.65 (tt, J=6.62, 3.42 Hz, 1H), 3.67-3.90 (m, 3H), 3.42-3.53 (m, 1H), 3.07 (s, 3H), 2.40 (d, J=7.53 Hz, 2H), 1.84-2.07 (m, 4H), 1.18 (t, J=7.53 Hz, 3H).

Example 254. (R)-Tetrahydrofuran-2-yl-[4-(4-thieno[2,3-b]pyridin-5-yl-phenoxy)-piperidin-1-yl]-methanone, TFA salt

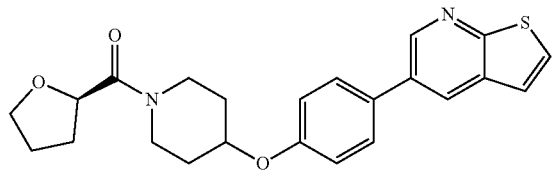 [SMILES: O=C([C@H]1CCCO1)N1CCC(Oc2ccc(-c3cnc4sccc4c3)cc2)CC1]

Analysis: LCMS m/z=409 (M+1); $^1$H NMR (400 MHz, CDCl$_3$) δ: 8.85 (d, J=2.01 Hz, 1H), 8.32 (d, J=2.01 Hz, 1H), 7.63 (d, J=5.77 Hz, 1H), 7.58 (d, J=8.53 Hz, 2H), 7.37 (d, J=6.02 Hz, 1H), 7.02-7.10 (m, 2H), 4.61-4.72 (m, 2H), 3.47-4.05 (m, 6H), 1.80-2.16 (m, 8H).

Example 255. Cyclopropyl-[4-(4-thieno[2,3-b]pyridin-5-yl-phenoxy)-piperidin-1-yl]-methanone, TFA salt

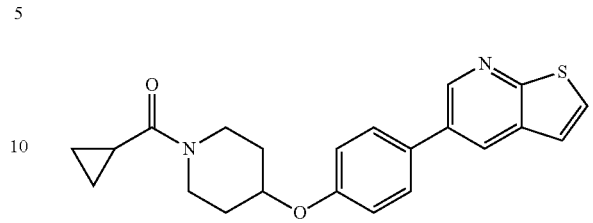

Analysis: LCMS m/z=379 (M+1); $^1$H NMR (400 MHz, CDCl$_3$) δ: 8.82 (d, J=2.26 Hz, 1H), 8.27 (d, J=2.26 Hz, 1H), 7.55-7.64 (m, 3H), 7.34 (d, J=5.77 Hz, 1H), 7.04-7.11 (m, 2H), 4.65 (tt, J=6.56, 3.36 Hz, 1H), 3.75-4.03 (m, 2H), 3.70 (ddd, J=13.49, 6.84, 4.02 Hz, 2H), 1.84-2.09 (m, 4H), 1.79 (tt, J=8.00, 4.67 Hz, 1H), 0.98-1.05 (m, 2H), 0.79 (dd, J=8.03, 3.01 Hz, 2H).

Example 256. 1-[4-(4-Imidazo[1,2-a]pyridin-6-yl-phenoxy)-piperidin-1-yl]-propan-1-one, TFA salt

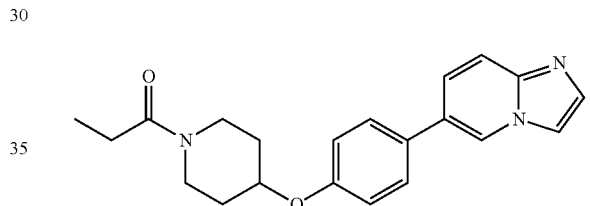

Analysis: LCMS m/z=350 (M+1); $^1$H NMR (400 MHz, CDCl$_3$) δ: 8.34-8.45 (m, 2H), 7.89-8.01 (m, 2H), 7.75 (d, J=1.76 Hz, 1H), 7.51 (d, J=8.78 Hz, 2H), 7.07 (d, J=8.78 Hz, 2H), 4.65 (tt, J=6.46, 3.33 Hz, 1H), 3.74 (br. s., 4H), 3.48-3.57 (m, 1H), 2.38-2.49 (m, 2H), 1.82-2.07 (m, 4H), 1.18 (t, J=7.40 Hz, 3H).

Example 257. {4-[4-(4-Chloroquinolin-7-yl)-phenoxy]-piperidin-1-yl}-(R)-tetrahydro-furan-2-yl-methanone, TFA salt

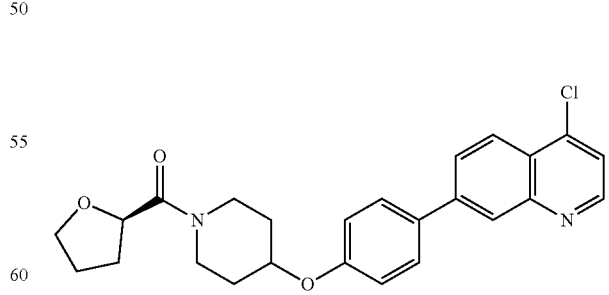

Analysis: LCMS m/z=437 (M+1); $^1$H NMR (400 MHz, CDCl$_3$) δ: 9.04 (d, J=5.52 Hz, 1H), 8.56 (s, 1H), 8.40 (d, J=9.03 Hz, 1H), 8.06-8.16 (m, 1H), 7.72-7.82 (m, 3H), 7.09 (d, J=8.78 Hz, 2H), 4.63-4.73 (m, 2H), 3.51-4.02 (m, 6H), 1.91-2.13 (m, 8H).

Example 258. {4-[4-(4-Chloroquinolin-7-yl)-phenoxy]-piperidin-1-yl}-cyclopropyl-methanone, TFA salt

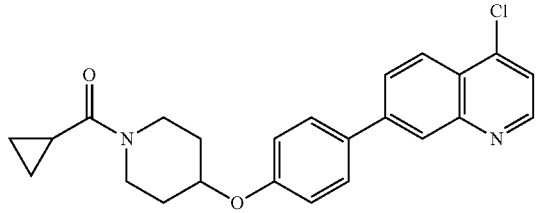 [SMILES: O=C(C1CC1)N1CCC(Oc2ccc(-c3ccc4c(Cl)ccnc4c3)cc2)CC1]

Analysis: LCMS m/z=407 (M+1); $^1$H NMR (400 MHz, CDCl$_3$) δ: 9.05 (d, J=5.52 Hz, 1H), 8.57 (d, J=1.51 Hz, 1H), 8.40 (d, J=8.78 Hz, 1H), 8.10 (dd, J=9.03, 1.76 Hz, 1H), 7.72-7.81 (m, 3H), 7.06-7.15 (m, 2H), 4.62-4.75 (m, 1H), 3.76-4.02 (m, 2H), 3.67-3.76 (m, 2H), 1.87-2.13 (m, 4H), 1.75-1.85 (m, 1H), 1.02 (dd, J=4.52, 2.76 Hz, 2H), 0.80 (dd, J=8.03, 3.01 Hz, 2H).

Example 259. 1-{4-[4-(4-Chloroquinolin-7-yl)-phenoxy]-piperidin-1-yl}-propan-1-one, TFA salt

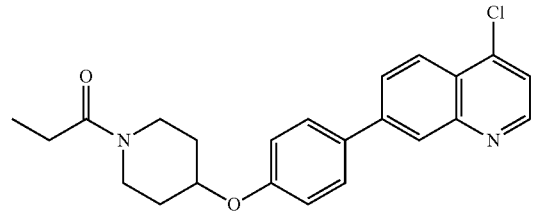 [SMILES: CCC(=O)N1CCC(Oc2ccc(-c3ccc4c(Cl)ccnc4c3)cc2)CC1]

Analysis: LCMS m/z=395 (M+1); $^1$H NMR (400 MHz, CDCl$_3$) δ: 9.03 (d, J=5.52 Hz, 1H), 8.55 (d, J=1.51 Hz, 1H), 8.39 (d, J=8.78 Hz, 1H), 8.08 (dd, J=8.78, 1.76 Hz, 1H), 7.67-7.80 (m, 3H), 7.09 (d, J=8.78 Hz, 2H), 4.61-4.73 (m, 1H), 3.54-3.92 (m, 4H), 2.41 (d, J=7.53 Hz, 2H), 1.83-2.06 (m, 4H), 1.18 (t, J=7.53 Hz, 3H).

Example 260. {4-[4-(8-Chloro-quinolin-7-yl)-phenoxy]-piperidin-1-yl}-(R)-tetrahydro-furan-2-yl-methanone, TFA salt

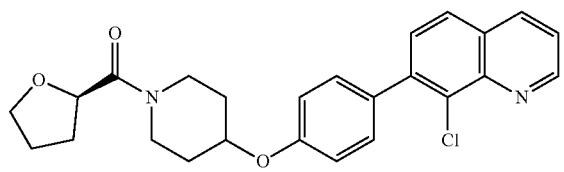 [SMILES: O=C([C@H]1CCCO1)N1CCC(Oc2ccc(-c3ccc4cccnc4c3Cl)cc2)CC1]

Analysis: LCMS m/z=437 (M+1); $^1$H NMR (400 MHz, CDCl$_3$) δ: 9.33 (d, J=4.52 Hz, 1H), 8.51-8.58 (m, 1H), 7.93 (d, J=8.53 Hz, 1H), 7.70-7.79 (m, 2H), 7.52 (d, J=8.53 Hz, 2H), 7.05 (d, J=8.78 Hz, 2H), 4.65-4.73 (m, 2H), 3.53-4.03 (m, 6H), 1.89-2.31 (m, 8H).

Example 261. 1-{4-[4-(8-Chloroquinolin-7-yl)-phenoxy]-piperidin-1-yl}-propan-1-one

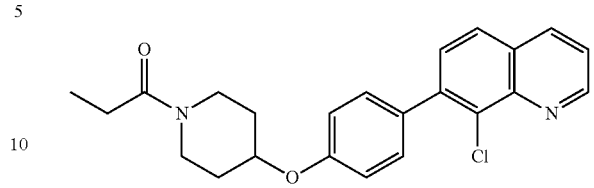

Analysis: LCMS m/z=395 (M+1); $^1$H NMR (400 MHz, CDCl$_3$) δ: 9.10 (dd, J=4.14, 1.63 Hz, 1H), 8.22 (dd, J=8.28, 1.51 Hz, 1H), 7.79 (d, J=8.53 Hz, 1H), 7.47-7.59 (m, 4H), 7.00-7.08 (m, 2H), 4.59-4.69 (m, 1H), 3.80-3.91 (m, 1H), 3.64-3.78 (m, 2H), 3.40-3.51 (m, 1H), 2.33-2.45 (m, 2H), 1.82-2.06 (m, 4H), 1.18 (t, J=7.53 Hz, 3H).

Example 262. {4-[4-(7-Methoxyquinolin-3-yl)-phenoxy]-piperidin-1-yl}-(R)-tetrahydro-furan-2-yl-methanone

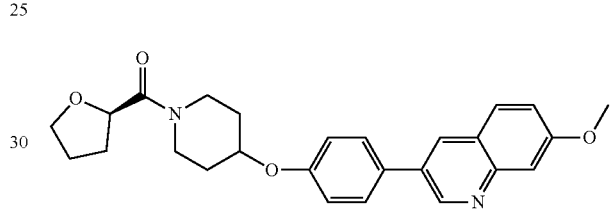

Step 1. 4-[4-(7-Methoxyquinolin-3-yl)-phenoxy]-piperidine-1-carboxylic acid t-butyl ester This compound was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 3-bromo-7-methoxyquinoline (443 mg, 1.86 mmol) in an analogous manner to Example 378. Product isolated as a solid (0.46 g, 85%). Analysis: LCMS m/z=435 (M+1).

Step 2. 7-Methoxy-3-[4-(piperidin-4-yloxy)-phenyl]-quinoline

This compound was prepared from 4-[4-(7-methoxyquinolin-3-yl)-phenoxy]-piperidine-1-carboxylic acid tert-butyl ester (0.46 g, 1.05 mmol) and TFA (2 mL) in an analogous manner to Example 378. Product isolated as a solid (0.24 g, 68%). Analysis: LCMS m/z=335 (M+1).

Step 3. {4-[4-(7-Methoxyquinolin-3-yl)-phenoxy]-piperidin-1-yl}-(R)-tetrahydrofuran-2-yl-methanone This compound was prepared from 7-methoxy-3-[4-(piperidin-4-yloxy)-phenyl]-quinoline (90 mg, 0.3 mmol) and (R)-tetrahydrofuran-2-carboxylic acid (52 uL, 0.54 mmol) in an analogous manner to Example 418. Product isolated as a solid (0.02 g, 20%). Analysis: LCMS m/z=433 (M+1). $^1$H NMR (DMSO-d6) δ: 9.14 (d, 1H, J=2.4 Hz), 8.49 (d, 1H, J=2.3 Hz), 7.94 (d, 1H, J=9.0 Hz), 7.79 (m, 2H), 7.41 (d, 1H, J=2.4 Hz), 7.29 (m, 1H), 7.15 (m, 2H), 4.72 (m, 2H), 3.93 (s, 3H), 3.77 (br m, 4H), 3.36 (m, 1H), 3.29 (m, 1H), 2.06 (br m, 4H), 1.84 (m, 2H), 1.60 (m, 2H).

Example 263. (R)-Tetrahydrofuran-2-yl-[4-(4-thieno[3,2-b]pyridin-6-yl-phenoxy)-piperidin-1-yl]-methanone, TFA salt

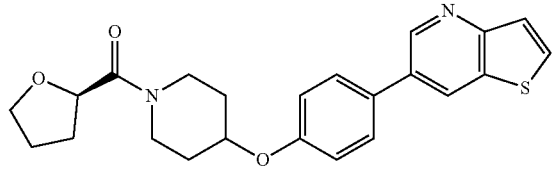 [SMILES: O=C([C@H]1CCCO1)N1CCC(Oc2ccc(-c3cnc4ccsc4c3)cc2)CC1]

Analysis: LCMS m/z=409 (M+1); $^1$H NMR (400 MHz, CDCl$_3$) δ; 9.10 (d, J=1.76 Hz, 1H), 8.71 (d, J=1.25 Hz, 1H), 8.05 (d, J=5.77 Hz, 1H), 7.94 (d, J=5.52 Hz, 1H), 7.62 (d, J=8.53 Hz, 2H), 7.06-7.14 (m, 2H), 4.66 (dd, J=7.40, 5.65 Hz, 2H), 3.64-4.01 (m, 6H), 2.24-2.38 (m, 1H), 1.86-2.16 (m, 7H).

Example 264. 1-[4-(4-Thieno[3,2-b]pyridin-6-yl-phenoxy)-piperidin-1-yl]-propan-1-one, TFA salt

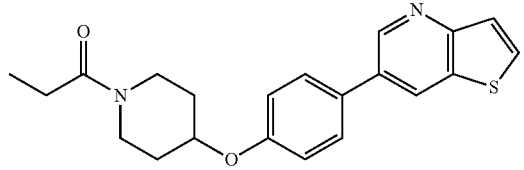 [SMILES: CCC(=O)N1CCC(Oc2ccc(-c3cnc4ccsc4c3)cc2)CC1]

Analysis: LCMS m/z=367 (M+1); $^1$H NMR (400 MHz, CDCl$_3$) δ: 9.11 (d, J=1.76 Hz, 1H), 8.73 (s, 1H), 8.06 (s, 1H), 7.92-8.00 (m, 1H), 7.62 (d, J=8.78 Hz, 2H), 7.08 (d, J=8.78 Hz, 2H), 4.59-4.73 (m, 1H), 3.75-3.84 (m, 2H), 3.49-3.59 (m, 2H), 2.38-2.50 (m, 2H), 1.86-2.06 (m, 4H), 1.19 (t, J=7.40 Hz, 3H).

Example 265. {4-[4-(3-Chloroquinolin-7-yl)-phenoxy]-piperidin-1-yl}-(R)-tetrahydro-furan-2-yl-methanone, TFA salt

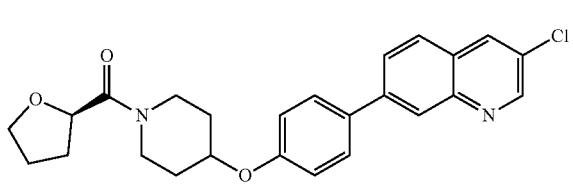 [SMILES: O=C([C@H]1CCCO1)N1CCC(Oc2ccc(-c3ccc4cc(Cl)cnc4c3)cc2)CC1]

Analysis: LCMS m/z=437 (M+1); $^1$H NMR (400 MHz, CDCl$_3$) δ: 8.93 (d, J=2.26 Hz, 1H), 8.34 (d, J=0.75 Hz, 1H), 8.27 (d, J=1.76 Hz, 1H), 7.83-7.93 (m, 2H), 7.70 (d, J=8.78 Hz, 2H), 7.06 (d, J=8.78 Hz, 2H), 4.66 (dd, J=7.40, 5.65 Hz, 2H), 3.46-4.01 (m, 6H), 2.28-2.34 (m, 1H), 1.87-2.15 (m, 7H).

Example 266. 1-{4-[4-(3-Chloroquinolin-7-yl)-phenoxy]-piperidin-1-yl}-propan-1-one, TFA salt

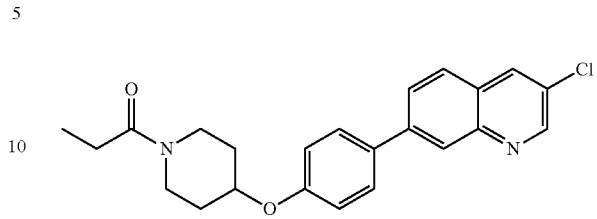

Analysis: LCMS m/z=395 (M+1); $^1$H NMR (400 MHz, CDCl$_3$) δ: 8.94 (d, J=2.26 Hz, 1H), 8.35 (s, 1H), 8.29 (d, J=2.26 Hz, 1H), 7.82-7.94 (m, 2H), 7.70 (d, J=8.78 Hz, 2H), 7.06 (d, J=8.78 Hz, 2H), 4.61-4.72 (m, 1H), 3.64-3.88 (m, 3H), 3.41-3.56 (m, 1H), 2.39-2.48 (m, 2H), 1.85-2.03 (m, 4H), 1.18-1.23 (m, 3H).

Example 267. [4-(4-Benzothiazol-5-yl-phenoxy)-piperidin-1-yl]-(R)-tetrahydrofuran-2-yl-methanone, TFA salt

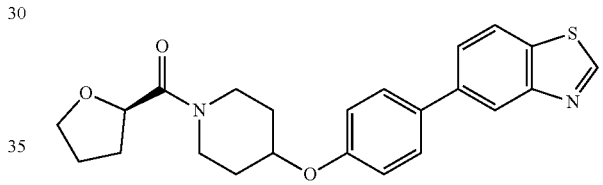

Analysis: LCMS m/z=409 (M+1); $^1$H NMR (400 MHz, CDCl$_3$) δ: 9.15 (s, 1H), 8.33 (d, J=1.25 Hz, 1H), 8.01 (d, J=8.28 Hz, 1H), 7.67-7.74 (m, 1H), 7.62 (d, J=8.53 Hz, 2H), 7.04 (d, J=8.78 Hz, 2H), 4.62-4.73 (m, 2H), 3.62-4.06 (m, 6H), 1.87-2.31 (m, 8H).

Example 268. [4-(4-Benzothiazol-5-yl-phenoxy)-piperidin-1-yl]-cyclopropylmethanone, TFA salt

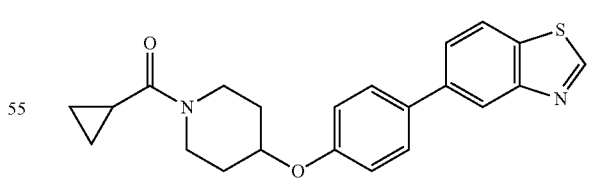

Analysis: LCMS m/z=379 (M+1); $^1$H NMR (400 MHz, CDCl$_3$) δ: 9.19 (s, 1H), 8.32-8.37 (m, 1H), 7.97-8.07 (m, 1H), 7.68-7.75 (m, 1H), 7.63 (d, J=8.78 Hz, 2H), 7.05 (d, J=8.78 Hz, 2H), 4.61-4.71 (m, 1H), 3.73-3.81 (m, 4H), 1.88-2.10 (m, 4H), 1.78-1.86 (m, 1H), 1.02-1.08 (m, 2H), 0.79-0.88 (m, 2H).

Example 269. 1-[4-(4-Benzothiazol-5-yl-phenoxy)-piperidin-1-yl]-propan-1-one; TFA salt

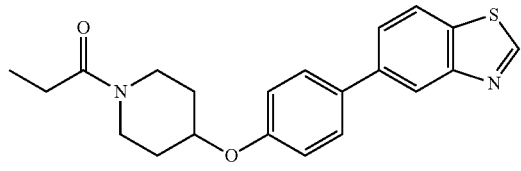 [SMILES: CCC(=O)N1CCC(Oc2ccc(-c3ccc4scnc4c3)cc2)CC1]

Analysis: LCMS m/z=367 (M+1); $^1$H NMR (400 MHz, CDCl$_3$) δ: 9.15-9.21 (m, 1H), 8.33 (d, J=1.25 Hz, 1H), 8.01 (d, J=8.28 Hz, 1H), 7.71 (dd, J=8.28, 1.51 Hz, 1H), 7.59-7.66 (m, 2H), 7.00-7.10 (m, 2H), 4.65 (br. s., 1H), 3.71-3.88 (m, 3H), 3.48-3.61 (m, 1H), 2.46 (d, J=7.53 Hz, 2H), 1.95 (br. s., 4H), 1.20 (t, J=7.53 Hz, 3H).

Example 270. Cyclopropyl-{4-[4-(1-methyl-1H-indazol-6-yl)-phenoxy]-piperidin-1-yl})-methanone. TFA salt

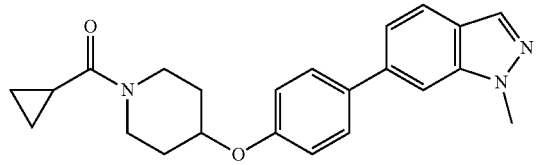 [SMILES: Cn1ncc2ccc(-c3ccc(OC4CCN(C(=O)C5CC5)CC4)cc3)cc21]

Analysis: LCMS m/z=376 (M+1); $^1$H NMR (400 MHz, CDCl$_3$) δ: 8.05 (1H, s), 7.79 (1H, d, J=8.5 Hz), 7.57-7.64 (2H, m), 7.51 (1H, s), 7.37-7.43 (1H, m), 7.04 (2H, d, J=8.8 Hz), 4.63-4.71 (1H, m), 3.78 (4H, br. s.), 1.87-2.07 (4H, m), 1.76-1.85 (1H, m), 0.99-1.10 (2H, m), 0.75-0.87 (2H, m).

Example 271. Cyclobutyl-{4-[4-(1-methyl-1H-indazol-6-yl)-phenoxy]-piperidin-1-yl}-methanone, TFA salt

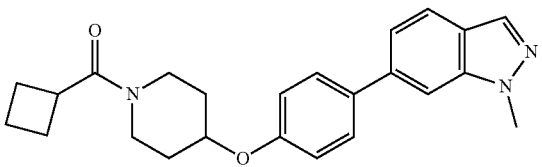 [SMILES: Cn1ncc2ccc(-c3ccc(OC4CCN(C(=O)C5CCC5)CC4)cc3)cc21]

Analysis: LCMS m/z=390 (M+1); $^1$H NMR (400 MHz, CD$_3$OD): δ: 8.37 (1H, d, J=1.0 Hz), 8.17 (1H, dd, J=8.5, 0.8 Hz), 8.02-8.11 (3H, m), 7.81 (1H, dd, J=8.5, 1.5 Hz), 7.39-7.52 (2H, m), 5.08 (1H, dt, J=7.0, 3.5 Hz), 4.24 (1H, td, J=8.7, 4.0 Hz), 4.03-4.15 (1H, m), 3.80-4.00 (3H, m), 2.54-2.77 (4H, m), 2.05-2.50 (6H, m).

Example 272. {4-[4-(8-Methoxyquinolin-7-yl)-phenoxy]-piperidin-1-yl}-(R)-tetrahydro-furan-2-yl-methanone, TFA salt

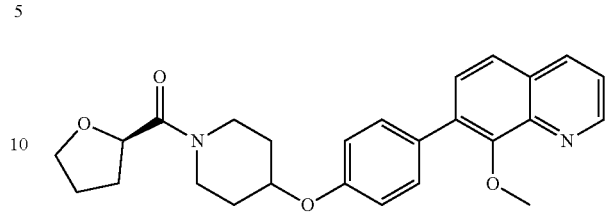

Analysis: LCMS m/z=433 (M+1); $^1$H NMR (400 MHz, CDCl$_3$) δ: 9.49 (dd, J=5.27, 1.51 Hz, 1H), 8.66-8.78 (m, 1H), 7.85 (s, 3H), 7.72 (d, J=8.78 Hz, 2H), 7.07 (d, J=9.04 Hz, 2H), 4.62-4.73 (m, 2H), 3.54-4.03 (m, 9H), 2.26-2.37 (m, 1H), 1.89-2.00 (m, 7H).

Example 273. 1-{4-[4-(8-Methoxyquinolin-7-yl)-phenoxy]-piperidin-1-yl}-propan-1-one, TFA salt.

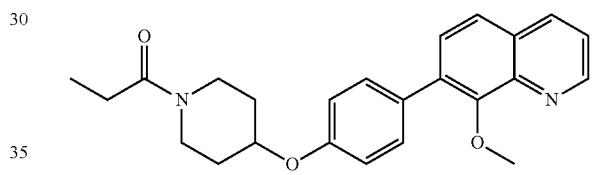

Analysis: LCMS m/z=433 (M+1); $^1$H NMR (400 MHz, CDCl$_3$) δ: 9.42-9.52 (m, 1H), 8.79 (dd, J=8.41, 1.13 Hz, 1H), 7.85-7.93 (m, 3H), 7.67-7.76 (m, 2H), 7.04-7.12 (m, 2H), 4.64-4.73 (m, 1H), 3.73-3.86 (m, 3H), 3.70 (s, 3H), 3.45-3.59 (m, 1H), 2.37-2.50 (m, 2H), 1.82-2.08 (m, 4H), 1.19 (t, J=7.53 Hz, 3H).

Example 274. Cyclopropyl-{4-[4-(8-methoxyquinolin-7-yl)-phenoxy]-piperidin-1-yl}-methanone, HCl

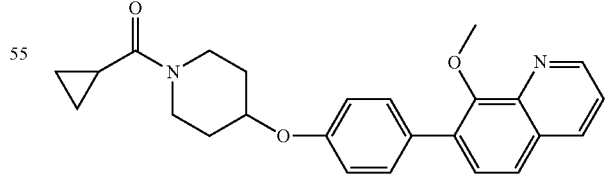

Analysis: LCMS m/z=403 (M+1); $^1$H NMR (400 MHz, CDCl$_3$) δ: 9.40 (d, J=4.52 Hz, 1H), 8.84 (d, J=7.78 Hz, 1H), 7.87-7.98 (m, 3H), 7.72-7.80 (m, 2H), 7.09 (d, J=8.78 Hz, 2H), 4.62-4.76 (m, 1H), 3.87 (s, 5H), 3.66-3.76 (m, 2H), 1.99-2.13 (m, 2H), 1.91 (br. s., 2H), 1.74-1.84 (m, 1H), 0.96-1.04 (m, 2H), 0.74-0.83 (m, 2H).

Example 275. {4-[4-(6-Methylquinolin-7-yl)-phenoxy]-piperidin-1-yl}-(R)-tetrahydro-furan-2-yl-methanone

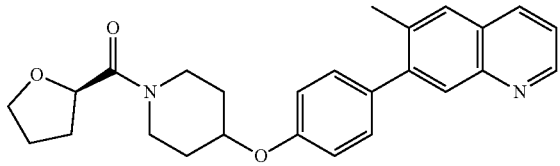 [SMILES: Cc1cc2cccnc2cc1-c1ccc(OC2CCN(C(=O)[C@H]3CCCO3)CC2)cc1]

Analysis: LCMS m/z=417 (M+1); $^1$H NMR (400 MHz, CDCl$_3$) δ: 8.87 (dd, J=4.27, 1.76 Hz, 1H), 8.09 (s, 1H), 7.95 (s, 1H), 7.68 (s, 1H), 7.33-7.40 (m, 3H), 7.01 (d, J=8.78 Hz, 2H), 4.66 (dd, J=7.15, 5.65 Hz, 2H), 3.49-4.01 (m, 6H), 2.44 (s, 3H), 2.28-2.37 (m, 1H), 1.85-2.11 (m, 7H).

Example 276. 1-{4-[4-(6-Methylquinolin-7-yl)-phenoxy]-piperidin-1-yl}-propan-1-one

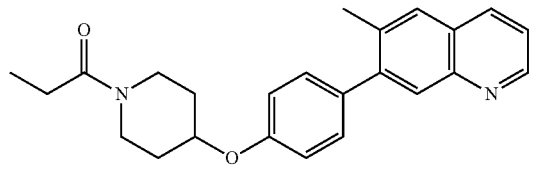 [SMILES: CCC(=O)N1CCC(Oc2ccc(-c3cc4ncccc4cc3C)cc2)CC1]

Analysis: LCMS m/z=375 (M+1); $^1$H NMR (400 MHz, CDCl$_3$) δ: 8.87 (dd, J=4.27, 1.76 Hz, 1H), 8.07-8.14 (m, 1H), 7.95 (s, 1H), 7.68 (s, 1H), 7.35 (d, J=8.78 Hz, 3H), 7.00 (d, J=8.78 Hz, 2H), 4.59-4.67 (m, 1H), 3.81-3.90 (m, 1H), 3.62-3.79 (m, 2H), 3.41-3.51 (m, 1H), 2.44 (s, 3H), 2.36-2.43 (m, 2H), 1.94-2.04 (m, 2H), 1.83-1.93 (m, 2H), 1.18 (t, J=7.53 Hz, 3H).

Example 277. 7-[4-(1-Propionyl-piperidin-4-yloxy)-phenyl]-quinoline-3-carbonitrile

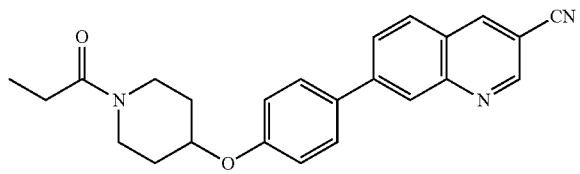 [SMILES: CCC(=O)N1CCC(Oc2ccc(-c3ccc4cc(C#N)cnc4c3)cc2)CC1]

Analysis: LCMS m/z=386 (M+1); $^1$H NMR (400 MHz, CDCl$_3$) δ: 9.04 (d, J=2.26 Hz, 1H), 8.53 (d, J=1.25 Hz, 1H), 8.32 (d, J=1.00 Hz, 1H), 7.93 (d, J=1.00 Hz, 2H), 7.72 (d, J=8.78 Hz, 2H), 7.07 (d, J=8.78 Hz, 2H), 4.59-4.71 (m, 1H), 3.79-3.88 (m, 1H), 3.65-3.77 (m, 2H), 3.39-3.51 (m, 1H), 2.39 (d, J=7.53 Hz, 2H), 1.96-2.03 (m, 2H), 1.82-1.94 (m, 2H), 1.18 (t, J=7.53 Hz, 3H).

Example 278. 7-{4-[1-((R)-Tetrahydrofuran-2-carbonyl)-piperidin-4-yloxy]-phenyl}-quinoline-3-carbonitrile

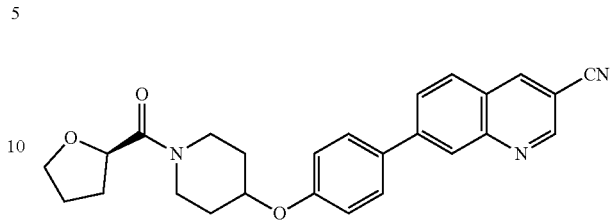

Analysis: LCMS m/z=428 (M+1); $^1$H NMR (400 MHz, CDCl$_3$) δ: 9.04 (d, J=2.01 Hz, 1H), 8.53 (dd, J=2.26, 0.75 Hz, 1H), 8.32 (d, J=1.00 Hz, 1H), 7.94 (d, J=1.26 Hz, 2H), 7.72 (d, J=8.78 Hz, 2H), 7.07 (d, J=8.78 Hz, 2H), 4.65 (dd, J=7.28, 5.52 Hz, 2H), 3.54-4.02 (m, 6H), 2.29-2.40 (m, 1H), 1.87-2.13 (m, 7H).

Example 279. 7-[4-(1-Cyclopropanecarbonyl-piperidin-4-yloxy)-phenyl]-quinoline-3-carbonitrile

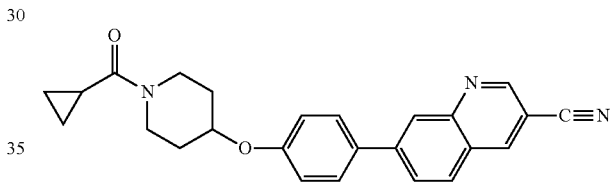

Analysis: LCMS m/z=398 (M+1); $^1$H NMR (400 MHz, CDCl$_3$) δ: 9.04 (d, J=2.01 Hz, 1H), 8.53 (dd, J=2.26, 0.75 Hz, 1H), 8.33 (d, J=0.75 Hz, 1H), 7.94 (d, J=1.00 Hz, 2H), 7.72 (d, J=8.78 Hz, 2H), 7.08 (d, J=9.03 Hz, 2H), 4.61-4.72 (m, 1H), 3.77-4.05 (m, 2H), 3.65-3.76 (m, 2H), 2.01 (s, 4H), 1.79 (s, 1H), 0.97-1.05 (m, 2H), 0.78 (dd, J=8.03, 3.01 Hz, 2H).

Example 280. 1-{4-[4-(3-Methylquinolin-7-yl)-phenoxy]-piperidin-1-yl}-propan-1-one

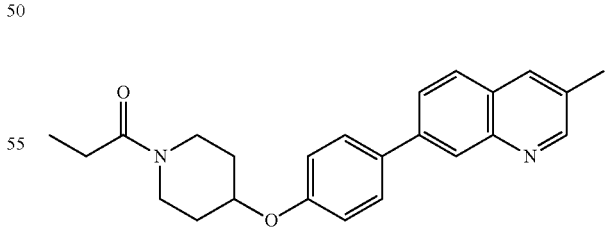

Analysis: LCMS m/z=375 (M+1); $^1$H NMR (400 MHz, CDCl$_3$) δ: 8.78 (d, J=2.01 Hz, 1H), 8.23 (s, 1H), 7.90-7.98 (m, 1H), 7.73-7.83 (m, 2H), 7.69 (d, J=8.78 Hz, 2H), 7.04 (d, J=8.78 Hz, 2H), 4.62 (tt, J=6.56, 3.36 Hz, 1H), 3.83 (br. s., 1H), 3.63-3.77 (m, 2H), 3.45 (dd, J=6.90, 4.39 Hz, 1H), 2.53 (s, 3H), 2.39 (d, J=7.03 Hz, 2H), 1.93-2.04 (m, 2H), 1.81-1.92 (m, 2H), 1.18 (t, J=7.53 Hz, 3H).

Example 281. {4-[4-(3-Methylquinolin-7-yl)-phenoxy]-piperidin-1-yl}-(R)-tetrahydro-furan-2-yl-methanone

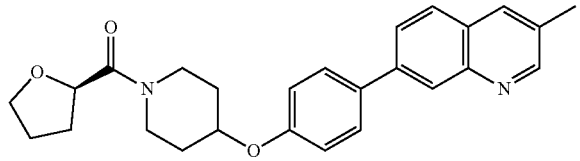 [SMILES: Cc1cnc2cc(-c3ccc(OC4CCN(C(=O)[C@H]5CCCO5)CC4)cc3)ccc2c1]

Analysis: LCMS m/z=417 (M+1); $^1$H NMR (400 MHz, CDCl$_3$) δ: 8.78 (d, J=2.01 Hz, 1H), 8.21-8.25 (m, 1H), 7.90-7.96 (m, 1H), 7.73-7.83 (m, 2H), 7.67-7.71 (m, 2H), 7.04 (d, J=9.04 Hz, 2H), 4.72-4.79 (m, 1H), 3.37-3.68 (m, 4H), 3.13 (s, 2H), 3.07 (s, 5H), 2.53 (s, 3H), 2.15-2.27 (m, 2H), 2.03 (br. s., 2H).

Example 282. Cyclopropyl-{4-[4-(3-methylquinolin-7-yl)-phenoxy]-piperidin-1-yl}-methanone

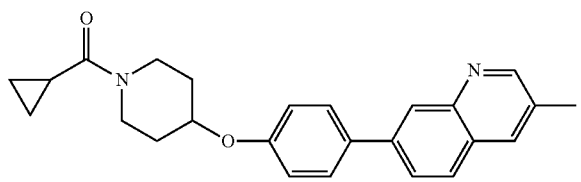 [SMILES: Cc1cnc2cc(-c3ccc(OC4CCN(C(=O)C5CC5)CC4)cc3)ccc2c1]

Analysis: LCMS m/z=387 (M+1); $^1$H NMR (400 MHz, CDCl$_3$) δ: 8.78 (d, J=2.26 Hz, 1H), 8.24 (s, 1H), 7.91-7.96 (m, 1H), 7.74-7.83 (m, 2H), 7.69 (d, J=8.78 Hz, 2H), 7.05 (d, J=8.78 Hz, 2H), 4.61-4.69 (m, 1H), 3.79-4.01 (m, 2H), 3.63-3.73 (m, 2H), 2.53 (s, 3H), 1.84-2.12 (m, 4H), 1.79 (s, 1H), 1.00 (dd, J=4.39, 2.89 Hz, 2H), 0.77 (dd, J=7.91, 3.14 Hz, 2H).

Example 283. {4-[4-(8-Methylimidazo[1,2-a]pyridin-6-yl)-phenoxy]-piperidin-1-yl}-(R)-tetrahydro-furan-2-yl-methanone

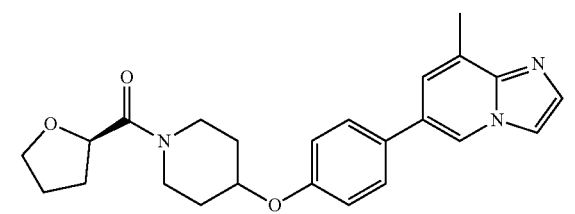 [SMILES: Cc1cc(-c2ccc(OC3CCN(C(=O)[C@H]4CCCO4)CC3)cc2)cn2ccnc12]

Analysis: LCMS m/z=406 (M+1); $^1$H NMR (400 MHz, CDCl$_3$) δ: 8.19 (d, J=0.75 Hz, 1H), 7.76 (s, 1H), 7.66 (d, J=1.51 Hz, 1H), 7.49 (d, J=8.53 Hz, 2H), 7.43 (br. s., 1H), 6.99-7.07 (m, 2H), 4.65 (dd, J=7.15, 5.65 Hz, 2H), 3.50-4.01 (m, 6H), 2.81 (s, 3H), 2.27-2.39 (m, 1H), 1.90-2.11 (m, 7H).

Example 284. 1-{4-[4-(8-Methylimidazo[1,2-a]pyridin-6-yl)-phenoxy]-piperidin-1-yl}-propan-1-one

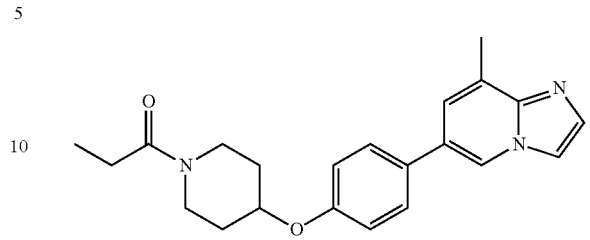

Analysis: LCMS m/z=364 (M+1); $^1$H NMR (400 MHz, CDCl$_3$) δ: 8.13 (dd, J=1.51, 0.75 Hz, 1H), 7.62 (dd, J=10.79, 1.00 Hz, 2H), 7.48 (d, J=8.78 Hz, 2H), 7.17-7.24 (m, 1H), 7.01 (d, J=8.78 Hz, 2H), 4.55-4.65 (m, 1H), 3.60-3.88 (m, 3H), 3.39-3.51 (m, 1H), 2.67 (s, 3H), 2.39 (d, J=7.53 Hz, 2H), 1.75-2.04 (m, 4H), 1.16-1.22 (m, 3H).

Example 285. {4-[4-(5-Methylimidazo[1,2-a]pyridin-6-yl)-phenoxy]-piperidin-1-yl}-(R)-tetrahydro-furan-2-yl-methanone

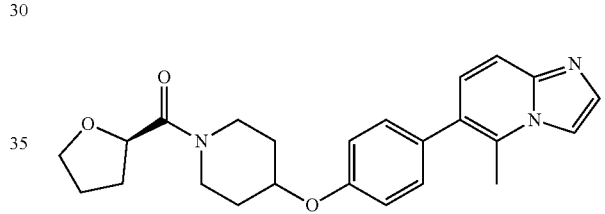

Analysis: LCMS m/z=406 (M+1); $^1$H NMR (400 MHz, CDCl$_3$) δ: 7.73 (d, J=1.25 Hz, 1H), 7.52-7.61 (m, 2H), 7.28 (s, 2H), 7.18 (d, J=9.03 Hz, 1H), 7.00 (d, J=8.78 Hz, 2H), 4.55-4.71 (m, 2H), 3.49-4.00 (m, 6H), 2.55 (s, 3H), 2.26-2.40 (m, 1H), 2.01 (s, 7H).

Example 286. 1-{4-[4-(5-Methylimidazo[1,2-a]pyridin-6-yl)-phenoxy]-piperidin-1-yl}-propan-1-one

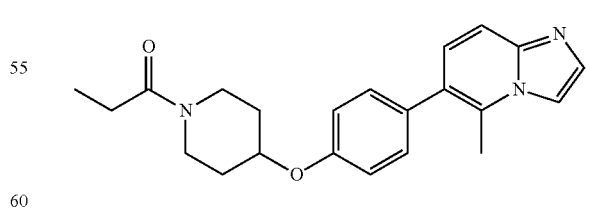

Analysis: LCMS m/z=364 (M+1); $^1$H NMR (400 MHz, CDCl$_3$) δ: 7.73 (d, J=1.26 Hz, 1H), 7.51-7.60 (m, 2H), 7.28 (s, 2H), 7.18 (d, J=9.29 Hz, 1H), 7.00 (d, J=8.78 Hz, 2H), 4.56-4.66 (m, 1H), 3.64-3.90 (m, 3H), 3.41-3.49 (m, 1H), 2.55 (s, 3H), 2.35-2.44 (m, 2H), 1.82-2.05 (m, 4H), 1.18 (t, J=7.53 Hz, 3H).

Example 287. Cyclopropyl-{4-[4-(5-methyl-imidazo[1,2-a]pyridin-6-yl)-phenoxy]-piperidin-1-yl})-methanone

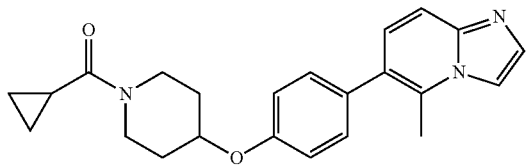 [SMILES: Cc1c(-c2ccc(OC3CCN(C(=O)C4CC4)CC3)cc2)ccc2nccn12]

Analysis: LCMS m/z=376 (M+1); $^1$H NMR (400 MHz, CDCl$_3$) δ: 7.73 (d, J=1.00 Hz, 1H), 7.58 (d, J=9.04 Hz, 1H), 7.53 (s, 1H), 7.26-7.29 (m, 3H), 7.18 (d, J=9.03 Hz, 1H), 6.98-7.05 (m, 2H), 4.58-4.67 (m, 1H), 3.79-4.03 (m, 2H), 3.64-3.73 (m, 2H), 2.55 (s, 3H), 2.01 (s, 4H), 1.75-1.83 (m, 1H), 1.01 (dd, J=4.39, 2.89 Hz, 2H), 0.78 (dd, J=7.91, 3.14 Hz, 2H).

Example 288. Cyclopropyl-{4-[4-(8-methylimidazo[1,2-a]pyridin-6-yl)-phenoxy]-piperidin-1-yl})-methanone

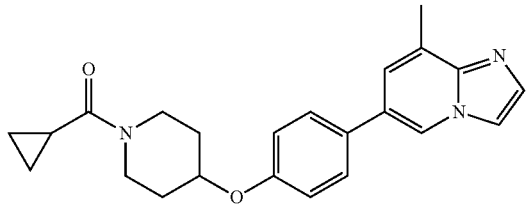 [SMILES: Cc1cc(-c2ccc(OC3CCN(C(=O)C4CC4)CC3)cc2)cn2ccnc12]

Analysis: LCMS m/z=376 (M+1); $^1$H NMR (400 MHz, CDCl$_3$) δ: 8.13 (d, J=0.75 Hz, 1H), 7.62 (dd, J=10.04, 1.25 Hz, 2H), 7.45-7.52 (m, 2H), 7.20 (d, J=1.25 Hz, 1H), 6.99-7.06 (m, 2H), 4.58-4.67 (m, 1H), 3.75-4.00 (m, 2H), 3.61-3.74 (m, 2H), 2.67 (s, 3H), 2.01 (s, 4H), 1.78 (s, 1H), 0.97-1.06 (m, 2H), 0.78 (dd, J=8.03, 3.01 Hz, 2H).

Example 289. {4-[4-(2,3-Dimethylimidazo[1,2-a]pyridin-6-yl)-phenoxy]-piperidin-1-yl}-(R)-tetrahydrofuran 2-yl-methanone

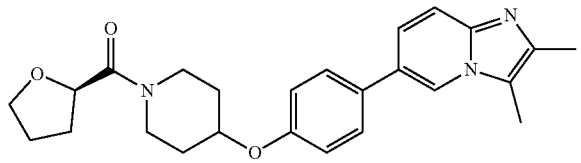 [SMILES: Cc1nc2ccc(-c3ccc(OC4CCN(C(=O)[C@H]5CCCO5)CC4)cc3)cn2c1C]

Analysis: LCMS m/z=420 (M+1); $^1$H NMR (400 MHz, CDCl$_3$) δ: 7.88 (s, 1H), 7.55 (dd, J=9.29, 0.75 Hz, 1H), 7.50 (d, J=8.53 Hz, 2H), 7.33 (dd, J=9.29, 1.76 Hz, 1H), 6.98-7.04 (m, 2H), 4.55-4.69 (m, 2H), 3.95 (s, 6H), 2.44 (d, J=3.51 Hz, 6H), 2.28-2.38 (m, 1H), 1.86-2.11 (m, 7H).

Example 290. 1-{4-[4-(2,3-Dimethylimidazo[1,2-a]pyridin-6-yl)-phenoxy]-piperidin-1-yl}-propan-1-one

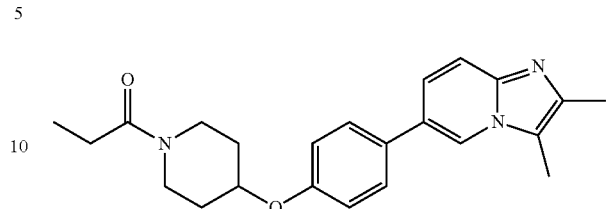

Analysis: LCMS m/z=378 (M+1); $^1$H NMR (400 MHz, CDCl$_3$) δ: 7.88 (s, 1H), 7.55 (d, J=9.29 Hz, 1H), 7.48-7.52 (m, 2H), 7.33 (dd, J=9.29, 1.76 Hz, 1H), 6.98-7.05 (m, 2H), 4.55-4.66 (m, 1H), 3.65-3.88 (m, 3H), 3.42-3.50 (m, 1H), 2.34-2.48 (m, 8H), 1.96 (d, J=4.02 Hz, 4H), 1.17 (t, J=7.40 Hz, 3H).

Example 291. Cyclopropyl-{4-[4-(2,3-dimethylimidazo[1,2-a]pyridin-6-yl)-phenoxy]-piperidin-1-yl}-methanone

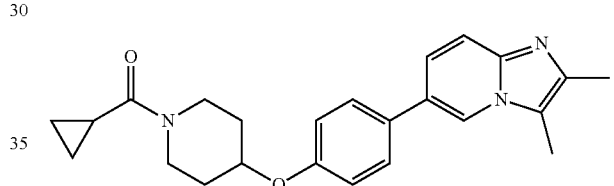

Analysis: LCMS m/z=390 (M+1); $^1$H NMR (400 MHz, CDCl$_3$) δ: 7.88 (s, 1H), 7.48-7.58 (m, 3H), 7.33 (dd, J=9.03, 1.76 Hz, 1H), 7.03 (d, J=8.78 Hz, 2H), 4.58-4.67 (m, 1H), 3.77-4.02 (m, 2H), 3.62-3.73 (m, 2H), 2.44 (d, J=3.51 Hz, 6H), 1.75-2.11 (m, 5H), 0.97-1.05 (m, 2H), 0.74-0.81 (m, 2H).

Example 292. {4-[4-(7-Methylimidazo[1,2-a]pyridin-6-yl)-phenoxy]-piperidin-1-yl}-(R)-tetrahydrofuran-2-yl-methanone

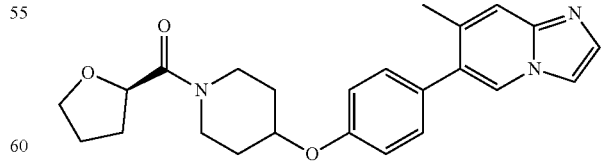

Analysis: LCMS m/z=406 (M+1); $^1$H NMR (400 MHz, CDCl$_3$) δ: 7.95 (s, 1H), 7.59 (d, J=1.26 Hz, 1H), 7.43-7.53 (m, 2H), 7.24 (s, 2H), 6.98 (d, J=8.78 Hz, 2H), 4.57-4.70 (m, 2H), 3.54-4.00 (m, 6H), 2.30-2.38 (m, 1H), 2.26 (s, 3H), 1.87-2.12 (m, 7H).

Example 293. 1-{4-[4-(7-Methylimidazo[1,2-a]pyridin-6-yl)-phenoxy]-piperidin-1-yl}-propan-1-one

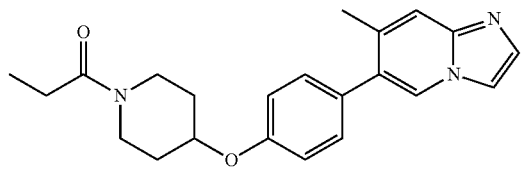 [SMILES: CCC(=O)N1CCC(Oc2ccc(-c3cn4ccnc4cc3C)cc2)CC1]

Analysis: LCMS m/z=364 (M+1); ¹H NMR (400 MHz, CDCl₃) δ: 7.94 (s, 1H), 7.59 (d, J=1.25 Hz, 1H), 7.46-7.52 (m, 2H), 7.24 (s, 2H), 6.98 (d, J=8.53 Hz, 2H), 4.53-4.65 (m, 1H), 3.63-3.89 (m, 3H), 3.40-3.50 (m, 1H), 2.38 (s, 2H), 2.26 (d, J=0.75 Hz, 3H), 1.79-2.04 (m, 4H), 1.18 (t, J=7.40 Hz, 3H).

Example 294. {4-[4-(5-Chloroimidazo[1,2-a]pyridin-6-yl)-phenoxy]-piperidin-1-yl}-(R)-tetrahydrofuran-2-yl-methanone

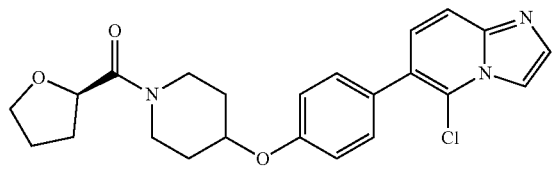 [SMILES: O=C([C@H]1CCCO1)N1CCC(Oc2ccc(-c3ccc4nccn4c3Cl)cc2)CC1]

Analysis: LCMS m/z=426 (M+1); ¹H NMR (400 MHz, CDCl₃) δ: 7.86 (d, J=0.75 Hz, 1H), 7.74 (d, J=1.25 Hz, 1H), 7.64 (d, J=9.03 Hz, 1H), 7.41 (d, J=8.53 Hz, 2H), 7.24 (s, 1H), 7.01 (d, J=8.78 Hz, 2H), 4.59-4.70 (m, 2H), 3.55-4.00 (m, 6H), 2.29-2.40 (m, 1H), 1.85-2.14 (m, 7H).

Example 295. {4-[4-(5-Chloroimidazo[1,2-a]pyridin-6-yl)-phenoxy]-piperidin-1-yl}-(R)-tetrahydrofuran-2-yl-methanone

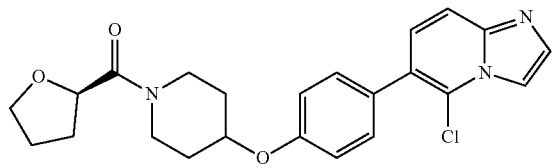 [SMILES: O=C([C@H]1CCCO1)N1CCC(Oc2ccc(-c3ccc4nccn4c3Cl)cc2)CC1]

Analysis: LCMS m/z=426 (M+1); ¹H NMR (400 MHz, CDCl₃) δ: 7.86 (d, J=0.75 Hz, 1H), 7.74 (d, J=1.25 Hz, 1H), 7.64 (d, J=9.03 Hz, 1H), 7.41 (d, J=8.53 Hz, 2H), 7.24 (s, 1H), 7.01 (d, J=8.78 Hz, 2H), 4.59-4.70 (m, 2H), 3.55-4.00 (m, 6H), 2.29-2.40 (m, 1H), 1.85-2.14 (m, 7H).

Example 296. 1-{4-[4-(5-Chloroimidazo[1,2-a]pyridin-6-yl)-phenoxy]-piperidin-1-yl}-propan-1-one

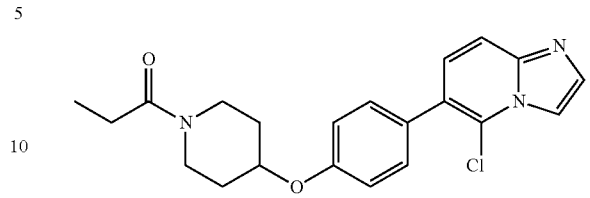

Analysis: LCMS m/z=384 (M+1); ¹H NMR (400 MHz, CDCl₃) δ: 7.85-7.88 (m, 1H), 7.74 (d, J=1.26 Hz, 1H), 7.64 (dd, J=9.03, 0.75 Hz, 1H), 7.41 (d, J=8.78 Hz, 2H), 7.24 (s, 1H), 6.98-7.04 (m, 2H), 4.57-4.65 (m, 1H), 3.71 (d, J=3.51 Hz, 3H), 3.41-3.51 (m, 1H), 2.38 (s, 2H), 1.82-2.05 (m, 4H), 1.18 (t, J=7.53 Hz, 3H).

Example 297. {4-[4-(5-Chloroimidazo[1,2-a]pyridin-6-yl)-phenoxy]-piperidin-1-yl})-cyclopropylmethanone

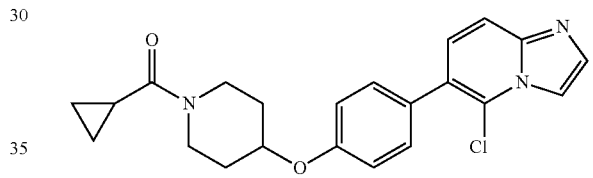

Analysis: LCMS m/z=396 (M+1); ¹H NMR (400 MHz, CDCl₃) δ: 7.86 (d, J=1.76 Hz, 1H), 7.74 (d, J=1.51 Hz, 1H), 7.64 (dd, J=9.29, 0.75 Hz, 1H), 7.39-7.44 (m, 2H), 7.24 (s, 1H), 6.99-7.06 (m, 2H), 4.61-4.67 (m, 1H), 3.78-4.01 (m, 2H), 3.66-3.73 (m, 2H), 1.79 (s, 5H), 1.00 (dd, J=4.52, 3.01 Hz, 2H), 0.78 (dd, J=8.03, 3.01 Hz, 2H).

Example 298. [4-(4-Imidazo[1,5-a]pyridin-6-yl-phenoxy)-piperidin-1-yl]-(R)-tetrahydro-furan-2-yl-methanone

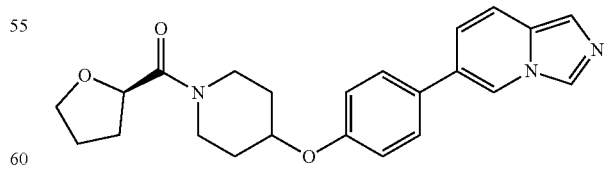

Analysis: LCMS m/z=392 (M+1); ¹H NMR (400 MHz, CDCl₃) δ: 8.17 (s, 1H), 8.05 (d, J=1.25 Hz, 1H), 7.42-7.53 (m, 4H), 6.93-7.05 (m, 3H), 4.58-4.70 (m, 2H), 3.54-4.02 (m, 6H), 2.28-2.39 (m, 1H), 2.01 (s, 7H).

Example 299. 1-[4-(4-Imidazo[1,5-a]pyridin-6-yl-phenoxy)-piperidin-1-yl]-propan-1-one

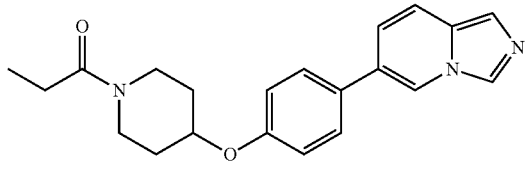 [SMILES: CCC(=O)N1CCC(Oc2ccc(-c3ccc4cncn4c3)cc2)CC1]

Analysis: LCMS m/z=350 (M+1); $^1$H NMR (400 MHz, CDCl$_3$) δ: 8.14 (s, 1H), 8.04 (q, J=1.17 Hz, 1H), 7.42-7.53 (m, 4H), 6.95-7.04 (m, 3H), 4.55-4.64 (m, 1H), 3.64-3.87 (m, 3H), 3.39-3.48 (m, 1H), 2.39 (d, J=7.28 Hz, 2H), 1.80-2.04 (m, 4H), 1.17 (t, J=7.40 Hz, 3H).

Example 300. Cyclopropyl-[4-(4-imidazo[1,5-a]pyridin-6-yl-phenoxy)-piperidin-1-yl]-methanone

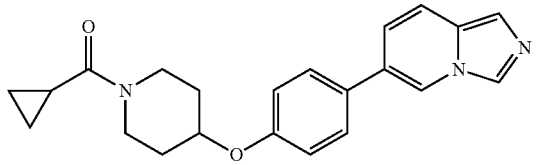 [SMILES: O=C(C1CC1)N1CCC(Oc2ccc(-c3ccc4cncn4c3)cc2)CC1]

Analysis: LCMS m/z=362 (M+1); $^1$H NMR (400 MHz, CDCl$_3$) δ: 8.15 (s, 1H), 8.05 (d, J=1.25 Hz, 1H), 7.42-7.53 (m, 4H), 7.02 (d, J=8.78 Hz, 3H), 4.57-4.67 (m, 1H), 3.77-4.01 (m, 2H), 3.63-3.72 (m, 2H), 1.74-2.09 (m, 5H), 0.97-1.04 (m, 2H), 0.75-0.82 (m, 2H).

Example 301. 1-[4-(4-Imidazo[1,5-a]pyridin-6-yl-phenoxy)-piperidine-1-carbonyl]-cyclopropanecarboxylic acid amide

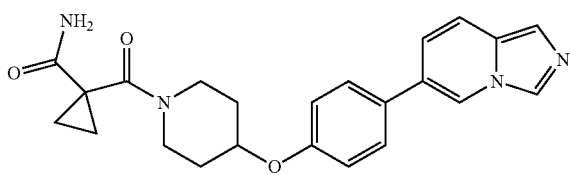 [SMILES: NC(=O)C1(C(=O)N2CCC(Oc3ccc(-c4ccc5cncn5c4)cc3)CC2)CC1]

Analysis: LCMS m/z=405 (M+1); $^1$H NMR (400 MHz, CDCl$_3$) δ: 8.15 (s, 1H), 8.04 (d, J=1.25 Hz, 1H), 7.41-7.52 (m, 4H), 6.94-7.05 (m, 3H), 5.89-6.04 (m, 1H), 5.33-5.47 (m, 1H), 4.60-4.67 (m, 1H), 3.67-3.90 (m, 4H), 1.88-2.02 (m, 4H), 1.47-1.53 (m, 2H), 1.23-1.29 (m, 2H).

Example 302. (1-Hydroxycyclopropyl)-[4-(4-imidazo[1,5-a]pyridin-6-yl-phenoxy)-piperidin-1-yl]-methanone

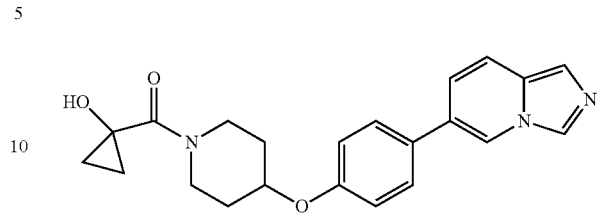

Analysis: LCMS m/z=378 (M+1); $^1$H NMR (400 MHz, CDCl$_3$) δ: 8.15 (s, 1H), 8.05 (d, J=1.25 Hz, 1H), 7.42-7.54 (m, 4H), 6.94-7.06 (m, 3H), 4.59-4.66 (m, 1H), 3.87-4.01 (m, 2H), 3.74 (br. s., 2H), 3.01-3.10 (m, 1H), 1.96-2.07 (m, 2H), 1.83-1.94 (m, 2H), 1.12-1.18 (m, 2H), 0.96-1.03 (m, 2H).

Example 303. (1-Hydroxycyclopropyl)-{4-[4-(8-methoxy-quinolin-7-yl)-phenoxy]-piperidin-1-yl}-methanone

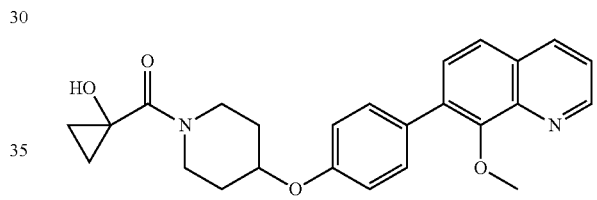

Analysis: LCMS m/z=419 (M+1); $^1$H NMR (400 MHz, CDCl$_3$) δ: 8.98 (dd, J=4.27, 1.76 Hz, 1H), 8.16 (dd, J=8.28, 1.76 Hz, 1H), 7.54-7.71 (m, 4H), 7.41 (dd, J=8.16, 4.14 Hz, 1H), 7.02-7.08 (m, 2H), 4.58-4.72 (m, 1H), 3.92-4.06 (m, 2H), 3.87 (s, 3H), 3.71-3.82 (m, 2H), 3.12-3.37 (m, 1H), 2.01-2.08 (m, 2H), 1.88-1.98 (m, 2H), 1.15 (d, J=2.76 Hz, 2H), 0.99 (d, J=2.51 Hz, 2H).

Example 304. (1-Hydroxymethylcyclopropyl)-{4-[4-(5-methyl-imidazo[1,2-a]pyridin-6-yl)-phenoxy]-piperidin-1-yl}-methanone

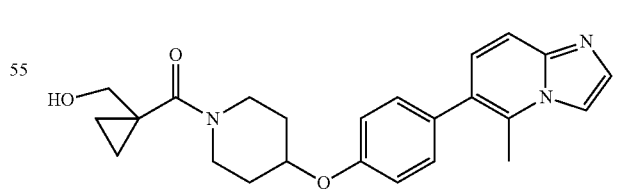

Analysis: LCMS m/z=406 (M+1); $^1$H NMR (400 MHz, CDCl$_3$) δ: 7.74 (d, J=1.25 Hz, 1H), 7.53-7.60 (m, 2H), 7.26-7.29 (m, 2H), 7.18 (d, J=9.03 Hz, 1H), 7.00 (d, J=8.78 Hz, 2H), 4.59-4.66 (m, 1H), 3.84-3.95 (m, 2H), 3.68 (s, 4H), 2.55 (s, 3H), 1.85-2.05 (m, 4H), 1.78-1.84 (m, 1H), 0.99-1.05 (m, 2H), 0.80-0.85 (m, 2H).

Example 305. (1-Aminocyclopropyl)-{4-[4-(5-methyl-imidazo[1,2-a]pyridin-6-yl)-phenoxy]-piperidin-1-yl}-methanone

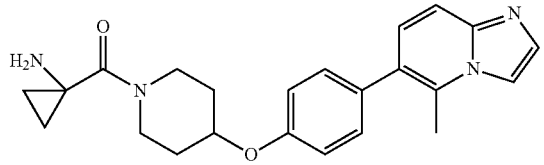 [SMILES: Cc1c(-c2ccc(OC3CCN(C(=O)C4(N)CC4)CC3)cc2)ccc2nccn12]

Analysis: LCMS m/z=391 (M+1); $^1$H NMR (400 MHz, CDCl$_3$) δ: 7.74 (d, J=1.25 Hz, 1H), 7.53-7.61 (m, 2H), 7.28 (d, J=8.78 Hz, 2H), 7.18 (d, J=9.29 Hz, 1H), 7.01 (d, J=8.78 Hz, 2H), 4.58-4.69 (m, 1H), 3.85-3.97 (m, 2H), 3.68-3.78 (m, 2H), 2.55 (s, 3H), 1.76-2.08 (m, 6H), 1.04 (d, J=2.26 Hz, 2H), 0.83 (d, J=2.26 Hz, 2H).

Example 306. (1-Hydroxycyclopropyl)-[4-(4-[1,2,4]triazolo[4,3-a]pyridin-7-yl-phenoxy)-piperidin-1-yl]-methanone

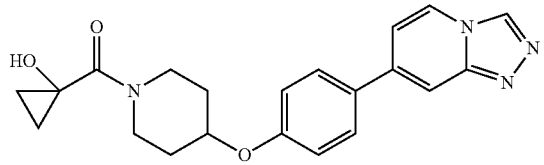 [SMILES: O=C(N1CCC(Oc2ccc(-c3ccn4cnnc4c3)cc2)CC1)C1(O)CC1]

Analysis: LCMS m/z=379 (M+1); $^1$H NMR (400 MHz, CDCl$_3$) δ: 8.81 (d, J=0.75 Hz, 1H), 8.12-8.20 (m, 1H), 7.88-7.94 (m, 1H), 7.61 (d, J=8.78 Hz, 2H), 7.13-7.17 (m, 1H), 7.05 (d, J=8.78 Hz, 2H), 4.59-4.71 (m, 1H), 3.87-4.02 (m, 2H), 3.68-3.82 (m, 2H), 2.90-2.98 (m, 1H), 1.97-2.09 (m, 2H), 1.84-1.94 (m, 2H), 1.12-1.19 (m, 2H), 0.97-1.04 (m, 2H).

Example 307. (R)-Tetrahydrofuran-2-yl-[4-(4-[1,2,4]triazolo[4,3-a]pyridin-7-yl-phenoxy)-piperidin-1-yl]-methanone

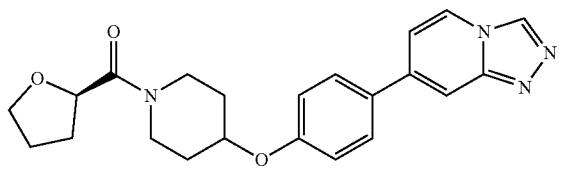 [SMILES: O=C([C@H]1CCCO1)N1CCC(Oc2ccc(-c3ccn4cnnc4c3)cc2)CC1]

Analysis: LCMS m/z=393 (M+1); $^1$H NMR (400 MHz, CDCl$_3$) δ: 8.80 (d, J=0.75 Hz, 1H), 8.15 (dd, J=7.28, 1.00 Hz, 1H), 7.88-7.93 (m, 1H), 7.61 (d, J=8.53 Hz, 2H), 7.13 (dd, J=7.28, 1.76 Hz, 1H), 7.04 (d, J=8.78 Hz, 2H), 4.59-4.71 (m, 2H), 3.51-4.01 (m, 6H), 2.28-2.39 (m, 1H), 1.87-2.11 (m, 7H).

Example 308. Cyclopropyl-[4-(4-[1,2,4]triazolo[4,3-a]pyridin-7-yl-phenoxy)-piperidin-1-yl]-methanone

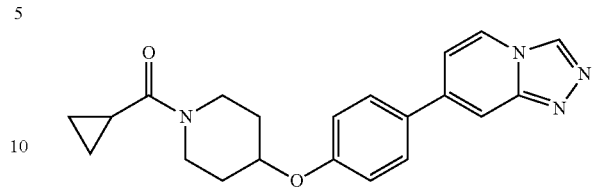

Analysis: LCMS m/z=363 (M+1); $^1$H NMR (400 MHz, CDCl$_3$) δ: 8.81 (s, 1H), 8.15 (dd, J=7.03, 1.00 Hz, 1H), 7.86-7.95 (m, 1H), 7.61 (d, J=8.78 Hz, 2H), 7.14 (dd, J=7.15, 1.63 Hz, 1H), 7.03-7.10 (m, 2H), 4.60-4.70 (m, 1H), 3.77-4.02 (m, 2H), 3.68 (ddd, J=13.36, 6.96, 4.02 Hz, 2H), 2.01 (s, 4H), 1.79 (t, J=4.64 Hz, 1H), 1.00 (dd, J=4.52, 3.01 Hz, 2H), 0.78 (dd, J=7.78, 3.01 Hz, 2H).

Example 309. (1-Hydroxycyclopropyl)-{4-[4-(5-methyl-imidazo[1,2-a]pyridin-6-yl)-phenoxy]-piperidin-1-yl}-methanone

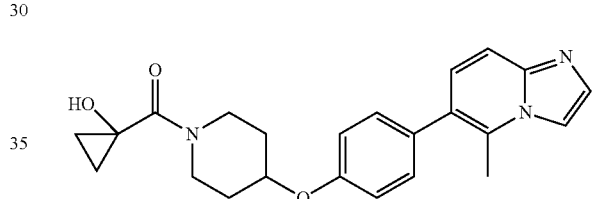

Analysis: LCMS m/z=392 (M+1); $^1$H NMR (400 MHz, CDCl$_3$) δ: 8.81 (s, 1H), 8.15 (dd, J=7.03, 1.00 Hz, 1H), 7.86-7.95 (m, 1H), 7.61 (d, J=8.78 Hz, 2H), 7.14 (dd, J=7.15, 1.63 Hz, 1H), 7.03-7.10 (m, 2H), 4.60-4.70 (m, 1H), 3.77-4.02 (m, 2H), 3.68 (ddd, J=13.36, 6.96, 4.02 Hz, 2H), 2.01 (s, 4H), 1.79 (t, J=4.64 Hz, 1H), 1.00 (dd, J=4.52, 3.01 Hz, 2H), 0.78 (dd, J=7.78, 3.01 Hz, 2H).

Example 310. 2-Hydroxy-2-methyl-1-{4-[4-(5-methyl-imidazo[1,2-a]pyridin-6-yl)-phenoxy]-piperidin-1-yl}-propan-1-one

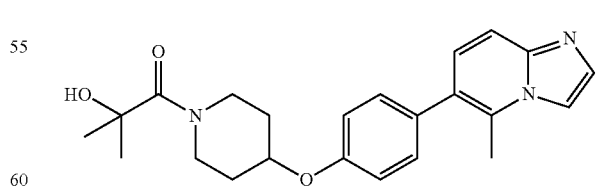

Analysis: LCMS m/z=394 (M+1); $^1$H NMR (400 MHz, CDCl$_3$) δ: 7.74 (d, J=1.25 Hz, 1H), 7.56-7.61 (m, 1H), 7.54 (s, 1H), 7.29 (s, 2H), 7.17-7.22 (m, 1H), 7.00 (d, J=8.78 Hz, 2H), 4.62-4.71 (m, 1H), 4.49 (s, 1H), 3.81-3.94 (m, 2H), 3.73 (s, 2H), 2.55 (s, 3H), 1.88-2.06 (m, 4H), 1.53 (s, 6H).

Example 311. {4-[4-(5-Methyl-[1,2,4]triazolo[1,5-a]pyridin-6-yl)-phenoxy]-piperidin-1-yl}-(R)-tetrahydrofuran-2-yl-methanone

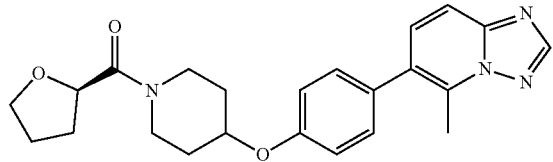 [SMILES: Cc1c(-c2ccc(OC3CCN(C(=O)[C@H]4CCCO4)CC3)cc2)ccc2ncnn12]

Analysis: LCMS m/z=407 (M+1); $^1$H NMR (400 MHz, CDCl$_3$) δ: 8.39 (s, 1H), 7.67 (s, 1H), 7.49 (d, J=9.03 Hz, 1H), 7.30 (d, J=8.53 Hz, 2H), 7.02 (d, J=8.78 Hz, 2H), 4.57-4.72 (m, 2H), 3.53-4.04 (m, 6H), 2.78 (s, 3H), 2.28-2.40 (m, 1H), 1.88-2.13 (m, 7H).

Example 312. (1-Hydroxycyclopropyl)-{4-[4-(5-methyl-[1,2,4]triazolo[1,5-a]pyridin-6-yl)-phenoxy]-piperidin-1-yl}-methanone

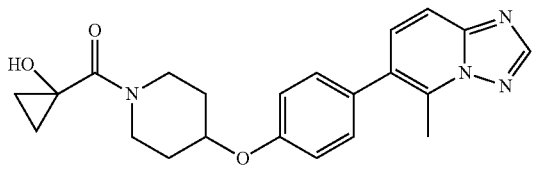 [SMILES: Cc1c(-c2ccc(OC3CCN(C(=O)C4(O)CC4)CC3)cc2)ccc2ncnn12]

Analysis: LCMS m/z=393 (M+1); $^1$H NMR (400 MHz, CDCl$_3$) δ: 8.39 (s, 1H), 7.66-7.73 (m, 1H), 7.47-7.54 (m, 1H), 7.28-7.34 (m, 2H), 7.30 (d, J=8.78 Hz, 2H), 7.03 (d, J=8.78 Hz, 2H), 4.61-4.69 (m, 1H), 3.90-4.03 (m, 2H), 3.69-3.81 (m, 2H), 2.78 (s, 4H), 1.99-2.09 (m, 2H), 1.87-1.97 (m, 2H), 1.14-1.19 (m, 2H), 1.00 (d, J=2.76 Hz, 2H).

Example 313. 1-{4-[4-(5-Methyl-[1,2,4]triazolo[1,5-a]pyridin-6-yl)-phenoxy]-piperidin-1-yl})-propan-1-one

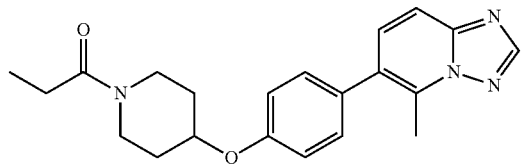 [SMILES: CCC(=O)N1CCC(Oc2ccc(-c3ccc4ncnn4c3C)cc2)CC1]

Analysis: LCMS m/z=365 (M+1); $^1$H NMR (400 MHz, CDCl$_3$) δ: 8.39 (s, 1H), 7.69 (d, J=9.04 Hz, 1H), 7.49 (d, J=9.03 Hz, 1H), 7.30 (d, J=8.78 Hz, 2H), 7.02 (d, J=8.78 Hz, 2H), 4.56-4.67 (m, 1H), 3.63-3.91 (m, 3H), 3.38-3.51 (m, 1H), 2.78 (s, 3H), 2.34-2.47 (m, 2H), 1.83-2.06 (m, 4H), 1.18 (s, 3H).

Example 314. Cyclopropyl-{4-[4-(5-methyl-[1,2,4]triazolo[1,5-a]pyridin-6-yl)-phenoxy]-piperidin-1-yl}-methanone

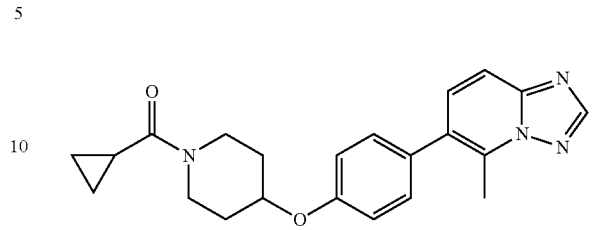

Analysis: LCMS m/z=377 (M+1); $^1$H NMR (400 MHz, CDCl$_3$) δ: 8.39 (s, 1H), 7.63-7.73 (m, 1H), 7.50 (d, J=9.29 Hz, 1H), 7.30 (d, J=8.78 Hz, 2H), 7.03 (d, J=8.78 Hz, 2H), 4.58-4.69 (m, 1H), 3.77-4.02 (m, 2H), 3.63-3.74 (m, 2H), 2.78 (s, 3H), 1.72-2.12 (m, 6H), 0.95-1.05 (m, 2H), 0.75-0.81 (m, 2H).

Example 315. {4-[4-(8-Methylquinolin-7-yl)-phenoxy]-piperidin-1-yl}-(1-trifluoro-methylcyclopropyl)-methanone

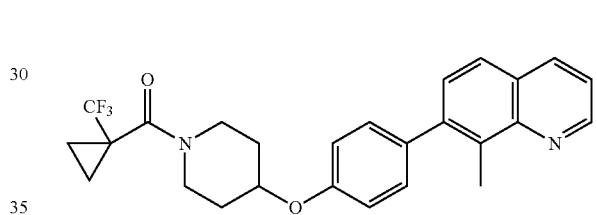

Analysis: LCMS m/z=455 (M+1); $^1$H NMR (400 MHz, CDCl$_3$) δ: 8.99 (dd, J=4.27, 1.76 Hz, 1H), 8.16 (dd, J=8.28, 1.76 Hz, 1H), 7.70 (d, J=8.53 Hz, 1H), 7.46 (d, J=8.28 Hz, 1H), 7.42 (dd, J=8.28, 4.27 Hz, 1H), 7.32-7.38 (m, 2H), 6.98-7.05 (m, 2H), 4.66 (t, J=3.51 Hz, 1H), 3.81 (br. s., 4H), 2.77 (s, 3H), 1.91-2.08 (m, 4H), 1.31-1.42 (m, 2H), 1.19 (s, 2H).

Example 316. (1-Aminocyclopropyl)-{4-[4-(8-methyl-quinolin-7-yl)-phenoxy]-piperidin-1-yl}-methanone

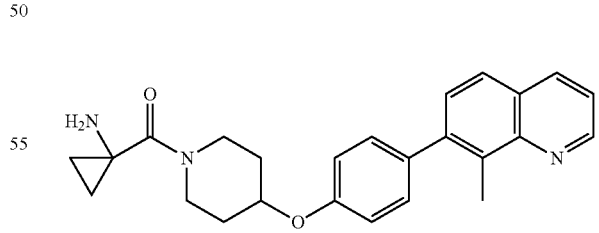

Analysis: LCMS m/z=402 (M+1); $^1$H NMR (400 MHz, CDCl$_3$) δ: 8.94-9.08 (m, 1H), 8.13-8.21 (m, 1H), 7.66-7.74 (m, 1H), 7.45-7.50 (m, 1H), 7.38-7.45 (m, 1H), 7.32-7.38 (m, 2H), 7.00-7.07 (m, 2H), 4.60-4.72 (m, 1H), 3.86-3.98 (m, 2H), 3.73 (dd, J=6.90, 4.14 Hz, 2H), 2.77 (s, 3H), 1.98-2.08 (m, 2H), 1.78-1.98 (m, 4H), 1.01-1.08 (m, 2H), 0.79-0.88 (m, 2H).

Example 317. {4-[4-(1-Methyl-1H-indazol-6-yl)-phenoxy]-piperidin-1-yl}-(R)-tetrahydrofuran-2-yl-methanone; compound with trifluoroacetic acid

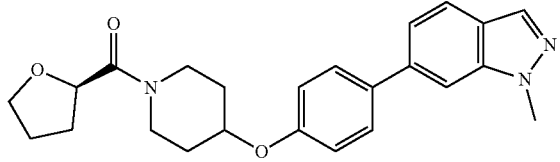 [SMILES: Cn1ncc2ccc(-c3ccc(OC4CCN(C(=O)[C@H]5CCCO5)CC4)cc3)cc21]

Analysis: LCMS m/z=406 (M+1); ¹H NMR (400 MHz, CDCl₃) δ: 8.04 (1H, d, J=1.0 Hz), 7.78 (1H, dd, J=8.5, 0.8 Hz), 7.61 (2H, d, J=8.5 Hz), 7.50 (1H, s), 7.40 (1H, dd, J=8.4, 1.4 Hz), 6.96-7.07 (2H, m), 4.66-4.72 (1H, m), 4.09-4.19 (3H, m), 3.40-4.05 (6H, m), 1.80-2.34 (8H, m).

Example 318. [4-(4-Imidazo[1,2-a]pyridin-6-yl-phenoxy)-piperidin-1-yl]-(R)-tetrahydro-furan-2-yl-methanone; compound with trifluoroacetic acid

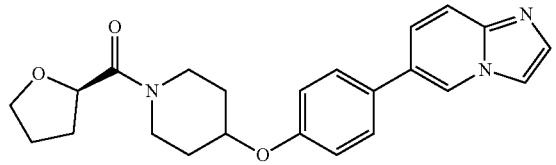 [SMILES: O=C([C@H]1CCCO1)N1CCC(Oc2ccc(-c3ccc4nccn4c3)cc2)CC1]

Analysis: LCMS m/z=392 (M+1); ¹H NMR (400 MHz, CDCl₃) δ: 8.26 (1H, s), 7.58-7.72 (3H, m), 7.48 (2H, d, J=8.5 Hz), 7.39 (1H, dd, J=9.3, 1.8 Hz), 7.02 (2H, d, J=8.5 Hz), 4.57-4.72 (2H, m), 3.43-4.03 (6H, m), 2.31 (1H, br. s.), 1.80-2.14 (7H, m).

Example 319. 1-{4-[4-(8-Methylquinolin-7-yl)-phenoxy]-piperidine-1-carbonyl}-cyclopropanecarbonitrile

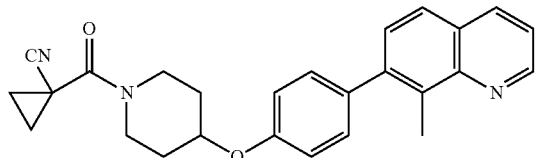

Analysis: LCMS m/z=412 (M+1); ¹H NMR (400 MHz, CDCl₃) δ: 8.99 (dd, J=4.27, 1.76 Hz, 1H), 8.16 (dd, J=8.28, 1.76 Hz, 1H), 7.70 (d, J=8.28 Hz, 1H), 7.47 (d, J=8.53 Hz, 1H), 7.33-7.44 (m, 3H), 6.99-7.09 (m, 2H), 4.68-4.77 (m, 1H), 3.65-4.10 (m, 4H), 2.77 (s, 3H), 1.94-2.19 (m, 4H), 1.65 (br. s., 4H).

Example 320. (1-Methylcyclopropyl)-{4-[4-(8-methyl-quinolin-7-yl)-phenoxy]-piperidin-1-yl}-methanone

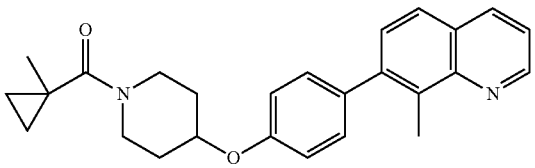 [SMILES: Cc1c(-c2ccc(OC3CCN(C(=O)C4(C)CC4)CC3)cc2)ccc2cccnc12]

Analysis: LCMS m/z=401 (M+1); ¹H NMR (400 MHz, CDCl₃) δ: 8.99 (dd, J=4.14, 1.88 Hz, 1H), 8.11-8.20 (m, 1H), 7.69 (s, 1H), 7.47 (d, J=8.53 Hz, 1H), 7.39-7.45 (m, 1H), 7.35 (d, J=8.53 Hz, 2H), 7.02 (d, J=8.78 Hz, 2H), 4.57-4.68 (m, 1H), 3.85-4.00 (m, 2H), 3.61-3.76 (m, 2H), 2.77 (s, 3H), 1.84-2.05 (m, 4H), 1.34 (s, 3H), 0.96 (d, J=1.76 Hz, 2H), 0.60 (d, J=1.76 Hz, 2H).

Example 321. ((S)-2,2-Dimethylcyclopropyl)-{4-[4-(8-methyl-quinolin-7-yl)-phenoxy]-piperidin-1-yl}-methanone

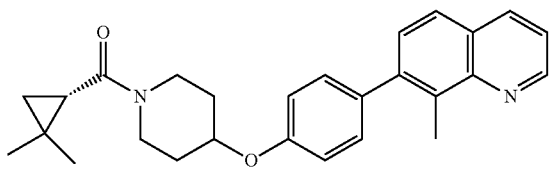 [SMILES: Cc1c(-c2ccc(OC3CCN(C(=O)[C@H]4CC4(C)C)CC3)cc2)ccc2cccnc12]

Analysis: LCMS m/z=415 (M+1); ¹H NMR (400 MHz, CDCl₃) δ: 8.99 (dd, J=4.02, 1.76 Hz, 1H), 8.16 (dd, J=8.16, 1.63 Hz, 1H), 7.70 (d, J=8.53 Hz, 1H), 7.48 (s, 1H), 7.42 (dd, J=8.03, 4.27 Hz, 1H), 7.35 (d, J=8.53 Hz, 2H), 7.03 (d, J=8.53 Hz, 2H), 4.63 (br. s., 1H), 3.56-4.02 (m, 4H), 2.77 (s, 3H), 1.82-2.14 (m, 4H), 1.18-1.28 (m, 5H), 1.08 (br. s., 3H), 0.68-0.77 (m, 1H).

Example 322. (2,2-Dimethylcyclopropyl)-{4-[4-(8-methyl-quinolin-7-yl)-phenoxy]-piperidin-1-yl}-methanone

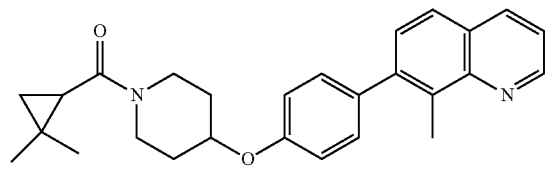 [SMILES: Cc1c(-c2ccc(OC3CCN(C(=O)C4CC4(C)C)CC3)cc2)ccc2cccnc12]

Analysis: LCMS m/z=415 (M+1); ¹H NMR (400 MHz, CDCl₃) δ: 8.99 (dd, J=3.89, 1.38 Hz, 1H), 8.16 (dd, J=8.16, 1.38 Hz, 1H), 7.70 (d, J=8.53 Hz, 1H), 7.39-7.51 (m, 2H), 7.35 (d, J=8.28 Hz, 2H), 7.03 (d, J=8.53 Hz, 2H), 4.63 (br. s., 1H), 3.59-4.02 (m, 4H), 2.77 (s, 3H), 1.84-2.12 (m, 4H), 1.14-1.26 (m, 5H), 1.07 (d, J=1.76 Hz, 3H), 0.73 (dd, J=7.78, 4.52 Hz, 1H).

Example 323. [4-[4-[8-(4-Methylpiperazin-1-yl)-7-quinolyl]phenoxy]-1-piperidyl]-[(2R)-tetrahydrofuran-2-yl]methanone

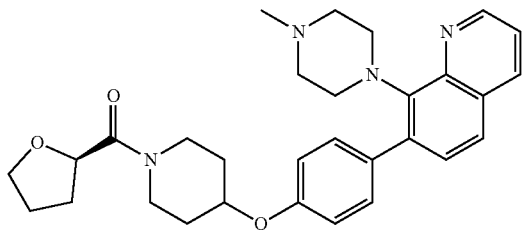 [SMILES: CN1CCN(c2c(-c3ccc(OC4CCN(C(=O)[C@H]5CCCO5)CC4)cc3)ccc3cccnc23)CC1]

Method A

Step 1 tert-Butyl 4-[4-[8-(4-methylpiperazin-1-yl)-7-quinolyl]phenoxy]piperidine-1-carboxylate To an oven dried flask under an atmosphere of argon was added tert-butyl 4-[4-(8-chloro-7-quinolyl)phenoxy]piperidine-1-carboxylate (0.200 g, 0.456 mmol), 1-methylpiperazine (0.06 mL, 0.5 mmol), palladium acetate (6.1 mg, 0.027 mmol), biphenyl-2-yl-di-tert-butyl-phosphane (16.3 mg, 0.0547 mmol), sodium tert-butoxide (0.0701 g, 0.729 mmol), followed by toluene (5 mL). The reaction mixture was purged under a nitrogen atmosphere and was stirred at 99° C. overnight. The reaction still contained ~50% unreacted starting material. Additional sodium tert-butoxide (0.0701 g, 0.729 mmol), biphenyl-2-yl-di-tert-butyl-phosphane (16.3 mg, 0.0547 mmol), palladium acetate (6.1 mg, 0.027 mmol), 1-methylpiperazine (0.06 mL, 0.5 mmol) were added. The reaction mixture was stirred for an additional 4 h. The solvent was evaporated under reduced pressure. The solids were diluted with brine (50 mL), extracted with EtOAc (3×50 mL), dried ($Na_2SO_4$) and the solvent evaporated under reduced pressure. The crude product was purified by on HPLC (reverse phase, 5-55% ACN/$H_2O$). The combined aqueous fractions were diluted with saturated $Na_2CO_3$ (25 mL) extracted with DCM (3×30 mL) to give tert-butyl 4-[4-[8-(4-methylpiperazin-1-yl)-7-quinolyl]phenoxy]piperidine-1-carboxylate (free base) as an off-white foam (50 mg, 20%); Analysis: LCMS m/z=503 (M+1); $^1$H NMR (400 MHz, $CDCl_3$) δ: 7.85-7.92 (m, 2H), 7.60-7.70 (m, 3H), 7.43-7.49 (m, 1H), 6.93-7.05 (m, 3H), 4.47-4.59 (m, 1H), 3.66-3.84 (m, 6H), 3.31-3.43 (m, 2H), 2.52-2.60 (m, 4H), 2.37 (s, 3H), 1.92-2.00 (m, 2H), 1.74-1.86 (m, 2H), 1.48 (s, 9H).

Step 2. 8-(4-Methylpiperazin-1-yl)-7-[4-(4-piperidyloxy)phenyl]quinoline hydrochloride To a stirred solution of tert-butyl 4-[4-[8-(4-methylpiperazin-1-yl)-7-quinolyl]-phenoxy]piperidine-1-carboxylate (50 mg, 0.1 mmol) in DCM (1 mL) was added 4.0 M of HCl in 1,4-dioxane (0.25 mL, 0.99 mmol) dropwise. The reaction was stirred at 35° C. 4 h and was concentrated under reduced pressure. The crude contents were re-dissolved in DCM (2×30 mL) and concentrated under reduced pressure. The crude product was trituated with $Et_2O$ (2×50 mL) to give the 8-(4-methylpiperazin-1-yl)-7-[4-(4-piperidyloxy)phenyl] quinoline HCl as an yellow solid (43 mg, 90%); Analysis: LCMS m/z=403 (M+1). This material was used in the next step without further purification.

Step 3. [4-[4-[8-(4-methylpiperazin-1-yl)-7-quinolyl]phenoxy]-1-piperidyl]-[(2R)-tetrahydrofuran-2-yl]methanone A solution of (R)-tetrahydrofuran-2-carboxylic acid (0.01 mL, 0.1 mmol), HATU (40 mg, 0.1 mmol) and DIPEA (0.07 mL, 0.4 mmol) in acetonitrile (0.4 mL) was stirred at room temperature for 10 min. 8-(4-Methylpiperazin-1-yl)-7-[4-(4-piperidyloxy)phenyl]quinoline dihydrochloride (43 mg, 0.098 mmol) was added and the mixture was stirred at room temperature for 1 h. The reaction was quenched by the addition of MeOH (1 mL) and the solvent was evaporated in vacuo. The crude product was purified by on HPLC (reverse phase, 5-50% ACN/$H_2O$). The combined aqueous fractions were diluted with saturated $Na_2CO_3$ (25 mL) extracted with DCM (3×30 mL) to give the desired product (free base) as on off-white foam. The compound was lyophilized to give [4-[4-[8-(4-methylpiperazin-1-yl)-7-quinolyl]phenoxy]-1-piperidyl]-[(2R)-tetrahydrofuran-2-yl]methanone as an off-white solid (20 mg, 39%); Analysis: LCMS m/z=501 (M+1); $^1$H NMR (400 MHz, $CDCl_3$) δ: 7.83-7.95 (m, 2H), 7.65 (dd, J=14.31, 8.28 Hz, 3H), 7.46 (dd, J=8.16, 1.38 Hz, 1H), 6.93-7.05 (m, 3H), 4.56-4.69 (m, 2H), 3.53-4.01 (m, 10H), 2.57 (t, J=4.64 Hz, 4H), 2.37 (s, 3H), 2.27-2.34 (m, 1H), 1.84-2.12 (m, 7H).

Example 324. [4-[4-(8-Amino-7-quinolyl)phenoxy]-1-piperidyl]-[(2R)-tetrahydrofuran-2-yl]methanone

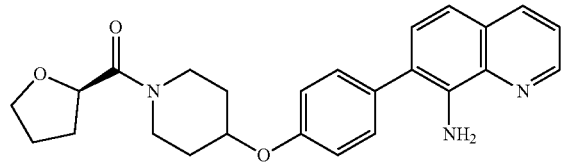 [SMILES: Nc1c(-c2ccc(OC3CCN(C(=O)[C@H]4CCCO4)CC3)cc2)ccc2cccnc12]

Method B

Step 1. tert-Butyl 4-[4-(8-amino-7-quinolyl)phenoxy]piperidine-1-carboxylate tert-Butyl 4-[4-(8-chloro-7-quinolyl)phenoxy]piperidine-1-carboxylate (0.300 g, 0.683 mmol), palladium acetate (15 mg, 0.068 mmol), (±)-BINAP (85 mg, 0.14 mmol), dicesium carbonate (668 mg, 2.05 mmol) and benzophenone imine (0.14 mL, 0.82 mmol) in toluene (6 mL) was degassed under an atmosphere of argon, then heated at 100° C. for 4 h. The solvent was then evaporated under reduced pressure. The solids were diluted with brine (50 mL), extracted with EtOAc (3×50 mL), dried ($Na_2SO_4$) and concentrated under reduced pressure. The resulting oil was purified on HPLC (reverse phase, 20-70% ACN/$H_2O$). The combined aqueous fractions were diluted with sat. $Na_2CO_3$ (50 mL) extracted with DCM (3×60 mL) to give the desired product (free base) as a brown oil. The crude product was purified by silica gel chromatography (0-50% EtOAc/hexanes) to give tert-butyl 4-[4-(8-amino-7-quinolyl)phenoxy]piperidine-1-carboxylate as an off-yellow oil (50 mg; 20%); Analysis: LCMS m/z=420 (M+1); $^1$H NMR (400 MHz, $CDCl_3$) δ: 8.78 (dd, J=4.14, 1.63 Hz, 1H), 8.08 (dd, J=8.28, 1.51 Hz, 1H), 7.46-7.56 (m, 2H), 7.31-7.42 (m, 2H), 7.19 (d, J=8.28 Hz, 1H), 7.00-7.09 (m, 2H), 5.04-5.29 (m, 2H), 4.53 (s, 1H), 3.67-3.83 (m, 2H), 3.37 (ddd, J=13.43, 7.78, 3.89 Hz, 2H), 1.96 (br. s., 2H), 1.82 (d, J=3.76 Hz, 2H), 1.49 (s, 9H).

Step 2. 7-[4-(4-Piperidyloxy)phenyl]quinolin-8-amine HCl

To a stirred solution of tert-butyl 4-[4-(8-amino-7-quinolyl)phenoxy]piperidine-1-carboxylate (50 mg, 0.1 mmol) in DCM (2 mL) was added 4.0 M of HCl in 1,4-dioxane (0.30 mL, 1.2 mmol) solution dropwise. The reaction was stirred at 35° C. 4 h and was then concentrated under reduced pressure. The crude contents were re-dissolved in DCM (2×30 mL) and concentrated under reduced pressure to give the desired product as yellow foam. The crude product was triturated with Et₂O (2×10 mL) to give 7-[4-(4-piperidyloxy)phenyl]quinolin-8-amine HCl as an yellow solid (35 mg; 80%); Analysis: LCMS m/z=320 (M+1). This material was used without further purification.

Step 3. [4-[4-(8-Amino-7-quinolyl)phenoxy]-1-piperidyl]-[(2R)-tetrahydrofuran-2-yl]methanone A solution of (R)-tetrahydrofuran-2-carboxylic acid (0.01 mL, 0.a mmol), HATU (39 mg, 0.10 mmol) and DIPEA (0.069 mL, 0.39 mmol) in acetonitrile (0.4 mL) was stirred at room temperature for 10 min. 7-[4-(4-piperidyloxy)phenyl]quinolin-8-amine HCl (35 mg, 0.098 mmol) was added and the mixture was stirred at room temperature for 1 hour. The reaction was quenched by addition of MeOH (1 mL). The solvent was evaporated in vacuo. The crude product was purified by HPLC (reverse phase, 13-55% ACN/H₂O). The combined aqueous fractions were diluted with sat. Na₂CO₃ (25 mL) extracted with DCM (3×30 mL) to give the desired product (free base) as an yellow foam. The product was triturated with Et₂O (5 mL) and hexanes (5 mL) to give [4-[4-(8-amino-7-quinolyl)phenoxy]-1-piperidyl]-[(2R)-tetrahydrofuran-2-yl]methanone as a light yellow solid (8 mg; 20%); Analysis: LCMS m/z=418 (M+1); $^1$H NMR (400 MHz, CDCl₃) δ: 8.80 (br. s., 1H), 8.16 (d, J=7.28 Hz, 1H), 7.51 (d, J=8.28 Hz, 2H), 7.34-7.46 (m, 2H), 7.22 (d, J=8.28 Hz, 1H), 7.05 (d, J=8.53 Hz, 2H), 4.68-6.04 (m, 2H), 4.65 (d, J=6.02 Hz, 2H), 3.55-4.02 (m, 6H), 2.26-2.40 (m, 1H), 1.87-2.14 (m, 7H).

The following compounds were synthesized using the procedures of Examples 323 or 324.

Example 325. {4-[4-(8-Methylaminoquinolin-7-yl)-phenoxy]-piperidin-1-yl}-(R)-tetrahydrofuran-2-yl-methanone

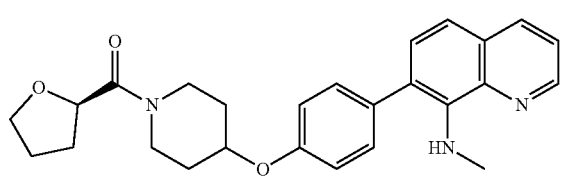 [SMILES: CNc1c(-c2ccc(OC3CCN(C(=O)[C@H]4CCCO4)CC3)cc2)ccc2cccnc12]

Analysis: LCMS m/z=432 (M+1); $^1$H NMR (400 MHz, CDCl₃) δ: 8.77 (dd, J=4.14, 1.63 Hz, 1H), 8.09 (dd, J=8.16, 1.63 Hz, 1H), 7.51 (d, J=8.53 Hz, 2H), 7.33-7.42 (m, 2H), 7.21 (d, J=8.53 Hz, 1H), 6.94-7.02 (m, 2H), 6.31-6.42 (m, 1H), 4.66 (dd, J=7.15, 5.65 Hz, 2H), 3.56-4.01 (m, 6H), 2.58 (s, 3H), 2.25-2.38 (m, 1H), 1.93 (br. s., 7H).

Example 326. 1-{4-[4-(8-Methylaminoquinolin-7-yl)-phenoxy]-piperidin-1-yl}-propan-1-one

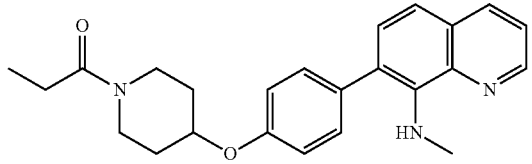 [SMILES: CCC(=O)N1CCC(Oc2ccc(-c3ccc4cccnc4c3NC)cc2)CC1]

Analysis: LCMS m/z=390 (M+1); $^1$H NMR (400 MHz, CDCl₃) δ: 8.77 (dd, J=4.27, 1.76 Hz, 1H), 8.09 (dd, J=8.28, 1.76 Hz, 1H), 7.47-7.56 (m, 2H), 7.33-7.44 (m, 2H), 7.21 (d, J=8.28 Hz, 1H), 6.98 (d, J=8.78 Hz, 2H), 6.31-6.45 (m, 1H), 4.60 (dt, J=6.53, 3.26 Hz, 1H), 3.80-3.90 (m, 1H), 3.63-3.79 (m, 2H), 3.39-3.51 (m, 1H), 2.58 (s, 3H), 2.36-2.45 (m, 2H), 1.80-2.05 (m, 4H), 1.18 (t, J=7.53 Hz, 3H).

Example 327. (4-{4-[8-(2-Methoxyethylamino)-quinolin-7-yl]-phenoxy}-piperidin-1-yl)-(R)-tetrahydrofuran-2-yl-methanone

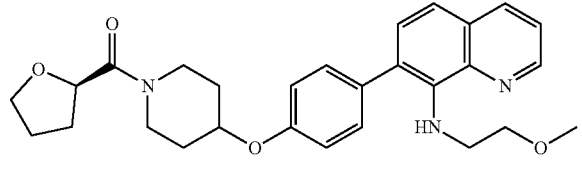 [SMILES: COCCNc1c(-c2ccc(OC3CCN(C(=O)[C@H]4CCCO4)CC3)cc2)ccc2cccnc12]

Analysis: LCMS m/z=476 (M+1); $^1$H NMR (400 MHz, CD₃OD): δ: 8.82 (dd, J=4.27, 1.76 Hz, 1H), 8.23 (dd, J=8.28, 1.76 Hz, 1H), 7.55 (d, J=8.53 Hz, 2H), 7.46-7.51 (m, 1H), 7.38 (s, 2H), 7.10 (d, J=8.53 Hz, 2H), 4.70-4.83 (m, 2H), 3.90 (s, 4H), 3.61-3.74 (m, 1H), 3.49-3.60 (m, 1H), 3.35-3.39 (m, 4H), 3.26 (s, 3H), 2.98 (t, J=5.40 Hz, 2H), 2.19-2.32 (m, 1H), 1.78-2.15 (m, 7H).

Example 328. 1-(4-{4-[8-(2-Methoxyethylamino)-quinolin-7-yl]-phenoxy}-piperidin-1-yl)-propan-1-one

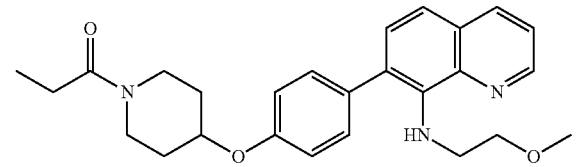 [SMILES: CCC(=O)N1CCC(Oc2ccc(-c3ccc4cccnc4c3NCCOC)cc2)CC1]

Analysis: LCMS m/z=434 (M+1); $^1$H NMR (400 MHz, CDCl₃) δ: 8.80 (dd, J=4.02, 1.51 Hz, 1H), 8.08 (dd, J=8.28, 1.51 Hz, 1H), 7.53 (d, J=8.53 Hz, 2H), 7.30-7.42 (m, 2H), 7.20-7.25 (m, 1H), 6.98 (d, J=8.53 Hz, 2H), 6.57 (br. s., 1H), 4.60 (br. s., 1H), 3.80-3.94 (m, 1H), 3.61-3.80 (m, 2H), 3.41-3.53 (m, 1H), 3.37 (t, J=5.52 Hz, 2H), 3.27 (s, 3H), 2.99 (t, J=5.40 Hz, 2H), 2.39 (q, J=7.45 Hz, 2H), 1.81-2.05 (m, 4H), 1.18 (t, J=7.53 Hz, 3H).

223

Example 329. (4-{4-[8-(2-Dimethylaminoethyl-amino)-quinolin-7-yl]-phenoxy}-piperidin-1-yl)-(R) tetrahydrofuran-2-yl-methanone

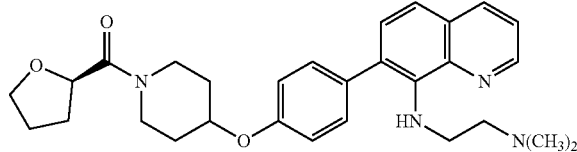 [SMILES: CN(C)CCNc1c(-c2ccc(OC3CCN(C(=O)[C@H]4CCCO4)CC3)cc2)ccc2cccnc12]

Analysis: LCMS m/z=489 (M+1); $^1$H NMR (400 MHz, CDCl$_3$) δ: 8.79 (dd, J=4.02, 1.76 Hz, 1H), 8.08 (dd, J=8.28, 1.76 Hz, 1H), 7.52 (d, J=8.28 Hz, 2H), 7.31-7.44 (m, 2H), 7.23 (d, J=8.53 Hz, 1H), 6.96-7.03 (m, 2H), 6.25-6.73 (m, 1H), 4.66 (dd, J=7.40, 5.65 Hz, 2H), 3.52-4.02 (m, 6H), 2.90 (t, J=6.53 Hz, 2H), 2.38 (t, J=6.40 Hz, 2H), 2.28-2.34 (m, 1H), 2.15 (s, 6H), 1.86-2.10 (m, 7H).

Example 330. 7-[4-(1-Propionyl-piperidin-4-yloxy)-phenyl]-quinoline-8-carbonitrile

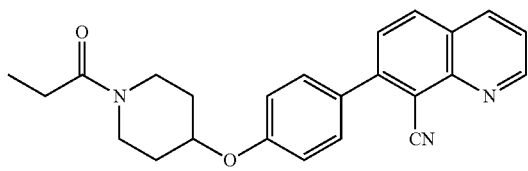 [SMILES: CCC(=O)N1CCC(Oc2ccc(-c3ccc4cccnc4c3C#N)cc2)CC1]

An oven dried round bottom flask was added 1-[4-[4-(8-chloro-7-quinolyl)-phenoxy]-1-piperidyl]propan-1-one (120 mg, 0.30 mmol), zinc cyanide (54 mg, 0.46 mmol), activated powdered zinc (4 mg, 0.06 mmol), [1,1'bis(diphenylphosphino)ferrocene]-dichloropalladium(II), complex (DPPF-Pd) with DCM (1:1) (12 mg, 0.015 mmol) and DMF (1 mL) under an atmosphere of nitrogen. The reaction mixture was heated at 90° C. and stirred overnight under an atmosphere of nitrogen. The reaction mixture was cooled rt and filtered through Celite, washed with EtOAc (2×20 mL) and concentrated under reduced pressure. The crude product was purified by HPLC (reverse phase, 23-65% ACN/H$_2$O). The combined aqueous fractions were diluted with sat. Na$_2$CO$_3$ (25 mL), extracted with DCM (3×30 mL) to give the desired product (free base) as an yellow oil. The sample was lyophilized overnight to give 7-[4-(1-propionyl-piperidin-4-yloxy)-phenyl]-quinoline-8-carbonitrile as on off-white solid (4.1 mg; 3.3%); Analysis: LCMS m/z=386 (M+1); $^1$H NMR (400 MHz, CDCl$_3$) δ: 9.14 (dd, J=4.27, 1.76 Hz, 1H), 8.22-8.29 (m, 1H), 8.06 (d, J=8.53 Hz, 1H), 7.70 (dd, J=8.78, 1.00 Hz, 3H), 7.52-7.57 (m, 1H), 7.06-7.12 (m, 2H), 4.61-4.70 (m, 1H), 3.78-3.90 (m, 1H), 3.65-3.77 (m, 2H), 3.40-3.51 (m, 1H), 2.40 (d, J=7.78 Hz, 2H), 1.95-2.05 (m, 2H), 1.81-1.92 (m, 2H), 1.17-1.21 (m, 3H).

224

Example 331. [4-[4-[8-(Dimethylamino)-7-quinolyl] phenoxy]-1-piperidyl]-[(2R)-tetrahydrofuran-2-yl] methanone

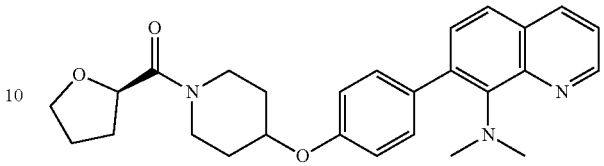

Step 1. Trifluoromethanesulfonic acid 7-bromoquinolin-8-yl ester

To a solution of 7-bromoquinolin-8-ol (5 g, 20 mmol) in DCM (120 mL) at 0° C. was added pyridine (9.02 mL, 112 mmol) and trifluoromethanesulfonic (triflic) anhydride (5.63 mL, 33.5 mmol). After stirring for 30 min at 0° C., the reaction was quenched with aq. sat. NaHCO$_3$ solution (25 mL). The organic layer was separated and the water layer was extracted with DCM (2×30 mL). The combined organic layers was washed with water (50 mL), brine (50 mL), dried (Na$_2$SO$_4$), and concentrated to give trifluoromethanesulfonic acid 7-bromoquinolin-8-yl ester as a grayish solid (7 g; 79%); LCMS m/z=357 (M+1). This material was used for next the step without further purification.

Step 2. 4-[4-(8-Trifluoromethanesulfonyloxy-quinolin-7-yl)-phenoxy]-piperidine-1-carboxylic acid tert-butyl ester A flask charged with 4-[4-(4,4,5,5-tetramethyl-1,3,2-dioxaborolan-2-yl)-phenoxy]-piperidine-1-carboxylic acid tert-butyl ester (5 g, 10 mmol), trifluoromethanesulfonic acid 7-bromo-quinolin-8-yl ester (4.86 g, 13.6 mmol), palladium acetate (280 mg, 1.2 mmol), triphenylphosphine (0.65 g, 2.5 mmol), 1,4-dioxane (60 mL) and 1.0 M of Na$_2$CO$_3$ in H$_2$O (62.0 mL, 62.0 mmol) was flashed with nitrogen for 5 min. The reaction was heated at 85° C. for 1.5 h. After cooling to room temp, the reaction was diluted with EtOAc (200 mL), washed with an aq. sat. NaHCO$_3$ solution (100 mL). The water layer was back-extracted with EtOAc (2×50 mL). The combined organic layers was washed with brine (50 mL), dried (Na$_2$SO$_4$), and concentrated. The crude was purified by silica gel chromatography (0-50% EtOAc/hexanes) to give 4-[4-(8-trifluoromethanesulfonyloxy-quinolin-7-yl)-phenoxy]-piperidine-1-carboxylic acid tert-butyl ester as a white solid (5 g; 60%); Analysis: LCMS m/z=553 (M+1); $^1$H NMR (400 MHz, CDCl$_3$) δ: 9.06-9.10 (m, 1H), 8.20-8.28 (m, 1H), 7.87 (d, J=8.53 Hz, 1H), 7.62 (d, J=8.53 Hz, 1H), 7.50-7.56 (m, 3H), 7.05 (d, J=9.03 Hz, 2H), 4.48-4.63 (m, 1H), 3.69-3.80 (m, 2H), 3.29-3.44 (m, 2H), 1.92-2.03 (m, 2H), 1.75-1.85 (m, 2H), 1.48 (s, 9H).

Step 3. tert-Butyl 4-[4-[8-(dimethylamino)-7-quinolyl]phenoxy]piperidine-1-carboxylate To an oven dried flask under an atmosphere of argon was added 4-[4-(8-trifluoro-methanesulfonyloxy-quinolin-7-yl)-phenoxy]-piperidine-1-carboxylic acid tert-butyl ester (1 g, 2 mmol), dimethylamine (2M solution in THF, 10.3 mL, 22.8 mmol), palladium acetate (51 mg, 0.23 mmol), (±)-BINAP (142 mg, 0.228 mmol), cesium carbonate (1.039 g, 3.189 mmol), followed by THF (10 mL). The reaction mixture was purged under an atmosphere of argon and was stirred at 65° C. for 20 h in a sealed tube. The solvent was evaporated under reduced pressure. The solids were diluted with brine (250 mL), extracted with EtOAc (3×50 mL), dried ($Na_2SO_4$) and the solvent evaporated under reduced pressure. The crude product was purified by on silica gel chromatography (0-30% EtOAc/hexanes). The combined aqueous fractions were evaporated under reduced pressure to yield the desired product as an yellow solid (420 mg; 40%). Analysis: LCMS m/z=448 (M+1); $^1$H NMR (400 MHz, $CDCl_3$) δ: 8.94 (dd, J=4.14, 1.88 Hz, 1H), 8.11 (dd, J=8.28, 1.76 Hz, 1H), 7.46-7.52 (m, 1H), 7.32-7.42 (m, 4H), 6.99 (d, J=8.78 Hz, 2H), 4.50-4.58 (m, 1H), 3.70-3.81 (m, 2H), 3.32-3.42 (m, 2H), 2.89 (s, 6H), 1.94-2.01 (m, 2H), 1.81 (dd, J=13.18, 3.89 Hz, 2H), 1.48 (s, 9H).

Step 4. N,N-Dimethyl-7-[4-(4-piperidyloxy)phenyl]quinolin-8-amine hydrochloride

To a stirred solution of tert-butyl 4-[4-[8-(dimethylamino)-7-quinolyl]phenoxy]-piperidine-1-carboxylate (420 mg, 0.94 mmol) in DCM (10 mL) was added 4.0 M of HCl in 1,4-dioxane (2.35 mL, 9.38 mmol) dropwise. The reaction was stirred at 35° C. (4 h) and was concentrated under reduced pressure. The crude contents were re-dissolved in DCM (2×30 mL) and concentrated under reduced pressure. The crude product was triturated with $Et_2O$ (2×25 mL) to give the desired N,N-dimethyl-7-[4-(4-piperidyloxy)phenyl]quinolin-8-amine HCl as an yellow solid (360 mg; 95%); LCMS m/z=348 (M+1). Used without further purification.

Step 5. [4-[4-[8-(Dimethylamino)-7-quinolyl]phenoxy]-1-piperidyl]-[(2R)-tetrahydrofuran-2-yl]methanone A solution of (R)-tetrahydrofuran-2-carboxylic acid (0.04 mL, 0.4 mmol), HATU (156 mg, 0.410 mmol) and DIPEA (0.27 mL, 1.6 mmol) in acetonitrile (2 mL) was stirred at room temperature for 10 min. [A] N,N-dimethyl-7-[4-(4-piperidyloxy)phenyl]quinolin-8-amine HCl (150 mg, 0.39 mmol) was added and the mixture was stirred at room temperature for 1 hour. The reaction was quenched by the addition of MeOH (1 mL). The solvent was evaporated in vacuo. The crude product was purified by on HPLC (reverse phase, 10-55% $ACN/H_2O$). The combined aqueous fractions were diluted with sat. $Na_2CO_3$ (25 mL) extracted with DCM (3×30 mL) to give the desired product (free base) as a an yellow solid (120 mg; 66%). Analysis: LCMS m/z=446 (M+1); $^1$H NMR (400 MHz, $CDCl_3$) δ: 8.95 (dd, J=4.14, 1.88 Hz, 1H), 8.09-8.16 (m, 1H), 7.46-7.56 (m, 1H), 7.32-7.42 (m, 4H), 6.93-7.06 (m, 2H), 4.55-4.73 (m, 2H), 3.53-4.04 (m, 6H), 2.90 (s, 6H), 2.26-2.41 (m, 1H), 1.89-2.14 (m, 7H).

The following compounds were synthesized using the procedure for example 331:

Example 332. 1-{4-[4-(8-Dimethylaminoquinolin-7-yl)-phenoxy]-piperidin-1-yl}-propan-1-one

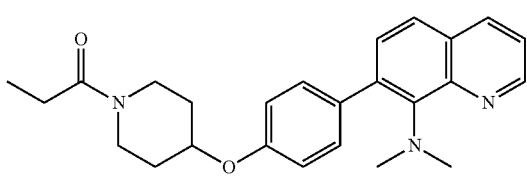 [SMILES: CCC(=O)N1CCC(Oc2ccc(-c3ccc4cccnc4c3N(C)C)cc2)CC1]

Analysis: LCMS m/z=404 (M+1); $^1$H NMR (400 MHz, $CDCl_3$) δ: 8.95 (dd, J=4.02, 1.76 Hz, 1H), 8.09-8.16 (m, 1H), 7.47-7.54 (m, 1H), 7.32-7.43 (m, 4H), 7.00 (d, J=8.53 Hz, 2H), 4.53-4.66 (m, 1H), 3.61-3.92 (m, 3H), 3.40-3.50 (m, 1H), 2.90 (s, 6H), 2.36-2.46 (m, 2H), 1.94-2.05 (m, 2H), 1.84-1.92 (m, 2H), 1.18 (t, J=7.53 Hz, 3H).

Example 333. Cyclopropyl-{4-[4-(8-dimethylamino-quinolin-7-yl)-phenoxy]-piperidin-1-yl}-methanone

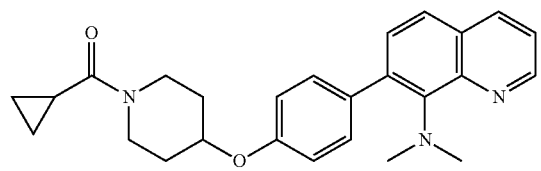 [SMILES: CN(C)c1c(-c2ccc(OC3CCN(C(=O)C4CC4)CC3)cc2)ccc2cccnc12]

Analysis: LCMS m/z=416 (M+1); $^1$H NMR (400 MHz, $CDCl_3$) δ: 8.95 (dd, J=4.27, 1.76 Hz, 1H), 8.08-8.18 (m, 1H), 7.47-7.56 (m, 1H), 7.33-7.44 (m, 4H), 7.01 (d, J=8.78 Hz, 2H), 4.57-4.68 (m, 1H), 3.82-4.02 (m, 2H), 3.64-3.73 (m, 2H), 2.90 (s, 6H), 2.01 (s, 5H), 1.01 (br. s., 2H), 0.78 (dd, J=8.03, 3.01 Hz, 2H).

Example 334. (4-{4-[8-(2-Pyrrolidin-1-yl-ethylamino)-quinolin-7-yl]-phenoxy}-piperidin-1-yl)-(R)-tetrahydrofuran-2-yl-methanone

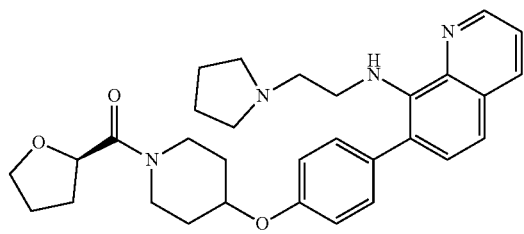 [SMILES: O=C([C@H]1CCCO1)N1CCC(Oc2ccc(-c3ccc4cccnc4c3NCCN3CCCC3)cc2)CC1]

Analysis: LCMS m/z=515 (M+1); $^1$H NMR (400 MHz, $CDCl_3$) δ: 8.78 (dd, J=4.02, 1.76 Hz, 1H), 8.05-8.12 (m, 1H), 7.53 (d, J=8.53 Hz, 2H), 7.34 (d, J=8.53 Hz, 2H), 7.23 (s, 1H), 6.98 (d, J=8.78 Hz, 2H), 6.36-6.76 (m, 1H), 4.58-4.70 (m, 2H), 3.48-4.04 (m, 6H), 2.94 (s, 2H), 2.54 (s, 2H), 2.24-2.40 (m, 5H), 1.84-2.13 (m, 7H), 1.70 (s, 4H).

Example 335. 1-(4-{4-[8-(2-Pyrrolidin-1-yl-ethylamino)-quinolin-7-yl]-phenoxy}-piperidin-1-yl)-propan-1-one

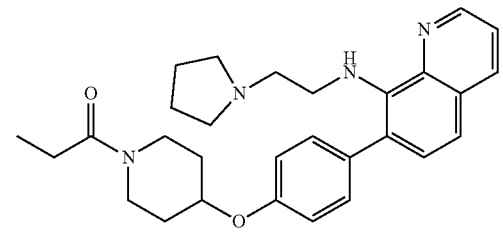 [SMILES: CCC(=O)N1CCC(Oc2ccc(-c3ccc4cccnc4c3NCCN3CCCC3)cc2)CC1]

Analysis: LCMS m/z=473 (M+1); $^1$H NMR (400 MHz, $CDCl_3$) δ: 8.78 (dd, J=4.27, 1.76 Hz, 1H), 8.08 (dd, J=8.28, 1.76 Hz, 1H), 7.50-7.57 (m, 2H), 7.30-7.40 (m, 2H), 7.22 (d, J=8.53 Hz, 1H), 6.92-7.02 (m, 2H), 6.32-6.75 (m, 1H), 4.52-4.67 (m, 1H), 3.63-3.90 (m, 3H), 3.39-3.51 (m, 1H), 2.94 (s, 2H), 2.54 (t, J=6.78 Hz, 2H), 2.33-2.45 (m, 6H), 1.82-2.02 (m, 4H), 1.68-1.76 (m, 4H), 1.18 (t, J=7.40 Hz, 3H)

Example 336. 7-[4-[[1-[(2R)-Tetrahydrofuran-2-carbonyl]-4 piperidyl]oxy]phenyl]quinoline-8-carboxamide

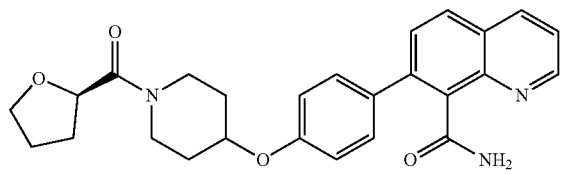 [SMILES: NC(=O)c1c(-c2ccc(OC3CCN(C(=O)[C@H]4CCCO4)CC3)cc2)ccc2cccnc12]

Step 1. tert-Butyl 4-[4-(8-cyano-7-quinolyl)phenoxy]piperidine-1-carboxylate

An oven dried round bottom flask was loaded with 4-[4-(8-trifluoromethane-sulfonyloxy-quinolin-7-yl)-phenoxy]-piperidine-1-carboxylic acid tert-butyl ester (1 g, 2 mmol), zinc cyanide (319 mg, 2.71 mmol), activated, powdered zinc (24 mg, 0.36 mmol), DPPF-Pd(II), complex with DCM (1:1) (74 mg, 0.090 mmol), and DMF (6 mL) under an atmosphere of nitrogen. The reaction mixture was lowered in a mantle pre-heated at 90° C. and stirred overnight at this temperature under an atmosphere of nitrogen. The reaction mixture was cooled to RT and filtered through Celite, washed with EtOAc (2×20 mL) and concentrated under reduced pressure. The crude product was purified by silica gel chromatography (0-60% EtOAc/hexanes). The combined fractions were evaporated under reduced pressure to give the tert-butyl 4-[4-(8-cyano-7-quinolyl)phenoxy]piperidine-1-carboxylate as a white solid (750 mg, 90%). Analysis: LCMS m/z=430 (M+1); $^1$H NMR (400 MHz, CDCl$_3$) δ: 9.10-9.22 (m, 1H), 8.21-8.30 (m, 1H), 8.05 (s, 1H), 7.69 (dd, J=8.66, 1.13 Hz, 3H), 7.50-7.59 (m, 1H), 7.07 (d, J=8.78 Hz, 2H), 4.52-4.67 (m, 1H), 3.65-3.83 (m, 2H), 3.32-3.49 (m, 2H), 1.94-2.03 (m, 2H), 1.78-1.88 (m, 2H), 1.48 (s, 9H).

Step 2. 7-[4-(4-Piperidyloxy)phenyl]quinoline-8-carboxamide; 2,2,2-trifluoroacetic acid To a stirred solution of tert-butyl 4-[4-(8-cyano-7-quinolyl)phenoxy]piperidine-1-carboxylate (250 mg, 0.58 mmol) in ethanol (4 mL) was added 0.5 M of sodium hydroxide in H$_2$O (12.8 mL, 6.40 mmol), followed by 30% aq. hydrogen peroxide (0.6 mL, 6 mmol). The reaction was stirred at 50° C. (24 h), but only 8-10% of desired product was observed. The reaction mixture was cooled to RT and neutralized with 10% aq. H$_2$SO$_4$ and was concentrated under reduced pressure. The crude reaction mixture was re-dissolved in 1-methoxy-2-propanol (10 mL). Solid sodium hydroxide (0.256 g, 6.40 mmol) was added, followed by H$_2$O (1 mL) and 30% aq. hydrogen peroxide (0.6 ml, 6 mmol). The reaction was heated at 98° C. (24 h) and this time ~40% of desired product was observed. Additional sodium hydroxide (0.256 g, 6.40 mmol) and 30% aq. hydrogen peroxide (0.6 ml, 6 mmol) was added. After additional heating at 98° C. (12 h), ~60% of desired product was observed. Additional sodium hydroxide (0.256, 6.4026 mmol) and 30% aq. hydrogen peroxide (0.6 ml, 6 mmol) was added and the reaction mixture was heated at 98° C. for additional 4 h. The reaction mixture was cooled to RT, neutralized with conc. aq. H$_2$SO$_4$ and evaporated under reduced pressure. The contents of the flask were dissolved in DMSO, the solids filtered and the resulting solution was purified by HPLC (reverse phase, 5-52% ACN/H$_2$O). The combined fractions were lyophilized to yield the desired product 7-[4-(4-piperidyloxy)phenyl]quinoline-8-carboxamide; 2,2,2-trifluoroacetic acid as an yellow solid (60 mg, 20%). Analysis: LCMS m/z=348 (M+1).

Step 3. 7-[4-[[1-[(2R)-Tetrahydrofuran-2-carbonyl]-4-piperidyl]oxy]phenyl]quinoline-8-carboxamide A solution of (R)-tetrahydrofuran-2-carboxylic acid (0.006 mL, 0.07 mmol), HATU (26 mg, 0.068 mmol) and DIPEA (0.045 mL, 0.26 mmol) in acetonitrile (0.2 mL, 5 mmol) was stirred at room temperature for 10 min. 7-[4-(4-piperidyloxy)phenyl]quinoline-8-carboxamide; TFA (30 mg, 0.06 mmol) was added and the mixture was stirred at RT for 1 hour. The reaction was quenched by addition of MeOH (1 mL). The solvent was evaporated in vacuo. The crude product was purified by HPLC (reverse phase, 5-52% ACN/H$_2$O). The combined aqueous fractions were diluted with sat. Na$_2$CO$_3$ (25 mL), extracted with DCM (3×30 mL) to give the desired product (free base) as a white solid. The product was lyophilized to give the 7-[4-[[1-[(2R)-tetrahydrofuran-2-carbonyl]-4 piperidyl]oxy]phenyl]quinoline-8-carboxamide as a white solid (25 mg, 80%). Analysis: LCMS m/z=446 (M+1); $^1$H NMR (400 MHz, CDCl$_3$) δ: 9.03 (dd, J=4.27, 1.76 Hz, 1H), 8.16-8.25 (m, 1H), 7.88-7.96 (m, 1H), 7.61 (s, 3H), 7.43-7.49 (m, 1H), 7.00 (d, J=8.78 Hz, 2H), 5.75-5.92 (m, 2H), 4.56-4.72 (m, 2H), 3.51-4.01 (m, 6H), 2.27-2.40 (m, 1H), 1.85-2.13 (m, 7H).

The following compound was synthesized using the procedure for Example 336:

Example 337. 7-[4-(1-Propionyl-piperidin-4-yloxy)-phenyl]-quinoline-8-carboxylic acid amide

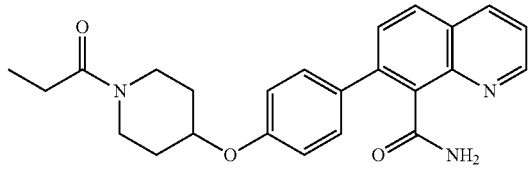 [SMILES: CCC(=O)N1CCC(Oc2ccc(-c3ccc4cccnc4c3C(N)=O)cc2)CC1]

Analysis: LCMS m/z=404 (M+1); $^1$H NMR (400 MHz, CDCl$_3$) δ: 9.03 (dd, J=4.27, 1.76 Hz, 1H), 8.17-8.26 (m, 1H), 7.90 (d, J=8.53 Hz, 1H), 7.60 (dd, J=8.66, 2.38 Hz, 3H), 7.41-7.50 (m, 1H), 7.00 (d, J=8.78 Hz, 2H), 5.79-5.94 (m, 2H), 4.55-4.67 (m, 1H), 3.63-3.92 (m, 3H), 3.40-3.54 (m, 1H), 2.34-2.47 (m, 2H), 1.83-2.03 (m, 4H), 1.18 (t, J=7.40 Hz, 3H).

Example 338. 1-(3-(4-(Quinolin-3-yl)phenoxy)azetidin-1-yl)propan-1-one

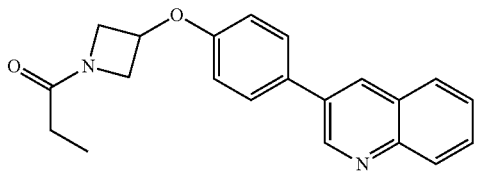 [SMILES: CCC(=O)N1CC(Oc2ccc(-c3cnc4ccccc4c3)cc2)C1]

Step 1. tert-Butyl 3-(4-bromophenoxy)azetidine-1-carboxylate

To tert-butyl 3-((methylsulfonyl)oxy)azetidine-1-carboxylate (7 g, 0.027 mol) and $Cs_2CO_3$ (10.9 g, 0.033 mol) in DMF (200 mL) was added 4-bromophenol (4.82 g, 0.027 mol). The reaction was heated to 80° C. for 18 h, and then cooled to RT. Ice water was added to the reaction mixture when a white solid tert-butyl 3-(4-bromophenoxy)azetidine-1-carboxylate was obtained which was filtered, washed with water and dried (6.5 g, 71%). Analysis: $^1$H NMR (400 MHz, DMSO-$d_6$) δ: 7.50-7.41 (m, 2H), 6.85-6.76 (m, 2H), 5.0-4.96 (m, 1H), 4.32-4.23 (m, 2H), 3.77 (m, 2H), 1.38 (s, 9H); LCMS (ESI): 328 (M+1).

Step 2. tert-Butyl 3-(4-(quinolin-3-yl)phenoxy)azetidine-1-carboxylate

A solution of tert-butyl 3-(4-bromophenoxy)azetidine-1-carboxylate (1.5 g, 4.57 mmol), quinolin-3-boronic acid (948 mg, 5.5 mmol) and $Na_2CO_3$ (1.2 g, 11.42 mmol) in 1,4-dioxane (60 mL) and water (15 mL) was degassed by argon for 15 min. Tetrakis(triphenylphosphine) palladium(0) (264 mg, 0.23 mmol) was then added under argon atmosphere and reaction mixture was heated at 100° C. for 15 h. The reaction mixture was cooled to RT and filtered through Celite pad, washed with ETOAc. Filtrate was washed with water and brine, dried over $Na_2SO_4$, filtered and concentrated. The crude product was purified by column chromatography (50% EtOAc-Hexane) to afford tert-butyl 3-(4-(quinolin-3-yl)phenoxy)azetidine-1-carboxylate (950 mg, 55%). Analysis: LCMS (ESI): 377 (M+1); $^1$H NMR (400 MHz, DMSO-$d_6$) δ: 9.22 (d, J=2.3 Hz, 1H), 8.58 (d, J=2.5 Hz, 1H), 8.03 (d, J=8.3 Hz, 2H), 7.84 (d, J=8.2 Hz, 2H), 7.81-7.70 (m, 1H), 7.63 (t, J=7.5 Hz, 1H), 7.02 (d, J=8.2 Hz, 2H), 5.08 (m, 1H), 4.35 (t, J=7.9 Hz, 2H), 3.84 (dd, J=10.1, 4.0 Hz, 2H), 1.40 (s, 9H).

Step 3. 3-(4-(Azetidin-3-yloxy)phenyl)quinoline hydrochloride

To a solution of t-butyl 3-(4-(quinolin-3-yl)phenoxy)azetidine-1-carboxylate (950 mg) in DCM (20 mL) was added 4M HCl in 1,4-dioxane (6 mL) at 0° C. The reaction mixture was stirred at RT for 2 h. After completion of the reaction, it was concentrated under reduced pressure to afford 3-(4-(azetidin-3-yloxy)phenyl)quinoline HCl (800 mg, 98%) which was used in the next step without further purification. Analysis: LCMS (ESI): 277 (M+1); $^1$H NMR (400 MHz, DMSO-$d_6$) δ: 9.24-9.19 (m, 1H), 8.57 (s, 1H), 8.03 (d, J=8.3 Hz, 2H), 7.78 (dd, J=33.2, 8.2 Hz, 3H), 7.63 (t, J=7.6 Hz, 1H), 6.99 (t, J=10.9 Hz, 2H), 5.76 (s, 1H), 5.11-5.06 (m, 1H), 3.87-3.78 (m, 2H), 3.55 (t, J=7.0 Hz, 1H), 1.23 (s, 1H).

Step 4. 1-(3-(4-(Quinolin-3-yl)phenoxy)azetidin-1-yl)propan-1-one

To a stirred solution of 3-(4-(azetidin-3-yloxy)phenyl)quinoline HCl (1 eq.) and $Et_3N$ (3 eq.) in DCM was added dropwise acid chloride (1.1 eq.) at 0° C. and the reaction mixture was then stirred at room temperature for 2 hour. On completion of reaction, the reaction mixture was diluted with DCM and washed with water. Organic layer was dried over $Na_2SO_4$, filtered and concentrated under reduced pressure. Purification by column chromatography using silica gel and 5-6% MeOH/DCM as eluent afforded 1-(3-(4-(quinolin-3-yl)phenoxy)azetidin-1-yl)propan-1-one. Analysis: mp 172° C.; LCMS (ESI): 333 (M+1); $^1$H NMR (400 MHz, DMSO-$d_6$) δ: 9.23 (d, J=2.4 Hz, 1H), 8.59 (d, J=2.4 Hz, 1H), 8.04 (d, J=8.5 Hz, 2H), 7.90-7.82 (m, 2H), 7.78-7.75 (m, 1H), 7.68-7.59 (m, 1H), 7.08-6.99 (m, 2H), 5.16-5.13 (m, 1H), 4.64-4.55 (m, 1H), 4.34 (dd, J=10.5, 6.5 Hz, 1H), 4.12 (dd, J=9.6, 3.8 Hz, 1H), 3.81 (dd, J=10.4, 3.8 Hz, 1H), 2.19-2.04 (m, 2H), 0.98 (q, J=7.5 Hz, 3H).

The following examples were prepared using the procedure to Example 338, using the requisite acid chloride in Step 4.

Example 339. 2-Methyl-1-(3-(4-(quinolin-3-yl)phenoxy)azetidin-1-yl)propan-1-one

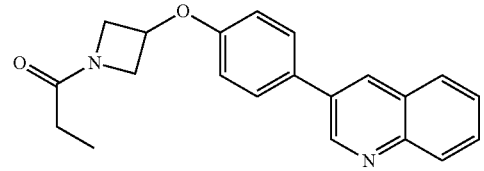 [SMILES: CCC(=O)N1CC(Oc2ccc(-c3cnc4ccccc4c3)cc2)C1]

Analysis: mp 162° C.; LCMS (ESI): 347 (M+1); $^1$H NMR (400 MHz, DMSO-$d_6$) δ: 9.23 (d, J=2.4 Hz, 1H), 8.59 (d, J=2.4 Hz, 1H), 8.04 (d, J=8.3 Hz, 2H), 7.91-7.81 (m, 2H), 7.80-7.71 (m, 1H), 7.64 (t, J=7.6 Hz, 1H), 7.04 (d, J=8.5 Hz, 2H), 5.14 (m, 1H), 4.66 (dd, J=9.3, 6.4 Hz, 1H), 4.39-4.29 (m, 1H), 4.16 (dd, J=9.4, 3.8 Hz, 1H), 3.81 (m, 1H), 0.99 (t, J=6.5 Hz, 7H).

Example 340. Cyclopropyl(3-(4-(quinolin-3-yl)phenoxy)azetidin-1-yl)methanone

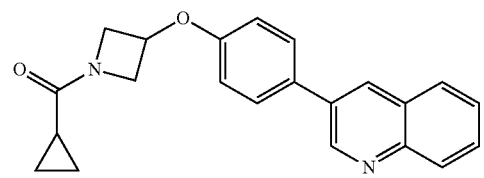 [SMILES: O=C(C1CC1)N1CC(Oc2ccc(-c3cnc4ccccc4c3)cc2)C1]

Analysis: mp 187° C.; LCMS (ESI): 345 (M+1); $^1$H NMR (400 MHz, DMSO-$d_6$) δ: 9.23 (d, J=2.4 Hz, 1H), 8.59 (d, J=2.4 Hz, 1H), 8.04 (d, J=8.5 Hz, 2H), 7.90-7.82 (m, 2H), 7.80-7.71 (m, 1H), 7.64 (t, J=7.5 Hz, 1H), 7.05 (d, J=8.6 Hz, 2H), 5.19-5.17 (m, 1H), 4.75 (t, J=8.1 Hz, 1H), 4.36 (dd, J=10.5, 6.5 Hz, 1H), 4.24 (dd, J=9.7, 3.7 Hz, 1H), 3.83 (dd, J=10.9, 3.9 Hz, 1H), 1.20-1.04 (m, 1H), 0.88-0.63 (m, 4H).

Example 341. 3-Methyl-1-(3-(4-(quinolin-3-yl)phenoxy)azetidin-1-yl)butan-1-one

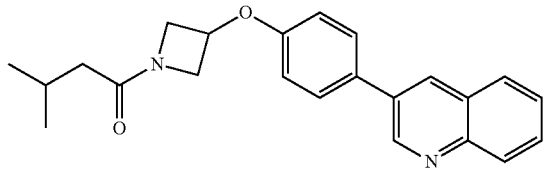 [SMILES: CC(C)CC(=O)N1CC(Oc2ccc(-c3cnc4ccccc4c3)cc2)C1]

Analysis: mp 201° C.; LCMS (ESI): 361 (M+1); $^1$H NMR (400 MHz, DMSO-$d_6$) δ: 9.23 (d, J=2.4 Hz, 1H), 8.58 (d, J=2.4 Hz, 1H), 8.03 (d, J=8.4 Hz, 2H), 7.85 (d, J=8.5 Hz, 2H), 7.80-7.59 (m, 2H), 7.04 (d, J=8.3 Hz, 2H), 5.15-5.12 (m, 1H), 4.60 (dd, J=9.6, 6.4 Hz, 1H), 4.34 (dd, J=10.6, 6.5 Hz, 1H), 4.11 (dd, J=9.7, 3.8 Hz, 1H), 3.81 (dd, J=10.8, 3.9 Hz, 1H), 2.49 (s, 1H), 1.98 (d, J=2.9 Hz, 2H), 0.96-0.79 (m, 6H).

Example 342. (S)-1-(3-(4-(Quinolin-7-yl)phenoxy)pyrrolidin-1-yl)propan-1-one, HCl

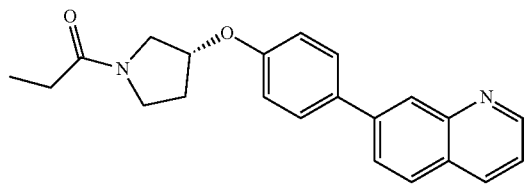 [SMILES: CCC(=O)N1CC[C@@H](Oc2ccc(-c3ccc4cccnc4c3)cc2)C1]

Step 1. (R)-1-(3-Hydroxypyrrolidin-1-yl)propan-1-one

To a solution of (R)-3-hydroxypyrrolidine (1.5 g, 0.017 mol) in DCM (20 mL) was added triethylamine (6.6 mL, 0.051 mol) at 0° C. The reaction mixture was stirred at 0° C. for 10 minutes, when propionyl chloride (1.59 g, 0.017 mol) was added dropwise, and the mixture was stirred at room temperature for 15 h. On completion of the reaction monitored by TLC, the reaction mixture was partitioned between DCM and water. The organic layer was washed with brine, dried over anhydrous sodium sulfate, filtered and concentrated under reduced pressure to obtain the crude product which was purified by column chromatography using silica gel to afford (R)-1-(3-hydroxypyrrolidin-1-yl)propan-1-one (2.3 g, 92%) as a colorless oil. Analysis: $^1$H NMR (400 MHz, CDCl$_3$) δ: 4.55-4.50 (m, 1H), 3.69-3.37 (m, 4H), 2.74-2.64 (m, 2H), 2.36-2.16 (m, 2H), 1.14 (t, J=7.5 Hz, 3H).

Step 2. (S)-1-(3-(4-Bromophenoxy)pyrrolidin-1-yl)propan-1-one (R)-1-(3-Hydroxypyrrolidin-1-yl)propan-1-one (2.3 g, 0.015 mol), was taken in DCM (30 mL) to which ADDP (4.8 g, 0.019 mol) was added at rt followed by addition of triphenylphosphine (5.01 g, 0.019 mol). 4-bromophenol (4.23 g, 0.019 mol) was then added and the reaction mixture was stirred at rt for 15 h. The reaction mixture was diluted with DCM and washed with 1N HCl solution, saturated NaCO$_3$ solution successively. Organic layer was separated, dried over Na$_2$SO$_4$, filtered and concentrated. The crude product was purified by column chromatography (neutral alumina, 2% MeoH in DCM), to afford (S)-1-(3-(4-bromophenoxy)pyrrolidin-1-yl)propan-1-one (1.9 g, 40%) as light yellow oil. Analysis: LCMS (ESI): 298 (M+1); $^1$H NMR (400 MHz, CDCl$_3$) δ: 7.53-7.33 (m, 2H), 6.80-6.70 (m, 2H), 4.86 (m, 1H), 3.86-3.52 (m, 4H), 2.39-2.00 (m, 4H), 1.16 (q, J=7.3 Hz, 3H).

Step 3. (S)-1-(3-(4-(Quinolin-7-yl)phenoxy)pyrrolidin-1-yl)propan-1-one hydrochloride A solution of (S)-1-(3-(4-bromophenoxy)pyrrolidin-1-yl)propan-1-one (300 mg, 1.0 mmol) in 1,4 dioxane:water (9 ml:3 ml) was added Na$_2$CO$_3$ (320 mg, 3 mmol), quinolin-7-boronic acid (209 mg, 1.2 mmol) and degassed with argon for 20 min. This was followed by addition of tetrakis Pd (12 mg, 0.01 mmol) and the reaction mixture was heated at 120° C. for 15 h. The reaction mixture was cooled to RT and filter through Celite bed, the filtrate was diluted ethyl acetate and washed with water. The organic layer was dried over Na$_2$SO$_4$, filtered and concentrated. Crude product was purified by column chromatography using silica gel (2-3% MeOH/DCM) to afford free base which was treated with 4M HCl in dioxane to afford (S)-1-(3-(4-(quinolin-7-yl)phenoxy)pyrrolidin-1-yl)propan-1-one HCl (110 mg, 32%) as a pale yellow sticky solid. Analysis: LCMS (ESI): 347 (M+1); $^1$H NMR (400 MHz, DMSO-$d_6$) δ: 9.22 (d, J=5.0 Hz, 1H), 9.01 (d, J=8.2 Hz, 1H), 8.46 (t, J=2.5 Hz, 1H), 8.35 (d, J=8.7 Hz, 1H), 8.23 (dd, J=8.7, 1.8 Hz, 1H), 7.98-7.82 (m, 3H), 7.23-7.13 (m, 2H), 5.13 (m, 1H), 3.75-3.30 (m, 4H), 2.33-2.07 (m, 4H), 1.23 (d, J=3.6 Hz, 3H).

Example 343. (S)-1-(3-(4-(Quinolin-3-yl)phenoxy)pyrrolidin-1-yl)propan-1-one, HCl

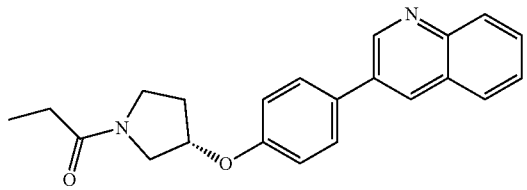 [SMILES: CCC(=O)N1CC[C@H](Oc2ccc(-c3cnc4ccccc4c3)cc2)C1]

This example was synthesized using the method for Example 341, using quinolin-3-boronic acid in Step 3.

Analysis: mp 60° C.; LCMS (ESI): 347 (M+1); $^1$H NMR (400 MHz, DMSO-$d_6$) δ: 9.67-9.61 (m, 1H), 9.45-9.39 (m, 1H), 8.44 (d, J=8.5 Hz, 1H), 8.38-8.31 (m, 1H), 8.1-808 (m, 1H), 8.04-7.90 (m, 3H), 7.25-7.15 (m, 2H), 5.16 (m, 1H), 3.69-3.49 (m, 3H), 3.43-3.30 (m, 1H), 2.35-2.02 (m, 4H), 1.13-0.93 (m, 3H).

The following examples were prepared by analogy to Examples 342 and 343, using (S)-3-hydroxypyrrolidine in Step 1.

Example 344 (R)-1-(3-(4-(Quinolin-7-yl)phenoxy)pyrrolidin-1-yl)propan-1-one, HCl

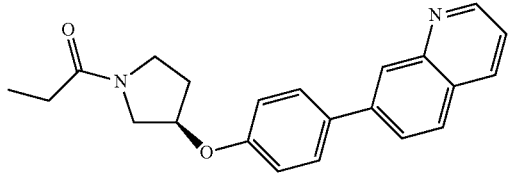 [SMILES: CCC(=O)N1CC[C@@H](Oc2ccc(-c3ccc4cccnc4c3)cc2)C1]

Analysis: mp 53° C.; LCMS (ESI): 347 (M+1); $^1$H NMR (400 MHz, DMSO-$d_6$) δ: 8.99 (s, 1H), 8.83 (d, J=7.4 Hz, 1H), 8.15 (s, 2H), 7.87-7.75 (m, 3H), 7.26 (s, 1H), 7.02 (d, J=8.2 Hz, 2H), 5.06 (s, 1H), 3.81-3.60 (m, 4H), 2.40-2.31 (m, 3H), 2.23 (s, 1H), 1.28-1.15 (m, 3H).

Example 345. (R)-1-(3-(4-(quinolin-3-yl)phenoxy)pyrrolidin-1-yl)propan-1-one, HCl

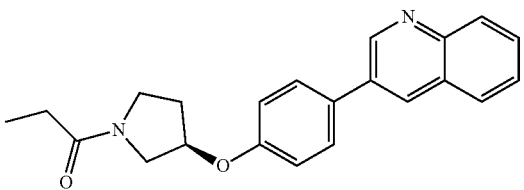 [SMILES: CCC(=O)N1CC[C@@H](Oc2ccc(-c3cnc4ccccc4c3)cc2)C1]

Analysis: mp 51° C.; LCMS (ESI): 347 (M+1); $^1$H NMR (400 MHz, DMSO-$d_6$) δ: 9.26-9.20 (m, 1H), 8.62-8.54 (m, 1H), 8.03 (d, J=8.4 Hz, 2H), 7.93-7.68 (m, 3H), 7.63 (t, J=7.6 Hz, 1H), 7.20-7.09 (m, 2H), 5.12 (t, J=3.3 Hz, 1H), 3.69-3.49 (m, 2H), 3.23 (d, J=4.7 Hz, 2H), 2.33-2.03 (m, 4H), 0.99 (m, 3H).

Example 346. 1-(4-(4-(5-Methylquinolin-7-yl)phenoxy)piperidin-1-yl)propan-1-one, HCl

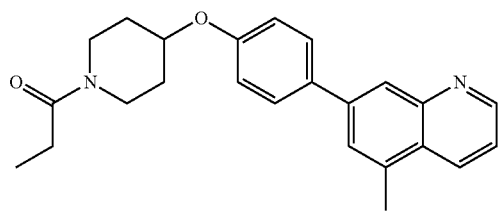 [SMILES: CCC(=O)N1CCC(Oc2ccc(-c3cc(C)c4cccnc4c3)cc2)CC1]

Step 1. 5-Bromo-7-methylquinoline and 7-Bromo-5-methylquinoline

To a mixture of 3-bromo-5-methylaniline (2.0 g), glycerol (2.8 eq.) and sodium-3-nitrobenzenesulphonate (1.8 eq.) in $H_2O$ (16 ml), conc. sulfuric acid (16 ml) was added at 0° C. dropwise. The reaction mixture was heated at 140° C. for 4 days. The reaction mixture was cooled to room & poured on ice, then carefully adjusted to basic pH (pH ~8) with aq. 20% NaOH solution. The mixture was then extracted with ethyl acetate (3×100 mL). Combined organic layer were dried over $Na_2SO_4$ and concentration give crude product which was purified preparative HPLC to afford 5-bromo-7-methylquinoline (240 mg) and 7-bromo-5-methylquinoline (210 mg).

Step 2. tert-Butyl 4-(4-(5-methylquinolin-7-yl)phenoxy)piperidine-1-carboxylate

To a degassed solution of 4-[4-(4,4,5,5-tetramethyl-[1,3,2]dioxaborolan-2-yl)-phenoxy]-piperidine-1-carboxylic acid tert-butyl ester (1 eq.), 5-Bromo-7-methylquinoline (1 eq.) and sodium carbonate (2.6 eq.) in dioxane/water (3:1), was added tetrakis-(triphenylphosphino)-palladium (13 mg, 0.012 mmol) and the reaction mixture was heated at 100° C. for 15 h when TLC confirmed completion of reaction. The reaction was filtered through a bed of Celite and the filtrate was diluted with ethyl acetate and washed with water. The combined organic phases was concentrated to get the crude product was purified by column chromatography using silica gel and 30-40% EtOAc/hexane as eluent to afford tert-butyl 4-(4-(5-methylquinolin-7-yl)phenoxy)-piperidine-1-carboxylate (64%). Analysis: LCMS (ESI): 419 (M+1); $^1$H NMR (400 MHz, DMSO-$d_6$) δ: 8.86 (d, J=4.2 Hz, 1H), 8.15 (d, J=8.6 Hz, 1H), 7.81 (s, 1H), 7.47-7.34 (m, 4H), 7.13 (d, J=8.4 Hz, 2H), 4.64 (m, 1H), 3.75-3.61 (m, 2H), 3.21 (m, 2H), 2.55 (s, 3H), 1.97 (m, 2H), 1.64-1.50 (m, 2H), 1.41 (s, 9H).

Step 3. 5-Methyl-7-(4-(piperidin-4-yloxy)phenyl)quinoline

To a solution of tert-butyl 4-(4-(5-methylquinolin-7-yl)phenoxy)piperidine-1-carboxylate (1 eq.) in DCM (20 mL) was added TFA (0.4 mL) at 0° C., and the reaction mixture was then stirred for 2 h at rt. Volatiles were removed at reduced pressure. Residue was triturated with ether to afford 5-methyl-7-(4-(piperidin-4-yloxy)phenyl)quinoline. Analysis: LCMS (ESI): 319 (M+1)

Step 4. 1-(4-(4-(5-Methylquinolin-7-yl)phenoxy)piperidin-1-yl)propan-1-one, HCl

To a solution of 5-methyl-7-(4-(piperidin-4-yloxy)phenyl)quinoline (1 eq.) in DCM (20 mL) was added at 0° C., $Et_3N$ (3 eq.) and propanoyl chloride (1 eq.) and the reaction mixture was stirred for 3 h at rt. On completion of reaction, the reaction mixture was diluted with DCM and washed with water. The organic layer was washed with brine, dried over $Na_2SO_4$, filtered and concentrated. The crude product was purified by column chromatography using silica gel and 2-3% MeOH/DCM as eluent. The purified free base was converted to the hydrochloride salt by treatment with 4M HCl in dioxane, followed by trituration in ethyl acetate: hexane, filtration and drying in vacuo to afford 1-(4-(4-(5-methylquinolin-7-yl)phenoxy)piperidin-1-yl)propan-1-one HCl. Analysis: LCMS (ESI): 375 (M+1); $^1$H NMR (400 MHz, DMSO-$d_6$) δ: 8.91 (d, J=4.2 Hz, 1H), 8.45 (d, J=8.4 Hz, 1H), 8.08 (s, 1H), 7.84-7.75 (m, 3H), 7.53 (m, 1H), 7.14 (d, J=8.4 Hz, 2H), 4.71 (m, 1H), 3.95-3.84 (m, 1H), 3.77-3.66 (m, 1H), 3.37 (m, 1H), 3.26 (m, 1H), 2.73 (s, 3H), 2.35 (q, J=7.4 Hz, 2H), 2.05-1.88 (m, 2H), 1.62 (m, 1H), 1.56 (m, 1H), 1.00 (t, J=7.4 Hz, 3H).

The following examples were prepared by analogy to Example 346, using the requisite heteroaryl bromide in Step b and acid chloride in Step d or with (R)-tetrahydrofuran-2-carboxylic acid in the presence of EDCI and HOBT for Step 4.

Example 347. Cyclopropyl(4-(4-(5-methylquinolin-7-yl)phenoxy)piperidin-1-yl)methanone, HCl

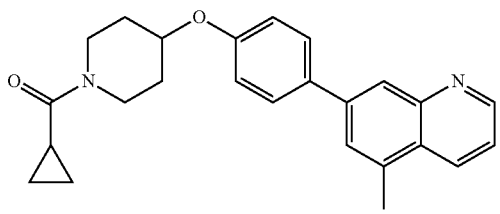 [SMILES: Cc1cc(-c2ccc(OC3CCN(C(=O)C4CC4)CC3)cc2)cc2ncccc12]

Analysis: LCMS (ESI): 387 (M+1); $^1$H NMR (400 MHz, DMSO-d$_6$) δ: 9.19 (d, J=5.0 Hz, 1H), 9.03 (d, J=8.4 Hz, 1H), 8.30 (s, 1H), 8.08 (s, 1H), 7.95-7.80 (m, 3H), 7.20 (d, J=8.8 Hz, 2H), 4.77 (m, 1H), 3.99 (m, 1H), 3.89 (m, 1H), 3.59 (m, 1H), 3.34 (m, 1H), 2.82 (s, 3H), 2.03 (m, 3H), 1.66 (m, 1H), 1.54 (m, 1H), 0.72 (m, 4H).

Example 348. 1-(4-(4-(7-methylquinolin-5-yl)phenoxy)piperidin-1-yl)propan-1-one HCl

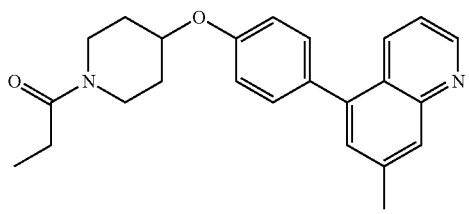 [SMILES: CCC(=O)N1CCC(Oc2ccc(-c3cc(C)cc4ncccc34)cc2)CC1]

Analysis: LCMS (ESI): 375 (M+1); $^1$H NMR (400 MHz, DMSO-d$_6$) δ: 9.23 (d, J=5.2 Hz, 1H), 8.85 (d, J=8.6 Hz, 1H), 8.14 (s, 1H), 7.94 (m, 1H), 7.74 (s, 1H), 7.46 (d, J=8.4 Hz, 2H), 7.20 (d, J=8.4 Hz, 2H), 4.75 (m, 1H), 3.91 (m, 1H), 3.78-3.65 (m, 1H), 3.44-3.21 (m, 2H), 2.67 (s, 3H), 2.36 (q, J=7.4 Hz, 2H), 2.04-1.93 (m, 2H), 1.61 (m, 1H), 1.56 (m, 1H), 1.00 (t, J=7.4 Hz, 3H).

Example 349. Cyclopropyl-{4-[4-(7-methyl-quinolin-5-yl)-phenoxy]-piperidin-1-yl}-methanone, HCl

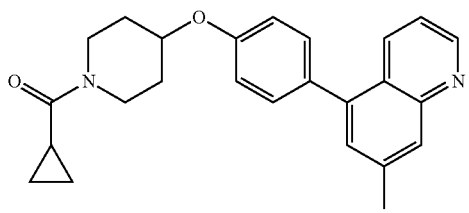 [SMILES: Cc1cc(-c2ccc(OC3CCN(C(=O)C4CC4)CC3)cc2)c2cccnc2c1]

Analysis: LCMS (ESI): 387 (M+1); $^1$H NMR (400 MHz, DMSO-d$_6$) δ: 9.19 (d, J=5.0 Hz, 1H), 8.76 (d, J=8.5 Hz, 1H), 8.08 (s, 1H), 7.87 (m, 1H), 7.69 (s, 1H), 7.48 (d, J=8.4 Hz, 2H), 7.21 (d, J=8.4 Hz, 2H), 4.77 (m, 1H), 4.01 (m, 1H), 3.91 (m, 1H), 3.60 (m, 1H), 3.31 (m, 1H), 2.66 (s, 3H), 2.09-1.94 (m, 3H), 1.68 (m, 1H), 1.57 (m, 1H), 0.79-0.66 (m, 4H).

Example 350. 1-(4-(4-(6-Methylquinolin-5-yl)phenoxy)piperidin-1-yl)propan-1-one HCl

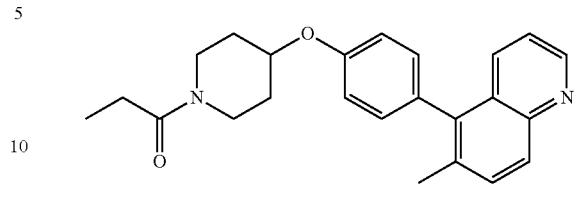

Analysis: LCMS (ESI): 375 (M+1); $^1$H NMR (400 MHz, DMSO-d6) δ: 8.82 (d, J=4.3 Hz, 1H), 7.95 (d, J=8.6 Hz, 1H), 7.72 (m, 2H), 7.41 (m, 1H), 7.17 (d, J=8.4 Hz, 2H), 7.14 (d, J=8.4 Hz, 2H), 4.71 (m, 1H), 3.95 (m, 1H), 3.75 (m, 1H), 3.37 (m, 1H), 3.24 (m, 1H), 2.36 (q, J=7.4 Hz, 2H), 2.24 (s, 3H), 2.02 (m, 2H), 1.66 (m, 1H), 1.55 (m, 1H), 0.99 (q, J=7.4 Hz, 3H).

Example 351. Cyclopropyl(4-(4-(6-methylquinolin-5-yl)phenoxy)piperidin-1-yl)methanone, HCl

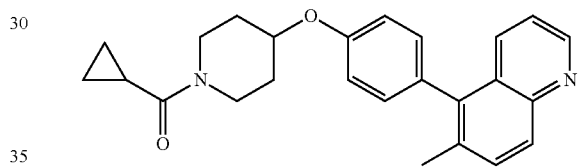

Analysis: LCMS (ESI): 387 (M+1); $^1$H NMR (400 MHz, DMSO-d$_6$) δ: 9.14 (d, J=4.9 Hz, 1H), 8.26 (m, 2H), 8.03 (d, J=8.8 Hz, 1H), 7.82 (m, 1H), 7.25 (d, J=8.4 Hz, 2H), 7.20 (d, J=8.4 Hz, 2H), 4.75 (m, 1H), 4.03 (m, 1H), 3.95 (m, 1H), 3.56 (m, 1H), 3.29 (m, 1H), 2.32 (s, 3H), 2.08-1.96 (m, 3H), 1.69 (s, 1H), 1.58 (s, 1H), 0.73 (m, 4H).

Example 352. (R)-(4-(4-(5-Methylquinolin-7-yl)phenoxy)piperidin-1-yl)(tetrahydrofuran-2-yl)methanone

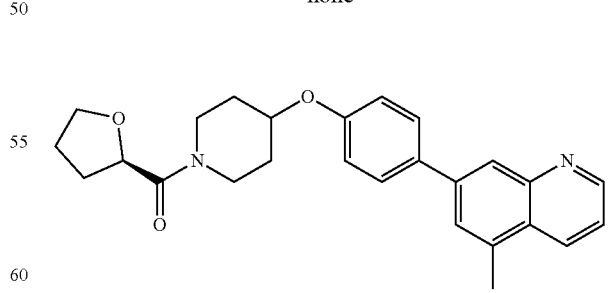

Analysis: LCMS (ESI): 417 (M+1); $^1$H NMR (400 MHz, DMSO-d$_6$) δ: 8.91 (d, J=4.2 Hz, 1H), 8.45 (m, 1H), 8.05 (s, 1H), 7.80 (m, 3H), 7.53 (m, 1H), 7.14 (d, J=8.6 Hz, 2H), 4.77-4.65 (m, 2H), 3.78 (m, 4H), 3.51 (m, 1H), 3.30 (m, 1H), 2.73 (s, 3H), 2.13-1.75 (m, 6H), 1.65-1.49 (m, 2H).

Example 353. (R)-(4-(4-(7-Methylquinolin-5-yl)phenoxy)piperidin-1-yl)(tetrahydrofuran-2-yl)methanone

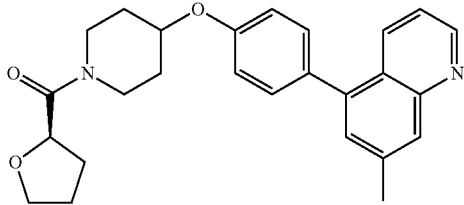 [SMILES: Cc1cc(-c2ccc(OC3CCN(C(=O)[C@H]4CCCO4)CC3)cc2)c2cccnc2c1]

Analysis: LCMS (ESI): 417 (M+1); $^1$H NMR (400 MHz, DMSO-$d_6$) δ: 8.86 (d, J=4.2 Hz, 1H), 8.15 (m, 1H), 7.82 (s, 1H), 7.48-7.35 (m, 4H), 7.15 (d, J=8.4 Hz, 2H), 4.77-4.65 (m, 2H), 3.96-3.69 (m, 4H), 3.51 (m, 1H), 3.21 (m, 1H), 2.56 (s, 3H), 2.13-1.74 (m, 6H), 1.73-1.51 (m, 2H).

Example 354. (R)-(4-(4-(6-Methylquinolin-5-yl)phenoxy)piperidin-1-yl)(tetrahydrofuran-2-yl)methanone

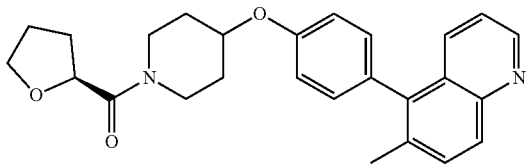 [SMILES: Cc1ccc2ncccc2c1-c1ccc(OC2CCN(C(=O)[C@@H]3CCCO3)CC2)cc1]

Analysis: LCMS (ESI): 417 (M+1); $^1$H NMR (400 MHz, DMSO-$d_6$) δ: 8.82 (d, J=4.1 Hz, 1H), 7.96 (d, J=8.6 Hz, 1H), 7.76-7.68 (m, 2H), 7.41 (m, 1H), 7.18 (m, 4H), 4.71 (m, 2H), 4.01-3.70 (m, 4H), 3.50 (m, 1H), 3.21 (m, 1H), 2.25 (s, 3H), 2.12-2.01 (m, 4H), 1.95-1.76 (m, 2H), 1.72-1.52 (m, 2H).

Example 355. (±)-(7S,8aS)-7-(4-(8-Methylquinolin-7-yl)phenoxy)hexahydroindolizin-3(2H)-one

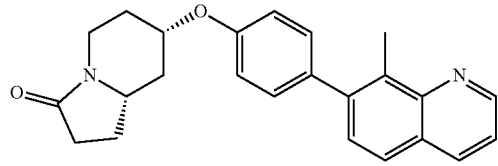 [SMILES: Cc1c(-c2ccc(O[C@H]3CCN4C(=O)CC[C@H]4C3)cc2)ccc2cccnc12]

Step 1. 7-(4-Fluorophenyl)-8-methylquinoline

A solution of 7-bromo-8-methylquinoline (1.0 g, 4.52 mmol), 4-fluorophenyl-boronic acid (0.74 g, 5.36 mmol) and $Na_2CO_3$ (1.62 g, 15.3 mmol) in 1,4-dioxane (20 mL) and water (4 mL) was degassed by argon for 30 min tetrakis (triphenylphosphine)palladium(0) (0.26 g, 0.22 mmol) was added and reaction mixture was heated at 100° C. for 15 h. The reaction mixture was cooled to RT and filtered through Celite pad, washed with ethyl acetate. Filtrate was washed with water and brine, dried over $Na_2SO_4$, filtered and concentrated. Purification was carried out by column chromatography to afford 7-(4-fluorophenyl)-8-methylquinoline (0.99 g, 92%). Analysis: LCMS (ESI): 238 (M+1); $^1$H NMR (400 MHz, $CDCl_3$) δ: 9.00 (dd, J=4.2, 1.9 Hz, 1H), 8.17 (dd, J=8.2, 1.9 Hz, 1H), 7.71 (d, J=8.4 Hz, 1H), 7.41-7.39 (m, 4H), 7.22-7.11 (m, 2H), 2.74 (s, 3H).

Step 2. (±)-(7S,8aS)-7-(4-(8-methylquinolin-7-yl)phenoxy)hexahydroindolizin-3(2H)-one To a solution of (±)-(7S,8aS)-7-hydroxyhexahydroindolizin-3(2H)-one (0.25 g, 1.61 mmol) (prepared according to Schoemaker, H. E. et al, *Tetrahedron*, 1978, 34, 163-172) in NMP, cooled at 0° C., was added NaH (60% in oil, 0.077 g, 1.93 mmol) and stirred at 0° C. for 30 min. To this solution 7-(4-fluorophenyl)-8-methylquinoline (0.4 g, 1.69 mmol) in NMP was added in dropwise fashion followed by heating at 100° C. for 12 h. The reaction mixture was quenched with water and extracted with ethyl acetate. The organic layer again washed with water, brine, was dried over $Na_2SO_4$ and concentrated. Residue was purified by column chromatography (silica, 3-5% methanol in DCM to afford (±)-(7S,8aS)-7-(4-(8-methylquinolin-7-yl)phenoxy)hexahydroindolizin-3(2H)-one (0.11 g, 18%). -LCMS (ESI): 373 (M+1); $^1$H NMR (400 MHz, $CDCL_3$) δ: 9.02-8.96 (m, 1H), 8.16 (dd, J=8.3, 1.9 Hz, 1H), 7.70 (d, J=8.4 Hz, 1H), 7.54-7.31 (m, 4H), 7.01 (dd, J=8.6, 2.5 Hz, 2H), 4.45-4.41 (m, 1H), 4.29-4.27 (m, 1H), 3.69-3.57 (m, 1H), 2.87-2.72 (m, 4H), 2.45 (s, 3H), 2.3-2.28 (m, 2H), 1.78-1.56 (m, 2H), 1.45-1.42 (m, 1H).

Example 356. (±)-(7R,8aS)-7-(4-(8-Methylquinolin-7-yl)phenoxy)hexahydroindolizin-3(2H)-one

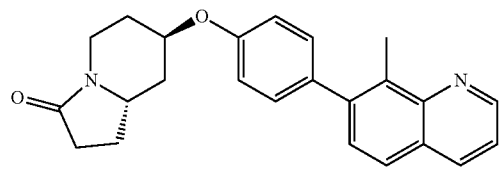 [SMILES: Cc1c(-c2ccc(O[C@@H]3CCN4C(=O)CC[C@H]4C3)cc2)ccc2cccnc12]

Step 1. 4-(8-Methylquinolin-7-yl)-phenol

A solution of 7-bromo-8-methylquinoline (1.0 g, 4.52 mmol), 4-hydroxyphenyl-boronic acid (0.76 g, 5.41 mmol) and $Na_2CO_3$ (1.62 g, 15.3 mmol) in 1,4-dioxane (20 mL) and water (4 mL) was degassed by argon for 30 min tetrakis (triphenylphosphine)palladium(0) (0.26 g, 0.22 mmol) was added and reaction mixture was heated at 100° C. for 15 h. The reaction mixture was cooled to rt and filtered through Celite pad, washed with ethyl acetate. Filtrate was washed with water and brine, dried over $Na_2SO_4$, filtered and concentrated. Purification was carried out by column chromatography to afford 4-(8-methylquinolin-7-yl)-phenol (1.0 g, 93%). Analysis: LCMS (ESI): 236 (M+1); $^1$H NMR (400 MHz, DMSO-$d_6$) δ: 9.57 (s, 1H), 8.96 (dd, J=4.2, 1.8 Hz, 1H), 8.35 (dd, J=8.2, 1.8 Hz, 1H), 7.83 (d, J=8.4 Hz, 1H), 7.53 (dd, J=8.2, 4.2 Hz, 1H), 7.45 (d, J=8.4 Hz, 1H), 7.30-7.20 (m, 2H), 6.93-6.84 (m, 2H), 2.67 (s, 3H).

Step 2. (±)-(7R,8aS)-7-(4-(8-methylquinolin-7-yl)phenoxy)hexahydroindolizin-3(2H)-one To a solution of (±)-(7S,8aS)-7-hydroxyhexahydroindolizin-3(2H)-one (0.4 g, 2.58 mmol) and 4-(8-methylquinolin- 7-yl)-phenol (0.63 g, 2.70 mmol) in THF, cooled at 0° C., was added triphenylphosphine (0.87 g, 3.35 mmol) and stirred at 0° C. for 20 min. To this solution was added di-tert-butyl azodicarboxylate (0.77 g, 3.35 mmol) followed by stirring at rt for 12 h. The reaction mixture was concentrated under reduced pressure. Residue was purified by column chromatography (silica, 1-2% methanol in DCM) to afford (±)-(7R,8aS)-7-(4-(8-methylquinolin-7-yl)phenoxy)hexahydroindolizin-3(2H)-one (0.12 g, 13%). Analysis: LCMS (ESI): 373 (M+1); $^1$H NMR (400 MHz, CDCl$_3$) δ: 9.00 (dd, J=4.1, 1.8 Hz, 1H), 8.16 (d, J=8.1 Hz, 1H), 7.70 (d, J=8.4 Hz, 1H), 7.50-7.27 (m, 4H), 7.02 (dd, J=8.7, 3.0 Hz, 2H), 4.83 (d, J=3.4 Hz, 1H), 4.11-3.91 (m, 2H), 3.18-3.16 (m, 1H), 2.78 (s, 3H), 2.49-2.17 (m, 4H), 2.14 (d, J=14.3 Hz, 1H), 1.76-1.56 (m, 2H), 1.47-1.45 (m, 1H).

Example 357. 2,2,2-Trifluoro-1-{4-[4-(8-methyl-quinolin-7-yl)-phenoxy]-piperidin-1-yl}-ethanone

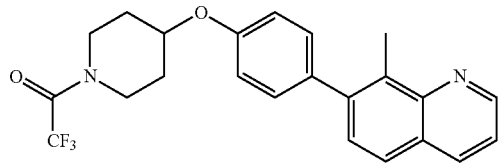 [SMILES: Cc1c(-c2ccc(OC3CCN(C(=O)C(F)(F)F)CC3)cc2)ccc2cccnc12]

Step 1. 4-[4-(8-Methylquinolin-7-yl)-phenoxy]-piperidine-1-carboxylic acid t-butyl ester 4-[4-(4,4,5,5-Tetramethyl-1,3,2-dioxaborolan-2-yl)-phenoxy]-piperidine-1-carboxylic acid tert-butyl ester (1.01 g, 2.51 mmol), 7-bromo-8-methylquinoline (0.556 g, 2.50 mmol), tetrakis(triphenylphosphine)palladium(0) (0.123 g, 0.106 mmol) and K$_2$CO$_3$ (0.556 g, 4.02 mmol) were combined in water (6.0 mL): 1,4-dioxane (24.0 mL). The mixture was briefly vacuum degassed then stirred at 80° C. under an atmosphere of nitrogen overnight. The mixture was cooled, partitioned between EtOAc (100 mL) and water (20 mL) and the layers wee separated. The aqueous layer was extracted with EtOAc (50 mL) and the combined organics were washed with brine (50 mL), dried over sodium sulfate and filtered through 2 mL silica gel. The filtrate was concentrated in vacuo to afford 4-[4-(8-methyl-quinolin-7-yl)-phenoxy]-piperidine-1-carboxylic acid t-butyl ester.

Step 2. 8-Methyl-7-[4-(piperidin-4-yloxy)-phenyl]-quinoline dihydrochloride

Crude 4-[4-(8-methyl-quinolin-7-yl)-phenoxy]-piperidine-1-carboxylic acid tert-butyl ester was dissolved in methanol (10.0 mL, 247 mmol) and 4.0 M of HCl in 1,4-dioxane (3.00 mL, 12.0 mmol) was added. After stirring overnight, the mixture was diluted with ethyl acetate: hexanes (1:1, 60 mL) and the resultant solids were collected by filtration, washed with ethyl acetate:hexanes (1:1, 10 mL) then dried in vacuo to afford 8-methyl-7-[4-(piperidin-4-yloxy)-phenyl]-quinoline dihydrochloride (0.830 g; 84.7%). Analysis: $^1$H NMR (400 MHz, DMSO-d$_6$) δ: 8.94-9.34 (3H, m), 8.62-8.94 (1H, m), 8.06 (1H, d, J=8.5 Hz), 7.73-7.87 (1H, m), 7.66 (1H, d, J=8.3 Hz), 7.43 (2H, d, J=8.8 Hz), 7.17 (2H, d, J=8.8 Hz), 4.60-5.00 (1H, m), 3.18-3.34 (2H, m), 2.99-3.15 (2H, m), 2.72 (3H, s), 2.10-2.23 (2H, m), 1.74-1.98 (2H, m).

Step 3. 2,2,2-Trifluoro-1-{4-[4-(8-methyl-quinolin-7-yl)-phenoxy]-piperidin-1-yl}-ethanone Trifluoroacetic anhydride (67.7 uL, 0.479 mmol) was added to 8-methyl-7-[4-(piperidin-4-yloxy)-phenyl]-quinoline 2HCl (0.125 g, 0.319 mmol) and DIPEA (0.250 mL, 1.44 mmol) in DMF (3.00 mL). After 2 h, the mixture was concentrated in vacuo. The residue was dissolved in DCM, applied to a silica gel loading cartridge (5 g) and purified on silica gel (24 g, 0-5% methanol:DCM) to afford 2,2,2-trifluoro-1-{4-[4-(8-methylquinolin-7-yl)-phenoxy]-piperidin-1-yl}-ethanone (92 mg, 69%) after reconcentration from ether. Analysis: LCMS (ESI): 415 (M+1); $^1$H NMR (400 MHz, DMSO-d$_6$) δ: 8.97 (1H, dd, J=4.3, 1.8 Hz), 8.37 (1H, dd, J=8.3, 1.8 Hz), 7.86 (1H, d, J=8.3 Hz), 7.55 (1H, dd, J=8.2, 4.1 Hz), 7.48 (1H, d, J=8.5 Hz), 7.39 (2H, d, J=7.6 Hz), 7.13 (2H, d, J=7.4 Hz), 4.68-4.84 (1H, m), 3.72-3.93 (2H, m), 3.47-3.66 (2H, m), 2.68 (3H, s), 1.99-2.15 (2H, m), 1.68-1.82 (2H, m); $^{19}$F NMR (377 MHz, DMSO-d$_6$) δ −68.07 (3F, s).

Example 358. 2,2-Difluoro-1-{4-[4-(8-methylquinolin-7-yl)-phenoxy]-piperidin-1-yl}-propan-1-one, HCl

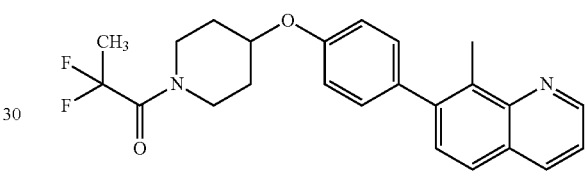

2,2-Difluoropropionic acid (0.0527 g, 0.479 mmol) in DMF (1.00 mL, 12.9 mmol) was added to 8-methyl-7-[4-(piperidin-4-yloxy)-phenyl]-quinoline 2HCl (0.125 g, 0.319 mmol) and DIPEA (0.250 mL, 1.44 mmol) in DMF (3.0 mL), then treated with HATU (0.146 g, 0.37 mmol). After 2 h, the mixture was concentrated in vacuo. The residue was dissolved in DCM, applied to a silica gel loading cartridge (5 g) and purified on silica gel (24 g, 0-5% methanol:DCM) to afford 2,2-difluoro-1-{4-[4-(8-methylquinolin-7-yl)-phenoxy]-piperidin-1-yl}-propan-1-one HCl (83 mg, 58%) after treatment of product fractions redissolved in methanol with 2M HCl in ether, reconcentrating from ether. Analysis: LCMS (ESI): 411 (M+1); $^1$H NMR (400 MHz, DMSO-d$_6$) δ: 9.10 (1H, dd, J=4.5, 1.5 Hz), 8.74 (1H, br. s.), 8.03 (1H, d, J=8.5 Hz), 7.79 (1H, dd, J=7.4, 4.6 Hz), 7.64 (1H, d, J=8.5 Hz), 7.41 (2H, d, J=8.8 Hz), 7.15 (2H, d, J=8.8 Hz), 4.74-4.84 (1H, m), 3.89 (2H, br. s.), 3.51-3.67 (1H, m), 3.46 (1H, t, J=9.3 Hz), 2.71 (3H, s), 2.04 (2H, br. s.), 1.83 (3H, t, J=20.1 Hz), 1.61-1.76 (2H, m); $^{19}$F NMR (377 MHz, DMSO-d6) δ −91.22 (d, J=27.2 Hz).

Example 359. 2-Fluoro-1-{4-[4-(8-methylquinolin-7-yl)-phenoxy]-piperidin-1-yl}-propan-1-one, HCl

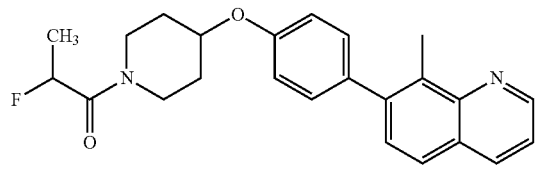 [SMILES: Cc1c(-c2ccc(OC3CCN(C(=O)C(C)F)CC3)cc2)ccc2cccnc12]

Prepared by analogy with Example 358. Analysis: LCMS (ESI): 393 (M+1); $^1$H NMR (400 MHz, DMSO-$d_6$) δ: 9.04 (1H, dd, J=4.4, 1.4 Hz), 8.59 (1H, d, J=6.5 Hz), 7.96 (1H, d, J=8.3 Hz), 7.65-7.78 (1H, m), 7.58 (1H, d, J=8.5 Hz), 7.31-7.45 (2H, m), 7.14 (2H, d, J=8.8 Hz), 5.56 (1H, dq, J=47.7, 6.5 Hz), 4.74 (1H, d, J=3.3 Hz), 3.91 (2H, m), 3.24-3.49 (2H, m), 2.69 (3H, s), 2.02 (2H, m), 1.64 (2H, m), 1.42 (3H, dd, J=24.9, 6.5 Hz).

Example 360. {exo-3-[4-(8-Methylquinolin-7-yl)-phenoxy]-8-aza-bicyclo[3.2.1]oct-8-yl}-(R)-tetrahydrofuran-2-yl-methanone, HCl

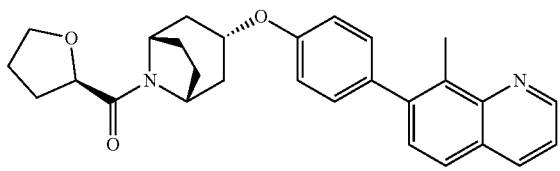 [SMILES: Cc1c(-c2ccc(O[C@@H]3C[C@H]4CC[C@@H](C3)N4C(=O)[C@H]3CCCO3)cc2)ccc2cccnc12]

Step 1. exo-3-[4-(8-Methyl-quinolin-7-yl)-phenoxy]-8-aza-bicyclo[3.2.1]octane-8-carboxylic acid tert-butyl ester exo-3-Hydroxy-8-aza-bicyclo[3.2.1]octane-8-carboxylic acid tert-butyl ester (379 mg, 1.67 mmol) and NaH, 60% dispersion in mineral oil (101 mg, 2.52 mmol) were combined in N-methylpyrrolidinone (NMP) (4.00 mL). After 20 min, a solution of 7-(4-fluoro-phenyl)-8-methyl-quinoline (294 mg, 1.24 mmol) in NMP (1.5 mL) was added and the mixture was heated at 100° C. for 48 h, at which point conversion had reached ca. 50% as determined by LCMS. The mixture was cooled, diluted with ethyl acetate (75 mL) and hexanes (25 mL) then washed with water (3×10 mL) and brine (30 mL), dried over sodium sulfate, filtered and concentrated in vacuo. The residue was dissolved in DCM, applied to a silica gel loading cartridge (5 g) and purified on silica gel (40 g, 0-40% ethyl acetate: hexane) to afford exo-3-[4-(8-methyl-quinolin-7-yl)-phenoxy]-8-aza-bicyclo[3.2.1]octane-8-carboxylic acid tert-butyl ester (0.192 g, 34.8%). Analysis: $^1$H NMR (400 MHz, methanol-$d_4$) δ: 8.89 (dd, J=4.3, 2.0 Hz, 1H) 8.32 (dd, J=8.3, 1.8 Hz, 1H) 7.79 (d, J=8.5 Hz, 1H) 7.51 (dd, J=8.3, 4.3 Hz, 1H) 7.47 (d, J=8.3 Hz, 1H) 7.32 (d, J=8.8 Hz, 2H) 7.07 (d, J=8.8 Hz, 2H) 4.86-4.95 (m, 1H) 4.25-4.32 (m, 2H) 2.68 (s, 3H) 2.17-2.26 (m, 2H) 2.01-2.08 (m, 2H) 1.83-1.93 (m, 2H) 1.66-1.79 (m, 2H) 1.51 (s, 9H).

Step 2. 7-{4-[exo-(8-Aza-bicyclo[3.2.1]oct-3-yl)oxy]-phenyl}-8-methyl-quinoline, 2HCL exo-3-[4-(8-Methylquinolin-7-yl)-phenoxy]-8-aza-bicyclo[3.2.1]octane-8-carboxylic acid tert-butyl ester (0.192 g, 0.432 mmol) and 4.0 M of HCl in 1,4-dioxane (0.450 mL, 1.80 mmol) were combined in methanol (7.0 mL) and stirred at room temp. After 22 h, the mixture was concentrated in vacuo to afford 7-{4-[exo-(8-aza-bicyclo[3.2.1]oct-3-yl)oxy]-phenyl}-8-methyl-quinoline 2HCl (0.180 g, 99.8%).

Step 3. {exo-3-[4-(8-Methylquinolin-7-yl)-phenoxy]-8-aza-bicyclo[3.2.1]oct-8-yl}-(R)-tetrahydrofuran-2-yl-methanone, HCl 7-{4-[exo-(8-Aza-bicyclo[3.2.1]oct-3-yl)oxy]-phenyl}-8-methylquinoline 2HCl (90.0 mg, 0.216 mmol), (R)-tetrahydrofuran-2-carboxylic acid (28.8 mg, 0.248 mmol) and DIPEA (0.225 mL, 1.29 mmol) were combined in DCM (3.0 mL) and HATU (102 mg, 0.270 mmol) was added. After 2 h, the mixture was diluted with EtOAc (20 mL), washed with saturated NaHCO$_3$ (5 mL) and brine (5 mL), dried over Na$_2$SO$_4$, filtered and concentrated in vacuo. The residue was dissolved in DCM, applied to a silica gel loading cartridge (5 g) and purified on silica gel (12 g, 10-70% ethyl acetate: hexane) to afford purified free base after concentration of product containing fractions. The free base was dissolved in methanol and treated with 4M HCl in dioxane then concentrated to afford {exo-3-[4-(8-methylquinolin-7-yl)-phenoxy]-8-aza-bicyclo[3.2.1]oct-8-yl}-(R)-tetrahydrofuran-2-yl-methanone HCl (95 mg, 92%). Analysis: LCMS (ESI): 443 (M+1); $^1$H NMR (400 MHz, DMSO-$d_6$) δ: 9.04 (d, J=3.0 Hz, 1H) 8.50-8.68 (m, 1H) 7.96 (d, J=8.3 Hz, 1H) 7.64-7.76 (m, 1H) 7.57 (d, J=8.5 Hz, 1H) 7.37 (d, J=8.8 Hz, 2H) 7.13 (d, J=8.5 Hz, 2H) 4.87-4.99 (m, 1H) 4.46-4.63 (m, 3H) 3.72-3.92 (m, 2H) 2.69 (s, 3H) 2.14-2.31 (m, 2H) 1.79-2.10 (m, 8H) 1.66-1.79 (m, 1H) 1.53-1.63 (m, 1H).

Example 361. 1-{exo-3-[4-(8-Methylquinolin-7-yl)-phenoxy]-8-aza-bicyclo[3.2.1]oct-8-yl})-propan-1-one HCl

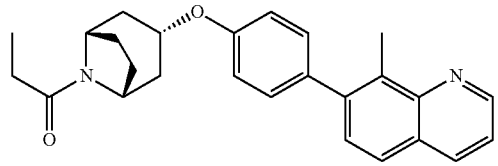 [SMILES: CCC(=O)N1[C@@H]2CC[C@H]1C[C@H](Oc1ccc(-c3ccc4cccnc4c3C)cc1)C2]

7-{4-[exo-(8-Aza-bicyclo[3.2.1]oct-3-yl)oxy]-phenyl}-8-methylquinoline 2HCl (90.0 mg, 0.216 mmol), and DIPEA (0.225 mL, 1.29 mmol) were combined in DCM (3.0 mL) and propanoyl chloride (22.9 mg, 0.248 mmol) was added. After 2 h, the mixture was diluted with ethyl acetate (20 mL), washed with saturated NaHCO$_3$ (5 mL) and brine (5 mL), dried over Na$_2$SO$_4$, filtered and concentrated in vacuo. The residue was dissolved in DCM, applied to a silica gel loading cartridge (5 g) and purified on silica gel (12 g, 10-60% ethyl acetate:hexane) to afford purified free base after concentration of product containing fractions. The free base was dissolved in methanol and treated with 4M HCl in dioxane then concentrated to afford 1-{exo-3-[4-(8-methylquinolin-7-yl)-phenoxy]-8-aza-bicyclo[3.2.1]oct-8-yl}-propan-1-one HCl (74 mg, 78%). Analysis: LCMS (ESI): 401 (M+1); $^1$H NMR (400 MHz, DMSO-$d_6$) δ: 9.10 (d, J=3.3 Hz, 1H) 8.68-8.84 (m, 1H) 8.04 (d, J=8.5 Hz, 1H) 7.75-7.86 (m, 1H) 7.64 (d, J=8.3 Hz, 1H) 7.38 (d, J=8.8 Hz, 2H) 7.14 (d, J=8.8 Hz, 2H) 4.93-4.98 (m, 1H) 4.53-4.58 (m, 1H) 4.31-4.37 (m, 1H) 2.70 (s, 3H) 2.13-2.44 (m, 4H) 1.79-2.03 (m, 4H) 1.50-1.62 (m, 2H) 1.02 (t, J=7.4 Hz, 3H).

Example 362. {2-Methyl-4-[4-(8-methylquinolin-7-yl)-phenoxy]-piperidin-1-yl}-(R)-tetrahydrofuran-2-yl-methanone, HCl

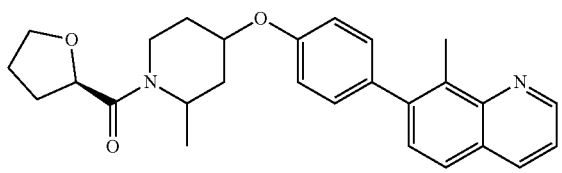 [SMILES: Cc1c(-c2ccc(OC3CCN(C(=O)[C@H]4CCCO4)C(C)C3)cc2)ccc2cccnc12]

Prepared as a mixture of four diastereomers, analogous to Example 360, using 4-hydroxy-2-methyl-piperidine-1-carboxylic acid tert-butyl ester in Step 1. Analysis: LCMS (ESI): 443 (M+1); $^1$H NMR (400 MHz, DMSO-d$_6$) δ: 9.08-9.16 (m, 1H) 8.75-8.89 (m, 1H) 8.02-8.15 (m, 1H) 7.80-7.93 (m, 1H) 7.64-7.73 (m, 1H) 7.37-7.47 (m, 2H) 7.07-7.19 (m, 2H) 4.84-4.92 (m, 1H) 4.57-4.76 (m, 2H) 3.71-3.84 (m, 2H) 2.66-2.76 (m, 9H) 1.76-2.19 (m, 6H) 1.13-1.47 (m, 3H).

Example 363. 1-{2-Methyl-4-[4-(8-methylquinolin-7-yl)-phenoxy]-piperidin-1-yl}-propan-1-one, HCl

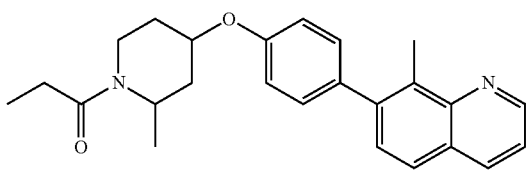 [SMILES: CCC(=O)N1CCC(Oc2ccc(-c3ccc4cccnc4c3C)cc2)CC1C]

Prepared as a 1:1 mixture of diastereomers, analogous to Example 361, using 4-hydroxy-2-methyl-piperidine-1-carboxylic acid tert-butyl ester and propanoyl chloride. Analysis: LCMS (ESI): 389 (M+1); $^1$H NMR (400 MHz, DMSO-d$_6$) δ: 9.01-9.12 (m, 1H) 8.58-8.78 (m, 1H) 7.94-8.08 (m, 1H) 7.68-7.84 (m, 1H) 7.56-7.67 (m, 1H) 7.34-7.47 (m, 2H) 7.06-7.18 (m, 2H) 4.78-4.94 (m, 1H) 4.30-4.52 (m, 1H) 3.64-3.73 (m, 1H) 3.28-3.52 (m, 1H) 2.67-2.73 (m, 3H) 2.29-2.39 (m, 1H) 1.87-2.22 (m, 2H) 1.16-1.36 (m, 3H) 0.95-1.07 (m, 3H).

Example 364. 1-{2-Methyl-4-[4-(8-methylquinolin-7-yl)-phenoxy]-piperidin-1-yl}-propan-1-one, HCl

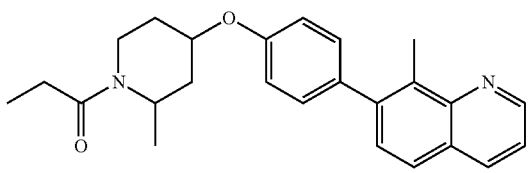 [SMILES: CCC(=O)N1CCC(Oc2ccc(-c3ccc4cccnc4c3C)cc2)CC1C]

Prepared as a 1:9 mixture of diastereomers, enriched in the more polar diastereo-mer, analogously to Example 361, using 4-hydroxy-2-methyl-piperidine-1-carboxylic acid tert-butyl ester and propanoyl chloride. Analysis: LCMS (ESI): 389 (M+1); $^1$H NMR (400 MHz, DMSO-d$_6$) δ: 9.01-9.12 (m, 1H) 8.58-8.78 (m, 1H) 7.94-8.08 (m, 1H) 7.68-7.84 (m, 1H) 7.56-7.67 (m, 1H) 7.34-7.47 (m, 2H) 7.06-7.18 (m, 2H) 4.78-4.94 (m, 1H) 4.30-4.52 (m, 1H) 3.64-3.73 (m, 1H) 3.28-3.52 (m, 1H) 2.67-2.73 (m, 3H) 2.29-2.39 (m, 1H) 1.87-2.22 (m, 2H) 1.16-1.36 (m, 3H) 0.95-1.07 (m, 3H).

Example 365. Cyclopropyl-{2-methyl-4-[4-(8-methylquinolin-7-yl)-phenoxy]-piperidin-1-yl}-methanone HCl

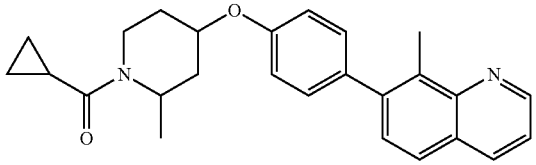 [SMILES: Cc1c(-c2ccc(OC3CCN(C(=O)C4CC4)C(C)C3)cc2)ccc2cccnc12]

Prepared as a racemic mixture of diastereomers, analogously to Example 361, using 4-hydroxy-2-methyl-piperidine-1-carboxylic acid tert-butyl ester and cyclopropyl carbonyl chloride. Analysis: LCMS (ESI): 401 (M+1); $^1$H NMR (400 MHz, DMSO-d$_6$) δ: 9.00-9.10 (m, 1H) 8.55-8.70 (m, 1H) 7.92-8.05 (m, 1H) 7.66-7.78 (m, 1H) 7.56-7.67 (m, 1H) 7.35-7.46 (m, 2H) 7.06-7.19 (m, 2H) 4.84-4.91 (m, 1H) 4.57-4.69 (m, 1H) 4.13-4.22 (m, 1H) 3.63-3.75 (m, 1H) 2.70 (s, 3H) 1.68-2.27 (m, 5H) 1.20-1.41 (m, 3H) 0.64-0.82 (m, 4H).

Example 366. {cis-3-Fluoro-4-[4-(8-methylquinolin-7-yl)-phenoxy]-piperidin-1-yl}-(R)-tetrahydrofuran-2-yl-methanone HCl

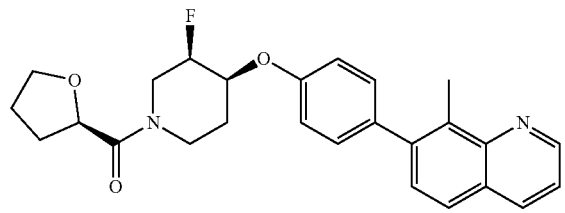 [SMILES: Cc1c(-c2ccc(O[C@H]3CCN(C(=O)[C@H]4CCCO4)C[C@H]3F)cc2)ccc2cccnc12]

Step 1. cis-3-Fluoro-4-[4-(8-methylquinolin-7-yl)-phenoxy]-piperidine-1-carboxylic acid t-butyl ester Di-t-butyl azodicarboxylate (0.405 g, 1.76 mmol) was added to a −10 OC solution of 4-(8-methyl-quinolin-7-yl)-phenol (0.267 g, 1.13 mmol), trans-3-Fluoro-4-hydroxy-piperidine-1-carboxylic acid t-butyl ester (0.387 g, 1.76 mmol), and triphenylphosphine (0.461 g, 1.76 mmol) in THF (12.0 mL). The mixture was allowed to slowly warm in the cooling bath then stirred overnight under an atmosphere of nitrogen. The mixture was heated at 60° C. for 24 h, resulting in significant conversion to product. The mixture was cooled and concentrated in vacuo onto silica gel (5 g) and purified on silica gel (80 g, 5-35% ethyl acetate:hexane) to afford cis-3-fluoro-4-[4-(8-methyl-quinolin-7-yl)-phenoxy]-piperidine-1-carboxylic acid tert-butyl ester (0.409 g, 82.6%). Analysis: LCMS (ESI): 437 (M+1); $^1$H NMR (400 MHz, methanol-d$_4$) δ 8.90 (dd, J=4.3, 1.8 Hz, 1H) 8.32 (dd, J=8.2, 1.9 Hz, 1H) 7.79 (d, J=8.5 Hz, 1H) 7.52 (dd, J=8.3, 4.3 Hz, 1H) 7.48 (d, J=8.3 Hz, 1H) 7.35 (d, J=8.8 Hz, 2H) 7.13 (d, J=8.5 Hz, 2H) 4.59-4.75 (m, 1H) 4.15-4.25 (m, 1H) 3.92-4.03 (m, 1H) 3.56-3.83 (m, 1H) 3.34-3.44 (m, 1H) 3.17-3.25 (m, 1H) 2.69 (s, 3H) 1.84-1.98 (m, 2H) 1.45 (s, 9H);

Step 2. 7-[4-(cis-3-Fluoropiperidin-4-yloxy)-phenyl]-8-methylquinoline 2HCl cis-3-Fluoro-4-[4-(8-methylquinolin-7-yl)-phenoxy]-piperidine-1-carboxylic acid t-butyl ester (0.495 g, 1.13 mmol)

and 4.0 M of HCl in 1,4-dioxane (3.0 mL, 12 mmol) were combined in methanol (10.0 mL) and aged at room temperature for 3 h. The mixture was concentrated in vacuo to afford 7-[4-(cis-3-fluoro-piperidin-4-yloxy)-phenyl]-8-methyl-quinoline 2HCl (0.449 g, 96.7%). Analysis: $^1$H NMR (400 MHz, methanol-d4) δ 9.21 (d, J=8.3 Hz, 1H) 9.17 (dd, J=5.5, 1.5 Hz, 1H) 8.23 (d, J=8.5 Hz, 1H) 8.11 (dd, J=8.2, 5.6 Hz, 1H) 7.88 (d, J=8.5 Hz, 1H) 7.47 (d, J=8.8 Hz, 2H) 7.25 (d, J=8.8 Hz, 2H) 5.15-5.35 (m, 1H) 4.87-4.98 (m, 1H) 3.69-3.86 (m, 1H) 3.39-3.57 (m, 3H) 2.78 (s, 3H) 2.23-2.35 (m, 2H); $^{19}$F NMR (377 MHz, methanol-d4) δ −192.91 (s, 1F).

Step 3. {cis-3-Fluoro-4-[4-(8-methylquinolin-7-yl)-phenoxy]-piperidin-1-yl}-(R)-tetrahydrofuran-2-yl-methanone HCl (R)-Tetrahydrofuran-2-carboxylic acid (47.4 mg, 0.408 mmol) HATU (168 mg, 0.443 mmol) were combined in DCM (1.6 mL, 24.8 mmol) and stirred for 30 min. A solution of 7-[4-(cis-3-fluoro-piperidin-4-yloxy)-phenyl]-8-methyl-quinoline 2HCl (148 mg, 0.362 mmol) and DIPEA (0.309 mL, 1.77 mmol) in DCM (4.8 mL) was then added. After stirring for 2 h, the mixture was diluted with ethyl acetate (15 mL) and satd. aq. NaHCO₃ (7 mL). The layers were separated, the aq. extracted with EtOAc (5 mL) and the combined organics were dried over sodium sulfate, filtered and concentrated. The residue was dissolved in DCM, applied to a silica gel loading cartridge (5 g) and purified on silica gel (24 g, 10-80% EtOAc:hexane) to afford {cis-3-fluoro-4-[4-(8-methylquinolin-7-yl)-phenoxy]-piperidin-1-yl}-(R)-tetrahydrofuran-2-yl-methanone HCl (0.131 g, 76.9%) as a 1:1 mixture of diastereomers, R-THF with 3R,4S piperidine and R-THF with 3S,4R piperidine after treatment of product containing fractions with 4.0 M of HCl in 1,4-dioxane (0.355 mL, 1.42 mmol) and reconcentration from methanol. Analysis: LCMS (ESI): 435 (M+1); $^1$H NMR (400 MHz, DMSO-d₆) δ: 9.06-9.17 (m, 1H) 8.70-8.96 (m, 1H) 7.99-8.11 (m, 1H) 7.76-7.88 (m, 1H) 7.61-7.70 (m, 1H) 7.40-7.49 (m, 2H) 7.14-7.27 (m, 2H) 4.91-5.14 (m, 1H) 4.79-4.90 (m, 1H) 4.62-4.76 (m, 1H) 3.93-4.55 (m, 2H) 3.59-3.84 (m, 3H) 2.71 (s, 3H) 1.93-2.11 (m, 3H) 1.72-1.85 (m, 2H) 1.21-1.33 (m, 4H); $^{19}$F NMR (377 MHz, DMSO-d6) δ −69.2 (s, 1F) and −71.1 (s, 1F).

The following examples were prepared by analogy with propanoyl chloride or cyclopropyl carbonyl chloride in Step c as required and the requisite N-Boc-piperidin-4-ol derivative.

Example 367. 1-{cis-3-Fluoro-4-[4-(8-methylquinolin-7-yl)-phenoxy]-piperidin-1-yl}-propan-1-one, HCl

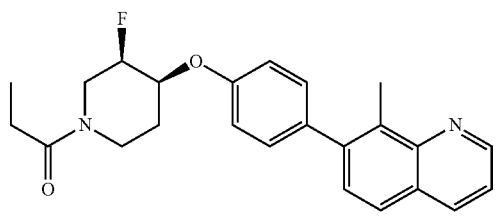 [SMILES: CCC(=O)N1CC[C@H](Oc2ccc(-c3ccc4cccnc4c3C)cc2)[C@H](F)C1]

Analysis: LCMS (ESI): 393 (M+1); $^1$H NMR (400 MHz, DMSO-d₆) δ: 9.02-9.10 (m, 1H) 8.59-8.69 (m, 1H) 7.95-8.03 (m, 1H) 7.70-7.77 (m, 1H) 7.55-7.64 (m, 1H) 7.37-7.45 (m, 2H) 7.13-7.22 (m, 2H) 4.90-5.13 (m, 1H) 4.77-4.88 (m, 1H) 4.47-4.54 (m, 1H) 4.29-4.37 (m, 1H) 4.09-4.19 (m, 1H) 3.66-3.91 (m, 1H) 3.42-3.57 (m, 1H) 3.12-3.34 (m, 1H) 2.28-2.43 (m, 2H) 1.89-1.97 (m, 1H) 0.95-1.06 (m, 3H).

Example 368. Cyclopropyl-{cis-3-fluoro-4-[4-(8-methylquinolin-7-yl)-phenoxy]-piperidin-1-yl}-methanone, HCl

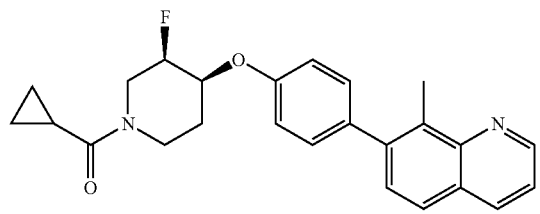 [SMILES: Cc1c(-c2ccc(O[C@H]3CCN(C(=O)C4CC4)C[C@H]3F)cc2)ccc2cccnc12]

Analysis: LCMS (ESI): 405 (M+1); $^1$H NMR (400 MHz, DMSO-d₆) δ: 9.00-9.10 (m, 1H) 8.58-8.67 (m, 1H) 7.98 (d, J=8.3 Hz, 1H) 7.68-7.76 (m, 1H) 7.59 (d, J=8.5 Hz, 1H) 7.42 (d, J=8.8 Hz, 2H) 7.19 (d, J=8.8 Hz, 2H) 4.93-5.15 (m, 1H) 4.78-4.90 (m, 1H) 4.44-4.55 (m, 1H) 4.21-4.35 (m, 1H) 3.37-3.52 (m, 1H) 2.70 (s, 3H) 1.93-2.07 (m, 2H) 1.66-1.81 (m, 1H) 0.67-0.80 (m, 5H).

Example 369. 1-{endo-3-[4-(8-Methylquinolin-7-yl)-phenoxy]-8-aza-bicyclo[3.2.1]oct-8-yl}-propan-1-one, HCl

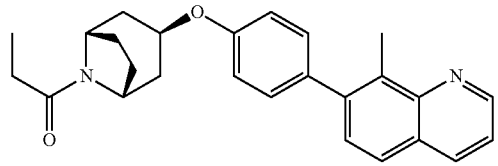 [SMILES: CCC(=O)N1[C@@H]2CC[C@H]1C[C@@H](Oc1ccc(-c3ccc4cccnc4c3C)cc1)C2]

Analysis: From exo-3-Hydroxy-8-aza-bicyclo[3.2.1]octane-8-carboxylic acid tert-butyl ester. LCMS (ESI): 401 (M+1); $^1$H NMR (400 MHz, DMSO-d₆) δ: 9.09 (dd, J=4.5, 1.3 Hz, 1H) 8.63-8.79 (m, 1H) 8.02 (d, J=8.5 Hz, 1H) 7.72-7.82 (m, 1H) 7.64 (d, J=8.3 Hz, 1H) 7.42 (d, J=8.8 Hz, 2H) 7.04 (d, J=8.8 Hz, 2H) 4.76-4.84 (m, 1H) 4.47-4.53 (m, 1H) 4.25-4.31 (m, 1H) 2.71 (s, 3H) 1.77-2.43 (m, 10H) 1.02 (t, J=7.4 Hz, 3H).

Example 370. Cyclopropyl-{endo-3-[4-(8-methylquinolin-7-yl)-phenoxy]-8-aza-bicyclo[3.2.1]oct-8-yl}-methanone, HCl

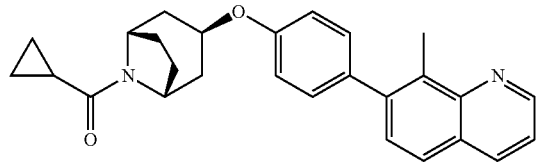 [SMILES: Cc1c(-c2ccc(O[C@H]3C[C@H]4CC[C@@H](C3)N4C(=O)C3CC3)cc2)ccc2cccnc12]

Analysis: LCMS (ESI): 413 (M+1); $^1$H NMR (400 MHz, DMSO-d₆) δ: 9.03-9.13 (m, 1H) 8.61-8.78 (m, 1H) 8.01 (d, J=8.5 Hz, 1H) 7.71-7.82 (m, 1H) 7.63 (d, J=8.5 Hz, 1H) 7.42

(d, J=8.8 Hz, 2H) 7.05 (d, J=8.8 Hz, 2H) 4.79-4.85 (m, 1H) 4.57-4.64 (m, 1H) 4.44-4.49 (m, 1H) 2.71 (s, 3H) 2.02-2.30 (m, 6H) 1.92 (d, J=7.8 Hz, 3H) 1.49-1.57 (m, 1H) 1.36-1.43 (m, 2H) 0.70-0.80 (m, 2H).

Example 371. {endo-3-[4-(8-Methylquinolin-7-yl)-phenoxy]-8-aza-bicyclo[3.2.1]oct-8-yl}-(R)-tetrahydrofuran-2-yl-methanone, HCl

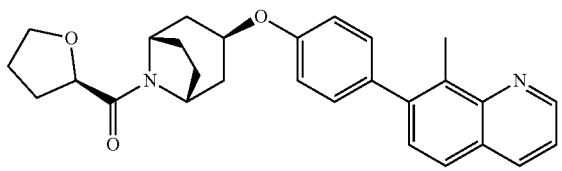 [SMILES: Cc1c(-c2ccc(O[C@H]3C[C@H]4CC[C@@H](C3)N4C(=O)[C@H]3CCCO3)cc2)ccc2cccnc12]

Analysis: LCMS (ESI): 443 (M+1); $^1$H NMR (400 MHz, DMSO-d$_6$) δ: 9.06 (d, J=2.8 Hz, 1H) 8.65 (br. s., 1H) 7.99 (d, J=8.8 Hz, 1H) 7.70-7.80 (m, 1H) 7.61 (d, J=8.3 Hz, 1H) 7.41 (d, J=8.5 Hz, 2H) 6.96-7.11 (m, 2H) 4.77-4.85 (m, 1H) 4.55-4.61 (m, 1H) 4.48-4.52 (m, 1H) 4.41-4.45 (m, 1H) 3.72-3.84 (m, 2H) 2.70 (s, 3H) 2.09-2.25 (m, 3H) 1.92-2.06 (m, 6H) 1.74-1.90 (m, 3H).

Example 372. {(trans)-3-Fluoro-4-[4-(8-methylquinolin-7-yl)-phenoxy]-piperidin-1-yl}-(R)-tetrahydrofuran-2-yl-methanone, HCl

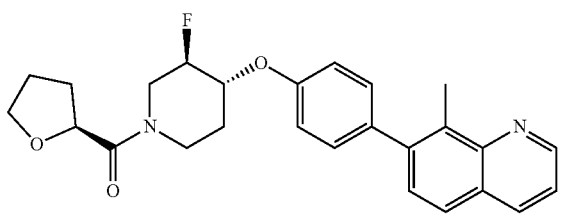 [SMILES: Cc1c(-c2ccc(O[C@@H]3CCN(C(=O)[C@@H]4CCCO4)C[C@H]3F)cc2)ccc2cccnc12]

Analysis: From cis-3-Fluoro-4-hydroxypiperidine-1-carboxylic acid t-butyl ester as a 1:1 mixture of diastereomers. LCMS (ESI): 435 (M+1); $^1$H NMR (400 MHz, DMSO-d$_6$, 95° C.) δ: 8.92-9.01 (m, 1H) 8.38-8.48 (m, 1H) 7.86 (d, J=8.3 Hz, 1H) 7.57 (dd, J=8.3, 4.3 Hz, 1H) 7.48 (d, J=8.5 Hz, 1H) 7.32-7.40 (m, 2H) 7.12-7.20 (m, 2H) 4.57-4.78 (m, 3H) 3.99-4.17 (m, 1H) 3.73-3.85 (m, 4H) 3.37-3.50 (m, 1H) 2.68 (s, 3H) 1.97-2.17 (m, 3H) 1.81-1.92 (m, 2H) 1.64-1.76 (m, 1H).

Example 373. 1-{trans-3-Fluoro-4-[4-(8-methylquinolin-7-yl)-phenoxy]-piperidin-1-yl}-propan-1-one, HCl

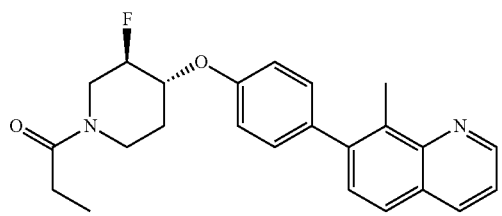 [SMILES: CCC(=O)N1CC[C@@H](Oc2ccc(-c3ccc4cccnc4c3C)cc2)[C@H](F)C1]

Analysis: LCMS (ESI): 393 (M+1); $^1$H NMR (400 MHz, DMSO-d$_6$) δ: 8.96 (dd, J=4.3, 1.8 Hz, 1H) 8.37 (dd, J=8.3, 1.8 Hz, 1H) 7.84 (d, J=8.3 Hz, 1H) 7.54 (dd, J=8.3, 4.3 Hz, 1H) 7.46 (d, J=8.5 Hz, 1H) 7.36 (d, J=8.8 Hz, 2H) 7.15 (d, J=8.8 Hz, 2H) 4.58-4.79 (m, 2H) 3.96-4.09 (m, 1H) 3.64-3.74 (m, 2H) 3.54-3.62 (m, 1H) 3.40-3.49 (m, 1H) 2.67 (s, 3H) 2.32-2.41 (m, 2H) 2.08-2.16 (m, 1H) 1.64-1.77 (m, 1H) 1.04 (t, J=7.4 Hz, 3H).

Example 374. Cyclopropyl-{trans-3-fluoro-4-[4-(8-methylquinolin-7-yl)-phenoxy]-piperidin-1-yl}-methanone, HCl

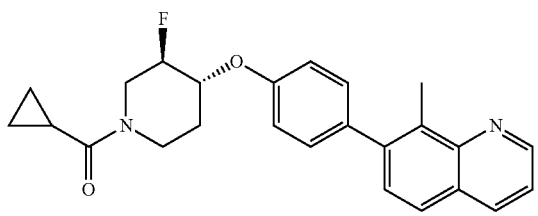 [SMILES: Cc1c(-c2ccc(O[C@@H]3CCN(C(=O)C4CC4)C[C@H]3F)cc2)ccc2cccnc12]

Analysis: LCMS (ESI): 405 (M+1); $^1$H NMR (400 MHz, DMSO-d$_6$, 95° C.) δ: 8.99 (dd, J=4.5, 1.8 Hz, 1H) 8.44 (dd, J=8.3, 1.8 Hz, 1H) 7.87 (d, J=8.5 Hz, 1H) 7.59 (dd, J=8.2, 4.4 Hz, 1H) 7.50 (d, J=8.3 Hz, 1H) 7.37 (d, J=8.8 Hz, 2H) 7.17 (d, J=8.8 Hz, 2H) 4.70-4.79 (m, 2H) 4.61-4.66 (m, 1H) 4.06-4.21 (m, 1H) 3.77-3.90 (m, 1H) 3.63-3.77 (m, 1H) 3.51-3.60 (m, 1H) 2.69 (s, 3H) 2.08-2.19 (m, 1H) 1.92-2.03 (m, 1H) 1.67-1.79 (m, 1H) 0.67-0.81 (m, 7H).

Example 375. 1-{3-Methyl-4-[4-(8-methylquinolin-7-yl)-phenoxy]-piperidin-1-yl}-propan-1-one, TFA salt

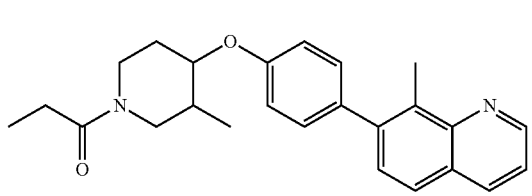 [SMILES: CCC(=O)N1CCC(Oc2ccc(-c3ccc4cccnc4c3C)cc2)C(C)C1]

From 4-Hydroxy-3-methyl-piperidine-1-carboxylic acid tert-butyl ester as a mixture of diastereomers. Analysis: LCMS (ESI): 389 (M+1); $^1$H NMR (400 MHz, DMSO-d$_6$) δ: 8.99-9.06 (m, 1H) 8.46-8.58 (m, 1H) 7.88-7.98 (m, 1H) 7.60-7.70 (m, 1H) 7.51-7.60 (m, 1H) 7.34-7.44 (m, 2H) 7.08-7.20 (m, 2H) 4.15-4.70 (m, 1H) 2.91-3.90 (m, 4H) 2.69 (s, 3H) 2.31-2.42 (m, 2H) 1.60-2.16 (m, 3H) 0.95-1.04 (m, 6H).

Example 376. Cyclopropyl-{3-methyl-4-[4-(8-methylquinolin-7-yl)-phenoxy]-piperidin-1-yl}-methanone, TFA salt

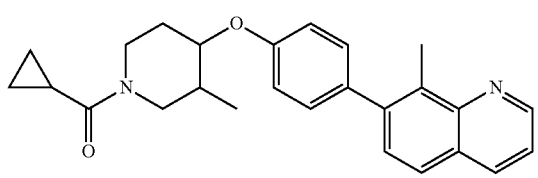 [SMILES: Cc1c(-c2ccc(OC3CCN(C(=O)C4CC4)CC3C)cc2)ccc2cccnc12]

Analysis: LCMS (ESI): 401 (M+1); $^1$H NMR (400 MHz, DMSO-d6) δ: 8.98-9.07 (1H, m), 8.52 (1H, d, J=7.8 Hz), 7.93 (1H, d, J=8.3 Hz), 7.65 (1H, dd, J=8.2, 4.4 Hz), 7.55 (1H, d, J=8.5 Hz), 7.36-7.43 (2H, m), 7.10-7.18 (2H, m), 4.62-4.74 (1H, m), 4.04-4.36 (1H, m), 3.74-3.90 (1H, m), 3.48-3.71 (1H, m), 2.96-3.48 (1H, m), 2.69 (3H, s), 1.62-2.26 (4H, m), 0.91-1.11 (3H, m), 0.67-0.82 (4H, m).

Example 377. {3-Methyl-4-[4-(8-methylquinolin-7-yl)-phenoxy]-piperidin-1-yl}-(R)-tetrahydrofuran-2-yl-methanone, TFA salt

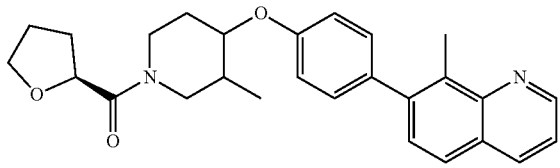 [SMILES: Cc1c(-c2ccc(OC3CCN(C(=O)[C@@H]4CCCO4)CC3C)cc2)ccc2cccnc12]

Analysis: LCMS (ESI): 431 (M+1); $^1$H NMR (400 MHz, DMSO-d$_6$) δ: 8.96-9.08 (1H, m), 8.47-8.60 (1H, m), 7.86-7.98 (1H, m), 7.61-7.71 (1H, m), 7.52-7.59 (1H, m), 7.35-7.43 (2H, m), 7.09-7.18 (2H, m), 4.59-4.84 (2H, m), 3.86-4.42 (1H, m), 2.90-3.84 (5H, m), 2.69 (3H, s), 1.61-2.22 (7H, m), 0.86-1.11 (3H, m).

Example 378. 1-{4-[4-(6-Phenyl-pyridin-3-yl)-phenoxy]-piperidin-1-yl}-propan-1-one

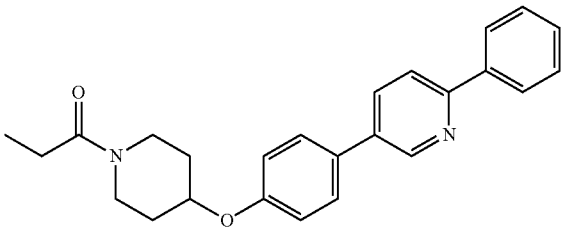 [SMILES: CCC(=O)N1CCC(Oc2ccc(-c3ccc(-c4ccccc4)nc3)cc2)CC1]

Step 1. 4-[4-(6-Phenylpyridin-3-yl)-phenoxy]-piperidine-1-carboxylic acid t-butyl ester To a schlenck flask was added 4-[4-(4,4,5,5-tetramethyl-1,3,2-dioxaborolan-2-yl)-phenoxy]-piperidine-1-carboxylic acid t-butyl ester (0.5 g, 1.24 mmol), 5-bromo-2-phenylpyridine (0.44 g, 1.86 mmol), tetrakis(triphenylphosphine)palladium(0) (0.14 g, 0.12 mmol), 1N sodium carbonate (3.72 mL, 3.72 mmol), followed by 1,4-dioxane (10 mL) and was degassed under an atmosphere of argon for 5 min and was heated at 100° C. overnight. The reaction was cooled, filtered through a pad of celite, washed with 1N sodium carbonate, water, brine, dried over sodium sulfate, and concentrated. The product was purified via silica gel chromatography (10-30% EtOAc/hexanes) and concentrated was isolated (0.48 g, 90%). Analysis: LCMS m/z=431 (M+1).

Step 2. 2-Phenyl-5-[4-(piperidin-4-yloxy)-phenyl]-pyridine

To a solution of 4-[4-(6-phenylpyridin-3-yl)-phenoxy]-piperidine-1-carboxylic acid t-butyl ester (0.48 g, 1.11 mmol) in DCM (10 mL) was added TFA (2 mL) dropwise and was stirred at rt for 1 h and concentrated. The reaction was partitioned between DCM/1N Na$_2$CO$_3$, washed with water/brine, dried over sodium sulfate, and concentrated. Product was isolated as a beige solid (0.37 g, 100%). LCMS m/z=331 (M+1).

Step 3

To 2-phenyl-5-[4-(piperidin-4-yloxy)-phenyl]-pyridine (94 mg, 0.28 mmol) in DCM (5 mL) was added TEA (1 mL, 7 mmol), followed by propanoyl chloride (40 uL, 0.5 mmol) dropwise and the reaction was stirred at rt for 1 h. The reaction was diluted with DCM, washed with 1N Na$_2$CO$_3$, water, and brine, dried over Na$_2$SO$_4$, and concentrated. The product was purified using the Gilson (0.1% TFA in water/0.1% TFA in acetonitrile gradient) and placed on the lyophilizer overnight. 1-{4-[4-(6-Phenyl-pyridin-3-yl)-phenoxy]-piperidin-1-yl}-propan-1-one TFA salt was isolated (0.07 g, 49%). Analysis: LCMS m/z=387 (M+1). $^1$H NMR (DMSO-d6) δ: 8.97 (m, 1H), 8.14 (m, 3H), 8.05 (d, 1H, J=8.3 Hz), 7.75 (d, 2H, J=8.7 Hz), 7.53 (m, 2H), 7.45 (m, 1H), 7.14 (d, 2H, J=8.8 Hz), 4.70 (m, 1H), 3.87 (m, 1H), 3.69 (m, 1H), 3.26 (m, 2H), 2.33 (m, 2H), 1.97 (m, 2H), 1.54 (m, 2H), 0.99 (t, 3H, J=7.4 Hz).

Example 379. 2-Methyl-1-{4-[4-(6-phenylpyridin-3-yl)-phenoxy]-piperidin-1-yl}-propan-1-one

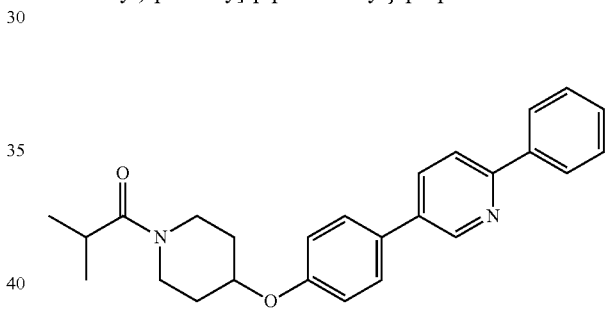

To 2-phenyl-5-[4-(piperidin-4-yloxy)-phenyl]-pyridine (94 mg, 0.28 mmol) in DCM (5 mL) was added triethylamine (1 mL, 7 mmol), followed by isobutyryl chloride (50 uL, 0.5 mmol) drop wise and the reaction was stirred at rt for 1 h and concentrated. The reaction was partitioned between DCM/1N sodium carbonate, washed with water/brine, dried over sodium sulfate, and concentrated. The product was purified via silica gel chromatography (8% methanol/DCM) and concentrated. 2-Methyl-1-{4-[4-(6-phenyl-pyridin-3-yl)-phenoxy]-piperidin-1-yl}-propan-1-one was isolated as a solid (0.07 g, 57%). Analysis: LCMS m/z=401 (M+1). $^1$H NMR (DMSO-d$_6$) δ: 8.96 (m, 1H), 8.14 (m, 3H), 8.03 (d, 1H, J=8.2 Hz), 7.72 (m, 2H), 7.51 (m, 2H), 7.44 (m, 1H), 7.14 (d, 2H, J=8.8 Hz), 4.71 (m, 1H), 3.88 (m, 1H), 3.77 (m, 1H), 3.40 (m, 1H), 3.26 (m, 1H), 2.90 (m, 1H), 1.99 (m, 2H), 1.53 (m, 2H), 1.01 (d, 6H, J=6.7 Hz).

The following examples were synthesized using the procedure for Examples 378 and 379.

Example 380. Cyclopropyl-{4-[4-(6-phenyl-pyridin-3-yl)-phenoxy]-piperidin-1-yl}-methanone

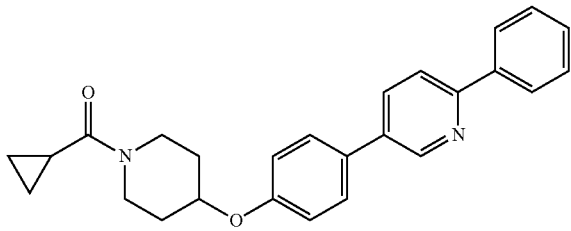 [SMILES: O=C(C1CC1)N1CCC(Oc2ccc(-c3ccc(-c4ccccc4)nc3)cc2)CC1]

Analysis: LCMS m/z=399 (M+1). $^1$H NMR (DMSO-d6) δ: 8.96 (m, 1H), 8.14 (m, 3H), 8.03 (d, 1H, J=8.2 Hz), 7.72 (m, 2H), 7.51 (m, 2H), 7.44 (m, 1H), 7.14 (d, 2H, J=8.8 Hz), 4.72 (m, 1H), 4.07 (m, 1H), 3.98 (m, 1H), 3.55 (m, 1H), 3.29 (m, 1H), 2.00 (m, 3H), 1.54-1.64 (br m, 2H), 0.71 (m, 4H).

Example 381. Cyclobutyl-{4-[4-(6-phenyl-pyridin-3-yl)-phenoxy]-piperidin-1-yl}-methanone

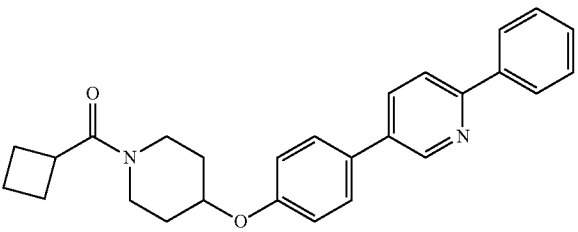 [SMILES: O=C(C1CCC1)N1CCC(Oc2ccc(-c3ccc(-c4ccccc4)nc3)cc2)CC1]

Analysis: LCMS m/z=413 (M+1). $^1$H NMR (DMSO-d6) δ: 8.96 (m, 1H), 8.14 (m, 3H), 8.03 (d, 1H, J=8.2 Hz), 7.72 (m, 2H), 7.51 (m, 2H), 7.44 (m, 1H), 7.14 (d, 2H, J=8.8 Hz), 4.69 (m, 1H), 3.85 (m, 1H), 3.56 (m, 1H), 3.36 (m, 1H), 3.25 (m, 2H), 2.09 (m, 4H), 1.92 (m, 3H), 1.74 (m, 1H), 1.55 (m, 2H).

Example 382. 1-{4-[4-(5-Phenylpyridin-3-yl)-phenoxy]-piperidin-1-yl}-propan-1-one

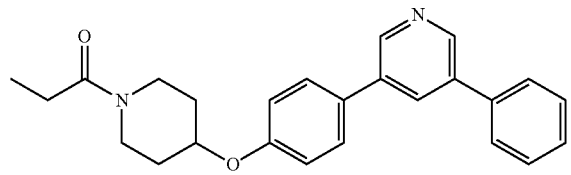 [SMILES: CCC(=O)N1CCC(Oc2ccc(-c3cncc(-c4ccccc4)c3)cc2)CC1]

Step 1. 4-[4-(5-Phenyl-pyridin-3-yl)-phenoxy]-piperidine-1-carboxylic acid tert-butyl ester The compound was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 3-bromo-5-phenylpyridine (0.44 g, 1.86 mmol) in an analogous manner to Example 378. Product was isolated as a solid (0.51 g, 96%). Analysis: LCMS m/z=431 (M+1).

Step 2. 3-Phenyl-5-[4-(piperidin-4-yloxy)-phenyl]-pyridine

The compound was prepared from 4-[4-(5-phenyl-pyridin-3-yl)-phenoxy]-piperidine-1-carboxylic acid tert-butyl ester (0.48 mg, 1.11 mmol) and TFA (2 mL) in an analogous manner to Example 378. The product was isolated as a solid (0.37 g, 100%). Analysis: LCMS m/z=331 (M+1).

Step 3. 1-{4-[4-(5-Phenylpyridin-3-yl)-phenoxy]-piperidin-1-yl}-propan-1-one The compound was prepared from 3-phenyl-5-[4-(piperidin-4-yloxy)-phenyl]-pyridine (95 mg, 0.29 mmol) and propanoyl chloride (40 uL, 0.5 mmol) in an analogous manner to Example 378 to give a solid (0.06 g, 54%). Analysis: LCMS m/z=387 (M+1). $^1$H NMR (DMSO-d6) δ: 8.82 (m, 2H), 8.25 (m, 1H), 7.83 (m, 2H), 7.77 (m, 2H), 7.53 (m, 2H), 7.45 (m, 1H), 7.12 (m, 2H), 4.71 (m, 1H), 3.86 (m, 1H), 3.70 (m, 1H), 3.27 (m, 2H), 2.33 (m, 2H), 1.97 (m, 2H), 1.61 (m, 2H), 0.99 (t, 3H, J=7.4 Hz).

Example 383. 2-Methyl-1-{4-[4-(5-phenylpyridin-3-yl)-phenoxy]-piperidin-1-yl}-propan-1-one

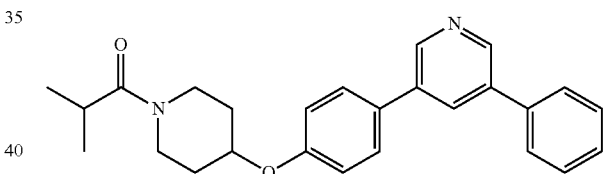

Analysis: LCMS m/z=401 (M+1). $^1$H NMR (DMSO-d6) δ: 8.82 (m, 2H), 8.25 (m, 1H), 7.83 (m, 2H), 7.77 (m, 2H), 7.53 (m, 2H), 7.45 (m, 1H), 7.12 (m, 2H), 4.72 (m, 1H), 3.87 (m, 1H), 3.76 (m, 1H), 3.41 (m, 1H), 3.29 (m, 1H), 2.90 (m, 1H), 1.99 (m, 2H), 1.54 (m, 2H), 1.01 (d, 6H, J=6.6 Hz).

Example 384. Cyclopropyl-{4-[4-(5-phenyl-pyridin-3-yl)-phenoxy]-piperidin-1-yl}-methanone, TFA salt

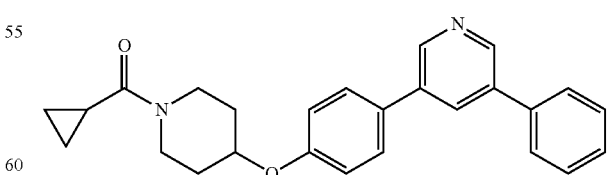

Analysis: LCMS m/z=399 (M+1). $^1$H NMR (DMSO-d6) δ: 8.94 (m, 2H), 8.52 (m, 1H), 7.90 (m, 4H), 7.56 (m, 2H), 7.49 (m, 1H), 7.18 (m, 2H), 4.76 (m, 1H), 3.99 (m, 1H), 3.89 (m, 1H), 3.56 (m, 1H), 3.29 (m, 1H), 2.00 (m, 3H), 1.55 (br m, 2H), 0.71 (m, 4H).

Example 385. Cyclobutyl-{4-[4-(5-phenylpyridin-3-yl)-phenoxy]-piperidin-1-yl}-methanone, TFA salt

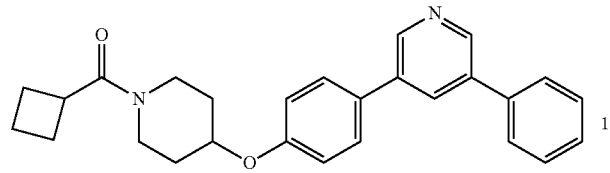

This example was synthesized from 3-phenyl-5-[4-(piperidin-4-yloxy)-phenyl]-pyridine (95 mg, 0.29 mmol) and cyclobutanecarbonyl chloride (60 uL, 0.5 mmol) to give a solid (0.08 g, 50%). Analysis: LCMS m/z=413 (M+1). $^1$H NMR (DMSO-d6) δ: 8.94 (m, 2H), 8.52 (m, 1H), 7.90 (m, 4H), 7.56 (m, 2H), 7.49 (m, 1H), 7.18 (m, 2H), 4.72 (m, 1H), 3.84 (m, 1H), 3.56 (m, 1H), 3.36 (m, 1H), 3.26 (m, 2H), 2.09 (br m, 4H), 1.93 (m, 3H), 1.74 (m, 1H), 1.56 (m, 2H).

Example 386. 1-{4-[4-(6-Morpholin-4-yl-pyridin-3-yl)-phenoxy]-piperidin-1-yl}-propan-1-one

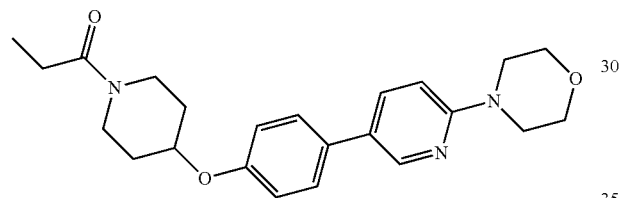

Step 1. 4-[4-(6-Morpholin-4-yl-pyridin-3-yl)-phenoxy]-piperidine-1-carboxylic acid t-butyl ester The compound was prepared from 4-(4-iodophenoxy)-piperidine-1-carboxylic acid tert-butyl ester (0.5 g, 1.24 mmol) and 4-[5-(4,4,5,5-tetramethyl-1,3,2-dioxaborolan-2-yl)-pyridin-2-yl]-morpholine (0.54 g, 1.86 mmol) as described previously. Product isolated as a solid (0.44 g, 81%). Analysis: LCMS m/z=440 (M+1).

Step 2. 4-{5-[4-(Piperidin-4-yloxy)-phenyl]-pyridin-2-yl}-morpholine

The compound was prepared from 4-[4-(6-morpholin-4-yl-pyridin-3-yl)-phenoxy]-piperidine-1-carboxylic acid t-butyl ester (0.44 mg, 1.01 mmol) and TFA (2 mL). The product isolated as a solid (0.34 g, 100%). Analysis: LCMS m/z=340 (M+1).

Step 3. 1-{4-[4-(6-Morpholin-4-yl-pyridin-3-yl)-phenoxy]-piperidin-1-yl}-propan-1-one The compound was prepared from 4-{5-[4-(piperidin-4-yloxy)-phenyl]-pyridin-2-yl}-morpholine (95 mg, 0.28 mmol) and propanoyl chloride (40 uL, 0.5 mmol). The product was isolated as a solid (0.04 g, 36%). Analysis: LC/MS 396 (M+1). $^1$H NMR (DMSO-d6) δ: 8.41 (d, 1H, J=2.3 Hz), 7.81 (m, 1H), 7.54 (m, 2H), 7.03 (m, 2H), 6.90 (d, 1H, J=8.8 Hz), 4.63 (m, 1H), 3.84 (m, 1H), 3.71 (m, 5H), 3.46 (m, 4H), 3.33 (m, 1H), 3.24 (m, 1H), 2.32 (m, 2H), 1.94 (m, 2H), 1.51 (m, 2H), 0.99 (t, 3H, J=7.4 Hz).

Example 387. Cyclopropyl-{4-[4-(6-morpholin-4-yl-pyridin-3-yl)-phenoxy]-piperidin-1-yl}-methanone

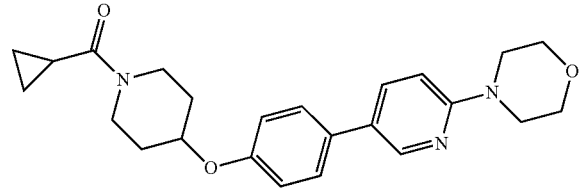 [SMILES: O=C(C1CC1)N1CCC(Oc2ccc(-c3ccc(N4CCOCC4)nc3)cc2)CC1]

This example was synthesized from 4-{5-[4-(piperidin-4-yloxy)-phenyl]-pyridin-2-yl}-morpholine (95 mg, 0.28 mmol) and cyclopropanecarbonyl chloride (40 μL, 0.5 mmol). The product was isolated as a solid (0.07 g, 61%). Analysis: LCMS m/z=408 (M+1). $^1$H NMR (DMSO-d6) δ: 8.41 (d, 1H, J=2.3 Hz), 7.81 (m, 1H), 7.54 (m, 2H), 7.03 (m, 2H), 6.90 (d, 1H, J=8.8 Hz), 4.66 (m, 1H), 3.96 (m, 1H), 3.87 (m, 1H), 3.71 (m, 4H), 3.53 (m, 1H), 3.46 (m, 4H), 3.29 (m, 1H), 1.99 (m, 2H), 1.97 (m, 1H), 1.63 (m, 1H), 1.52 (m, 1H), 0.71 (m, 4H).

Example 388. Cyclobutyl-{4-[4-(6-morpholin-4-yl-pyridin-3-yl)-phenoxy]-piperidin-1-yl}-methanone

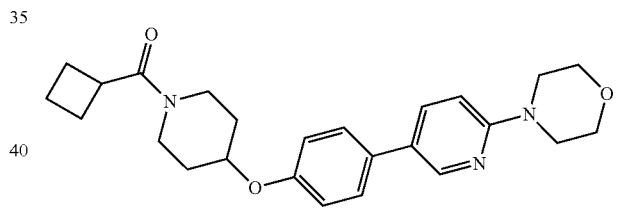

Synthesized from 4-{5-[4-(piperidin-4-yloxy)-phenyl]-pyridin-2-yl}-morpholine (95 mg, 0.28 mmol) and cyclobutanecarbonyl chloride (50 uL, 0.5 mmol). Product isolated as a solid (0.06 g, 51%). Analysis: LCMS m/z=422 (M+1). $^1$H NMR (DMSO-d6) δ: 8.41 (d, 1H, J=2.3 Hz), 7.81 (m, 1H), 7.54 (m, 2H), 7.03 (m, 2H), 6.90 (d, 1H, J=8.8 Hz), 4.62 (m, 1H), 3.86 (m, 1H), 3.71 (m, 4H), 3.58 (m, 1H), 3.46 (m, 4H), 3.33 (m, 1H), 3.23 (m, 2H), 2.06-2.19 (br m, 4H), 1.90 (m, 3H), 1.74 (m, 1H), 1.49 (m, 2H).

Example 389. 1-{4-[4-(6-Phenoxy-pyridin-3-yl)-phenoxy]-piperidin-1-yl}-propan-1-one

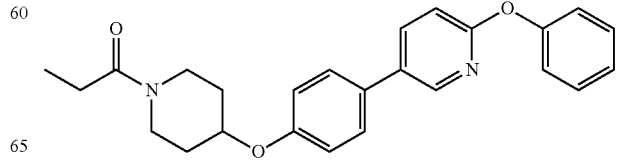

Step 1. 4-[4-(6-Phenoxy-pyridin-3-yl)-phenoxy]-piperidine-1-carboxylic acid t-butyl ester The compound was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 5-bromo-2-phenoxy-pyridine (0.47 g, 1.86 mmol) in an analogous manner to Example 378. Product isolated as a solid (0.44 g, 80%). Analysis: LCMS m/z=447 (M+1).

Step 2. 2-Phenoxy-5-[4-(piperidin-4-yloxy)-phenyl]-pyridine

The compound was prepared from 4-[4-(6-phenoxy-pyridin-3-yl)-phenoxy]-piperidine-1-carboxylic acid tert-butyl ester (0.44 g, 0.99 mmol) and TFA (2 mL). The product was isolated as a solid (0.32 g, 95%). Analysis: LCMS m/z=347 (M+1).

Step 3. 1-{4-[4-(6-Phenoxypyridin-3-yl)-phenoxy]-piperidin-1-yl}-propan-1-one The compound was prepared from 2-phenoxy-5-[4-(piperidin-4-yloxy)-phenyl]-pyridine (95 mg, 0.27 mmol) and propanoyl chloride (40 uL, 0.5 mmol) to give a solid (0.07 g, 60%). Analysis: LCMS m/z=403 (M+1). $^1$H NMR (DMSO-d6) δ: 8.40 (d, 1H, J=2.2 Hz), 8.08 (m, 1H), 7.58 (m, 2H), 7.43 (m, 2H), 7.22 (m, 1H), 7.16 (m, 2H), 7.09 (m, 3H), 4.66 (m, 1H), 3.89 (m, 1H), 3.71 (m, 1H), 3.35 (m, 1H), 3.24 (m, 1H), 2.32 (m, 2H), 1.95 (m, 2H), 1.49-1.62 (br m, 2H), 0.99 (t, 3H, J=7.4 Hz).

Example 390. Cyclopropyl-{4-[4-(6-phenoxy-pyridin-3-yl)-phenoxy]-piperidin-1-yl}-methanone

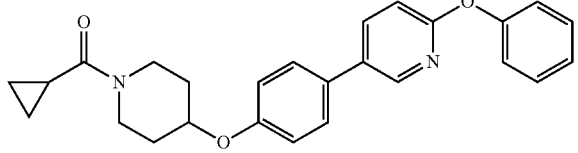

This example was synthesized from 2-phenoxy-5-[4-(piperidin-4-yloxy)-phenyl]-pyridine (95 mg, 0.27 mmol) and cyclopropanecarbonyl chloride (40 uL, 0.5 mmol) to give a solid (0.08 g, 70%). Analysis: LCMS m/z=415 (M+1). $^1$H NMR (DMSO-d6) δ: 8.40 (d, 1H, J=2.2 Hz), 8.08 (m, 1H), 7.58 (m, 2H), 7.43 (m, 2H), 7.22 (m, 1H), 7.16 (m, 2H), 7.09 (m, 3H), 4.70 (m, 1H), 3.97 (m, 1H), 3.87 (m, 1H), 3.54 (m, 1H), 3.26 (m, 1H), 1.91-2.02 (br m, 3H), 1.62 (m, 1H), 1.52 (m, 1H), 0.71 (m, 4H).

Example 391. Cyclobutyl-{4-[4-(6-phenoxy-pyridin-3-yl)-phenoxy]-piperidin-1-yl}-methanone

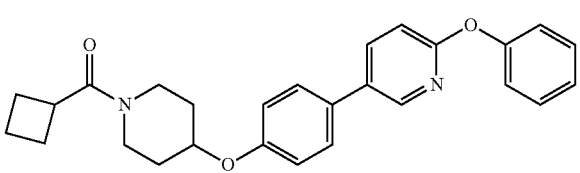 [SMILES: O=C(C1CCC1)N1CCC(Oc2ccc(-c3ccc(Oc4ccccc4)nc3)cc2)CC1]

This example was synthesized from 2-phenoxy-5-[4-(piperidin-4-yloxy)-phenyl]-pyridine (95 mg, 0.27 mmol) and cyclobutanecarbonyl chloride (50 uL, 0.5 mmol) to give a solid (0.09 g, 72%). Analysis: LCMS m/z=429 (M+1). $^1$H NMR (DMSO-d6) δ: 8.40 (d, 1H, J=2.2 Hz), 8.08 (m, 1H), 7.58 (m, 2H), 7.43 (m, 2H), 7.22 (m, 1H), 7.16 (m, 2H), 7.09 (m, 3H), 4.65 (m, 1H), 3.87 (m, 1H), 3.55 (m, 1H), 3.35 (m, 1H), 3.23 (m, 2H), 2.06-2.19 (br m, 4H), 1.90 (br m, 3H), 1.74 (m, 1H), 1.53 (m, 2H).

Example 392. 1-{4-[4-(6-Phenylaminopyridin-3-yl)-phenoxy]-piperidin-1-yl}-propan-1-one, TFA salt

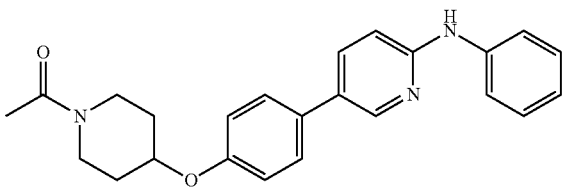 [SMILES: CC(=O)N1CCC(Oc2ccc(-c3ccc(Nc4ccccc4)nc3)cc2)CC1]

Step 1. 4-[4-(6-Phenylaminopyridin-3-yl)-phenoxy]-piperidine-1-carboxylic acid t-butyl ester The compound was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and (5-bromo-pyridin-2-yl)-phenyl-amine (0.46 g, 1.86 mmol) to give a solid. Analysis: LCMS m/z=446 (M+1).

Step 2. Phenyl-{5-[4-(piperidin-4-yloxy)-phenyl]-pyridin-2-yl}-amine

The compound was prepared from 4-[4-(6-phenylaminopyridin-3-yl)-phenoxy]-piperidine-1-carboxylic acid tert-butyl ester and trifluoroacetic acid (2 mL). Product isolated as a solid. Analysis: LCMS m/z=346 (M+1).

Step 3. 1-{4-[4-(6-Phenylaminopyridin-3-yl)-phenoxy]-piperidin-1-yl}-propan-1-one, TFA salt The compound was prepared from phenyl-{5-[4-(piperidin-4-yloxy)-phenyl]-pyridin-2-yl}-amine (95 mg, 0.27 mmol) and propanoyl chloride (40 uL, 0.5 mmol). Product isolated as a solid (0.03 g, 21%). Analysis: LCMS m/z 402 (M+1). $^1$H NMR (DMSO-d6) δ: 9.55 (br s, 1H), 8.36 (d, 1H, J=2.2 Hz), 7.99 (m, 1H), 7.59 (m, 4H), 7.34 (m, 2H), 7.08 (m, 4H), 4.66 (m, 1H), 3.85 (m, 1H), 3.71 (m, 1H), 3.25 (m, 2H), 2.33 (m, 2H), 1.95 (m, 2H), 1.47-1.64 (br m, 2H), 0.99 (t, 3H, J=7.3 Hz).

Example 393. Cyclopropyl-{4-[4-(6-phenylaminopyridin-3-yl)-phenoxy]-piperidin-1-yl}-methanone, TFA salt

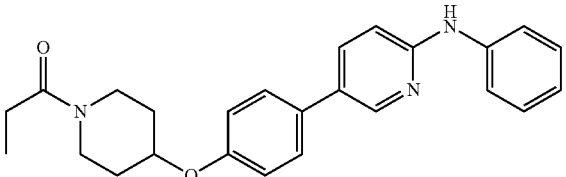

Prepared from phenyl-{5-[4-(piperidin-4-yloxy)-phenyl]-pyridin-2-yl}-amine (95 mg, 0.27 mmol) and cyclopropanecarbonyl chloride (40 uL, 0.5 mmol) to give a solid (0.08 g, 55%). Analysis: LCMS m/z=414 (M+1). $^1$H NMR (DMSO-d6) δ: 9.55 (br s, 1H), 8.36 (d, 1H, J=2.2 Hz), 7.99 (m, 1H), 7.59 (m, 4H), 7.34 (m, 2H), 7.08 (m, 4H), 4.68 (m, 1H), 3.88-3.97 (br m, 2H), 3.54 (m, 1H), 3.27 (m, 1H), 1.91-2.02 (br m, 3H), 1.49-1.79 (br m, 2H), 1.01 (m, 4H).

Example 394. Cyclobutyl-{4-[4-(6-phenylaminopyridin-3-yl)-phenoxy]-piperidin-1-yl}-methanone, TFA salt

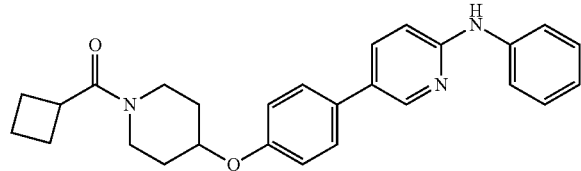 [SMILES: O=C(C1CCC1)N1CCC(Oc2ccc(-c3ccc(Nc4ccccc4)nc3)cc2)CC1]

This example was synthesized from phenyl-{5-[4-(piperidin-4-yloxy)-phenyl]-pyridin-2-yl}-amine (95 mg, 0.27 mmol) and cyclobutanecarbonyl chloride (50 uL, 0.5 mmol) to give a solid (0.05 g, 34%). LCMS m/z=428 (M+1). $^1$H NMR (DMSO) δ: 9.55 (br s, 1H), 8.36 (d, 1H, J=2.2 Hz), 7.99 (m, 1H), 7.59 (m, 4H), 7.34 (m, 2H), 7.08 (m, 4H), 4.64 (m, 1H), 3.84 (m, 1H), 3.58 (m, 1H), 3.35 (m, 1H), 3.21 (m, 2H), 2.05-2.19 (br m, 4H), 1.85-1.94 (br m, 3H), 1.74 (m, 1H), 1.53 (m, 2H).

Example 395. 1-[4-(2'-Fluoro-3'-pyridin-2-yl-biphenyl-4-yloxy)-piperidin-1-yl]-propan-1-one

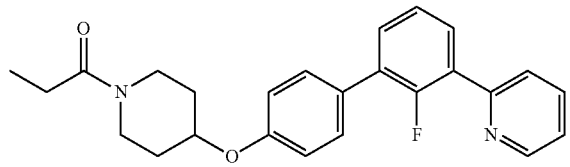

Step 1

To a schlenck flask was added (3-bromo-2-fluorophenyl) boronic acid (0.5 g, 2.28 mmol), 2-bromopyridine (0.32 mL, 3.43 mmol), tetrakis(triphenylphosphine)palladium(0) (0.26 g, 0.23 mmol), 1N Na$_2$CO$_3$ (6.9 mL, 6.86 mmol), followed by 1,4-dioxane (10 mL) and was degassed under an atmosphere of argon for 5 min and was heated at 100° C. for 1 h. The reaction was cooled, filtered through a pad of celite, washed with 1N Na$_2$CO$_3$, water and brine, dried over sodium sulfate, and concentrated. The product was purified via silica gel chromatography (10% ethyl acetate/hexanes) and concentrated to give 2-(3-bromo-2-fluoro-phenyl)-pyridine (0.54 g, 94%). Analysis: LCMS m/z=253 (M+1).

Step 2

4-(2'-Fluoro-3'-pyridin-2-yl-biphenyl-4-yloxy)-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid tert-butyl ester (0.5 g, 1.24 mmol) and 2-(3-bromo-2-fluoro-phenyl)-pyridine (0.54 g, 2.15 mmol) Analysis: LCMS m/z=449 (M+1).

Step 3

2-[2-Fluoro-4'-(piperidin-4-yloxy)-biphenyl-3-yl]-pyridine was prepared from 4-(2'-fluoro-3'-pyridin-2-yl-biphenyl-4-yloxy)-piperidine-1-carboxylic acid tert-butyl ester and trifluoroacetic acid (2 mL) to give a solid. Analysis: LCMS m/z=349 (M+1).

Step 4

1-[4-(2'-Fluoro-3'-pyridin-2-yl-biphenyl-4-yloxy)-piperidin-1-yl]-propan-1-one was prepared from 2-[2-fluoro-4'-(piperidin-4-yloxy)-biphenyl-3-yl]-pyridine (73 mg, 0.21 mmol) and propanoyl chloride (30 uL, 0.4 mmol). Product isolated as a solid (0.03 g, 35%). Analysis: LCMS m/z=405 (M+H). $^1$H NMR (DMSO-d6) δ: 8.73 (m, 1H), 7.93 (m, 1H), 7.81 (m, 2H), 7.54 (m, 3H), 7.38 (m, 2H), 7.11 (d, 2H, J=8.7 Hz), 4.69 (m, 1H), 3.87 (m, 1H), 3.69 (m, 1H), 3.34 (m, 1H), 3.25 (m, 1H), 2.35 (m, 2H), 1.97 (m, 2H), 1.54 (br m, 2H), 0.99 (t, 3H, J=7.3 Hz).

Example 396. Cyclopropyl-[4-(2'-fluoro-3'-pyridin-2-yl-biphenyl-4-yloxy)-piperidin-1-yl]-methanone

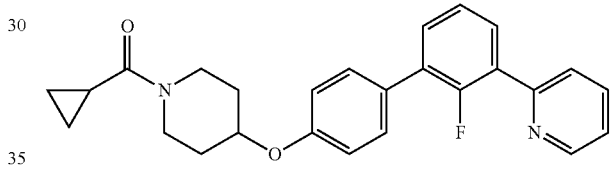

To 2-[2-fluoro-4'-(piperidin-4-yloxy)-biphenyl-3-yl]-pyridine (73 mg, 0.21 mmol) in DCM (4 mL) was added triethylamine (0.7 mL, 5 mmol), followed by cyclopropanecarbonyl chloride (30 uL, 0.4 mmol) dropwise and the reaction was stirred at rt for 1 h and concentrated. The reaction was partitioned between DCM and 1N Na$_2$CO$_3$, washed with water/brine, dried over sodium sulfate, and concentrated. The product was purified using the Gilson (0.1% TFA in water/0.1% TFA in acetonitrile gradient), diluted clean fractions with DCM, washed with 1N sodium carbonate/brine, dried over sodium sulfate, and concentrated to give a solid (0.03 g, 25%). Analysis: LCMS m/z=417 (M+1). $^1$H NMR (DMSO-d6) δ: 8.73 (m, 1H), 7.93 (m, 1H), 7.81 (m, 2H), 7.54 (m, 3H), 7.38 (m, 2H), 7.11 (d, 2H, J=8.7 Hz), 4.71 (m, 1H), 3.99 (m, 1H), 3.89 (m, 1H), 3.55 (m, 1H), 3.29 (m, 1H), 2.00 (br m, 3H), 1.54-1.64 (br m, 2H), 0.71 (m, 4H).

Example 397. 1-{4-[4-(5-Phenoxypyridin-3-yl)-phenoxy]-piperidin-1-yl}-propan-1-one, TFA

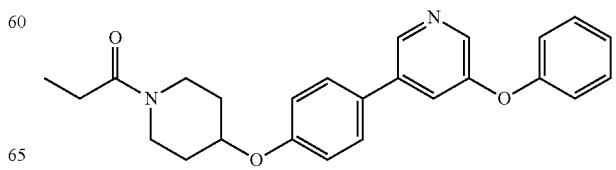

Step 1

4-[4-(5-Phenoxypyridin-3-yl)-phenoxy]-piperidine-1-carboxylic acid t-butyl ester was prepared from 4-(4-iodophenoxy)-piperidine-1-carboxylic acid t-butyl ester (0.5 g, 1.24 mmol) and (5-phenoxy-3-pyridyl)boronic acid (0.4 g, 1.86 mmol). LCMS m/z=447 (M+1).

Step 2

3-Phenoxy-5-[4-(piperidin-4-yloxy)-phenyl]-pyridine was prepared from 4-[4-(5-phenoxypyridin-3-yl)-phenoxy]-piperidine-1-carboxylic acid t-butyl ester and TFA (2 mL). Analysis: LCMS m/z=347 (M+1).

Step 3. 1-{4-[4-(5-Phenoxypyridin-3-yl)-phenoxy]-piperidin-1-yl}-propan-1-one TFA salt was prepared from 3-phenoxy-5-[4-(piperidin-4-yloxy)-phenyl]-pyridine (90 mg, 0.2 mmol) and propanoyl chloride (40 uL, 0.4 mmol) to give a solid (0.09 g, 70%). Analysis: LCMS m/z=403 (M+1). $^1$H NMR (DMSO-d6) δ: 8.72 (br s, 1H), 8.34 (br s, 1H), 7.77 (m, 1H), 7.69 (m, 2H), 7.46 (m, 2H), 7.23 (m, 1H), 7.11 (m, 4H), 4.69 (m, 1H), 3.85 (m, 1H), 3.71 (m, 1H), 3.36 (m, 2H), 2.32 (m, 2H), 1.95 (m, 2H), 1.48-1.62 (br m, 2H), 0.99 (t, 3H, J=7.4 Hz).

Example 398. Cyclobutyl-[4-(2'-fluoro-3'-pyridin-2-yl-biphenyl-4-yloxy)-piperidin-1-yl]-methanone, HCl

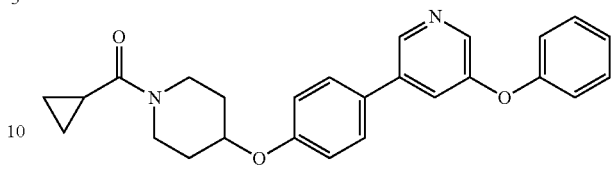

To 2-[2-fluoro-4'-(piperidin-4-yloxy)-biphenyl-3-yl]-pyridine (73 mg, 0.21 mmol) in DCM (4 mL) was added TEA (0.7 mL, 5 mmol), followed by cyclobutanecarbonyl chloride (40 uL, 0.4 mmol) dropwise and the reaction was stirred at rt for 1 h. The reaction was partitioned between DCM/1N Na$_2$CO$_3$, washed with water/brine, dried over Na$_2$SO$_4$, and concentrated. The product was purified using Gilson (0.1% TFA in water/0.1% TFA in acetonitrile gradient), clean fractions diluted with DCM, washed with 1N Na$_2$CO$_3$/water/brine, dried over Na$_2$SO$_4$, and concentrated. The compound was dissolved in DCM, 2M of HCl in diethyl ether (105 uL, 0.21 mmol) was added and concentrated, then dried under vacuum at 65° C. overnight to give a solid (0.03 g, 31%). Analysis: LCMS m/z=431 (M+1). $^1$H NMR (DMSO-d6) δ: 8.79 (m, 1H), 8.07 (m, 1H), 7.92 (m, 1H), 7.80 (m, 1H), 7.57 (m, 4H), 7.41 (m, 1H), 7.11 (m, 2H), 4.68 (m, 1H), 3.89 (m, 1H), 3.56 (m, 1H), 3.36 (m, 1H), 3.24 (m, 2H), 2.05-2.22 (br m, 4H), 1.92 (br m, 3H), 1.74 (m, 1H), 1.55 (m, 2H).

Example 399. Cyclopropyl-{4-[4-(5-phenoxy-pyridin-3-yl)-phenoxy]-piperidin-1-yl}-methanone, HCl

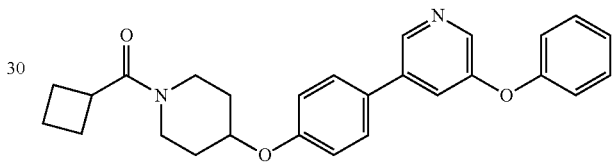

The compound was prepared from 3-phenoxy-5-[4-(piperidin-4-yloxy)-phenyl]-pyridine (90 mg, 0.2 mmol) and cyclopropanecarbonyl chloride (40 uL, 0.4 mmol). Product isolated as a solid (0.05 g, 40%). Analysis: LCMS m/z=415 (M+1). $^1$H NMR (DMSO-d6) δ: 8.73 (m, 1H), 8.34 (d, 1H, J=2.2 Hz), 7.81 (m, 1H), 7.70 (m, 2H), 7.45 (m, 2H), 7.22 (m, 1H), 7.16 (m, 4H), 4.72 (m, 1H), 3.97 (m, 1H), 3.87 (m, 1H), 3.54 (m, 1H), 3.26 (m, 1H), 1.90-2.02 (br m, 3H), 1.62 (br m, 2H), 0.70 (m, 4H).

Example 400. Cyclobutyl-{4-[4-(5-phenoxypyridin-3-yl)-phenoxy]-piperidin-1-yl}-methanone, HCl

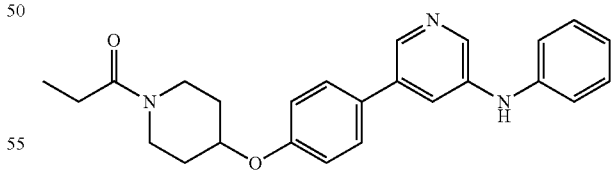

This example was prepared from 3-phenoxy-5-[4-(piperidin-4-yloxy)-phenyl]-pyridine (90 mg, 0.2 mmol) and cyclobutanecarbonyl chloride (50 uL, 0.4 mmol) to give a solid (0.04 g, 30%). Analysis: LCMS m/z=429 (M+1). $^1$H NMR (DMSO-d6) δ: 8.74 (d, 1H, J=1.7 Hz), 8.35 (d, 1H, J=2.5H), 7.83 (m, 1H), 7.70 (m, 2H), 7.47 (m, 2H), 7.24 (m, 1H), 7.16 (m, 2H), 7.09 (m, 2H), 4.68 (m, 1H), 3.85 (m, 1H), 3.58 (m, 1H), 3.35 (m, 1H), 3.23 (m, 2H), 2.04-2.21 (br m, 4H), 1.92 (br m, 3H), 1.74 (m, 1H), 1.51 (m, 2H).

Example 401. 1-{4-[4-(5-Phenylaminopyridin-3-yl)-phenoxy]-piperidin-1-yl}-propan-1-one, TFA salt

Step 1

4-[4-(5-Bromopyridin-3-yl)-phenoxy]-piperidine-1-carboxylic acid t-butyl ester was prepared from 4-(4-iodophenoxy)-piperidine-1-carboxylic acid t-butyl ester (0.5 g, 1.24 mmol) and (5-bromo-3-pyridyl)boronic acid (0.38 g, 1.86 mmol) in an analogous manner to Example 378. Product isolated as a solid (0.14 g, 25%). Analysis: LCMS m/z=434 (M+1).

Step 2

To an oven dried schlenck flask under an atmosphere of argon was charged with 4-[4-(5-bromo-pyridin-3-yl)-phenoxy]-piperidine-1-carboxylic acid t-butyl ester (0.14 g, 0.31 mmol), aniline (0.04 mL, 0.47 mmol), tris(dibenzylideneacetone)dipalladium(0) (28 mg, 0.02 mmol), 9,9-dimethyl-4,5-bis(diphenylphosphino)xanthene (36 mg, 0.06 mmol), sodium t-butoxide (90 mg, 0.94 mmol), followed by 1,4-dioxane (5 mL) and the reaction was degassed 3-times under an atmosphere of argon and was heated at 100° C. for 2 h. The mixture was cooled, filtered through a pad of celite, washed with DCM, and concentrated. The product was purified via silica gel chromatography (10-30% EtOAc/hexanes) and concentrated. 4-[4-(5-Phenylamino-pyridin-3-yl)-phenoxy]-piperidine-1-carboxylic acid t-butyl ester was isolated (0.12 g, 88%). Analysis: LCMS m/z=446 (M+1).

Step 3

Phenyl-{5-[4-(piperidin-4-yloxy)-phenyl]-pyridin-3-yl}-amine was prepared from 4-[4-(5-phenylamino-pyridin-3-yl)-phenoxy]-piperidine-1-carboxylic acid t-butyl ester (0.12 g, 0.27 mmol) and TFA (1 mL) in an analogous manner to Example 599b. Product isolated as a solid (0.07 g, 75%). Analysis: LCMS m/z=346 (M+1).

Step 4

The product was prepared from phenyl-{5-[4-(piperidin-4-yloxy)-phenyl]-pyridin-3-yl}-amine (71 mg, 0.20 mmol) and propanoyl chloride (21 uL, 0.25 mmol) in an analogous manner to Example 599c. Product isolated as a solid (0.04 g, 33%). Analysis: LCMS m/z=402 (M+1). $^1$H NMR (DMSO-d6) δ: 9.00 (s, 1H), 8.45 (d, 1H, J=1 Hz), 8.32 (d, 1H, J=2.1 Hz), 7.95 (m, 1H), 7.66 (m, 2H), 7.39 (m, 2H), 7.27 (m, 2H), 7.15 (m, 2H), 7.05 (m, 1H), 4.71 (m, 1H), 3.87 (m, 1H), 3.72 (m, 1H), 3.36 (m, 1H), 3.25 (m, 1H), 2.33 (m, 2H), 1.91-1.97 (br m, 2H), 1.50-1.63 (br m, 2H), 0.99 (t, 3H, J=7.4 Hz).

Example 402. 1-{4-[4-(2-Phenylpyridin-4-yl)-phenoxy]-piperidin-1-yl}-propan-1-one, TFA

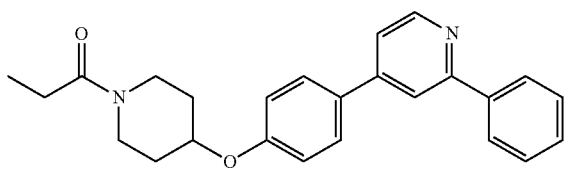 [SMILES: CCC(=O)N1CCC(Oc2ccc(-c3ccnc(-c4ccccc4)c3)cc2)CC1]

Step 1

4-[4-(2-Bromopyridin-4-yl)-phenoxy]-piperidine-1-carboxylic acid tert-butyl ester was prepared from 4-(4-iodophenoxy)-piperidine-1-carboxylic acid tert-butyl ester (0.5 g, 1.24 mmol) and (2-bromo-4-pyridyl)boronic acid (0.38 g, 1.86 mmol) Product isolated as a solid (0.19 g, 36%). Analysis: LCMS m/z 434 (M+1).

Step 2

4-[4-(2-Phenylpyridin-4-yl)-phenoxy]-piperidine-1-carboxylic acid tert-butyl ester was prepared from 4-[4-(2-bromopyridin-4-yl)-phenoxy]-piperidine-1-carboxylic acid tert-butyl ester (0.19 g, 0.44 mmol) and phenylboronic acid (81 mg, 0.67 mmol). Product isolated as a solid. Analysis: LCMS m/z=431 (M+1).

Step 3

2-Phenyl-4-[4-(piperidin-4-yloxy)-phenyl]-pyridine was prepared from 4-[4-(2-phenylpyridin-4-yl)-phenoxy]-piperidine-1-carboxylic acid tert-butyl ester and TFA (1 mL). Product isolated as a solid. Analysis: LCMS m/z=331 (M+1).

Step 4

The title product was prepared from 2-phenyl-4-[4-(piperidin-4-yloxy)-phenyl]-pyridine (56 mg, 0.17 mmol) and propanoyl chloride (29 uL, 0.34 mmol). Product isolated as a solid (0.05 g, 59%). Analysis: LCMS m/z 387 (M+1). $^1$H NMR (DMSO-d6) δ: 8.74 (d, 1H, J=5.6 Hz), 8.33 (s, 1H), 8.15 (m, 2H), 7.98 (m, 2H), 7.87 (d, 1H, J=4.4 Hz), 7.56 (m, 3H), 7.19 (m, 2H), 4.77 (m, 1H), 3.87 (m, 1H), 3.72 (m, 1H), 3.24-3.38 (m, 2H), 2.33 (m, 2H), 1.98 (m, 2H), 1.53-1.65 (br m, 2H), 0.99 (t, 3H, J=7.4 Hz).

Example 403. Cyclopropyl-{4-[4-(2-phenylpyridin-4-yl)-phenoxy]-piperidin-1-yl}-methanone, TFA salt

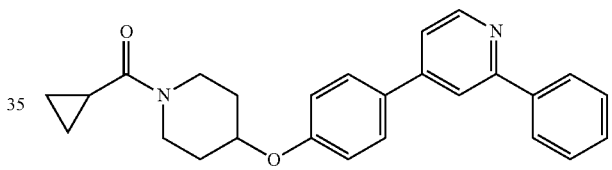

This example was prepared from 2-phenyl-4-[4-(piperidin-4-yloxy)-phenyl]-pyridine (56 mg, 0.17 mmol) and cyclopropanecarbonyl chloride (31 uL, 0.34 mmol). Product isolated as a solid (0.35 g, 40%). Analysis: LCMS m/z=399 (M+1). $^1$H NMR (DMSO-d6) δ: 8.74 (d, 1H, J=5.6 Hz), 8.33 (s, 1H), 8.15 (m, 2H), 7.98 (m, 2H), 7.87 (d, 1H, J=4.4 Hz), 7.56 (m, 3H), 7.19 (m, 2H), 4.79 (m, 1H), 3.89-3.98 (br m, 2H), 3.57 (m, 1H), 3.29 (m, 1H), 2.00 (br m, 3H), 1.50-1.79 (br m, 2H), 0.71 (m, 4H).

Example 404. 1-{4-[4-(2-Phenylaminopyridin-4-yl)-phenoxy]-piperidin-1-yl}-propan-1-one

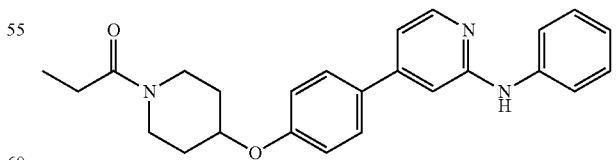

Step 1

4-[4-(2-Chloropyridin-4-yl)-phenoxy]-piperidine-1-carboxylic acid t-butyl ester was prepared from 4-(4-iodophenoxy)-piperidine-1-carboxylic acid t-butyl ester (0.5 g, 1.24 mmol) and 2-chloropyridine-4-boronic acid (0.29 g, 1.86 mmol). Product isolated as a solid (0.24 g, 49%). Analysis: LCMS m/z 389 (M+1).

Step 2

4-[4-(2-Phenylaminopyridin-4-yl)-phenoxy]-piperidine-1-carboxylic acid tert-butyl ester was prepared from 4-[4-(2-chloro-pyridin-4-yl)-phenoxy]-piperidine-1-carboxylic acid tert-butyl ester (0.24 g, 0.61 mmol) and aniline (0.08 mL, 0.91 mmol) in an analogous manner to Example 402, Step 2. Product isolated as a solid (0.19 g, 69%). Analysis: LCMS m/z 446 (M+1).

Step 3

Phenyl-{4-[4-(piperidin-4-yloxy)-phenyl]-pyridin-2-yl}-amine was prepared from 4-[4-(2-phenylaminopyridin-4-yl)-phenoxy]-piperidine-1-carboxylic acid tert-butyl ester (0.19 g, 0.42 mmol) and trifluoroacetic acid (1 mL). Product isolated as a solid (0.14 g, 100%). Analysis: LCMS m/z 346 (M+1).

Step 4

The title product was prepared from phenyl-{4-[4-(piperidin-4-yloxy)-phenyl]-pyridin-2-yl}-amine (73 mg, 0.21 mmol) and propanoyl chloride (28 uL, 0.32 mmol) in an analogous manner to Example 396. Product isolated as a solid (0.03 g, 35%). Analysis: LCMS m/z=402 (M+1). $^1$H NMR (DMSO-d6) δ: 9.04 (s, 1H), 8.17 (d, 1H, J=5.4 Hz), 7.70 (d, 2H, J=7.6 Hz), 7.65 (d, 2H, J=8.8 Hz), 7.26 (m, 2H), 7.13 (d, 2H, J=8.8 Hz), 7.02 (m, 2H), 6.88 (m, 1H), 4.69 (m, 1H), 3.88 (m, 1H), 3.70 (m, 1H), 3.37 (m, 1H), 3.25 (m, 1H), 2.33 (m, 2H), 1.96 (br m, 2H), 1.50-1.63 (br m, 2H), 0.99 (t, 3H, J=7.4 Hz).

Example 405. Cyclopropyl-{4-[4-(2-phenylaminopyridin-4-yl)-phenoxy]-piperidin-1-yl}-methanone

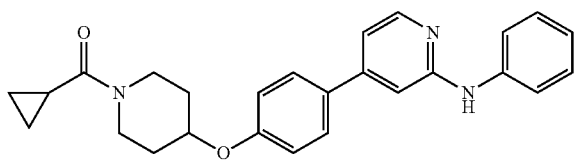 [SMILES: O=C(C1CC1)N1CCC(Oc2ccc(-c3ccnc(Nc4ccccc4)c3)cc2)CC1]

This example was prepared from phenyl-{4-[4-(piperidin-4-yloxy)-phenyl]-pyridin-2-yl}-amine (73 mg, 0.21 mmol) and cyclopropanecarbonyl chloride (29 uL, 0.32 mmol) in an analogous manner to Example 396. Product isolated as a solid (0.04 g, 40%). Analysis: LCMS m/z=414 (M+1). $^1$H NMR (DMSO-d6) δ: 9.04 (s, 1H), 8.17 (d, 1H, J=5.4 Hz), 7.70 (d, 2H, J=7.6 Hz), 7.65 (d, 2H, J=8.8 Hz), 7.26 (m, 2H), 7.13 (d, 2H, J=8.8 Hz), 7.02 (m, 2H), 6.88 (m, 1H), 4.72 (m, 1H), 3.98 (m, 1H), 3.89 (m, 1H), 3.55 (m, 1H), 3.29 (m, 1H), 1.94-2.03 (br m, 3H), 1.54-1.64 (br m, 2H), 0.71 (m, 4H).

Example 406. 1-[4-(2'-Methyl-3'-pyridin-2-yl-biphenyl-4-yloxy)-piperidin-1-yl]-propan-1-one; TFA salt

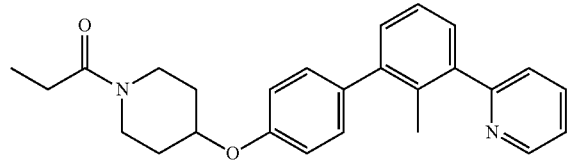 [SMILES: CCC(=O)N1CCC(Oc2ccc(-c3cccc(-c4ccccn4)c3C)cc2)CC1]

Step 1

2-(3-Bromo-2-methylphenyl)-pyridine was prepared from 3-bromo-2-methyl-phenylboronic acid (0.5 g, 2.33 mmol) and 2-bromopyridine (0.33 mL, 3.49 mmol) in an analogous manner to Example 378. Product isolated as a solid (0.5 g, 87%). Analysis: LCMS m/z 249 (M+1).

Step 2

4-(2'-Methyl-3'-pyridin-2-yl-biphenyl-4-yloxy)-piperidine-1-carboxylic acid tert-butyl ester was prepared from 4-[4-(4,4,5,5-tetramethyl-1,3,2-dioxaborolan-2-yl)-phenoxy]-piperidine-1-carboxylic acid tert-butyl ester (0.5 g, 1.24 mmol) and 2-(3-bromo-2-methyl-phenyl)-pyridine (0.46 g, 1.86 mmol) in an analogous manner to Example 378. Product isolated as a solid (0.5 g, 89%). Analysis: LCMS m/z 445 (M+1).

Step 3

2-[2-Methyl-4'-(piperidin-4-yloxy)-biphenyl-3-yl]-pyridine was prepared from 4-(2'-methyl-3'-pyridin-2-yl-biphenyl-4-yloxy)-piperidine-1-carboxylic acid tert-butyl ester (0.5 g, 1.11 mmol) and TFA (2 mL) in an analogous manner to Example 378, step 2. Product isolated as a solid (0.3 g, 87%). Analysis: LCMS m/z 345 (M+1).

Step 4

The title product was prepared from 2-[2-methyl-4'-(piperidin-4-yloxy)-biphenyl-3-yl]-pyridine (110 mg, 0.32 mmol) and propanoyl chloride (50 uL, 0.5 mmol) in an analogous manner to Example 378 step 3. Product isolated as a solid (0.07 g, 40%). Analysis: LCMS m/z=401 (M+1). $^1$H NMR (DMSO-d6) δ: 8.78 (d, 1H, J=4.5 Hz), 8.17 (m, 1H), 7.78 (d, 1H, J=7.8 Hz), 7.63 (m, 1H), 7.39 (m, 2H), 7.30 (m, 3H), 7.08 (d, 2H, J=8.6 Hz), 4.66 (m, 1H), 3.90 (m, 1H), 3.71 (m, 1H), 3.33 (m, 1H), 3.24 (m, 1H), 2.33 (m, 2H), 2.12 (s, 3H), 1.96 (m, 2H), 1.51-1.63 (br m, 2H), 0.99 (t, 3H, J=7.4 Hz).

Example 407. Cyclopropyl-[4-(2'-methyl-3'-pyridin-2-yl-biphenyl-4-yloxy)-piperidin-1-yl]-methanone, TFA salt

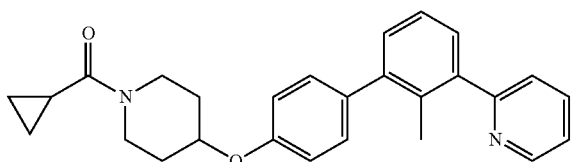

The title compound was prepared from 2-[2-methyl-4'-(piperidin-4-yloxy)-biphenyl-3-yl]-pyridine (110 mg, 0.32 mmol) and cyclopropanecarbonyl chloride (50 μL, 0.5 mmol) in an analogous manner to Example 378 step 3. Product isolated as a solid (0.14 g, 80%). Analysis: LCMS m/z=413 (M+1). ¹H NMR (DMSO-d6) δ: 8.78 (d, 1H, J=4.5 Hz), 8.17 (m, 1H), 7.78 (d, 1H, J=7.8 Hz), 7.63 (m, 1H), 7.39 (m, 2H), 7.30 (m, 3H), 7.08 (d, 2H, J=8.6 Hz), 4.68 (m, 1H), 3.99 (m, 1H), 3.90 (m, 1H), 3.54 (m, 1H), 3.26 (m, 1H), 2.12 (s, 3H), 2.00 (br m, 3H), 1.54-1.64 (br m, 2H), 0.71 (m, 4H).

Example 408. Cyclobutyl-[4-(2'-methyl-3'-pyridin-2-yl-biphenyl-4-yloxy)-piperidin-1-yl]-methanone, TFA salt

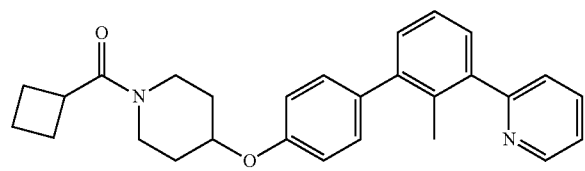 [SMILES: Cc1c(-c2ccc(OC3CCN(C(=O)C4CCC4)CC3)cc2)cccc1-c1ccccn1]

The title compound was prepared from 2-[2-methyl-4'-(piperidin-4-yloxy)-biphenyl-3-yl]-pyridine (110 mg, 0.32 mmol) and cyclobutanecarbonyl chloride (60 uL, 0.5 mmol) in an analogous manner to Example 378 step 3. Product isolated as a solid (0.08 g, 43%). Analysis: LCMS m/z=427 (M+1). ¹H NMR (DMSO-d6) δ: 8.78 (d, 1H, J=4.5 Hz), 8.17 (m, 1H), 7.78 (d, 1H, J=7.8 Hz), 7.63 (m, 1H), 7.39 (m, 2H), 7.30 (m, 3H), 7.08 (d, 2H, J=8.6 Hz), 4.65 (m, 1H), 3.90 (m, 1H), 3.57 (m, 1H), 3.36 (m, 1H), 3.23 (m, 2H), 2.15 (m, 2H), 2.11 (s, 3H), 2.09 (m, 2H), 1.93 (m, 3H), 1.74 (m, 1H), 1.53 (m, 2H).

Example 409. 1-{4-[4-(2-Phenoxypyridin-4-yl)-phenoxy]-piperidin-1-yl}-propan-1-one

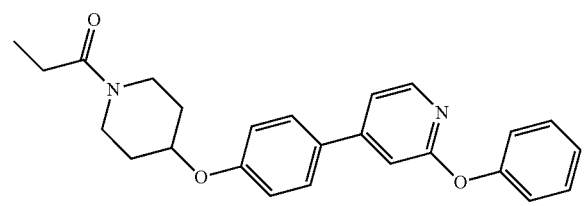 [SMILES: CCC(=O)N1CCC(Oc2ccc(-c3ccnc(Oc4ccccc4)c3)cc2)CC1]

Step 1

4-[4-(2-Fluoropyridin-4-yl)-phenoxy]-piperidine-1-carboxylic acid tert-butyl ester was prepared from 4-(4-iodophenoxy)-piperidine-1-carboxylic acid t-butyl ester (0.5 g, 1.24 mmol) and 2-fluoropyridine-4-boronic acid (0.26 g, 1.86 mmol) in an analogous manner to Example 378. Product isolated as a solid (0.2 g, 44%). Analysis: LCMS m/z 373 (M+1).

Step 2

2-Fluoro-4-[4-(piperidin-4-yloxy)-phenyl]-pyridine was prepared from 4-[4-(2-fluoropyridin-4-yl)-phenoxy]-piperidine-1-carboxylic acid tert-butyl ester (0.2 g, 0.55 mmol) and trifluoroacetic acid (1 mL) in an analogous manner to Example 378 step 2. Product isolated as a solid (0.15 g, 98%). Analysis: LCMS m/z 273 (M+1).

Step 3

Phenol (59 mg, 0.63 mmol) in DMF (5 mL) at 0° C. was added NaH, 60% disp. in mineral oil (65 mg, 1.62 mmol). After stirring 0.5 h at rt, 1-{4-[4-(2-fluoropyridin-4-yl)-phenoxy]-piperidin-1-yl}-propan-1-one (0.17 g, 0.52 mmol) was added dropwise in DMF (2 mL) and the reaction was stirred at 100° C. overnight. The reaction was diluted with EtOAc, was washed with water/brine, dried over Na₂SO₄, and concentrated. The product was purified using the Gilson (0.1% TFA in water/0.1% TFA in acetonitrile gradient). The clean fractions were diluted with DCM, washed with 1N Na₂CO₃/water/brine, dried over Na₂SO₄, concentrated, and dried under high vacuum at 50° C. overnight. 1-{4-[4-(2-phenoxy-pyridin-4-yl)-phenoxy]-piperidin-1-yl}-propan-1-one was isolated as a solid (0.05 g, 21%). Analysis: LCMS m/z=403 (M+1). ¹H NMR (DMSO-d6) δ: 8.15 (d, 1H, J=5.3 Hz), 7.79 (m, 2H), 7.42 (m, 3H), 7.30 (s, 1H), 7.21 (m, 1H), 7.13 (m, 4H), 4.71 (m, 1H), 3.90 (m, 1H), 3.70 (m, 1H), 3.35 (m, 1H), 3.25 (m, 1H), 2.33 (m, 2H), 1.97 (br m, 2H), 1.50-1.62 (br m, 2H), 0.99 (t, 3H, J=7.3 Hz).

Example 410. 1-{4-[4-(4-Methoxypyrazolo[1,5-a]pyridin-6-yl)-phenoxy]-piperidin-1-yl}-propan-1-one, HCl

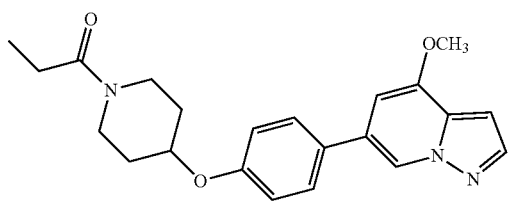 [SMILES: CCC(=O)N1CCC(Oc2ccc(-c3cc(OC)c4ccnn4c3)cc2)CC1]

Step 1

6-Bromopyrazolo[1,5-a]pyridin-4-ol (0.5 g, 2.35 mmol) in DMF (5 mL) under an atmosphere of nitrogen was added cesium carbonate (2.3 g, 7.04 mmol), followed by methyl iodide (0.22 mL, 3.52 mmol) and the reaction was heated at 80° C. for 1 h. The reaction was cooled at rt, diluted with ethyl acetate, washed with water several times, washed with brine, dried over sodium sulfate, and concentrated. The product was purified via silica gel chromatography (10% ethyl acetate/hexanes) and concentrated. 6-Bromo-4-methoxy-pyrazolo[1,5-a]pyridine was isolated as a solid (0.43 g, 80%). Analysis: LCMS m/z=228 (M+1).

Step 2

4-[4-(4-Methoxypyrazolo[1,5-a]pyridin-6-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 6-bromo-4-methoxypyrazolo[1,5-a]pyridine (0.42 g, 1.86 mmol) in an analogous manner to Example 378. Product isolated as a solid (0.4 g, 78%). Analysis: LCMS m/z 424 (M+1).

Step 3

4-Methoxy-6-[4-(piperidin-4-yloxy)-phenyl]-pyrazolo[1,5-a]pyridine was prepared from 4-[4-(4-methoxy-pyrazolo

[1,5-a]pyridin-6-yl)-phenoxy]-piperidine-1-carboxylic acid tert-butyl ester (0.4 g, 0.97 mmol) and TFA (2 mL) in an analogous manner to Example 378 step 2. Product isolated as a solid (0.25 g, 79%). Analysis: LCMS m/z 324 (M+1).

Step 4

The title compound was prepared from 4-methoxy-6-[4-(piperidin-4-yloxy)-phenyl]-pyrazolo[1,5-a]pyridine (82 mg, 0.25 mmol) and propanoyl chloride (40 uL, 0.4 mmol) in an analogous manner to Example 398. Product isolated as a solid (0.07 g, 62%). Analysis: LCMS m/z=380 (M+1). $^1$H NMR (DMSO-d6) δ: 8.57 (s, 1H), 7.94 (d, 1H, J=2.2 Hz), 7.73 (d, 2H, J=8.7 Hz), 7.51 (br m, 1H), 7.10 (d, 2H, J=8.8 Hz), 6.89 (s, 1H), 6.62 (m, 1H), 4.69 (m, 1H), 4.03 (s, 3H), 3.85 (m, 1H), 3.68 (m, 1H), 3.35 (br m, 2H), 2.33 (m, 2H), 1.96 (m, 2H), 1.51-1.63 (br m, 2H), 0.99 (t, 3H, J=7.3 Hz).

Example 411. Cyclopropyl-{4-[4-(4-methoxypyrazolo[1,5-a]pyridin-6-yl)-phenoxy]-piperidin-1-yl}-methanone, HCl

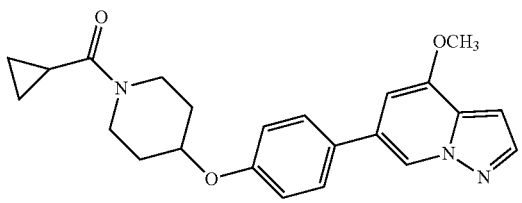 [SMILES: COc1cc(-c2ccc(OC3CCN(C(=O)C4CC4)CC3)cc2)cn2nccc12]

This example was prepared from 4-methoxy-6-[4-(piperidin-4-yloxy)-phenyl]-pyrazolo[1,5-a]pyridine (82 mg, 0.25 mmol) and cyclopropanecarbonyl chloride (40 uL, 0.4 mmol) in an analogous manner to Example 398. Product isolated as a solid (0.08 g, 72%). Analysis: LCMS m/z=392 (M+1). $^1$H NMR (DMSO-d6) δ: 8.57 (s, 1H), 7.94 (d, 1H, J=2.2 Hz), 7.73 (d, 2H, J=8.7 Hz), 7.10 (d, 2H, J=8.8 Hz), 6.89 (s, 1H), 6.62 (m, 1H), 4.71 (m, 1H), 4.20 (br m, 1H), 4.02 (s, 3H), 3.97 (m, 1H), 3.87 (m, 1H), 3.56 (m, 1H), 3.29 (m, 1H), 2.00 (br m, 3H), 1.54-1.64 (br m, 2H), 0.71 (m, 4H).

Example 412. Cyclobutyl-{4-[4-(4-methoxypyrazolo[1,5-a]pyridin-6-yl)-phenoxy]-piperidin-1-yl}-methanone, HCl

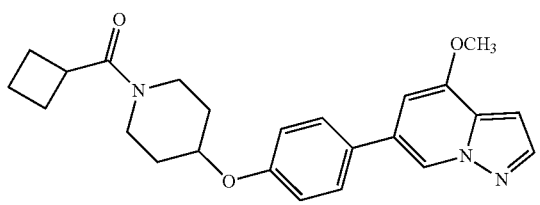 [SMILES: COc1cc(-c2ccc(OC3CCN(C(=O)C4CCC4)CC3)cc2)cn2nccc12]

This example was prepared from 4-methoxy-6-[4-(piperidin-4-yloxy)-phenyl]-pyrazolo[1,5-a]pyridine (82 mg, 0.25 mmol) and cyclobutanecarbonyl chloride (50 uL, 0.4 mmol) in an analogous manner to Example 398. Product isolated as a solid (0.04 g, 36%). Analysis: LCMS m/z=406 (M+1). $^1$H NMR (DMSO-d6) δ: 8.57 (s, 1H), 7.94 (d, 1H, J=2.2 Hz), 7.73 (d, 2H, J=8.7 Hz), 7.10 (d, 2H, J=8.8 Hz), 6.89 (s, 1H), 6.62 (m, 1H), 4.70 (m, 1H), 4.45 (br m, 1H), 4.02 (s, 3H), 3.88 (m, 1H), 3.59 (m, 1H), 3.36 (m, 1H), 3.26 (m, 2H), 2.07-2.51 (br m, 7H), 1.74 (m, 1H), 1.55 (m, 2H).

Example 413. 1-{4-[4-(3-Chloroisoquinolin-6-yl)-phenoxy]-piperidin-1-yl}-propan-1-one

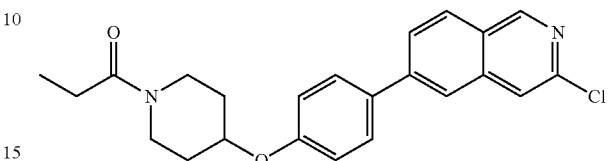

Step 1

4-[4-(3-Chloroisoquinolin-6-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 6-bromo-3-chloro-isoquinoline (0.3 g, 1.24 mmol) in an analogous manner to Example 378. Product isolated as a solid (0.47 g, 87%). Analysis: LCMS m/z 439 (M+1).

Step 2

3-Chloro-6-[4-(piperidin-4-yloxy)-phenyl]-isoquinoline was prepared from 4-[4-(3-chloro-isoquinolin-6-yl)-phenoxy]-piperidine-1-carboxylic acid tert-butyl ester (0.23 g, 0.52 mmol) and trifluoroacetic acid (1 mL) in an analogous manner to Example 378 step 2. Product isolated as a solid (0.15 g, 86%). Analysis: LCMS m/z 339 (M+1).

Step 3

The title compound was prepared from 3-chloro-6-[4-(piperidin-4-yloxy)-phenyl]-isoquinoline (75 mg, 0.22 mmol) and propanoyl chloride (30 uL, 0.4 mmol) in an analogous manner to Example 396. Product isolated as a solid (0.03 g, 34%). Analysis: LCMS m/z=395 (M+1). $^1$H NMR (DMSO-d6) δ: 9.19 (s, 1H), 8.21 (m, 2H), 8.03 (m, 2H), 7.80 (m, 2H), 7.15 (m, 2H), 4.72 (m, 1H), 3.88 (m, 1H), 3.69 (m, 1H), 3.35 (m, 1H), 3.27 (m, 1H), 2.35 (m, 2H), 1.97 (br m, 2H), 1.52-1.64 (br m, 2H), 1.00 (t, 3H, J=7.3 Hz).

Example 414. {4-[4-(3-Chloroisoquinolin-6-yl)-phenoxy]-piperidin-1-yl}-cyclopropyl-methanone

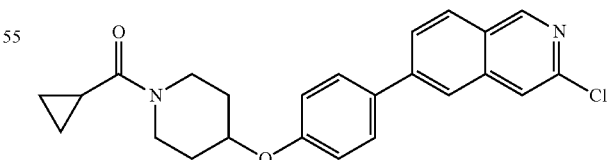

This example was prepared from 3-chloro-6-[4-(piperidin-4-yloxy)-phenyl]-isoquinoline (75 mg, 0.22 mmol) and cyclopropanecarbonyl chloride (30 uL, 0.4 mmol) in an analogous manner to Example 396. Product isolated as a solid (0.05 g, 56%). Analysis: LCMS m/z=407 (M+1). $^1$H NMR (DMSO-d6) δ: 9.19 (s, 1H), 8.21 (m, 2H), 8.03 (m, 2H), 7.80 (m, 2H), 7.15 (m, 2H), 4.75 (m, 1H), 4.02 (m, 1H), 3.89 (m, 1H), 3.56 (m, 1H), 3.29 (m, 1H), 2.00 (br m, 3H), 1.56-1.66 (br m, 2H), 0.71 (m, 4H).

Example 415. 1-{4-[4-(3-Methoxyisoquinolin-6-yl)-phenoxy]-piperidin-1-yl}-propan-1-one

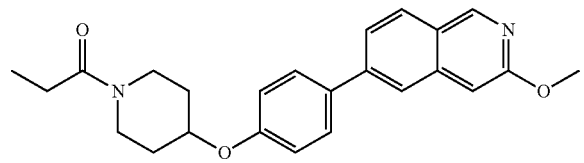 [SMILES: CCC(=O)N1CCC(Oc2ccc(-c3ccc4cnc(OC)cc4c3)cc2)CC1]

Step 1

4-[4-(3-Methoxy-isoquinolin-6-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.57 g, 1.40 mmol) and 6-bromo-3-methoxy-isoquinoline (0.5 g, 2.10 mmol) in an analogous manner to Example 378. Product isolated as a solid (0.51 g, 84%). Analysis: LCMS m/z 435 (M+1).

Step 2

3-Methoxy-6-[4-(piperidin-4-yloxy)-phenyl]-isoquinoline was prepared from 4-[4-(3-methoxy-isoquinolin-6-yl)-phenoxy]-piperidine-1-carboxylic acid tert-butyl ester (0.51 g, 1.2 mmol) and TFA (2 mL) in an analogous manner to Example 378 step 2. Product isolated as a solid (0.36 g, 91%). Analysis: LCMS m/z 335 (M+1).

Step 3

The title compound was prepared from 3-methoxy-6-[4-(piperidin-4-yloxy)-phenyl]-isoquinoline (89 mg, 0.27 mmol) and propanoyl chloride (40 uL, 0.4 mmol) in an analogous manner to Example 379. Product isolated as a solid (0.06 g, 58%). Analysis: LCMS m/z=391 (M+1). $^1$H NMR (DMSO-d6) δ: 9.04 (s, 1H), 8.04 (m, 2H), 7.95 (m, 3H), 7.20 (s, 1H), 7.14 (m, 2H), 4.71 (m, 1H), 3.95 (s, 3H), 3.87 (m, 1H), 3.69 (m, 1H), 3.35 (m, 1H), 3.26 (m, 1H), 2.35 (m, 2H), 1.98 (br m, 2H), 1.52-1.64 (br m, 2H), 0.99 (t, 3H, J=7.4 Hz).

Example 416. Cyclopropyl-{4-[4-(3-methoxyisoquinolin-6-yl)-phenoxy]-piperidin-1-yl}-methanone

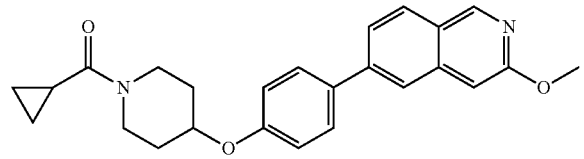 [SMILES: COc1cc2cc(-c3ccc(OC4CCN(C(=O)C5CC5)CC4)cc3)ccc2cn1]

This example was synthesized from 3-methoxy-6-[4-(piperidin-4-yloxy)-phenyl]-isoquinoline (89 mg, 0.27 mmol) and cyclopropanecarbonyl chloride (40 uL, 0.4 mmol) in an analogous manner to Example 396. Product isolated as a solid (0.08 g, 75%). Analysis: LCMS m/z=403 (M+1). $^1$H NMR (DMSO-d6) δ: 9.04 (s, 1H), 8.04 (m, 2H), 7.75 (m, 3H), 7.20 (s, 1H), 7.14 (m, 2H), 4.73 (m, 1H), 4.00 (m, 1H), 3.95 (s, 3H), 3.90 (m, 1H), 3.56 (m, 1H), 3.29 (m, 1H), 2.00 (br m, 3H), 1.65 (br m, 2H), 0.74 (m, 4H).

Example 417. Cyclobutyl-{4-[4-(3-methoxyisoquinolin-6-yl)-phenoxy]-piperidin-1-yl}-methanone

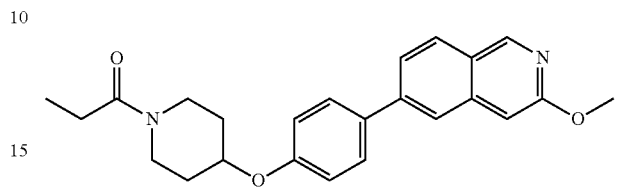

This example was synthesized from 3-methoxy-6-[4-(piperidin-4-yloxy)-phenyl]-isoquinoline (89 mg, 0.27 mmol) and cyclobutanecarbonyl chloride (50 uL, 0.4 mmol) in an analogous manner to Example 396. Product isolated as a solid (0.08 g, 68%). Analysis: LCMS m/z=417 (M+1). $^1$H NMR (DMSO-d6) δ: 9.04 (s, 1H), 8.04 (m, 2H), 7.95 (m, 3H), 7.20 (s, 1H), 7.14 (m, 2H), 4.69 (m, 1H), 3.95 (s, 3H), 3.85 (m, 1H), 3.56 (m, 1H), 3.36 (m, 1H), 3.25 (m, 2H), 2.17 (br m, 4H), 1.92 (br m, 3H), 1.75 (m, 1H), 1.53 (m, 2H).

Example 418. {4-[4-(3-Methoxy-isoquinolin-6-yl)-phenoxy]-piperidin-1-yl}-(R)-tetrahydrofuran-2-yl-methanone

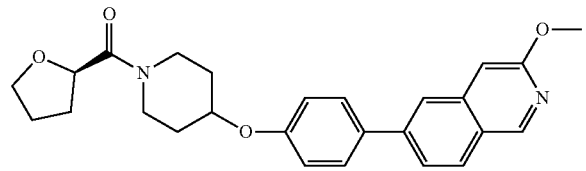 [SMILES: COc1cc2cc(-c3ccc(OC4CCN(C(=O)[C@H]5CCCO5)CC4)cc3)ccc2cn1]

To 3-ethoxy-6-[4-(piperidin-4-yloxy)-phenyl]-isoquinoline (0.09 g, 0.27 mmol) in DMF (3 mL) was added HATU (0.15 g, 0.4 mmol), DIPEA (0.14 mL, 0.8 mmol), followed by (R)-tetrahydrofuran-2-carboxylic acid (0.05 mL, 0.53 mmol) and the mixture was stirred at rt for 1 h. The mixture was poured into ethyl acetate, washed with 1N sodium carbonate/brine, dried over sodium sulfate, and concentrated. The product was purified using the Gilson (0.1% TFA in water/0. 1% TFA in acetonitrile gradient), diluted clean fractions with DCM, washed with 1N sodium carbonate/brine, dried over sodium sulfate, and concentrated. {4-[4-(3-Methoxy-isoquinolin-6-yl)-phenoxy]-piperidin-1-yl}-(R)-tetrahydrofuran-2-yl-methanone was isolated as a solid (0.09 g, 74%). Analysis: LCMS m/z=433 (M+1). $^1$H NMR (DMSO-d6) δ: 9.04 (s, 1H), 8.04 (m, 2H), 7.95 (m, 3H), 7.20 (s, 1H), 7.14 (m, 2H), 4.69 (m, 2H), 3.95 (s, 3H), 3.77 (m, 4H), 3.42 (m, 2H), 2.01 (br m, 4H), 1.84 (m, 2H), 1.63 (m, 2H).

Example 419. 1-{4-[4-(1-Chloroisoquinolin-6-yl)-phenoxy]-piperidin-1-yl}-propan-1-one

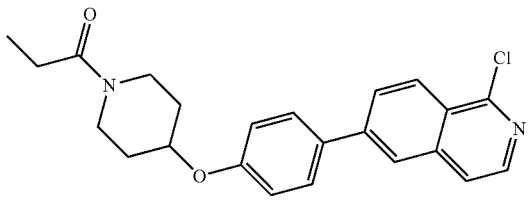 [SMILES: CCC(=O)N1CCC(Oc2ccc(-c3ccc4c(Cl)nccc4c3)cc2)CC1]

Step 1

4-[4-(1-Chloroisoquinolin-6-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 6-bromo-1-chloro-isoquinoline (0.3 g, 1.24 mmol) in an analogous manner to Example 378. Product isolated as a solid (0.2 g, 36%). Analysis: LCMS m/z 439 (M+1).

Step 2

1-Chloro-6-[4-(piperidin-4-yloxy)-phenyl]-isoquinoline was prepared from 4-[4-(1-chloroisoquinolin-6-yl)-phenoxy]-piperidine-1-carboxylic acid tert-butyl ester (0.2 g, 0.45 mmol) and TFA (1 mL) in an analogous manner to Example 378 step 2. Product isolated as a solid (0.14 g, 93%). Analysis: LCMS m/z 339 (M+1).

Step 3

The title compound was prepared from 1-chloro-6-[4-(piperidin-4-yloxy)-phenyl]-isoquinoline (70 mg, 0.2 mmol) and propanoyl chloride (30 uL, 0.4 mmol) in an analogous manner to Example 379. Product isolated as a solid (0.04 g, 40%). Analysis: LCMS m/z=395 (M+1). $^1$H NMR (DMSO-d6) δ: 8.31 (m, 3H), 8.15 (m, 1H), 7.93 (m, 1H), 7.84 (m, 2H), 7.18 (m, 2H), 4.73 (m, 1H), 3.87 (m, 1H), 3.69 (m, 1H), 3.35 (m, 1H), 3.27 (m, 1H), 2.34 (m, 2H), 1.98 (br m, 2H), 1.52-1.64 (br m, 2H), 1.00 (t, 3H, J=7.4 Hz).

Example 420. {4-[4-(1-Chloroisoquinolin-6-yl)-phenoxy]-piperidin-1-yl}-cyclopropyl-methanone

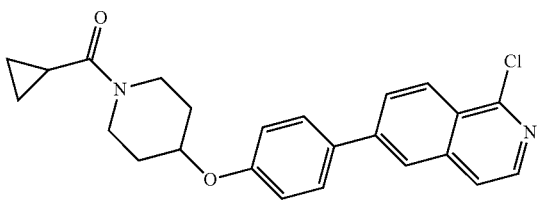 [SMILES: O=C(C1CC1)N1CCC(Oc2ccc(-c3ccc4c(Cl)nccc4c3)cc2)CC1]

This example was synthesized from 1-chloro-6-[4-(piperidin-4-yloxy)-phenyl]-isoquinoline (70 mg, 0.2 mmol) and cyclopropanecarbonyl chloride (30 uL, 0.4 mmol) in an analogous manner to Example 396. Product isolated as a solid (0.04 g, 50%). Analysis: LCMS m/z=407 (M+1). $^1$H NMR (DMSO-d6) δ: 8.31 (m, 3H), 8.15 (m, 1H), 7.93 (m, 1H), 7.84 (m, 2H), 7.18 (m, 2H), 4.75 (m, 1H), 3.99 (m, 1H), 3.89 (m, 1H), 3.56 (m, 1H), 3.29 (m, 1H), 2.04 (br m, 3H), 1.55-1.65 (br m, 2H), 0.74 (m, 4H).

Example 421. 1-{4-[4-(3-Dimethylaminoisoquinolin-6-yl)-phenoxy]-piperidin-1-yl}-propan-1-one

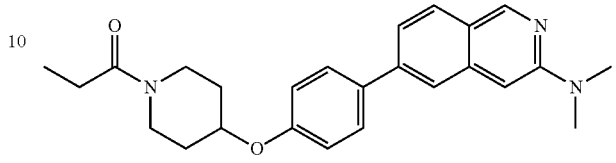

Step 1

4-[4-(3-Chloroisoquinolin-6-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 6-bromo-3-chloroisoquinoline (0.3 g, 1.24 mmol) in an analogous manner to Example 378. Product isolated as a solid (0.47 g, 87%). Analysis: LCMS m/z 439 (M+1).

Step 2

To an oven dried flask under an atmosphere of argon was added 4-[4-(3-chloroisoquinolin-6-yl)-phenoxy]-piperidine-1-carboxylic acid t-butyl ester (0.2 g, 0.46 mmol), 2M of dimethylamine in THF (0.68 mL, 1.37 mmol), cinnamyl-palladium chloride dimer (24 mg, 0.05 mmol), di(1-adamantyl)-2-dimethylaminophenylphosphine (38 mg, 0.09 mmol), sodium t-butoxide (0.13 g, 1.37 mmol), followed by toluene (40 mL) and the reaction was degassed 3 times under an atmosphere of argon and was stirred at 90° C. overnight. Cooled at rt, diluted with DCM, filtered through a pad of celite, washed with water/brine, dried over sodium sulfate, and concentrated. The product was purified via silica gel chromatography (10-20% EtOAc/hexanes) and concentrated. 4-[4-(3-Dimethylamino-isoquinolin-6-yl)-phenoxy]-piperidine-1-carboxylic acid t-butyl ester was isolated as a solid (0.1 g, 53%). Analysis: LCMS m/z 448 (M+1).

Step 3

Dimethyl-{6-[4-(piperidin-4-yloxy)-phenyl]-isoquinolin-3-yl}-amine was prepared from 4-[4-(3-dimethylamino-isoquinolin-6-yl)-phenoxy]-piperidine-1-carboxylic acid tert-butyl ester (0.1 g, 0.24 mmol) and TFA (1 mL) in an analogous manner to Example 378 step 2. Product isolated as a solid (0.08 g, 92%). Analysis: LCMS m/z 348 (M+1).

Step 4

The title compound was prepared from dimethyl-{6-[4-(piperidin-4-yloxy)-phenyl]-isoquinolin-3-yl}-amine (76 mg, 0.22 mmol) and propanoyl chloride (30 uL, 0.4 mmol) in an analogous manner to Example 396. Product isolated as a solid (0.04 g, 45%). Analysis: LCMS m/z=404 (M+1). $^1$H NMR (DMSO-d6) δ: 8.92 (s, 1H), 7.84 (m, 2H), 7.71 (m, 2H), 7.50 (m, 1H), 7.12 (d, 2H, J=8.8 Hz), 6.79 (s, 1H), 4.69 (m, 1H), 3.90 (m, 1H), 3.69 (m, 1H), 3.37 (m, 1H), 3.29 (m, 1H), 3.11 (s, 6H), 2.35 (m, 2H), 1.98 (br m, 2H), 1.51-1.64 (br m, 2H), 0.99 (t, 3H, J=7.3 Hz).

Example 422. 1-{4-[4-(3-Aminoisoquinolin-6-yl)-phenoxy]-piperidin-1-yl}-propan-1-one

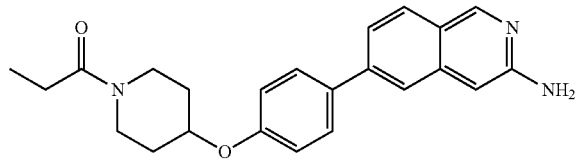 [SMILES: CCC(=O)N1CCC(Oc2ccc(-c3ccc4cnc(N)cc4c3)cc2)CC1]

Step 1

4-[4-(4,4,5,5-Tetramethyl-1,3,2-dioxaborolan-2-yl)-phenoxy]-piperidine was prepared from 4-[4-(4,4,5,5-tetramethyl-1,3,2-dioxaborolan-2-yl)-phenoxy]-piperidine-1-carboxylic acid t-butyl ester (0.3 g, 0.74 mmol) and TFA (1 mL) in an analogous manner to Example 378 step 2. Product isolated as a solid (0.2 g, 87%). Analysis: LCMS m/z 304 (M+1).

Step 2

1-{4-[4-(4,4,5,5-Tetramethyl-1,3,2-dioxaborolan-2-yl)-phenoxy]-piperidin-1-yl}-propan-1-one was prepared from the Step 1 product (97 mg, 0.32 mmol) and propanoyl chloride (50 uL, 0.5 mmol) in an analogous manner to Example 378 step 3. Product isolated as a solid (0.11 g, 97%). Analysis: LCMS m/z=360 (M+1).

Step 3

1-{4-[4-(3-Aminoisoquinolin-6-yl)-phenoxy]-piperidin-1-yl}-propan-1-one was prepared from the Step 2 product (0.11 g, 0.32 mmol) and 6-bromoisoquinolin-3-ylamine (0.11 g, 0.48 mmol) in an analogous manner to Example 378. Product isolated as a solid (0.05 g, 42%). Analysis: LCMS m/z=376 (M+1). ¹H NMR (DMSO-d6) δ: 8.78 (s, 1H), 7.84 (d, 1H, J=8.6 Hz), 7.70 (m, 3H), 7.44 (m, 1H), 7.11 (m, 2H), 6.65 (s, 1H), 5.91 (s, 2H), 4.69 (m, 1H), 3.88 (m, 1H), 3.69 (m, 1H), 3.34 (m, 1H), 3.29 (m, 1H), 2.33 (m, 2H), 1.96 (br m, 2H), 1.50-1.64 (br m, 2H), 0.99 (t, 3H, J=7.3 Hz).

Example 423. {4-[4-(3-Aminoisoquinolin-6-yl)-phenoxy]-piperidin-1-yl}-cyclopropyl-methanone

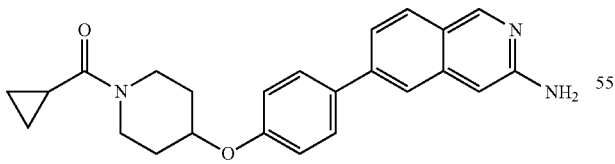

Step 1

Cyclopropyl-{4-[4-(4,4,5,5-tetramethyl-1,3,2-dioxaborolan-2-yl)-phenoxy]-piperidin-1-yl}-methanone was prepared from 4-[4-(4,4,5,5-tetramethyl-1,3,2-dioxaborolan-2-yl)-phenoxy]-piperidine (97 mg, 0.32 mmol) and cyclopropanecarbonyl chloride (50 uL, 0.5 mmol) in an analogous manner to Example 378 step 3. Product isolated as a solid (0.12 g, 100%). Analysis: LCMS m/z=372 (M+1).

Step 2

The title compound was prepared form the Step 2 product (0.13 g, 0.35 mmol) and 6-bromoisoquinolin-3-ylamine (0.12 g, 0.52 mmol) in an analogous manner to Example 378. Product isolated as a solid (0.07 g, 52%). Analysis: LCMS m/z=388 (M+1). ¹H NMR (DMSO-d6) δ: 8.78 (s, 1H), 7.84 (d, 1H, J=8.6 Hz), 7.70 (m, 3H), 7.44 (m, 1H), 7.11 (m, 2H), 6.65 (s, 1H), 5.91 (s, 2H), 4.71 (m, 1H), 3.98 (m, 1H), 3.88 (m, 1H), 3.56 (m, 1H), 3.29 (m, 1H), 2.00 (br m, 3H), 1.54-1.64 (br m, 2H), 0.71 (m, 4H).

Example 424. {4-[4-(4-Methoxypyrazolo[1,5-a]pyridin-6-yl)-phenoxy]-piperidin-1-yl}-(R)-tetrahydrofuran-2-yl-methanone, HCl

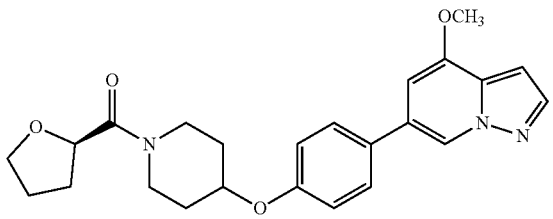 [SMILES: COc1cc(-c2ccc(OC3CCN(C(=O)[C@H]4CCCO4)CC3)cc2)cn2nccc12]

To 4-methoxy-6-[4-(piperidin-4-yloxy)-phenyl]-pyrazolo[1,5-a]pyridine (0.09 g, 0.28 mmol) in DMF (3 mL) was added HATU (0.16 g, 0.42 mmol), DIPEA (0.15 mL, 0.84 mmol), followed by (R)-tetrahydrofuran-2-carboxylic acid (0.05 mL, 0.56 mmol) and was stirred at rt for 1 h. The solution was poured into EtOAc, washed with 1N Na₂CO₃/brine, dried over sodium sulfate, and concentrated. The product was purified using the Gilson (0.1% TFA in water/0.1% TFA in acetonitrile gradient), diluted clean fractions with DCM, washed with 1N Na₂CO₃/brine, dried over sodium sulfate, and concentrated. Dissolved compound in DCM, 2 M of HCl in diethyl ether (0.14 mL, 0.28 mmol) was added and concentrated. Dried sample under high vacuum at 40° C. overnight. {4-[4-(4-Methoxypyrazolo[1,5-a]pyridin-6-yl)-phenoxy]-piperidin-1-yl}-(R)-tetrahydrofuran-2-yl-methanone; HCl was isolated as a solid (0.03 g, 24%). Analysis: LCMS m/z=422 (M+1). ¹H NMR (DMSO-d6) δ: 8.57 (s, 1H), 7.94 (d, 1H, J=2.2 Hz), 7.73 (m, 2H), 7.10 (d, 2H, J=8.7 Hz), 6.89 (s, 1H), 6.62 (m, 1H), 4.68 (m, 2H), 4.02 (s, 3H), 3.78 (m, 4H), 3.37 (m, 1H), 3.25 (m, 1H), 1.80-2.08 (br m, 6H), 1.53-1.65 (br m, 2H).

Example 425. 1-{4-[4-(1-Methylisoquinolin-6-yl)-phenoxy]-piperidin-1-yl}-propan-1-one

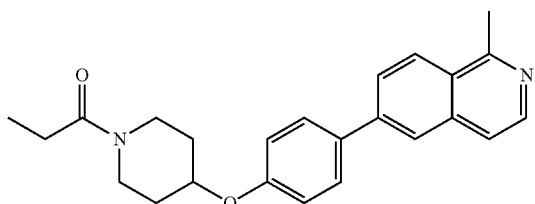

Step 1

4-[4-(1-Chloroisoquinolin-6-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 6-bromo-1-chloroisoquinoline (0.3 g, 1.24 mmol)) in an analogous manner to Example 378. Product isolated as a solid (0.14 g, 26%). Analysis: LCMS m/z 439 (M+1).

Step 2

To an oven dried schlenck flask under an atmosphere of argon was added 4-[4-(1-chloroisoquinolin-6-yl)-phenoxy]-piperidine-1-carboxylic acid tert-butyl ester (0.14 g, 0.32 mmol), methylboronic acid (96 mg, 1.59 mmol), DPPF-Pd(II) complex with DCM (1:1) (52 mg, 0.06 mmol), potassium phosphate (338 mg, 1.59 mmol), followed by 1,4-dioxane (5 mL) and was degassed under an atmosphere of argon for 5 min and was heated at 99° C. overnight. The reaction was cooled, filtered through a pad of celite, washed with 1N sodium carbonate/water/brine, dried over sodium sulfate, and concentrated. The product was purified via silica gel chromatography (10-50% ethyl acetate/hexanes) and concentrated. 4-[4-(1-methyl-isoquinolin-6-yl)-phenoxy]-piperidine-1-carboxylic acid t-butyl ester was isolated as a solid (0.06 g, 46%). Analysis: LCMS m/z 419 (M+1).

Step 3

1-Methyl-6-[4-(piperidin-4-yloxy)-phenyl]-isoquinoline was prepared from 4-[4-(1-methyl-isoquinolin-6-yl)-phenoxy]-piperidine-1-carboxylic acid tert-butyl ester (0.06 g, 0.14 mmol) and trifluoroacetic acid (1 mL) in an analogous manner to Example 378. Product isolated as a solid (0.05 g, 100%). Analysis: LCMS m/z 319 (M+1).

Step d

The title compound was prepared from the Step 3 product (60 mg, 0.2 mmol) and propanoyl chloride (30 uL, 0.4 mmol) in an analogous manner to Example 396. Product isolated as a solid (0.03 g). Analysis: LCMS m/z=375 (M+1). $^1$H NMR (DMSO-d6) δ: 8.34 (d, 1H, J=5.7 Hz), 8.23 (m, 1H), 8.17 (m, 1H), 7.98 (m, 1H), 7.81 (m, 2H), 7.70 (m, 1H), 7.13 (m, 2H), 4.71 (m, 1H), 3.87 (m, 1H), 3.69 (m, 1H), 3.35 (m, 1H), 3.29 (m, 1H), 2.89 (s, 3H), 2.35 (m, 2H), 1.98 (br m, 2H), 1.52-1.65 (br m, 2H), 1.00 (t, 3H, J=7.3 Hz).

Example 426. 1-{4-[4-(4-Hydroxypyrazolo[1,5-a]pyridin-6-yl)-phenoxy]-piperidin-1-yl}-propan-1-one

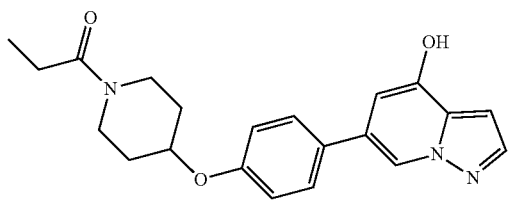 [SMILES: CCC(=O)N1CCC(Oc2ccc(-c3cc(O)c4ccnn4c3)cc2)CC1]

This example was synthesized from 1-{4-[4-(4,4,5,5-tetramethyl-1,3,2-dioxaborolan-2-yl)-phenoxy]-piperidin-1-yl}-propan-1-one (0.1 g, 0.28 mmol) and 6-bromo-pyrazolo[1,5-a]pyridin-4-ol (89 mg, 0.42 mmol) in an analogous manner to Example 378. Product isolated as a solid (0.03 g, 29%). Analysis: LCMS m/z=366 (M+1). $^1$H NMR (DMSO-d6) δ: 10.61 (s, 1H), 8.46 (m, 1H), 7.89 (d, 1H, J=2.2 Hz), 7.60 (m, 2H), 7.08 (m, 2H), 6.72 (m, 1H), 6.63 (m, 1H), 4.66 (m, 1H), 3.89 (m, 1H), 3.72 (m, 1H), 3.35 (m, 1H), 3.25 (m, 1H), 2.33 (m, 2H), 1.95 (br m, 2H), 1.48-1.62 (br m, 2H), 0.99 (t, 3H, J=7.3 Hz).

Example 427. Cyclobutyl-{4-[4-(4-hydroxy-pyrazolo[1,5-a]pyridin-6-yl)-phenoxy]-piperidin-1-yl}-methanone

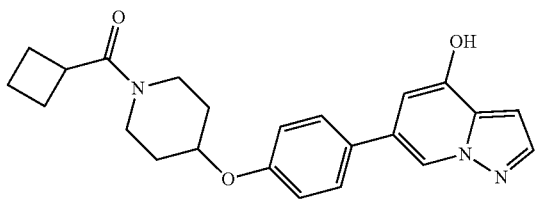 [SMILES: O=C(C1CCC1)N1CCC(Oc2ccc(-c3cc(O)c4ccnn4c3)cc2)CC1]

Cyclobutyl-{4-[4-(4-hydroxy-pyrazolo[1,5-a]pyridin-6-yl)-phenoxy]-piperidin-1-yl}-methanone 1-{4-[4-(4,4,5,5-tetramethyl-1,3,2-dioxaborolan-2-yl)-phenoxy]-piperidin-1-yl}-propan-1-one (0.1 g, 0.28 mmol) and 6-bromo-pyrazolo[1,5-a]pyridin-4-ol (91 mg, 0.43 mmol) in an analogous manner to Example 378. Product isolated as a solid (0.04 g, 37%). Analysis: LCMS m/z=392 (M+1). $^1$H NMR (DMSO-d$_6$) δ: 10.61 (s, 1H), 8.46 (m, 1H), 7.89 (d, 1H, J=2.2 Hz), 7.60 (m, 2H), 7.08 (m, 2H), 6.72 (m, 1H), 6.63 (m, 1H), 4.65 (m, 1H), 3.85 (m, 1H), 3.55 (m, 1H), 3.36 (m, 1H), 3.24 (m, 2H), 2.14 (m, 4H), 1.92 (m, 3H), 1.74 (m, 1H), 1.54 (m, 2H).

Example 428. {4-[4-(1-Chloroisoquinolin-6-yl)-phenoxy]-piperidin-1-yl}-cyclobutyl-methanone

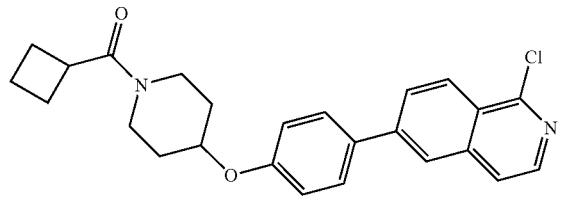 [SMILES: O=C(C1CCC1)N1CCC(Oc2ccc(-c3ccc4c(Cl)nccc4c3)cc2)CC1]

This example was synthesized from 1-chloro-6-[4-(piperidin-4-yloxy)-phenyl]-isoquinoline (40 mg, 0.1 mmol) and cyclobutanecarbonyl chloride (20 uL, 0.2 mmol) in an analogous manner to Example 379. Product isolated as a solid (0.03 g, 50%). Analysis: LCMS m/z=421 (M+1). $^1$H NMR (DMSO-d6) δ: 8.31 (m, 3H), 8.15 (m, 1H), 7.93 (m, 1H), 7.84 (m, 2H), 7.18 (m, 2H), 4.72 (m, 1H), 3.85 (m, 1H), 3.56 (m, 1H), 3.36 (m, 1H), 3.29 (m, 2H), 2.17 (m, 2H), 2.09 (m, 2H), 1.93 (m, 3H), 1.74 (m, 1H), 1.56 (m, 2H).

Example 429. {4-[4-(1-Chloroisoquinolin-6-yl)-phenoxy]-piperidin-1-yl}-(R)-tetrahydro-furan-2-yl-methanone

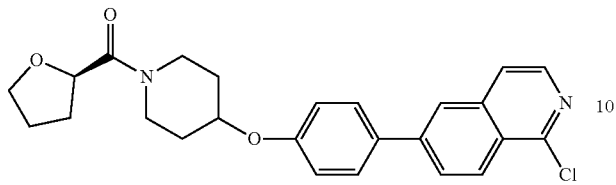

This example was synthesized from 1-chloro-6-[4-(piperidin-4-yloxy)-phenyl]-isoquinoline (0.04 g, 0.12 mmol) and (R)-tetrahydrofuran-2-carboxylic acid (0.02 mL, 0.24 mmol) in an analogous manner to Example 418. Product isolated as a solid (0.02 g, 39%). Analysis: LCMS m/z=437 (M+1). $^1$H NMR (DMSO-d6) δ: 8.31 (m, 3H), 8.15 (m, 1H), 7.93 (m, 1H), 7.84 (m, 2H), 7.18 (m, 2H), 4.75 (m, 1H), 4.69 (m, 1H), 3.77 (m, 4H), 3.34 (m, 1H), 3.29 (m, 1H), 2.01 (m, 4H), 1.84 (m, 2H), 1.52-1.65 (br m, 2H).

Example 430. 1-{4-[4-(3-Methylisoquinolin-6-yl)-phenoxy]-piperidin-1-yl}-propan-1-one

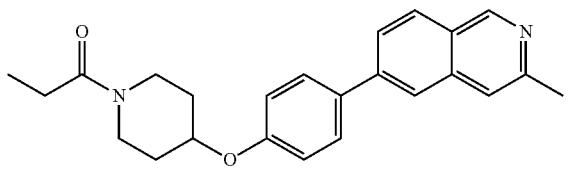 [SMILES: CCC(=O)N1CCC(Oc2ccc(-c3ccc4cnc(C)cc4c3)cc2)CC1]

Step 1

To an oven-dried schlenck flask under an atmosphere of argon was added 4-[4-(3-chloroisoquinolin-6-yl)-phenoxy]-piperidine-1-carboxylic acid t-butyl ester (0.44 g, 1 mmol), methylboronic acid (301 mg, 5.02 mmol), amphos (142 mg, 0.2 mmol), cesium carbonate (1.64 g, 5.02 mmol), followed by 1,4-dioxane (60 mL) and was degassed under an atmosphere of argon for 5 min and was heated at 99° C. overnight. The reaction was cooled, filtered through a pad of celite, washed with 1N sodium carbonate, water, brine, dried over sodium sulfate, and concentrated. The product was purified via silica gel chromatography (10-30% ethyl acetate/hexanes) and concentrated. 4-[4-(3-methyl-isoquinolin-6-yl)-phenoxy]-piperidine-1-carboxylic acid tert-butyl ester was isolated as a solid (0.11 g, 27%). Analysis: LCMS m/z=419 (M+1).

Step 2

3-Methyl-6-[4-(piperidin-4-yloxy)-phenyl]-isoquinoline was prepared from 4-[4-(3-methylisoquinolin-6-yl)-phenoxy]-piperidine-1-carboxylic acid tert-butyl ester (0.11 g, 0.27 mmol) and trifluoroacetic acid (1 mL) in an analogous manner to Example 378. Product isolated as a solid (0.08 g, 87%). Analysis: LCMS m/z=319 (M+1).

Step 3

The title compound was prepared from 3-methyl-6-[4-(piperidin-4-yloxy)-phenyl]-isoquinoline (75 mg, 0.24 mmo) and propanoyl chloride (30 uL, 0.4 mmol) in an analogous manner to Example 396. Product isolated as a solid (0.05 g, 51%). Analysis: LCMS m/z=375 (M+1). $^1$H NMR (DMSO-d6) δ: 9.20 (s, 1H), 8.12 (d, 1H, J=8.6 Hz), 8.07 (s, 1H), 7.90 (m, 1H), 7.78 (m, 2H), 7.66 (s, 1H), 7.15 (d, 2H, J=8.8 Hz), 4.71 (m, 1H), 3.88 (m, 1H), 3.73 (m, 1H), 3.36 (m, 1H), 3.29 (m, 1H), 2.61 (s, 3H), 2.33 (m, 2H), 1.98 (br m, 2H), 1.52-1.64 (br, m, 2H), 0.99 (t, 3H, J=7.4 Hz).

Example 431. {4-[4-(1-Methylisoquinolin-6-yl)-phenoxy]-piperidin-1-yl}-(R)-tetrahydro-furan-2-yl-methanone

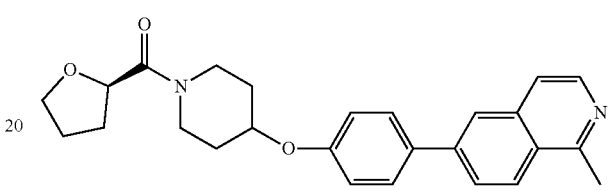

This example was synthesized from 1-methyl-6-[4-(piperidin-4-yloxy)-phenyl]-isoquinoline (50 mg, 0.2 mmol) and (R)-tetrahydrofuran-2-carboxylic acid (30 uL, 0.31 mmol) in an analogous manner to Example 639. Product isolated as a solid. Analysis: LCMS m/z=417 (M+1). $^1$H NMR (DMSO-d6) δ: 8.34 (d, 1H, J=5.8 Hz), 8.25 (d, 1H, J=8.7 Hz), 8.18 (m, 1H), 7.98 (m, 1H), 7.81 (d, 2H. J=8.7 Hz), 7.70 (d, 1H, J=5.8 Hz), 7.16 (d, 2H, J=8.7 Hz), 4.69 (m, 2H), 3.77 (m, 4H), 3.43 (m, 1H), 3.26 (m, 1H), 2.89 (s, 3H), 2.01 (br m, 4H), 1.84 (m, 2H), 1.52-1.66 (br m, 2H).

Example 432. {4-[4-(1-Methoxyisoquinolin-6-yl)-phenoxy]-piperidin-1-yl}-(R)-tetrahydro-furan-2-yl-methanone

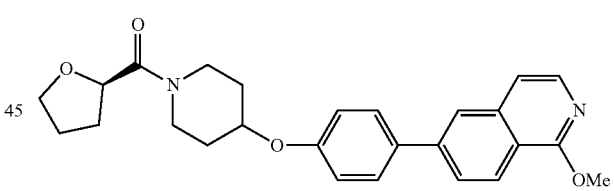

Step 1

4-[4-(1-Methoxyisoquinolin-6-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 6-bromo-1-methoxy-isoquinoline (443 mg, 1.86 mmol) in an analogous manner to Example 378. Product isolated as a solid. Analysis: LCMS m/z=435 (M+1).

Step 2

1-Methoxy-6-[4-(piperidin-4-yloxy)-phenyl]-isoquinoline was prepared from the step 1 product and trifluoroacetic acid (2 mL) in an analogous manner to Example 378. Product isolated as a solid. Analysis: LCMS m/z=335 (M+1).

Step 3

The title compound was prepared from 1-methoxy-6-[4-(piperidin-4-yloxy)-phenyl]-isoquinoline (0.09 g, 0.27 mmol) and (R)-tetrahydrofuran-2-carboxylic acid (0.05 mL, 0.53 mmol) in an analogous manner to Example 418. Product isolated as a solid (0.04 g, 30%). Analysis: LCMS m/z=433 (M+1). ¹H NMR (DMSO-d6) δ: 8.21 (d, 1H, J=8.7 Hz), 8.13 (s, 1H), 8.02 (d, 1H, J=5.8 Hz), 7.92 (m, 1H), 7.79 (d, 2H, J=8.7 Hz), 7.43 (d, 1H, J=5.7 Hz), 7.15 (d, 2H, J=8.7 Hz), 4.73 (m, 2H), 4.07 (s, 3H), 3.75 (br m, 4H), 3.42 (m, 1H), 3.25 (m, 1H), 2.01 (br m, 4H), 1.84 (m, 2H), 1.54-1.66 (br m, 2H).

Example 433. 1-{4-[4-(1-Methoxyisoquinolin-6-yl)-phenoxy]-piperidin-1-yl}-propan-1-one

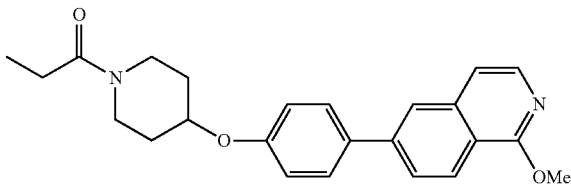 [SMILES: CCC(=O)N1CCC(Oc2ccc(-c3ccc4c(OC)nccc4c3)cc2)CC1]

This example was synthesized from 1-methoxy-6-[4-(piperidin-4-yloxy)-phenyl]-isoquinoline (0.09 g, 0.27 mmol) and propanoyl chloride (40 uL, 0.4 mmol) in an analogous manner to Example 379. Product isolated as a solid (0.06 g, 53%). Analysis: LCMS m/z=391 (M+1). ¹H NMR (DMSO-d6) δ: 8.21 (d, 1H, J=8.7 Hz), 8.13 (s, 1H), 8.02 (d, 1H, J=5.8 Hz), 7.92 (m, 1H), 7.79 (d, 2H, J=8.7 Hz), 7.43 (d, 1H, J=5.7 Hz), 7.15 (d, 2H, J=8.7 Hz), 4.71 (m, 1H), 4.07 (s, 3H), 3.88 (m, 1H), 3.72 (m, 1H), 3.35 (m, 1H), 3.26 (m, 1H), 2.33 (m, 2H), 1.98 (br m, 2H), 1.52-1.64 (br m, 2H), 0.99 (t, 3H, J=7.4 Hz).

Example 434. Cyclobutyl-{4-[4-(1-methoxyisoquinolin-6-yl)-phenoxy]-piperidin-1-yl}-methanone

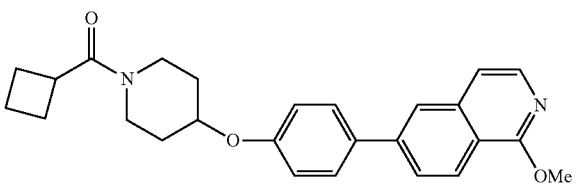 [SMILES: COc1nccc2cc(-c3ccc(OC4CCN(C(=O)C5CCC5)CC4)cc3)ccc12]

This example was synthesized from 1-methoxy-6-[4-(piperidin-4-yloxy)-phenyl]-isoquinoline (0.09 g, 0.27 mmol) and cyclobutanecarbonyl chloride (50 uL, 0.4 mmol) in an analogous manner to Example 396. Product isolated as a solid (0.07 g, 60%). Analysis: LCMS m/z=417 (M+1). ¹H NMR (DMSO-d6) δ: 8.21 (d, 1H, J=8.7 Hz), 8.13 (s, 1H), 8.02 (d, 1H, J=5.8 Hz), 7.92 (m, 1H), 7.79 (d, 2H, J=8.7 Hz), 7.43 (d, 1H, J=5.7 hZ), 7.15 (d, 2H, J=8.7 Hz), 4.70 (m, 1H), 4.07 (m, 3H), 3.88 (m, 1H), 3.56 (m, 1H), 3.36 (m, 1H), 3.25 (m, 2H), 2.07-2.20 (br m, 4H), 1.92 (br m, 3H), 1.74 (m, 1H), 1.56 (m, 2H).

Example 435. Cyclopropyl-{4-[4-(1-methoxyisoquinolin-6-yl)-phenoxy]-piperidin-1-yl}-methanone

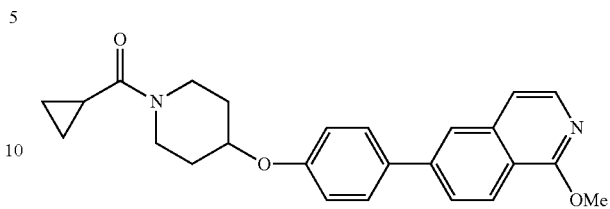

This example was synthesized from 1-methoxy-6-[4-(piperidin-4-yloxy)-phenyl]-isoquinoline (0.09 g, 0.27 mmol) and cyclopropanecarbonyl chloride (40 uL, 0.4 mmol) analogous manner to Example 396. Product isolated as a solid (0.03 g, 29%). Analysis: LCMS m/z=403 (M+1). ¹H NMR (DMSO-d6) δ: 8.21 (d, 1H, J=8.7 Hz), 8.13 (s, 1H), 8.02 (d, 1H, J=5.8 Hz), 7.92 (m, 1H), 7.79 (d, 2H, J=8.7 Hz), 7.43 (d, 1H, J=5.7 Hz), 7.15 (d, 2H, J=8.7 Hz), 4.73 (m, 1H), 4.07 (s, 3H), 3.98 (m, 1H), 3.88 (m, 1H), 3.56 (m, 1H), 3.29 (m, 1H), 2.00 (br m, 3H), 1.55-1.64 (br m, 2H), 0.71 (m, 4H).

Example 436. {4-[4-(3-Aminoisoquinolin-6-yl)-phenoxy]-piperidin-1-yl}-(R)-tetrahydro-furan-2-yl-methanone

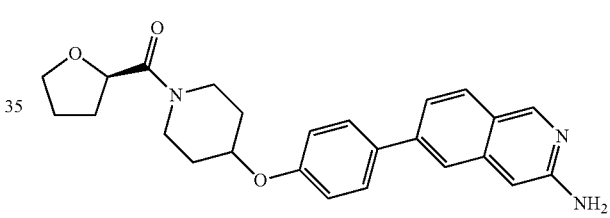

Step 1

To 4-[4-(4,4,5,5-tetramethyl-1,3,2-dioxaborolan-2-yl)phenoxy]piperidine (0.09 g, 0.3 mmol) in DMF (3 mL) was added HATU (0.17 g, 0.44 mmol), DIPEA (0.15 mL, 0.88 mmol), followed by (R)-tetrahydrofuran-2-carboxylic acid (0.05 mL, 0.59 mmol) and was stirred at RT for 1 h. The solution was poured into ethyl acetate, washed with 1N sodium carbonate/brine, dried over sodium sulfate, and concentrated. [(2R)-tetrahydrofuran-2-yl]-[4-[4-(4,4,5,5-tetramethyl-1,3,2-dioxaborolan-2-yl)phenoxy]-1-piperidyl]methanone was isolated (0.05 g, 46%). Analysis: LCMS m/z=402 (M+1).

Step 2

To an oven dried schlenck flask was added [(2R)-tetrahydrofuran-2-yl]-[4-[4-(4,4,5,5-tetramethyl-1,3,2-dioxaborolan-2-yl)phenoxy]-1-piperidyl]methanone (0.11 g, 0.26 mmol), 6-bromoisoquinolin-3-ylamine (0.09 g, 0.39 mmol), tetrakis(triphenylphosphine)palladium(0) (0.03 g, 0.03 mmol), 1N Na₂CO₃ (0.79 mL, 0.79 mmol), followed by 1,4-dioxane (2 mL) and was degassed under an atmosphere of argon for 5 min and was heated at 99° C. for 2 h. The reaction was cooled, filtered through a pad of celite, washed with 1N Na₂CO₃/water/brine, dried over sodium sulfate, and concentrated. The product was purified using the Gilson (0.1% TFA in water/0.1% TFA in acetonitrile gradient), diluted clean fractions with DCM, washed with 1N Na₂CO₃/brine, dried over sodium sulfate, and concentrated. {4-[4-(3-aminoisoquinolin-6-yl)-phenoxy]-piperidin-1-yl}-(R)-tetrahydrofuran-2-yl-methanone was isolated as a solid (0.04 g, 34%). Analysis: LCMS m/z=403 (M+1). ¹H NMR (DMSO-d6) δ: 8.78 (s, 1H), 7.84 (d, 1H, J=8.6 Hz), 7.70 (m, 3H), 7.44 (m, 2H), 7.11 (m, 2H), 6.65 (s, 1H), 5.91 (s, 2H), 4.68 (m, 2H), 3.76 (m, 4H), 3.41 (m, 1H), 3.29 (m, 1H), 2.01 (br m, 4H), 1.84 (m, 2H) 1.51-1.65 (br m, 2H).

Example 437. {4-[4-(3-Methylisoquinolin-6-yl)-phenoxy]-piperidin-1-yl}-(R)-tetrahydro-furan-2-yl-methanone

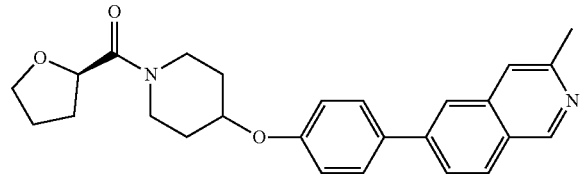 [SMILES: Cc1cc2cc(-c3ccc(OC4CCN(C(=O)[C@H]5CCCO5)CC4)cc3)ccc2cn1]

This example was synthesized from 3-methyl-6-[4-(piperidin-4-yloxy)-phenyl]-isoquinoline (0.14 g, 0.43 mmol) and (R)-tetrahydrofuran-2-carboxylic acid (0.08 mL, 0.86 mmol) in an analogous manner to Example 418. Product isolated as a solid (0.06 g, 30%). Analysis: LCMS m/z=417 (M+1). ¹H NMR (DMSO-d₆) δ: 9.20 (s, 1H), 8.12 (d, 1H, J=8.6 Hz), 8.07 (s, 1H), 7.90 (m, 1H), 7.78 (m, 2H), 7.66 (s, 1H), 7.15 (d, 2H, J=8.8 Hz), 4.69 (m, 2H), 3.73-3.80 (m, 4H), 3.37 (m, 1H), 3.30 (m, 1H), 2.61 (s, 3H), 2.00 (br m, 4H), 1.84 (m, 2H), 1.53-1.65 (br m, 2H).

Example 438. {4-[4-(1-Ethylisoquinolin-6-yl)-phenoxy]-piperidin-1-yl}-(R)-tetrahydro-furan-2-yl-methanone, HCl

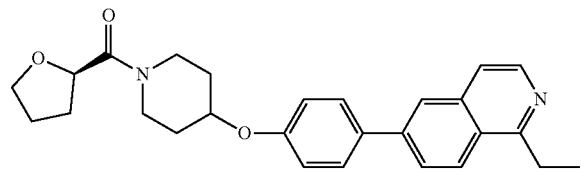 [SMILES: CCc1nccc2cc(-c3ccc(OC4CCN(C(=O)[C@H]5CCCO5)CC4)cc3)ccc12]

Step 1

4-[4-(1-Ethylisoquinolin-6-yl)-phenoxy]-piperidine-1-carboxylic acid t-butyl ester was prepared from 4-[4-(1-chloroisoquinolin-6-yl)-phenoxy]-piperidine-1-carboxylic acid tert-butyl ester (0.12 g, 0.26 mmol) and ethyl boronic acid (0.1 g, 1.31 mmol) in an analogous manner to Example 425 step 2. Product isolated as a solid. Analysis: LCMS m/z=433 (M+1).

Step 2

1-Ethyl-6-[4-(piperidin-4-yloxy)-phenyl]-isoquinoline was prepared from the Step 1 product and TFA (0.8 mL) in an analogous manner to Example 378. Product isolated as a solid. Analysis: LCMS m/z=333 (M+1).

Step 3

The title compound was prepared from the Step 2 product (42 mg, 0.13 mmol) and (R)-tetrahydrofuran-2-carboxylic acid (24 uL, 0.25 mmol) in an analogous manner to Example 424. Product isolated as a solid (0.04 g, 59%). Analysis: LCMS m/z=431 (M+1). ¹H NMR (DMSO-d6) δ: 8.65 (d, 1H, J=9.0 Hz), 8.54 (s, 1H), 8.48 (d, 1H, J=6.4 Hz), 8.31 (d, 1H, J=8.0 Hz), 8.24 (d, 1H, J=6.0 Hz), 7.94 (d, 2H, J=8.8 Hz), 7.22 (d, 2H, J=8.8 Hz), 4.78 (m, 1H), 4.69 (m, 1H), 3.77 (m, 4H), 3.54 (m, 2H), 3.35 (m, 1H), 3.26 (m, 1H), 2.00 (br m, 4H), 1.84 (m, 2H), 1.50-1.66 (br m, 2H), 1.43 (t, 3H, J=7.5 Hz).

Example 439. 1-{4-[4-(1-Cyclopropyl-isoquinolin-6-yl)-phenoxy]-piperidin-1-yl}-propan-1-one

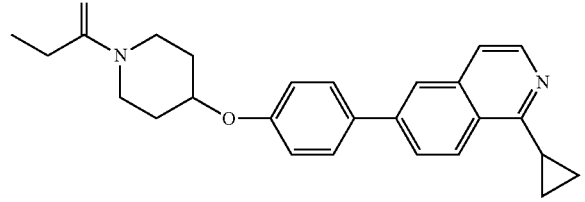

Step 1. 4-[4-(1-Cyclopropylisoquinolin-6-yl)-phenoxy]-piperidine-1-carboxylic acid tert-butyl ester was prepared from 4-[4-(1-chloroisoquinolin-6-yl)-phenoxy]-piperidine-1-carboxylic acid tert-butyl ester (0.24 g, 0.55 mmol) and cyclopropyl boronic acid (0.24 g, 2.76 mmol) in an analogous manner to Example 425 step 2. Product isolated as a solid (0.15 g, 61%). Analysis: LCMS m/z=445 (M+1)

Step 2

1-Cyclopropyl-6-[4-(piperidin-4-yloxy)-phenyl]-isoquinoline was prepared from the Step 1 product (0.15 g, 0.33 mmol) and TFA (2 mL) in an analogous manner to Ex. 378. Product isolated as a solid (0.12 g, 100%). Analysis: LCMS m/z=345 (M+1).

Step 3

The title compound was prepared from 1-cyclopropyl-6-[4-(piperidin-4-yloxy)-phenyl]-isoquinoline (59 mg, 0.17 mmol) and propanoyl chloride (20 uL, 0.3 mmol) in an analogous manner to Example 379. Product isolated as a solid (0.03 g, 48%). Analysis: LCMS m/z=401 (M+1). ¹H NMR (DMSO-d6) δ: 8.56 (d, 1H, J=9.0 Hz), 8.31 (d, 1H, J=5.6 Hz), 8.17 (s, 1H), 7.99 (m, 1H), 7.82 (m, 2H), 7.61 (d, 1H, J=5.6 Hz), 7.16 (m, 2H), 4.71 (m, 1H), 3.87 (m, 1H), 3.69 (m, 1H), 3.36 (m, 1H), 3.27 (m, 1H), 2.94 (m, 1H), 2.35 (m, 2H), 1.98 (br m, 2H), 1.53-1.65 (br m, 2H), 1.07-1.15 (m, 4H), 1.00 (t, 3H, J=7.4 Hz).

Example 440. {4-[4-(1-Cyclopropylisoquinolin-6-yl)-phenoxy]-piperidin-1-yl}-(R)-tetrahydrofuran-2-yl-methanone

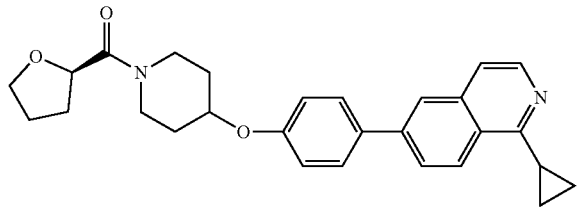 [SMILES: O=C([C@H]1CCCO1)N1CCC(Oc2ccc(-c3ccc4c(C5CC5)nccc4c3)cc2)CC1]

This example was synthesized from 1-cyclopropyl-6-[4-(piperidin-4-yloxy)-phenyl]-isoquinoline (59 mg, 0.17 mmol) and (R)-tetrahydrofuran-2-carboxylic acid (33 uL, 0.34 mmol) in an analogous manner to Example 418. Product isolated as a solid (0.05 g, 62%). Analysis: LCMS m/z=443 (M+1). $^1$H NMR (DMSO-d6) δ: 8.56 (d, 1H, J=9.0 Hz), 8.31 (d, 1H, J=5.6 Hz), 8.17 (s, 1H), 7.99 (m, 1H), 7.82 (m, 2H), 7.61 (d, 1H, J=5.6 Hz), 7.16 (m, 2H), 4.69 (m, 2H), 3.77 (br m, 4H), 3.36 (m, 1H), 3.29 (m, 1H), 2.94 (m, 1H), 2.01 (br m, 4H), 1.84 (m, 2H), 1.53-1.66 (br m, 2H), 1.07-1.15 (br m, 4H)

Example 441. 1-{4-[4-(7-Methoxy-6-methylquinolin-3-yl)-phenoxy]-piperidin-1-yl}-propan-1-one

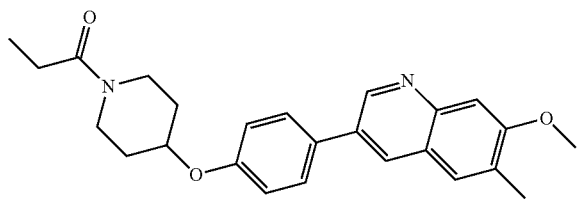 [SMILES: CCC(=O)N1CCC(Oc2ccc(-c3cnc4cc(OC)c(C)cc4c3)cc2)CC1]

Step 1

4-[4-(7-Methoxy-6-methylquinolin-3-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid tert-butyl ester (0.5 g, 1.24 mmol) and 3-bromo-7-methoxy-6-methylquinoline (469 mg, 1.86 mmol) in an analogous manner to Example 378. Product isolated as a solid (0.56 g, 100%). LCMS m/z=449 (M+1).

Step 2

The Step 1 product (0.56 g, 1.27 mmol) was dissolved in DCM (6 mL), TFA (2 mL) was added dropwise and the reaction was stirred at rt for 1 h and concentrated. The product was partitioned between DCM/1N sodium carbonate, washed with brine, dried over sodium sulfate, and concentrated. The product was dissolved DCM, 2M of hydrogen chloride in diethyl ether (1.24 mL, 2.48 mmol) was added and concentrated. 4-[4-(7-Methoxy-6-methyl-quinolin-3-yl)-phenoxy]-piperidine 2HCl was isolated as a solid (419 mg 78%). Analysis: LCMS m/z=349 (M+1).

Step 3

The title compound was prepared from the step 2 product (90 mg, 0.2 mmol) and propanoyl chloride (30 uL, 0.4 mmol) in an analogous manner to Example 396. Product isolated as a solid (0.05 g, 50%). Analysis: LCMS m/z=405 (M+1). $^1$H NMR (DMSO-d6) δ: 9.06 (d, 1H, J=2.3 Hz), 8.37 (d, 1H, J=2.3 Hz), 7.75 (m, 3H), 7.36 (s, 1H), 7.14 (d, 2H, J=8.7 Hz), 4.70 (m, 1H), 3.96 (s, 3H), 3.87 (m, 1H), 3.69 (m, 1H), 3.36 (m, 1H), 3.29 (m, 1H), 2.35 (m, 5H), 1.97 (br m, 2H), 1.52-1.64 (br m, 2H), 0.99 (t, 3H, J=7.4 Hz).

Example 442. Cyclopropyl-{4-[4-(7-methoxy-6-methylquinolin-3-yl)-phenoxy]-piperidin-1-yl}-methanone

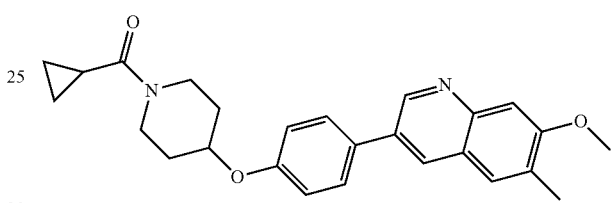

This example was synthesized from 4-[4-(7-methoxy-6-methylquinolin-3-yl)-phenoxy]-piperidine, 2HCl (90 mg, 0.2 mmol) and cyclopropanecarbonyl chloride (30 uL, 0.4 mmol) in an analogous manner to Example 396. Product isolated as a solid (0.06 g, 70%). Analysis: LCMS m/z=417 (M+1). $^1$H NMR (DMSO-d6) δ: 9.06 (d, 1H, J=2.3 Hz), 8.37 (d, 1H, J=2.2 Hz), 7.75 (m, 3H), 7.36 (s, 1H), 7.14 (d, 2H, J=8.7 Hz), 4.72 (m, 1H), 4.14 (m, 1H), 3.96 (s, 3H), 3.90 (m, 1H), 3.36 (m, 1H), 3.29 (m, 1H), 2.35 (s, 3H), 2.00 (br m, 3H), 1.55-1.64 (br m, 2H), 0.71 (m, 4H).

Example 443. {4-[4-(7-Methoxy-6-methylquinolin-3-yl)-phenoxy]-piperidin-1-yl}-(R)-tetrahydrofuran-2-yl-methanone

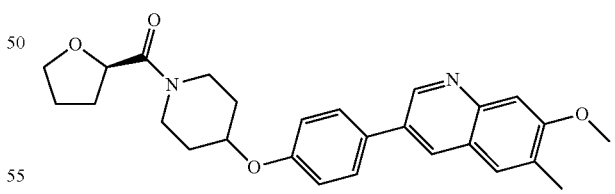

This example was synthesized from 4-[4-(7-methoxy-6-methylquinolin-3-yl)-phenoxy]-piperidine 2HCl (90 mg, 0.2 mmol) and (R)-tetrahydrofuran-2-carboxylic acid (41 uL, 0.43 mmol) in an analogous manner to Example 418. Product isolated as a solid (0.06 g, 60%). Analysis: LCMS m/z=447 (M+1). $^1$H NMR (DMSO-d6) δ: 9.06 (d, 1H, J=2.3 Hz), 8.37 (d, 1H, J=2.2 Hz), 7.75 (m, 3H), 7.36 (s, 1H), 7.14 (d, 2H, J=8.7 Hz), 4.69 (m, 2H), 3.96 (s, 3H), 3.77 (m, 4H), 3.42 (m, 1H), 3.29 (m, 1H), 2.35 (s, 3H), 2.01 (br m, 4H), 1.84 (m, 2H), 1.52-1.66 (br m, 2H).

Example 444. 1-{4-[4-(6-Fluoro-7-methoxyquinolin-3-yl)-phenoxy]-piperidin-1-yl}-propan-1-one

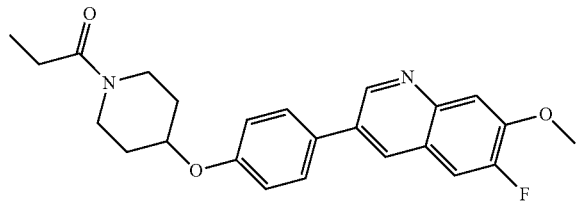

Step 1

4-[4-(6-Fluoro-7-methoxyquinolin-3-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 3-bromo-6-fluoro-7-methoxyquinoline (476 mg, 1.86 mmol) in an analogous manner to Example 378. Product isolated as a solid (0.5 g, 88%). Analysis: LCMS m/z=453 (M+1).

Step 2

6-Fluoro-7-methoxy-3-[4-(piperidin-4-yloxy)-phenyl]-quinoline was prepared from the Step 1 product (0.5 g, 1.1 mmol) and TFA (2 mL) in an analogous manner to Ex. 378. Product isolated as a solid (0.36 g, 93%). Analysis: LCMS m/z=353 (M+1).

Step 3

The title compound was prepared from the Step 2 product above (90 mg, 0.2 mmol) and propanoyl chloride (40 uL, 0.4 mmol) in an analogous manner to Example 396. Product isolated as a solid. Analysis: LCMS m/z=409 (M+1). $^1$H NMR (DMSO-d6) δ: 9.13 (d, 1H, J=2.2 Hz), 8.47 (d, 1H, J=2.2 Hz), 7.76 (m, 3H), 7.60 (d, 1H, J=8.4 Hz), 7.14 (m, 2H), 4.71 (m, 1H), 4.02 (s, 3H), 3.90 (m, 1H), 3.69 (m, 1H), 3.36 (m, 1H), 3.29 (m, 1H), 2.35 (m, 2H), 2.07 (br m, 2H), 1.52-1.64 (br m, 2H), 0.99 (t, 3H, J=7.4 Hz).

Example 445. Cyclopropyl-{4-[4-(6-fluoro-7-methoxyquinolin-3-yl)-phenoxy]-piperidin-1-yl}-methanone

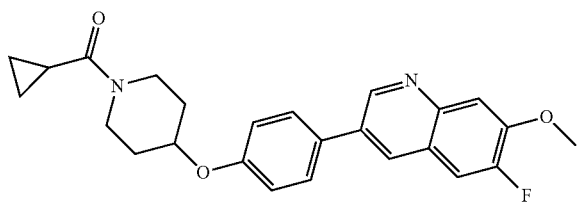 [SMILES: COc1cc2ncc(-c3ccc(OC4CCN(C(=O)C5CC5)CC4)cc3)cc2cc1F]

This example was synthesized from 6-fluoro-7-methoxy-3-[4-(piperidin-4-yloxy)-phenyl]-quinoline (90 mg, 0.2 mmol) and cyclopropanecarbonyl chloride (40 uL, 0.4 mmol) in an analogous manner to Example 396. Product isolated as a solid (0.06 g, 60%). Analysis: LCMS m/z=421 (M+1). $^1$H NMR (DMSO-d6) δ: 9.13 (d, 1H, J=2.2 Hz), 8.47 (d, 1H, J=2.2 Hz), 7.76 (m, 3H), 7.60 (d, 1H, J=8.4 Hz), 7.14 (m, 2H), 4.73 (m, 1H), 4.02 (s, 3H), 4.00 (m, 1H), 3.88 (m, 1H), 3.57 (m, 1H), 3.29 (m, 1H), 2.00 (br m, 3H), 1.54-1.65 (br m, 2H), 0.71 (m, 4H).

Example 446. {4-[4-(6-Fluoro-7-methoxyquinolin-3-yl)-phenoxy]-piperidin-1-yl}-(R)-tetrahydrofuran-2-yl-methanone

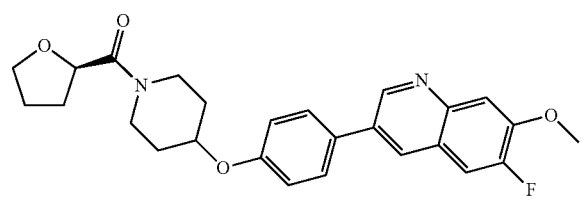

This example was synthesized from 6-fluoro-7-methoxy-3-[4-(piperidin-4-yloxy)-phenyl]-quinoline (90 mg, 0.2 mmol) and (R)-tetrahydrofuran-2-carboxylic acid (49 uL, 0.51 mmol) in an analogous manner to Example 418. Product isolated as a solid (0.04 g, 30%). Analysis: LCMS m/z=451 (M+1). $^1$H NMR (DMSO-d$_6$) δ: 9.13 (d, 1H, J=2.2 Hz), 8.47 (d, 1H, J=2.2 Hz), 7.76 (m, 3H), 7.60 (d, 1H, J=8.4 Hz), 7.14 (m, 2H), 4.69 (m, 2H), 4.02 (s, 3H), 3.77 (br m, 4H), 3.43 (m, 1H), 3.25 (m, 1H), 2.01 (br m, 4H), 1.84 (m, 2H), 1.51-1.66 (br m, 2H).

Example 447. 1-{4-[4-(6-Chloro-7-methoxyquinolin-3-yl)-phenoxy]-piperidin-1-yl}-propan-1-one

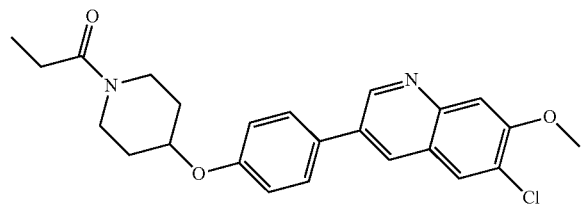 [SMILES: CCC(=O)N1CCC(Oc2ccc(-c3cnc4cc(OC)c(Cl)cc4c3)cc2)CC1]

Step 1

4-[4-(6-Chloro-7-methoxyquinolin-3-yl)-phenoxy]-piperidine-1-carboxylic acid tert-butyl ester was prepared from 4-[4-(4,4,5,5-tetramethyl-1,3,2-dioxaborolan-2-yl)-phenoxy]-piperidine-1-carboxylic acid tert-butyl ester (0.5 g, 1.24 mmol) and 3-bromo-6-chloro-7-methoxy-quinoline (338 mg, 1.24 mmol) in an analogous manner to Example 378. Product isolated as a solid (0.5 g, 86%). Analysis: LCMS m/z=469 (M+1).

Step 2

4-[4-(6-Chloro-7-methoxyquinolin-3-yl)-phenoxy]-piperidine 2HCl was prepared from the step 1 product above (0.5 g, 1.06 mmol) and TFA (2 mL) in an analogous manner to Example 441 step 2. Product isolated as a solid (0.4 g, 85%). Analysis: LCMS m/z=369 (M+1).

Step 3

The title compound was prepared from the step 2 product above (90 mg, 0.2 mmol) and propanoyl chloride (30 uL, 0.4 mmol) in an analogous manner to Example 396. Product isolated as a solid (0.05 g, 50%). Analysis: LCMS m/z=425 (M+1). ¹H NMR (DMSO-d6) δ: 9.17 (d, 1H, J=2.4 Hz), 8.48 (d, 1H, J=2.3 Hz), 8.17 (s, 1H), 7.76 (m, 2H), 7.57 (s, 1H), 7.16 (m, 2H), 4.71 (m, 1H), 4.03 (s, 3H), 3.88 (m, 1H), 3.73 (m, 1H), 3.35 (m, 1H), 3.29 (m, 1H), 2.33 (m, 2H), 1.98 (br m, 2H), 1.52-1.64 (br m, 2H), 0.99 (t, 3H, J=7.4 Hz).

Example 448. {4-[4-(6-Chloro-7-methoxyquinolin-3-yl)-phenoxy]-piperidin-1-yl}-cyclopropylmethanone

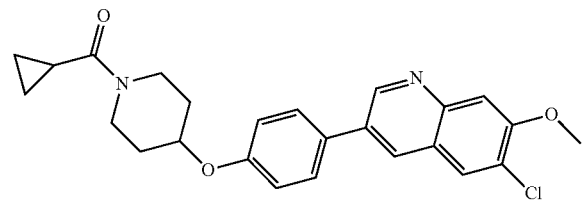 [SMILES: COc1cc2ncc(-c3ccc(OC4CCN(C(=O)C5CC5)CC4)cc3)cc2cc1Cl]

This example was synthesized from 4-[4-(6-chloro-7-methoxy-quinolin-3-yl)-phenoxy]-piperidine 2HCl (90 mg, 0.2 mmol) and cyclopropanecarbonyl chloride (30 uL, 0.4 mmol) in an analogous manner to Example 396. Product isolated as a solid (0.06 g, 60%). Analysis: LCMS m/z=437 (M+1). ¹H NMR (DMSO-d6) δ: 9.17 (d, 1H, J=2.4 Hz), 8.48 (d, 1H, J=2.3 Hz), 8.17 (s, 1H), 7.76 (m, 2H), 7.57 (s, 1H), 7.16 (m, 2H), 4.73 (m, 1H), 4.03 (s, 3H), 3.89 (m, 2H), 3.56 (m, 1H), 3.29 (m, 1H), 2.00 (br m, 3H), 1.55-1.64 (br m, 2H), 0.71 (m, 4H).

Example 449. {4-[4-(6-Chloro-7-methoxyquinolin-3-yl)-phenoxy]-piperidin-1-yl}-(R)-tetrahydrofuran-2-yl-methanone

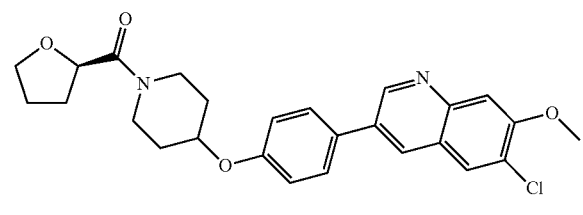 [SMILES: COc1cc2ncc(-c3ccc(OC4CCN(C(=O)[C@H]5CCCO5)CC4)cc3)cc2cc1Cl]

This example was synthesized from 4-[4-(6-chloro-7-methoxyquinolin-3-yl)-phenoxy]-piperidine 2HCl (90 mg, 0.2 mmol) and (R)-tetrahydrofuran-2-carboxylic acid (41 uL, 0.43 mmol) in an analogous manner to Example 418. Product isolated as a solid (0.05 g, 50%). Analysis: LCMS m/z=467 (M+1). ¹H NMR (DMSO-d6) δ: 9.17 (d, 1H, J=2.4 Hz), 8.48 (d, 1H, J=2.3 Hz), 8.17 (s, 1H), 7.76 (m, 2H), 7.57 (s, 1H), 7.16 (m, 2H), 4.73 (m, 1H), 4.03 (s, 3H), 3.87 (m, 4H), 3.36 (m, 1H), 3.29 (m, 1H), 2.01 (m, 4H), 1.84 (m, 2H), 1.52-1.66 (br m, 2H).

Example 450. {4-[4-(6-Methoxyquinolin-3-yl)-phenoxy]-piperidin-1-yl}-(R)-tetrahydro-furan-2-yl-methanone, HCl

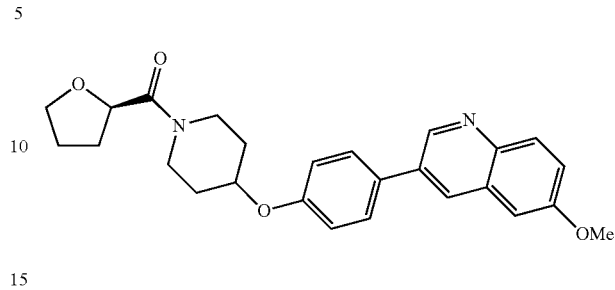

Step 1

4-[4-(6-Methoxyquinolin-3-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 3-bromo-6-methoxy-quinoline (295 mg, 1.24 mmol) in an analogous manner to Example 378. Product isolated as a solid (0.52 g, 96%). Analysis: LCMS m/z=435 (M+1).

Step 2

4-[4-(6-Methoxyquinolin-3-yl)-phenoxy]-piperidine 2HCl was prepared from the Step 1 product above (0.52 g, 1.2 mmol) and TFA (2 mL) in an analogous manner to Ex. 441 step 2. Product isolated as a solid (0.39 g, 80%). Analysis: LCMS m/z=335 (M+1).

Step 3

The title compound was prepared from the Step 2 product above (90 mg, 0.2 mmol) and (R)-tetrahydrofuran-2-carboxylic acid (41 uL, 0.43 mmol) in an analogous manner to Example 424. Product isolated as a solid (0.07 g, 60%). Analysis: LCMS m/z=433 (M+1). ¹H NMR (DMSO-d6) δ: 9.26 (d, 1H, J=1.8 Hz), 8.86 (s, 1H), 8.08 (d, 1H, J=10.0 Hz), 7.88 (d, 2H, J=8.8 Hz), 7.55 (m, 2H), 7.21 (d, 2H, J=8.8 Hz), 4.75 (m, 1H), 4.69 (m, 1H), 3.95 (s, 3H), 3.77 (br m, 4H), 3.23-3.48 (br m, 2H), 1.99 (br m, 4H), 1.84 (m, 2H), 1.52-1.67 (br m, 2H).

Example 451. {4-[4-(3-Isopropoxyisoquinolin-6-yl)-phenoxy]-piperidin-1-yl}-(R)-tetrahydrofuran-2-yl-methanone

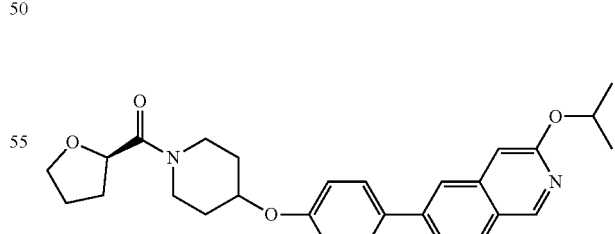

Step 1

To 6-bromoisoquinolin-3-ol (0.5 g, 2.23 mmol) in DMF (4 mL) under a nitrogen atmosphere was added cesium carbonate (2.18 g, 6.69 mmol), followed by isopropyl iodide (0.22 mL, 2.23 mmol) and the reaction was heated at 80° C.

for 2 h. The reaction was cooled at RT, diluted with EtOAc, washed with water several times, washed with brine, dried over Na$_2$SO$_4$, and concentrated. The product was purified via silica gel chromatography (5% EtOAc/hexanes) and concentrated. 6-Bromo-3-isopropoxyisoquinoline was isolated as a solid (0.2 g, 33%). Analysis: LCMS m/z=267 (M+1).

Step 2

4-[4-(3-Isopropoxy-isoquinolin-6-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.25 g, 0.61 mmol) and 6-bromo-3-isopropoxy-isoquinoline (195 mg, 0.73 mmol) in an analogous manner to Example 378. Product isolated as a solid (0.25 g, 89%). Analysis: LCMS m/z=463 (M+1).

Step 3

3-Isopropoxy-6-[4-(piperidin-4-yloxy)-phenyl]-isoquinoline was prepared from the Step 2 product above (0.25 g, 0.54 mmol) and TFA (1 mL) in an analogous manner to Example 378 step 2. Product isolated as a solid (0.19 g, 98%). Analysis: LCMS m/z=363 (M+1).

Step 4

{4-[4-(3-Isopropoxyisoquinolin-6-yl)-phenoxy]-piperidin-1-yl}-(R)-tetrahydro-furan-2-yl-methanone was prepared from the Step 3 product above (90 mg, 0.2 mmol and (R)-tetrahydrofuran-2-carboxylic acid (27 uL, 0.28 mmol) in an analogous manner to Example 418. isolated as a solid (0.08 g, 60%). Analysis: LCMS m/z=461 (M+1). $^1$H NMR (DMSO-d6) δ: 8.99-9.06 (m, 1H), 8.02-8.09 (m, 1H), 7.98-8.02 (m, 1H), 7.68-7.79 (m, 3H), 7.11-7.17 (m, 3H), 5.25-5.34 (m, 1H), 4.64-4.78 (m. 2H), 3.69-3.86 (m, 4H), 3.33-3.38 (m, 1H), 3.20-3.29 (m, 1H), 1.89-2.13 (m, 4H), 1.75-1.88 (m, 2H), 1.44-1.70 (m, 2H), 1.34 (d, 6H, J=6.3 Hz)

Example 452. {4-[4-(1-Morpholin-4-yl-isoquinolin-6-yl)-phenoxy]-piperidin-1-yl}-(R)-tetrahydrofuran-2-yl-methanone

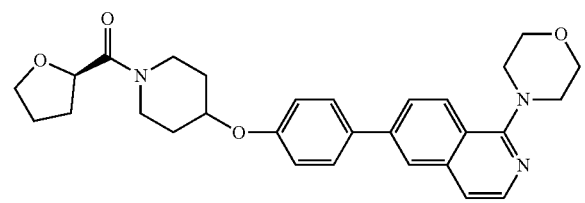 [SMILES: O=C([C@H]1CCCO1)N1CCC(Oc2ccc(-c3ccc4c(N5CCOCC5)nccc4c3)cc2)CC1]

Step 1

To an oven dried flask under an atmosphere of argon was added 4-[4-(1-chloro-isoquinolin-6-yl)-phenoxy]-piperidine-1-carboxylic acid t-butyl ester (0.2 g, 0.46 mmol), morpholine (0.08 mL, 0.91 mmol), cinnamylpalladium chloride dimer (24 mg, 0.046 mmol), di(1-adamantyl)-2-dimethylaminophenylphosphine (38 mg, 0.09 mmol), sodium t-butoxide (0.13 g, 1.37 mmol), followed by toluene (10 mL) and the reaction was degassed 3× under an atmosphere of argon and was stirred at 99° C. overnight. The reaction was cooled at rt, diluted with DCM, filtered through a pad of celite, washed with water/brine, dried over sodium sulfate, and concentrated. The product was purified via silica gel chromatography (10-30-50% ethyl acetate/hexanes) and concentrated. 4-[4-(1-Morpholin-4-yl-isoquinolin-6-yl)-phenoxy]-piperidine-1-carboxylic acid tert-butyl ester was isolated as a solid (0.1 g, 43%). Analysis: LCMS m/z=490 (M+1).

Step 2

1-Morpholin-4-yl-6-[4-(piperidin-4-yloxy)-phenyl]-isoquinoline was prepared from the Step 1 product above (0.1 g, 0.2 mmol) and TFA (1 mL) in an analogous manner to Example 378. Product isolated as a solid (0.07 g, 88%). Analysis: LCMS m/z=390 (M+1).

Step 3

The title compound was prepared from the Step 2 product above (67 mg, 0.17 mmol) and (R)-tetrahydrofuran-2-carboxylic acid (18 uL, 0.19 mmol) in an analogous manner to Example 418. Product isolated as a solid (0.06 g, 72%). Analysis: LCMS m/z=488 (M+1). $^1$H NMR (DMSO-d6) δ: 8.12 (m, 3H), 7.89 (m, 1H), 7.78 (d, 2H, J=8.7 Hz), 7.45 (d, 1H, J=5.8 Hz), 7.15 (d, 2H, J=8.7 Hz), 4.69 (m, 2H), 3.86 (m, 4H), 3.76 (m, 4H), 3.22-3.45 (br m, 6H), 2.01 (br m, 4H), 1.84 (m, 2H), 1.54-1.65 (br m, 2H).

Example 453. {4-[4-(1-Dimethylaminoisoquinolin-6-yl)-phenoxy]-piperidin-1-yl}-(R)-tetrahyrofuran-2-yl methananone, HCl

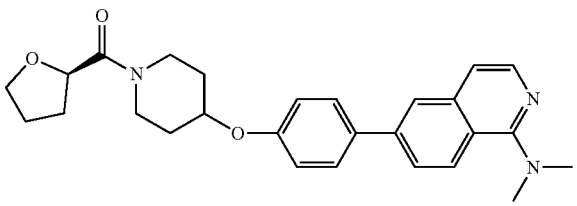 [SMILES: CN(C)c1nccc2cc(-c3ccc(OC4CCN(C(=O)[C@H]5CCCO5)CC4)cc3)ccc12]

Step 1

4-[4-(1-Dimethylaminoisoquinolin-6-yl)-phenoxy]-piperidine-1-carboxylic acid t-butyl ester was prepared from 4-[4-(1-chloroisoquinolin-6-yl)-phenoxy]-piperidine-1-carboxylic acid t-butyl ester (0.2 g, 0.46 mmol) and 2M dimethylamine in THF (0.46 mL, 0.91 mmol) in an analogous manner to Example 673a. Product isolated as a solid (0.1 g, 52%). Analysis: LCMS m/z=448 (M+1).

Step 2

Dimethyl-{6-[4-(piperidin-4-yloxy)-phenyl]-isoquinolin-1-yl}-amine was prepared from the Step 1 product above (0.1 g, 0.24 mmol) and TFA (1 mL) in an analogous manner to Example 599b. Product isolated as a solid (0.06 g, 67%). LCMS m/z=348 (M+1).

Step 3

The title compound was prepared the Step 2 product above (55 mg, 0.16 mmol) and (R)-tetrahydrofuran-2-carboxylic acid (17 uL, 0.17 mmol) in an analogous manner to Example 645. Product isolated as a solid (0.04 g, 52%). Analysis: LCMS m/z=446 (M+1). $^1$H NMR (DMSO-d6) δ: 12.84 (br s, 1H), 8.43 (d, 1H, J=9.0 Hz), 8.28 (s, 1H), 8.02 (m, 1H), 7.87 (d, 2H, J=8.8 Hz), 7.75 (d, 1H, J=6.3 Hz), 7.41 (d, 1H, J=6.6 Hz), 7.19 (d, 2H, J=8.8 Hz), 4.75 (m, 1H), 4.69 (m, 1H), 3.76 (br m, 4H), 3.44 (s, 3H), 3.41 (s, 3H), 3.33 (m, 1H), 3.25 (m, 1H), 1.99 (br m, 4H), 1.84 (m, 2H), 1.52-1.68 (br m, 2H).

Example 454. {4-[4-(1-Aminoisoquinolin-6-yl)-phenoxy]-piperidin-1-yl}-(R)-tetrahydro-furan-2-yl-methanone

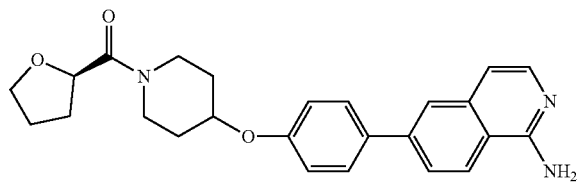 [SMILES: Nc1nccc2cc(-c3ccc(OC4CCN(C(=O)[C@H]5CCCO5)CC4)cc3)ccc12]

This example was synthesized from [(2R)-tetrahydro-furan-2-yl]-[4-[4-(4,4,5,5-tetramethyl-1,3,2-dioxaborolan-2-yl)phenoxy]-1-piperidyl]methanone (0.1 g, 0.2 mmol) and 6-bromoisoquinolin-1-ylamine (67 mg, 0.3 mmol) in an analogous manner to Example 436. Product isolated as a solid (0.03 g, 30%). Analysis: LCMS m/z=418 (M+1). $^1$H NMR (DMSO-d6) δ: 8.28 (m, 1H), 7.95 (s, 1H), 7.75 (m, 4H), 7.12 (m, 2H), 6.95 (m, 3H), 4.72 (m, 2H), 3.80 (m, 4H), 3.36 (m, 1H), 3.29 (m, 1H), 1.99 (br m, 4H), 1.82 (m, 2H), 1.60 (br m, 2H).

Example 455. {4-[4-(1-Dimethylaminoisoquinolin-6-yl)-phenoxy]-piperidin-1-yl}-(R)-tetrahydrofuran-2-yl-methanone, 2HCL

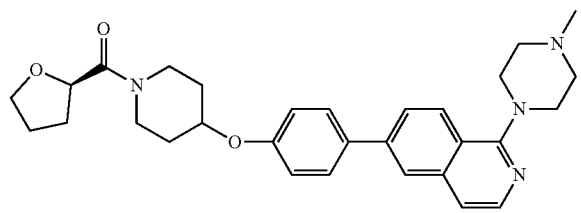 [SMILES: CN1CCN(c2nccc3cc(-c4ccc(OC5CCN(C(=O)[C@H]6CCCO6)CC5)cc4)ccc23)CC1]

Step 1

4-{4-[1-(4-Methylpiperazin-1-yl)-isoquinolin-6-yl]-phenoxy}-piperidine-1-carboxylic acid t-butyl ester was prepared from 4-[4-(1-chloro-isoquinolin-6-yl)-phenoxy]-piperidine-1-carboxylic acid t-butyl ester (0.2 g, 0.46 mmol) and 1-methylpiperazine (0.1 mL, 0.91 mmol) in an analogous manner to Example 452. Product isolated as a solid (0.08 g, 36%). Analysis: LCMS m/z=503 (M+1).

Step 2

The step 1 product above was dissolved in DCM (4 mL), TFA (1 mL) was added dropwise and was stirred at rt for 1 h and concentrated. 1-(4-Methylpiperazin-1-yl)-6-[4-(piperidin-4-yloxy)-phenyl]-isoquinoline di-trifluoroacetate was isolated as the crude product. Analysis: LCMS m/z=403 (M+1).

Step 3

The title compound was prepared from 4-{4-[1-(4-methylpiperazin-1-yl)-isoquinolin-6-yl]-phenoxy}-piperidine tri-trifluoroacetate (14 mg, 0.19 mmol) and (R)-tetrahydrofuran-2-carboxylic acid (20 uL, 0.21 mmol) in an analogous manner to Example 424. Product isolated as a solid (0.04 g, 37%). Analysis: LCMS m/z=501 (M+1). $^1$H NMR (DMSO-d6) δ: 11.13 (br s, 1H), 8.26 (s, 1H), 8.22 (d, 1H, J=8.8 Hz), 8.09 (d, 1H, J=6.0 Hz), 7.98 (m, 1H), 7.83 (d, 2H, J=8.8 Hz), 7.60 (d, 1H, J=6.2 Hz), 7.18 (d, 2H, J=8.8 Hz), 4.69 (m, 2H), 3.25-4.04 (br m, 15H), 2.87 (s, 3H), 2.02 (m, 4H), 1.84 (m, 2H), 1.52-1.66 (br m, 2H).

Example 456. {4-[4-(1-Methylaminoisoquinolin-6-yl)-phenoxy]-piperidin-1-yl}-(R)-tetrahydrofuran-2-yl-methanone

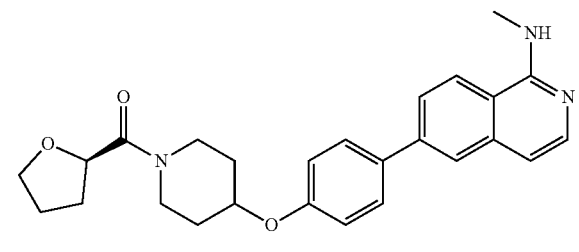 [SMILES: CNc1nccc2cc(-c3ccc(OC4CCN(C(=O)[C@H]5CCCO5)CC4)cc3)ccc12]

Step 1

4-[4-(1-Methylaminoisoquinolin-6-yl)-phenoxy]-piperidine-1-carboxylic acid t-butyl ester was prepared from 4-[4-(1-chloroisoquinolin-6-yl)-phenoxy]-piperidine-1-carboxylic acid t-butyl ester (0.09 g, 0.2 mmol) and 2M methylamine in THF (0.2 mL, 0.4 mmol) in an analogous manner to Example 452. Product isolated as a solid (0.07 g, 80%). Analysis: LCMS m/z=434 (M+1).

Step 2

Methyl-{6-[4-(piperidin-4-yloxy)-phenyl]-isoquinolin-1-yl}-amine was prepared from the Step 1 product above (0.07 g, 0.16 mmol) and TFA (0.5 mL) in an analogous manner to Example 379. Product isolated as a solid (0.05 g, 100%). LCMS m/z=334 (M+1).

Step 3

The title compound was prepared from the Step 2 product above (53 mg, 0.16 mmol) and (R)-tetrahydrofuran-2-carboxylic acid (15 uL, 0.16 mmol) in an analogous manner to Example 418. Product isolated as a solid (0.02 g, 29%). Analysis: LCMS m/z=432 (M+1). $^1$H NMR (DMSO-d6) δ: 8.22 (m, 1H), 8.92 (m, 1H), 7.75 (m, 3H), 7.45 (m, 1H), 7.12 (m, 2H), 6.90 (m, 1H), 4.72 (m, 2H), 3.80 (m, 4H), 3.36 (m, 1H), 3.29 (m, 1H), 2.98 (m, 3H), 2.00 (br m, 4H), 1.85 (m, 2H), 1.52-1.64 (br m, 2H).

Example 457. 1-{4-[4-(4-Methylisoquinolin-6-yl)-phenoxy]-piperidin-1-yl}-propan-1-one HCl

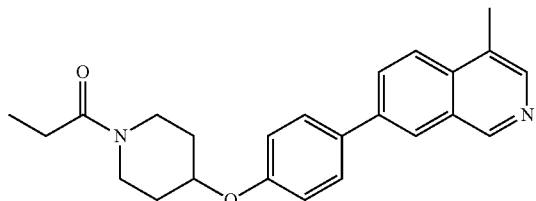

Step 1

4-[4-(4-Methylisoquinolin-6-yl)-phenoxy]-piperidine-1-carboxylic acid tert-butyl ester was prepared from 4-[4-(4,4,5,5-tetramethyl-1,3,2-dioxaborolan-2-yl)-phenoxy]-piperidine-1-carboxylic acid tert-butyl ester (0.5 g, 1.24 mmol) and 6-bromo-4-methyl-isoquinoline (0.33 g, 1.49 mmol) in an analogous manner to Example 378. Product isolated as a solid (0.55 g, 100%). Analysis: LCMS m/z=419 (M+1).

Step 2

4-[4-(4-Methylisoquinolin-6-yl)-phenoxy]-piperidine, 2HCl was prepared from the Step 1 product above (0.55 g, 1.32 mmol) and TFA (1 mL) in an analogous manner to Ex. 662b. Product isolated as a solid (0.39 g, 76%). Analysis: LCMS m/z=319 (M+1).

Step 3

The title compound was prepared from the Step two product above (90 mg, 0.2 mmol) and propanoyl chloride (30 uL, 0.4 mmol) in an analogous manner to Example 619. Product isolated as a solid (0.04 g, 40%). Analysis: LCMS m/z=375 (M+1). $^1$H NMR (DMSO-d6) δ: 9.68 (s, 1H), 8.50-8.62 (m, 2H), 8.42 (s, 1H), 8.27-8.35 (m, 1H), 7.98 (d, 2H, J=8.8 Hz), 7.21 (d, 2H, J=8.8 Hz), 4.66-5.01 (m, 1H), 4.01-4.32 (brm, 1H), 3.79-3.96 (m, 1H), 3.60-3.76 (m, 1H), 3.15-3.40 (m, 2H), 2.82 (s, 3H), 2.35 (d, 2H, J=7.5 Hz), 1.82-2.13 (m, 2H), 1.45-1.77 (m, 2H), 1.00 (t, 3H, J=7.4 Hz).

Example 458

Cyclopropyl-{4-[4-(4-methylisoquinolin-6-yl)-phenoxy]-piperidin-1-yl}-methanone, HCl

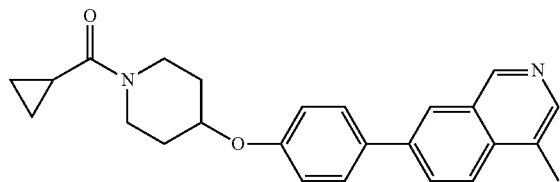 [SMILES: Cc1cncc2cc(-c3ccc(OC4CCN(C(=O)C5CC5)CC4)cc3)ccc12]

This example was synthesized from 4-[4-(4-methylisoquinolin-6-yl)-phenoxy]-piperidine, 2HCl (90 mg, 0.2 mmol) and cyclopropanecarbonyl chloride (40 uL, 0.4 mmol) in an analogous manner to Example 398. Product isolated as a solid (0.06 g, 60%). Analysis: LCMS m/z=387 (M+1). $^1$H NMR (DMSO-d$_6$) δ: 9.67 (s, 1H), 8.49-8.60 (m, 2H), 8.42 (s, 1H), 8.25-8.35 (m, 1H), 7.99 (d, 2H, J=8.8 Hz), 7.22 (d, 2H, J=8.8 Hz), 4.65-4.99 (m, 1H), 3.43-4.17 (m, 4H), 3.18-3.38 (m, 1H), 2.82 (s, 3H), 1.81-2.23 (m, 3H), 1.41-1.79 (m, 2H), 0.52-0.92 (m, 4H).

Example 459. {4-[4-(4-Methylisoquinolin-6-yl)-phenoxy]-piperidin-1-yl}-(R)-tetrahydrofuran-2-yl-methanone, HCl

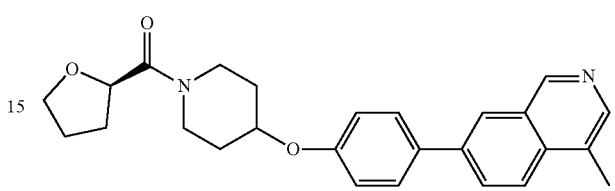

This example was synthesized from 4-[4-(4-methylisoquinolin-6-yl)-phenoxy]-piperidine, 2HCl (90 mg, 0.2 mmol) and (R)-tetrahydrofuran-2-carboxylic acid (0.02 mL, 0.25 mmol) in an analogous manner to Example 424. Product isolated as a solid (0.07 g, 62%). Analysis: LCMS m/z=417 (M+1). $^1$H NMR (DMSO-d6) δ: 9.65 (s, 1H), 8.48-8.59 (m, 2H), 8.40 (s, 1H), 8.32 (m, 1H), 7.98 (d, 2H, J=8.8 Hz), 7.21 (d, 2H, J=8.5 Hz), 4.54-4.87 (m, 2H), 3.52-3.92 (m, 5H), 3.20-3.50 (m, 2H), 2.82 (s, 3H), 1.93-2.18 (m, 4H), 1.73-1.90 (m, 2H), 1.45-1.66 (m, 2H).

Example 460. 1-{4-[4-(5-Methylquinolin-3-yl)-phenoxy]-piperidin-1-yl}-propan-1-one, HCl

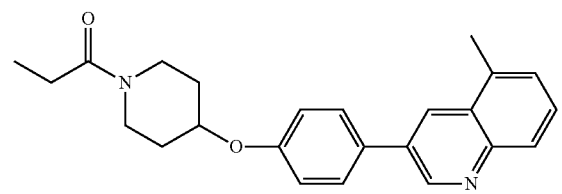 [SMILES: CCC(=O)N1CCC(Oc2ccc(-c3cnc4cccc(C)c4c3)cc2)CC1]

Step 1

4-[4-(5-Chloroquinolin-3-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 3-bromo-5-chloro-quinoline (0.36 g, 1.49 mmol) in an analogous manner to Example 378. Product isolated as a solid. Analysis: LCMS m/z=439 (M+1).

Step 2

4-[4-(5-Methyl-quinolin-3-yl)-phenoxy]-piperidine-1-carboxylic acid t-butyl ester was prepared from the Step 1 product above (0.58 g, 1.32 mmol) and methylboronic acid (396 mg, 6.62 mmol) in an analogous manner to Example 430. Product isolated as a solid. Analysis: LCMS m/z=419 (M+1).

Step 3

4-[4-(5-Methyl-quinolin-3-yl)-phenoxy]-piperidine 2HCl was prepared from the Step 2 product above and TFA (2 mL)

in an analogous manner to Example 441 step 2. Product isolated as a solid. LCMS m/z=319 (M+1).

Step 4

The title compound was prepared from the Step 3 product above (90 mg, 0.2 mmol) and propanoyl chloride (30 uL, 0.4 mmol) in an analogous manner to Example 398. Product isolated as a solid (0.05 g, 50%). Analysis: LCMS m/z=375 (M+1). $^1$H NMR (DMSO-d6) δ: 9.39 (s, 1H), 8.83-8.90 (m, 1H), 8.01 (d, 1H, J=8.8 Hz), 7.93 (d, 2H, J=8.8 Hz), 7.74-7.83 (m, 1H), 7.55-7.64 (m, 1H), 7.20 (d, 2H, J=8.8 Hz), 4.70-4.81 (m, 1H), 4.40 (br m, 1H), 3.82-3.97 (m, 1H), 3.63-3.79 (m, 1H), 3.19-3.47 (m, 2H), 2.80 (s, 3H), 2.28-2.42 (m, 2H), 1.87-2.09 (m, 2H), 1.47-1.72 (m, 2H), 1.00 (t, 3H, J=7.4 Hz).

Example 461. Cyclopropyl-{4-[4-(5-methyl-quinolin-3-yl)-phenoxy]-piperidin-1-yl}-methanone, HCl

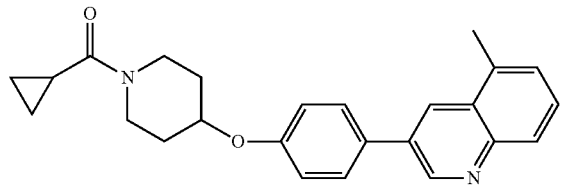 [SMILES: Cc1cccc2ncc(-c3ccc(OC4CCN(C(=O)C5CC5)CC4)cc3)cc12]

This example was synthesized from 4-[4-(5-methylquinolin-3-yl)-phenoxy]-piperidine, 2HCl (90 mg, 0.2 mmol) and cyclopropanecarbonyl chloride (40 uL, 0.4 mmol) in an analogous manner to Example 398. Product isolated as a solid (0.05 g, 50%). Analysis: LCMS m/z=387 (M+1). $^1$H NMR (DMSO-d6) δ: 9.48 (s, 1H), 8.93-9.08 (m, 1H), 8.04-8.13 (m, 1H), 7.97 (d, 2H, J=8.5 Hz), 7.79-7.89 (m, 1H), 7.50-7.72 (m, 1H), 7.23 (d, 2H, J=8.8 Hz), 4.68-4.88 (m, 1H), 3.78-4.09 (m, 2H), 3.53-3.69 (m, 1H), 3.22-3.38 (m, 1H), 2.83 (s, 3H), 1.86-2.17 (m, 3H), 1.46-1.77 (m, 2H), 0.73 (d, 4H, J=8.8 Hz).

Example 462. {4-[4-(5-Methylquinolin-3-yl)-phenoxy]-piperidin-1-yl}-(R)-tetrahydro-furan-2-yl-methanone, HCl

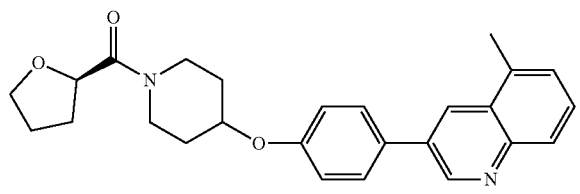 [SMILES: Cc1cccc2ncc(-c3ccc(OC4CCN(C(=O)[C@H]5CCCO5)CC4)cc3)cc12]

This example was synthesized from 4-[4-(5-methylquinolin-3-yl)-phenoxy]-piperidine 2HCl (90 mg, 0.2 mmol) and (R)-tetrahydrofuran-2-carboxylic acid (0.02 mL, 0.25 mmol) in an analogous manner to Example 424. Product isolated as a solid (0.06 g, 53%). Analysis: LCMS m/z=417 (M+1). $^1$H NMR (DMSO-d6) δ: 9.45 (d, 1H, J=1.8 Hz), 8.96 (s, 1H), 8.02-8.10 (m, 1H), 7.96 (d, 2H, J=8.8 Hz), 7.74-7.86 (m, 1H), 7.58-7.70 (m, 1H), 7.21 (d, 2H, J=8.5 Hz), 4.59- 4.84 (m, 2H), 3.76 (d, 4H, J=6.8 Hz), 3.17-3.57 (m, 2H), 2.82 (s, 3H), 1.91-2.15 (m, 4H), 1.76-1.89 (m, 2H), 1.46-1.71 (m, 2H).

Example 463. 1-{4-[4-(5-Methoxyquinolin-3-yl)-phenoxy]-piperidin-1-yl}-propan-1-one, HCl

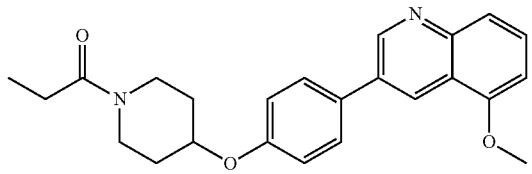 [SMILES: CCC(=O)N1CCC(Oc2ccc(-c3cnc4cccc(OC)c4c3)cc2)CC1]

Step 1

4-[4-(5-Methoxyquinolin-3-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 3-bromo-5-methoxy-quinoline (0.35 g, 1.49 mmol) in an analogous manner to Example 378. Product isolated as a solid. (0.53 g, 100%). Analysis: LCMS m/z=435 (M+1).

Step 2

5-Methoxy-3-[4-(piperidin-4-yloxy)-phenyl]-quinoline 2HCl was prepared from the product of Step 1 above (0.53 g, 1.24 mmol) and TFA (2 mL) in an analogous manner to Example 461. Product isolated as a solid (0.48 g, 95%). LCMS m/z=335 (M+1).

Step 3

The title compound was prepared from the Step 2 product above (90 mg, 0.2 mmol) and propanoyl chloride (30 uL, 0.4 mmol) in an analogous manner to Example 398. Product isolated as a solid (0.05 g, 50%). LCMS m/z=391 (M+1). $^1$H NMR (DMSO) δ: 9.43 (d, 1H, J=2.2 Hz), 8.95 (s, 1H), 7.89 (m, 3H), 7.79 (m, 1H), 7.26 (m, 1H), 7.19 (m, 2H), 4.74 (m, 1H), 4.07 (s, 3H), 3.88 (m, 1H), 3.69 (m, 1H), 3.25-3.39 (br m, 2H), 2.34 (m, 2H), 1.98 (m, 2H), 1.53-1.68 (br m, 2H), 1.00 (t, 3H, J=7.4 Hz).

Example 464. Cyclopropyl-{4-[4-(5-methoxyquinolin-3-yl)-phenoxy]-piperidin-1-yl}-methanone

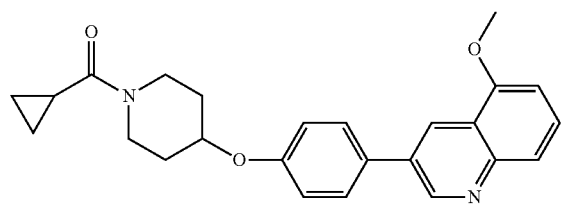 [SMILES: COc1cccc2ncc(-c3ccc(OC4CCN(C(=O)C5CC5)CC4)cc3)cc12]

This example was synthesized from 5-methoxy-3-[4-(piperidin-4-yloxy)-phenyl]-quinoline, 2HCl (90 mg, 0.2 mmol) and cyclopropanecarbonyl chloride (40 uL, 0.4 mmol) in an analogous manner to Example 619. Product isolated as a solid (0.07 g, 70%). Analysis: LCMS m/z=403

(M+1). ¹H NMR (DMSO-d6) δ: 9.44 (d, 1H, J=2.3 Hz), 8.97 (s, 1H), 7.89 (m, 3H), 7.79-7.81 (m, 1H), 7.24-7.29 (m, 1H), 7.20 (d, 2H, J=8.8 Hz), 4.60-4.90 (m, 1H), 4.08 (s, 3H), 3.96-4.02 (m, 1H), 3.81-3.92 (m, 1H), 3.51-3.70 (m, 1H), 3.20-3.38 (m, 1H), 2.01 (m, 3H), 1.45-1.77 (m, 2H), 0.64-0.77 (m, 4H).

Example 465. {4-[4-(5-Methoxyquinolin-3-yl)-phenoxy]-piperidin-1-yl}-(R)-tetrahydro-furan-2-yl-methanone, HCl

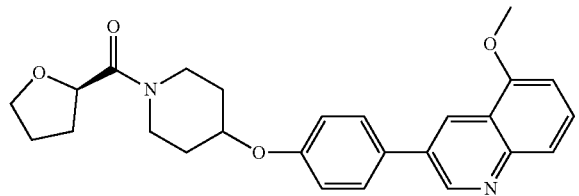 [SMILES: COc1cccc2ncc(-c3ccc(OC4CCN(C(=O)[C@H]5CCCO5)CC4)cc3)cc12]

This example was synthesized from 5-methoxy-3-[4-(piperidin-4-yloxy)-phenyl]-quinoline, 2HCl (90 mg, 0.2 mmol) and (R)-tetrahydrofuran-2-carboxylic acid (0.02 mL, 0.24 mmol) in an analogous manner to Example 424. Product isolated as a solid (0.06 g, 58%). Analysis: LCMS m/z=433 (M+1). ¹H NMR (DMSO-d₆) δ: 9.44 (d, 1H, J=2.3 Hz), 8.97 (s, 1H), 7.89 (m, 3H), 7.73-7.81 (m, 1H), 7.23-7.32 (m, 1H), 7.19 (d, 2H, J=8.8 Hz), 4.62-4.84 (m, 2H), 4.08 (s, 3H), 3.76 (m, 4H), 3.08-3.56 (m, 2H), 2.00 (m, 4H), 1.74-1.92 (m, 2H), 1.41-1.70 (m, 2H).

Example 466. Cyclopropyl-[4-(4-isoquinolin-6-yl-phenoxy)-piperidin-1-yl]-methanone

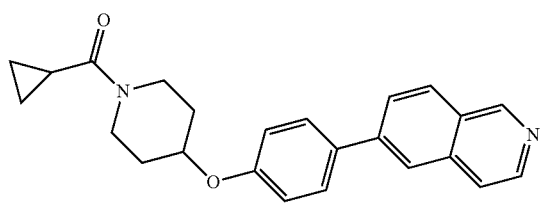 [SMILES: O=C(C1CC1)N1CCC(Oc2ccc(-c3ccc4cnccc4c3)cc2)CC1]

Step 1

4-(4-Isoquinolin-6-yl-phenoxy)-piperidine-1-carboxylic acid t-butyl ester was prepared from 4-(4-iodo-phenoxy)-piperidine-1-carboxylic acid t-butyl ester (0.5 g, 1.24 mmol) and 6-isoquinolylboronic acid (0.26 g, 1.49 mmol) in an analogous manner to Example 378. Product was isolated as a solid (0.33 g, 65%). Analysis: LCMS m/z=405 (M+1).

Step 2

6-[4-(Piperidin-4-yloxy)-phenyl]-isoquinoline was prepared from the Step 1 product above (0.33 g, 0.8 mmol) and TFA (2 mL) in an analogous manner to Example 378. Product isolated as a solid (0.24 g, 97%). Analysis: LCMS m/z=305 (M+1).

Step 3

The title compound was prepared from the Step 2 product above and cyclopropanecarbonyl chloride (40 uL, 0.5 mmol) in an analogous manner to Example 396. Product isolated as a solid (0.06 g, 50%). Analysis: LCMS m/z=373 (M+1). ¹H NMR (DMSO-d6) δ: 9.31 (s, 1H), 8.50 (d, 1H, J=5.8 Hz), 8.19 (m, 2H), 8.01 (d, 1H, J=1.8 Hz), 7.81 (m, 3H), 7.16 (d, 2H, J=8.8 Hz), 4.70-4.83 (m, 1H), 3.83-4.07 (m, 2H), 3.52-3.64 (m, 1H), 3.24-3.31 (m, 1H), 1.90-2.09 (m, 3H), 1.49-1.72 (m, 2H), 0.73 (m, 4H).

Example 467. [4-[4-(6-Isoquinolyl)phenoxy]-1-piperidyl]-[(2R)-tetrahydrofuran-2-yl]methanone HCl

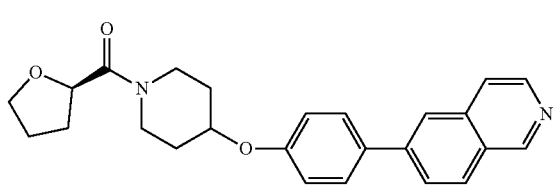

This example was synthesized from 6-[4-(piperidin-4-yloxy)-phenyl]-isoquinoline (0.09 g, 0.30 mmol) and (R)-tetrahydrofuran-2-carboxylic acid (0.03 mL, 0.33 mmol) in an analogous manner to Example 424. Product isolated as a solid (0.08 g, 59%). Analysis: LCMS m/z=403 (M+1). ¹H NMR (DMSO-d6) δ: 9.78 (s, 1H), 8.61-8.68 (m, 1H), 8.47-8.58 (m, 2H), 8.29-8.42 (m, 2H), 7.93 (d, 2H, J=8.8 Hz), 7.09-7.27 (m, 2H), 4.74-4.83 (m, 1H), 4.70 (m, 1H), 3.77 (s, 4H), 3.20-3.53 (m, 2H), 1.91-2.13 (m, 4H), 1.76-1.91 (m, 2H), 1.47-1.73 (m, 2H).

Example 468. {4-[4-(5-Methylisoquinolin-6-yl)-phenoxy]-piperidin-1-yl}-(R)-tetrahydro-furan-2-yl-methanone, HCl

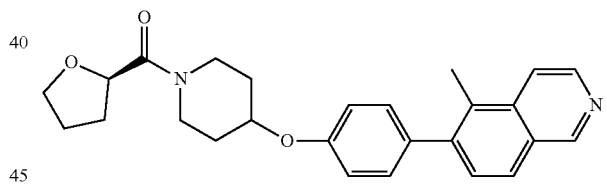

Step 1

To 6-methoxy-5-methyl-isoquinoline (0.14 g, 0.81 mmol) under an atmosphere of nitrogen in DCM (10 mL) at 0° C. was added 1M of BBr₃ in DCM (2.85 mL, 2.85 mmol) and the reaction was warmed to RT overnight. The reaction was poured slowly into sat. sodium bicarbonate (30 mL) at 0° C. with vigorous stirring, extracted, washed with water/brine, dried over sodium sulfate, and concentrated. 5-Methyl-isoquinolin-6-ol was isolated as crude product (0.1 g, 83%). Analysis: LCMS m/z=160 (M+1).

Step 2

To a solution of 5-methylisoquinolin-6-ol (0.13 g, 0.8 mmol) in DMF (3 mL) and DIPEA (0.42 mL, 2.39 mmol) was added N-phenylbis(trifluoromethanesulphonimide) (0.31 g, 0.88 mmol) and was stirred at RT for 30 min. The reaction was diluted with ethyl acetate, washed with water/brine, and concentrated. The product was purified via silica gel chromatography (10-30% EtOAc/hexanes) and concentrated. Trifluoromethanesulfonic acid 5-methyl-isoquinolin-6-yl ester was isolated as a solid (0.14 g, 59%). Analysis: LCMS m/z=292 (M+1).

Step 3

4-[4-(5-Methylisoquinolin-6-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.16 g, 0.4 mmol) and the Step 2 product above (0.14 g, 0.47 mmol) in an analogous manner to Example 378. Product isolated as a solid (0.13 g, 75%). Analysis: LCMS m/z=419 (M+1).

Step 4

5-Methyl-6-[4-(piperidin-4-yloxy)-phenyl]-isoquinoline was prepared from the Step 3 product above (0.14 g, 0.3 mmol) and TFA (0.5 mL) in an analogous manner to Ex. 378. Product isolated as a solid (0.09 g, 89%). Analysis: LCMS m/z=319 (M+1).

Step 5

The title compound was prepared from the step 4 product above (0.09 g, 0.27 mmol) and (R)-tetrahydrofuran-2-carboxylic acid (0.03 mL, 0.3 mmol) in an analogous manner to Example 424. Product isolated as a solid (0.09 g, 74%). Analysis: LCMS m/z=417 (M+1). $^1$H NMR (DMSO-d6) δ: 9.83 (s, 1H), 8.72 (d, 1H, J=6.5 Hz), 8.51 (d, 1H, J=6.8 Hz), 8.38 (d, 1H, J=8.5 Hz), 7.87 (d, 1H, J=8.8 Hz), 7.43 (d, 2H, J=8.8 Hz), 7.17 (d, 2H, J=8.5 Hz), 4.70 (m, 2H), 3.68-3.97 (m, 4H), 3.20-3.51 (m, 2H), 2.67 (s, 3H), 2.02 (br m, 4H), 1.78-1.92 (m, 2H), 1.49-1.73 (m, 2H).

Example 469. 1-[4-[4-(1,4-Dimethyl-6-isoquinolyl)phenoxy]-1-piperidyl]propan-1-one, HCl

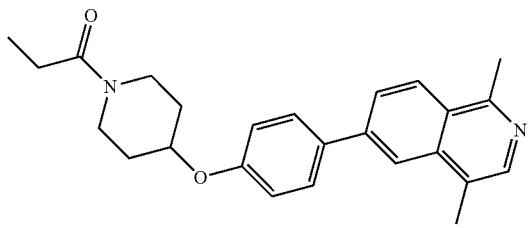 [SMILES: CCC(=O)N1CCC(Oc2ccc(-c3ccc4c(C)ncc(C)c4c3)cc2)CC1]

Step 1

4-[4-(1-Chloro-4-methyl-isoquinolin-6-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 6-bromo-1-chloro-4-methylisoquinoline (0.32 g, 1.24 mmol) in an analogous manner to Example 378. Product isolated as a solid (0.4 g, 70%). Analysis: LCMS m/z=453 (M+1).

Step 2

To a schlenck flask under an atmosphere of argon was added the Step 1 product above (0.4 g, 0.87 mmol), methylboronic acid (0.26 g, 4.34 mmol), DPPF-Pd(II), complex with DCM (1:1) (142 mg, 0.17 mmol), potassium phosphate (0.92 g, 4.34 mmol), followed by 1,4-dioxane (10 mL) and was degassed under an atmosphere of argon for 5 min and was heated at 99° C. for 2 h. The reaction was cooled, filtered through a pad of celite, washed with 1N Na$_2$CO$_3$/water/brine, dried over sodium sulfate, and concentrated. The product was purified via silica gel chromatography using (20-50% EtOAc/hexanes) and concentrated. T-butyl 4-[4-(1,4-dimethyl-6-isoquinolyl)phenoxy]piperidine-1-carboxylate was dissolved in DCM (7 mL), TFA (2 mL) was added dropwise and the reaction was stirred at rt for 1 h and concentrated. The reaction was partitioned between DCM/1N sodium carbonate, washed with brine, dried over sodium sulfate, and concentrated. The product was dissolved in DCM, 2M of HCl in diethyl ether (0.43 mL, 0.87 mmol) was added and was concentrated. 1,4-Dimethyl-6-[4-(4-piperidyloxy)phenyl]isoquinoline dihydrochloride was isolated as a solid (0.22 g, 62%). LCMS m/z=333 (M+1).

Step 3

1-[4-[4-(1,4-Dimethyl-6-isoquinolyl)phenoxy]-1-piperidyl]propan-1-one HCl was prepared from 1,4-dimethyl-6-[4-(4-piperidyloxy)phenyl]isoquinoline 2HCl (72 mg, 0.18 mmol) and propanoyl chloride (30 uL, 0.3 mmol) in an analogous manner to Example 398. Product isolated as a solid (0.04 g, 53%). Analysis: LCMS m/z=389 (M+1). $^1$H NMR (DMSO-d$_6$) δ: 8.60 (d, 1H, J=8.8 Hz), 8.29-8.41 (m, 3H), 7.99 (d, 2H, J=8.8 Hz), 7.21 (d, 2H, J=8.8 Hz), 4.71-4.84 (m, 1H), 3.83-3.96 (m, 1H), 3.67-3.77 (m, 1H), 3.23-3.64 (br m, 3H), 3.17 (s, 3H), 2.78 (s, 3H), 2.35 (m, 2H), 1.86-2.10 (m, 2H), 1.48-1.72 (m, 2H), 1.00 (t, 3H, J=7.4 Hz).

Example 470. Cyclopropyl-[4-[4-(1,4-dimethyl-6-isoquinolyl)phenoxy]-1-piperidyl]methanone, HCl

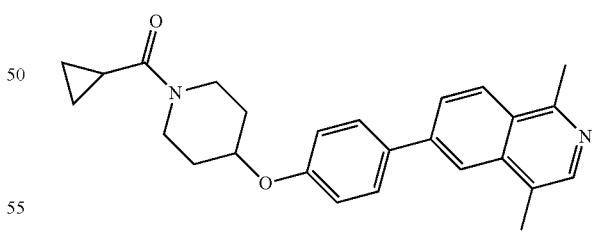

This example was synthesized from 1,4-dimethyl-6-[4-(4-piperidyloxy)phenyl]isoquinoline, 2HCl (72 mg, 0.18 mmol) and cyclopropanecarbonyl chloride (30 uL, 0.3 mmol) in an analogous manner to Example 398. Product isolated as a solid (0.04 g, 52%). Analysis: LCMS m/z=401 (M+1). $^1$H NMR (DMSO-d$_6$) δ: 8.60 (d, 1H, J=9.0 Hz), 8.29-8.42 (m, 3H), 7.99 (d, 2H, J=8.8 Hz), 7.22 (d, 2H, J=8.8 Hz), 4.80 (m, 1H), 3.83-4.10 (m, 2H), 3.24-3.69 (m, 3H), 3.17 (s, 3H), 2.78 (s, 3H), 1.88-2.11 (m, 3H), 1.47-1.76 (m, 2H), 0.64-0.76 (m, 4H).

Example 471. [4-[4-(1,4-Dimethyl-6-isoquinolyl)phenoxy]-1-piperidyl]-[(2R)-tetrahydrofuran-2-yl]methanone, HCl

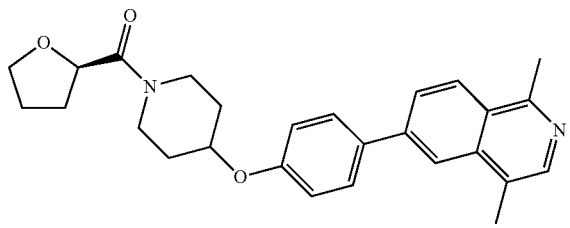 [SMILES: Cc1cnc(C)c2ccc(-c3ccc(OC4CCN(C(=O)[C@H]5CCCO5)CC4)cc3)cc12]

This example was synthesized from 1,4-dimethyl-6-[4-(4-piperidyloxy)phenyl]-isoquinoline 2HCl (72 mg, 0.18 mmol) and (R)-tetrahydrofuran-2-carboxylic acid (19 uL, 0.2 mmol) in an analogous manner to Example 424. Product isolated as a solid (0.03 g, 36%). LCMS m/z=432 (M+1). $^1$H NMR (DMSO) δ: 8.59 (d, 1H, J=8.8 Hz), 8.28-8.42 (m, 3H), 7.99 (d, 2H, J=8.8 Hz), 7.21 (d, 2H, J=8.5 Hz), 4.85 (m, 1H), 4.64 (m, 1H), 3.70-3.95 (m, 4H), 3.23-3.61 (m, 3H), 3.15 (s, 3H), 2.78 (s, 3H), 1.92-2.15 (m, 4H), 1.79-1.91 (m, 2H), 1.50-1.73 (m, 2H).

Example 472. 1-[4-[4-(1,5-Dimethyl-6-isoquinolyl)phenoxy]-1-piperidyl]propan-1-one HCl

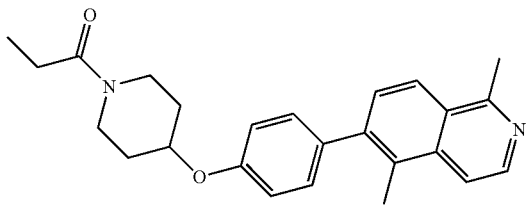 [SMILES: CCC(=O)N1CCC(Oc2ccc(-c3ccc4c(C)nccc4c3C)cc2)CC1]

Step 1

5-Chloro-6-methoxy-1-methylisoquinoline was prepared from 1,5-dichloro-6-methoxyisoquinoline (0.5 g, 2.19 mmol) and methylboronic acid (656 mg, 11 mmol) in an analogous manner to Example 425. Product isolated as a solid (0.4 g, 91%). LCMS m/z=208 (M+1).

Step 2

6-Methoxy-1,5-dimethylisoquinoline was prepared from the Step 1 product above (0.4 g, 1.99 mmol) and methylboronic acid (597 mg, 9.97 mmol) an analogous manner to Example 430. Product isolated as a solid (0.37 g, 100%). Analysis: LCMS m/z=188 (M+1).

Step 3

1,5-Dimethylisoquinolin-6-ol was prepared from 6-methoxy-1,5-dimethylisoquinoline (0.4 g, 2.06 mmol) and 1M of BBr$_3$ in DCM (7.2 mL, 7.2 mmol) an analogous manner to Example 468. Product was isolated (0.25 g, 69%). Analysis: LCMS m/z=174 (M+1).

Step 4

Trifluoromethanesulfonic acid 1,5-dimethylisoquinolin-6-yl ester was prepared from 1,5-dimethylisoquinolin-6-ol (0.25 g, 1.42 mmol) and N-phenylbis(trifluoromethanesulphonimide) (0.56 g, 1.56 mmol) an analogous manner to Example 468. Product was isolated as a solid (0.22 g, 50%). Analysis: LCMS m/z=306 (M+1).

Step 5

To a schlenck flask was added 4-[4-(4,4,5,5-tetramethyl-1,3,2-dioxaborolan-2-yl)-phenoxy]-piperidine-1-carboxylic acid t-butyl ester (0.25 g, 0.61 mmol), the Step 4 product above (0.22 g, 0.71 mmol), tetrakis(triphenylphosphine)palladium(0) (0.07 g, 0.06 mmol), 1M of Na$_2$CO$_3$ (1.82 mL, 1.82 mmol), followed by 1,4-dioxane (6 mL) and was degassed under Argon for 5 min and was heated at 99° C. overnight. The reaction was cooled, filtered through a pad of celite, washed with 1N Na$_2$CO$_3$/water/brine, dried over Na$_2$SO$_4$, and concentrated. The product was purified via silica gel chromatography (20-50% EtOAc/hexanes) and concentrated. T-butyl 4-[4-(1,5-dimethyl-6-isoquinolyl)phenoxy]piperidine-1-carboxylate was dissolved in DCM (6 mL), TFA (0.8 mL) was added dropwise and was stirred at rt for 2 h and concentrated. The compound was partitioned between DCM/1N Na$_2$CO$_3$, washed with water/brine, dried over Na$_2$SO$_4$, and concentrated. The product was dissolved in DCM, 2M of HCl in diethyl ether (0.3 mL, 0.61 mmol) was added and was concentrated. 1,5-Dimethyl-6-[4-(piperidin-4-yloxy)-phenyl]-isoquinoline was isolated as a solid (0.22 g, 90%). Analysis: LCMS m/z=333 (M+1).

Step 6

The title compound was prepared from 1,5-dimethyl-6-[4-(4-piperidyloxy)phenyl]-isoquinoline 2HCl (74 mg, 0.18 mmol) and propanoyl chloride (30 uL, 0.3 mmol) an analogous manner to Example 619. Product isolated as a solid (0.05 g, 64%). Analysis: LCMS m/z=389 (M+1). $^1$H NMR (DMSO-d6) δ: 8.53 (d, 1H, J=6.8 Hz), 8.41 (d, 1H, J=8.8 Hz), 8.34 (d, 1H, J=6.3 Hz), 7.83 (d, 1H, J=8.8 Hz), 7.42 (d, 2H, J=8.8 Hz), 7.16 (d, 2H, J=8.5 Hz), 4.73 (m, 1H), 3.86-3.99 (m, 1H), 3.73 (m, 1H), 3.22-3.45 (br m, 2H), 3.19 (s, 3H), 2.65 (s, 3H), 2.36 (m, 2H), 1.97 (m, 2H), 1.48-1.75 (m, 2H), 1.00 (t, 3H, J=7.4 Hz).

Example 473. Cyclopropyl-[4-[4-(1,5-dimethyl-6-isoquinolyl)phenoxy]-1-piperidyl]methanone HCl

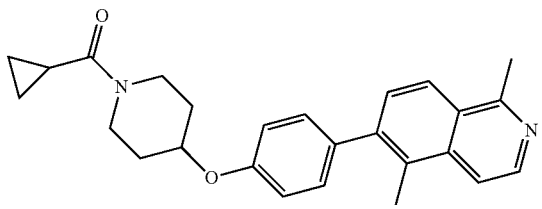 [SMILES: Cc1nccc2c(C)c(-c3ccc(OC4CCN(C(=O)C5CC5)CC4)cc3)ccc12]

This example was synthesized from 1,5-dimethyl-6-[4-(4-piperidyloxy)phenyl]isoquinoline, 2HCl (74 mg, 0.18 mmol) and cyclopropanecarbonyl chloride (30 uL, 0.3 mmol) in an analogous manner to Example 398. Product isolated as a solid (0.05 g, 56%). Analysis: LCMS m/z=401 (M+1). $^1$H NMR (DMSO-d$_6$) δ: 8.55 (d, 1H, J=7.0 Hz), 8.44

(d, 1H, J=8.8 Hz), 8.38 (d, 1H, J=6.8 Hz), 7.86 (d, 1H, J=8.8 Hz), 7.40-7.46 (m, 2H), 7.13-7.20 (m, 2H), 4.68-4.83 (m, 1H), 3.81-4.08 (m, 2H), 3.49-3.65 (m, 2H), 3.23-3.36 (m, 1H), 3.20 (s, 3H), 2.67 (s, 3H), 1.91-2.14 (m, 3H), 1.50-1.76 (m, 2H), 0.66-0.78 (m, 4H).

Example 474. [4-[4-(1,5-Dimethyl-6-isoquinolyl)phenoxy]-1-piperidyl]-[(2R)-tetrahydrofuran-2-yl]methanone, HCl

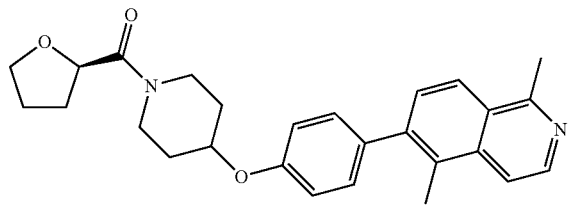 [SMILES: Cc1nccc2c(C)c(-c3ccc(OC4CCN(C(=O)[C@H]5CCCO5)CC4)cc3)ccc12]

This example was synthesized from 1,5-dimethyl-6-[4-(4-piperidyloxy)phenyl]-isoquinoline, 2HCl (74 mg, 0.18 mmol) and (R)-tetrahydrofuran-2-carboxylic acid (19 uL, 0.2 mmol) in an analogous manner to Example 424. Product isolated as a solid (0.04 g, 47%). Analysis: LCMS m/z=432 (M+1). $^1$H NMR (DMSO-$d_6$) δ: 8.54 (d, 1H, J=7.0 Hz), 8.44 (d, 1H, J=8.8 Hz), 8.39 (d, 1H, J=6.8 Hz), 7.86 (d, 1H, J=8.8 Hz), 7.42 (d, 2H, J=8.8 Hz), 7.17 (d, 2H, J=8.5 Hz), 4.70 (m, 2H), 3.52-3.96 (br m, 5H), 3.23-3.51 (br m, 2H), 3.21 (s, 3H), 2.66 (s, 3H), 1.93-2.11 (m, 4H), 1.76-1.91 (m, 2H), 1.49-1.72 (m, 2H).

Example 475. [4-[4-(8-Cyclopropyl-7-quinolyl)phenoxy]-1-piperidyl]-[(2R)-tetrahydrofuran-2-yl]methanone, HCl

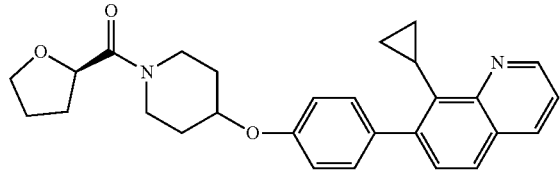 [SMILES: O=C([C@H]1CCCO1)N1CCC(Oc2ccc(-c3ccc4cccnc4c3C3CC3)cc2)CC1]

Step 1 t-Butyl 4-[4-(8-chloro-7-quinolyl)phenoxy]piperidine-1-carboxylate was prepared from 4-[4-(4,4,5,5-tetramethyl-1,3,2-dioxaborolan-2-yl)-phenoxy]-piperidine-1-carboxylic acid t-butyl ester (0.25 g, 0.62 mmol) and 7-bromo-8-chloroquinoline (0.17 g, 0.68 mmol) in an analogous manner to Example 378. Product isolated as a solid (0.23 g, 85%). Analysis: LCMS m/z=439 (M+1).

Step 2

To a schlenck flask under an atmosphere of argon was added the Step 1 product (0.23 g, 0.53 mmol), cyclopropyl boronic acid (0.23 g, 2.63 mmol), amphos (74.5 mg, 0.11 mmol), cesium carbonate (0.86 g, 2.63 mmol), followed by 1,4-dioxane (20 mL)/Water (0.670 mL) and was degassed under an atmosphere of argon for 5 min and was heated at 120° C. for 4 h and cooled at RT. The reaction was filtered through a pad of celite, washed with DCM, washed with water/brine, dried over sodium sulfate, and concentrated. The product was purified via silica gel chromatography using Prep TLC plates (30% EtOAc/hexanes) and concentrated. Tert-butyl 4-[4-(8-cyclopropyl-7-quinolyl)phenoxy]piperidine-1-carboxylate was dissolved in DCM (4 mL), TFA (1 mL) was added and was stirred at rt for 2 h and concentrated. The product was washed with 1N Na$_2$CO$_3$/brine, dried over sodium sulfate, and concentrated. 8-Cyclopropyl-7-[4-(piperidin-4-yloxy)-phenyl]-quinoline was isolated as a yellow oil (0.05 g, 29%). LCMS m/z=345 (M+1).

Step 3

[4-[4-(8-Cyclopropyl-7-quinolyl)phenoxy]-1-piperidyl]-[(2R)-tetrahydrofuran-2-yl]-methanone HCl was prepared from the Step 2 product above (52 mg, 0.15 mmol) and (R)-tetrahydrofuran-2-carboxylic acid (16 uL, 0.17 mmol) in an analogous manner to Example 424. Product isolated as a solid (0.04 g, 55%). Analysis: LCMS m/z=444 (M+1). $^1$H NMR (DMSO-$d_6$) δ: 9.23 (s, 1H), 8.95-9.12 (br m, 1H), 8.15-8.26 (m, 1H), 7.95-8.06 (m, 1H), 7.78-7.88 (m, 1H), 7.57 (d, 2H, J=8.5 Hz), 7.15 (d, 2H, J=8.5 Hz), 4.71 (m, 2H), 4.30 (br m, 1H), 3.66-3.97 (m, 4H), 3.18-3.54 (m, 2H), 2.39-2.47 (m, 1H), 1.94-2.12 (m, 4H), 1.84 (m, 2H), 1.48-1.73 (m, 2H), 0.88-1.12 (m, 2H), 0.23-0.39 (m, 2H).

Example 476. {4-[4-(3-Ethylisoquinolin-6-yl)-phenoxy]-piperidin-1-yl}-(R)-tetrahydro-furan-2-yl-methanone

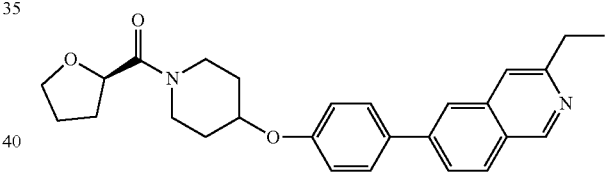

Step 1

4-[4-(3-Ethyl-isoquinolin-6-yl)-phenoxy]-piperidine-1-carboxylic acid t-butyl ester was prepared from 4-[4-(3-chloroisoquinolin-6-yl)-phenoxy]-piperidine-1-carboxylic acid t-butyl ester (0.67 g, 1.53 mmol) and ethyl boronic acid (0.57 g, 7.65 mmol) analogous to Example 430. Product isolated as a solid. Analysis: LCMS m/z=433 (M+1).

Step 2

3-Ethyl-6-[4-(piperidin-4-yloxy)-phenyl]-isoquinoline was prepared from the Step 1 product above and TFA (2 mL) in an analogous manner to Example 378. Product isolated as a solid (0.09 g, 97%). Analysis: LCMS m/z=333 (M+1).

Step 3

{4-[4-(3-Ethylisoquinolin-6-yl)-phenoxy]-piperidin-1-yl}-(R)-tetrahydrofuran-2-yl-methanone was prepared from the Step 2 product above (88 mg, 0.26 mmol) and (R)-tetrahydrofuran-2-carboxylic acid (51 uL, 0.53 mmol) in an analogous manner to Example 418. Product isolated as a solid (0.05 g, 40%). Analysis: LCMS m/z=431 (M+1). $^1$H NMR (DMSO-d6) δ: 9.22 (s, 1H), 8.12 (d, 2H, J=8.8 Hz), 7.91 (m, 1H), 7.79 (d, 2H, J=8.8 Hz), 7.66 (s, 1H), 7.15 (d, 2H, J=8.7 Hz), 4.69 (m, 2H), 3.77 (br m, 4H), 3.36 (m, 1H), 3.25 (m, 1H), 2.90 (m, 2H), 2.01 (br m, 4H), 1.84 (m, 2H), 1.52-1.66 (br m, 2H), 1.32 (t, 3H, J=7.6 Hz).

Example 477. Cyclopropyl-{4-[4-(7-fluoroquinolin-3-yl)-phenoxy]-piperidin-1-yl}-methanone

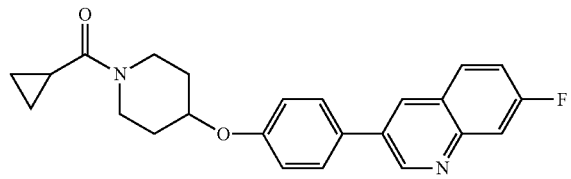 [SMILES: O=C(C1CC1)N1CCC(Oc2ccc(-c3cnc4cc(F)ccc4c3)cc2)CC1]

Step 1

4-[4-(7-Fluoroquinolin-3-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 3-bromo-7-fluoroquinoline (0.28 g, 1.24 mmol) in an analogous manner to Example 378. Product isolated as a solid. Analysis: LCMS m/z=423 (M+1).

Step 2

7-Fluoro-3-[4-(piperidin-4-yloxy)-phenyl]-quinoline was prepared from the Step 1 product above and TFA (2 mL) in an analogous manner to Example 378. Product isolated as a solid (0.29 g, 96%). Analysis: LCMS m/z=323 (M+1).

Step 3

The title compound was prepared from the Step 2 product above (95 mg, 0.29 mmol) and cyclopropanecarbonyl chloride (40 uL, 0.5 mmol) in an analogous manner to Example 396. Product isolated as a solid (0.06 g, 52%). Analysis: LCMS m/z=391 (M+1). $^1$H NMR (DMSO-d$_6$) δ: 9.25 (s, 1H), 8.64 (s, 1H), 8.12 (m, 1H), 7.81 (m, 2H), 7.76 (m, 1H), 7.58 (m, 1H), 7.18 (m, 2H), 4.74 (m, 1H), 3.98 (m, 1H), 3.89 (m, 1H), 3.56 (m, 1H), 3.29 (m, 1H), 2.00 (br m, 3H), 1.55-1.66 (br m, 2H), 0.74 (m, 4H).

Example 478. 1-{4-[4-(7-Fluoroquinolin-3-yl)-phenoxy]-piperidin-1-yl}-propan-1-one

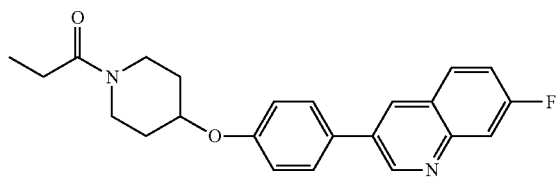 [SMILES: CCC(=O)N1CCC(Oc2ccc(-c3cnc4cc(F)ccc4c3)cc2)CC1]

This example was synthesized from 7-fluoro-3-[4-(piperidin-4-yloxy)-phenyl]-quinoline (95 mg, 0.29 mmol) and propanoyl chloride (40 uL, 0.5 mmol) in an analogous manner to Example 396. Product isolated as a solid (0.02 g, 19%). Analysis: LCMS m/z=379 (M+1). $^1$H NMR (DMSO-d$_6$) δ: 9.25 (s, 1H), 8.64 (s, 1H), 8.12 (m, 1H), 7.81 (m, 2H), 7.76 (m, 1H), 7.58 (m, 1H), 7.18 (m, 2H), 4.72 (m, 1H), 3.87 (m, 1H), 3.69 (m, 1H), 3.35 (m, 1H), 3.27 (m, 1H), 2.35 (m, 2H), 1.98 (br m, 2H), 1.50-1.65 (br m, 2H), 1.00 (t, 3H, J=7.4 Hz).

Example 479. {4-[4-(7-Fluoroquinolin-3-yl)-phenoxy]-piperidin-1-yl}-(R)-tetrahydro-furan-2-yl-methanone

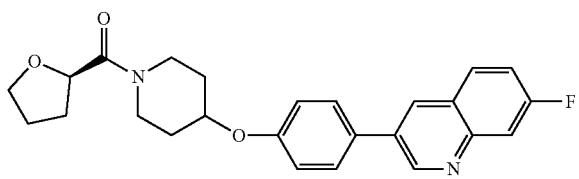 [SMILES: O=C([C@H]1CCCO1)N1CCC(Oc2ccc(-c3cnc4cc(F)ccc4c3)cc2)CC1]

This example was synthesized from 7-fluoro-3-[4-(piperidin-4-yloxy)-phenyl]-quinoline (95 mg, 0.29 mmol) and (R)-tetrahydrofuran-2-carboxylic acid (60 uL, 0.63 mmol) in an analogous manner to Example 418. Product isolated as a solid (0.09 g, 65%). Analysis: LCMS m/z=421 (M+1). $^1$H NMR (DMSO-d$_6$) δ: 9.25 (s, 1H), 8.64 (s, 1H), 8.12 (m, 1H), 7.81 (m, 2H), 7.76 (m, 1H), 7.58 (m, 1H), 7.18 (m, 2H), 4.71 (m, 2H), 3.77 (br m, 4H), 3.36 (m, 1H), 3.26 (m, 1H), 2.02 (m, 4H), 1.84 (m, 2H), 1.52-1.66 (m, 2H).

Example 480. {4-[4-(3-Cyclopropylisoquinolin-6-yl)-phenoxy]-piperidin-1-yl}-(R)-tetrahydrofuran-2-yl-methanone

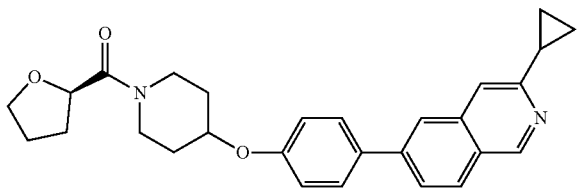 [SMILES: O=C([C@H]1CCCO1)N1CCC(Oc2ccc(-c3ccc4cnc(C5CC5)cc4c3)cc2)CC1]

Step 1

4-[4-(3-Cyclopropylisoquinolin-6-yl)-phenoxy]-piperidine-1-carboxylic acid t-butyl ester was prepared from 4-[4-(3-chloroisoquinolin-6-yl)-phenoxy]-piperidine-1-carboxylic acid t-butyl ester (0.59 g, 1.35 mmol) and cyclopropyl boronic acid (0.58 g, 6.74 mmol) in an analogous manner to Example 430. Product isolated as a solid (0.08 g, 14%). Analysis: LCMS m/z=445 (M+1).

Step 2

3-Cyclopropyl-6-[4-(piperidin-4-yloxy)-phenyl]-isoquinoline was prepared from the Step 1 product above (0.08 g, 0.19 mmol) and TFA (4 mL) in an analogous manner to Example 378. Product isolated as a solid (0.06 g, 95%). Analysis: LCMS m/z=345 (M+1).

Step 3

{4-[4-(3-Cyclopropylisoquinolin-6-yl)-phenoxy]-piperidin-1-yl}-(R)-tetrahydro-furan-2-yl-methanone was prepared from the Step 3 product above (61 mg, 0.18 mmol) and (R)-tetrahydrofuran-2-carboxylic acid (34 uL, 0.35 mmol) in an analogous manner to Example 418. Product isolated as a solid (0.03 g, 41%). Analysis: LCMS m/z=443 (M+1). $^1$H NMR (DMSO-d$_6$) δ: 9.14 (s, 1H), 8.05 (d, 2H, J=9.4 Hz), 7.86 (m, 1H), 7.76 (m, 2H), 7.70 (s, 1H), 7.15 (d, 2H, J=8.7 Hz), 4.69 (m, 2H), 3.77 (br m, 4H), 3.36 (m, 1H), 3.29 (m, 1H), 2.22 (m, 1H), 2.01 (m, 4H), 1.80 (m, 2H), 1.54-1.65 (br m, 2H), 0.99 (m, 4H).

Example 481. Cyclopropyl-{4-[4-(1-methylisoquinolin-6-yl)-phenoxy]-piperidin-1-yl}-methanone

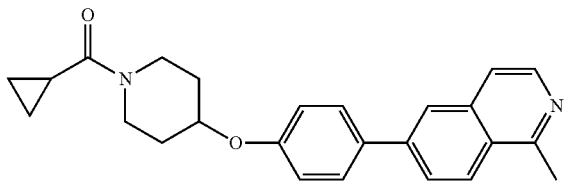 [SMILES: Cc1nccc2cc(-c3ccc(OC4CCN(C(=O)C5CC5)CC4)cc3)ccc12]

This example was synthesized from 1-methyl-6-[4-(piperidin-4-yloxy)-phenyl]-isoquinoline (63 mg, 0.20 mmol) and cyclopropanecarbonyl chloride (30 uL, 0.3 mmol) in an analogous manner to Example 396. Product isolated as a solid (0.05 g, 63%). Analysis: LCMS m/z=387 (M+1). $^1$H NMR (DMSO-d$_6$) δ: 8.34 (d, 1H, J=5.8 Hz), 8.25 (d, 1H J=8.7 Hz), 8.18 (m, 1H), 7.98 (m, 1H), 7.81 (d, 2H, J=8.7 Hz), 7.70 (d, 1H, J=5.8 Hz), 7.16 (d, 2H, J=8.7 Hz), 4.74 (m, 1H), 3.98 (m, 1H), 3.89 (m, 1H), 3.56 (m, 1H), 3.29 (m, 1H), 2.70 (s, 3H), 2.00 (br m, 3H), 1.55-1.65 (br m, 2H), 0.71 (m, 4H).

Example 482. {4-[4-(7-Methylquinolin-3-yl)-phenoxy]-piperidin-1-yl}-(R)-tetrahydro-furan-2-yl-methanone, HCl

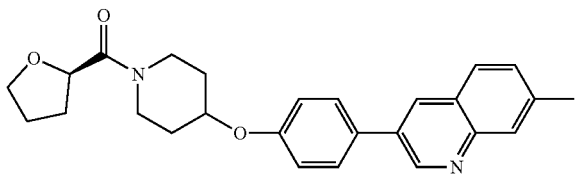 [SMILES: Cc1ccc2cc(-c3ccc(OC4CCN(C(=O)[C@H]5CCCO5)CC4)cc3)cnc2c1]

This example was synthesized from 7-methyl-3-[4-(piperidin-4-yloxy)-phenyl]-quinoline (90 mg, 0.3 mmol) and (R)-tetrahydrofuran-2-carboxylic acid (54 uL, 0.57 mmol) in an analogous manner to Example 424. Product isolated as a solid (0.06 g, 50%). LCMS m/z=417 (M+1). $^1$H NMR (DMSO-d$_6$) δ: 9.28 (s, 1H), 8.71 (s, 1H), 7.93 (d, 1H, J=7.9 Hz), 7.86 (m, 2H), 7.67 (d, 1H, J=6.9 Hz), 7.57 (m, 1H), 7.19 (d, 2H, J=8.6 Hz), 5.58 (br m, 1H), 4.74 (m, 2H), 3.77 (m, 4H), 3.35-3.48 (br m, 2H), 2.76 (s, 3H), 2.02 (br m, 4H), 1.84 (m, 2H), 1.52-1.69 (br m, 2H).

Example 483. 1-{4-[4-(6-Methylquinolin-3-yl)-phenoxy]-piperidin-1-yl}-propan-1-one, HCl

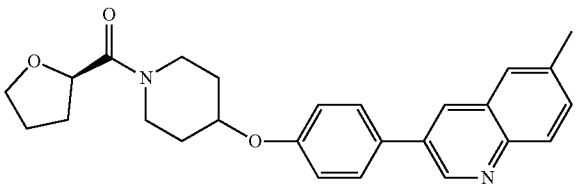 [SMILES: Cc1ccc2ncc(-c3ccc(OC4CCN(C(=O)[C@H]5CCCO5)CC4)cc3)cc2c1]

Step 1

4-[4-(6-Methylquinolin-3-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 3-bromo-6-methyl-quinoline (413 mg, 1.86 mmol) in an analogous manner to Example 378. Product isolated as a solid (0.49 g, 94%). Analysis: LCMS m/z=419 (M+1).

Step 2

6-Methyl-3-[4-(piperidin-4-yloxy)-phenyl]-quinoline was prepared from the Step 2 product above (0.49 g, 1.16 mmol) and TFA (2 mL) in an analogous manner to Example 378. Product isolated as a solid (0.35 g, 94%). Analysis: LCMS m/z=319 (M+1).

Step 3

The title compound was prepared from the Step 2 product above (86 mg, 0.27 mmol) and propanoyl chloride (40 uL, 0.5 mmol) in an analogous manner to Example 398. Product isolated as a solid (0.06 g, 54%). Analysis: LCMS m/z=375 (M+1). $^1$H NMR (DMSO-d6) δ: 9.38 (s, 1H), 8.94 (s, 1H), 8.13 (d, 1H, J=8.6 Hz), 7.96 (s, 1H), 7.90 (m, 2H), 7.80 (m, 1H), 7.21 (m, 2H), 4.75 (m, 1H), 3.89 (m, 1H), 3.70 (m, 1H), 3.25-3.38 (br m, 2H), 2.56 (s, 3H), 2.34 (m, 2H), 1.99 (br m, 2H), 1.51-1.67 (br m, 2H), 1.00 (t, 3H, J=7.4 Hz).

Example 484. Cyclopropyl-{4-[4-(6-methylquinolin-3-yl)-phenoxy]-piperidin-1-yl}-methanone, HCl

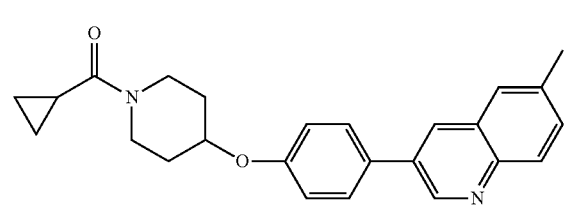

This example was synthesized from 6-methyl-3-[4-(piperidin-4-yloxy)-phenyl]-quinoline (86 mg, 0.27 mmol) and cyclopropanecarbonyl chloride (40 uL, 0.5 mmol) in an analogous manner to Example 398. Product isolated as a solid (0.06 g, 61%). Analysis: LCMS m/z=387 (M+1). $^1$H NMR (DMSO-d$_6$) δ: 9.38 (s, 1H), 8.94 (s, 1H), 8.13 (d, 1H, J=8.6 Hz), 7.96 (s, 1H), 7.90 (m, 2H), 7.80 (m, 1H), 7.21 (m, 2H), 4.77 (m, 1H), 3.99 (m, 1H), 3.89 (m, 1H), 3.57 (m, 1H), 3.30 (m, 1H), 2.56 (s, 3H), 2.01 (br m, 3H), 1.50-1.66 (br m, 2H), 0.72 (m, 4H).

Example 485. {4-[4-(6-Methylquinolin-3-yl)-phenoxy]-piperidin-1-yl}-(R)-tetrahydro-furan-2-yl-methanone, HCl

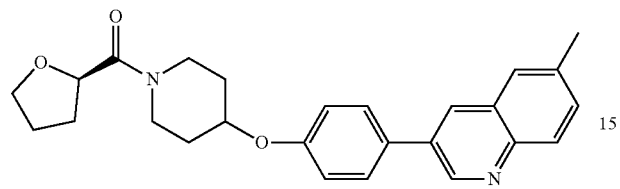

This example was synthesized from 6-methyl-3-[4-(piperidin-4-yloxy)-phenyl]-quinoline (86 mg, 0.27 mmol) and (R)-tetrahydrofuran-2-carboxylic acid (52 uL, 0.54 mmol) in an analogous manner to Example 424. Product isolated as a solid (0.05 g, 41%). Analysis: LCMS m/z=417 (M+1). $^1$H NMR (DMSO-d$_6$) δ: 9.38 (s, 1H), 8.94 (s, 1H), 8.13 (d, 1H, J=8.6 Hz), 7.96 (s, 1H), 7.90 (m, 2H), 7.80 (m, 1H), 7.21 (m, 2H), 4.76 (m, 1H), 4.69 (m, 1H), 3.77 (m, 4H), 3.23-3.48 (br m, 2H), 2.56 (s, 3H), 1.99 (br m, 4H), 1.84 (br m, 2H), 1.54-1.67 (br m, 2H).

Example 486. 1-{4-[4-(8-Methylquinolin-3-yl)-phenoxy]-piperidin-1-yl}-propan-1-one, HCl

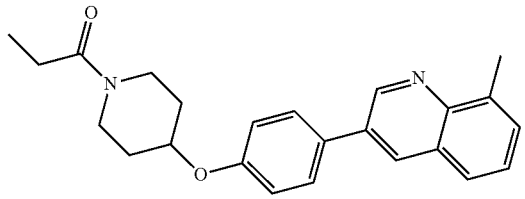 [SMILES: CCC(=O)N1CCC(Oc2ccc(-c3cnc4c(C)cccc4c3)cc2)CC1]

Step 1

4-[4-(8-Methylquinolin-3-yl)-phenoxy]-piperidine-1-carboxylic acid t-butyl ester was prepared from 4-[4-(4,4,5,5-tetramethyl-1,3,2-dioxaborolan-2-yl)-phenoxy]-piperidine-1-carboxylic acid t-butyl ester (0.5 g, 1.24 mmol) and 3-bromo-8-methyl-quinoline (413 mg, 1.86 mmol) in an analogous manner to Example 378. Product isolated as a solid (0.49 g, 94%). Analysis: LCMS m/z=419 (M+1).

Step 2

8-Methyl-3-[4-(piperidin-4-yloxy)-phenyl]-quinoline was prepared from the Step 1 product above (0.49 g, 1.17 mmol) and TFA (2 mL) in an analogous manner to Example 378. Product isolated as a solid (0.36 g, 98%). Analysis: LCMS m/z=319 (M+1).

Step 3

The title compound was prepared the Step 2 product above (91 mg, 0.28 mmol) and propanoyl chloride (40 uL, 0.5 mmol) in an analogous manner to Example 424. Product isolated as a solid (0.07 g, 59%). Analysis: LCMS m/z=375 (M+1). $^1$H NMR (DMSO-d$_6$) δ: 9.46 (s, 1H), 9.14 (s, 1H), 8.17 (d, 1H, J=8.4 Hz), 8.05 (s, 1H), 7.92 (d, 2H, J=8.8 Hz), 7.72 (m, 1H), 7.21 (d, 2H, J=8.8 Hz), 4.75 (m, 1H), 3.90 (m, 1H), 3.87 (m, 1H), 3.24-3.38 (br m, 2H), 2.61 (s, 3H), 2.34 (m, 2H), 1.92 (br m, 2H), 1.50-1.67 (m, 2H), 1.00 (t, 3H, J=7.4 Hz).

Example 487 Cyclopropyl-{4-[4-(8-methylquinolin-3-yl)-phenoxy]-piperidin-1-yl}-methanone

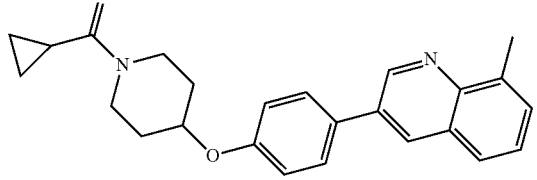

This example was synthesized from 8-methyl-3-[4-(piperidin-4-yloxy)-phenyl]-quinoline (91 mg, 0.28 mmol) and cyclopropanecarbonyl chloride (40 uL, 0.5 mmol) in an analogous manner to Example 396. Product isolated as a solid (0.03 g, 28%). Analysis: LCMS m/z=387 (M+1). $^1$H NMR (DMSO-d$_6$) δ: 9.17 (d, 1H, J=2.4 Hz), 8.51 (d, 1H, J=2.1 Hz), 7.93 (m, 1H), 7.79 (m, 3H), 7.48 (m, 1H), 7.15 (m, 2H), 4.74 (m, 1H), 3.98 (m, 1H), 3.89 (m, 1H), 3.36 (m, 2H), 2.54 (s, 3H), 2.00 (br m, 3H), 1.55-1.66 (br m, 2H), 0.71 (m, 4H).

Example 488. {4-[4-(8-Methylquinolin-3-yl)-phenoxy]-piperidin-1-yl}-(R)-tetrahydro-furan-2-yl-methanone

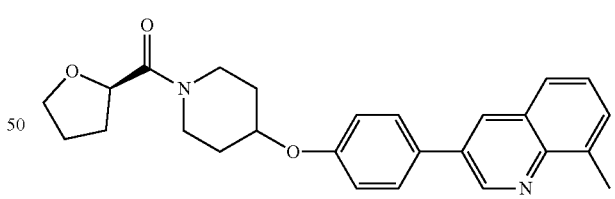

This example was synthesized from 8-methyl-3-[4-(piperidin-4-yloxy)-phenyl]-quinoline (91 mg, 0.28 mmol) and (R)-tetrahydrofuran-2-carboxylic acid (55 uL, 0.57 mmol) in an analogous manner to Example 418. Product isolated as a solid (0.05 g, 45%). Analysis: LCMS m/z=417 (M+1). $^1$H NMR (DMSO-d$_6$) δ: 9.17 (d, 1H, J=2.4 Hz), 8.51 (d, 1H, J=2.1 Hz), 7.93 (m, 1H), 7.79 (m, 3H), 7.48 (m, 1H), 7.15 (m, 2H), 4.73 (m, 2H), 3.71-3.87 (br m, 4H), 3.37 (m, 1H), 3.25 (m, 1H), 2.54 (s, 3H), 2.01 (br m, 4H), 1.84 (m, 2H), 1.53-1.66 (br m, 2H).

Example 489 4-(3',4'-Dimethoxybiphenyl-4-yloxy)-piperidine-1-carboxylic acid t-butyl ester

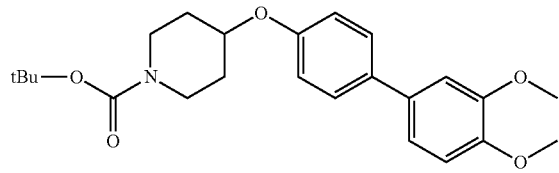 [SMILES: COc1ccc(-c2ccc(OC3CCN(C(=O)OC(C)(C)C)CC3)cc2)cc1OC]

Palladium acetate (0.008 g, 0.04 mmol), triphenylphosphine (0.023 g, 0.088 mmol) and 1,4-dioxane (4.6 mL) were combined and stirred. 4-(4-Iodophenoxy)-piperidine-1-carboxylic acid t-butyl ester (0.408 g, 1.01 mmol), 3,4-dimethoxyphenylboronic acid (0.218 g, 1.20 mmol), DMF (6.7 mL), 1 M of aqueous $Na_2CO_3$ solution (1.5 mL, 1.5 mmol) was added and the reaction was purged with nitrogen and heated at 80° C. for 2 hours. The reaction was concentrated and the residue was dissolved in EtOAc, washed with 1M $Na_2CO_3$, water, and brine. The organic phase was dried over $MgSO_4$, filtered, concentrated and purified by normal phase chromatography eluting with EtOAc/hexane to yield 220 mg (53%) of an off-white solid. Analysis: LCMS: m/z=314 (M+1); $^1$H NMR (400 MHz, $CDCl_3$) δ: 7.46 (m, 2H), 7.07 (m, 2H), 6.94 (m, 3H), 4.50 (m, 1H), 3.94 (s, 3H), 3.91 (s, 3H), 3.72 (m, 2H), 3.36 (m, 2H), 1.93 (m, 2H), 1.79 (m, 2H), 1.48 (s, 9H).

Example 490. 4-(4'-Cyano-biphenyl-4-yloxy)-piperidine-1-carboxylic acid t-butyl ester

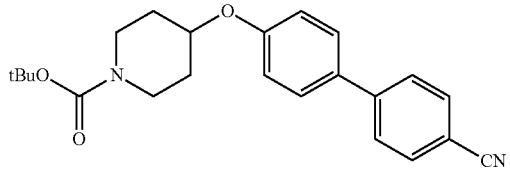 [SMILES: CC(C)(C)OC(=O)N1CCC(Oc2ccc(-c3ccc(C#N)cc3)cc2)CC1]

This example was prepared using the previous procedure with 4-cyanophenyl-boronic acid to yield the title compound, a white solid (60). Analysis: LCMS: m/z=379 (M+1); $^1$H NMR (400 MHz, DMSO-$d_6$) δ: 7.85 (m, 4H), 7.70 (m, 2H), 7.10 (m, 2H), 4.65 (m, 1H), 3.67 (m, 2H), 3.20 (m, 2H), 1.94 (m, 2H), 1.54 (m, 2H), 1.41 (s, 9H).

Example 491. 1-[4-(3',4'-Dimethoxy-biphenyl-4-yloxy)-piperidin-1-yl]-propan-1-one

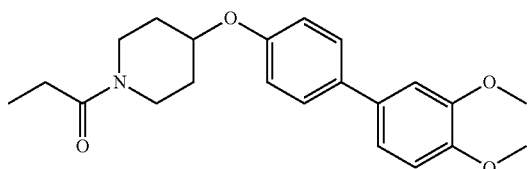

Step 1

4-(3',4'-Dimethoxybiphenyl-4-yloxy)-piperidine-1-carboxylic acid t-butyl ester (0.200 g, 0.484 mmol) and 4 M of HCl in 1,4-dioxane (5.0 mL, 20 mmol) were stirred at 60° C. for 80 min. The reaction was concentrated and the residue was dissolved in ethyl acetate, washed with 1M $Na_2CO_3$, water, and brine. The organic phase was dried with magnesium sulfate, filtered, concentrated and purified by normal phase chromatography eluting with DCM then 60/40/0.4 DCM/methanol/isopropylamine to yield 82 mg (54%) of a white solid. Analysis: LCMS: m/z=314 (M+1); $^1$H NMR (400 MHz, DMSO-$d_6$) δ: 7.53 (m, 2H), 7.12 (m, 2H), 6.99 (m, 3H), 4.41 (m, 1H), 3.83 (s, 3H), 3.77 (s, 3H), 2.94 (m, 2H), 2.57 (m, 2H), 1.91 (m, 2H), 1.45 (m, 2H).

Step 2

4-(3',4'-Dimethoxybiphenyl-4-yloxy)-piperidine (0.032 g, 0.10 mmol) and DIPEA (0.0534 mL, 0.306 mmol) in THF (2 mL) was added propanoyl chloride (18 uL, 0.20 mmol) and stirred at rt for 1 h. The reaction was concentrated, dissolved in EtOAc, and washed with 1 M aqueous $Na_2CO_3$, water, and brine. Organic phase was dried with $MgSO_4$, filtered and concentrated. The residue was purified by normal phase chromatography eluting with hexane/ethyl acetate to yield 21.5 mg (57%) of a yellow solid. Analysis: LCMS m/z=370 (M+1); $^1$H NMR (400 MHz, DMSO-$d_6$) δ: 7.55 (m, 2H), 7.13 (m, 2H), 7.01 (m, 3H), 4.64 (m, 1H), 3.89 (m, 1H), 3.88 (s, 3H), 3.77 (s, 3H), 3.69 (m, 1H), 3.36 (m, 1H), 3.25 (m, 1H), 2.33 (m, 2H), 1.93 (m, 2H), 1.56 (m, 2H), 0.99 (m, 3H).

Example 492. 1-[4-(3',4'-Dimethoxybiphenyl-4-yloxy)-piperidin-1-yl]-2-methyl-propan-1-one

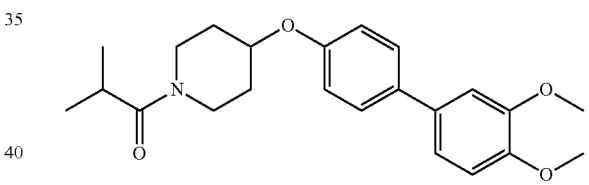

This example was synthesized using isobutyryl chloride to yield a yellow solid (70%). Analysis: LCMS m/z=384 (M+1); $^1$H NMR (400 MHz, DMSO-$d_6$) δ: 7.55 (m, 2H), 7.13 (m, 2H), 7.01 (m, 3H), 4.65 (m, 1H), 3.86 (m, 1H), 3.83 (s, 3H), 3.77 (s, 3H), 3.76 (m, 1H), 3.39 (m, 1H), 3.26 (m, 1H), 2.90 (m, 1H), 1.97 (m, 2H), 1.54 (m, 2H), 1.00 (d, 6H, J=6.7 Hz)

The following examples were synthesized using the procedure for Examples 541 and 543.

Example 493. 4'-(1-Propionyl-piperidin-4-yloxy)-biphenyl-4-carbonitrile

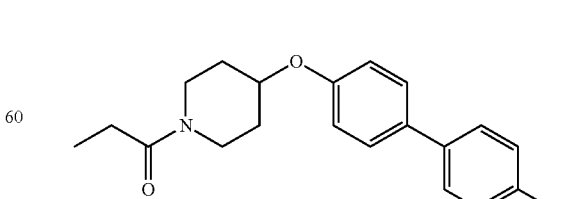

The product was isolated as a white solid. Analysis: LCMS m/z=335 (M+1); $^1$H NMR (400 MHz, DMSO-$d_6$) δ:

7.86 (m, 4H), 7.70 (m, 2H), 7.11 (m, 2H), 4.71 (m, 1H), 3.87 (m, 1H), 3.68 (m, 1H), 3.25 (m, 2H), 2.34 (m, 2H), 1.91 (m, 2H), 1.55 (m, 2H), 0.99 (m, 3H).

Example 494. 4'-(1-Isobutyrylpiperidin-4-yloxy)-biphenyl-4-carbonitrile

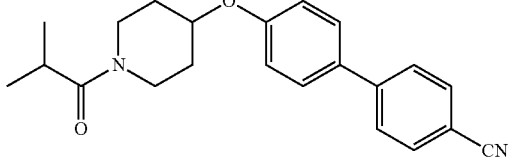

Analysis: LCMS m/z=349 (M+1); $^1$H NMR (400 MHz, DMSO-d$_6$) δ: 7.86 (m, 4H), 7.70 (m, 2H), 7.11 (m, 2H), 4.72 (m, 1H), 3.83 (m, 2H), 3.33 (m, 2H), 2.90 (m, 1H), 1.98 (m, 2H), 1.57 (m, 2H), 1.00 (d, 6H, J=6.7 Hz).

Example 495. 4'-(1-Cyclopropanecarbonyl-piperidin-4-yloxy)-biphenyl-4-carbonitrile

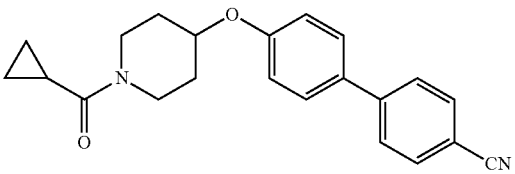 [SMILES: N#Cc1ccc(-c2ccc(OC3CCN(C(=O)C4CC4)CC3)cc2)cc1]

Analysis: LCMS: m/z=347 (M+1); $^1$H NMR (400 MHz, DMSO-d$_6$) δ: 7.86 (m, 4H), 7.71 (m, 2H), 7.12 (m, 2H), 4.73 (m, 1H), 3.94 (m, 2H), 3.54 (m, 1H), 3.27 (m, 1H), 1.96 (m, 3H), 1.58 (m, 2H), 0.71 (m, 4H).

Example 496. 1-[4-(3-Quinolin-3-yl-phenoxy)-piperidin-1-yl]-propan-1-one

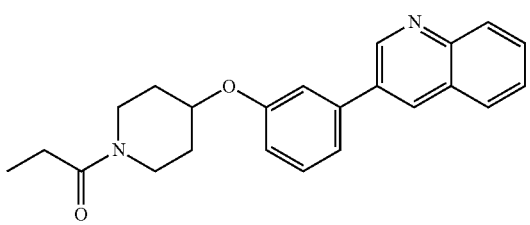 [SMILES: CCC(=O)N1CCC(Oc2cccc(-c3cnc4ccccc4c3)c2)CC1]

This example was synthesized from 4-(3-bromophenoxy)-piperidine-1-carboxylic acid t-butyl ester. Analysis: LCMS: m/z=361 (M+1); $^1$H NMR (400 MHz, DMSO-d$_6$) δ: 9.25 (d, 1H, J=2.3 Hz), 8.66 (m, 1H), 8.06 (m, 2H), 7.78 (m, 1H), 7.66 (m, 1H), 7.46 (m, 3H), 7.09 (m, 1H), 4.79 (m, 1H), 3.89 (m, 1H), 3.72 (m, 1H), 3.33 (m, 2H), 2.34 (m, 2H), 1.99 (m, 2H), 1.59 (m, 2H), 1.00 (m, 3H).

Example 497. Cyclopropyl-[4-(3-quinolin-3-yl-phenoxy)-piperidin-1-yl]-methanone

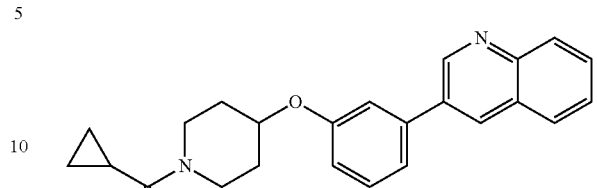

Analysis: LCMS: m/z=3732 (M+1); $^1$H NMR (400 MHz, DMSO-d$_6$) δ: 9.25 (d, 1H, J=2.4 Hz), 8.67 (m, 1H), 8.05 (m, 2H), 7.78 (m, 1H), 7.66 (m, 1H), 7.48 (m, 3H), 7.10 (m, 1H), 4.82 (m, 1H), 3.99 (m, 2H), 3.57 (m, 1H), 3.33 (m, 1H), 2.01 (m, 3H), 1.62 (m, 2H), 0.72 (m, 4H).

Example 498. 1-{4-[4-(5,6-Dimethoxypyridin-3-yl)-phenoxy]-piperidin-1-yl}-propan-1-one

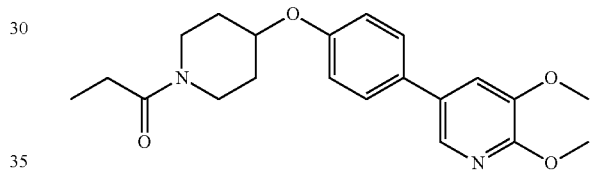

Analysis: LCMS: m/z=371 (M+1); $^1$H NMR (400 MHz, DMSO-d$_6$) δ: 7.93 (d, 1H, J=1.6 Hz), 7.60 (d, 2H, J=8.6 Hz), 7.48 (s, 1H), 7.07 (d, 2H, J=8.6 Hz), 4.67 (m, 1H), 3.87 (m, 7H), 3.70 (m, 1H), 3.27 (m, 2H), 2.33 (m, 2H), 1.93 (m, 2H), 1.58 (m, 2H), 0.99 (m, 3H).

Example 499. Cyclopropyl-{4-[4-(5,6-dimethoxypyridin-3-yl)-phenoxy]-piperidin-1-yl}-methanone

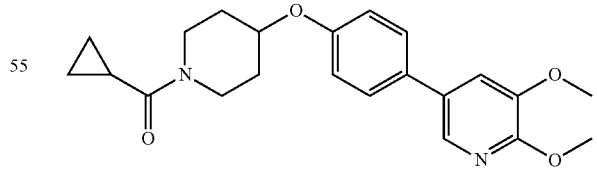

Analysis: LCMS: m/z=383 (M+1); $^1$H NMR (400 MHz, DMSO-d$_6$) δ: 7.93 (d, 1H, J=2.0 Hz), 7.61 (d, 2H, J=8.8 Hz), 7.47 (d, 1H, J=2.0 Hz), 7.07 (d, 2H, J=8.8 Hz), 4.69 (m, 1H), 3.97 (m, 1H), 3.88 (m, 7H), 3.56 (m, 1H), 3.28 (m, 1H), 1.97 (m, 3H), 1.57 (m, 2H), 0.71 (m, 4H).

Example 500. 1-[4-(3',4'-Dichlorobiphenyl-4-yloxy)-piperidin-1-yl]-propan-1-one

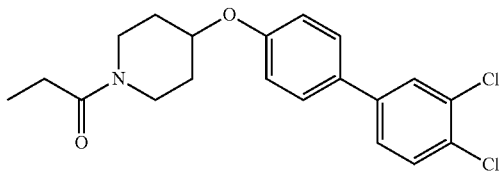 [SMILES: CCC(=O)N1CCC(Oc2ccc(-c3ccc(Cl)c(Cl)c3)cc2)CC1]

Analysis: LCMS: m/z=378 (M+1); $^1$H NMR (400 MHz, DMSO-d$_6$) δ: 7.88 (d, 1H, J=2.0 Hz), 7.66 (m, 4H), 7.08 (d, 2H, J=8.8 Hz), 4.69 (m, 1H), 3.87 (m, 1H), 3.69 (m, 1H), 3.25 (m, 2H), 2.33 (m, 2H), 1.96 (m, 2H), 1.56 (m, 2H), 0.99 (m, 3H).

Example 501. Cyclopropyl-[4-(3',4'-dichlorobiphenyl-4-yloxy)-piperidin-1-yl]-methanone

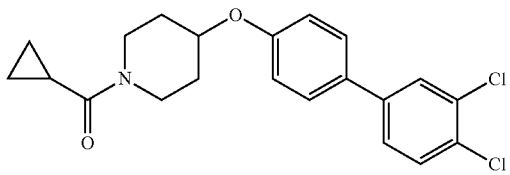 [SMILES: O=C(C1CC1)N1CCC(Oc2ccc(-c3ccc(Cl)c(Cl)c3)cc2)CC1]

Analysis: LCMS: m/z=390 (M+1); $^1$H NMR (400 MHz, DMSO-d$_6$) δ: 7.88 (d, 1H, J=2.0 Hz), 7.66 (m, 4H), 7.09 (d, 2H, J=8.8 Hz), 4.71 (m, 1H), 3.93 (m, 2H), 3.56 (m, 1H), 3.25 (m, 1H), 1.97 (m, 3H), 1.58 (m, 2H), 0.71 (m, 4H).

Example 502. 1-{4-[4-(2,3-Dihydro-1,4-benzodioxin-6-yl)-phenoxy]-piperidin-1-yl}-propan-1-one

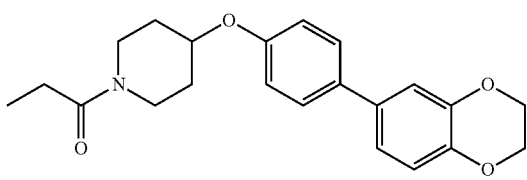 [SMILES: CCC(=O)N1CCC(Oc2ccc(-c3ccc4c(c3)OCCO4)cc2)CC1]

Analysis: LCMS: m/z=368 (M+1); $^1$H NMR (400 MHz, DMSO-d$_6$) δ: 7.49 (d, 2H, J=8.8 Hz), 7.03 (m, 4H), 6.89 (d, 1H, J=8.4 Hz), 4.63 (m, 1H), 4.26 (s, 4H), 3.87 (m, 1H), 3.68 (m, 1H), 3.24 (m, 2H), 2.33 (m, 2H), 1.93 (m, 2H), 1.55 (m, 2H), 0.99 (m, 3H).

Example 503. Cyclopropyl-{4-[4-(2,3-dihydro-1,4-benzodioxin-6-yl)-phenoxy]-piperidin-1-yl})-methanone

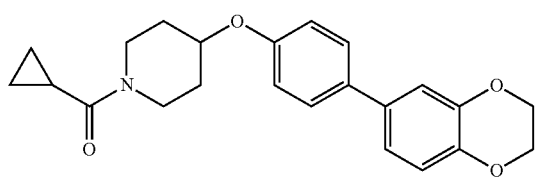 [SMILES: O=C(C1CC1)N1CCC(Oc2ccc(-c3ccc4c(c3)OCCO4)cc2)CC1]

Analysis: LCMS: m/z=380 (M+1); $^1$H NMR (400 MHz, DMSO-d$_6$) δ: 7.50 (d, 2H, J=8.8 Hz), 7.04 (m, 4H), 6.89 (m, 1H), 4.65 (m, 1H), 4.26 (s, 4H), 3.93 (m, 2H), 3.54 (m, 1H), 3.26 (m, 1H), 1.96 (m, 3H), 1.57 (m, 2H), 0.71 (m, 4H).

Example 504. 1-[4-(4'-Benzyloxy-2'-fluoro-biphenyl-4-yloxy)-piperidin-1-yl]-propan-1-one

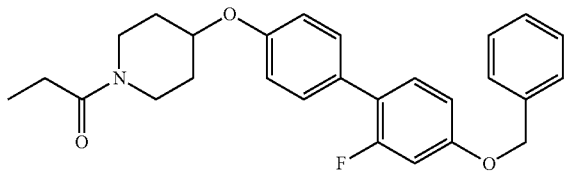 [SMILES: CCC(=O)N1CCC(Oc2ccc(-c3ccc(OCc4ccccc4)cc3F)cc2)CC1]

Analysis: LCMS: m/z=434; $^1$H NMR (400 MHz, DMSO-d$_6$) δ: 7.41 (m, 8H), 6.99 (m, 4H), 5.16 (s, 2H), 4.65 (m, 1H), 3.87 (m, 1H), 3.69 (m, 1H), 3.30 (m, 2H), 2.33 (m, 2H), 1.94 (m, 2H), 1.56 (m, 2H), 0.99 (m, 3H).

Example 505. [4-(4'-Benzyloxy-2'-fluorobiphenyl-4-yloxy)-piperidin-1-yl]-cyclopropyl-methanone

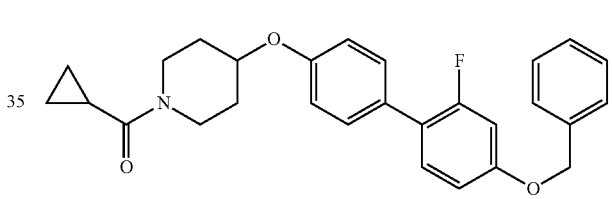

Analysis: LCMS: m/z=446; $^1$H NMR (400 MHz, DMSO-d$_6$) δ: 7.41 (m, 8H), 7.06 (d, 2H, J=8.8 Hz), 6.96 (m, 2H), 5.16 (s, 2H), 4.68 (m, 1H), 3.93 (m, 2H), 3.54 (m, 1H), 3.27 (m, 1H), 1.97 (m, 3H), 1.58 (m, 2H), 0.71 (m, 4H).

Example 506. 1-[4-(5'-Benzyloxy-3'-fluorobiphenyl-4-yloxy)-piperidin-1-yl]-propan-1-one

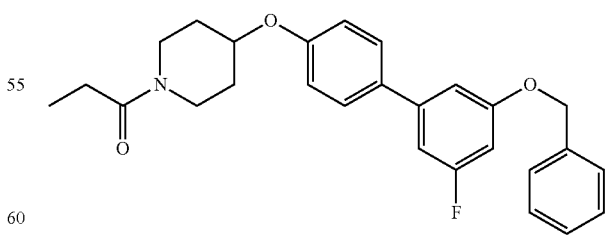

Analysis: LCMS: m/z=434; $^1$H NMR (400 MHz, DMSO-d$_6$) δ: 7.63 (m, 2H), 7.48 (m, 2H), 7.41 (m, 2H), 7.34 (m, 1H), 7.07 (m, 4H), 6.85 (m, 1H), 5.19 (s, 2H), 4.68 (m, 1H), 3.87 (m, 1H), 3.68 (m, 1H), 3.28 (m, 2H), 2.34 (m, 2H), 1.93 (m, 2H), 1.56 (m, 2H), 0.99 (m, 3H).

Example 507. [4-(5'-Benzyloxy-3'-fluorobiphenyl-4-yloxy)-piperidin-1-yl]-cyclopropyl-methanone

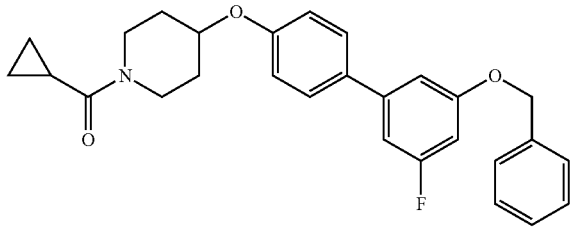 [SMILES: O=C(C1CC1)N1CCC(Oc2ccc(-c3cc(F)cc(OCc4ccccc4)c3)cc2)CC1]

Analysis: LCMS: m/z=446; $^1$H NMR (400 MHz, DMSO-$d_6$) δ: 7.63 (m, 2H), 7.48 (m, 2H), 7.41 (m, 2H), 7.35 (m, 1H), 7.07 (m, 4H), 6.85 (m, 1H), 5.20 (s, 2H), 4.70 (m, 1H), 3.93 (m, 2H), 3.55 (m, 1H), 3.28 (m, 1H), 1.97 (m, 3H), 1.58 (m, 2H), 0.71 (m, 4H).

Example 508. 1-[4-(4'-Phenoxybiphenyl-4-yloxy)-piperidin-1-yl]-propan-1-one

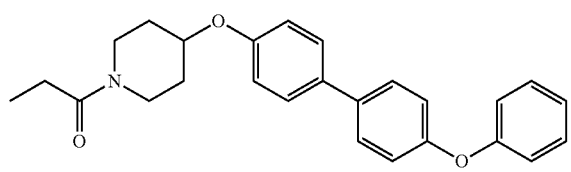 [SMILES: CCC(=O)N1CCC(Oc2ccc(-c3ccc(Oc4ccccc4)cc3)cc2)CC1]

Analysis: LCMS: m/z=402; $^1$H NMR (400 MHz, DMSO-$d_6$) δ: 8.75 (m, 2H), 7.62 (m, 2H), 7.56 (m, 2H), 7.41 (m, 2H), 7.16 (m, 1H), 7.05 (m, 6H), 4.65 (m, 1H), 3.88 (m, 1H), 3.69 (m, 1H), 3.27 (m, 2H), 2.34 (m, 2H), 1.95 (m, 2H), 1.56 (m, 2H), 0.99 (m, 3H).

Example 509. Cyclopropyl-[4-(4'-phenoxybiphenyl-4-yloxy)-piperidin-1-yl]-methanone

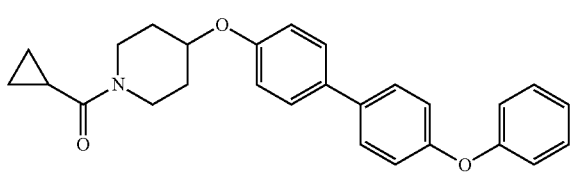 [SMILES: O=C(C1CC1)N1CCC(Oc2ccc(-c3ccc(Oc4ccccc4)cc3)cc2)CC1]

Analysis: LCMS: m/z=414; $^1$H NMR (400 MHz, DMSO-$d_6$) δ: 7.60 (m, 4H), 7.41 (m, 2H), 7.16 (m, 1H), 7.06 (m, 6H), 4.68 (m, 1H), 3.94 (m, 2H), 3.55 (m, 1H), 3.27 (m, 1H), 1.97 (m, 3H), 1.58 (m, 2H), 0.71 (m, 4H).

Example 510. 1-[4-(3'-Phenoxybiphenyl-4-yloxy)-piperidin-1-yl]-propan-1-one

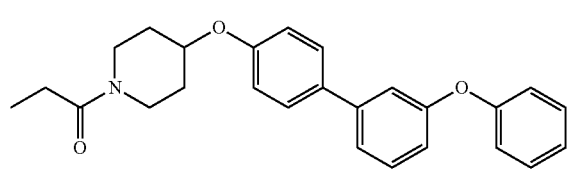 [SMILES: CCC(=O)N1CCC(Oc2ccc(-c3cccc(Oc4ccccc4)c3)cc2)CC1]

Analysis: LCMS: m/z=402; $^1$H NMR (400 MHz, DMSO-$d_6$) δ: 7.56 (m, 2H), 7.41 (m, 4H), 7.23 (m, 1H), 7.16 (m, 1H), 7.06 (m, 4H), 6.92 (m, 1H), 4.65 (m, 1H), 3.87 (m, 1H), 3.69 (m, 1H), 3.27 (m, 2H), 2.33 (m, 2H), 1.95 (m, 2H), 1.56 (m, 2H), 0.99 (m, 3H).

Example 511. Cyclopropyl-[4-(3'-phenoxybiphenyl-4-yloxy)-piperidin-1-yl]-methanone

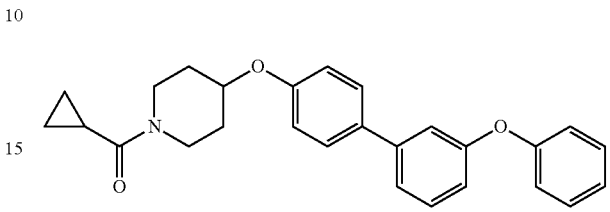

Analysis: LCMS: m/z=414; $^1$H NMR (400 MHz, DMSO-$d_6$) δ: 7.57 (m, 2H), 7.42 (m, 4H), 7.23 (m, 1H), 7.16 (m, 1H), 7.06 (m, 4H), 6.93 (m, 1H), 4.68 (m, 1H), 3.93 (m, 2H), 3.54 (m, 1H), 3.27 (m, 1H), 1.96 (m, 3H), 1.58 (m, 2H), 0.71 (m, 4H).

Example 512. 2-Methyl-1-[4-(4-quinolin-7-yl-benzenesulfonyl)-piperidin-1-yl]-propan-1-one

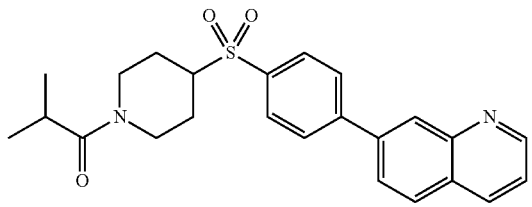 [SMILES: CC(C)C(=O)N1CCC(S(=O)(=O)c2ccc(-c3ccc4cccnc4c3)cc2)CC1]

Step 1. 1-[4-(4-Bromobenzenesulfonyl)-piperidin-1-yl]-2-methyl-propan-1-one 4-(4-Bromobenzenesulfonyl)piperidine HCl (0.300 g, 0.881 mmol) suspended in THF (5 mL) was added DIPEA (0.767 mL, 4.40 mmol) at rt. Isobutyryl chloride (0.186 mL, 1.76 mmol) was added dropwise and the mixture stirred 4 h and concentrated. The residue was partitioned between EtOAc and 1N $Na_2CO_3$, washed with water and brine then dried. The product was triturated with ether to give a white solid (275 mg, 85%). LCMS m/z=375 (M+1); $^1$H NMR ($CDCl_3$) δ: 7.70 (s, 4H), 4.76 (m, 1H), 4.09 (m, 1H), 2.98-3.14 (m, 2H), 2.69-2.77 (m, 1H), 2.48 (m, 1H), 2.11 (m, 1H), 1.95 (m, 1H), 1.60-1.72 (m, 2H), 1.10 (d, 6H, J=7 Hz).

Step 2. 2-Methyl-1-[4-(4-quinolin-7-yl-benzenesulfonyl)-piperidin-1-yl]-propan-1-one Palladium acetate (0.00195 g, 0.00868 mmol) and triphenylphosphine (0.00911 g, 0.0347 mmol) in 1,4-dioxane (2 mL, 20 mmol) were stirred under an atmosphere of nitrogen for 15 min. 1-[4-(4-Bromobenzenesulfonyl)-piperidin-1-yl]-2-methyl-propan-1-one (0.0650 g, 0.174 mmol), quinoline-7-boronic acid (0.0360 g, 0.208 mmol), DMF (4 mL) and 1 M of sodium carbonate (0.695 mL) were added and heated at 80° C. for 16 h. The mixture was concentrated, dissolved in EtOAc and washed with 1N $Na_2CO_3$, water and brine then dried over $MgSO_4$. The product was purified on ISCO (95/5 DCM/MeOH). The HCl salt was synthesized by adding 1N HCl-ether to an EtOAC solution of the base, and crystallizing the white solid from acetone-ether. Analysis: LCMS m/z=423 (M+1); ¹H NMR (DMSO) δ: 9.14 (d, 1H, J=3 Hz), 8.77 (d, 1H, J=8 Hz), 8.50 (s, 1H), 8.30 (d, 1H, J=8.7 Hz), 8.16-8.20 (m, 3H), 8.02 (d, 2H, J=8.6 Hz), 7.81 (dd, 1H, J=4, 8 Hz), 4.49 (d, 1H, J=12 Hz), 4.05 (d, 1H, J=12 Hz), 3.63-3.69 (m, 1H), 3.03 (t, 1H, J=12 Hz), 2.84 (q, 1H, J=7.6 Hz), 1.92 (bm, 2H), 1.47 (m, 1H), 1.35 (m, 1H), 0.96 (d, 6H, J=7 Hz). The following examples were synthesized using 1-[4-(4-bromobenzenesulfonyl)piperidin-1-yl]-2-methyl-propan-1-one and the appropriate boronic acid by the previous procedure.

Example 513. 1-[4-(4-Isoquinolin-7-yl-benzenesulfonyl)-piperidin-1-yl]-2-methylpropan-1-one

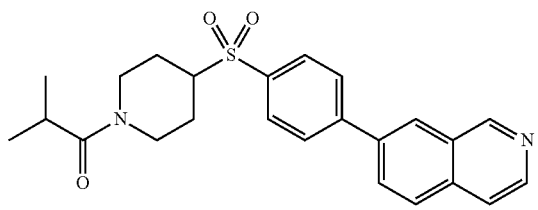 [SMILES: CC(C)C(=O)N1CCC(S(=O)(=O)c2ccc(-c3ccc4ccncc4c3)cc2)CC1]

Analysis: LCMS m/z=423 (M+1); ¹H NMR (CDCl₃) δ: 9.36 (s, 1H), 8.60 (d, 1H, J=6 Hz), 8.27 (s, 1H), 8.00 (d, 2H, J=8.5 Hz), 7.97 (s, 2H), 7.91 (d, 2H, J=8.5 Hz), 7.71 (d, 1H, J=6 Hz), 4.78 (d, 1H, J=10 Hz), 4.09 (d, 1H, J=10 Hz), 3.18 (tt, 1H, J=4, 12 Hz), 3.04 (t, 1H, J=12 Hz), 2.76 (q, 1H, J=6 Hz), 2.51 (t, 1H, J=12 Hz), 2.20 (d, 1H, J=12 Hz), 2.02 (d, 1H, J=12 Hz), 1.67-1.73 (m, 3H), 1.10 (d, 6H, J=8 Hz).

Example 514. 1-[4-(4-Isoquinolin-6-yl-benzenesulfonyl)-piperidin-1-yl]-2-methyl-propan-1-one

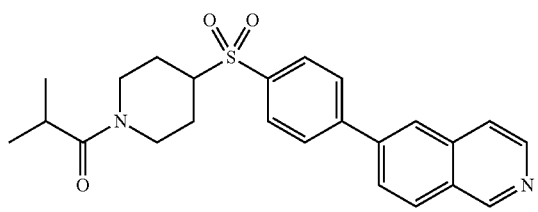 [SMILES: CC(C)C(=O)N1CCC(S(=O)(=O)c2ccc(-c3ccc4cnccc4c3)cc2)CC1]

Analysis: LCMS m/z=423 (M+1); ¹H NMR (DMSO-d₆) δ: 9.22 (s, 1H), 8.60 (d, 1H, J=6 Hz), 8.12 (d, 1H, J=8.3 Hz), 8.05 (s, 1H), 8.00 (d, 2H, J=8.3 Hz), 7.91 (d, 2H, J=8.3 Hz), 7.86 (dd, 1H, J=2, 8 Hz), 7.74 (d, 1H, J=6 Hz), 4.78 (d, 1H, J=12 Hz), 4.10 (d, 1H, J=12 Hz), 3.19 (tt, 1H, J=4, 12 Hz), 3.04 (t, 1H, J=12 Hz), 2.76 (q, 1H, J=7 Hz), 2.51 (t, 1H, J=12.5 Hz), 2.21 (d, 1H, J=10.4 Hz), 2.01 (d, 1H, J=12 Hz), 1.68-1.78 (m, 2H), 1.10 (d, 6H, J=7 Hz).

Example 515 1-[4-(4-Benzofuran-5-yl-benzenesulfonyl)-piperidin-1-yl]-2-methyl-propan-1-one

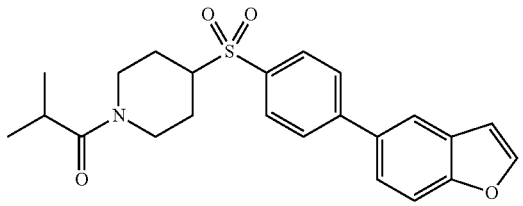 [SMILES: CC(C)C(=O)N1CCC(S(=O)(=O)c2ccc(-c3ccc4occc4c3)cc2)CC1]

Analysis: LCMS m/z=412 (M+1); ¹H NMR (CDCl₃) δ: 7.92 (d, 2H, J=8 Hz), 7.83 (d, 1H, J=2 Hz), 7.81 (d, 2H, J=8 Hz), 7.70 (d, 1 h, J=2 Hz), 7.61 (d, 1H, J=8.6 Hz), 7.54 (dd, 1H, J=2, 8 Hz), 6.86 (d, 1H, J=2 Hz), 4.78 (d, 1H, J=11 Hz), 4.08 (d, 1H, J=11 Hz), 3.16 (tt, 1H, J=4, 12 Hz), 3.03 (t, 1H, J=12 Hz), 2.76 (q, 1H, J=7 Hz), 2.51 (t, 1H, J=12 Hz, 2.18 (d, 1H, J=11 Hz), 2.00 (d, 1H, J=12 Hz), 1.61-1.73 (m, 2H), 1.10 (d, 6H, J=7 Hz).

Example 516. 1-(4-((4-(quinolin-7-yl)phenyl)thio)piperidin-1-yl)propan-1-one, HCl

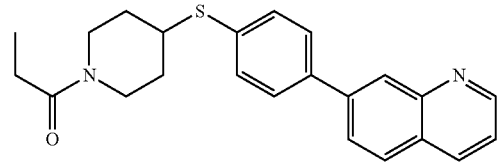 [SMILES: CCC(=O)N1CCC(Sc2ccc(-c3ccc4cccnc4c3)cc2)CC1]

Step 1. 1-(4-((4-Bromophenyl)thio)piperidin-1-yl)propan-1-one

To a solution of 4-((4-bromophenyl)thio)piperidine (500 mg, 1.83 mmol) in DCM (10 mL) was added TEA (0.8 mL, 5.5 mmol) at RT and the reaction mixture was cooled to 0° C. when propionyl chloride (254 mg, 2.75 mol) was added dropwise. The reaction was then stirred at rt for 15 h. On completion, the reaction was diluted with DCM and washed with water. The organic layer was dried over Na₂SO₄, concentrated and the crude product was purified by column chromatography using silica gel to afford 1-(4-((4-bromophenyl)thio)piperidin-1-yl)propan-1-one (600 mg, 90%) as a colorless oil. Analysis: ¹H NMR (400 MHz, CD₃OD) δ: 7.49 (m, 2H), 7.35 (m, 2H), 4.30 (m, 1H), 3.91 (m, 1H), 3.42 (m, 1H), 3.23 (m, 1H), 2.95 (m, 1H), 2.39 (q, J=7.5 Hz, 2H), 1.99 (m, 2H), 1.48 (m, 2H), 1.10 (t, J=7.5 Hz, 3H).

Step 2. 1-(4-((4-(Quinolin-7-yl)phenyl)thio)piperidin-1-yl)propan-1-one, HCl

To a solution of the Step 1 product (1 equiv) in 1,4 dioxane: water (3:1) was added Na₂CO₃ (3 equiv) and quinolin-7-boronic acid (1.2 equiv) and the reaction mixture was degassed with argon for 20 min. This was followed by addition of tetrakis(triphenylphosphine)palladium (0.01 equiv) and the reaction mixture was heated at 100° C. for 15 h. The reaction mixture was cooled to rt and filtered through celite, the filtrate concentrated, diluted with EtOAc and washed with water. The organic layer was dried over Na₂SO₄, filtered and concentrated. The crude product was purified by column chromatography using silica gel to obtain the free base which was converted to the hydrochloride salt by treatment with 4M HCl in dioxane to afford 1-(4-((4-(quinolin-7-yl)phenyl)thio)piperidin-1-yl)propan-1-one hydrochloride (32%). mp 188° C.; Analysis: LCMS (ESI) 377 (M+1); ¹H NMR (400 MHz, DMSO-d₆) δ: 9.29 (d, J=5.2 Hz, 1H), 9.13 (d, J=8.3 Hz, 1H), 8.61 (s, 1H), 8.43 (d, J=8.7 Hz, 1H), 8.29 (d, J=8.7 Hz, 1H), 8.03 (dd, J=8.3, 5.2 Hz, 1H), 7.86 (d, J=8.4 Hz, 2H), 7.61 (d, J=8.4 Hz, 2H), 4.21 (d, J=13.3 Hz, 1H), 3.81 (d, J=13.3 Hz, 1H), 3.68 (m, 1H), 3.19 (m, 1H), 2.88 (m, 1H), 2.31 (t, J=7.4 Hz, 2H), 1.99 (m, 2H), 1.56-1.29 (m, 2H), 0.97 (t, J=7.4 Hz, 3H).

The following examples were prepared by analogy to Example 516, using requisite heteroaryl boronic acid and acid chloride.

Example 517. 1-(4-((4-(Isoquinolin-6-yl)phenyl)thio)piperidin-1-yl)propan-1-one, HCl

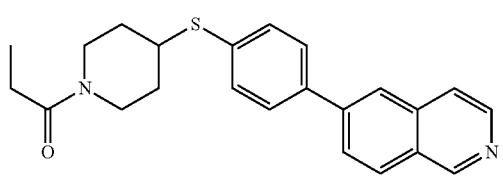 [SMILES: CCC(=O)N1CCC(Sc2ccc(-c3ccc4cnccc4c3)cc2)CC1]

Analysis: mp 222° C.; ¹H NMR (400 MHz, DMSO-d₆) δ: 9.89 (s, 1H), 8.74-8.58 (m, 3H), 8.49 (d, J=6.6 Hz, 1H), 8.40 (d, J=8.7 Hz, 1H), 7.95 (d, J=8.4 Hz, 2H), 7.64 (d, J=8.4 Hz, 2H), 4.21 (m, 1H), 3.82 (m, 1H), 3.71 (m, 1H), 3.20 (m, 1H), 2.89 (m, 1H), 2.31 (q, J=7.4 Hz, 2H), 1.99 (m, 2H), 1.47 (m, 1H), 1.38 (m, 1H), 0.97 (t, J=7.4 Hz, 3H).

Example 518. 1-(4-((4-(Quinolin-3-yl)phenyl)thio)piperidin-1-yl)propan-1-one, HCl

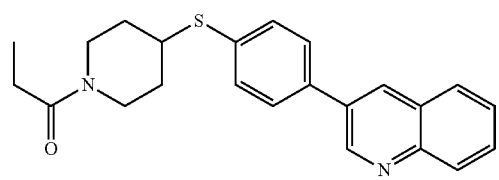 [SMILES: CCC(=O)N1CCC(Sc2ccc(-c3cnc4ccccc4c3)cc2)CC1]

Analysis: mp 70° C.; ¹H NMR (400 MHz, CD₃OD) δ: 9.15 (s, 1H), 8.60 (s, 1H), 8.11-8.00 (m, 2H), 7.85-7.75 (m, 2H), 7.71-7.51 (m, 4H), 4.32 (m, 1H), 3.93 (m, 1H), 3.55 (m, 1H), 3.00 (m, 1H), 2.41 (q, J=7.5 Hz, 2H), 2.07 (m, 1H), 1.64-1.54 (m, 1H), 1.56-1.47 (m, 1H), 1.34-1.20 (m, 2H), 1.11 (t, J=7.5 Hz, 3H).

Example 519. 1-(4-((4-(Isoquinolin-4-yl)phenyl)thio)piperidin-1-yl)propan-1-one, HCl

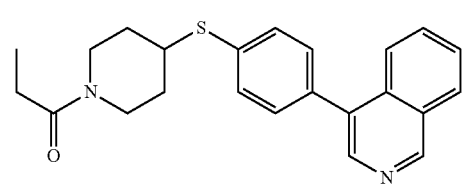 [SMILES: CCC(=O)N1CCC(Sc2ccc(-c3cncc4ccccc34)cc2)CC1]

Analysis: mp 88° C.; ¹H NMR (400 MHz, DMSO-d₆) δ: 9.95 (s, 1H), 8.70-8.62 (m, 2H), 8.21 (m, 1H), 8.12-8.01 (m, 2H), 7.62 (m, 4H), 4.22 (m, 1H), 3.82 (m, 1H), 3.72 (m, 1H), 3.21 (m, 1H), 2.92 (m, 1H), 2.32 (q, J=7.4 Hz, 2H), 2.07-1.96 (m, 2H), 1.58-1.32 (m, 2H), 0.98 (t, J=7.4 Hz, 3H).

Example 520. 1-(4-((4-(Isoquinolin-6-yl)phenyl)thio)piperidin-1-yl)propan-1-one, HCl

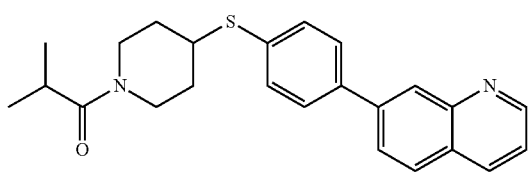 [SMILES: CC(C)C(=O)N1CCC(Sc2ccc(-c3ccc4cccnc4c3)cc2)CC1]

Analysis: mp 120° C.; LCMS (ESI): 391 (M+H)+; ¹H NMR (400 MHz, DMSO-d₆) δ: 9.23 (d, J=5.0 Hz, 1H), 9.00 (d, J=8.3 Hz, 1H), 8.53 (s, 1H), 8.37 (d, J=8.7 Hz, 1H), 8.23 (d, J=8.7 Hz, 1H), 7.94 (dd, J=8.3, 5.0 Hz, 1H), 7.86 (d, J=8.4 Hz, 2H), 7.60 (d, J=8.4 Hz, 2H), 4.22 (d, J=13.5 Hz, 1H), 3.80 (d, J=13.5 Hz, 1H), 3.68 (m, 1H), 3.23 (m, 1H), 2.87 (m, 2H), 2.00 (m, 2H), 1.47 (m, 1H), 1.36 (m, 1H), 0.98 (d, J=6.0 Hz, 6H).

Example 521. 1-(4-((4-(Isoquinolin-6-yl)phenyl)thio)piperidin-1-yl)-2-methylpropan-1-one HCl

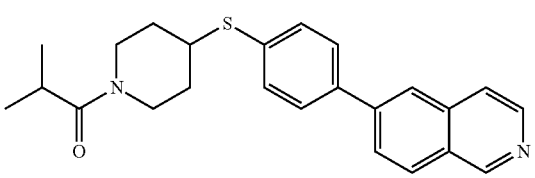 [SMILES: CC(C)C(=O)N1CCC(Sc2ccc(-c3ccc4cnccc4c3)cc2)CC1]

Analysis: mp 228° C.; LCMS (ESI): 391 (M+H)+; ¹H NMR (400 MHz, DMSO-d₆) δ: 9.82 (s, 1H), 8.70-8.52 (m, 3H), 8.40 (d, J=6.0 Hz, 1H), 8.34 (d, J=8.4 Hz, 1H), 7.93 (d, J=8.0 Hz, 2H), 7.60 (d, J=8.0 Hz, 2H), 4.26-4.17 (m, 1H), 3.91 (m, 1H), 3.70 (m, 1H), 3.24 (m, 1H), 2.86 (m, 2H), 2.07-1.93 (m, 2H), 1.51-1.33 (m, 2H), 0.98 (d, J=6.7 Hz, 6H).

Example 522. 2-Methyl-1-(4-((4-(quinolin-3-yl)phenyl)thio)piperidin-1-yl)propan-1-one, HCl

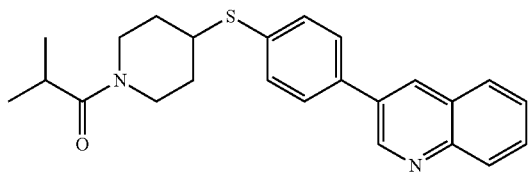 [SMILES: CC(C)C(=O)N1CCC(Sc2ccc(-c3cnc4ccccc4c3)cc2)CC1]

Analysis: mp 130° C.; LCMS (ESI): 391 (M+H)+; ¹H NMR (400 MHz, DMSO-d₆) δ: 9.48 (s, 1H), 9.09 (s, 1H), 8.22 (d, J=8.6 Hz, 2H), 7.96 (d, J=8.6 Hz, 2H), 7.82 (t, J=7.6 Hz, 1H), 7.67-7.50 (m, 3H), 4.22 (m, 1H), 3.91 (m, 1H), 3.69

(m, 1H), 3.23 (m, 1H), 2.87 (m, 2H), 2.06-1.92 (m, 2H), 1.45-1.31 (m, 2H), 0.98 (d, J=6.5 Hz, 6H).

Example 523. 1-(4-((4-(Isoquinolin-4-yl)phenyl)thio)piperidin-1-yl)-2-methylpropan-1-one HCl

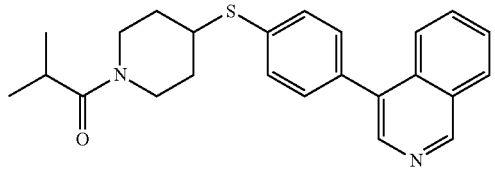 [SMILES: CC(C)C(=O)N1CCC(Sc2ccc(-c3cncc4ccccc34)cc2)CC1]

Analysis: mp 120° C.; LCMS (ESI): 391 (M+H)+; $^1$H NMR (400 MHz, DMSO-$d_6$) δ: 9.80 (s, 1H), 8.64 (s, 1H), 8.55 (d, J=8.2 Hz, 1H), 8.12 (m, 1H), 8.07-7.96 (m, 2H), 7.67-7.50 (m, 4H), 4.24 (m, 1H), 3.92 (m, 1H), 3.71 (m, 1H), 3.25 (m, 1H), 2.88 (m, 2H), 2.03 (m, 2H), 1.49 (m, 1H), 1.39 (m, 1H), 0.99 (d, J=7.0 Hz, 6H).

Example 524. 1-{4-[Methyl-(4-quinolin-3-yl-phenyl)-amino]-piperidin-1-yl}-propan-1-one, HCl

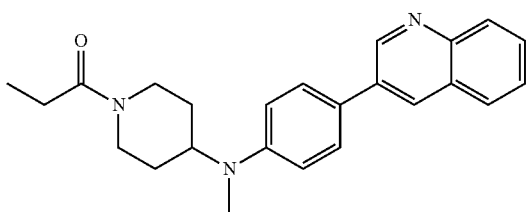 [SMILES: CCC(=O)N1CCC(N(C)c2ccc(-c3cnc4ccccc4c3)cc2)CC1]

Step 1. 4-[(4-Bromophenyl)-methyl-amino]-piperidine-1-carboxylic acid tert-butyl ester A mixture of 4-(4-bromophenylamino)-piperidine-1-carboxylic acid t-butyl ester (1.5 g, 4.22 mmol), $K_2CO_3$ (2.91 g, 21.1 mmol), methyl iodide (788 µL, 12.6 mmol), and acetonitrile (30 mL) was heated at 80° C. for 24 h. After cooled to RT, the reaction mixture was concentrated. The residue was diluted with DCM (100 mL), washed with $H_2O$, brine, dried ($Na_2SO_4$), and concentrated. The residue was purified by chromatography on silica gel (0-10% MeOH/DCM) gave 1.0 g (64%) of colorless oil. Analysis: $^1$H NMR (400 MHz, DMSO-$d_6$) δ: 7.25-7.31 (2H, m), 6.74-6.80 (2H, m), 3.97-4.10 (2H, m), 3.73-3.85 (1H, m), 2.74-2.92 (2H, m), 2.66 (3H, s), 1.48-1.63 (4H, m), 1.40 (9H, s).

Step 2 4-[Methyl-(4-quinolin-3-yl-phenyl)-amino]-piperidine-1-carboxylic acid t-butyl ester A flask charged with 4-[(4-bromophenyl)-methylamino]-piperidine-1-carboxylic acid t-butyl ester (1.0 g, 2.71 mmol), 3-quinolineboronic acid (482 mg, 2.79 mmol), palladium acetate (61 mg, 0.271 mmol), triphenylphosphine (142 mg, 0.542 mmol), 1.0 M of $Na_2CO_3$ (13.5 mL, 13.5 mmol), 1,4-dioxane (10 mL), and DMF (10 mL) was flashed with nitrogen for 15 min. The reaction mixture was heated at 85° C. for 4 h then RT over 2 days. The reaction mixture was concentrated and the residue was diluted with EtOAc (100 mL), washed with 1M $Na_2CO_3$ solution (35 mL), the water layer was back extracted with EtOAc (50 mL). The combined organic layers were washed with $H_2O$, brine, dried ($Na_2SO_4$), and concentrated. The residue was chromatography on silica gel (0-70% EtOAc/Hexanes) afforded 586 mg (52%) of light brownish oil. Analysis: $^1$H NMR (400 MHz, DMSO-$d_6$) δ: 9.21-9.23 (1H, m), 8.48-8.50 (1H, m), 7.98-8.02 (2H, m), 7.72-7.76 (2H, m), 7.67-7.72 (1H, m), 7.57-7.63 (1H, m), 6.96-7.01 (2H, m), 4.01-4.12 (2H, m), 3.90-4.00 (1H, m), 2.82-2.97 (2H, m), 2.78 (3H, s), 1.53-1.70 (4H, m), 1.42 (9H, s) ppm.

Step 3. Methylpiperidin-4-yl-(4-quinolin-3-yl-phenyl)-amine

To a solution of 4-[methyl-(4-quinolin-3-yl-phenyl)-amino]-piperidine-1-carboxylic acid t-butyl ester (586 mg, 1.40 mmol) in DCM (20 mL) was added 4.0 M of HCl in 1,4-dioxane (3.51 mL, 14.0 mmol) dropwise. After 18 h, the red solid precipitation was collected by filtration, washed with DCM, dried to give 630 mg (100%) of the HCl salt. Analysis: $^1$H NMR (400 MHz, DMSO-$d_6$) δ: 9.58-9.61 (1H, m), 9.28-9.32 (1H, m), 8.99-9.22 (2H, m), 8.36-8.42 (1H, m), 8.28-8.33 (1H, m), 8.00-8.06 (1H, m), 7.87-7.96 (3H, m), 7.12-7.17 (1H, m), 4.13-4.25 (1H, m), 3.32-3.41 (2H, m), 3.00-3.14 (2H, m), 2.87 (3H, s), 2.00-2.15 (2H, m), 1.76-1.87 (2H, m).

Step 4

A vial charged with methyl-piperidin-4-yl-(4-quinolin-3-yl-phenyl)-amine 3HCl (110 mg, 0.26 mmol), DIPEA (449 µL, 2.58 mmol) in DCM (7 mL) was added propanoyl chloride (25 µL, 0.28 mmol). After 30 min, the reaction was quenched with MeOH (3 mL) and concentrated. The residue was purified by prep-HPLC and the isolated fractions were combined, neutralized with saturated $NaHCO_3$ solution (25 mL), extracted with DCM (3×25 mL). The combined organic layers were dried ($Na_2SO_4$), and concentrated. The product was dissolved in DCM (~5 mL) and mixed with 1.2 equivalents of 0.5 M HCl in MeOH and concentrated. The residue was dissolved in a small amount of DCM and concentrated—this procedure was repeated several times, collected and dried to give 91 mg (86%) of red solid. Analysis: LCMS m/z 374 (M+1); $^1$H NMR (400 MHz, DMSO-$d_6$) δ: 9.55-9.61 (1H, m), 9.24-9.30 (1H, m), 8.26-8.39 (2H, m), 7.93-8.08 (3H, m), 7.86-7.93 (1H, m), 7.16-7.49 (1H, m), 4.49-4.60 (2H, m), 3.92-4.10 (2H, m), 3.06-3.19 (1H, m), 2.85-3.00 (3H, m), 2.55-2.70 (1H, m), 2.34 (2H, q, J=7.5 Hz), 1.47-1.85 (4H, m), 1.00 (3H, t, J=7.4 Hz). The following compounds were synthesized using the procedure for Example 524.

Example 525. Cyclopropyl-{4-[methyl-(4-quinolin-3-yl-phenyl)-amino]-piperidin-1-yl}-methanone, HCl

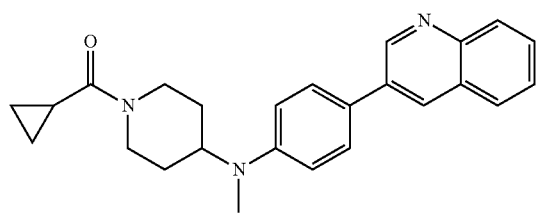 [SMILES: CN(c1ccc(-c2cnc3ccccc3c2)cc1)C1CCN(C(=O)C2CC2)CC1]

The product was isolated as a red solid. Analysis: LCMS m/z 386 (M+1); $^1$H NMR (400 MHz, DMSO-$d_6$) δ: 9.57-9.61 (1H, m), 9.26-9.31 (1H, m), 8.34-8.39 (1H, m), 8.27-8.33 (1H, m), 7.94-8.07 (3H, m), 7.86-7.93 (1H, m), 6.90-7.75 (2H, m), 4.47-4.58 (1H, m), 4.34-4.45 (1H, m), 4.01-4.13 (1H, m), 3.12-3.28 (1H, m), 2.83-3.04 (3H, m), 2.54-2.74 (1H, m), 1.96-2.05 (1H, m), 1.65-1.91 (3H, m), 1.51-1.65 (1H, m), 0.64-0.81 (4H, m).

Example 526. 1-[4-(4-Quinolin-3-yl-phenylamino)-piperidin-1-yl]-propan-1-one, HCl

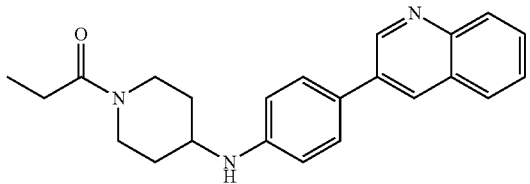 [SMILES: CCC(=O)N1CCC(Nc2ccc(-c3cnc4ccccc4c3)cc2)CC1]

The product was isolated as a dark-red solid. Analysis: LCMS m/z 360 (M+1); $^1$H NMR (400 MHz, DMSO-$d_6$) δ: 9.52-9.57 (1H, m), 9.18-9.24 (1H, m), 8.24-8.35 (2H, m), 7.96-8.04 (1H, m), 7.82-7.91 (3H, m), 6.94-7.06 (2H, m), 4.27-4.37 (1H, m), 3.82-3.92 (1H, m), 3.59-3.71 (1H, m), 3.11-3.22 (1H, m), 2.74-2.86 (1H, m), 2.34 (2H, q, J=7.3 Hz), 1.89-2.04 (2H, m), 1.25-1.47 (2H, m), 1.00 (3H, t, J=7.4 Hz).

Example 527. Cyclopropyl-[4-(4-quinolin-3-yl-phenylamino)-piperidin-1-yl]-methanone, HCl

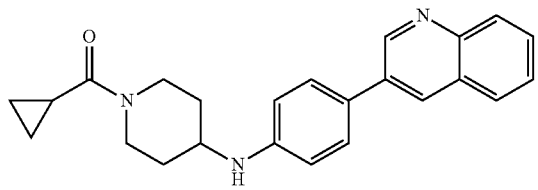 [SMILES: O=C(C1CC1)N1CCC(Nc2ccc(-c3cnc4ccccc4c3)cc2)CC1]

The product was isolated as a dark-red solid. Analysis: LCMS m/z 372 (M+1); $^1$H NMR (400 MHz, DMSO-$d_6$) δ: 9.49-9.53 (1H, m), 9.13-9.19 (1H, m), 8.22-8.32 (2H, m), 7.94-8.01 (1H, m), 7.80-7.90 (3H, m), 6.91-7.02 (2H, m), 4.19-4.34 (2H, m), 3.62-3.73 (1H, m), 3.22-3.37 (1H, m), 2.77-2.92 (1H, m), 1.88-2.09 (3H, m), 1.25-1.51 (2H, m), 0.68-0.76 (4H, m).

Example 528. {4-[Methyl-(4-quinolin-3-yl-phenyl)-amino]-piperidin-1-yl}-(R)-tetrahydrofuran-2-yl-methanone, HCl

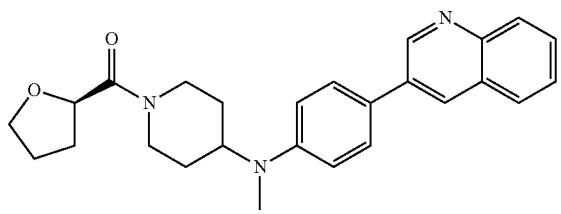 [SMILES: CN(c1ccc(-c2cnc3ccccc3c2)cc1)C1CCN(C(=O)[C@H]2CCCO2)CC1]

A mixture of methylpiperidin-4-yl-(4-quinolin-3-yl-phenyl)-amine; 3HCl (110 mg, 0.26 mmol), (R)-tetrahydrofuran-2-carboxylic acid (27 μL, 0.28 mmol), HATU (117 mg, 0.31 mmol), DIPEA (449 μL, 2.58 mmol) in DCM (5 mL) was stirred at RT for 1 h. The solvent was removed and the residue was purified by pre-HPLC. The isolated fractions were combined, neutralized with sat. NaHCO$_3$ solution (25 mL), extracted with DCM (3×25 mL). The combined organic layers were dried (Na$_2$SO$_4$), and concentrated. The product was dissolved in DCM (~5 mL) and mixed with 1.2 equivalent of 0.5 M HCl in MeOH and concentrated. The residue was dissolved in a small amount of DCM and concentrated—repeated this procedure several times, dried to give 108 mg (93%) of red solid. Analysis: LCMS m/z 416 (M+1); $^1$H NMR (400 MHz, DMSO-$d_6$) δ: 9.55-9.61 (1H, m), 9.23-9.29 (1H, m), 8.25-8.38 (2H, m), 7.93-8.06 (3H, m), 7.85-7.92 (1H, m), 6.88-7.71 (2H, m), 4.65-4.71 (1H, m), 4.46-4.51 (1H, m), 4.02-4.17 (2H, m), 3.69-3.85 (2H, m), 3.06-3.24 (1H, m), 2.81-3.00 (3H, m), 2.61-2.76 (1H, m), 1.92-2.15 (2H, m), 1.48-1.91 (6H, m).

Example 529. N-Ethyl-4-[4-(2-hydroxy-8-methyl-7-quinolyl)phenoxy]piperidine-1-carboxamide

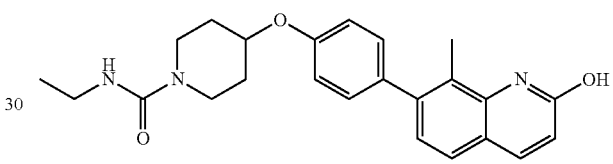

Step 1. tert-Butyl 4-[4-(2-methoxy-8-methyl-7-quinolyl)phenoxy]piperidine-1-carboxylate Palladium acetate (0.028 g, 0.124 mmol) and triphenylphosphine (0.13 g, 0.50 mmol) in dioxane (10 mL) were stirred 15 min under an atmosphere of nitrogen. 4-[4-(4,4,5,5-tetramethyl-1,3,2-dioxaborolan-2-yl)-phenoxy]-piperidine-1-carboxylic acid tert-butyl ester (1.00 g, 2.5 mmol), 7-bromo-8-methyl-2-methoxyquinoline (0.688 g, 2.73 mmol), DMF (10 mL) and 1 M Na$_2$CO$_3$ (7 mL) were added and heated at 90° C. for 18 h. The mixture was concentrated, dissolved in EtOAc, washed with 1N Na$_2$CO$_3$, water and brine, then dried (MgSO$_4$). The product was purified by ISCO (silica get, 80 g column; 20-80% EtOAc/hexanes) to give a white solid (0.8 g, 72%). Analysis: LCMS m/z=449 (M+1). $^1$H NMR (CDCl$_3$) δ 7.98 (d, J=8.8 Hz, 1H), 7.59 (d, J=8.0 Hz, 1H), 7.35-7.31 (m, 2H), 7.28 (d, J=8.3 Hz, 1H), 7.04-6.95 (m, 2H), 6.90 (d, J=8.8 Hz, 1H), 4.54 (dquin, J=7.1, 3.3 Hz, 1H), 4.09 (s, 3H), 3.83-3.67 (m, 2H), 3.45-3.29 (m, 2H), 2.65 (s, 3H), 2.04-1.93 (m, 2H), 1.89-1.75 (m, 2H), 1.48 (s, 9H).

Step 2. 8-Methyl-7-[4-(4-piperidyloxy)phenyl]quinolin-2-ol, HCl tert-Butyl 4-[4-(2-methoxy-8-methyl-7-quinolyl)phenoxy]piperidine-1-carboxylate (750 mg. 1.7 mmol) in 4N HCl in dioxane (10 mL) was heated at 70° C. for 12 h and concentrated. The solid was triturated with ether, collected and dried to give 600 mg (97%) of a tan solid as the HCl salt. LCMS=335 m/z (M+1); 1H NMR (DMSO-d6) δ 10.84 (br s, 1H), 8.76 (br s, 2H), 7.93 (d, J=9.5 Hz, 1H), 7.55 (d, J=8.0 Hz, 1H), 7.29 (d, J=8.8 Hz, 2H), 7.09 (d, J=8.8 Hz, 2H), 7.05

(d, J=8.0 Hz, 1H), 6.52 (d, J=9.5 Hz, 1H), 4.72 (dt, J=7.2, 3.8 Hz, 1H), 3.26 (br s, 2H), 3.10 (br d, J=5.8 Hz, 2H), 2.31 (s, 3H), 2.24-2.08 (m, 2H), 1.96-1.78 (m, 2H).

Step 3. N-Ethyl-4-[4-(2-hydroxy-8-methyl-7-quinolyl)phenoxy]piperidine-1-carboxamide 8-Methyl-7-[4-(4-piperidyloxy)phenyl]quinolin-2-ol HCl (100 mg, 0.27 mmol), isocyanatoethane (38 mg, 0.43 mmol), diisopropylethylamine (0.14 mL) in DCM (3 mL) was stirred at rt for 4 h. The mixture was concentrated, dissolved in EtOAc and washed with 1N Na₂CO₃ and brine and then dried (MgSO₄). The product was chromatographed on Isco (12 g silica gel, 0-5% MeOH/DCM) to give a white solid. Analysis: LCMS m/z=406 (M+1); ¹H NMR (DMSO-d₆ (deuterated dimethylsulfoxide)) δ: 10.82 (s, 1H), 7.92 (d, J=9.5 Hz, 1H), 7.54 (d, J=8.0 Hz, 1H), 7.26 (d, J=8.8 Hz, 2H), 7.10-6.97 (m, 3H), 6.57-6.45 (m, 2H), 4.59 (dt, J=8.1, 4.4 Hz, 1H), 3.75-3.63 (m, 2H), 3.17-3.01 (m, 4H), 2.31 (s, 3H), 2.02-1.87 (m, 2H), 1.59-1.46 (m, 2H), 1.01 (t, J=7.2 Hz, 3H)

The following examples were synthesized using the procedure of Example 73, Method A.

Example 530. 4-[4-(8-Methyl-7-quinolyl)phenoxy]-N-(2-pyrrolidin-1-ylethyl)piperidine-1-carboxamide HCl

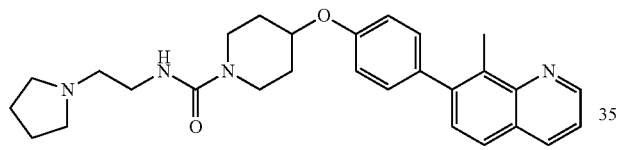

LCMS m/z=459 (M+1); ¹H NMR (CHLOROFORM-d) δ: 8.99 (dd, J=4.3, 1.8 Hz, 1H), 8.16 (dd, J=8.3, 1.8 Hz, 1H), 7.69 (d, J=8.3 Hz, 1H), 7.47 (d, J=8.3 Hz, 1H), 7.41 (dd, J=8.2, 4.1 Hz, 1H), 7.33 (d, J=8.5 Hz, 2H), 7.00 (d, J=8.8 Hz, 2H), 6.84 (br s, 1H), 4.61-4.52 (m, 1H), 3.89-3.78 (m, 2H), 3.71-3.63 (m, 2H), 3.54-3.42 (m, 3H), 3.28-3.19 (m, 2H), 2.77 (s, 3H), 2.17 (br s, 4H), 2.10-1.96 (m, 3H), 1.93-1.80 (m, 4H)

Example 531. 4-[4-(8-Methyl-7-quinolyl)phenoxy]-N-(2-morpholinoethyl)piperidine-1-carboxamide HCl

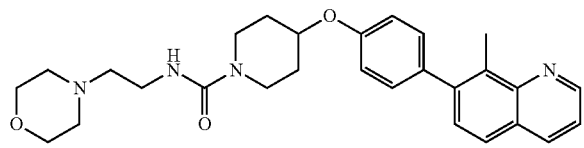 [SMILES: Cc1c(-c2ccc(OC3CCN(C(=O)NCCN4CCOCC4)CC3)cc2)ccc2cccnc12]

LCMS m/z=475 (M+1); ¹H NMR (400 MHz, DMSO-d6) δ:10.62 (br s, 1H), 9.07 (d, J=3.0 Hz, 1H), 8.66 (br s, 1H), 8.00 (br d, J=8.3 Hz, 1H), 7.75 (br s, 1H), 7.61 (d, J=8.5 Hz, 1H), 7.40 (d, J=8.8 Hz, 2H), 7.12 (d, J=8.8 Hz, 2H), 7.03 (br s, 1H), 4.66 (dt, J=8.0, 4.2 Hz, 1H), 3.97 (br d, J=10.5 Hz, 4H), 3.79 (br t, J=11.3 Hz, 4H), 3.50 (br d, J=12.3 Hz, 2H), 3.44 (br d, J=7.0 Hz, 2H), 3.24-3.02 (m, 7H), 2.70 (s, 3H), 1.98 (br d, J=8.5 Hz, 2H), 1.63-1.53 (m, 2H)

Example 532. (4-Isopropylpiperazin-1-yl)-[4-[4-(8-methyl-7-quinolyl)phenoxy]-1-piperidyl]methanone, HCl

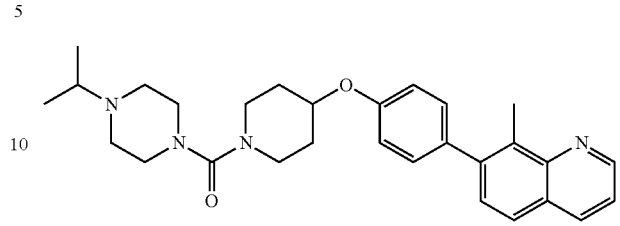

Step 1. 4-Nitrophenyl) 4-[4-(8-methyl-7-quinolyl)phenoxy]piperidine-1-carboxylate 8-Methyl-7-[4-(4-piperidyloxy)phenyl]quinoline (0.8 g, 2.51 mmol) in DCM (15 mL) was added TEA (0.70 mL, 5.03 mmol) and (4-nitrophenyl) carbonochloridate (0.66 g, 3.27 mmol) on an ice bath. The solution was stirred for 2 h at rt and then concentrated. The residue was dissolved in EtOAc and washed with 1N Na₂CO₃, and brine then dried over MgSO₄. The product was purified by ISCO (80 g silica gel, 30-60% EtOAc/hexanes). The fractions containing pure product were concentrated to give a white solid (900 mg, 73%). This material was used in the next step. Analysis: LCMS m/z=484 (M+1); ¹H NMR (400 MHz, DCCl₃) δ: 9.00 (dd, J=4.3, 1.8 Hz, 1H), 8.32-8.24 (m, 2H), 8.20-8.13 (m, 1H), 7.71 (d, J=8.5 Hz, 1H), 7.47 (d, J=8.3 Hz, 1H), 7.43 (dd, J=8.3, 4.3 Hz, 1H), 7.38-7.31 (m, 3H), 7.10-6.99 (m, 2H), 4.68 (tt, J=6.2, 3.3 Hz, 1H), 3.96-3.63 (m, 4H), 2.78 (s, 3H), 2.14-1.94 (m, 4H)

Step 2. (4-Isopropylpiperazin-1-yl)-[4-[4-(8-methyl-7-quinolyl)phenoxy]-1-piperidyl]methanone, HCl (4-Nitrophenyl) 4-[4-(8-methyl-7-quinolyl)phenoxy]piperidine-1-carboxylate (0.04 g, 0.082 mmol), 1-isopropylpiperazine (0.042 g, 0.33 mmol), and 1,4-dioxane (1 mL) was heated at 125° C. for a total of 4 h on the microwave. The mixture was diluted in EtOAc, washed with 1N Na₂CO₃ and brine then dried over MgSO₄. The product was purified by ISCO (4 g, MeOH/DCM 0-10%) to give an oil. The HCl salt was synthesized by adding 2N HCl-ether to a DCM solution of base to give a light yellow solid (25 mg, 58%). Analysis: LCMS m/z=473 (M+1); ¹H NMR (400 MHz, DMSO-d6) δ: 10.61 (br s, 1H), 9.07 (br d, J=3.3 Hz, 1H), 8.66 (br s, 1H), 8.00 (br d, J=8.3 Hz, 1H), 7.75 (br s, 1H), 7.61 (br d, J=8.5 Hz, 1H), 7.40 (d, J=8.5 Hz, 2H), 7.13 (d, J=8.5 Hz, 2H), 4.68 (br s, 1H), 3.66 (br d, J=13.6 Hz, 2H), 3.59-3.44 (m, 3H), 3.40-3.27 (m, 4H), 3.15 (br t, J=9.5 Hz, 2H), 3.07-2.95 (m, 2H), 2.70 (s, 3H), 1.99 (br s, 2H), 1.69-1.58 (m, 2H), 1.28 (d, J=6.5 Hz, 6H).

Example 533. (4-Methylpiperazin-1-yl)-[4-[4-(8-methyl-7-quinolyl)phenoxy]-1-piperidyl]methanone, HCl

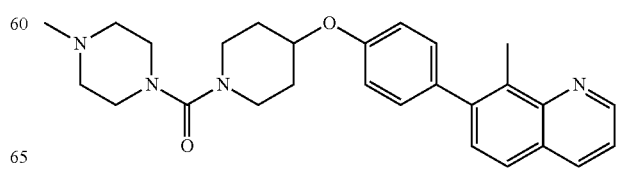

(4-Nitrophenyl) 4-[4-(8-methyl-7-quinolyl)phenoxy]piperidine-1-carboxylate (0.1 g, 0.21 mmol), 1-methylpiperazine (0.1 g, 1.0 mmol), and 1,4-dioxane (2 mL) was heated at 125° C. for a total of 4 h on the microwave. The mixture was diluted in EtOAc, washed with 1N Na$_2$CO$_3$ and brine then dried over MgSO$_4$. The product was purified by ISCO (4 g, MeOH/DCM 0-10%) to give an oil. The HCl salt was synthesized by adding 2N HCl-ether to a DCM solution of base, and concentrating to give a yellow salt (55 mg, 59%). Analysis: LCMS m/z=445 (M+1); $^1$H NMR (400 MHz, DMSO-d6) δ: 10.75 (br s, 1H), 9.08 (br d, J=3.5 Hz, 1H), 8.68 (br s, 1H), 8.01 (br d, J=8.8 Hz, 1H), 7.77 (br s, 1H), 7.62 (br d, J=8.3 Hz, 1H), 7.40 (br d, J=8.5 Hz, 2H), 7.13 (br d, J=8.8 Hz, 2H), 4.68 (br s, 1H), 3.66 (br d, J=14.1 Hz, 2H), 3.53 (br d, J=13.3 Hz, 2H), 3.41-3.33 (m, 2H), 3.26-3.12 (m, 4H), 3.07-2.97 (m, 2H), 2.80-2.76 (m, 3H), 2.71 (s, 3H), 1.99 (br s, 2H), 1.65 (br d, J=9.0 Hz, 2H).

Example 534. [4-[4-(8-Methyl-7-quinolyl)phenoxy]-1-piperidyl]-(4-morpholino-1-piperidyl)methanone, HCl

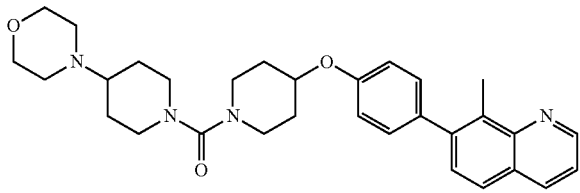 [SMILES: Cc1c(-c2ccc(OC3CCN(C(=O)N4CCC(N5CCOCC5)CC4)CC3)cc2)ccc2cccnc12]

(4-Nitrophenyl) 4-[4-(8-methyl-7-quinolyl)phenoxy]piperidine-1-carboxylate (0.075 g, 0.16 mmol), 4-(4-piperidyl)morpholine (0.13 g, 0.78 mmol) and 1-methyl-2-pyrrolidinone (2.058 g, 2 mL, 20.76 mmol) was heated at 155° C. for 1.5 h on the microwave. The mixture was diluted in EtOAc, washed with 1N Na$_2$CO$_3$ and brine then dried over MgSO$_4$. The product was purified by ISCO (4 g, MeOH/DCM 0-10%) to give an solid. This material was triturated with ether and hexanes then collected to give a white solid (40 mg. 49%). Analysis: LCMS m/z=515 (M+1); $^1$H NMR (CHLOROFORM-d) δ: 8.99 (dd, J=4.3, 1.8 Hz, 1H), 8.16 (dd, J=8.3, 1.8 Hz, 1H), 7.70 (d, J=8.3 Hz, 1H), 7.47 (d, J=8.5 Hz, 1H), 7.41 (dd, J=8.2, 4.1 Hz, 1H), 7.37-7.31 (m, 2H), 7.01 (d, J=8.8 Hz, 2H), 4.55 (dt, J=7.1, 3.6 Hz, 1H), 3.82-3.68 (m, 6H), 3.64-3.50 (m, 2H), 3.28-3.12 (m, 2H), 2.84-2.78 (m, 2H), 2.77 (s, 3H), 2.57 (br s, 3H), 2.42-2.27 (m, 1H), 2.10-1.98 (m, 2H), 1.90-1.81 (m, 4H), 1.55-1.43 (m, 2H)

Example 535. (4-Ethyl 1piperazin-1-yl)-[4-[4-(8-methyl-7-quinolyl)phenoxy]-1-piperidyl]methanone tosylate

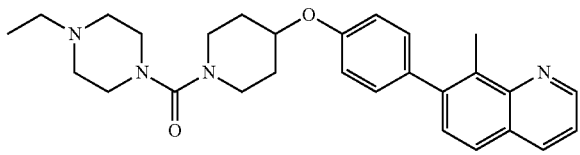 [SMILES: CCN1CCN(C(=O)N2CCC(Oc3ccc(-c4ccc5cccnc5c4C)cc3)CC2)CC1]

(4-Nitrophenyl) 4-[4-(8-methyl-7-quinolyl)phenoxy]piperidine-1-carboxylate (0.1 g, 0.21 mmol), 1-ethylpiperazine (0.12 g, 1.03 mmol), and 1-methyl-2-pyrrolidinone (1 mL) was heated at 160° C. for 1 h on the microwave. The mixture was diluted in EtOAc, washed with 1N Na$_2$CO$_3$ and brine then dried over MgSO$_4$. The product was purified by ISCO (4 g, MeOH/DCM 0-10%) to give an oil. The tosylate salt was synthesized by adding p-toluenesulfonic acid monohydrate in acetone (2 mL) to an acetone solution of base and concentrating. The light yellow solid was suspended in DCM and ether added, the product collected and dried under vacuum (75 mg, 68%). Analysis: LCMS m/z=459 (M+1); $^1$H NMR (400 MHz, DMSO-d6) δ: 9.32 (br s, 1H), 9.02 (br d, J=3.0 Hz, 1H), 8.52 (br s, 1H), 7.93 (br d, J=8.3 Hz, 1H), 7.65 (br s, 1H), 7.54 (br d, J=7.8 Hz, 1H), 7.47 (d, J=8.0 Hz, 4H), 7.39 (d, J=8.5 Hz, 2H), 7.15-7.08 (m, 6H), 4.68 (br s, 1H), 3.68 (br d, J=13.8 Hz, 2H), 3.54 (br d, J=14.3 Hz, 2H), 3.45 (br d, J=11.5 Hz, 2H), 3.21-2.95 (m, 8H), 2.68 (s, 3H), 2.29 (s, 6H), 1.99 (br s, 2H), 1.65 (br d, J=8.3 Hz, 2H), 1.22 (t, J=7.3 Hz, 3H)

Example 536. N-Ethyl-4-[4-(7-methylpyrazolo[1,5-a]pyridin-6-yl)phenoxy]piperidine-1-carboxamide

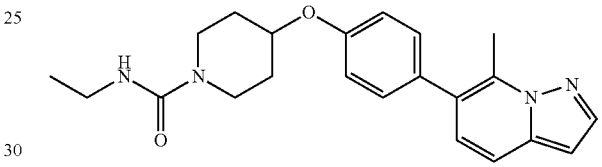

7-Methyl-6-[4-(4-piperidyloxy)phenyl]pyrazolo[1,5-a]pyridine dihydrochloride (0.08 g, 0.21 mmol) and triethylamine (0.09 mL) in DCM (3 mL) was added isocyanatoethane (0.03 g, 0.022 mL, 0.42 mmol) dropwise. After stirring at rt for 4 h the solution was concentrated, dissolved in EtOAc, washed with 1N Na$_2$CO$_3$ and brine and then dried over MgSO$_4$. The product was purified by ISCO (12 g silica gel, 40-90% EtOAc/hexanes), and crystallized from ether to give a white solid (60 mg, 75%); LCMS m/z=379 (M+1); $^1$H NMR (400 MHz, CHLOROFORM-d) δ: 8.03 (d, J=2.3 Hz, 1H), 7.50 (d, J=9.0 Hz, 1H), 7.29 (d, J=8.5 Hz, 2H), 7.11 (d, J=9.0 Hz, 1H), 6.99 (d, J=8.8 Hz, 2H), 6.59 (d, J=2.3 Hz, 1H), 4.56 (dt, J=6.8, 3.5 Hz, 1H), 4.43 (br s, 1H), 3.75-3.61 (m, 2H), 3.42-3.26 (m, 4H), 2.75 (s, 3H), 2.00 (td, J=8.6, 3.9 Hz, 2H), 1.91-1.78 (m, 2H), 1.17 (t, J=7.3 Hz, 3H).

Example 537. N-Isopropoxy-4-[4-(7-methylpyrazolo[1,5-a]pyridin-6-yl)phenoxy]piperidine-1-carboxamide

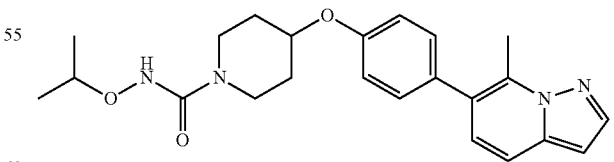

O-Isopropylhydroxylamine hydrochloride (0.073 g, 0.66 mmol), DCI (0.107 g, 0.658 mmol) DIEA in dichloroethane (4 mL) was stirred for 2 h at rt. 7-Methyl-6-[4-(4-piperidyloxy)phenyl]pyrazolo[1,5-a]pyridine dihydrochloride (0.125 g, 0.329 mmol) was added and stirred at rt overnight. The mixture was concentrated, dissolved in EtOAc, washed with brine and then dried over MgSO₄. The product was purified by ISCO (12 g silica gel, 40-90% EtOAc/hexanes). The product was crystallized from ether and hexanes to give a white solid (70 mg, 52%). LCMS m/z=409 (M+1); ¹H NMR (400 MHz, DCCl₃) δ: 8.03 (d, J=2.3 Hz, 1H), 7.55-7.45 (m, 1H), 7.34-7.27 (m, 2H), 7.11 (d, J=9.0 Hz, 1H), 7.05-6.96 (m, 2H), 6.93 (s, 1H), 6.59 (d, J=2.3 Hz, 1H), 4.59 (tt, J=6.5, 3.3 Hz, 1H), 4.06 (spt, J=6.2 Hz, 1H), 3.75-3.61 (m, 2H), 3.43 (ddd, J=13.4, 7.0, 3.9 Hz, 2H), 2.75 (s, 3H), 2.07-1.95 (m, 2H), 1.93-1.80 (m, 2H), 1.25 (d, J=6.0 Hz, 6H).

Example 538. N-Ethoxyoxy-4-[4-(7-methylpyrazolo[1,5-a]pyridin-6-yl)phenoxy]piperidine-1-carboxamide

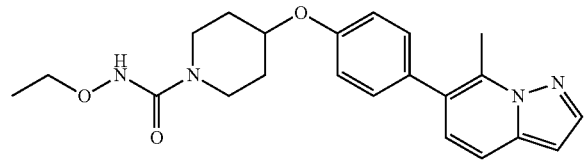

Synthesized using by the method of Example 538 using O-ethylhydroxylamine hydrochloride. LCMS m/z=395 (M+1); 1H NMR (400 MHz, CHLOROFORM-d) δ: 8.03 (d, J=2.3 Hz, 1H), 7.55-7.45 (m, 1H), 7.30 (d, J=8.5 Hz, 2H), 7.11 (d, J=9.0 Hz, 1H), 7.05-6.92 (m, 3H), 6.59 (d, J=2.3 Hz, 1H), 4.59 (dt, J=6.5, 3.2 Hz, 1H), 3.93 (q, J=7.0 Hz, 2H), 3.75-3.62 (m, 2H), 3.47-3.41 (m, 2H), 2.75 (s, 3H), 2.07-1.95 (m, 2H), 1.93-1.82 (m, 2H), 1.27 (t, J=7.0 Hz, 3H)

Example 539. N-Methoxyoxy-4-[4-(7-methylpyrazolo[1,5-a]pyridin-6-yl)phenoxy]piperidine-1-carboxamide

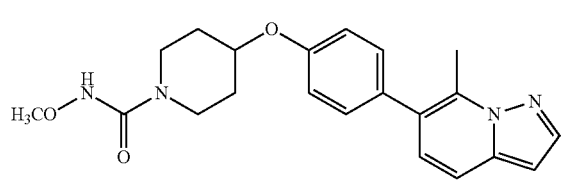 [SMILES: CONC(=O)N1CCC(Oc2ccc(-c3ccc4ccnn4c3C)cc2)CC1]

Synthesized using by the method of Example 538 using O-methylhydroxylamine hydrochloride. LCMS m/z=381 (M+1); 1H NMR (400 MHz, CCCl₃) δ: 8.05 (d, J=2.0 Hz, 1H), 7.51 (d, J=9.0 Hz, 1H), 7.30 (d, J=8.5 Hz, 2H), 7.14 (d, J=9.0 Hz, 1H), 6.99 (d, J=8.5 Hz, 2H), 6.60 (d, J=2.3 Hz, 1H), 4.62-4.57 (m, 1H), 3.74 (s, 3H), 3.66 (br dd, J=8.7, 4.6 Hz, 2H), 3.46-3.40 (m, 2H), 2.77 (s, 3H), 2.02-1.96 (m, 2H), 1.92-1.87 (m, 2H)

Example 540. N-(Cyclopropylmethyl)-4-[4-(8-methyl-7-quinolyl)phenoxy]piperidine-1-carboxamide, HCl

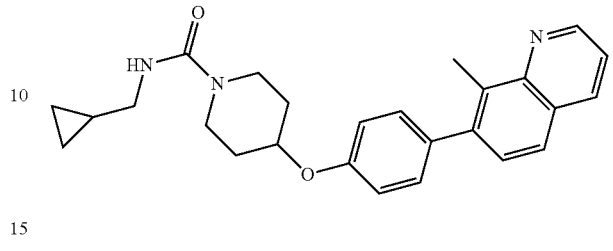

1-Isocyanato-2-methylpropane (30.5 mg, 0.302 mmol) was added to a solution of 8-methyl-7-[4-(4-piperidyloxy)phenyl]quinoline dihydrochloride (80 mg, 0.25 mmol), and N,N-diisopropylethylamine (0.131 mL, 0.751 mmol) in dichloromethane (3 mL) at 0° C. After stirring for 1 h, the reaction was concentrated and partitioned between EtOAc and 1 M Na₂CO₃. The organic layer was washed with brine, and then dried over MgSO₄, filtered and concentrated in vacuo. The product was purified on ISCO (12 g silica gel column, 45-90% EtOAc in hexanes) to yield an oil. The HCl salt was synthesized by adding 1 mL of 4M HCl-dioxane solution to a methanol solution of base. The salt was concentrated to yield N-(cyclopropylmethyl)-4-[4-(8-methyl-7-quinolyl)phenoxy]piperidine-1-carboxamide HCl (72 mg, 63%). Analysis: LCMS m/z=416 (M+1); ¹H NMR (400 MHz, DCCl₃) δ: 9.46 (1H, br d, J=4.0 Hz), 8.86 (1H, d, J=8.0 Hz), 8.00 (1H, d, J=8.5 Hz), 7.89-7.96 (1H, m), 7.83 (1H, d, J=8.5 Hz), 7.33 (2H, d, J=8.8 Hz), 7.07 (2H, d, J=8.8 Hz), 4.64 (1H, dt, J=6.5, 3.0 Hz), 3.71 (2H, ddd, J=13.0, 8.8, 3.5 Hz), 3.32-3.46 (2H, m), 3.13 (2H, d, J=7.3 Hz), 3.08 (1H, s), 3.04-3.10 (1H, m), 2.07-2.22 (2H, m), 1.86-2.02 (3H, m), 0.93-1.10 (1H, m), 0.46-0.62 (2H, m), 0.15-0.27 (2H, m), 0.04-0.05 (1H, m).

The following examples were made using the previous procedure.

Example 541. N-Isobutyl-4-[4-(8-methyl-7-quinolyl)phenoxy]piperidine-1-carboxamide, HCl

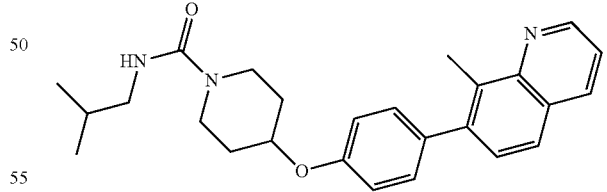

Using 8-methyl-7-[4-(4-piperidyloxy)phenyl]quinoline 2HCl and 1-isocyanato-2-methylpropane. Analysis: LCMS m/z=418 (M+1); ¹H NMR (400 MHz, DCCl₃) δ: 9.46 (1H, br d, J=4.3 Hz), 8.87 (1H, d, J=7.3 Hz), 8.00 (1H, d, J=8.5 Hz), 7.93 (1H, dd, J=8.3, 5.3 Hz), 7.83 (1H, d, J=8.5 Hz), 7.30-7.38 (2H, m), 7.02-7.13 (2H, m), 4.68 (1H, dt, J=6.0, 3.0 Hz), 3.73 (2H, ddd, J=13.0, 9.3, 3.5 Hz), 3.31-3.47 (2H, m), 3.12 (2H, d, J=6.8 Hz), 3.07 (3H, s), 2.15-2.29 (2H, m), 1.98-2.11 (2H, m), 1.84 (1H, dt, J=13.5, 6.7 Hz), 0.96 (6H, d, J=6.8 Hz).

Example 542. N-(2-Methoxyethyl)-4-[4-(8-methyl-7-quinolyl)phenoxy]piperidine-1-carboxamide HCl

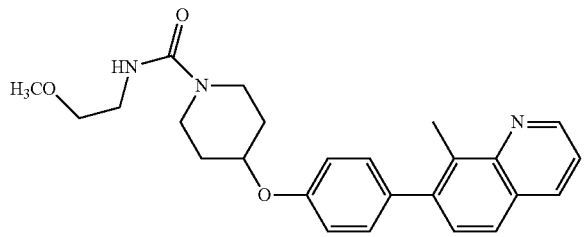 [SMILES: COCCNC(=O)N1CCC(Oc2ccc(-c3ccc4cccnc4c3C)cc2)CC1]

Using 8-methyl-7-[4-(4-piperidyloxy)phenyl]quinoline 2HCl and 1-isocyanato-2-methoxyethane. Analysis: LCMS m/z=420 (M+1); $^1$H NMR (400 MHz, DCCl$_3$) δ: 9.46 (1H, br s), 8.96 (1H, br d, J=4.3 Hz), 7.91-8.18 (2H, m), 7.83 (1H, br d, J=8.0 Hz), 7.24-7.40 (2H, m), 7.06 (2H, br d, J=8.3 Hz), 4.80-5.28 (1H, m), 4.62 (1H, br s), 3.60-3.87 (2H, m), 3.24-3.59 (11H, m), 3.06 (3H, s), 1.95-2.22 (2H, m), 1.87 (2H, br d, J=6.5 Hz).

Example 543. N-Isopropoxy-4-[4-(8-methyl-7-quinolyl)phenoxy]piperidine-1-carboxamide

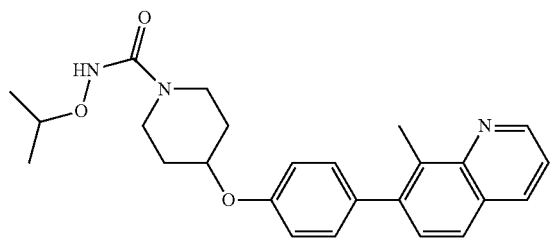 [SMILES: Cc1c(-c2ccc(OC3CCN(C(=O)NOC(C)C)CC3)cc2)ccc2cccnc12]

At 0° C., 8-methyl-7-[4-(4-piperidyloxy)phenyl]quinolone 2 HCl (100 mg, 0.31 mmol) in DCM (3 mL) was treated with N,N-diisopropylethylamine (0.219 mL, 1.26 mmol) and then triphosgene (95.1 mg, 0.314 mmol). Upon competition of the acid chloride, the reaction was partitioned between CH$_2$Cl$_2$ and brine, the organic layers separated and dried over MgSO$_4$, then concentrated in vacuo to a brown oil. To the oil in 1,2 dichloroethane, was added DIPEA (0.219 mL, 1.26 mmol), and then O-isopropylhydroxylamine hydrochloride (72 mg, 0.63 mmol) and heated to 70° C. for 20 h. The reaction was concentrated, dissolved in EtOAc, washed with brine, and then dried over MgSO$_4$. The product was purified by Gilson, (10-55% ACN with 0.1% TFA/H$_2$O with 0.1% TFA). The product was concentrated with toluene, then free based with Na$_2$CO$_3$ to yield N-isopropoxy-4-[4-(8-methyl-7-quinolyl)phenoxy]piperidine-1-carboxamide (39 mg, 30%). LCMS m/z=420 (M+1); $^1$H NMR (400 MHz, DMSO-d$_6$) δ: 9.50 (1H, s), 8.97 (1H, dd, J=4.3, 1.8 Hz), 8.36 (1H, dd, J=8.3, 1.8 Hz), 7.85 (1H, d, J=8.3 Hz), 7.55 (1H, dd, J=8.2, 4.1 Hz), 7.47 (1H, d, J=8.5 Hz), 7.37 (2H, d, J=8.5 Hz), 7.10 (2H, d, J=8.8 Hz), 4.63 (1H, dt, J=8.2, 4.3 Hz), 3.88 (1H, quin, J=6.2 Hz), 3.55-3.72 (2H, m), 3.04-3.25 (2H, m), 2.68 (3H, s), 1.79-2.09 (2H, m), 1.56 (2H, ddt, J=12.9, 8.6, 4.3, 4.3 Hz), 1.23 (1H, s), 1.12 (6H, d, J=6.3 Hz).

Example 544. N-Isobutoxy-4-[4-(8-methyl-7-quinolyl)phenoxy]piperidine-1-carboxamide

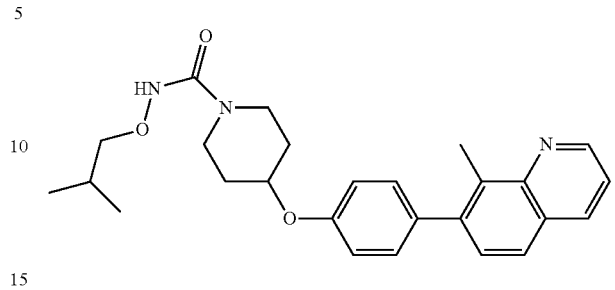

Step 1

8-Methyl-7-[4-(4-piperidyloxy)phenyl]quinoline (300 mg, 0.9422 mmol) in DCM (10 mL) at 0° C., was treated with DIPEA (2 equiv., 1.884 mmol) and triphosgene (1 equiv., 0.942 mmol). After 2 h, the solution was partitioned between DCM and brine, the organic layer dried over MgSO$_4$, filtered and concentrated to yield 4-[4-(8-methyl-7-quinolyl)phenoxy]piperidine-1-carbonyl chloride.

Step 2

4-[4-(8-Methyl-7-quinolyl)phenoxy]piperidine-1-carbonyl chloride (0.10 g, 0.26 mmol) in DCE (2 mL), was added DIPEA (0.22 mL, 1.26 mmol), and o-isobutylhydroxylamine HCl (0.068 g, 0.53 mmol). The reaction was heated to 70° C. for 5 h, cooled to rt diluted with EtOAc and washed with water and brine then dried over MgSO$_4$. The product was purified by GILSON (Gemini-NX-5u, C18 110A 150× 30 mm 5 micron column), (15-60% ACN/H$_2$O with 0.1% TFA). The fractions with product were concentrated, and free based with Na$_2$CO$_3$ to yield N-isobutoxy-4-[4-(8-methyl-7-quinolyl)phenoxy]piperidine-1-carboxamide (39 mg, 34%). Analysis: LCMS m/z=434 (M+1); 1H NMR (400 MHz, DMSO-d$_6$) δ: 9.65 (1H, s), 8.97 (1H, dd, J=4.1, 1.9 Hz), 8.36 (1H, dd, J=8.3, 1.8 Hz), 7.85 (1H, d, J=8.3 Hz), 7.55 (1H, dd, J=8.2, 4.1 Hz), 7.47 (1H, d, J=8.5 Hz), 7.34-7.40 (2H, m), 7.06-7.13 (2H, m), 4.63 (1H, dt, J=7.9, 4.1 Hz), 3.55-3.71 (2H, m), 3.49 (2H, d, J=6.8 Hz), 3.05-3.20 (2H, m), 2.68 (3H, s), 1.78-2.03 (3H, m), 1.56 (2H, td, J=8.5, 4.5 Hz), 0.90 (6H, d, J=6.5 Hz).

Example 545. N-(2-Dimethylaminoethyl)-4-[4-(8-methyl-7-quinolyl)phenoxy]piperidine-1-carboxamide HCl

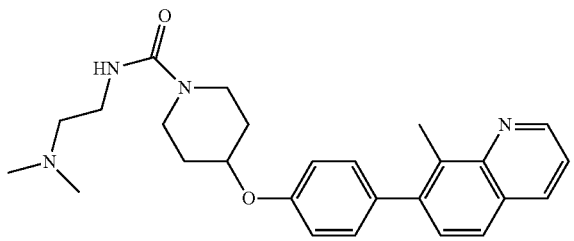 [SMILES: Cc1c(-c2ccc(OC3CCN(C(=O)NOCC(C)C)CC3)cc2)ccc2cccnc12]

Prepared using 4-[4-(8-methyl-7-quinolyl)phenoxy]piperidine-1-carbonyl chloride and N,N-dimethylethylenediamine. Analysis: LCMS m/z=433 (M+1); $^1$H NMR (400 MHz, DMSO-d$_6$) δ: 9.77 (1H, br s), 8.97-9.06 (1H, m), 8.53 (1H, br s), 7.94 (1H, br d, J=9.0 Hz), 7.66 (1H, br s), 7.55 (1H, d, J=8.3 Hz), 7.39 (2H, d, J=8.8 Hz), 7.12 (2H, d, J=8.8 Hz), 6.86-6.99 (1H, m), 4.59-4.75 (1H, m), 3.67-3.81 (2H, m), 3.32-3.45 (2H, m), 3.03-3.27 (4H, m), 2.80 (6H, d, J=5.0 Hz), 2.69 (3H, s), 1.97 (2H, br s), 1.48-1.71 (2H, m)

Example 546. 2-Morpholinoethyl 4-[4-(8-methyl-7-quinolyl)phenoxy]piperidine-1-carboxylate 2HCl

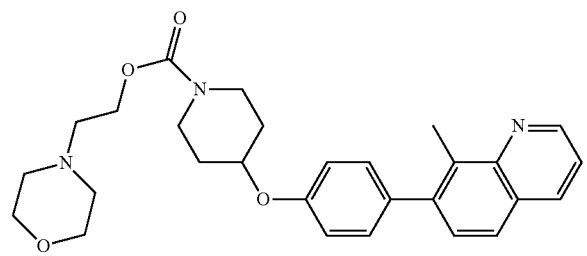 [SMILES: Cc1c(-c2ccc(OC3CCN(C(=O)OCCN4CCOCC4)CC3)cc2)ccc2cccnc12]

Prepared using 4-[4-(8-methyl-7-quinolyl)phenoxy]piperidine-1-carbonyl chloride and 2-morpholinoethanol. Analysis: LCMS m/z=460 (M+1); $^1$H NMR (400 MHz, DMSO-d$_6$) δ:11.70 (1H, br s), 9.17 (1H, dd, J=4.8, 1.3 Hz), 8.92 (1H, br d, J=6.8 Hz), 8.03-8.22 (1H, m), 7.92 (1H, br dd, J=7.9, 4.9 Hz), 7.61-7.83 (1H, m), 7.32-7.52 (2H, m), 7.12-7.18 (2H, m), 4.71 (1H, dt, J=7.8, 4.1 Hz), 4.34-4.49 (2H, m), 3.63-4.05 (6H, m), 3.23-3.47 (6H, m), 3.07-3.17 (2H, m), 2.75 (3H, s), 2.01 (2H, dt, J=6.7, 3.0 Hz), 1.52-1.75 (2H, m).

Example 547. 2-Pyrrolidin-1-ylethyl 4-[4-(8-methyl-7-quinolyl)phenoxy]piperidine-1-carboxylate, 2HCl

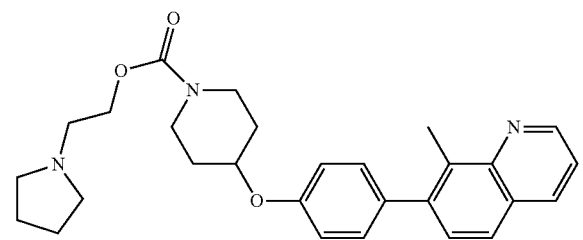 [SMILES: Cc1c(-c2ccc(OC3CCN(C(=O)OCCN4CCCC4)CC3)cc2)ccc2cccnc12]

Synthesized using 4-[4-(8-methyl-7-quinolyl)phenoxy]piperidine-1-carbonyl chloride and N-(2-hydroxyethyl)pyrrolidine. Analysis: LCMS m/z=460 (M+1); $^1$H NMR (400 MHz, DMSO-d$_6$) δ: 11.28 (1H, br s), 9.17 (1H, dd, J=4.9, 1.4 Hz), 8.92 (1H, br d, J=7.5 Hz), 8.12 (1H, d, J=8.5 Hz), 7.91 (1H, br dd, J=7.8, 5.0 Hz), 7.72 (1H, d, J=8.5 Hz), 7.34-7.51 (2H, m), 7.15 (2H, d, J=8.8 Hz), 4.71 (1H, dt, J=7.7, 4.0 Hz), 4.28-4.43 (2H, m), 3.69-3.94 (2H, m), 3.55 (2H, br dd, J=10.3, 5.0 Hz), 3.26-3.48 (4H, m), 2.91-3.12 (2H, m), 2.75 (3H, s), 1.81-2.10 (6H, m), 1.54-1.73 (2H, m).

Example 548. N-[2-(1H-Imidazol-4-yl)ethyl]-4-[4-(8-methyl-7-quinolyl)phenoxy]piperidine-1-carboxamide, 2HCl

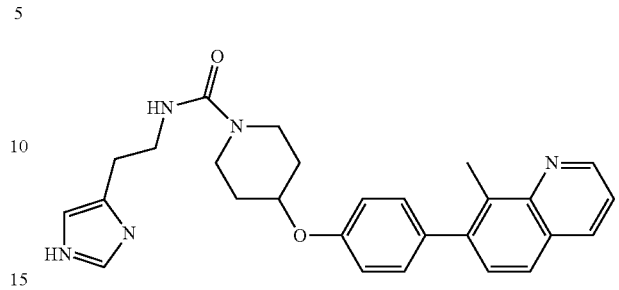

Synthesized using 4-[4-(8-methyl-7-quinolyl)phenoxy]piperidine-1-carbonyl chloride and histamine. Analysis: LCMS m/z=456 (M+1); $^1$NMR (400 MHz, DMSO-d$_6$) δ: 14.52 (1H, br s), 14.28 (1H, br s), 9.12 (1H, br d, J=3.3 Hz), 9.03 (1H, s), 8.79 (1H, br s), 8.06 (1H, br d, J=8.5 Hz), 7.84 (1H, br s), 7.67 (1H, d, J=8.5 Hz), 7.45 (1H, s), 7.41 (2H, d, J=8.8 Hz), 7.13 (2 H, d, J=8.8 Hz), 6.80 (1H, br s), 4.64 (1H, dt, J=8.2, 4.2 Hz), 3.61-3.77 (2H, m), 3.35 (2H, br t, J=6.7 Hz), 3.07-3.20 (2H, m), 2.82 (2H, t, J=6.8 Hz), 2.73 (3H, s), 1.93 (2H, br dd, J=10.7, 5.6 Hz), 1.45-1.61 (2H, m).

Example 549. 4-[4-(8-Methyl-7-quinolyl)phenoxy]-N-tetrahydropyran-4-yl-piperidine-1-carboxamide, HCl

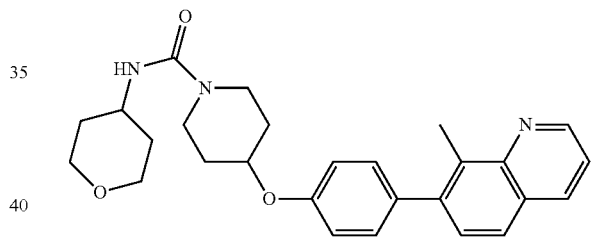

Synthesized using 4-[4-(8-methyl-7-quinolyl)phenoxy]piperidine-1-carbonyl chloride and 4-aminotetrahydropyran. Analysis: LCMS m/z=446 (M+1); $^1$H NMR (400 MHz, DMSO-d$_6$) δ: 9.03-9.17 (1H, m), 8.76 (1H, br s), 8.05 (2H, br d, J=8.3 Hz), 7.81 (1H, br s), 7.65 (2H, d, J=8.5 Hz), 7.28-7.52 (2H, m), 7.06-7.21 (2H, m), 6.33 (2H, br s), 4.63 (1H, br d, J=4.3 Hz), 3.83 (2H, br dd, J=11.9, 2.1 Hz), 3.54-3.78 (3H, m), 3.31 (2H, td, J=11.7, 1.9 Hz), 3.05-3.21 (2H, m), 2.71 (3H, s), 1.86-2.03 (2H, m), 1.68 (2H, br dd, J=12.4, 2.4 Hz), 1.34-1.60 (4H, m).

Example 550. Isobutyl 4-[4-(8-methyl-7-quinolyl)phenoxy]piperidine-1-carboxylate, HCl

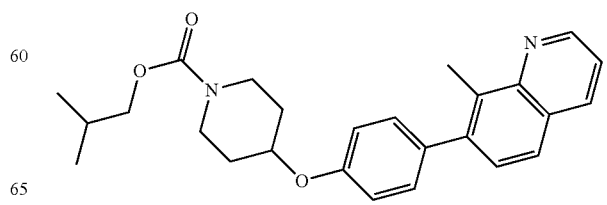

Isobutyl chloroformate (0.085 mL, 0.64 mmol) was added to a solution of 8-methyl-7-[4-(4-piperidyloxy)phenyl]quinoline (100 mg, 0.3141 mmol) and DIPEA (0.11 mL) in 1,2-dichloroethane (5 mL) at 0° C. After 0.5 h, the reaction was diluted with EtOAc and washed with water, H$_2$O and brine; then dried over MgSO$_4$. The product was purified by GILSON (Gemini-NX-5u, C18 110A 150×30 mm 5 micron column), (5-60% ACN/H$_2$O with 0.1% TFA) to yield isobutyl 4-[4-(8-methyl-7-quinolyl)phenoxy]piperidine-1-carboxylate HCl (15 mg, 10%) Analysis: LCMS m/z=419 (M+1); 1H NMR (400 MHz, DMSO-d$_6$) δ: 9.04 (1H, dd, J=4.4, 1.6 Hz), 8.58 (1H, br s), 7.96 (1H, br d, J=8.3 Hz), 7.62-7.75 (1H, m), 7.57 (1H, d, J=8.3 Hz), 7.33-7.45 (2H, m), 7.04-7.17 (2H, m), 4.68 (1H, dt, J=8.0, 4.0 Hz), 3.81 (4H, d, J=6.5 Hz), 3.29 (2H, br s), 2.69 (3H, s), 1.93-2.07 (2H, m), 1.88 (1H, dt, J=13.4, 6.7 Hz), 1.60 (2H, dtd, J=12.9, 8.7, 8.7, 4.1 Hz), 0.90 (6H, d, J=6.8 Hz).

Example 551. Allyl 4-[4-(8-methyl-7-quinolyl)phenoxy]piperidine-1-carboxylate, HCl

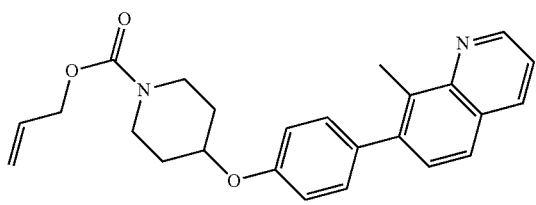 [SMILES: C=CCOC(=O)N1CCC(Oc2ccc(-c3ccc4cccnc4c3C)cc2)CC1]

Synthesized using 8-methyl-7-[4-(4-piperidyloxy)phenyl]quinolone 2 HCl and allyl chloroformate. Analysis: LCMS m/z=403 (M+1); $^1$H NMR (400 MHz, DMSO-d$_6$) δ: 9.17 (1H, dd, J=4.8, 1.3 Hz), 8.94 (1H, br d, J=7.3 Hz), 8.13 (1H, d, J=8.5 Hz), 8.04-8.21 (1H, m), 7.93 (1H, br dd, J=7.9, 5.1 Hz), 7.73 (1H, d, J=8.5 Hz), 7.42 (2H, d, J=8.5 Hz), 7.15 (2H, d, J=8.5 Hz), 5.80-6.12 (1H, m), 5.30 (1H, dq, J=17.3, 1.7 Hz), 5.21 (1H, dq, J=10.5, 1.5 Hz), 4.70 (1H, dt, J=7.8, 4.1 Hz), 4.55 (2H, dt, J=5.3, 1.5 Hz), 3.61-3.88 (2H, m), 3.32 (2H, br s), 2.75 (3H, s), 2.00 (2H, ddd, J=9.5, 6.1, 2.8 Hz), 1.45-1.73 (2H, m).

Example 552. N-Cyclobutyl-4-[4-(8-methyl-7-quinolyl)phenoxy]piperidine-1-carboxamide HCl

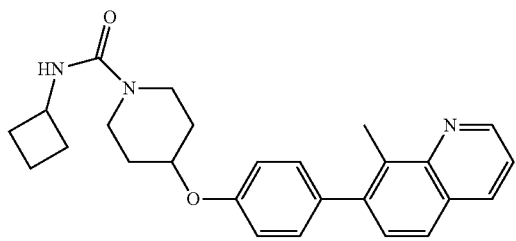 [SMILES: Cc1c(-c2ccc(OC3CCN(C(=O)NC4CCC4)CC3)cc2)ccc2cccnc12]

Synthesized using 4-[4-(8-methyl-7-quinolyl)phenoxy]piperidine-1-carbonyl chloride and cyclobutylamine. Analysis: LCMS m/z=416 (M+1); $^1$H NMR (400 MHz, DMSO-d$_6$) δ: 9.15 (1H, dd, J=4.8, 1.5 Hz), 8.88 (1H, br d, J=7.3 Hz), 8.10 (1H, br d, J=8.5 Hz), 7.89 (1H, br dd, J=7.9, 4.9 Hz), 7.71 (1H, d, J=8.5 Hz), 7.32-7.50 (2H, m), 7.00-7.20 (2H, m), 6.67 (1H, br s), 4.63 (1H, dt, J=8.2, 4.3 Hz), 4.11 (1H, brt, J=8.4 Hz), 3.57-3.85 (2H, m), 2.92-3.26 (2H, m), 2.73 (3H, s), 2.01-2.19 (2H, m), 1.77-1.99 (4H, m), 1.36-1.68 (4H, m).

Example 553: Cyclopropylmethyl 4-[4-(8-methyl-7-quinolyl)phenoxy]piperidine-1-carboxylate HCl

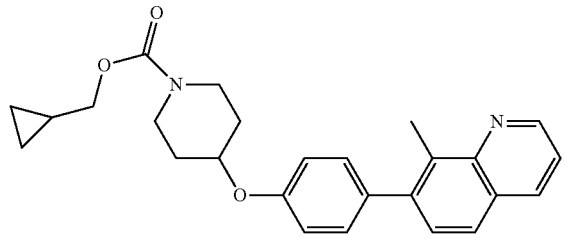 [SMILES: Cc1c(-c2ccc(OC3CCN(C(=O)OCC4CC4)CC3)cc2)ccc2cccnc12]

Synthesized using 4-[4-(8-methyl-7-quinolyl)phenoxy]piperidine-1-carbonyl chloride and cyclopropanemethanol. Analysis: LCMS m/z=417 (M+1); $^1$H NMR (400 MHz, DMSO-d$_6$) δ: 9.11 (1H, dd, J=4.6, 1.4 Hz), 8.77 (1H, br s), 8.05 (1H, br d, J=8.3 Hz), 7.75-7.95 (1H, m), 7.66 (1H, d, J=8.3 Hz), 7.30-7.50 (2H, m), 7.06-7.27 (2H, m), 4.68 (1H, tt, J=7.8, 3.8 Hz), 3.86 (2H, d, J=7.0 Hz), 3.68-3.80 (2H, m), 3.29 (2H, br s), 2.72 (3H, s), 1.84-2.06 (2H, m), 1.61 (2H, dtd, J=12.9, 8.7, 8.7, 4.0 Hz), 1.03-1.22 (1H, m), 0.38-0.59 (2H, m), 0.14-0.36 (2H, m).

Example 554. 4-[4-(8-Methyl-7-quinolyl)phenoxy]piperidine-1-carbohydroxamic acid, HCl

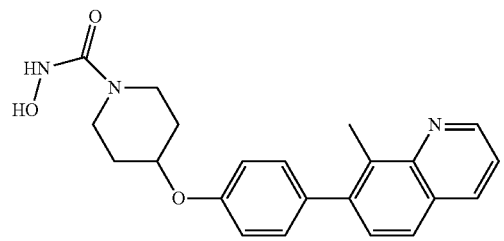 [SMILES: Cc1c(-c2ccc(OC3CCN(C(=O)NO)CC3)cc2)ccc2cccnc12]

Synthesized using 4-[4-(8-methyl-7-quinolyl)phenoxy]piperidine-1-carbonyl chloride, and hydroxylamine HCl. Analysis: LCMS m/z=378 (M+1); $^1$H NMR (400 MHz, DMSO-d$_6$) δ: 9.13 (1H, br d, J=3.8 Hz), 8.84 (1H, br s), 8.08 (1H, br d, J=8.3 Hz), 7.86 (1H, br s), 7.69 (1H, br d, J=8.3 Hz), 7.37-7.44 (2H, m), 7.09-7.18 (2H, m), 4.66 (1H, dt, J=8.0, 4.2 Hz), 3.57-3.77 (2H, m), 3.03-3.22 (2H, m), 2.72 (3H, s), 1.87-2.08 (2H, m), 1.55 (2H, td, J=8.6, 4.4 Hz).

Example 555. 2-Methoxyethyl 4-[4-(8-methyl-7-quinolyl)phenoxy]piperidine-1-carboxylate, HCl

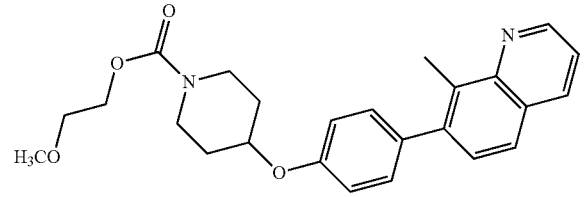 [SMILES: COCCOC(=O)N1CCC(Oc2ccc(-c3ccc4cccnc4c3C)cc2)CC1]

Synthesized using 8-methyl-7-[4-(4-piperidyloxy)phenyl]quinolone and 2-methoxyethyl chloroformate. Analysis: LCMS m/z=421 (M+1); $^1$H NMR (400 MHz, DMSO-$d_6$) δ: 9.15 (1H, dd, J=4.8, 1.3 Hz), 8.89 (1H, br s), 8.11 (1H, br d, J=8.5 Hz), 7.81-7.95 (1H, m), 7.71 (1H, d, J=8.3 Hz), 7.32-7.48 (2H, m), 7.08-7.22 (2H, m), 4.69 (1H, dt, J=7.8, 4.1 Hz), 4.01-4.21 (2H, m), 3.68-3.85 (2H, m), 3.45-3.63 (2H, m), 3.28 (5H, s), 2.73 (3H, s), 1.99 (2H, ddd, J=9.6, 6.0, 3.0 Hz), 1.61 (2H, dtd, J=12.9, 8.7, 8.7, 3.9 Hz).

Example 556. Tetrahydropyran-4-yl 4-[4-(8-methyl-7-quinolyl)phenoxy]piperidine-1-carboxylate

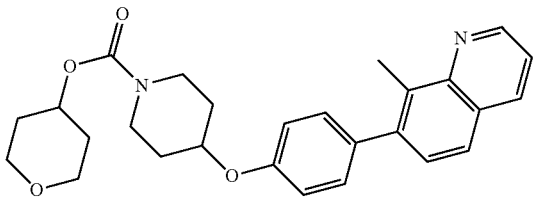 [SMILES: Cc1c(-c2ccc(OC3CCN(C(=O)OC4CCOCC4)CC3)cc2)ccc2cccnc12]

Step 1

Added pyridine (0.317 mL, 3.92 mmol) to a solution of triphosgene (0.326 g, 1.08 mmol) in THF (10 mL) at 0° C. and stirred for 10 min, then tetrahydropyran-4-ol (200 mg, 1.958 mmol), was added and stirred 45 min while warming to rt. The reaction was concentrated, dissolved in EtOAc (20 mL) and washed with water (20 mL) and then brine. The EtOAc layer was dried over MgSO$_4$, filtered and concentrated to yield tetrahydropyran-4-yl carbonochloridate.

Step 2

Synthesized using 8-methyl-7-[4-(4-piperidyloxy)phenyl]quinolone and tetrahydropyran-4-yl carbonochloridate. Analysis: LCMS m/z=447 (m+1); $^1$H NMR (400 MHz, DMSO-$d_6$) δ: 8.97 (1 h, dd, j=4.1, 1.9 hz), 8.37 (1 h, dd, j=8.2, 1.9 hz), 7.85 (1 h, d, j=8.3 hz), 7.55 (1 h, dd, j=8.2, 4.1 hz), 7.48 (1 h, d, j=8.5 hz), 7.34-7.41 (2 h, m), 7.07-7.15 (2 h, m), 4.76 (1 h, tt, j=8.3, 4.1 hz), 4.67 (1 h, dt, j=7.8, 4.1 hz), 3.69-3.86 (4 h, m), 3.47 (2 h, ddd, j=11.6, 8.7, 3.0 hz), 3.34 (2 h, br s), 2.68 (3 h, s), 1.93-2.07 (2 h, m), 1.79-1.92 (2 h, m), 1.45-1.69 (4 h, m).

Example 557. Tetrahydropyran-3-yl 4-[4-(8-methyl-7-quinolyl)phenoxy]piperidine-1-carboxylate

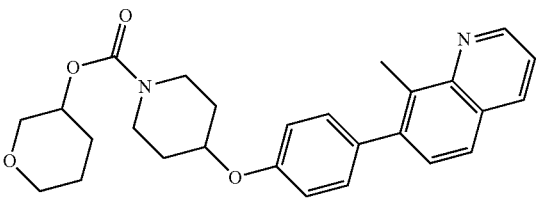 [SMILES: Cc1c(-c2ccc(OC3CCN(C(=O)OC4CCCOC4)CC3)cc2)ccc2cccnc12]

Synthesized using 8-methyl-7-[4-(4-piperidyloxy)phenyl]quinolone and tetrahydropyran-3-yl carbonochloridate by the method of Example 557. Analysis: LCMS m/z=447 (M+1); 1H NMR (400 MHz, DMSO-$d_6$) δ: 8.97 (1H, dd, J=4.3, 1.8 Hz), 8.37 (1H, dd, J=8.3, 1.8 Hz), 7.85 (1H, d, J=8.5 Hz), 7.55 (1H, dd, J=8.2, 4.1 Hz), 7.48 (1H, d, J=8.5 Hz), 7.38 (2H, d, J=8.5 Hz), 7.11 (2H, d, J=8.8 Hz), 4.61-4.75 (1H, m), 4.56 (1H, dt, J=6.0, 3.0 Hz), 3.65-3.85 (3H, m), 3.55 (2H, t, J=5.3 Hz), 3.46 (1H, dd, J=11.7, 5.6 Hz), 3.33 (2H, s), 2.68 (3H, s), 1.85-2.06 (3H, m), 1.42-1.81 (5H, m).

Example 558. [4-[4-(8-Methyl-7-quinolyl)phenoxy]-1-piperidyl]-(oxazinan-2-yl)methanone

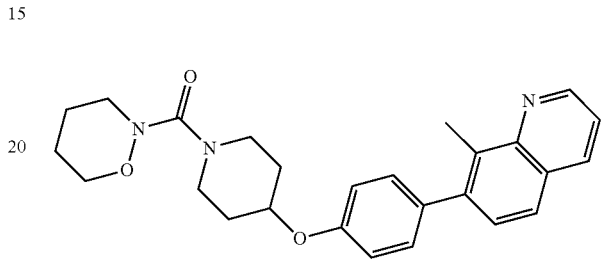

Synthesized using 4-[4-(8-methyl-7-quinolyl)phenoxy]piperidine-1-carbonyl chloride and 1,2-oxazinane HCl. Analysis: LCMS m/z=432 (M+1); $^1$H NMR (400 MHz, DMSO-$d_6$) δ: 8.97 (1H, dd, J=4.3, 1.8 Hz), 8.37 (1H, dd, J=8.3, 1.8 Hz), 7.85 (1H, d, J=8.5 Hz), 7.52-7.61 (1H, m), 7.51-7.52 (1H, m), 7.48 (1H, d, J=8.3 Hz), 7.37 (2H, d, J=8.8 Hz), 7.11 (2H, d, J=8.8 Hz), 4.68 (1H, tt, J=7.9, 3.7 Hz), 3.90 (2H, t, J=4.9 Hz), 3.65-3.78 (2H, m), 3.21-3.30 (4H, m), 2.68 (3H, s), 2.01 (2H, ddd, J=9.5, 5.9, 3.1 Hz), 1.54-1.74 (6H, m).

Example 559. Tetrahydrofuran-3-yl 4-[4-(8-methyl-7-quinolyl)phenoxy]piperidine-1-carboxylate

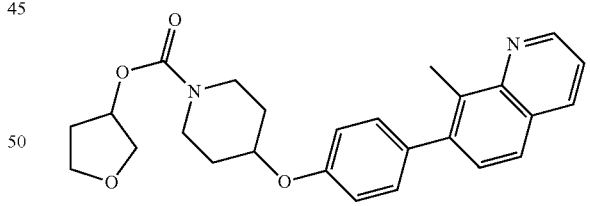

Synthesized using 8-methyl-7-[4-(4-piperidyloxy)phenyl]quinolone and tetrahydrofuran-3-yl carbonochloridate. Analysis LCMS m/z=433 (M+1); $^1$H NMR (400 MHz, DMSO-$d_6$) δ: 8.97 (1H, dd, J=4.3, 1.8 Hz), 8.36 (1H, dd, J=8.3, 2.0 Hz), 7.85 (1H, d, J=8.5 Hz), 7.52-7.60 (1H, m), 7.48 (1H, d, J=8.5 Hz), 7.37 (2H, d, J=8.8 Hz), 7.11 (2H, d, J=8.8 Hz), 5.15 (1H, td, J=4.3, 2.1 Hz), 4.58-4.72 (1H, m), 3.63-3.90 (6H, m), 3.15-3.42 (2H, m), 2.68 (3H, s), 2.05-2.20 (1H, m), 1.84-2.03 (3H, m), 1.61 (2H, ddt, J=12.8, 8.6, 4.4, 4.4 Hz).

Example 560. N-(Cyclobutylmethyl)-4-[4-(8-methyl-7-quinolyl)phenoxy]piperidine-1-carboxamide

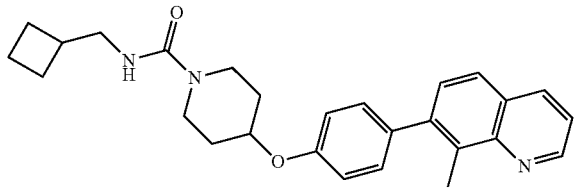 [SMILES: Cc1c(-c2ccc(OC3CCN(C(=O)NCC4CCC4)CC3)cc2)ccc2cccnc12]

Synthesized using 4-[4-(8-methyl-7-quinolyl)phenoxy]piperidine-1-carbonyl chloride and cyclobutylmethylamine. Analysis: LCMS m/z=430 (M+1); $^1$H NMR (400 MHz, DMSO-$d_6$) δ: 8.97 (1H, dd, J=4.3, 1.8 Hz), 8.37 (1H, dd, J=8.3, 1.8 Hz), 7.85 (1H, d, J=8.3 Hz), 7.55 (1H, dd, J=8.3, 4.3 Hz), 7.48 (1H, d, J=8.5 Hz), 7.32-7.40 (2H, m), 7.00-7.16 (2H, m), 6.52 (1H, t, J=5.5 Hz), 4.61 (1H, dt, J=8.3, 4.2 Hz), 3.64-3.83 (2H, m), 2.93-3.20 (4H, m), 2.68 (3H, s), 2.40 (1H, dq, J=15.0, 7.5 Hz), 1.88-2.02 (4H, m), 1.73-1.87 (2H, m), 1.41-1.71 (4H, m).

Example 561. Cyclobutyl 4-[4-(8-methyl-7-quinolyl)phenoxy]piperidine-1-carboxylate

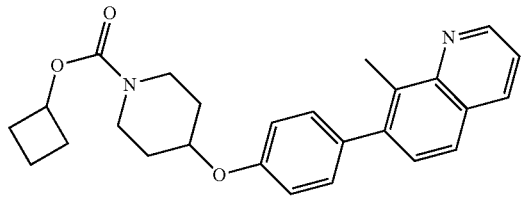 [SMILES: Cc1c(-c2ccc(OC3CCN(C(=O)OC4CCC4)CC3)cc2)ccc2cccnc12]

Synthesized using 8-methyl-7-[4-(4-piperidyloxy)phenyl]quinolone and cyclobutyl carbonochloridate. Analysis: LCMS m/z=417 (M+1); 1H NMR (400 MHz, DMSO-$d_6$) δ: 8.97 (1H, dd, J=4.1, 1.9 Hz), 8.37 (1H, dd, J=8.2, 1.9 Hz), 7.85 (1H, d, J=8.3 Hz), 7.55 (1H, dd, J=8.2, 4.1 Hz), 7.48 (1H, d, J=8.5 Hz), 7.37 (2H, d, J=8.8 Hz), 7.10 (2H, d, J=8.8 Hz), 4.84 (1H, dd, J=7.9, 7.2 Hz), 4.65 (1H, dt, J=8.0, 4.2 Hz), 3.73 (2H, br d, J=12.8 Hz), 3.34 (6H, br s), 2.63-2.77 (3H, m), 2.16-2.33 (2H, m), 1.88-2.05 (4H, m), 1.46-1.80 (4H, m)

Example 562. Azepan-1-yl-[4-[4-(8-methyl-7-quinolyl)phenoxy]-1-piperidyl]methanone

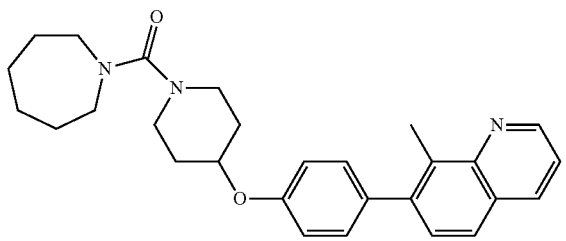 [SMILES: Cc1c(-c2ccc(OC3CCN(C(=O)N4CCCCCC4)CC3)cc2)ccc2cccnc12]

Synthesized using 4-[4-(8-methyl-7-quinolyl)phenoxy]piperidine-1-carbonyl chloride and hexamethyleneimine. Analysis: LCMS m/z=444 (M+1); $^1$H NMR (400 MHz, DMSO-$d_6$) δ: 8.97 (1H, dd, J=4.1, 1.9 Hz), 8.36 (1H, dd, J=8.3, 2.0 Hz), 7.85 (1H, d, J=8.3 Hz), 7.55 (1H, dd, J=8.2, 4.1 Hz), 7.47 (1H, d, J=8.5 Hz), 7.37 (2H, d, J=8.8 Hz), 7.10 (2H, d, J=8.8 Hz), 4.61 (1H, dt, J=8.0, 4.2 Hz), 3.20-3.44 (8H, m), 2.97 (2H, ddd, J=12.9, 9.5, 2.9 Hz), 2.68 (3H, s), 1.93-2.08 (2H, m), 1.58-1.77 (6H, m), 1.36-1.55 (4H, m).

Example 563. N-Butyl-4-[4-(5-chloroimidazo[1,2-a]pyridin-6-yl)phenoxy]piperidine-1-carboxamide

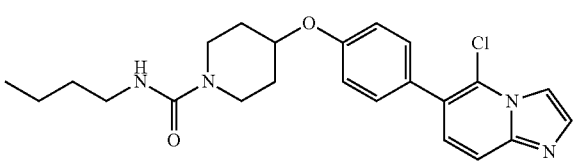

Step 1. tert-Butyl 4-[4-(5-chloroimidazo[1,2-a]pyridin-6-yl)phenoxy]piperidine-1-carboxylate Palladium acetate (0.046 g, 0.205 mmol), triphenylphosphine (0.202 g, 0.770 mmol) and 1,4-dioxane (10 g, 9 mL, 100 mmol) were combined in a flask and stirred for 40 min under nitrogen. 6-Bromo-5-chloroimidazo[1,2-a]pyridine (1.008 g, 4.35 mmol), tert-butyl 4-[4-(4,4,5,5-tetramethyl-1,3,2-dioxaborolan-2-yl)phenoxy]piperidine-1-carboxylate (1.514 g, 3.754 mmol), 1 M Na$_2$CO$_3$ in water (14.9 mL, 10 mmol) and DMF (10 g, 20 mL, 200 mmol) were then added. The reaction was purged with argon and heated at 80° C. under nitrogen for 4 h. The reaction was then cooled to rt, diluted with ETOAc and washed with 1N Na$_2$CO$_3$, and brine, then dried over sodium sulfate, filtered and concentrated. The residue was purified by Isco normal phase chromatography, eluting with EtOAc/heptane to give an off-white solid (519 mg, 70%). LC-MS: m/z=428 (M+1); $^1$H NMR (400 MHz, DMSO-$d_6$) δ 8.11 (m, 1H), 7.78 (m, 1H), 7.73 (d, 1H, J=9.2 Hz), 7.48 (m, 2H), 7.38 (d, 1H, J=9.2 Hz), 7.13 (m, 2H), 4.68-4.64 (m, 1H), 3.74-3.69 (m, 2H), 3.28-3.20 (m, 2H), 2.01-1.96 (m, 2H), 1.62-1.54 (m, 2H), 1.44 (s, 9H).

Step 2. 5-chloro-6-[4-(4-piperidyloxy)phenyl]imidazo[1,2-a]pyridine tert-Butyl 4-[4-(5-chloroimidazo[1,2-a]pyridin-6-yl)phenoxy]piperidine-1-carboxylate (0.519 g, 1.213 mmol) and aqueous HCl (6 M) (3 mL, 18 mmol) were combined in a flask and stirred at RT for 2 h. The reaction was concentrated; the residue was dissolved in EtOAc and washed with NaHCO$_3$ solution, water and brine. The aqueous phase was back extracted several times with EtOAc. The organic phase was dried over MgSO$_4$, filtered and concentrated to give an off-white solid (330 mg, 79%). LC-MS: m/z=328 (M+1); $^1$H NMR (400 MHz, DMSO-$d_6$) δ: 8.10 (m, 1H), 7.78 (d, 1H, J=1.3 Hz), 7.72 (m, 1H), 7.46 (m, 2H), 7.37 (d, 1H, J=9.2 Hz), 7.09 (m, 2H), 4.52-4.46 (m, 1H), 3.01-2.96 (m, 2H), 2.65-2.59 (m, 2H), 1.99-1.95 (m, 2H), 1.55-1.46 (m, 2H).

Step 3. N-Butyl-4-[4-(5-chloroimidazo[1,2-a]pyridin-6-yl)phenoxy]piperidine-1-carboxamide 5-Chloro-6-[4-(4-piperidyloxy)phenyl]imidazo[1,2-a]pyridine (0.068 g, 0.2074 mmol), DIPEA (0.081 g, 0.11 mL, 0.61 mmol) and DCM (3 g, 2 mL, 40 mmol) were combined in a vial. Butyl isocyanate (0.030 g, 0.034 mL, 0.30 mmol) was added, and the reaction was stirred at rt for 17 h. The reaction was washed with 1 N aqueous $Na_2CO_3$ solution, then brine. The organic layer was dried over $MgSO_4$, filtered and concentrated. The residue was purified by Isco normal phase chromatography eluting with 0% to 8% methanol in DCM to give a white solid (62 mg, 70%). mp: 171-177° C.; HPLC 5.25 min. rt=2.359 min.; LC-MS: m/z=427 (M+1); $^1$H NMR (400 MHz, DMSO-$d_6$) δ: 8.08 (m, 1H), 7.76 (d, 1H, J=1.3 Hz), 7.70 (m, 1H), 7.46 (m, 2H), 7.36 (m, 1H), 7.10 (m, 2H), 6.48 (m, 1H), 4.64-4.60 (m, 1H), 3.72-3.69 (m, 2H), 3.14-3.08 (m, 2H), 3.04-2.99 (m, 2H), 1.93 (m, 2H), 1.56-1.47 (m, 2H), 1.43-1.36 (m, 2H), 1.34-1.22 (m, 2H), 0.88 (m, 3H).

Example 564. 4-[4-(5-Chloroimidazo[1,2-a]pyridin-6-yl)phenoxy]-N-ethyl-piperidine-1-carboxamide

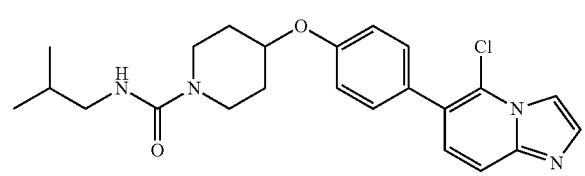 [SMILES: CC(C)CNC(=O)N1CCC(Oc2ccc(-c3ccc4nccn4c3Cl)cc2)CC1]

The title compound, a white solid, was prepared in a manner similar to the procedure used to prepare Example 564 in 68% yield. mp: 189-193° C.; HPLC 5.25 min. rt=1.970 min.; LC-MS: m/z=399 (M+1); 1H NMR (400 MHz, DMSO-$d_6$) δ: 8.08 (s, 1H), 7.76 (d, 1H, J=1.3 Hz), 7.70 (d, 1H, J=9.3 Hz), 7.46 (m, 2H), 7.36 (d, 1H, J=9.2 Hz), 7.10 (m, 2H), 6.50 (m, 1H), 4.64-4.60 (m, 1H), 3.72-3.68 (m, 2H), 3.14-3.02 (m, 4H), 1.94 (m, 2H), 1.56-1.49 (m, 2H), 1.01 (m, 3H).

Example 565. 4-[4-(5-Chloroimidazo[1,2-a]pyridin-6-yl)phenoxy]-N-isobutyl-piperidine-1-carboxamide

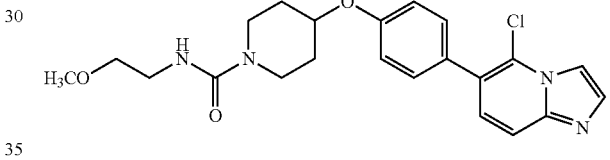

This compound was prepared in a manner similar to the procedure described in Example 564 in 67% yield. mp: 201° C.; LC-MS: m/z=427 (M+1); $^1$H NMR (400 MHz, DMSO-$d_6$) δ: 8.08 (s, 1H), 7.76 (d, 1H, J=1.2 Hz), 7.70 (d, 1H, J=9.2 Hz), 7.46 (m, 2H), 7.36 (d, 1H, J=9.2 Hz), 7.10 (m, 2H), 6.54 (m, 1H), 4.65-4.60 (m, 1H), 3.75-3.71 (m, 2H), 3.15-3.09 (m, 2H), 2.86-2.83 (m, 2H), 1.95-1.91 (m, 2H), 1.73-1.67 (m, 1H), 1.55-1.47 (m, 2H), 0.84-0.82 (d, 6H, J=6.7 Hz).

Example 566. 4-[4-(5-Chloroimidazo[1,2-a]pyridin-6-yl)phenoxy]-N-propyl-piperidine-1-carboxamide

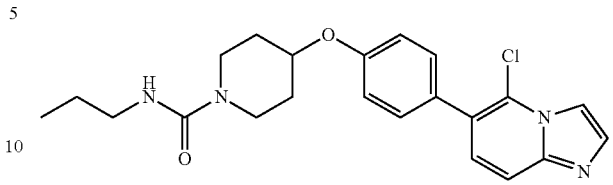

The title compound was prepared in a manner similar to the procedure used to prepare Example 564 to give a white solid in 56% yield. mp: 184° C.; LC-MS: m/z=413 (M+1); $^1$H NMR (400 MHz, DMSO-$d_6$) δ: 8.08 (s, 1H), 7.76 (d, 1H, J=1.3 Hz), 7.70 (m, 1H), 7.48-7.44 (m, 2H), 7.36 (d, 1H, J=9.2 Hz), 7.10 (m, 2H), 6.51 (m, 1H), 4.65-4.60 (m, 1H), 3.74-3.68 (m, 2H), 3.15-3.08 (m, 2H), 3.01-2.96 (m, 2H), 1.93 (m, 2H), 1.56-1.47 (m, 2H), 1.46-1.37 (m, 2H), 0.85-0.81 (m, 3H).

Example 567. 4-[4-(5-Chloroimidazo[1,2-a]pyridin-6-yl)phenoxy]-N-(2-methoxyethyl)piperidine-1-carboxamide

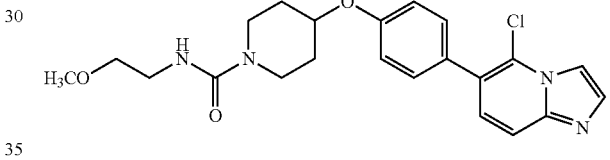

The title compound was prepared in a manner similar to the procedure used to prepare Example 564 in 30% yield. mp: 135-138° C.; LC-MS: m/z=429 (M+1); $^1$H NMR (400 MHz, DMSO-$d_6$) δ: 8.09 (s, 1H), 7.76 (d, 1H, J=1.2 Hz), 7.70 (d, 1H, J=9.6 Hz), 7.45 (m, 2H), 7.36 (d, 1H, J=9.2 Hz), 7.10 (m, 2H), 6.58 (m, 1H), 4.65-4.60 (m, 1H), 3.73-3.69 (m, 2H), 3.37-3.27 (m, 2H), 3.24 (s, 3H), 3.20-3.09 (m, 4H), 1.94 (m, 2H), 1.55-1.49 (m, 2H).

Example 568. 4-[4-(5-Chloroimidazo[1,2-a]pyridin-6-yl)phenoxy]-N-(cyclopropylmethyl)-piperidine-1-carboxamide

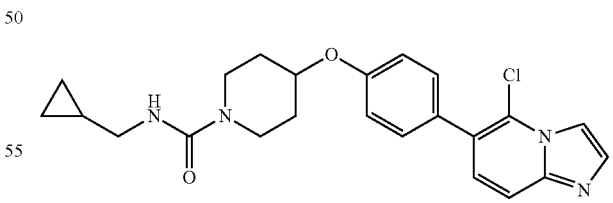

The title compound was prepared in a manner similar to the procedure used to prepare Example 564 in 75% yield. mp: 183° C.-185° C.; LC-MS: m/z=425 (M+1); 1H NMR (400 MHz, DMSO-$d_6$) δ: 8.08 (s, 1H), 7.76 (d, 1H, J=0.3 Hz), 7.70 (d, 1H, J=9.1 Hz), 7.46 (m, 2H), 7.36 (d, 1H, J=9.2 Hz), 7.11 (m, 2H), 6.59 (m, 1H), 4.65-4.60 (m, 1H), 3.74-3.69 (m, 2H), 3.16-3.09 (m, 2H), 2.93-2.90 (m, 2H), 1.96-1.93 (m, 2H), 1.57-1.49 (m, 2H), 0.98-0.88 (m, 1H), 0.39-0.35 (m, 2H), 0.16-0.13 (m, 2H)

Example 569. 4-[4-(5-Chloroimidazo[1,2-a]pyridin-6-yl)phenoxy]-N-isopropoxy-piperidine-1-carboxamide

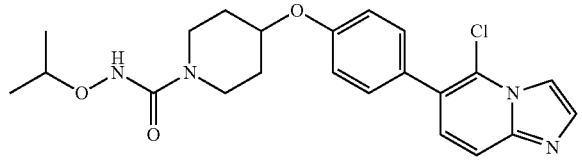

5-Chloro-6-[4-(4-piperidyloxy)phenyl]imidazo[1,2-a]pyridine HCl (0.053 g, 0.1455 mmol) and TEA (0.08 mL, 0.574 mmol) in DCM (2 mL) was added triphosgene (0.043 g, 0.144904 mmol) and the reaction stirred at rt for 2 h. Additional portions of triphosgene (25 mg) and TEA (20 uL) were added, the reaction was stirred for additional 30 min, then concentrated. The residue was dissolved in 1,2-dichloroethane (3 mL) and DIPEA (0.11 mL, 0.631 mmol) was added followed by O-isopropylhydroxylamine HCl (0.041 g, 0.36748 mmol). The reaction was heated at 70° C. for 5 h then stirred at rt for 16 h. The reaction was concentrated, diluted with EtOAc, washed with 1N aqueous $Na_2CO_3$, and then brine. The organic phase was dried over $MgSO_4$, filtered and concentrated. The residue was purified by Isco normal phase chromatography (methanol/DCM) then further purified by preparatory HPLC and lyophilized. The lyophilized material was diluted with EtOAc, washed with 1 N aqueous $Na_2CO_3$, then brine, dried over magnesium sulfate, filtered and concentrated to yield a white solid (24 mg, 37%). mp: 175° C.; LC-MS: m/z=429 (M+1); $^1$H NMR (400 MHz, MeOD) δ: 8.04 (s, 1H), 7.72 (s, 1H), 7.63 (d, 1H, J=9.2 Hz), 7.45-7.39 (m, 3H), 7.08 (m, 2H), 4.70-4.65 (m, 1H), 3.99-3.93 (m, 1H), 3.38-3.33 (m, 2H), 2.04-1.98 (m, 2H), 1.79-1.71 (m, 2H), 1.21 (d, 6H, J=6.2 Hz).

Example 570. 4-[4-(5-Chloroimidazo[1,2-a]pyridin-6-yl)phenoxy]-N-isopropyl-piperidine-1-carboxamide

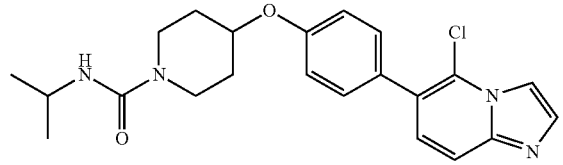 [SMILES: CC(C)NC(=O)N1CCC(Oc2ccc(-c3ccc4nccn4c3Cl)cc2)CC1]

The title compound was prepared in a manner similar in 45% yield. mp: 220° C.; LC-MS: m/z=413 (M+1); $^1$H NMR (400 MHz, DMSO-$d_6$) δ: 8.09 (s, 1H), 7.76 (d, 1H, J=1.3 Hz), 7.72-7.69 (m, 1H), 7.36 (d, 1H, J=9.2 Hz), 7.11 (m, 2H), 6.21 (d, 1H, J=7.6 Hz), 4.63-4.59 (m, 1H), 3.79-3.69 (m, 3H), 3.13-3.07 (m, 2H), 1.95-1.92 (m, 2H), 1.56-1.47 (m, 2H), 1.06 (d, 6H, J=6.6 Hz).

Example 571. 4-[4-(5-Chloroimidazo[1,2-a]pyridin-6-yl)phenoxy]-N-isobutoxy-piperidine-1-carboxamide

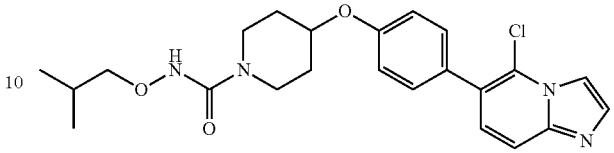

The title compound was prepared in a manner similar in 19% yield. mp: 157° C.; LC-MS: m/z=443 (M+1); $^1$H NMR (400 MHz, MeOD) δ: 8.04 (s, 1H), 7.72 (d, 1H, J=1.3 Hz), 7.63 (d, 1H, J=9.2 Hz), 7.45-7.40 (m, 3H), 7.08 (m, 2H), 4.70-4.65 (m, 1H), 3.70-3.64 (m, 2H), 3.57 (d, 2H, J=6.8 Hz), 3.37-3.32 (m, 2H), 2.04-1.94 (m, 3H), 1.79-1.71 (m, 2H), 0.95 (d, 6H, J=6.7 Hz).

Example 572. 4-[4-(5-Chloroimidazo[1,2-a]pyridin-6-yl)phenoxy]-N-isopentyl-piperidine-1-carboxamide

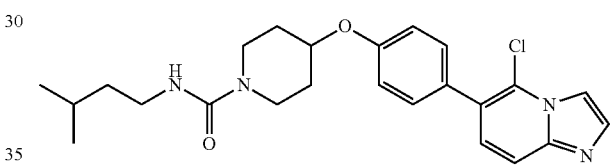

The title compound was prepared in a manner similar in 65% yield. mp: 185° C.; LC-MS: m/z=441 (M+1); 1H NMR (400 MHz, DMSO-$d_6$) δ: 8.09 (m, 1H), 7.76 (d, 1H, J=1.3 Hz), 7.71 (m, 1H), 7.46 (m, 2H), 7.36 (d, 1H, J=9.2 Hz), 7.10 (m, 2H), 6.47 (m, 1H), 4.63-4.60 (m, 1H), 3.72-3.69 (m, 2H), 3.16-3.01 (m, 4H), 1.94-1.91 (m, 2H), 1.60-1.47 (m, 3H), 1.33-1.28 (m, 2H), 0.87 (d, 6H, J=6.6 Hz).

Example 573. 4-[4-(5-Chloroimidazo[1,2-a]pyridin-6-yl)phenoxy]-N-ethoxy-piperidine-1-carboxamide

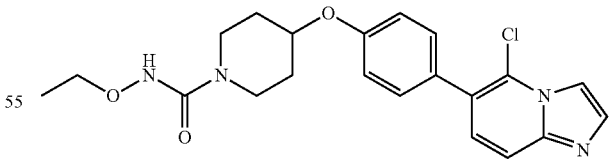

The title compound was prepared in a manner similar to the procedure used to prepare Example 7 in 28% yield. mp: 210° C.; LC-MS: m/z=443 (M+1); $^1$H NMR (400 MHz, DMSO-$d_6$) δ: 9.66 (s, 1H), 8.09 (s, 1H), 7.76 (d, 1H, J=1.2 Hz), 7.70 (d, 1H, J=9.2 Hz), 7.46 (m, 2H), 7.36 (d, 1H, J=9.2 Hz), 7.10 (m, 2H), 4.66-4.62 (m, 1H), 3.77-3.72 (m, 2H), 3.66-3.60 (m, 2H), 3.15-3.10 (m, 2H), 1.95 (m, 2H), 1.58-1.50 (m, 2H), 1.14-1.11 (m, 3H).

Example 574. 4-[4-(8-Methyl-7-quinolyl)phenoxy]-N-propoxy-piperidine-1-carboxamide

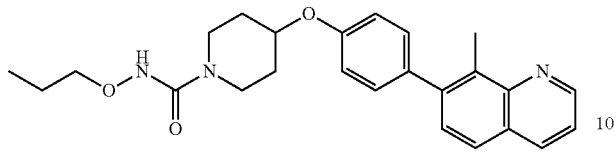

1,1'-Carbonyldiimidazole (0.082 g, 0.506 mmol), O-propylhydroxylamine HCl (0.05 g, 0.43 mmol) and DIPEA (0.11 mL, 0.63 mmol) in DCM (2.0 mL) and THF (0.5 mL) was stirred at rt for 2 h. In a separate vial, 8-methyl-7-[4-(4-piperidyloxy)phenyl]quinoline (0.097 g, 0.305 mmol), DIPEA (0.11 mL, 0.63 mmol) and DCM (2.5 mL) were combined, added to the reaction and stirred at rt for 24 h. The reaction was diluted with EtOAc and washed with saturated NH$_4$Cl solution, water, saturated NaHCO$_3$ solution, and then brine. The organic layer was dried over Na$_2$SO4, filtered and concentrated. The residue was triturated with ether, and dried under reduced pressure at 40° C. to yield a solid (65 mg, 51%) mp: 75° C.; LC-MS: m/z=420 (M+1); 1H NMR (400 MHz, DMSO-d$_6$) δ: 9.65 (s, 1H), 8.97 (m, 1H), 8.36 (m, 1H), 7.85 (d, 1H, J=8.4 Hz), 7.55 (m, 1H), 7.47 (d, 1H, J=8.4 Hz), 7.37 (m, 2H), 7.10 (m, 2H), 4.65-4.61 (m, 1H), 3.68-3.62 (m, 4H), 3.16-3.10 (m, 2H), 2.68 (s, 3H), 1.96 (m, 2H), 1.59-1.50 (m, 4H), 0.92-0.88 (m, 3H).

Example 575. 4-[4-(5-Chloroimidazo[1,2-a]pyridin-6-yl)phenoxy]piperidine-1-carbohydroxamic acid

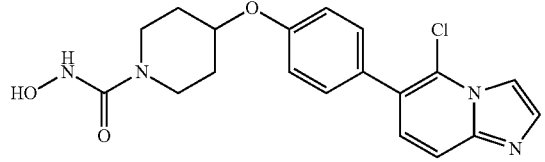 [SMILES: O=C(NO)N1CCC(Oc2ccc(-c3ccc4nccn4c3Cl)cc2)CC1]

The title compound was prepared in a manner similar to the previous procedure using hydroxylamine HCl in a 10% yield. mp: 232° C.; LC-MS: m/z=387 (M+1); $^1$H NMR (400 MHz, DMSO-d$_6$) δ: 9.08 (s, 1H), 8.09 (s, 1H), 7.99 (s, 1H), 7.76 (d, 1H, J=1.3 Hz), 7.70 (m, 1H), 7.46 (m, 2H), 7.36 (d, 1H, J=9.2 Hz), 7.11 (m, 2H), 4.66-4.61 (m, 1H), 3.69-3.64 (m, 2H), 3.16-3.09 (m, 2H), 1.96-1.92 (m, 2H), 1.57-1.50 (m, 2H).

Example 576. 4-[4-(5-Chloroimidazo[1,2-a]pyridin-6-yl)phenoxy]-N-propoxy-piperidine-1-carboxamide

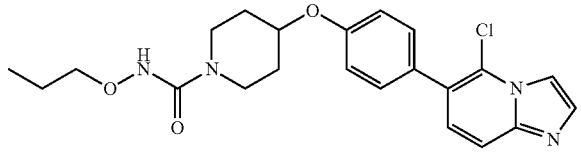

The title compound was prepared in a manner similar to the procedure in 82% yield. LC-MS: m/z=429 (M+1); 1H NMR (400 MHz, DMSO-d$_6$) δ: 9.64 (s, 1H), 8.09 (s, 1H), 7.76 (d, 1H, J=1.2 Hz), 7.70 (m, 1H), 7.46 (m, 2H), 7.36 (d, 1H, J=9.2 Hz), 7.10 (m, 2H), 4.67-4.61 (m, 1H), 3.68-3.61 (m, 4H), 3.15-3.10 (m, 2H), 1.97-1.92 (m, 2H), 1.58-1.50 (m, 4H).

Example 577. 4-[4-(5-Chloroimidazo[1,2-a]pyridin-6-yl)phenoxy]piperidine-1-carboxamide

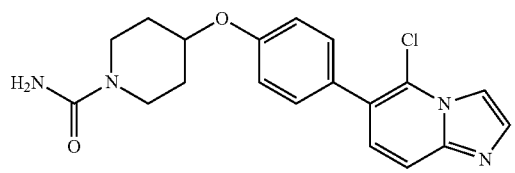 [SMILES: NC(=O)N1CCC(Oc2ccc(-c3ccc4nccn4c3Cl)cc2)CC1]

The title compound was prepared in a similar manner similar using isocyanato-(trimethyl)silane to give a 36% yield. mp: 204° C.; LC-MS: m/z=371 (M+1); $^1$H NMR (400 MHz, DMSO-d$_6$) δ: 8.09 (s, 1H), 7.76 (d, 1H, J=1.3 Hz), 7.70 (m, 1H), 7.46 (m, 2H), 7.36 (d, 1H, J=9.2 Hz), 7.11 (m, 2H), 5.97 (s, 2H), 4.65-4.59 (m, 1H), 3.73-3.67 (m, 2H), 3.15-3.09 (m, 2H), 1.95-1.91 (m, 2H), 1.57-1.48 (m, 2H).

Example 578. N-Ethyl-4-[4-(1-methyl-6-isoquinolyl)phenoxy]piperidine-1-carboxamide

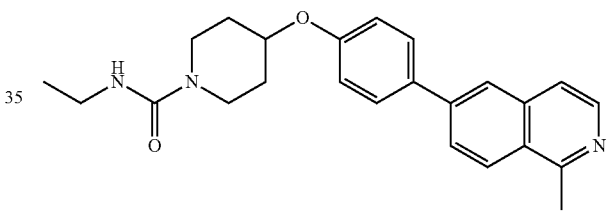 [SMILES: CCCNC(=O)N1CCC(Oc2ccc(-c3ccc4c(C)nccc4c3)cc2)CC1]

The title compound was prepared in a manner similar in 60% yield. mp: 211° C.; LC-MS: m/z=390 (M+1); 1H NMR (400 MHz, DMSO-d$_6$) δ: 8.33 (d, 1H, J=5.8 Hz), 8.25 (d, 1H, J=8.8 Hz), 8.17 (d, 1H, J=1.7 Hz), 7.97 (m, 1H), 7.79 (m, 2H), 7.69 (d, 1H, J=5.8 Hz), 7.14 (m, 2H), 6.51 (m, 1H), 4.67-4.62 (m, 1H), 3.72-3.67 (m, 2H), 3.16-3.02 (m, 4H), 2.89 (s, 3H), 1.95-1.92 (m, 2H), 1.57-1.48 (m, 2H), 1.03-0.99 (m, 3H).

Example 579. 4-[4-(1-Methyl-6-isoquinolyl)phenoxy]-N-propyl-piperidine-1-carboxamide

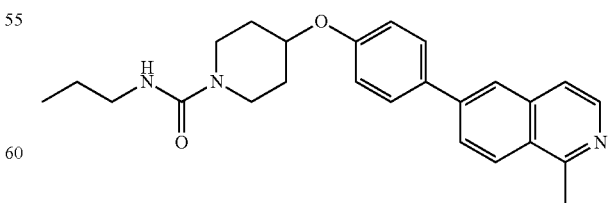

The title compound was prepared in a manner similar in 75% yield. mp: 181° C.; LC-MS: m/z=404 (M+1); $^1$H NMR (400 MHz, DMSO-d$_6$) δ: 8.34 (d, 1H, J=5.8 Hz), 8.25 (d, 1H, J=8.8 Hz), 8.17 (d, 1H, J=1.7 Hz), 7.97 (m, 1H), 7.79

(m, 2H), 7.69 (d, 1H, J=5.8 Hz), 7.14 (m, 2H), 6.52 (m, 1H), 4.67-4.62 (m, 1H), 3.73-3.68 (m, 2H), 3.16-3.10 (m, 2H), 3.01-2.96 (m, 2H), 2.89 (s, 3H), 1.95 (m, 2H), 1.56-1.48 (m, 2H), 1.46-1.36 (m, 2H), 0.85-0.81 (m, 3H).

Example 580. N-Isobutyl-4-[4-(1-methyl-6-isoquinolyl)phenoxy]piperidine-1-carboxamide

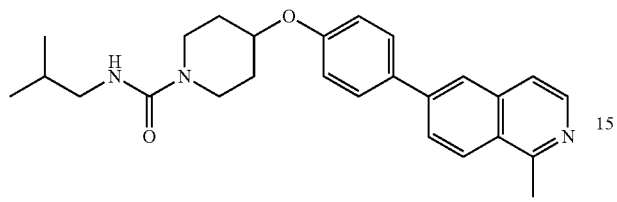

The title compound was prepared in a manner similar to the previous procedure in 24% yield. mp: 157° C.; LC-MS: m/z=418 (M+1); $^1$H NMR (400 MHz, DMSO-$d_6$) δ: 8.34 (d, 1H, J=5.8 Hz), 8.24 (d, 1H, J=8.8 Hz), 8.17 (d, 1H, J=1.7 Hz), 7.97 (m, 1H), 7.79 (m, 2H), 7.69 (d, 1H, J=5.8 Hz), 7.13 (m, 2H), 6.54 (m, 1H), 4.67-4.63 (m, 1H), 3.74-3.70 (m, 2H), 3.17-3.10 (m, 2H), 2.89 (s, 3H), 2.86-2.83 (m, 2H), 1.95-1.92 (m, 2H), 1.75-1.65 (m, 1H), 1.55-1.48 (m, 2H), 0.83 (d, 6H, J=6.7 Hz).

Example 581. 4-[4-(1-Methyl-6-isoquinolyl)phenoxy]piperidine-1-carboxamide

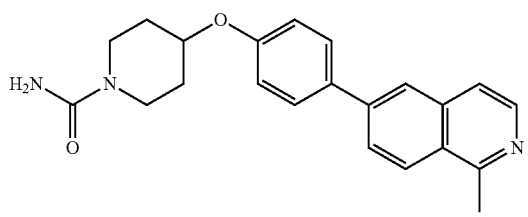 [SMILES: Cc1nccc2cc(-c3ccc(OC4CCN(C(N)=O)CC4)cc3)ccc12]

The title compound was prepared in a similar manner using isocyanato(trimethyl)-silane in 64% yield. mp: 232° C.; LC-MS: m/z=362 (M+1); 1H NMR (400 MHz, DMSO-$d_6$) δ: 8.34 (d, 1H, J=5.8 Hz), 8.25 (d, 1H, J=8.8 Hz), 8.18 (d, 1H, J=1.7 Hz), 7.97 (m, 1H), 7.80 (m, 2H), 7.70 (d, 1H, J=5.8 Hz), 7.14 (m, 2H), 5.98 (s, 2H), 4.68-4.62 (m, 1H), 3.72-3.66 (m, 2H), 3.17-3.11 (m, 2H), 2.89 (s, 3H), 1.96-1.91 (m, 2H), 1.57-1.49 (m, 2H).

Example 582. N-(Cyclopropylmethyl)-4-[4-(1-methyl-6-isoquinolyl)phenoxy]piperidine-1-carboxamide

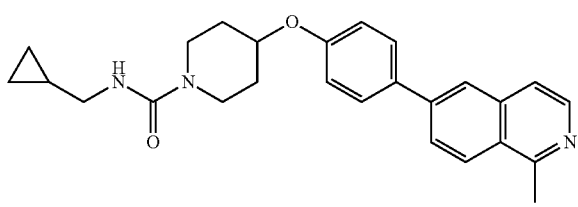 [SMILES: Cc1nccc2cc(-c3ccc(OC4CCN(C(=O)NCC5CC5)CC4)cc3)ccc12]

The title compound was prepared in a similar manner similar in 37% yield. mp: 188° C.; LC-MS: m/z=416 (M+1); $^1$H NMR (400 MHz, DMSO-$d_6$) δ 8.33 (d, 1H, J=5.8 Hz), 8.25 (d, 1H, J=8.8 Hz), 8.17 (d, 1H, J=1.7 Hz), 7.98 (m, 1H), 7.79 (m, 2H), 7.69 (d, 1H, J=5.8 Hz), 7.14 (m, 2H), 6.60 (m, 1H), 4.67-4.62 (m, 1H), 3.73-3.68 (m, 2H), 3.17-3.11 (m, 2H), 2.93-2.89 (m, 5H), 1.95-1.92 (m, 2H), 1.57-1.49 (m, 2H), 0.98-0.88 (m, 1H), 0.39-0.35 (m, 2H), 0.16-0.13 (m, 2H).

Example 583. N-Isopropoxy-4-[4-(1-methyl-6-isoquinolyl)phenoxy]piperidine-1-carboxamide

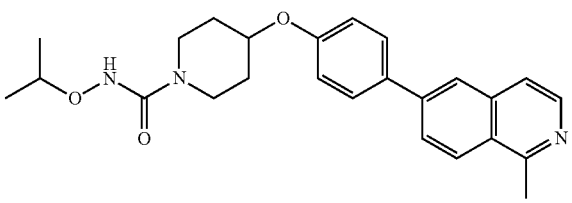 [SMILES: Cc1nccc2cc(-c3ccc(OC4CCN(C(=O)NOC(C)C)CC4)cc3)ccc12]

The title compound was prepared in a similar manner similar in 55% yield. mp: 189° C.; HPLC 5.25 min. rt=2.223 min.; LC-MS: m/z=420 (M+1); $^1$H NMR (400 MHz, DMSO-$d_6$) δ: 9.50 (s, 1H), 8.34 (d, 1H, J=5.8 Hz), 8.25 (d, 1H, J=8.8 Hz), 8.17 (d, 1H, J=1.7 Hz), 7.97 (m, 1H), 7.79 (m, 2H), 7.69 (d, 1H, J=5.8 Hz), 7.13 (m, 2H), 4.69-4.64 (m, 1H), 3.90-3.84 (m, 1H), 3.67-3.61 (m, 2H), 3.17-3.11 (m, 2H), 2.89 (s, 3H), 1.97-1.92 (m, 2H), 1.59-1.50 (m, 2H), 1.12 (d, 6H, J=6.2 Hz).

Example 584. 4-[4-(1-Methyl-6-isoquinolyl)phenoxy]-N-propoxypiperidine-1-carboxamide

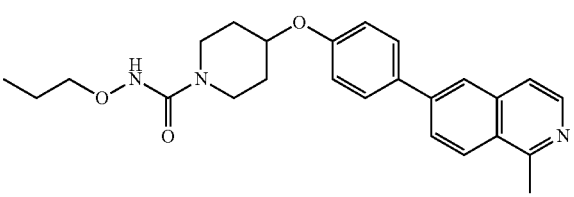 [SMILES: CCCONC(=O)N1CCC(Oc2ccc(-c3ccc4c(C)nccc4c3)cc2)CC1]

The title compound was prepared in a similar manner in 59% yield. mp: 165° C.; LC-MS: m/z=420 (M+1); $^1$H NMR (400 MHz, DMSO-$d_6$) δ: 9.64 (s, 1H), 8.34 (d, 1H, J=5.8 Hz), 8.25 (d, 1H, J=8.8 Hz), 8.17 (d, 1H, J=1.6 Hz), 7.97 (m, 1H), 7.80 (m, 2H), 7.69 (d, 1H, J=5.8 Hz), 7.14 (m, 2H), 4.68-4.64 (m, 1H), 3.68-3.59 (m, 4H), 3.17-3.11 (m, 2H), 2.89 (s, 3H), 1.99-1.93 (m, 2H), 1.59-1.50 (m, 4H), 0.92-0.88 (m, 3H).

Example 585. 4-[4-(1-Methyl-6-isoquinolyl)phenoxy]piperidine-1-carbohydroxamic acid

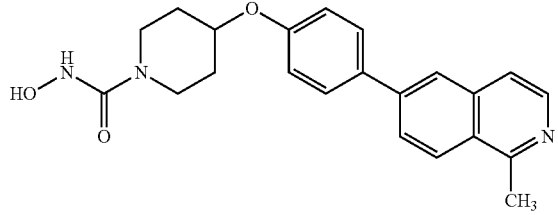 [SMILES: Cc1nccc2cc(-c3ccc(OC4CCN(C(=O)NO)CC4)cc3)ccc12]

The title compound was prepared in a similar manner using hydroxylamine HCl in 7% yield. mp: 185° C.; LC-MS: m/z=378 (M+1); $^1$H NMR (400 MHz, DMSO-d$_6$) δ: 9.09 (br s, 1H), 8.55 (d, 1H, J=9.0 Hz), 8.50 (s, 1H), 8.46 (d, 1H, J=6.4 Hz), 8.29 (m, 1H), 8.19 (m, 1H), 7.92 (m, 2H), 7.19 (m, 2H), 4.72-4.68 (m, 1H), 3.68-3.62 (m, 2H), 3.18-3.13 (m, 5H), 1.96-1.93 (m, 2H), 1.58-1.50 (m, 2H)

Example 586. N-Ethoxy-4-[4-(1-methyl-6-isoquinolyl)phenoxy]piperidine-1-carboxamide

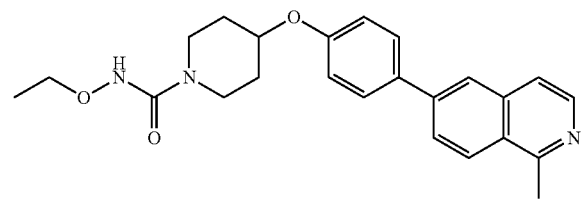 [SMILES: CCONC(=O)N1CCC(Oc2ccc(-c3ccc4c(C)nccc4c3)cc2)CC1]

The title compound was prepared in a similar manner similar in 16% yield. mp: 208° C.; LC-MS: m/z=406 (M+1); 1H NMR (400 MHz, DMSO-d$_6$) δ: 9.66 (s, 1H), 8.34 (d, 1H, J=5.8 Hz), 8.25 (d, 1H, J=8.8 Hz), 8.17 (d, 1H, J=1.8 Hz), 7.97 (m, 1H), 7.80 (m, 2H), 7.69 (d, 1H, J=5.9 Hz), 7.14 (m, 2H), 4.68-4.64 (m, 1H), 3.77-3.72 (m, 2H), 3.64-3.60 (m, 2H), 3.17-3.11 (m, 2H), 2.89 (s, 3H), 1.96-1.92 (m, 2H), 1.59-1.50 (m, 2H), 1.14-1.11 (m, 3H).

Example 587. N-Ethoxy-4-[4-(4-methyl-3-quinolyl)phenoxy]piperidine-1-carboxamide

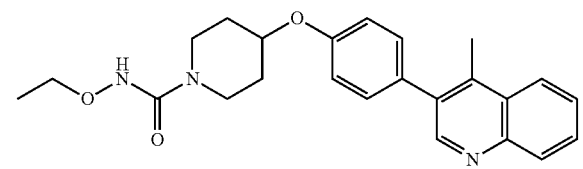 [SMILES: CCONC(=O)N1CCC(Oc2ccc(-c3cnc4ccccc4c3C)cc2)CC1]

The title compound was prepared in a similar manner in 59% yield. mp: 152° C.; LC-MS: m/z=406 (M+1); $^1$H NMR (400 MHz, DMSO-d$_6$) δ: 9.66 (s, 1H), 8.73 (s, 1H), 8.19 (d, 1H, J=8.3 Hz), 8.04 (d, 1H, J=8.2 Hz), 7.79-7.75 (m, 1H), 7.70-7.66 (m, 1H), 7.40 (d, 2H, J=8.6 Hz), 7.13 (d, 2H, J=8.6 Hz), 4.67-4.63 (m, 1H), 3.78-3.73 (m, 2H), 3.66-3.63 (m, 2H), 3.17-3.11 (m, 2H), 2.63 (s, 3H), 1.99-1.95 (m, 2H), 1.60-1.52 (m, 2H), 1.15-1.11 (m, 3H) Example 588. N-Isopropoxy-4-[4-(4-methyl-3-quinolyl)phenoxy]piperidine-1-carboxamide

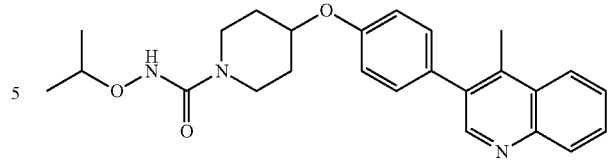 [SMILES: CCCONC(=O)N1CCC(Oc2ccc(-c3cnc4ccccc4c3C)cc2)CC1]

The title compound was prepared in a similar manner in 51% yield. mp: 80° C.; LC-MS: m/z=420 (M+1); $^1$H NMR (400 MHz, DMSO-d$_6$) δ: 9.51 (s, 1H), 8.73 (s, 1H), 8.19 (d, 1H, J=7.7 Hz), 8.04 (d, 1H, J=8.3 Hz), 7.79-7.75 (m, 1H), 7.70-7.66 (m, 1H), 7.40 (m, 2H), 7.13 (m, 2H), 4.67-4.63 (m, 1H), 3.92-3.83 (m, 1H), 3.68-3.63 (m, 2H), 3.17-3.11 (m, 2H), 2.63 (s, 3H), 1.99-1.95 (m, 2H), 1.60-1.52 (m, 2H), 1.12 (d, 6H, J=6.2 Hz).

Example 589. 4-[4-(4-Methyl-3-quinolyl)phenoxy]-N-propoxy-piperidine-1-carboxamide

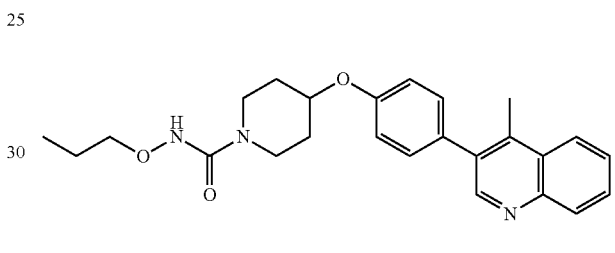

The title compound was prepared in a similar manner tin 61% yield. mp: 75° C.; LC-MS: m/z=420 (M+1); $^1$H NMR (400 MHz, DMSO-d$_6$) δ: 9.65 (s, 1H), 8.73 (s, 1H), 8.18 (d, 1H, J=7.7 Hz), 8.04 (d, 1H, J=8.0 Hz), 7.79-7.75 (m, 1H), 7.70-7.66 (m, 1H), 7.40 (m, 2H), 7.13 (m, 2H), 4.67-4.63 (m, 1H), 3.68-3.62 (m, 4H), 3.17-3.10 (m, 2H), 2.63 (s, 3H), 1.99-1.95 (m, 2H), 1.59-1.52 (m, 4H), 0.92-0.88 (m, 3H).

Example 590. N-Isobutyl-4-[4-(4-methyl-3-quinolyl)phenoxy]piperidine-1-carboxamide

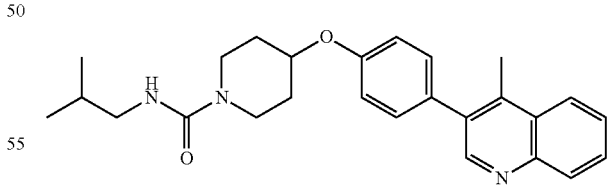

The title compound was prepared in a similar manner in 54% yield. mp: 153° C.; HPLC 5.25 min. rt=2.490 min.; LC-MS: m/z=418 (M+1); $^1$H NMR (400 MHz, DMSO-d$_6$) δ: 8.73 (s, 1H), 8.19 (d, 1H, J=7.7 Hz), 8.04 (d, 1H, J=7.6 Hz), 7.79-7.75 (m, 1H), 7.70-7.66 (m, 1H), 7.40 (m, 2H), 7.13 (m, 2H), 6.56-6.53 (m, 1H), 4.66-4.62 (m, 1H), 3.76-3.72 (m, 2H), 3.16-3.10 (m, 2H), 2.87-2.84 (m, 2H), 2.63 (s, 3H), 1.95 (m, 2H), 1.74-1.67 (m, 1H), 1.57-1.49 (m, 2H), 0.83 (d, 6H, J=6.7 Hz).

Example 591. 4-[4-(4-Methyl-3-quinolyl)phenoxy]-N-propyl-piperidine-1-carboxamide

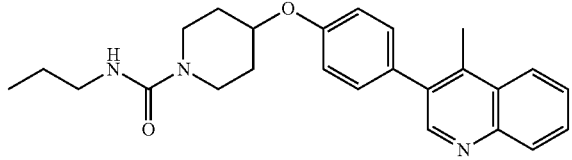 [SMILES: CCCNC(=O)N1CCC(Oc2ccc(-c3cnc4ccccc4c3C)cc2)CC1]

The title compound was prepared in a similar manner in 64% yield. mp: 171° C.; min; LC-MS: m/z=404 (M+1); 1H NMR (400 MHz, DMSO-d$_6$) δ 8.73 (s, 1H), 8.19 (m, 1H), 8.04 (m, 1H), 7.79-7.74 (m, 1H), 7.70-7.66 (m, 1H), 7.41-7.38 (m, 2H), 7.13 (m, 2H), 6.53 (m, 1H), 4.65-4.61 (m, 1H), 3.75-3.70 (m, 2H), 3.15-3.09 (m, 2H), 3.01-2.96 (m, 2H), 2.63 (s, 3H), 1.99-1.94 (m, 2H), 1.57-1.49 (m, 2H), 1.46-1.37 (m, 2H), 0.85-0.82 (m, 3H).

Example 592. N-Ethyl-4-[4-(5-methylimidazo[1,2-a]pyridin-6-yl)phenoxy]piperidine-1-carboxamide

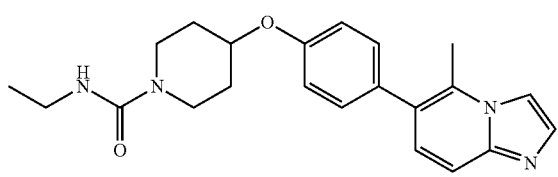 [SMILES: CCNC(=O)N1CCC(Oc2ccc(-c3ccc4nccn4c3C)cc2)CC1]

To a suspension of 5-methyl-6-[4-(4-piperidyloxy)phenyl]imidazo[1,2-a]pyridine 2HCl (0.060 g, 0.158 mmol) in anhydrous DCM (3.0 mL) in a scintillation vial at RT under N$_2$ was added DIPEA (0.0826 mL, 0.0612 g, 0.473 mmol) followed by isocyanatoethane (0.0187 mL, 0.0168 g, 0.237 mmol). The solution was stirred at RT overnight. Saturated aqueous NaHCO$_3$ solution (3 mL) was added to the reaction. The vial was shaken and the layers separated. The organic layer was withdrawn via a syringe and loaded directly onto a 24 g silica gel ISCO column (repeated with 2×2 mL of DCM). Flash chromatography on the ISCO (0 to 100% (33% 20:1:1 EtOH:NH$_4$OH:H$_2$O-67% EtOAc)-100 to 0% hexanes) yielded the desired compound as a white solid (0.041 g, 69%). Analysis: LCMS m/z=379 (M+1); $^1$H NMR (400 MHz, DMSO-d$_6$) δ: 7.89 (s, 1H), 7.68 (d, J=1.3 Hz, 1H), 7.53 (d, J=9.0 Hz, 1H), 7.37-7.31 (m, 2H), 7.20 (d, J=9.3 Hz, 1H), 7.11-7.05 (m, 2H), 6.50 (t, J=5.3 Hz, 1H), 4.60 (tt, J=8.1, 3.8 Hz, 1H), 3.76-3.65 (m, 2H), 3.16-3.00 (m, 4H), 2.54 (s, 3H), 1.99-1.88 (m, 2H), 1.58-1.46 (m, 2H), 1.02 (t, J=7.0 Hz, 3H).

Example 593. N-Isobutyl-4-[4-(5-methylimidazo[1,2-a]pyridin-6-yl)phenoxy]piperidine-1-carboxamide

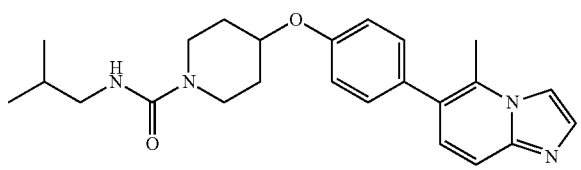 [SMILES: Cc1c(-c2ccc(OC3CCN(C(=O)NCC(C)C)CC3)cc2)ccc2nccn12]

To a suspension of 5-methyl-6-[4-(4-piperidyloxy)phenyl]imidazo[1,2-a]pyridine 2HCl (0.0600 g, 0.158 mmol) in anhydrous DCM (3.0 mL) in a scintillation vial at RT under N$_2$ was added DIPEA (0.0826 mL, 0.0612 g, 0.473 mmol) followed by 1-isocyanato-2-methylpropane (0.0235 g, 0.237 mmol). The solution stirred at RT overnight. Saturated aqueous NaHCO$_3$ solution (3 mL) was added to the reaction. The vial was shaken and the layers allowed to separate. The organic layer was withdrawn via a syringe and needle and loaded directly onto a 24 g silica gel ISCO column (repeated with 2×2 mL of DCM). Flash chromatography on the ISCO (0 to 100% (33% 20:1:1 EtOH:NH$_4$OH:H$_2$O-67% EtOAc)-100 to 0% hexanes) yielded the desired compound as a white solid (0.047 g, 73%). Analysis: LCMS m/z=407 (M+1); $^1$H NMR (400 MHz, DMSO-d$_6$) δ: 7.89 (s, 1H), 7.68 (d, J=1.0 Hz, 1H), 7.53 (d, J=9.0 Hz, 1H), 7.37-7.30 (m, 2H), 7.20 (d, J=9.3 Hz, 1H), 7.12-7.05 (m, 2H), 6.54 (t, J=5.5 Hz, 1H), 4.61 (tt, J=8.2, 3.9 Hz, 1H), 3.78-3.67 (m, 2H), 3.12 (ddd, J=13.2, 9.7, 3.0 Hz, 2H), 2.85 (dd, J=6.8, 5.8 Hz, 2H), 2.54 (s, 3H), 1.99-1.88 (m, 2H), 1.70 (dquin, J=13.6, 6.8 Hz, 1H), 1.58-1.45 (m, 2H), 0.83 (d, J=6.8 Hz, 6H).

Example 594. 4-[4-(5-Methylimidazo[1,2-a]pyridin-6-yl)phenoxy]-N-propyl-piperidine-1-carboxamide

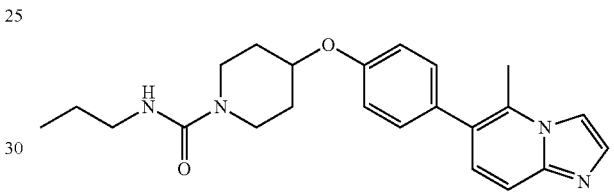

To a suspension of 5-methyl-6-[4-(4-piperidyloxy)phenyl]imidazo[1,2-a]pyridine 2HCl (0.0600 g, 0.158 mmol) in anhydrous DCM (3.0 mL) in a scintillation vial at RT under N$_2$ was added DIPEA (0.0826 mL, 0.0612 g, 0.473 mmol) followed by 1-isocyanatopropane (0.0222 mL, 0.0201 g, 0.237 mmol). The solution was stirred at RT overnight. Saturated aqueous NaHCO$_3$ solution (3 mL) was added to the reaction. The vial was shaken and the layers allowed to separate. The organic layer was withdrawn via a syringe and needle and loaded directly onto a 24 g silica gel ISCO column (repeated with 2×2 mL of DCM). Flash chromatography on the ISCO (0 to 100% (33% 20:1:1 EtOH: NH$_4$OH: H$_2$O-67% EtOAc)-100 to 0% hexanes) yielded the desired compound as a white solid (0.050 g, 81%). Analysis: LCMS m/z=393 (M+1); $^1$H NMR (400 MHz, DMSO-d$_6$) δ: 7.89 (s, 1H), 7.68 (d, J=1.3 Hz, 1H), 7.53 (d, J=9.0 Hz, 1H), 7.37-7.30 (m, 2H), 7.20 (d, J=9.0 Hz, 1H), 7.11-7.05 (m, 2H), 6.51 (t, J=5.4 Hz, 1H), 4.65-4.55 (m, 1H), 3.77-3.66 (m, 2H), 3.11 (ddd, J=13.2, 9.6, 3.0 Hz, 2H), 3.03-2.94 (m, 2H), 2.54 (s, 3H), 1.99-1.88 (m, 2H), 1.58-1.47 (m, 2H), 1.42 (sxt, J=7.3 Hz, 2H), 0.83 (t, J=7.4 Hz, 3H).

Example 595. N-(Cyclopropylmethyl)-4-[4-(5-methylimidazo[1,2-a]pyridin-6-yl)-phenoxy]piperidine-1-carboxamide

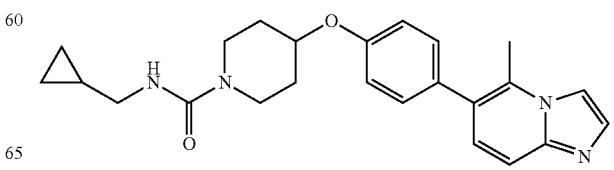

To a suspension of 5-methyl-6-[4-(4-piperidyloxy)phenyl]imidazo[1,2-a]pyridine 2HCl (0.0600 g, 0.158 mmol) in anhydrous DCM (3.0 mL) in a scintillation vial at RT under N₂ was added DIPEA (0.0826 mL, 0.0612 g, 0.473 mmol) followed by isocyanatomethylcyclopropane (0.0230 g, 0.237 mmol). The solution was stirred at RT overnight. Saturated aqueous NaHCO₃ solution (3 mL) was added to the reaction. The vial was shaken and the layers allowed to separate. The organic layer was withdrawn via a syringe and needle and loaded directly onto a 24 g silica gel ISCO column (repeated with 2×2 mL of DCM). Flash chromatography on the ISCO (0 to 100% (33% 20:1:1 EtOH: NH₄OH: H₂O-67% EtOAc)-100 to 0% hexanes) yielded the desired compound as a white solid (0.053 g, 83%). Analysis: LCMS m/z=405 (M+1); ¹H NMR (400 MHz, DMSO-d₆) δ: 7.74 (s, 1H), 7.52 (d, J=1.0 Hz, 1H), 7.38 (d, J=9.3 Hz, 1H), 7.22-7.16 (m, 2H), 7.05 (d, J=9.3 Hz, 1H), 6.97-6.90 (m, 2H), 6.45 (t, J=5.6 Hz, 1H), 4.46 (tt, J=8.1, 3.8 Hz, 1H), 3.62-3.52 (m, 2H), 2.97 (ddd, J=13.2, 9.5, 3.1 Hz, 2H), 2.76 (t, J=6.0 Hz, 2H), 2.39 (s, 3H), 1.84-1.74 (m, J=9.3 Hz, 1H), 1.84-1.74 (m, 2H), 1.44-1.31 (m, 2H), 0.84-0.73 (m, 1H), 0.25-0.18 (m, 2H), 0.03-0.04 (m, 2H).

Example 596. 4-[4-(5-Methylimidazo[1,2-a]pyridin-6-yl)phenoxy]-N-(3-pyridyl)piperidine-1-carboxamide

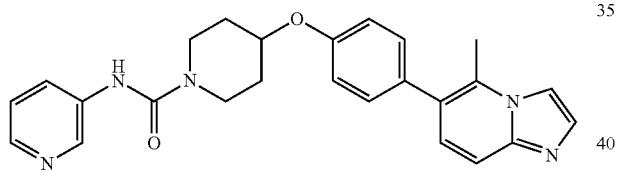

To a suspension of 5-methyl-6-[4-(4-piperidyloxy)phenyl]imidazo[1,2-a]pyridine 2HCl (0.0700 g, 0.184 mmol) in anhydrous DCM (3.0 mL) in a scintillation vial at RT under N₂ was added DIPEA (0.0963 mL, 0.0714 g, 0.552 mmol) followed by 3-isocyanatopyridine (0.0442 g, 0.368 mmol). The solution was stirred at RT overnight. Saturated aqueous NaHCO₃ solution (3 mL) was added to the reaction. The vial was shaken and the layers allowed to separate. The organic layer was concentrated and the residue was purified by preparative HPLC on the Gilson (5 to 40% MeCN-95 to 60% water (both with 0.1% TFA) over 15 min.; Phenomenex Gemini 5 m NX-C₁₈ 100 Å 150×30 mm column). The fractions were combined and partitioned between saturated aqueous NaHCO₃ solution and DCM, then separated, dried with Na₂SO₄, and concentrated to yield the desired compound as the free base, an off-white solid (0.049 g, 62%). Analysis: LCMS m/z=428 (M+1); ¹H NMR (400 MHz, DMSO-d₆) δ: 8.76 (s, 1H), 8.65 (d, J=2.3 Hz, 1H), 8.15 (dd, J=4.8, 1.5 Hz, 1H), 7.91-7.86 (m, 2H), 7.68 (d, J=1.0 Hz, 1H), 7.53 (d, J=9.0 Hz, 1H), 7.38-7.33 (m, 2H), 7.27 (dd, J=8.7, 4.4 Hz, 1H), 7.21 (d, J=9.3 Hz, 1H), 7.14-7.09 (m, 2H), 4.69 (tt, J=8.0, 4.0 Hz, 1H), 3.93-3.81 (m, 2H), 3.39-3.36 (m, 1H), 2.55 (s, 3H), 2.04 (ddd, J=9.4, 6.0, 3.1 Hz, 2H), 1.70-1.59 (m, 2H).

Example 597. N-(2-Methoxyethyl)-4-[4-(5-methylimidazo[1,2-a]pyridin-6-yl)phenoxy]piperidine-1-carboxamide

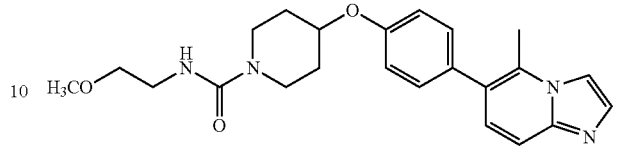

To a suspension of 5-methyl-6-[4-(4-piperidyloxy)phenyl]imidazo[1,2-a]pyridine 2HCl (0.0600 g, 0.158 mmol) in anhydrous DCM (3.0 mL) in a scintillation vial at RT under N₂ was added DIPEA (0.0826 mL, 0.0612 g, 0.473 mmol) followed by 1-isocyanato-2-methoxyethane (0.0239 g, 0.237 mmol). The solution was stirred at RT overnight. Saturated aqueous NaHCO₃ solution (3 mL) was added to the reaction. The vial was shaken and the layers allowed to separate. The organic layer was withdrawn via a syringe and needle and loaded directly onto a 24 g silica gel ISCO column (repeated with 2×2 mL of DCM). Flash chromatography on the ISCO (0 to 100% (33% 20:1:1 EtOH:NH₄OH: H₂O-67% EtOAc)-100 to 0% hexanes) yielded the desired compound as an off-white solid (0.062 g, 96%). Analysis: LCMS m/z=409 (M+1); ¹H NMR (400 MHz, DMSO-d₆) δ: 7.89 (s, 1H), 7.67 (d, J=1.3 Hz, 1H), 7.53 (d, J=9.3 Hz, 1H), 7.36-7.31 (m, 2H), 7.20 (d, J=9.0 Hz, 1H), 7.11-7.06 (m, 2H), 6.58 (t, J=5.5 Hz, 1H), 4.60 (tt, J=8.1, 3.9 Hz, 1H), 3.76-3.65 (m, 2H), 3.36-3.33 (m, 2H), 3.24 (s, 3H), 3.22-3.08 (m, 4H), 2.54 (s, 3H), 1.98-1.89 (m, 2H), 1.58-1.46 (m, 2H).

Example 598. [4-[4-(5-Methylimidazo[1,2-a]pyridin-6-yl)phenoxy]-1-piperidyl]-(4-methylpiperazin-1-yl)methanone

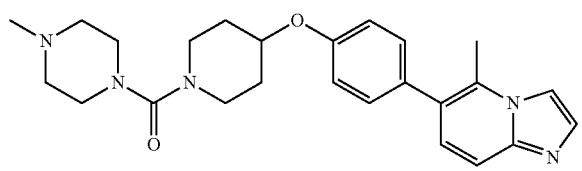 [SMILES: Cc1c(-c2ccc(OC3CCN(C(=O)N4CCN(C)CC4)CC3)cc2)ccc2nccn12]

Step 1. (4-Nitrophenyl) 4-[4-(5-methylimidazo[1,2-a]pyridin-6-yl)phenoxy]piperidine-1-carboxylate To a solution of 4-nitrophenyl chloroformate (0.233 g, 1.16 mmol) in anhydrous DCM (2.0 mL) in a scintillation vial in a bath of cool tap water under N₂ was added a suspension of 5-methyl-6-[4-(4-piperidyloxy)phenyl]imidazo[1,2-a]pyridine 2HCl (0.400 g, 1.05 mmol) and TEA (0.484 mL, 0.351 g, 3.47 mmol) in anhydrous DCM (2.0 mL+2×1.0 mL rinse). The reaction stirred for 60 min. The suspension was partitioned between DCM and water and separated. The aqueous layer was re-extracted with DCM. The organic layers were combined and washed with brine, then dried over Na₂SO₄, filtered, and concentrated. Silica gel chromatography on the ISCO (0 to 100% (20% MeOH-80% EtOAc)-100 to 0% hexanes; 40 g column) yielded the desired compounds as a yellowish foam (0.330 g, 66%).

Analysis: LCMS m/z=473 (M+1); $^1$H NMR (400 MHz, DCCl$_3$) δ: 8.30-8.24 (m, 2H), 7.75 (d, J=1.3 Hz, 1H), 7.62 (d, J=9.3 Hz, 1H), 7.55 (s, 1H), 7.35-7.27 (m, 4H), 7.21 (d, J=9.0 Hz, 1H), 7.05-7.00 (m, 2H), 4.67 (tt, J=6.3, 3.3 Hz, 1H), 3.95-3.63 (m, 4H), 2.57 (s, 3H), 2.12-1.94 (m, 5H).

Step 2. [4-[4-(5-Methylimidazo[1,2-a]pyridin-6-yl)phenoxy]-1-piperidyl]-(4-methylpiperazin-1-yl)methanone A mixture of (4-nitrophenyl) 4-[4-(5-methylimidazo[1,2-a]pyridin-6-yl)phenoxy]-piperidine-1-carboxylate (0.060 g, 0.13 mmol), 1-methylpiperazine (0.070 mL, 0.064 g, 0.63 mmol), and K$_2$CO$_3$ (0.026 g, 0.19 mmol) in anhydrous DMF (2.0 mL) in a small microwave vial under Ar was heated in the microwave at 150° C. for 15 min. The mixture was partitioned between DCM and saturated aqueous NaHCO$_3$ solution and separated. The aqueous layer was re-extracted with 40 mL of DCM. The organic layers were combined and washed with water, then brine, then dried over Na$_2$SO$_4$, filtered, and concentrated. The residue was purified by preparative HPLC on the Gilson (5 to 40% MeCN-95 to 60% water (both with 0.1% TFA) over 15 min.; Phenomenex Gemini 5 m NX-C$_{18}$ 100 Å 150×30 mm column). The good fractions were combined and partitioned between saturated aqueous NaHCO$_3$ solution and DCM, then separated, dried with Na$_2$SO$_4$, and concentrated to yield the desired compound as the free base, a yellow solid. Analysis: LCMS m/z=434 (M+1); $^1$H NMR (400 MHz, DMSO-d$_6$) δ: 7.89 (s, 1H), 7.67 (d, J=1.3 Hz, 1H), 7.53 (d, J=9.0 Hz, 1H), 7.37-7.31 (m, 2H), 7.20 (d, J=9.3 Hz, 1H), 7.11-7.05 (m, 2H), 4.62 (tt, J=8.0, 3.8 Hz, 1H), 3.51-3.41 (m, 2H), 3.20-3.11 (m, 4H), 3.06 (ddd, J=13.0, 9.3, 3.0 Hz, 2H), 2.54 (s, 3H), 2.28 (t, J=4.8 Hz, 4H), 2.17 (s, 3H), 2.02-1.92 (m, 2H), 1.67-1.55 (m, 2H).

Example 599. N,N-Dimethyl-4-[4-(5-methylimidazo[1,2-a]pyridin-6-yl)phenoxy]piperidine-1-carboxamide

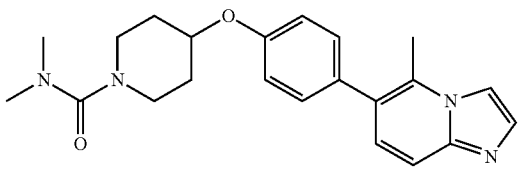 [SMILES: Cc1c(-c2ccc(OC3CCN(C(=O)N(C)C)CC3)cc2)ccc2nccn12]

A mixture of (4-nitrophenyl) 4-[4-(5-methylimidazo[1,2-a]pyridin-6-yl)-phenoxy]piperidine-1-carboxylate (0.060 g, 0.13 mmol), O-isopropylhydroxylamine HCl (0.043 g, 0.38 mmol), and K$_2$CO$_3$ (0.079 g, 0.57 mmol) in anhydrous DMF (2.0 mL) in a small microwave vial under Ar was heated in the microwave at 150° C. for 15 min. LC-MS showed primarily unreacted starting material and ~22% of the N,N-dimethylurea product derived from high-temperature decomposition of the DMF. The reaction was heated an additional 45 min. at 150° C., and LCMS showed almost exclusively the unintended N,N-dimethylurea product. The mixture was partitioned between DCM and saturated aqueous NaHCO$_3$ solution and separated. The aqueous layer was re-extracted with 40 mL of DCM. The organic layers were combined and washed with water, then brine, then dried over Na$_2$SO$_4$, filtered, and concentrated. Silica gel chromatography on the ISCO (0 to 100% (33% 20:1:1 EtOH:NH$_4$OH: H$_2$O-67% EtOAc)-100 to 0% hexanes) yielded the compound as a tan solid (0.034 g, 71%). Analysis: LCMS m/z=379 (M+1); $^1$H NMR (400 MHz, DMSO-d$_6$) δ: 7.89 (s, 1H), 7.68 (d, J=1.0 Hz, 1H), 7.53 (d, J=9.3 Hz, 1H), 7.37-7.31 (m, 2H), 7.21 (d, J=9.0 Hz, 1H), 7.11-7.06 (m, 2H), 4.62 (tt, J=8.1, 3.9 Hz, 1H), 3.47-3.39 (m, 2H), 3.02 (ddd, J=13.1, 9.4, 3.1 Hz, 2H), 2.75 (s, 6H), 2.54 (s, 3H), 2.04-1.93 (m, 2H), 1.68-1.56 (m, 2H).

Example 600. N-Isopropoxy-4-[4-(5-methylimidazo[1,2-a]pyridin-6-yl)phenoxy]piperidine-1-carboxamide

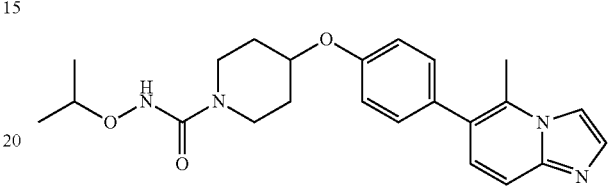

Step 1

To a solution of triphosgene (0.049 g, 0.17 mmol) in anhydrous DCM (2.0 mL) in a large scintillation vial at 0° C. under N$_2$ was added a solution of 5-methyl-6-[4-(4-piperidyloxy)-phenyl]imidazo[1,2-a]pyridine 2HCl (0.060 g, 0.16 mmol) and TEA (0.088 mL, 0.064 g, 0.63 mmol) in anhydrous DCM (1.5 mL+2×0.5 mL rinses) dropwise. The yellowish solution stirred at 0° C. for about 60 min. The reaction was concentrated to yield a yellowish solid.

Step 2

In a separate vial, O-isopropylhydroxylamine HCl (0.053 g, 0.47 mmol) was suspended in anhydrous 1,2-dichloroethane (1.5 mL), and DIPEA (0.12 mL, 0.092 g, 0.71 mmol) was added. The resulting solution was added dropwise to the vial containing the carbamoyl chloride, which was then heated to 70° C. before the heat was turned off and the reaction stirred at RT overnight. The mixture was partitioned between EtOAc and saturated aqueous NaHCO$_3$ solution and separated. The organic layer was washed with water, then brine, then dried over Na$_2$SO$_4$, filtered, and concentrated. Silica gel chromatography on the ISCO (0 to 100% (33% 20:1:1 EtOH:NH$_4$OH:H$_2$O-67% EtOAc)-100 to 0% hexanes; 24 g column) yielded the desired compound as an off-white solid (0.034 g, 53%). Analysis: LCMS m/z=409 (M+1); $^1$H NMR (400 MHz, DMSO-d6) δ: 9.50 (s, 1H), 7.89 (s, 1H), 7.68 (d, J=1.3 Hz, 1H), 7.53 (d, J=9.3 Hz, 1H), 7.37-7.30 (m, 2H), 7.20 (d, J=9.3 Hz, 1H), 7.11-7.05 (m, 2H), 4.62 (tt, J=8.0, 3.8 Hz, 1H), 3.87 (spt, J=6.2 Hz, 1H), 3.70-3.59 (m, 2H), 3.13 (ddd, J=13.1, 9.5, 3.3 Hz, 2H), 2.54 (s, 3H), 2.00-1.89 (m, 2H), 2.00-1.89 (m, 2H), 1.60-1.48 (m, 2H), 1.12 (d, J=6.3 Hz, 6H).

Example 601. N-Isobutoxy-4-[4-(5-methylimidazo[1,2-a]pyridin-6-yl)phenoxy]piperidine-1-carboxamide

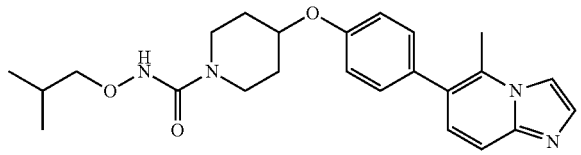 [SMILES: Cc1c(-c2ccc(OC3CCN(C(=O)NOCC(C)C)CC3)cc2)ccc2nccn12]

Step 1

To a solution of triphosgene (0.049 g, 0.17 mmol) in anhydrous DCM (2.0 mL) in a large scintillation vial at 0° C. under $N_2$ was added a solution of 5-methyl-6-[4-(4-piperidyloxy)phenyl]imidazo[1,2-a]pyridine 2HCl (0.060 g, 0.16 mmol) and TEA (0.088 mL, 0.064 g, 0.63 mmol) in anhydrous DCM (1.5 mL+2×0.5 mL rinses) dropwise. The yellowish solution stirred at 0° C. for about 60 min. The reaction was concentrated to yield a yellowish solid.

Step 2

In a separate vial, O-isobutylhydroxylamine HCl (0.059 g, 0.47 mmol) was suspended in anhydrous 1,2-dichloroethane (1.5 mL), and DIPEA (0.12 mL, 0.092 g, 0.71 mmol) was added. The resulting solution was added dropwise to the vial containing the carbamoyl chloride, which was then heated to 80° C. for several hours. The mixture was partitioned between EtOAc and saturated aqueous $NaHCO_3$ solution and separated. The organic layer was washed with water, then brine, then dried over $Na_2SO_4$, filtered, and concentrated. Silica gel chromatography on the ISCO (0 to 100% (33% 20:1:1 EtOH: $NH_4OH:H_2O$-67% EtOAc)-100 to 0% hexanes; 24 g column) yielded the desired compound as an off-white solid (0.030 g, 45%). Analysis: LCMS m/z=423 (M+1); $^1$H NMR (400 MHz, DMSO-$d_6$) δ: 9.64 (s, 1H), 7.89 (s, 1H), 7.68 (d, J=1.3 Hz, 1H), 7.53 (d, J=9.3 Hz, 1H), 7.37-7.30 (m, 2H), 7.20 (d, J=9.3 Hz, 1H), 7.11-7.05 (m, 2H), 4.66-4.57 (m, J=8.1, 4.1, 4.1 Hz, 1H), 3.68-3.57 (m, 2H), 3.49 (d, J=6.8 Hz, 2H), 3.18-3.08 (m, 2H), 2.54 (s, 3H), 1.99-1.90 (m, 2H), 1.90-1.80 (m, 1H), 1.60-1.48 (m, 2H), 0.89 (d, J=6.8 Hz, 6H).

Example 602. Isobutyl 4-[4-(5-methylimidazo[1,2-a]pyridin-6-yl)phenoxy]piperidine-1-carboxylate

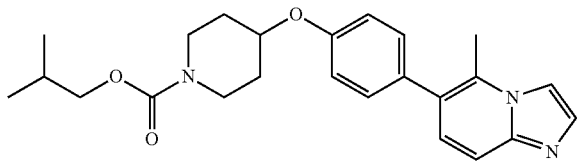 [SMILES: Cc1c(-c2ccc(OC3CCN(C(=O)OCC(C)C)CC3)cc2)ccc2nccn12]

To a solution of isobutyl carbonochloridate (0.031 mL, 0.032 g, 0.24 mmol) in anhydrous DCM (1.5 mL) in a large scintillation vial at 0° C. under $N_2$ was added a solution of 5-methyl-6-[4-(4-piperidyloxy)phenyl]imidazo[1,2-a]pyridine 2HCl (0.060 g, 0.16 mmol) and DIPEA (0.11 mL, 0.082 g, 0.63 mmol) in anhydrous DCM (1.0 mL+2×0.5 mL rinse) dropwise. The reaction was stirred at 0° C. for 90 min. The reaction was quenched by adding 3 mL of saturated aqueous $NaHCO_3$ solution, then partitioned between EtOAc and additional saturated aqueous $NaHCO_3$ solution and separated. The organic layer was washed with water, then brine, then dried over $Na_2SO_4$, filtered, and concentrated. Silica gel chromatography on the ISCO (0 to 80% (33% 20:1:1 EtOH: $NH_4OH:H_2O$-67% EtOAc)-100 to 20% hexanes; 24 g column) yielded the desired compound as an off-white solid (0.047 g, 73%). Analysis: LCMS m/z=408 (M+1); $^1$H NMR (400 MHz, DMSO-$d_6$) δ: 7.89 (s, 1H), 7.68 (d, J=1.3 Hz, 1H), 7.53 (d, J=9.0 Hz, 1H), 7.37-7.31 (m, 2H), 7.21 (d, J=9.3 Hz, 1H), 7.12-7.06 (m, 2H), 4.65 (tt, J=7.9, 3.7 Hz, 1H), 3.80 (d, J=6.5 Hz, 2H), 3.78-3.69 (m, 2H), 3.31-3.20 (m, 2H), 2.54 (s, 3H), 2.02-1.93 (m, 2H), 1.88 (dquin, J=13.3, 6.7 Hz, 1H), 1.59 (dtd, J=12.8, 8.6, 3.9 Hz, 2H), 0.90 (d, J=6.8 Hz, 6H).

Example 603. N-Isopropyl-4-[4-(5-methylimidazo[1,2-a]pyridin-6-yl)phenoxy]piperidine-1-carboxamide

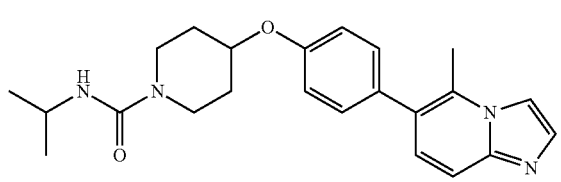 [SMILES: Cc1c(-c2ccc(OC3CCN(C(=O)NC(C)C)CC3)cc2)ccc2nccn12]

To a suspension of 5-methyl-6-[4-(4-piperidyloxy)phenyl]imidazo[1,2-a]pyridine 2HCl (0.0600 g, 0.158 mmol) in anhydrous DCM (3.0 mL) in a scintillation vial at RT under $N_2$ was added DIPEA (0.0826 mL, 0.0612 g, 0.473 mmol) followed by 2-isocyanatopropane (0.0232 mL, 0.0201 g, 0.237 mmol). The solution stirred at RT overnight. Saturated aqueous $NaHCO_3$ solution (3 mL) was added to the reaction. The vial was shaken and the layers allowed to separate. The organic layer was withdrawn via a syringe and needle and loaded directly onto a 24 g silica gel ISCO column (repeated with 2×2 mL of DCM). Flash chromatography on the ISCO (0 to 100% (33% 20:1:1 EtOH: $NH_4OH:H_2O$-67% EtOAc)-100 to 0% hexanes) yielded the desired compound as a white solid (0.051 g, 82%). Analysis: LCMS m/z=393 (M+1); $^1$H NMR (400 MHz, DMSO-$d_6$) δ: 7.89 (s, 1H), 7.68 (d, J=1.3 Hz, 1H), 7.53 (d, J=9.3 Hz, 1H), 7.37-7.31 (m, 2H), 7.21 (d, J=9.3 Hz, 1H), 7.12-7.05 (m, 2H), 6.21 (d, J=7.8 Hz, 1H), 4.65-4.55 (m, 1H), 3.83-3.66 (m, 3H), 3.10 (ddd, J=13.1, 9.6, 3.1 Hz, 2H), 2.54 (s, 3H), 1.98-1.88 (m, 2H), 1.58-1.45 (m, 2H), 1.06 (d, J=6.5 Hz, 6H).

Example 604. 4-[4-(5-Methylimidazo[1,2-a]pyridin-6-yl)phenoxy]-N-(1-methylpyrazol-4-yl)piperidine-1-carboxamide

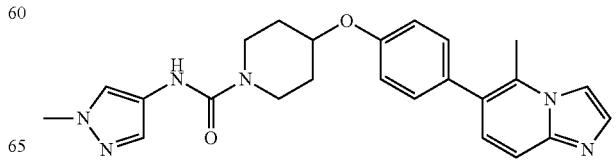

To a suspension of 5-methyl-6-[4-(4-piperidyloxy)phenyl]imidazo[1,2-a]pyridine 2HCl (0.0600 g, 0.158 mmol) in anhydrous DCM (3.0 mL) in a scintillation vial at RT under $N_2$ was added DIPEA (0.0826 mL, 0.0612 g, 0.473 mmol) followed by 4-isocyanato-1-methyl-pyrazole (0.0291 g, 0.237 mmol). The solution stirred at RT overnight. The mixture was partitioned between EtOAc and saturated aqueous $NaHCO_3$ solution and separated. The organic layer was washed with water, then brine, then dried over $Na_2SO_4$, filtered, and concentrated. The residue was purified by preparative HPLC on the Gilson (5 to 50% MeCN-95 to 50% water (both with 0.1% TFA) over 15 min.; Phenomenex Gemini 5 m NX-$C_{18}$ 100 Å 150×30 mm column). The good fractions were combined and partitioned between saturated aqueous $NaHCO_3$ solution and DCM, then separated, dried with $Na_2SO_4$, and concentrated to yield the desired compound as the free base, an off-white solid (0.048 g, 71%). Analysis: LCMS m/z=431 (M+1); $^1$H NMR (400 MHz, DMSO-$d_6$) δ: 8.55 (s, 1H), 7.90 (s, 1H), 7.68 (s, 1H), 7.67 (s, 1H), 7.53 (d, J=9.0 Hz, 1H), 7.38-7.31 (m, 3H), 7.21 (d, J=9.3 Hz, 1H), 7.13-7.07 (m, 2H), 4.70-4.61 (m, J=8.0, 4.2, 4.2 Hz, 1H), 3.85-3.77 (m, 2H), 3.75 (s, 3H), 3.25 (ddd, J=13.2, 9.6, 3.0 Hz, 2H), 2.55 (s, 3H), 2.04-1.95 (m, 2H), 1.64-1.54 (m, 2H).

Example 605. tert-Butyl 4-[4-(5-methylimidazo[1,2-a]pyridin-6-yl)phenoxy]piperidine-1-carboxylate

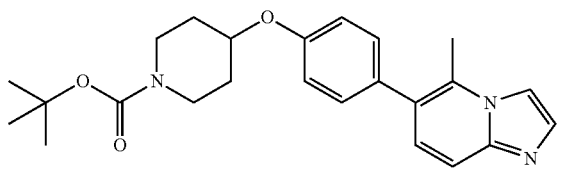 [SMILES: Cc1c(-c2ccc(OC3CCN(C(=O)OC(C)(C)C)CC3)cc2)ccc2nccn12]

Triphenylphosphine (0.702 g, 2.68 mmol) and palladium (II) acetate (0.150 g, 0.669 mmol) were placed in a pressure flask, then dissolved in 1,4-dioxane (27 mL). Nitrogen gas was bubbled through the solution for several minutes, then the flask was capped and stirred at RT for 30 min. While again bubbling $N_2$ through the mixture, tert-butyl 4-[4-(4,4,5,5-tetramethyl-1,3,2-dioxaborolan-2-yl)phenoxy]piperidine-1-carboxylate (5.40 g, 13.4 mmol), 6-bromo-5-methyl-imidazo[1,2-a]pyridine (2.97 g, 14.1 mmol), DMF (38 mL), and 1 M aqueous $Na_2CO_3$ solution (40.2 mmol) were added, and the flask was capped and heated to 80° C. for about eight hours before the heat was turned off and the reaction was stirred at RT overnight. The mixture was concentrated, then partitioned between EtOAc and saturated aqueous $NaHCO_3$ solution and separated. The aqueous layer was re-extracted with 100 mL of EtOAc. The organic layers were combined and washed with water (2×), then brine, then dried over $Na_2SO_4$, filtered, and concentrated. Silica gel chromatography on the ISCO (0 to 100% (20% 20:1:1 EtOH:$NH_4OH$:$H_2O$-80% EtOAc)-100 to 0% hexanes; 120 g column) yielded the desired compound as a white solid. Analysis: LCMS m/z=408 (M+1); $^1$H NMR (400 MHz, DMSO-d6) δ: 7.89 (s, 1H), 7.68 (d, J=1.0 Hz, 1H), 7.53 (d, J=9.0 Hz, 1H), 7.37-7.31 (m, 2H), 7.20 (d, J=9.3 Hz, 1H), 7.12-7.06 (m, 2H), 4.63 (tt, J=8.0, 3.7 Hz, 1H), 3.74-3.65 (m, 2H), 3.26-3.14 (m, J=9.5, 9.5 Hz, 2H), 2.54 (s, 3H), 2.00-1.90 (m, 2H), 1.61-1.50 (m, 2H), 1.41 (s, 9H).

Example 606. 4-[4-(5-Methylimidazo[1,2-a]pyridin-6-yl)phenoxy]-N-(2,2,2-trifluoro-ethyl)piperidine-1-carboxamide

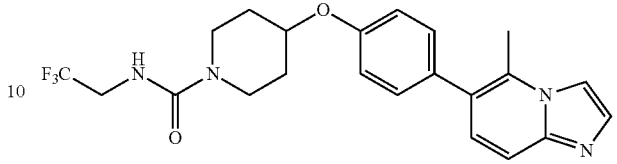

To a solution of 1,1'-carbonyldiimidazole (0.0426 g, 0.263 mmol) in a 4:1 mixture of anhydrous DCM (1.60 mL) and THF (0.40 mL) in a large scintillation vial at RT under $N_2$ was added 2,2,2-trifluoroethanamine (0.0125 mL, 0.0173 g, 0.175 mmol). The solution stirred at RT for about two hours before adding a solution of 5-methyl-6-[4-(4-piperidyloxy)phenyl]imidazo[1,2-a]pyridine 2HCl (0.0832 g, 0.219 mmol) and DIPEA (0.0916 mL, 0.0679 g, 0.525 mmol) in anhydrous DCM (1.0 mL+2×0.5 mL rinses) dropwise. The reaction was stirred at RT for 72 hours. The mixture was partitioned between EtOAc and saturated aqueous $NaHCO_3$ solution and separated. The organic layer was washed with water, then brine, then dried over $Na_2SO_4$, filtered, and concentrated. The residue was purified by preparative HPLC on the Gilson (10 to 50% MeCN-90 to 50% water (both with 0.1% TFA) over 15 min.; Phenomenex Gemini 5 m NX-$C_{18}$ 100 Å 150×30 mm column). The fractions were combined and partitioned between saturated aqueous $NaHCO_3$ solution and DCM, then separated, dried with $Na_2SO_4$, and concentrated to yield the desired compound as the free base, an off-white solid (0.038 g, 50%). Analysis: LCMS m/z=433 (M+1); $^1$H NMR (400 MHz, DMSO-$d_6$) δ 7.90 (s, 1H), 7.68 (s, 1H), 7.53 (d, J=9.3 Hz, 1H), 7.37-7.31 (m, 2H), 7.24-7.16 (m, 2H), 7.12-7.06 (m, 2H), 4.69-4.59 (m, J=8.0, 4.2, 4.2 Hz, 1H), 3.84 (qd, J=9.8, 6.3 Hz, 2H), 3.78-3.70 (m, 2H), 3.20 (ddd, J=13.2, 9.6, 3.0 Hz, 2H), 2.54 (s, 3H), 2.01-1.91 (m, 2H), 1.60-1.49 (m, 2H). $^{19}$F NMR (377 MHz, DMSO-d6) δ −71.22 (s, 1F).

Example 607. 4-[4-(5-Methylimidazo[1,2-a]pyridin-6-yl)phenoxy]-N-propoxy-piperidine-1-carboxamide

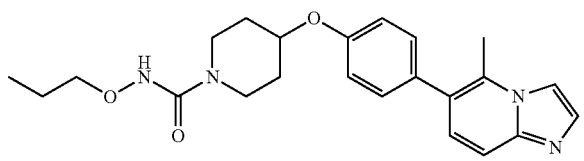 [SMILES: CCCONC(=O)N1CCC(Oc2ccc(-c3ccc4nccn4c3C)cc2)CC1]

To a solution of 1,1'-carbonyldiimidazole (0.051 g, 0.31 mmol) in a 4:1 mixture of anhydrous DCM (1.60 mL) and THF (0.40 mL) in a large scintillation vial at RT under $N_2$ was added a solution of O-propylhydroxylamine HCl (0.032 g, 0.29 mmol) and DIPEA (0.058 mL, 0.043 g, 0.34 mmol) in the 4:1 solvent mixture (1.0 mL+2×0.5 mL rinses) dropwise. The solution stirred at RT for about two hours before adding a solution of 5-methyl-6-[4-(4-piperidyloxy)phenyl]imidazo[1,2-a]pyridine 2HCl (0.085 g, 0.22 mmol) and DIPEA (0.058 mL, 0.043 g, 0.34 mmol) in anhydrous DCM (1.0 mL+2×0.5 mL rinses) dropwise. The reaction was stirred at RT for two hours. The mixture was partitioned between EtOAc and saturated aqueous NaHCO₃ solution and separated. The organic layer was washed with water, then brine, then dried over Na₂SO₄, filtered, and concentrated. Silica gel chromatography on the ISCO (0 to 100% (33% 20:1:1 EtOH: NH₄OH:H₂O-67% EtOAc)-100 to 0% hexanes; 24 g column) yielded an off-white solid. The compound was partitioned between DCM and saturated aqueous NH₄Cl solution and separated. The aqueous layer was re-extracted with DCM. The organic layers were combined and washed with water, saturated aqueous NaHCO₃ solution, and brine, then dried over Na₂SO₄, filtered, and concentrated to yield the desired compound as an off-white solid (0.058 g, 64%). Analysis: LCMS m/z=409 (M+1); ¹H NMR (400 MHz, DMSO-d₆) δ: 9.64 (s, 1H), 7.89 (s, 1H), 7.68 (d, J=1.3 Hz, 1H), 7.53 (d, J=9.3 Hz, 1H), 7.37-7.31 (m, 2H), 7.20 (d, J=9.0 Hz, 1H), 7.12-7.05 (m, 2H), 4.62 (tt, J=7.9, 3.7 Hz, 1H), 3.69-3.59 (m, 4H), 3.13 (ddd, J=13.2, 9.5, 3.1 Hz, 2H), 2.54 (s, 3H), 2.00-1.89 (m, 2H), 1.60-1.48 (m, 4H), 0.90 (t, J=7.5 Hz, 3H).

Example 608. N-Ethoxy-4-[4-(5-methylimidazo[1,2-a]pyridin-6-yl)phenoxy]piperidine-1-carboxamide

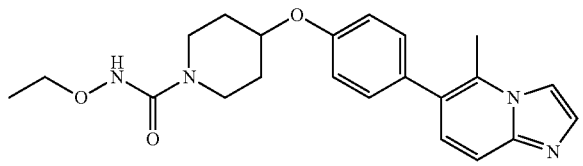 [SMILES: CCONC(=O)N1CCC(Oc2ccc(-c3ccc4nccn4c3C)cc2)CC1]

To a solution of 1,1'-carbonyldiimidazole (0.051 g, 0.32 mmol) in a 4:1 mixture of anhydrous DCM (2.00 mL) and THF (0.50 mL) in a large scintillation vial at RT under N₂ was added DIPEA (0.073 mL, 0.054 g, 0.42 mmol) followed by O-ethylhydroxylamine HCl (0.029 g, 0.29 mmol). The mixture was stirred at RT for about two hours before adding a solution of 5-methyl-6-[4-(4-piperidyloxy)phenyl]imidazo[1,2-a]pyridine 2HCl (0.080 g, 0.21 mmol) and DIPEA (0.073 mL, 0.054 g, 0.42 mmol) in anhydrous DCM (1.0 mL+2×0.5 mL rinses) dropwise. The resulting mixture was stirred at RT overnight. The mixture was partitioned between EtOAc and saturated aqueous NH₄Cl solution and separated. The organic layer was washed with 15 mL of water, saturated aqueous NaHCO₃ solution, and brine, then dried over Na₂SO₄, filtered, and concentrated. Silica gel chromatography on the ISCO (0 to 100% (33% 20:1:1 EtOH:NH₄OH:H₂O-67% EtOAc)-100 to 0% hexanes; 24 g column) yielded the desired compound as a white solid (0.073 g, 88%). Analysis: LCMS m/z=395 (M+1); ¹H NMR (400 MHz, DMSO-d₆) δ: 9.66 (s, 1H), 7.89 (s, 1H), 7.68 (d, J=1.3 Hz, 1H), 7.53 (d, J=9.3 Hz, 1H), 7.37-7.31 (m, 2H), 7.20 (d, J=9.3 Hz, 1H), 7.11-7.06 (m, 2H), 4.67-4.57 (m, J=8.0, 4.3, 4.3 Hz, 1H), 3.75 (q, J=7.0 Hz, 2H), 3.68-3.58 (m, 2H), 3.13 (ddd, J=13.2, 9.5, 3.1 Hz, 2H), 2.54 (s, 3H), 2.00-1.89 (m, 2H), 1.60-1.48 (m, 2H), 1.13 (t, J=7.0 Hz, 3H).

Example 609. 2-Amino-1-[4-[4-(8-methyl-7-quinolyl)phenoxy]-1-piperidyl]ethanone, 2HCl

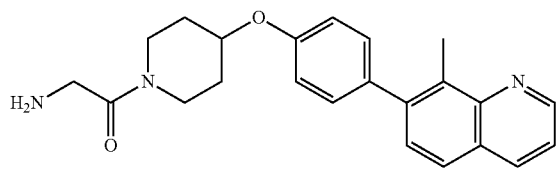 [SMILES: Cc1c(-c2ccc(OC3CCN(C(=O)CN)CC3)cc2)ccc2cccnc12]

Step 1

To a suspension of 2-(tert-butoxycarbonylamino)acetic acid (0.053 g, 0.30 mmol) and HATU (0.11 g, 0.30 mmol) in anhydrous DCM (2.0 mL) in a large scintillation vial at RT under N₂ was added DIPEA (0.18 mL, 0.13 g, 1.0 mmol). The mixture stirred for 20 min. before adding 8-methyl-7-[4-(4-piperidyloxy)phenyl]quinolone (0.080 g, 0.25 mmol) and stirring at RT overnight. The mixture was partitioned between EtOAc and saturated aqueous NH₄Cl solution and separated. The organic layer was washed with water, saturated aqueous NaHCO₃ solution, and brine, then dried over Na₂SO₄, filtered, and concentrated. Silica gel chromatography on the ISCO (0 to 100% EtOAc-100 to 0% hexanes; 24 g column) yielded tert-butyl N-[2-[4-[4-(8-methyl-7-quinolyl)phenoxy]-1-piperidyl]-2-oxo-ethyl]carbamate as an off-white foam.

Step 2

To a solution of tert-butyl N-[2-[4-[4-(8-methyl-7-quinolyl)phenoxy]-1-piperidyl]-2-oxo-ethyl]carbamate (0.120 g, 0.252 mmol) in anhydrous EtOAc (3.0 mL) in a small RBF at RT under N₂ was added HCl (4 mol/L) in 1,4-dioxane (3.0 mL, 12 mmol) dropwise. A yellowish precipitate formed immediately. The reaction stirred at RT for about two hours. The reaction was concentrated. The residue was partitioned between EtOAc and saturated aqueous NH₄Cl solution and separated. The organic layer was washed with water, saturated aqueous NaHCO₃ solution, and brine, then dried over Na₂SO₄, filtered and concentrated to yield a yellowish oil. The material was transferred to a vial, then dissolved in 0.5 mL of DCM before adding 0.250 mL of the 4.0 M HCl-dioxane solution while stirring. A precipitate formed immediately. The reaction was concentrated and dried under vacuum to yield the desired product as the dihydrochloride salt, a yellow solid (0.090 g, 80%). Analysis: LCMS m/z=376 (M+1); ¹H NMR (400 MHz, DMSO-d⁶) δ: 9.06 (dd, J=4.3, 1.5 Hz, 1H), 8.69-8.51 (m, 1H), 8.14 (t, J=5.0 Hz, 3H), 7.98 (d, J=8.5 Hz, 1H), 7.72 (dd, J=7.7, 4.4 Hz, 1H), 7.59 (d, J=8.3 Hz, 1H), 7.41 (d, J=8.8 Hz, 2H), 7.14 (d, J=8.8 Hz, 2H), 4.76 (tt, J=7.6, 3.6 Hz, 1H), 3.92 (d, J=5.8 Hz, 3H), 3.42-3.31 (m, 3H), 2.71 (s, 3H), 2.10-1.95 (m, 1H), 2.10-1.95 (m, 2H), 1.77-1.66 (m, 1H), 1.66-1.54 (m, J=12.6, 8.5, 4.1, 4.1 Hz, 1H).

Example 610. (2R)-2-Amino-1-[4-[4-(8-methyl-7-quinolyl)phenoxy]-1-piperidyl]propan-1-one, 2HCl

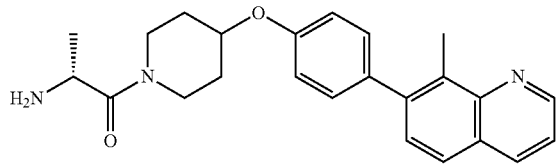 [SMILES: Cc1c(-c2ccc(OC3CCN(C(=O)[C@@H](C)N)CC3)cc2)ccc2cccnc12]

Step 1

To a suspension of (2R)-2-(tert-butoxycarbonylamino)propanoic acid (0.057 g, 0.30 mmol) and HATU (0.11 g, 0.30 mmol) in anhydrous DCM (2.00 mL) in a large scintillation vial at RT under $N_2$ was added DIPEA (0.18 mL, 0.13 g, 1.0 mmol). The mixture stirred for ~20 min. before adding 8-methyl-7-[4-(4-piperidyloxy)phenyl]quinoline (0.080 g, 0.25 mmol) and stirring at RT overnight. The mixture was partitioned between EtOAc and saturated aqueous $NH_4Cl$ solution and separated. The organic layer was washed with water, saturated aqueous $NaHCO_3$ solution, and brine, then dried over $Na_2SO_4$, filtered, and concentrated to yield a cloudy, colorless oil. Silica gel chromatography on the ISCO (0 to 100% EtOAc-100 to 0% hexanes; 24 g column) yielded tert-butyl N-[(1R)-1-methyl-2-[4-[4-(8-methyl-7-quinolyl)phenoxy]-1-piperidyl]-2-oxo-ethyl]carbamate as a white foam.

Step 2

To a solution of tert-butyl N-[(1R)-1-methyl-2-[4-[4-(8-methyl-7-quinolyl)phenoxy]-1-piperidyl]-2-oxo-ethyl]carbamate in anhydrous EtOAc (5.0 mL) in a small RBF at RT under $N_2$ was added HCl (4 mol/L) in 1,4-dioxane (5.0 mL, 20 mmol) dropwise. The mixture stirred for several hours before the reaction was concentrated to yield the desired product as the dihydrochloride salt, a yellow solid (0.116 g, 100%). Analysis: LCMS m/z=390 (M+1); $^1$H NMR (400 MHz, DMSO-$d_6$) δ: 9.08 (dd, J=4.4, 1.1 Hz, 1H), 8.67 (d, J=6.3 Hz, 1H), 8.18 (d, J=4.0 Hz, 3H), 8.01 (d, J=8.5 Hz, 1H), 7.75 (dd, J=7.8, 4.5 Hz, 1H), 7.61 (d, J=8.5 Hz, 1H), 7.41 (d, J=8.0 Hz, 2H), 7.15 (d, J=8.5 Hz, 2H), 4.84-4.69 (m, 1H), 4.47-4.35 (m, 1H), 4.22-4.09 (m, 1H), 4.06-3.97 (m, J=12.3 Hz, 1H), 3.52-3.44 (m, 5H), 3.34-3.25 (m, 1H), 2.71 (s, 3H), 2.11-1.92 (m, 3H), 1.77-1.53 (m, 2H), 1.34 (dd, J=6.8, 2.3 Hz, 3H).

Example 611. N-Methoxy-4-[4-(5-methylimidazo[1,2-a]pyridin-6-yl)phenoxy]piperidine-1-carboxamide

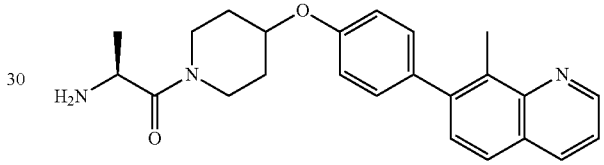

To a solution of 1,1'-carbonyldiimidazole (0.051 g, 0.32 mmol) in a 4:1 mixture of anhydrous DCM (2.00 mL) and THF (0.50 mL) in a large scintillation vial at RT under $N_2$ was added DIPEA (0.073 mL, 0.054 g, 0.42 mmol) followed by O-methylhydroxylamine HCl (0.025 g, 0.29 mmol). The solution stirred at RT for about two hours before adding additional DIPEA (0.073 mL, 0.054 g, 0.42 mmol) and 5-methyl-6-[4-(4-piperidyloxy)phenyl]imidazo[1,2-a]pyridine 2HCl (0.080 g, 0.21 mmol). The resulting mixture was stirred at RT overnight. The mixture was partitioned between EtOAc and saturated aqueous $NH_4Cl$ solution and separated. The organic layer was washed with water, saturated aqueous $NaHCO_3$ solution, and brine, then dried over $Na_2SO_4$, filtered, and concentrated. Silica gel chromatography on the ISCO (0 to 100% (33% 20:1:1 EtOH: $NH_4OH$: $H_2O$-67% EtOAc)-100 to 0% hexanes; 24 g column) yielded the desired product as a white solid (0.061 g, 76%). Analysis: LCMS m/z=381 (M+1); $^1$H NMR (400 MHz, DMSO-$d_6$) δ: 9.74 (s, 1H), 7.89 (s, 1H), 7.68 (d, J=1.3 Hz, 1H), 7.53 (d, J=9.0 Hz, 1H), 7.37-7.30 (m, 2H), 7.20 (d, J=9.0 Hz, 1H), 7.11-7.05 (m, 2H), 4.62 (tt, J=8.0, 3.7 Hz, 1H), 3.68-3.57 (m, 2H), 3.54 (s, 3H), 3.18-3.08 (m, 2H), 2.54 (s, 3H), 2.00-1.89 (m, 2H), 1.61-1.49 (m, 2H).

Example 612. (2S)-2-Amino-1-[4-[4-(8-methyl-7-quinolyl)phenoxy]-1-piperidyl]propan-1-one 2HCl

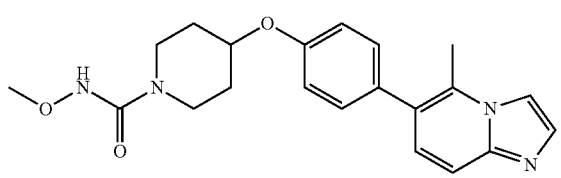 [SMILES: CONC(=O)N1CCC(Oc2ccc(-c3ccc4nccn4c3C)cc2)CC1]

Step 1

To a suspension of (2S)-2-(tert-butoxycarbonylamino)propanoic acid (0.057 g, 0.30 mmol) and HATU (0.11 g, 0.30 mmol) in anhydrous DCM in a scintillation vial at RT under $N_2$ was added DIPEA (0.18 mL, 0.13 g, 1.0 mmol). The mixture stirred for ~20 min. before adding 8-methyl-7-[4-(4-piperidyloxy)phenyl]quinoline (0.080 g, 0.25 mmol) and stirring at RT overnight. The mixture was partitioned between EtOAc and saturated aqueous $NH_4Cl$ solution and separated. The organic layer was washed with water, saturated aqueous $NaHCO_3$ solution, and brine, then dried over $Na_2SO_4$, filtered, and concentrated. Silica gel chromatography on the ISCO (0 to 100% EtOAc-100 to 0% hexanes; 24 g column) yielded tert-butyl N-[(1S)-1-methyl-2-[4-[4-(8-methyl-7-quinolyl)phenoxy]-1-piperidyl]-2-oxo-ethyl]carbamate as a white foam.

Step 2

To a solution of tert-butyl N-[(1S)-1-methyl-2-[4-[4-(8-methyl-7-quinolyl)phenoxy]-1-piperidyl]-2-oxo-ethyl]carbamate in anhydrous EtOAc (5.0 mL) in a small RBF at RT under $N_2$ was added HCl (4 mol/L) in 1,4-dioxane solution (5.0 mL, 20 mmol) dropwise. The mixture stirred for several hours before the reaction was concentrated to yield the desired product as the dihydrochloride salt, a yellow solid (0.113 g, 97%). Analysis: LCMS m/z=390 (M+1); $^1$H NMR (400 MHz, DMSO-$d_6$) δ: 9.08 (dd, J=4.4, 1.4 Hz, 1H), 8.68 (d, J=6.8 Hz, 1H), 8.18 (d, J=4.3 Hz, 3H), 8.01 (d, J=8.5 Hz, 1H), 7.76 (dd, J=7.8, 4.3 Hz, 1H), 7.62 (d, J=8.3 Hz, 1H), 7.42 (d, J=8.0 Hz, 2H), 7.15 (d, J=8.8 Hz, 2H), 4.84-4.69 (m, 1H), 4.47-4.36 (m, 1H), 4.14-4.10 (m, 1H), 4.07-3.96 (m, J=12.8 Hz, 1H), 3.33-3.25 (m, 1H), 2.71 (s, 3H), 2.11-1.93 (m, 4H), 1.77-1.53 (m, 2H), 1.34 (dd, J=6.9, 2.4 Hz, 3H).

Example 613. 4-[4-(5-Methylimidazo[1,2-a]pyridin-6-yl)phenoxy]piperidine-1-carbohydroxamic acid

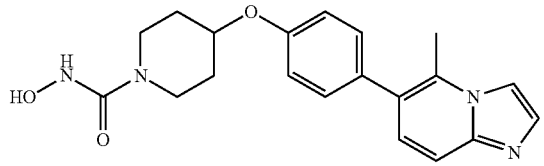 [SMILES: Cc1c(-c2ccc(OC3CCN(C(=O)NO)CC3)cc2)ccc2nccn12]

Step 1

To a solution of triphosgene (0.064 g, 0.22 mmol) in anhydrous 1,2-dichloroethane (2.0 mL) in a large scintillation vial at 0° C. under $N_2$ was added a solution of 5-methyl-6-[4-(4-piperidyloxy)phenyl]imidazo[1,2-a]pyridine 2HCl (0.075 g, 0.20 mmol) and DIPEA (0.14 mL, 0.10 g, 0.79 mmol) in anhydrous 1,2-dichloroethane (1.0 mL+2×0.5 mL rinses) dropwise. The yellowish solution stirred at 0° C. for about 60 min. Additional DIPEA (0.14 mL, 0.10 g, 0.79 mmol) was added, followed immediately by hydroxylamine HCl (0.041 g, 0.59 mmol). The resulting solution was heated to 75° C. After several hours, LC-MS showed primarily starting material, and no obvious sign of the desired product. Additional DIPEA (0.210 mL, 0.15 g, 1.19 mmol) and hydroxylamine HCl (0.041 g, 0.59 mmol) were added, and the reaction was heated to 70° C. overnight. The mixture was partitioned between DCM and saturated aqueous $NaHCO_3$ solution and separated. The aqueous layer was re-extracted with DCM. The organic layers were combined and washed with water, then brine, then dried over $Na_2SO_4$, filtered, and concentrated. The residue was purified by preparative HPLC on the Gilson (5 to 40% MeCN-95 to 60% water (both with 0.1% TFA) over 15 min.; Phenomenex Gemini 5 m NX-$C_{18}$ 100 Å 150×30 mm column). The fractions were combined and partitioned between saturated aqueous $NaHCO_3$ solution and DCM, then separated, dried with $Na_2SO_4$, and concentrated to yield the desired compound as the free base, a white solid (0.017 g, 24%). Analysis: LCMS m/z=367 (M+1); $^1$H NMR (400 MHz, DMSO-$d_6$) δ: 9.08 (d, J=2.0 Hz, 1H), 8.00 (d, J=2.0 Hz, 1H), 7.89 (s, 1H), 7.68 (d, J=1.3 Hz, 1H), 7.53 (d, J=9.3 Hz, 1H), 7.37-7.30 (m, 2H), 7.20 (d, J=9.3 Hz, 1H), 7.12-7.05 (m, 2H), 4.62 (tt, J=8.1, 3.8 Hz, 1H), 3.71-3.61 (m, 2H), 3.13 (ddd, J=13.2, 9.5, 3.1 Hz, 2H), 2.54 (s, 3H), 1.99-1.89 (m, 2H), 1.59-1.47 (m, 2H).

Example 614. 2-(Dimethylamino)-1-[4-[4-(8-methyl-7-quinolyl)phenoxy]-1-piperidyl]ethanone

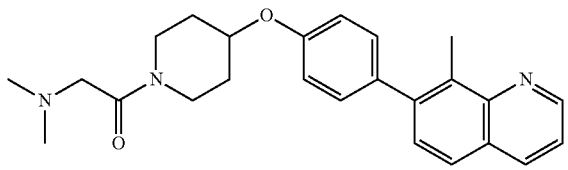 [SMILES: Cc1c(-c2ccc(OC3CCN(C(=O)CN(C)C)CC3)cc2)ccc2cccnc12]

To a suspension of 2-(dimethylamino)acetic acid (0.027 g, 0.26 mmol) and HATU (0.10 g, 0.26 mmol) in anhydrous DCM (2.00 mL) in a scintillation vial at RT under $N_2$ was added DIPEA (0.15 mL, 0.11 g, 0.88 mmol). The mixture stirred for ~20 min. before adding 8-methyl-7-[4-(4-piperidyloxy)phenyl]quinoline (0.070 g, 0.22 mmol) and stirring at RT overnight. The mixture was partitioned between EtOAc and saturated aqueous $NH_4Cl$ solution and separated. The organic layer was washed with water, saturated aqueous $NaHCO_3$ solution, and brine, then dried over $Na_2SO_4$, filtered, and concentrated. Silica gel chromatography on the ISCO (0 to 100% (40% 20:1:1 EtOH:$NH_4OH$:$H_2O$-60% EtOAc)-100 to 0% hexanes; 24 g column) yielded the desired compound as an off-white solid (0.088 g, 99%). Analysis: LCMS m/z=404 (M+1); $^1$H NMR (400 MHz, DMSO-$d_6$) δ: 8.97 (dd, J=4.3, 1.8 Hz, 1H), 8.37 (dd, J=8.2, 1.9 Hz, 1H), 7.86 (d, J=8.5 Hz, 1H), 7.59-7.52 (m, 1H), 7.48 (d, J=8.3 Hz, 1H), 7.42-7.35 (m, 2H), 7.15-7.08 (m, 2H), 4.77-4.68 (m, 1H), 3.97-3.86 (m, 1H), 3.80-3.69 (m, J=13.8 Hz, 1H), 3.60 (br. s., 2H), 2.68 (s, 3H), 2.45 (s, 6H), 2.10-1.93 (m, 2H), 1.75-1.64 (m, 1H), 1.64-1.53 (m, 1H).

Example 615. 4-[4-(5-Methylimidazo[1,2-a]pyridin-6-yl)phenoxy]piperidine-1-carboxamide

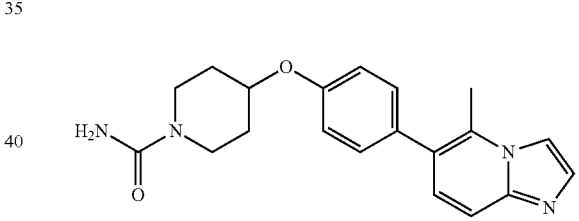

To a solution of 1,1'-carbonyldiimidazole (0.048 g, 0.30 mmol) in anhydrous DMF (2.0 mL) in a scintillation vial at RT under $N_2$ was added $NH_4Cl$ (0.018 g, 0.35 mmol) followed by DIPEA (0.17 mL, 0.13 g, 0.99 mmol). The solution was stirred at RT for about two hours, and the solid $NH_4Cl$ gradually dissolved. 5-Methyl-6-[4-(4-piperidyloxy)-phenyl]imidazo[1,2-a]pyridine 2HCl (0.075 g, 0.20 mmol) was then added, and the reaction was stirred at RT overnight. The mixture was partitioned between EtOAc and saturated aqueous $NH_4Cl$ solution and separated. The organic layer was washed with water, saturated $NaHCO_3$ solution, and brine, then dried over $Na_2SO_4$, filtered, and concentrated. Silica gel chromatography on the ISCO (0 to 100% (40% 20:1:1 EtOH: $NH_4OH$:$H_2O$-60% EtOAc)-100 to 0% hexanes; 24 g column) yielded the desired compound as a white solid (0.049 g, 71%). Analysis: LCMS m/z=351 (M+1); $^1$H NMR (400 MHz, DMSO-$d_6$) δ: 7.89 (s, 1H), 7.68 (d, J=1.3 Hz, 1H), 7.53 (d, J=9.3 Hz, 1H), 7.37-7.30 (m, 2H), 7.21 (d, J=9.3 Hz, 1H), 7.12-7.05 (m, 2H), 5.97 (s, 2H), 4.61 (tt, J=8.2, 3.9 Hz, 1H), 3.75-3.65 (m, 2H), 3.12 (ddd, J=13.2, 9.5, 3.1 Hz, 2H), 2.54 (s, 3H), 1.99-1.88 (m, 2H), 1.59-1.46 (m, 2H).

Example 616. [(2R)-1-Methylpyrrolidin-2-yl]-[4-[4-(8-methyl-7-quinolyl)phenoxy]-1-piperidyl]methanone

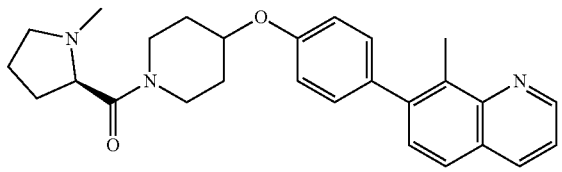 [SMILES: Cc1c(-c2ccc(OC3CCN(C(=O)[C@H]4CCCN4C)CC3)cc2)ccc2cccnc12]

To a suspension of (2R)-1-methylpyrrolidine-2-carboxylic acid HCl (0.037 g, 0.23 mmol) and HATU (0.079 g, 0.21 mmol) in anhydrous DCM (2.00 mL) in a scintillation vial at RT under $N_2$ was added DIPEA (0.13 mL, 0.097 g, 0.75 mmol). The mixture stirred for ~20 min. before adding 8-methyl-7-[4-(4-piperidyloxy)phenyl]quinoline (0.060 g, 0.19 mmol) and stirring at RT for ~72 hours. The mixture was partitioned between EtOAc and saturated aqueous $NH_4Cl$ solution and separated. The organic layer was washed with water, saturated aqueous $NaHCO_3$ solution, and brine, then dried over $Na_2SO_4$, filtered, and concentrated. Silica gel chromatography on the ISCO (0 to 100% (50% 20:1:1 $EtOH:NH_4OH:H_2O$-50% EtOAc)-100 to 0% hexanes; 24 g column) yielded the desired compound as an off-white solid (0.077 g, 95%). Analysis: LCMS m/z=430 (M+1); $^1$H NMR (400 MHz, DMSO-$d_6$) δ: 8.97 (dd, J=4.3, 1.8 Hz, 1H), 8.37 (dd, J=8.3, 1.8 Hz, 1H), 7.86 (d, J=8.5 Hz, 1H), 7.59-7.52 (m, 1H), 7.48 (d, J=8.5 Hz, 1H), 7.38 (d, J=8.8 Hz, 2H), 7.16-7.08 (m, 2H), 4.78-4.67 (m, J=3.5 Hz, 1H), 4.05-3.75 (m, 2H), 3.66 (br. s., 1H), 3.54-3.43 (m, J=9.5 Hz, 1H), 3.25-3.16 (m, 1H), 2.68 (s, 3H), 2.44 (s, 3H), 2.26 (br. s., 1H), 2.11-1.93 (m, 2H), 1.92-1.68 (m, 4H), 1.68-1.51 (m, 2H).

Example 617. [(2S)-1-Methylpyrrolidin-2-yl]-[4-[4-(8-methyl-7-quinolyl)phenoxy]-1-piperidyl]methanone

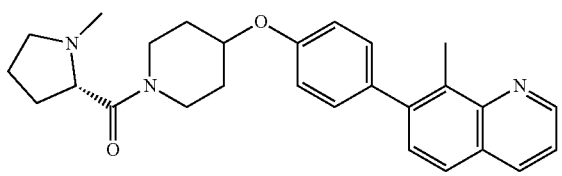 [SMILES: Cc1c(-c2ccc(OC3CCN(C(=O)[C@@H]4CCCN4C)CC3)cc2)ccc2cccnc12]

To a suspension of (2S)-1-methylpyrrolidine-2-carboxylic acid hydrate (0.033 g, 0.23 mmol) and HATU (0.079 g, 0.21 mmol) in anhydrous DCM (2.00 mL) in a scintillation vial at RT under $N_2$ was added DIPEA (0.13 mL, 0.097 g, 0.75 mmol). The mixture stirred for ~20 min. before adding 8-methyl-7-[4-(4-piperidyloxy)phenyl]quinoline (0.060 g, 0.19 mmol) and stirring at RT for ~72 hours. The mixture was partitioned between EtOAc and saturated aqueous $NH_4Cl$ solution and separated. The organic layer was washed with water, saturated aqueous $NaHCO_3$ solution, and brine, then dried over $Na_2SO_4$, filtered, and concentrated. Silica gel chromatography on the ISCO (0 to 100% (50% 20:1:1 $EtOH:NH_4OH:H_2O$-50% EtOAc)-100 to 0% hexanes; 24 g column) yielded the desired compound as an off-white solid (0.077 g, 95%). Analysis: LCMS m/z=430 (M+1); $^1$H NMR (400 MHz, DMSO-$d_6$) δ 8.97: (dd, J=4.0, 1.8 Hz, 1H), 8.37 (dd, J=8.3, 1.8 Hz, 1H), 7.86 (d, J=8.5 Hz, 1H), 7.58-7.52 (m, 1H), 7.48 (d, J=8.3 Hz, 1H), 7.42-7.35 (m, J=8.5 Hz, 2H), 7.16-7.08 (m, 2H), 4.78-4.67 (m, 1H), 4.72 (dt, J=7.0, 3.5 Hz, 1H), 4.07-3.58 (m, 4H), 3.52-3.40 (m, 2H), 3.28-3.16 (m, 2H), 2.68 (s, 3H), 2.60-2.52 (m, 1H), 2.45 (s, 3H), 2.27 (br. s., 1H), 1.99 (s, 2H), 1.93-1.67 (m, 4H), 1.67-1.52 (m, 2H).

Example 618. S-Isopropyl 4-[4-(8-methyl-7-quinolyl)phenoxy]piperidine-1-carbothioate

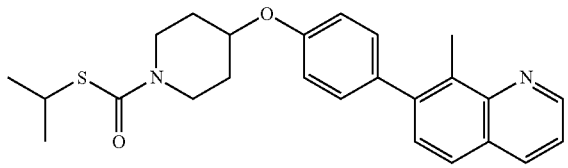 [SMILES: Cc1c(-c2ccc(OC3CCN(C(=O)SC(C)C)CC3)cc2)ccc2cccnc12]

To a solution of 8-methyl-7-[4-(4-piperidyloxy)phenyl]quinoline (0.060 g, 0.19 mmol) in anhydrous DCM (2.0 mL) in a large scintillation vial at 0° C. under $N_2$ was added a solution of DIPEA (0.066 mL, 0.049 g, 0.38 mmol) followed by S-isopropyl chloromethanethioate (0.035 mL, 0.039 g, 0.28 mmol) dropwise. The mixture was stirred at 0° C. for ~90 min. The reaction was quenched by adding ~2 mL of saturated aqueous $NaHCO_3$ solution, then partitioned between EtOAc and saturated aqueous $NH_4Cl$ solution and separated. The organic layer was washed with water, saturated aqueous $NaHCO_3$ solution, and brine, then dried over $Na_2SO_4$, filtered, and concentrated. Silica gel chromatography on the ISCO (0 to 100% EtOAc-100 to 0% hexanes; 24 g column) yielded the desired product as an off-white waxy solid (0.0706 g, 89%). Analysis: LCMS m/z=421 (M+1); $^1$H NMR (400 MHz, DMSO-$d_6$) δ: 8.97 (dd, J=4.0, 1.8 Hz, 1H), 8.37 (dd, J=8.2, 1.9 Hz, 1H), 7.85 (d, J=8.5 Hz, 1H), 7.55 (dd, J=8.2, 4.1 Hz, 1H), 7.48 (d, J=8.5 Hz, 1H), 7.41-7.34 (m, 2H), 7.15-7.07 (m, 2H), 4.75-4.67 (m, 1H), 3.77 (br. s., 2H), 3.55-3.43 (m, 1H), 3.42-3.36 (m, 2H), 2.68 (s, 3H), 2.05-1.94 (m, 2H), 1.63 (dtd, J=12.7, 8.5, 4.0 Hz, 2H), 1.29 (d, J=6.8 Hz, 6H).

Example 619. 2-Amino-2-methyl-1-[4-[4-(8-methyl-7-quinolyl)phenoxy]-1-piperidyl]propan-1-one

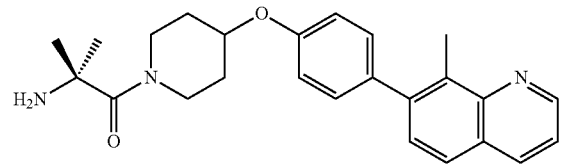

Step 1

To a suspension of 2-(tert-butoxycarbonylamino)-2-methyl-propanoic acid (0.054 g, 0.26 mmol) and HATU (0.10 g, 0.26 mmol) in anhydrous DCM (2.00 mL) in a large scintillation vial at RT under $N_2$ was added DIPEA (0.15 mL, 0.11 g, 0.88 mmol). The mixture stirred for ~20 min. before adding 8-methyl-7-[4-(4-piperidyloxy)phenyl]quinoline (0.070 g, 0.22 mmol) and stirring at RT overnight. The mixture was partitioned between EtOAc and saturated aqueous NH₄Cl solution and separated. The organic layer was washed with water, saturated aqueous NaHCO₃ solution, and brine, then dried over Na₂SO₄, filtered, and concentrated. Silica gel chromatography on the ISCO (0 to 100% EtOAc-hexanes; 24 g column) yielded tert-butyl N-[1,1-dimethyl-2-[4-[4-(8-methyl-7-quinolyl)phenoxy]-1-piperidyl]-2-oxo-ethyl]carbamate as a white foam.

Step 2

To a solution of tert-butyl N-[1,1-dimethyl-2-[4-[4-(8-methyl-7-quinolyl)phenoxy]-1-piperidyl]-2-oxo-ethyl]carbamate in anhydrous EtOAc (10 mL) in a small RBF at RT under N₂ was added HCl (4 mol/L) in 1,4-dioxane (5 mL, 20 mmol) dropwise. A yellow precipitate immediately began to form. The mixture stirred overnight. The reaction was concentrated to yield a tan solid. Analysis showed that some hydrolysis of the amide had occurred. The residue was purified by preparative HPLC on the Gilson (5 to 40% MeCN-95 to 60% water (both with 0.1% TFA) over 15 min.; Phenomenex Gemini 5 µm NX-C₁₈ 100 Å 150×30 mm column). The good fractions were combined and partitioned between saturated aqueous NaHCO₃ solution and DCM, then separated, dried with Na₂SO₄, and concentrated to yield the desired compound as the free base, a white solid (0.0488 g, 55%). Analysis: LCMS m/z=404 (M+1); ¹H NMR (400 MHz, DMSO-d₆) δ: 8.97 (dd, J=4.1, 1.9 Hz, 1H), 8.37 (dd, J=8.3, 1.8 Hz, 1H), 7.85 (d, J=8.3 Hz, 1H), 7.59-7.52 (m, 1H), 7.48 (d, J=8.5 Hz, 1H), 7.41-7.34 (m, 2H), 7.15-7.06 (m, 2H), 4.69 (tt, J=7.9, 3.9 Hz, 1H), 4.29 (br. s., 2H), 3.75-3.41 (m, 2H), 2.68 (s, 3H), 2.05-1.88 (m, 3H), 1.67-1.54 (m, 2H), 1.28 (s, 6H).

Example 620. [4-[4-(8-Methyl-7-quinolyl)phenoxy]-1-piperidyl]-[(2R)-pyrrolidin-2-yl]methanone

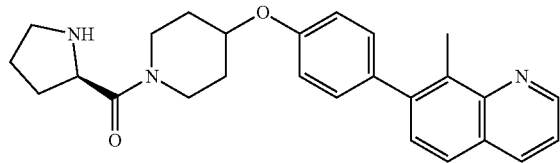 [SMILES: Cc1c(-c2ccc(OC3CCN(C(=O)[C@H]4CCCN4)CC3)cc2)ccc2cccnc12]

Step 1

To a suspension of (2R)-1-tert-butoxycarbonylpyrrolidine-2-carboxylic acid (0.049 g, 0.23 mmol) and HATU (0.079 g, 0.21 mmol) in anhydrous DCM (2.00 mL) in a scintillation vial at RT under N₂ was added DIPEA (0.13 mL, 0.097 g, 0.75 mmol). The mixture stirred for ~20 min. before adding 8-methyl-7-[4-(4-piperidyloxy)phenyl]quinoline (0.060 g, 0.19 mmol) and stirring at RT for ~72 hours. The reaction was partitioned between EtOAc and saturated aqueous NH₄Cl solution and separated. The organic layer was washed with water, saturated aqueous NaHCO₃ solution, and brine, then dried over Na₂SO₄, filtered, and concentrated. Silica gel chromatography on the ISCO (0 to 100% (10% 20:1:1 EtOH:NH₄OH:H₂O-90% EtOAc)-100 to 0% hexanes; 24 g column) yielded tert-butyl (2R)-2-[4-[4-(8-methyl-7-quinolyl)phenoxy]piperidine-1-carbonyl]pyrrolidine-1-carboxylate as a white foam.

Step 2

To a solution of tert-butyl (2R)-2-[4-[4-(8-methyl-7-quinolyl)phenoxy]piperidine-1-carbonyl]pyrrolidine-1-carboxylate in anhydrous DCM (3 mL) in a small RBF at RT under N₂ was added trifluoroacetic acid (1 mL, 1.508 g, 13.23 mmol). The mixture stirred at RT for ~2 hours before the reaction was concentrated. In order to generate the free base, the residue was dissolved in methanol and loaded onto a Phenomenex Strata-X-C 33u Polymeric Strong Cation 2 g/20 mL Giga Tube, then eluted using 2.0 M ammonia in methanol. The eluent was concentrated to yield the desired compound as an off-white solid (0.0691 g, 88%). Analysis: LCMS m/z=416 (M+1); ¹H NMR (400 MHz, DMSO-d₆) δ: 8.97 (dd, J=4.0, 1.8 Hz, 1H), 8.37 (dd, J=8.3, 1.8 Hz, 1H), 7.86 (d, J=8.3 Hz, 1H), 7.55 (dd, J=8.2, 4.1 Hz, 1H), 7.48 (d, J=8.5 Hz, 1H), 7.42-7.34 (m, 2H), 7.16-7.08 (m, 2H), 4.72 (qt, J=7.7, 3.8 Hz, 1H), 3.99-3.85 (m, 2H), 3.85-3.71 (m, 1H), 3.02 (dt, J=10.6, 5.4 Hz, 1H), 2.72-2.63 (m, 4H), 2.11-1.92 (m, 3H), 1.76-1.51 (m, 5H).

Example 621. [4-[4-(8-Methyl-7-quinolyl)phenoxy]-1-piperidyl]-[(2S)-pyrrolidin-2-yl]methanone

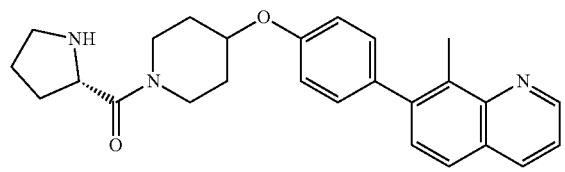 [SMILES: Cc1c(-c2ccc(OC3CCN(C(=O)[C@@H]4CCCN4)CC3)cc2)ccc2cccnc12]

Step 1

To a suspension of (2S)-1-tert-butoxycarbonylpyrrolidine-2-carboxylic acid (0.049 g, 0.23 mmol) and HATU (0.079 g, 0.21 mmol) in anhydrous DCM (2.00 mL) in a scintillation vial at RT under N₂ was added DIPEA (0.13 mL, 0.097 g, 0.75 mmol). The mixture stirred for ~20 min. before adding 8-methyl-7-[4-(4-piperidyloxy)phenyl]quinoline (0.060 g, 0.19 mmol) and stirring at RT for ~72 hours. The reaction was partitioned between EtOAc and saturated aqueous NH₄Cl solution and separated. The organic layer was washed with water, saturated aqueous NaHCO₃ solution, and brine, then dried over Na₂SO₄, filtered, and concentrated. Silica gel chromatography on the ISCO (0 to 100% (10% 20:1:1 EtOH:NH₄OH:H₂O-90% EtOAc)-100 to 0% hexanes; 24 g column) yielded tert-butyl (2S)-2-[4-[4-(8-methyl-7-quinolyl)phenoxy]piperidine-1-carbonyl]pyrrolidine-1-carboxylate as a white foam.

Step 2

To a solution of tert-butyl (2S)-2-[4-[4-(8-methyl-7-quinolyl)phenoxy]piperidine-1-carbonyl]pyrrolidine-1-carboxylate in anhydrous DCM (3 mL) in a small RBF at RT under N₂ was added trifluoroacetic acid (1 mL, 1.508 g, 13.23 mmol). The mixture stirred at RT for ~2 hours before the reaction was concentrated. In order to generate the free base, the residue was dissolved in methanol and loaded onto a Phenomenex Strata-X-C 33u Polymeric Strong Cation 2 g/20 mL Giga Tube, then eluted using 2.0 M ammonia in methanol. The eluent was concentrated to yield the desired compound as an off-white solid (0.0641 g, 82%). Analysis:

LCMS m/z=416 (M+1); 1H NMR (400 MHz, DMSO-d6) δ: 8.97 (dd, J=4.1, 1.9 Hz, 1H), 8.37 (dd, J=8.3, 1.8 Hz, 1H), 7.86 (d, J=8.5 Hz, 1H), 7.55 (dd, J=8.3, 4.0 Hz, 1H), 7.48 (d, J=8.3 Hz, 1H), 7.41-7.35 (m, 2H), 7.16-7.08 (m, J=8.5 Hz, 2H), 4.78-4.65 (m, J=7.7, 7.7, 3.6, 3.6 Hz, 1H), 4.00-3.85 (m, 2H), 3.85-3.71 (m, J=15.4, 15.4 Hz, 1H), 3.01 (dt, J=10.6, 5.4 Hz, 1H), 2.71-2.61 (m, 4H), 2.10-1.93 (m, 3H), 1.76-1.51 (m, 5H).

Example 622. [1-(Methylamino)cyclopropyl]-[4-[4-(8-methyl-7-quinolyl)phenoxy]-1-piperidyl]methanone

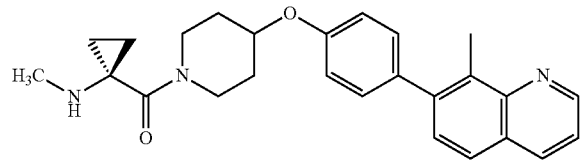

Step 1

1-[tert-butoxycarbonyl(methyl)amino]cyclopropanecarboxylic acid. To a solution of 1-(tert-butoxycarbonylamino)cyclopropanecarboxylic acid (0.250 g, 1.24 mmol) in anhydrous THF (6.2 mL) in a small RBF at 0° C. under N₂ was added iodomethane (0.155 mL, 0.353 g, 2.48 mmol) followed by NaH (0.149 g, 3.73 mmol). Gas was vigorously evolved. After ~15 min., the ice bath was removed, and the mixture was stirred at RT overnight. The white suspension was cooled to 0° C. and quenched by carefully adding water dropwise until gas was no longer evolved. The reaction was concentrated to remove the THF, and the residue was dissolved in ~10 mL of water. This aqueous layer was extracted with 15 mL of ether; the ether layer was then extracted with 10 mL of saturated aqueous NaHCO₃ solution. The two aqueous layers were combined in a flask with 10 mL of EtOAc, cooled to 0° C., and acidified to pH ~2 by dropwise addition of 10% aqueous KHSO₄ solution. The mixture was transferred to a separatory funnel with 10 mL of additional EtOAc, the layers were separated, and the aqueous layer was re-extracted with 2×20 mL of EtOAc. The organic layers were combined and washed with 5 mL of water, then brine, then dried over Na₂SO₄, filtered, concentrated, and dried under vacuum to yield the desired compound as a white, waxy solid (0.264 g, 99%). ¹H NMR (400 MHz, DMSO-d₆) δ 12.46 (br. s., 1H), 2.84-2.71 (m, 3H), 1.42-1.32 (m, 10H), 1.18-1.08 (m, 2H).

Step 2

To a suspension of 1-[tert-butoxycarbonyl(methyl)amino]cyclopropanecarboxylic acid (0.053 g, 0.24 mmol) and HATU (0.079 g, 0.21 mmol) in anhydrous DCM (2.00 mL) in a large scintillation vial at RT under N₂ was added DIPEA (0.13 mL, 0.097 g, 0.75 mmol). The mixture stirred for ~20 min. before adding 8-methyl-7-[4-(4-piperidyloxy)phenyl]quinoline (0.060 g, 0.19 mmol) and stirring at RT overnight. The mixture was partitioned between EtOAc and sat. aqueous NH₄Cl solution and separated. The organic layer was washed with water, sat. NaHCO₃ solution, and brine, then dried over Na₂SO₄, filtered, and concentrated. Silica gel chromatography on the ISCO (0 to 100% EtOAc-100 to 0% hexanes; 24 g column) yielded tert-butyl N-methyl-N-[1-[4-[4-(8-methyl-7-quinolyl)phenoxy]piperidine-1-carbonyl]cyclopropyl]carbamate as a white foam.

Step 3

To a solution of tert-butyl N-methyl-N-[1-[4-[4-(8-methyl-7-quinolyl)phenoxy]piperidine-1-carbonyl]cyclopropyl]carbamate in anhydrous DCM (3.0 mL) in a small RBF at RT under N₂ was added trifluoroacetic acid (0.5 mL, 0.8 g, 7 mmol). After ~2 hrs., the reaction was concentrated. In order to generate the free base, the residue was dissolved in methanol and loaded onto a Phenomenex Strata-X-C 33u Polymeric Strong Cation 2 g/20 mL Giga Tube, then eluted using 2.0 M ammonia in methanol. The eluent was concentrated to yield the desired compound as a white solid (0.0511 g, 65%). Analysis: LCMS m/z=416 (M+1); ¹H NMR (400 MHz, DMSO-d₆) δ: 8.97 (dd, J=4.3, 1.8 Hz, 1H), 8.37 (dd, J=8.3, 1.8 Hz, 1H), 7.86 (d, J=8.3 Hz, 1H), 7.55 (dd, J=8.2, 4.1 Hz, 1H), 7.48 (d, J=8.3 Hz, 1H), 7.41-7.34 (m, 2H), 7.12 (s, 1H), 7.15-7.09 (m, 2H), 4.71 (tt, J=7.9, 3.7 Hz, 1H), 4.02 (br. s., 2H), 2.68 (s, 3H), 2.23 (s, 3H), 2.06-1.96 (m, J=11.3 Hz, 2H), 1.70-1.53 (m, J=8.5 Hz, 2H), 0.87-0.80 (m, 2H), 0.70-0.63 (m, 2H).

Example 623. 3-Amino-1-[4-[4-(8-methyl-7-quinolyl)phenoxy]-1-piperidyl]propan-1-one, 2HCl

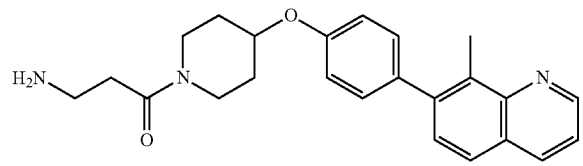 [SMILES: Cc1c(-c2ccc(OC3CCN(C(=O)CCN)CC3)cc2)ccc2cccnc12]

Step 1

To a suspension of 3-(tert-butoxycarbonylamino)propanoic acid (0.043 g, 0.23 mmol) and HATU (0.079 g, 0.21 mmol) in anhydrous DCM (2.00 mL) in a scintillation vial at RT under N₂ was added DIPEA (0.13 mL, 0.097 g, 0.75 mmol). The mixture stirred for ~20 min. before adding 8-methyl-7-[4-(4-piperidyloxy)phenyl]quinolone (0.060 g, 0.19 mmol) and stirring at RT overnight. The mixture was partitioned between EtOAc and saturated aqueous NH₄Cl solution and separated. The organic layer was washed with water, saturated aqueous NaHCO₃ solution, and brine, then dried over Na₂SO₄, filtered, and concentrated. Silica gel chromatography on the ISCO (0 to 100% EtOAc-100 to 0% hexanes; 24 g column) yielded tert-butyl N-[3-[4-[4-(8-methyl-7-quinolyl)phenoxy]-1-piperidyl]-3-oxo-propyl]carbamate as a white foam/clear, colorless oil.

Step 2

To a solution of tert-butyl N-[3-[4-[4-(8-methyl-7-quinolyl)phenoxy]-1-piperidyl]-3-oxo-propyl]carbamate (0.080 g, 0.16 mmol) in anhydrous DCM (5 mL) in a small RBF at RT under N₂ was added 4.0 M HCl in 1,4-Dioxane (5 mL, 20 mmol) dropwise. The mixture became cloudy after several minutes, and then became clearer as a small amount of precipitate stuck to the walls of the flask. The reaction stirred at RT for about two hours before the mixture was concentrated. In order to generate the free base, the residue was dissolved in methanol and loaded onto a Phenomenex Strata-X-C 33u Polymeric Strong Cation 2 g/20 mL Giga Tube, then eluted using 2.0 M ammonia in methanol. The eluent was concentrated. When several attempts to concentrate the compound from dichloromethane/ether failed to yield an easily weighable solid, the HCl salt was synthesized by dissolving the compound in anhydrous dichloromethane and treating with a slight excess of 2.0 M HCl-ether. Concentration and drying under vacuum yielded the desired compound as the dihydrochloride salt, a yellow solid (0.0652 g, 75%). Analysis: LCMS m/z=390 (M+1); $^1$H NMR (400 MHz, DMSO-d$_6$) δ: 9.00 (dd, J=4.3, 1.8 Hz, 1H), 8.46 (d, J=7.8 Hz, 1H), 7.90 (d, J=8.3 Hz, 1H), 7.80 (br. s., 3H), 7.61 (dd, J=8.2, 4.1 Hz, 1H), 7.52 (d, J=8.5 Hz, 1H), 7.42-7.36 (m, 2H), 7.16-7.09 (m, 2H), 4.73 (tt, J=7.8, 3.7 Hz, 1H), 3.98-3.89 (m, 1H), 3.71 (dt, J=13.7, 5.1 Hz, 1H), 3.01 (sxt, J=5.9 Hz, 2H), 2.74 (t, J=6.3 Hz, 2H), 2.69 (s, 3H), 2.11-1.93 (m, 2H), 1.75-1.54 (m, 2H).

Example 624. 2-Isopropoxy-1-[4-[4-(8-methyl-7-quinolyl)phenoxy]-1-piperidyl]ethanone, HCl

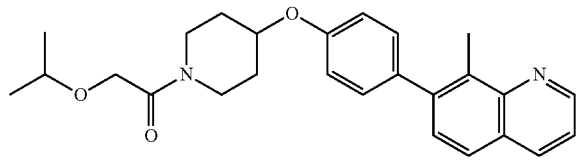 [SMILES: Cc1c(-c2ccc(OC3CCN(C(=O)COC(C)C)CC3)cc2)ccc2cccnc12]

To a suspension of 2-isopropoxyacetic acid (0.027 g, 0.23 mmol) and HATU (0.079 g, 0.21 mmol) in anhydrous DCM (2.00 mL) in a scintillation vial at RT under N$_2$ was added DIPEA (0.13 mL, 0.097 g, 0.75 mmol). The mixture stirred for ~20 min. before adding 8-methyl-7-[4-(4-piperidyloxy)phenyl]quinoline (0.060 g, 0.19 mmol) and stirring at RT overnight. The mixture was partitioned between EtOAc and saturated aqueous NH$_4$Cl solution and separated. The organic layer was washed with water, saturated aqueous NaHCO$_3$ solution, and brine, then dried over Na$_2$SO$_4$, filtered, and concentrated. Silica gel chromatography on the ISCO (0 to 100% EtOAc-100 to 0% hexanes; 24 g column) yielded a clear, colorless oil. The HCl salt was synthesized by dissolving the compound in anhydrous dichloromethane and treating with a slight excess of 2.0 M HCl-ether, then concentrating and drying under vacuum to yield the desired compound as a yellow solid (0.0627 g, 73%). Analysis: LCMS m/z=419 (M+1); $^1$H NMR (400 MHz, DMSO-d$_6$) δ: 9.08 (dd, J=4.5, 1.5 Hz, 1H), 8.69 (d, J=7.8 Hz, 1H), 8.01 (d, J=8.3 Hz, 1H), 7.76 (dd, J=8.0, 4.5 Hz, 1H), 7.62 (d, J=8.5 Hz, 1H), 7.44-7.36 (m, 2H), 7.18-7.10 (m, 2H), 4.72 (tt, J=7.8, 3.6 Hz, 1H), 4.11 (d, J=1.3 Hz, 2H), 3.93-3.84 (m, 2H), 3.78-3.69 (m, J=12.5 Hz, 3H), 3.40-3.32 (m, 2H), 3.32-3.23 (m, 2H), 2.71 (s, 3H), 2.09-1.92 (m, J=19.3 Hz, 2H), 1.74-1.62 (m, 1H), 1.62-1.50 (m, 1H), 1.12 (d, J=6.0 Hz, 6H).

Example 625. [2-[4-[4-(8-Methyl-7-quinolyl)phenoxy]-1-piperidyl]-2-oxo-ethyl]acetate

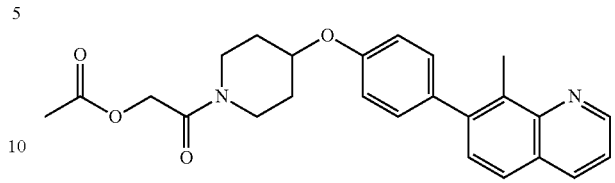

To a solution of 8-methyl-7-[4-(4-piperidyloxy)phenyl]quinoline (0.060 g, 0.19 mmol) and DIPEA (0.13 mL, 0.097 g, 0.75 mmol) in anhydrous DCM (2.00 mL) in a scintillation vial at RT under N$_2$ was added (2-chloro-2-oxo-ethyl) acetate (0.026 mL, 0.033 g, 0.24 mmol) dropwise. The mixture was stirred at RT overnight. The mixture was partitioned between EtOAc and saturated aqueous NH$_4$Cl solution and separated. The organic layer was washed with water, saturated aqueous NaHCO$_3$ solution, and brine, then dried over Na$_2$SO$_4$, filtered, and concentrated. Silica gel chromatography on the ISCO (0 to 100% EtOAc-100 to 0% hexanes; 24 g column) yielded the desired compound as an off-white solid (0.065 g, 82%). Analysis: LCMS m/z=419 (M+1); $^1$H NMR (400 MHz, DMSO-d$_6$) δ: 8.97 (dd, J=4.1, 1.9 Hz, 1H), 8.37 (dd, J=8.3, 1.8 Hz, 1H), 7.86 (d, J=8.5 Hz, 1H), 7.55 (dd, J=8.2, 4.1 Hz, 1H), 7.48 (d, J=8.5 Hz, 1H), 7.41-7.35 (m, 2H), 7.15-7.09 (m, J=8.8 Hz, 2H), 4.81 (s, 2H), 4.72 (tt, J=7.7, 3.7 Hz, 1H), 3.91-3.79 (m, 1H), 3.70-3.58 (m, J=14.1 Hz, 1H), 3.31-3.25 (m, 1H), 2.68 (s, 3H), 2.09 (s, 3H), 2.07-1.91 (m, 2H), 1.75-1.63 (m, 1H), 1.63-1.51 (m, 1H).

Example 626. 2-Hydroxy-1-[4-[4-(8-methyl-7-quinolyl)phenoxy]-1-piperidyl]ethanone

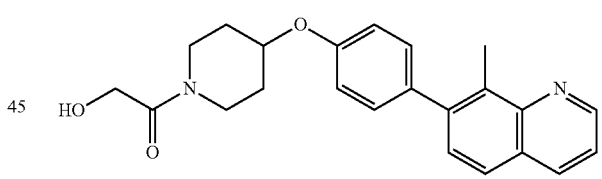

To a suspension of [2-[4-[4-(8-methyl-7-quinolyl)phenoxy]-1-piperidyl]-2-oxo-ethyl] acetate (0.060 g, 0.14 mmol) in methanol (2 mL) in a scintillation vial at RT under N$_2$ was added 1.0 N aqueous lithium hydroxide solution (0.22 mL, 0.22 mmol). The mixture became homogeneous, and was stirred at RT for ~2.5 hrs. before adding 1.0 N aqueous HCl solution (0.220 mL, 0.22 mmol), then partially concentrating to remove the methanol. The residue was partitioned between ethyl acetate and saturated aqueous NH$_4$Cl solution and separated. The organic layer was washed with water, saturated NaHCO$_3$ solution, and brine, then dried over Na$_2$SO$_4$, filtered, and concentrated to yield the desired compound as an off-white solid (0.0509 g, 94%). Analysis: LCMS m/z=377 (M+1); $^1$H NMR (400 MHz, DMSO-d$_6$) δ: 8.97 (dd, J=4.3, 1.8 Hz, 1H), 8.37 (dd, J=8.3, 1.8 Hz, 1H), 7.85 (d, J=8.3 Hz, 1H), 7.59-7.52 (m, 1H), 7.48 (d, J=8.3 Hz, 1H), 7.42-7.34 (m, 2H), 7.15-7.08 (m, 2H), 4.71 (tt, J=7.8, 3.7 Hz, 1H), 4.54 (t, J=5.5 Hz, 1H), 4.12 (d, J=5.5 Hz, 2H), 3.97-3.84 (m, 1H), 3.67-3.55 (m, J=14.3 Hz, 1H), 3.32-3.24 (m, 2H), 2.68 (s, 3H), 2.07-1.93 (m, 2H), 1.73-1.52 (m, 2H).

Example 627. (1-Aminocyclobutyl)-[4-[4-(8-methyl-7-quinolyl)phenoxy]-1-piperidyl]methanone

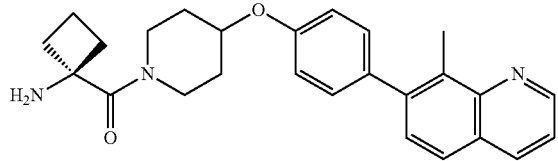

Step 1

To a suspension of 1-(tert-butoxycarbonylamino)cyclobutanecarboxylic acid (0.053 g, 0.24 mmol) and HATU (0.079 g, 0.21 mmol) in anhydrous DCM (2.00 mL) in a scintillation vial at RT under $N_2$ was added DIPEA (0.13 mL, 0.097 g, 0.75 mmol). The mixture stirred for ~20 min. before adding 8-methyl-7-[4-(4-piperidyloxy)phenyl]quinoline (0.060 g, 0.19 mmol) and stirring at RT overnight. The mixture was partitioned between EtOAc and saturated aqueous $NH_4Cl$ solution and separated. The organic layer was washed with water, saturated aqueous $NaHCO_3$ solution, and brine, then dried over $Na_2SO_4$, filtered, and concentrated. Silica gel chromatography on the ISCO (0 to 100% EtOAc-100 to 0% hexanes; 24 g column) yielded tert-butyl N-[1-[4-[4-(8-methyl-7-quinolyl)phenoxy]piperidine-1-carbonyl]cyclobutyl]carbamate as a white foam.

Step 2

To a solution of tert-butyl N-[1-[4-[4-(8-methyl-7-quinolyl)phenoxy]piperidine-1-carbonyl]cyclobutyl]carbamate in anhydrous DCM (5.0 mL) in a small RBF at RT under $N_2$ was added 4.0 M HCl in 1,4-dioxane (5.0 mL, 20 mmol) dropwise. The reaction was stirred at RT for about two hours before it was concentrated to yield a yellow solid. The residue was purified by preparative HPLC on the Gilson (5 to 40% MeCN-95 to 60% water (both with 0.1% TFA) over 15 min.; Phenomenex Gemini 5 m NX-$C_{18}$ 100 Å 150×30 mm column). The good fractions were combined and partitioned between saturated aqueous $NaHCO_3$ solution and DCM, then separated, dried with $Na_2SO_4$, and concentrated to yield the desired compound as the free base, a clear, colorless oil which eventually crystallized into a white solid. (0.0409 g, 52%). Analysis: LCMS m/z=416 (M+1); $^1$H NMR (400 MHz, DMSO-$d_6$) δ 8.97 (dd, J=4.1, 1.9 Hz, 1H), 8.36 (dd, J=8.2, 1.9 Hz, 1H), 7.85 (d, J=8.3 Hz, 1H), 7.55 (dd, J=8.2, 4.1 Hz, 1H), 7.48 (d, J=8.5 Hz, 1H), 7.41-7.34 (m, 2H), 7.15-7.07 (m, 2H), 4.74-4.64 (m, J=7.9, 4.1, 4.1 Hz, 1H), 3.88 (br. s., 2H), 3.26 (br. s., 1H), 2.68 (s, 3H), 2.59-2.52 (m, 2H), 2.21 (br. s., 2H), 1.97 (br. s., 2H), 1.93-1.79 (m, 3H), 1.74-1.44 (m, 3H).

Example 628

N-Ethyl-4-(4-imidazo[1,2-a]pyridin-7-ylphenoxy)piperidine-1-carboxamide, HCl

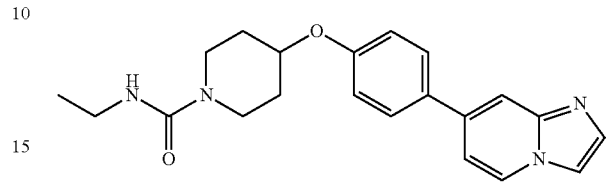

Step 1 tert-Butyl 4-(4-imidazo[1,2-a]pyridin-7-ylphenoxy)piperidine-1-carboxylate HCl Palladium acetate (0.021 g, 0.094 mmol) and triphenylphosphine (0.10 g, 0.38 mmol) were combined in a flask in 1,4-dioxane (6.0 mL). After stirring for 30 min, DMF (5.7 g, 6.0 mL, 78 mmol), tert-butyl 4-[4-(4,4,5,5-tetramethyl-1,3,2-dioxaborolan-2-yl)phenoxy]piperidine-1-carboxylate (0.75 g, 1.9 mmol), 7-bromoimidazo[1,2-a]pyridine (0.44 g, 2.2 mmol) and aq. $Na_2CO_3$ (0.5 M) (12.0 mL, 6.0 mmol) were added and the flask was heated under nitrogen at 90° C. overnight. The mixture was diluted with water (60 mL) then extracted with EtOAc (3×50 mL). The organic extracts were combined, washed with brine (50 mL), dried over sodium sulfate filtered and concentrated in vacuo. The residue was dissolved in EtOAc (40 mL) then treated with 2M HCl in ether (1.5 mL) with stirring. The resultant solids were collected by filtration, washed with EtOAc (30 mL) and hexane (10 mL), then dried on a Buchner funnel to afford tert-butyl 4-(4-imidazo[1,2-a]pyridin-7-ylphenoxy)piperidine-1-carboxylate HCl (0.495 g, 62% Yield) as a beige solid. LCMS (ESI): 394 (M+1); $^1$H NMR (400 MHz, DMSO-$d_6$) δ 8.91 (d, J=7.2 Hz, 1H), 8.30 (d, J=1.5 Hz, 1H), 8.14 (d, J=2.0 Hz, 1H), 8.09 (s, 1H), 7.93-7.84 (m, 3H), 7.19 (d, J=8.8 Hz, 2H), 4.71 (dt, J=7.8, 4.1 Hz, 1H), 3.73-3.51 (m, 2H), 3.29-3.14 (m, 2H), 1.97-1.88 (m, 2H), 1.61-1.51 (m, 2H), 1.41 (s, 9H).

Step 2. 7-[4-(4-Piperidyloxy)phenyl]imidazo[1,2-a]pyridine 2HCl

Acetyl chloride (0.6 g, 0.5 mL, 7 mmol) was added to ethanol (10.0 mL) and the mixture was then added to tert-butyl 4-(4-imidazo[1,2-a]pyridin-7-ylphenoxy)piperidine-1-carboxylate HCl (0.495 g, 1.15 mmol). After stirring at room temperature for 1 h, the mixture was heated at 60° C. for 3 h. The mixture was cooled to room temperature then diluted with ether (10 mL), which resulted in formation of a gum. The mixture was transferred to a tared flask using methanol then concentrated in vacuo and dried in vacuo to afford 7-[4-(4-piperidyloxy)phenyl]imidazo[1,2-a]pyridine 2HCl (0.415 g, 1.13 mmol, 98.4% Yield) as a yellow solid with trace ethanol remaining. LCMS (ESI): 294 (M+1); $^1$H NMR (400 MHz, DMSO-$d_6$) δ: 9.13 (br s, 2H), 8.97-8.93 (m, 1H), 8.32 (d, J=2.0 Hz, 1H), 8.17 (d, J=2.0 Hz, 1H), 8.12-8.09 (m, 1H), 7.95-7.86 (m, 3H), 7.22 (d, J=9.0 Hz, 2H), 4.86-4.75 (m, 1H), 3.31-3.18 (m, 2H), 3.15-3.02 (m, 2H), 2.23-2.10 (m, 2H), 1.96-1.82 (m, 2H).

Step 3. N-Ethyl-4-(4-imidazo[1,2-a]pyridin-7-ylphenoxy)piperidine-1-carboxamide HCl A mixture of 7-[4-(4-piperidyloxy)phenyl]imidazo[1,2-a]pyridine 2HCl (0.095 g, 0.26 mmol) and DIPEA (0.15 g, 0.20 mL, 1.1 mmol) in THF (5.0 mL) with ACN (1.0 mL) was treated at room temperature with ethyl isocyanate (0.045 g, 0.050 mL, 0.63 mmol). After stirring overnight the mixture was partitioned between saturated aq. NaHCO$_3$ (10 mL) and DCM (5 mL). The layers were separated, the aq. phase further extracted with DCM (2×10 mL) and the combined organics were dried over sodium sulfate, filtered and concentrated in vacuo. The residue was dissolved in DCM, applied to a silica gel loading cartridge (5 g) and purified on silica gel (12 g, 0-7% methanol:DCM). Product fractions were combined, treated with 2M HCl in ether (1 mL) then concentrated in vacuo. The residue was reconcentrated from ethanol then dried in vacuo to afford N-ethyl-4-(4-imidazo[1,2-a]pyridin-7-ylphenoxy)piperidine-1-carboxamide HCl (0.069 g, 0.17 mmol, 66% Yield) as a hard orange foam. LCMS (ESI): 365 (M+1); $^1$H NMR (400 MHz, DMSO-d$_6$) δ 14.39 (br s, 1H), 8.93 (d, J=7.3 Hz, 1H), 8.32 (d, J=1.8 Hz, 1H), 8.17 (d, J=1.8 Hz, 1H), 8.10 (s, 1H), 7.92-7.87 (m, 3H), 7.19 (d, J=8.8 Hz, 2H), 6.63-6.46 (m, 1H), 4.74-4.66 (m, 1H), 3.73-3.68 (m, 2H), 3.17-3.08 (m, 2H), 3.05 (q, J=7.2 Hz, 2H), 1.98-1.89 (m, 1H), 1.57-1.46 (m, 2H), 1.01 (t, J=7.2 Hz, 3H).

Example 629. N-Ethyl-4-[4-(8-methylimidazo[1,2-a]pyridin-7-yl)phenoxy]piperidine-1-carboxamide, HCl

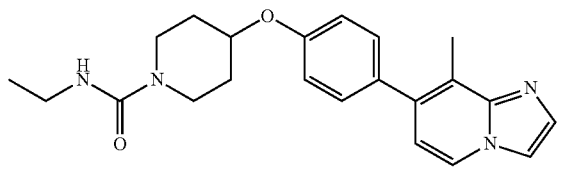 [SMILES: CCNC(=O)N1CCC(Oc2ccc(-c3ccn4ccnc4c3C)cc2)CC1]

Step 1. 7-Bromo-8-methyl-imidazo[1,2-a]pyridine

A mixture of 4-bromo-3-methyl-pyridin-2-amine (0.45 g, 2.4 mmol) and bromo-acetaldehyde diethyl acetal (0.98 g, 0.75 mL, 5.0 mmol) in ethanol (2.4 mL) was treated with 48% aq. HBr (0.37 g, 0.25 mL, 2.2 mmol) then the mixture was heated at 60° C. in a resealable vial. After stirring for seven days, the mixture was cooled to room temperature, treated with 0.5M Na$_2$CO$_3$ (10 mL) then extracted with DCM (10 mL then 5 mL). The organic extract was dried over Na$_2$SO$_4$, filtered and concentrated in vacuo. The residue was dissolved in DCM, applied to a silica gel loading cartridge (5 g) and purified on silica gel (40 g, 0-5% methanol:DCM) to afford 7-bromo-8-methyl-imidazo[1,2-a]pyridine (0.436 g, 2.07 mmol, 86% Yield) after concentration of product containing fractions. LCMS (ESI): 211 (M+1); $^1$H NMR (400 MHz, DMSO-d$_6$) δ: 8.39-8.35 (m, 1H), 7.96 (d, J=1.3 Hz, 1H), 7.55 (d, J=1.3 Hz, 1H), 7.05 (d, J=7.3 Hz, 1H), 2.56 (s, 3H).

Step 2. tert-Butyl 4-[4-(8-methylimidazo[1,2-a]pyridin-7-yl)phenoxy]piperidine-1-carboxylate Analogous to Example 628 Step 1, 7-bromo-8-methyl-imidazo[1,2-a]pyridine and tert-butyl 4-[4-(4,4,5,5-tetramethyl-1,3,2-dioxaborolan-2-yl)phenoxy]piperidine-1-carboxylate were coupled to prepare tert-butyl 4-[4-(8-methylimidazo[1,2-a]pyridin-7-yl)phenoxy]piperidine-1-carboxylate (0.68 g, 81% yield). LCMS (ESI): 408 (M+1); $^1$H NMR (400 MHz, DMSO-d$_6$) δ: 8.42 (d, J=7.0 Hz, 1H), 7.93 (d, J=1.3 Hz, 1H), 7.56 (d, J=1.0 Hz, 1H), 7.35 (d, J=8.8 Hz, 2H), 7.08 (d, J=8.8 Hz, 2H), 6.80 (d, J=7.0 Hz, 1H), 4.63 (tt, J=8.0, 3.7 Hz, 1H), 3.75-3.63 (m, 2H), 3.26-3.16 (m, 2H), 2.46 (s, 3H), 1.98-1.89 (m, 2H), 1.62-1.49 (m, 2H), 1.41 (s, 9H).

Step 3. 8-Methyl-7-[4-(4-piperidyloxy)phenyl]imidazo[1,2-a]pyridine, 2HCl

Analogous to Example 628 Step 2, tert-butyl 4-[4-(8-methylimidazo[1,2-a]pyridin-7-yl)phenoxy]piperidine-1-carboxylate was converted to 8-methyl-7-[4-(4-piperidyloxy)-phenyl]imidazo[1,2-a]pyridine 2HCl (0.65 g, 99% yield). MS (ESI): 308 (M+1); 1H NMR (400 MHz, DMSO-d$_6$) δ: 14.71 (br s, 1H), 9.08 (br s, 2H), 8.81 (d, J=6.8 Hz, 1H), 8.38 (d, J=2.3 Hz, 1H), 8.25 (d, J=2.0 Hz, 1H), 7.52-7.40 (m, 3H), 7.19 (d, J=8.8 Hz, 2H), 4.81-4.74 (m, 1H), 3.31-3.19 (m, 2H), 3.15-3.04 (m, 2H), 2.56 (s, 3H), 2.21-2.10 (m, 2H), 1.95-1.84 (m, 2H).

Step 3. 8-Methyl-7-[4-(4-piperidyloxy)phenyl]imidazo[1,2-a]pyridine, 2HCl

Analogous to Example 628 Step 3 8-methyl-7-[4-(4-piperidyloxy)phenyl]-imidazo[1,2-a]pyridine 2HCl (0.110 g, 0.289 mmol) was converted to N-ethyl-4-[4-(8-methylimidazo[1,2-a]pyridin-7-yl)phenoxy]piperidine-1-carboxamide HCl (0.091 g, 0.22 mmol, 76% Yield). LCMS (ESI): 379 (M+1); $^1$H NMR (400 MHz, DMSO-d$_6$) δ: 14.52 (br s, 1H), 8.80 (d, J=6.8 Hz, 1H), 8.38 (d, J=2.0 Hz, 1H), 8.26 (d, J=2.0 Hz, 1H), 7.49-7.41 (m, 3H), 7.16 (d, J=8.5 Hz, 2H), 6.56-6.48 (m, 1H), 4.69-4.62 (m, 1H), 3.76-3.67 (m, 2H), 3.18-3.01 (m, 4H), 2.55 (s, 3H), 1.99-1.89 (m, 2H), 1.58-1.47 (m, 2H), 1.01 (t, J=7.0 Hz, 3H).

Example 630. N-Isopropoxy-4-[4-(8-methylimidazo[1,2-a]pyridin-7-yl)phenoxy]piperidine-1-carboxamide, HCl

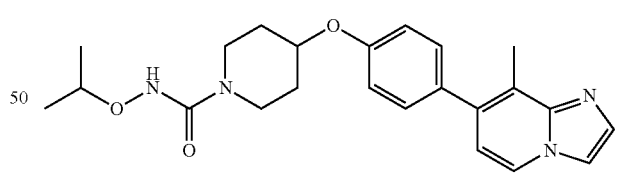

A mixture of O-isopropylhydroxylamine HCl (0.058 g, 0.52 mmol), N,N'-carbonyldiimidazole (0.071 g, 0.44 mmol) and DIPEA (0.37 g, 0.50 mL, 2.9 mmol) in DCM (3.0 mL) was stirred for 2 h, then 8-methyl-7-[4-(4-piperidyloxy)phenyl]imidazo[1,2-a]pyridine 2HCl (0.076 g, 0.20 mmol) was added to the reaction. After stirring overnight, the reaction solution was applied to a silica gel loading column (25 g) then purified on silica gel (12 g, 0-5% methanol:DCM). Product containing fractions were concentrated in vacuo then reconcentrated from ethanolic HCl (1 mL, 1M) and ethanol to afford N-isopropoxy-4-[4-(8-methylimidazo[1,2-a]pyridin-7-yl)phenoxy]piperidine-1-carboxamide HCl (0.063 g, 0.14 mmol, 71% Yield) as a white foam after drying in vacuo. LCMS (ESI)=409 (M+1); ¹H NMR (400 MHz, DMSO-d₆) δ: 14.51 (br s, 1H), 9.52 (s, 1H), 8.79 (d, J=7.0 Hz, 1H), 8.36 (d, J=2.3 Hz, 1H), 8.23 (d, J=2.0 Hz, 1H), 7.47-7.41 (m, 3H), 7.16 (d, J=8.8 Hz, 2H), 4.70-4.64 (m, 1H), 3.87 (quin, J=6.1 Hz, 1H), 3.71-3.60 (m, 2H), 3.14 (ddd, J=13.1, 9.5, 3.3 Hz, 2H), 2.55 (s, 3H), 1.99-1.91 (m, 2H), 1.59-1.50 (m, 2H), 1.12 (d, J=6.3 Hz, 6H).

Example 631. 4-[4-(8-Methylimidazo[1,2-a]pyridin-7-yl)phenoxy]-N-propyl-piperidine-1-carboxamide, HCl

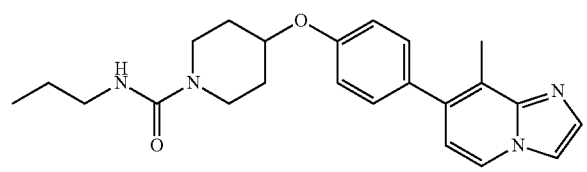 [SMILES: CCCNC(=O)N1CCC(Oc2ccc(-c3ccn4ccnc4c3C)cc2)CC1]

Analogous to Example 628 Step 3, 8-methyl-7-[4-(4-piperidyloxy)phenyl]-imidazo[1,2-a]pyridine 2HCl (0.076 g, 0.20 mmol) was reacted with propyl isocyanate to afford 4-[4-(8-methylimidazo[1,2-a]pyridin-7-yl)phenoxy]-N-propyl-piperidine-1-carboxamide HCl (0.063 g, 0.15 mmol, 73% Yield). LCMS (ESI)=393 (M+1); ¹H NMR (400 MHz, DMSO-d₆) δ: 14.73 (br s, 1H), 8.82 (d, J=6.8 Hz, 1H), 8.39 (d, J=2.0 Hz, 1H), 8.25 (d, J=2.0 Hz, 1H), 7.49-7.41 (m, 3H), 7.16 (d, J=8.8 Hz, 2H), 6.56 (br s, 1H), 4.70-4.62 (m, 1H), 3.78-3.67 (m, 2H), 3.18-3.06 (m, 2H), 3.03-2.92 (m, 2H), 2.57 (s, 3H), 2.00-1.88 (m, 2H), 1.57-1.47 (m, 2H), 1.47-1.36 (m, 2H), 0.83 (t, J=7.4 Hz, 3H).

Example 632. N-Isobutyl-4-[4-(8-methylimidazo[1,2-a]pyridin-7-yl)phenoxy]piperidine-1-carboxamide

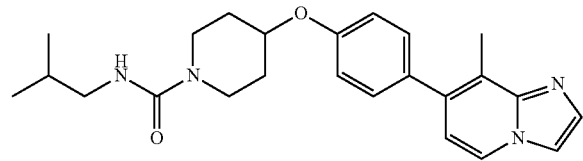 [SMILES: Cc1c(-c2ccc(OC3CCN(C(=O)NCC(C)C)CC3)cc2)ccn2ccnc12]

Analogous to Example 628 Step 3, 8-methyl-7-[4-(4-piperidyloxy)phenyl]imidazo[1,2-a]pyridine 2HCl (0.076 g, 0.20 mmol) was reacted with isobutyl isocyanate to afford N-isobutyl-4-[4-(8-methylimidazo[1,2-a]pyridin-7-yl)phenoxy]piperidine-1-carboxamide (0.055 g, 0.14 mmol, 68% Yield). LCMS (ESI)=407 (M+1); ¹H NMR (400 MHz, DMSO-d₆) δ 8.42 (d, J=7.0 Hz, 1H), 7.93 (d, J=1.3 Hz, 1H), 7.56 (d, J=1.3 Hz, 1H), 7.35 (d, J=7.8 Hz, 2H), 7.08 (d, J=7.9 Hz, 2H), 6.80 (d, J=7.0 Hz, 1H), 6.54 (t, J=5.5 Hz, 1H), 4.65-4.56 (m, 1H), 3.76-3.68 (m, 2H), 3.16-3.07 (m, 2H), 2.85 (dd, J=6.9, 5.9 Hz, 2H), 2.46 (s, 3H), 1.97-1.89 (m, 2H), 1.75-1.65 (m, 1H), 1.56-1.46 (m, 2H), 0.83 (d, J=6.5 Hz, 6H).

Example 633. N-Isobutyl-4-[4-(7-methylpyrazolo[1,5-a]pyridin-6-yl)phenoxy]piperidine-1-carboxamide

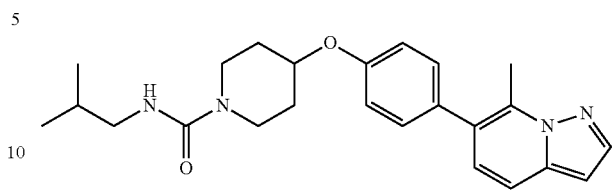

This compound may be synthesized using the procedure for example 537 using 1-isocyanato-2-methylpropane.

Example 634. 4-[4-(7-Methylpyrazolo[1,5-a]pyridin-6-yl)phenoxy]piperidine-1-carboxamide

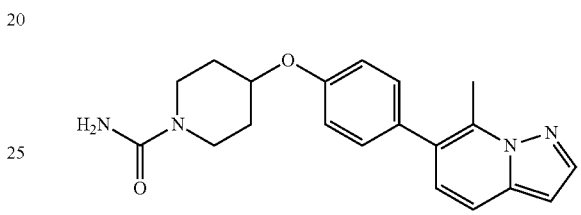

This compound may be synthesized using the procedure for example 539 with 7-methyl-6-[4-(4-piperidyloxy)phenyl]pyrazolo[1,5-a]pyridine 2HCl.

Example 635. 4-[4-(7-Methylpyrazolo[1,5-a]pyridin-6-yl)phenoxy]piperidine-1-carbohydroxamic acid

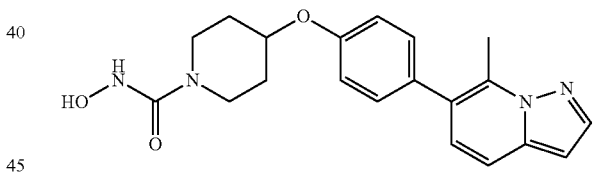

This compound may be synthesized using the procedure for example 576 starting with 7-methyl-6-[4-(4-piperidyloxy)phenyl]pyrazolo[1,5-a]pyridine dihydrochloride.

Example 636. N,N-Dimethyl-4-[4-(7-methylpyrazolo[1,5-a]pyridin-6-yl)phenoxy]piperidine-1-carboxamide

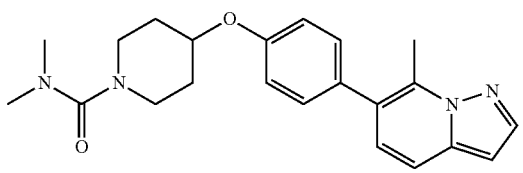 [SMILES: Cc1c(-c2ccc(OC3CCN(C(=O)N(C)C)CC3)cc2)ccc2ccnn12]

This compound may be synthesized using the procedure for example 89 starting with 7-methyl-6-[4-(4-piperidyloxy)phenyl]pyrazolo[1,5-a]pyridine 2HCl and dimethylamine.

Example 637. [4-[4-(7-Methylpyrazolo[1,5-a]pyridin-6-yl)phenoxy]-1-piperidyl]-pyrrolidin-1-yl-methanone

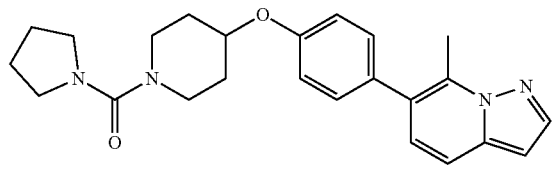 [SMILES: Cc1c(-c2ccc(OC3CCN(C(=O)N4CCCC4)CC3)cc2)ccc2ccnn12]

This compound may be synthesized using the procedure for example 94 starting with 7-methyl-6-[4-(4-piperidyloxy)phenyl]pyrazolo[1,5-a]pyridine 2HCl and pyrrolidine.

Example 638. [(3S)-3-Fluoropyrrolidin-1-yl]-[4-[4-(7-methylpyrazolo[1,5-a]pyridin-6-yl)phenoxy]-1-piperidyl]methanone

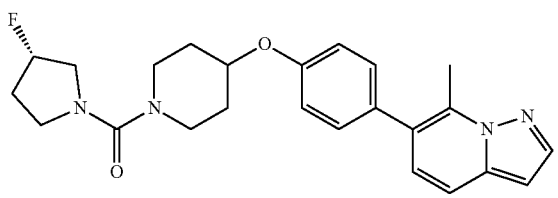 [SMILES: Cc1c(-c2ccc(OC3CCN(C(=O)N4CC[C@H](F)C4)CC3)cc2)ccc2ccnn12]

This compound may be synthesized using the procedure for example 94 starting with 7-methyl-6-[4-(4-piperidyloxy)phenyl]pyrazolo[1,5-a]pyridine 2HCl and S-3-fluoropyrrolidine.

Example 639. [(3R)-3-Fluoropyrrolidin-1-yl]-[4-[4-(7-methylpyrazolo[1,5-a]pyridin-6-yl)phenoxy]-1-piperidyl]methanone

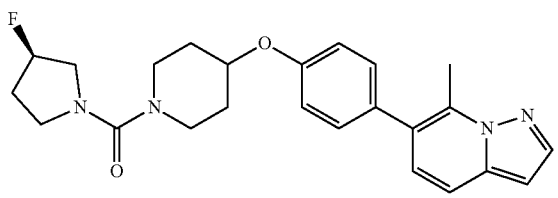 [SMILES: Cc1c(-c2ccc(OC3CCN(C(=O)N4CC[C@@H](F)C4)CC3)cc2)ccc2ccnn12]

This compound may be synthesized using the procedure for example 94 starting with 7-methyl-6-[4-(4-piperidyloxy)phenyl]pyrazolo[1,5-a]pyridine 2HCl and R-3-fluoropyrrolidine.

Example 640. 4-[4-(7-Methylpyrazolo[1,5-a]pyridin-6-yl)phenoxy]-N-methyl sulfanyl-piperidine-1-carboxamide This compound may be synthesized using the procedure for example 94 starting with 7-methyl-6-[4-(4-piperidyloxy)phenyl]pyrazolo[1,5-a]pyridine 2HCl and methanesulfenamide

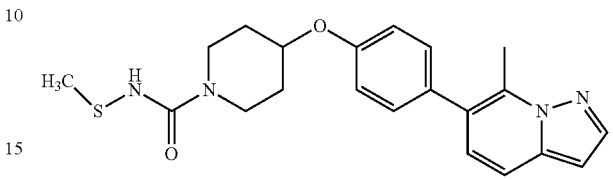

Example 641. N-Ethylsulfanyl-4-[4-(7-methylpyrazolo[1,5-a]pyridin-6-yl)phenoxy]piperidine-1-carboxamide This compound may be synthesized using the procedure for example 94 starting with 7-methyl-6-[4-(4-piperidyloxy)phenyl]pyrazolo[1,5-a]pyridine 2HCl and ethylsulfenamide

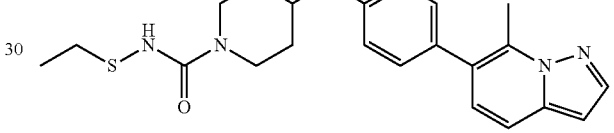

Example 642. 4-[4-(4-Methyl-3-quinolyl)phenoxy]-N-methylsulfanyl-piperidine-1-carboxamide This compound may be synthesized using the procedure for example 94 starting with 4-methyl-3-[4-(4-piperidyloxy)phenyl]quinolone 2HCl and methanesulfenamide.

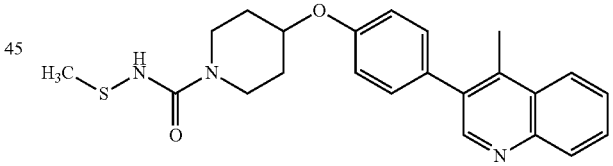

Example 643. 4-[4-(4-Methyl-3-quinolyl)phenoxy]-N-ethylsulfanyl-piperidine-1-carboxamide This compound may be synthesized using the procedure for example 94 starting with 4-methyl-3-[4-(4-piperidyloxy)phenyl]quinolone 2HCl and methanesulfenamide

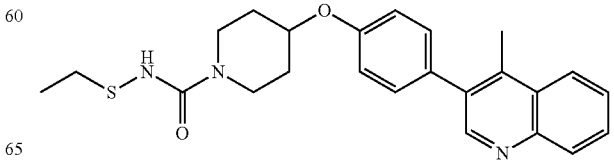

Example 644. 1-[4-[4-(7-Methylpyrazolo[1,5-a]pyridin-6-yl)phenoxy]piperidine-1-carbonyl]pyrrolidin-2-one This compound may be synthesized using 7-methyl-6-[4-(4-piperidyloxy)phenyl]-pyrazolo[1,5-a]pyridine 2HCl and pyrrolidin-2-one

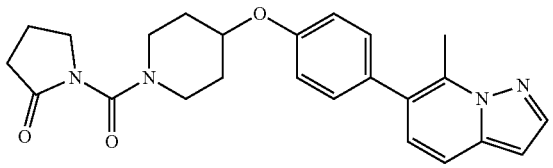 [SMILES: Cc1c(-c2ccc(OC3CCN(C(=O)N4CCCC4=O)CC3)cc2)ccc2ccnn12]

Example 645. 1-[4-[4-(4-Methyl-3-quinolyl)phenoxy]piperidine-1-carbonyl]pyrrolidin-2-one This compound may be synthesized using 4-methyl-3-[4-(4-piperidyloxy)phenyl]-quinolone 2HCl and pyrrolidin-2-one

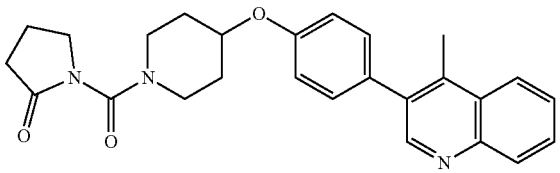 [SMILES: Cc1c(-c2ccc(OC3CCN(C(=O)N4CCCC4=O)CC3)cc2)cnc2ccccc12]

Example 646. 4-[4-(7-Methylpyrazolo[1,5-a]pyridin-6-yl)phenoxy]-N-propyl-piperidine-1-carboxamide This compound may be synthesized using the procedure for example 537 using 7-methyl-6-[4-(4-piperidyloxy)phenyl]pyrazolo[1,5-a]pyridine 2HCl and 1-isocyanato-3-propane

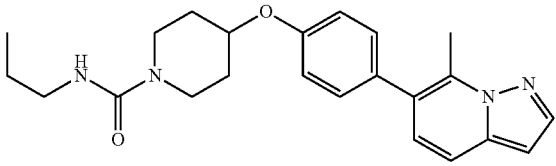 [SMILES: CCCNC(=O)N1CCC(Oc2ccc(-c3ccc4ccnn4c3C)cc2)CC1]

Example 647. N-ethyl-4-[4-(2-fluoro-8-methyl-7-quinolyl)phenoxy]piperidine-1-carboxamide

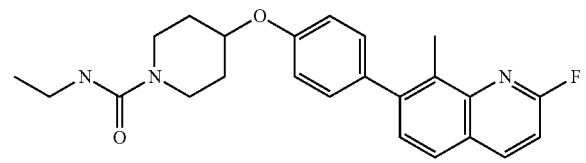 [SMILES: CCNC(=O)N1CCC(Oc2ccc(-c3ccc4ccc(F)nc4c3C)cc2)CC1]

This compound may be synthesized using the procedure for example 88 with 7-bromo-2-fluoro-8-methyl-quinoline in place of 7-bromo-8-methyl-quinoline using the intermediate of example 529 step 2, and reacting with phosphorus oxychloride followed by reaction with tetrabutylammonium fluoride.

A number of embodiments of the invention have been described herein. Nevertheless, As those skilled in the art will appreciate, numerous modifications and variations of the present invention are possible in light of the above teachings; without departing from the scope of the invention that is disclosed herein. It is therefore understood that within the scope of the appended claims, the invention may be practiced otherwise than as specifically described herein, and the scope of the invention is intended to encompass all such variations.

What is claimed is:

1. A pharmaceutical composition comprising at least one compound according to Formula V(a):

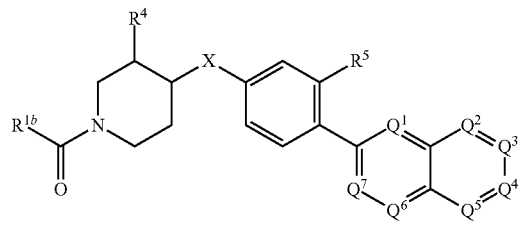

V(a)

or a pharmaceutically acceptable salt thereof, wherein:

$R^{1b}$ is selected from —$NR^7R^8$ and —$N(OR^8)R^7$;

$R^4$ is selected from —H, —($C_1$-$C_6$) alkyl, —OH, —O($C_1$-$C_6$) alkyl, halogen, and —CN;

X is selected from —O— and —S—;

$R^5$ is selected from —H, —$C_1$-$C_7$ hydrocarbyl, —$C_3$-$C_6$ heterocyclyl; halogen, —($C_1$-$C_3$) haloalkyl, —$OR^{7a}$, —CN, —$NR^{7a}R^{8a}$, —$O(CH_2)_nNR^{7a}R^{8a}$, —$O(CH_2)_nOR^{8a}$, —$NR^{8a}(CH_2)_nNR^{7a}R^{8a}$, —$NR^{8a}(CH_2)_nOR^{8a}$, —C(=O)$NR^{7a}R^{8a}$, —C(=O)$OR^{7a}$, 5-6 membered heteroaryl and substituted 5-6 membered heteroaryl;

n is an integer selected from 1, 2, 3, and 4;

$R^7$ is selected from —H, —($C_1$-$C_7$) hydrocarbyl, substituted —($C_1$-$C_7$) hydrocarbyl, —C(=O)$R^8$, and —($C_1$-$C_6$) heteroalkyl;

$R^8$ is selected from —H, and —($C_1$-$C_6$) alkyl, wherein $R^7$ can optionally be structurally connected to $R^8$ to form a 5 to 7 membered heterocyclyl ring;

$R^{7a}$ is selected from —H, —($C_1$-$C_7$) hydrocarbyl, substituted —($C_1$-$C_7$) hydrocarbyl, —C(=O)$R^8$, and —($C_1$-$C_6$) heteroalkyl;

$R^{8a}$ is selected from —H, and —($C_1$-$C_6$) alkyl, wherein $R^{7a}$ can optionally be structurally connected to $R^{8a}$ to form a 5 to 7 membered heterocyclyl ring;

$Q^1$, $Q^2$, $Q^3$, $Q^4$, $Q^5$, $Q^6$ and $Q^7$ are independently selected from N and C—$R^{12}$, provided that 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$;

each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_p$-(5-6 membered heterocyclyl), —O($CH_2$)$_p$—O($C_1$-$C_6$) alkyl, —$NH_2$, —CN, —NH($C_1$-$C_6$) alkyl, —N($C_1$-$C_6$ alkyl)$_2$, —NH($CH_2$)$_p$—O($C_1$-$C_6$) alkyl, —NH($CH_2$)$_p$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$; and p is an integer selected independently from 1, 2, 3, and 4; and at least one pharmaceutically acceptable excipient.

2. The pharmaceutical composition according to claim 1, wherein X is —O—.

3. The pharmaceutical composition according to claim 1, wherein $R^5$ is selected from —H, —($C_1$-$C_7$) hydrocarbyl, and halogen.

4. The pharmaceutical composition according to claim 1, wherein one of $Q^1$, $Q^2$, $Q^3$, $Q^4$, $Q^5$, $Q^6$ and $Q^7$ is N, and the remainder of $Q^1$, $Q^2$, $Q^3$, $Q^4$, $Q^5$, $Q^6$ and $Q^7$ are C—$R^{12}$.

5. The pharmaceutical composition according to claim 4, wherein one of $Q^2$ and $Q^6$ is N; the other of $Q^2$ and $Q^6$ is C—$R^{12}$; and $Q^1$, $Q^3$, $Q^4$, $Q^5$ and $Q^7$ are C—$R^{12}$.

6. The pharmaceutical composition according to claim 1, wherein the compound according to Formula V(a) is selected from:

isoxazolidin-2-yl-[4-(4-quinolin-3-yl-phenoxy)-piperidin-1-yl]-methanone;
[4-(4-isoquinolin-3-yl-phenoxy)-piperidin-1-yl]-isoxazolidin-2-yl-methanone; isoxazolidin-2-yl-{4-[4-(8-methylquinolin-7-yl)-phenoxy]-piperidin-1-yl}-methanone;
{4-[4-(4-chloroquinolin-3-yl)-phenoxy]-piperidin-1-yl}-isoxazolidin-2-yl-methanone;
{4-[4-(8-chloroquinolin-7-yl)-phenoxy]-piperidin-1-yl}-isoxazolidin-2-yl-methanone;
isoxazolidin-2-yl-{4-[4-(4-methylquinolin-3-yl)-phenoxy]-piperidin-1-yl}-methanone;
isoxazolidin-2-yl-{4-[4-(8-methoxyquinolin-7-yl)-phenoxy]-piperidin-1-yl}-methanone;
isoxazolidin-2-yl-{4-[4-(7-methylquinolin-3-yl)-phenoxy]-piperidin-1-yl}-methanone;
isoxazolidin-2-yl-[4-(4-quinoxalin-2-yl-phenoxy)-piperidin-1-yl]-methanone;
4-[4-(4-methylquinolin-3-yl)-phenoxy]-piperidine-1-carboxylic acid methoxyamide;
4-[4-(4-methylquinolin-3-yl)-phenoxy]-piperidine-1-carboxylic acid methoxymethylamide;
4-[4-(4-methylquinolin-3-yl)-phenoxy]-piperidine-1-carboxylic acid ethylamide;
4-[4-(8-methoxyquinolin-7-yl)-phenoxy]-piperidine-1-carboxylic acid methylamide;
4-[4-(8-methoxyquinolin-7-yl)-phenoxy]-piperidine-1-carboxylic acid ethylamide;
4-[4-(4-methylquinolin-3-yl)-phenoxy]-piperidine-1-carboxylic acid hydroxyamide;
N-ethyl-4-[4-(8-methyl-7-quinolyl)phenoxy]piperidine-1-carboxamide;
N,N-dimethyl-4-[4-(8-methyl-7-quinolyl)phenoxy]piperidine-1-carboxamide;
N-methoxy-4-[4-(8-methyl-7-quinolyl)phenoxy]piperidine-1-carboxamide;
N-isopropyl-4-[4-(8-methyl-7-quinolyl)phenoxy]piperidine-1-carboxamide;
N-ethoxy-4-[4-(8-methyl-7-quinolyl)phenoxy]piperidine-1-carboxamide;
[4-[4-(8-methyl-7-quinolyl)phenoxy]-1-piperidyl]-pyrrolidin-1-yl-methanone;
N-methyl-4-[4-(8-methyl-7-quinolyl)phenoxy]piperidine-1-carboxamide;
4-[4-(8-methyl-7-quinolyl)phenoxy]-N-propyl-piperidine-1-carboxamide;
4-[4-(8-methyl-7-quinolyl)phenoxy]piperidine-1-carboxamide;
[4-[4-(8-methyl-7-quinolyl)phenoxy]-1-piperidyl]-(1-piperidyl)methanone;
[4-[4-(8-methyl-7-quinolyl)phenoxy]-1-piperidyl]-morpholinomethanone;
N-methoxy-4-[4-(8-methoxy-7-quinolyl)phenoxy]piperidine-1-carboxamide;
3-[4-(4-quinolin-3-yl-phenoxy)-piperidine-1-carbonyl]-oxazolidin-2-one;
1-[4-(4-quinolin-3-yl-phenoxy)-piperidine-1-carbonyl]-pyrrolidin-2-one;
N-ethyl-4-[4-(2-hydroxy-8-methyl-7-quinolyl)phenoxy]piperidine-1-carboxamide;
4-[4-(8-methyl-7-quinolyl)phenoxy]-N-(2-pyrrolidin-1-ylethyl)piperidine-1-carboxamide; 4-[4-(8-methyl-7-quinolyl)phenoxy]-N-(2-morpholinoethyl)piperidine-1-carboxamide;
(4-isopropylpiperazin-1-yl)-[4-[4-(8-methyl-7-quinolyl)phenoxy]-1-piperidyl]methanone; (4-methylpiperazin-1-yl)-[4-[4-(8-methyl-7-quinolyl)phenoxy]-1-piperidyl]methanone;
[4-[4-(8-methyl-7-quinolyl)phenoxy]-1-piperidyl]-(4-morpholino-1-piperidyl)methanone; (4-ethylpiperazin-1-yl)-[4-[4-(8-methyl-7-quinolyl)phenoxy]-1-piperidyl]methanone;
N-(cyclopropylmethyl)-4-[4-(8-methyl-7-quinolyl)phenoxy]piperidine-1-carboxamide;
N-isobutyl-4-[4-(8-methyl-7-quinolyl)phenoxy]piperidine-1-carboxamide;
N-(2-methoxyethyl)-4-[4-(8-methyl-7-quinolyl)phenoxy]piperidine-1-carboxamide;
N-isopropoxy-4-[4-(8-methyl-7-quinolyl)phenoxy]piperidine-1-carboxamide;
N-isobutoxy-4-[4-(8-methyl-7-quinolyl)phenoxy]piperidine-1-carboxamide;
N-(2-dimethylaminoethyl)-4-[4-(8-methyl-7-quinolyl)phenoxy]piperidine-1-carboxamide; N-[2-(1H-imidazol-4-yl)ethyl]-4-[4-(8-methyl-7-quinolyl)phenoxy], piperidine-1-carboxamide;
4-[4-(8-methyl-7-quinolyl)phenoxy]-N-tetrahydropyran-4-yl-piperidine-1-carboxamide; N-cyclobutyl-4-[4-(8-methyl-7-quinolyl)phenoxy]piperidine-1-carboxamide;
4-[4-(8-methyl-7-quinolyl)phenoxy]piperidine-1-carbohydroxamic acid;
[4-[4-(8-methyl-7-quinolyl)phenoxy]-1-piperidyl]-(oxazinan-2-yl)methanone;
N-(cyclobutylmethyl)-4-[4-(8-methyl-7-quinolyl)phenoxy]piperidine-1-carboxamide; azepan-1-yl-[4-[4-(8-methyl-7-quinolyl)phenoxy]-1-piperidyl]methanone;
4-[4-(8-methyl-7-quinolyl)phenoxy]-N-propoxy-piperidine-1-carboxamide;
N-ethyl-4-[4-(1-methyl-6-isoquinolyl)phenoxy]piperidine-1-carboxamide;
4-[4-(1-methyl-6-isoquinolyl)phenoxy]-N-propyl-piperidine-1-carboxamide;
N-isobutyl-4-[4-(1-methyl-6-isoquinolyl)phenoxy]piperidine-1-carboxamide;
4-[4-(1-methyl-6-isoquinolyl)phenoxy]piperidine-1-carboxamide;
N-(cyclopropylmethyl)-4-[4-(1-methyl-6-isoquinolyl)phenoxy]piperidine-1-carboxamide; N-isopropoxy-4-[4-(1-methyl-6-isoquinolyl)phenoxy]piperidine-1-carboxamide;
4-[4-(1-methyl-6-isoquinolyl)phenoxy]-N-propoxypiperidine-1-carboxamide;
4-[4-(1-methyl-6-isoquinolyl)phenoxy]piperidine-1-carbohydroxamic acid;
N-ethoxy-4-[4-(1-methyl-6-isoquinolyl)phenoxy]piperidine-1-carboxamide;

N-ethoxy-4-[4-(4-methyl-3-quinolyl)phenoxy]piperidine-1-carboxamide;

N-isopropoxy-4-[4-(4-methyl-3-quinolyl)phenoxy]piperidine-1-carboxamide;

4-[4-(4-methyl-3-quinolyl)phenoxy]-N-propoxy-piperidine-1-carboxamide;

N-isobutyl-4-[4-(4-methyl-3-quinolyl)phenoxy]piperidine-1-carboxamide;

4-[4-(4-methyl-3-quinolyl)phenoxy]-N-propyl-piperidine-1-carboxamide;

4-[4-(4-methyl-3-quinolyl)phenoxy]-N-methylsulfanyl-piperidine-1-carboxamide;

4-[4-(4-methyl-3-quinolyl)phenoxy]-N-ethylsulfanyl-piperidine-1-carboxamide,

1-[4-[4-(4-methyl-3-quinolyl)phenoxy]piperidine-1-carbonyl]pyrrolidin-2-one;

or a pharmaceutically acceptable salt thereof.

7. The pharmaceutical composition according to claim 6, further comprising an antipsychotic agent.

8. The pharmaceutical composition according to claim 7, wherein the antipsychotic agent is clozapine, risperidone, aripiprazole, olanzapine, quetiapine or ziprasidone or a combination thereof.

9. The pharmaceutical composition according to claim 1, wherein the compound of formula (Va) is

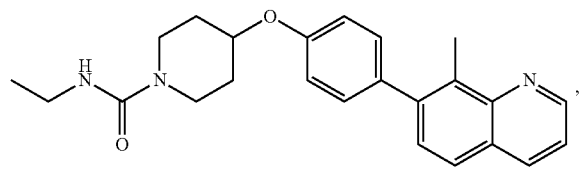 [SMILES: CCNC(=O)N1CCC(Oc2ccc(-c3ccc4cccnc4c3C)cc2)CC1]

or a pharmaceutically acceptable salt thereof.

10. The pharmaceutical composition according to claim 1, wherein the compound of formula (Va) is

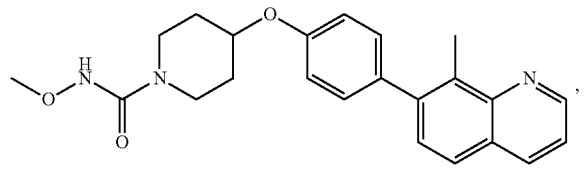 [SMILES: CONC(=O)N1CCC(Oc2ccc(-c3ccc4cccnc4c3C)cc2)CC1]

or a pharmaceutically acceptable salt thereof.

11. A method of treating a subject suffering from a disorder mediated by fatty acid synthase, comprising administering to the subject a therapeutically effective amount of a pharmaceutical composition according to claim 1.

12. A compound having the formula:

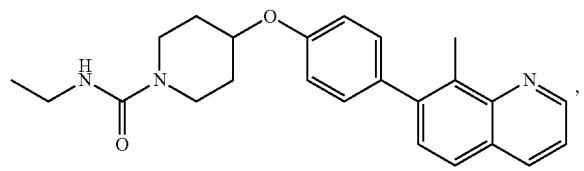 [SMILES: CCNC(=O)N1CCC(Oc2ccc(-c3ccc4cccnc4c3C)cc2)CC1]

or a pharmaceutically acceptable salt thereof.

13. A compound having the formula:

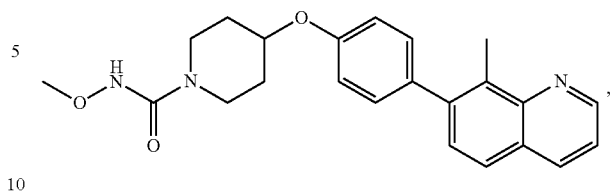

or a pharmaceutically acceptable salt thereof.

14. A method of treating a subject suffering from a disorder mediated by fatty acid synthase, comprising administering to the subject a therapeutically effective amount of a compound according to Formula V(a):

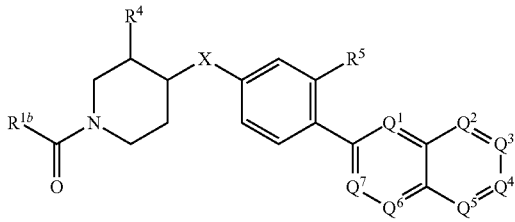

or a pharmaceutically acceptable salt thereof, wherein:

$R^{1b}$ is selected from —$NR^7R^8$ and —$N(OR^8)R^7$;

$R^4$ is selected from —H, —($C_1$-$C_6$) alkyl, —OH, —O($C_1$-$C_6$) alkyl, halogen, and —CN;

X is selected from —O— and —S—;

$R^5$ is selected from —H, —$C_1$-$C_7$ hydrocarbyl, —$C_3$-$C_6$ heterocyclyl; halogen, —($C_1$-$C_3$) haloalkyl, —$OR^{7a}$, —CN, —$NR^{7a}R^{8a}$, —$O(CH_2)_nNR^{7a}R^{8a}$, —$O(CH_2)_nOR^{8a}$, —$NR^{8a}(CH_2)_nNR^{7a}R^{8a}$, —$NR^{8a}(CH_2)_nOR^{8a}$, —C(=O)$NR^{7a}R^{8a}$, —C(=O)$OR^{7a}$, 5-6 membered heteroaryl and substituted 5-6 membered heteroaryl;

n is an integer selected from 1, 2, 3, and 4;

$R^7$ is selected from —H, —($C_1$-$C_7$) hydrocarbyl, substituted —($C_1$-$C_7$) hydrocarbyl, —C(=O)$R^8$, and —($C_1$-$C_6$) heteroalkyl;

$R^8$ is selected from —H, and —($C_1$-$C_6$) alkyl, wherein $R^7$ can optionally be structurally connected to $R^8$ to form a 5 to 7 membered heterocyclyl ring;

$R^{7a}$ is selected from —H, —($C_1$-$C_7$) hydrocarbyl, substituted —($C_1$-$C_7$) hydrocarbyl, —C(=O)$R^8$, and —($C_1$-$C_6$) heteroalkyl;

$R^{8a}$ is selected from —H, and —($C_1$-$C_6$) alkyl, wherein $R^{7a}$ can optionally be structurally connected to $R^{8a}$ to form a 5 to 7 membered heterocyclyl ring;

$Q^1$, $Q^2$, $Q^3$, $Q^4$, $Q^5$, $Q^6$ and $Q^7$ are independently selected from N and C—$R^{12}$, provided that 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$;

each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —O($CH_2$)$_p$-(5-6 membered heterocyclyl), —O($CH_2$)$_p$—O($C_1$-$C_6$) alkyl, —$NH_2$, —CN, —NH($C_1$-$C_6$) alkyl, —N($C_1$-$C_6$ alkyl)$_2$, —NH($CH_2$)$_p$—O($C_1$-$C_6$) alkyl, —NH($CH_2$)$_p$—N($C_1$-$C_6$ alkyl)$_2$, —C(=O)$NH_2$, —C(=O)NH($C_1$-$C_6$) alkyl, and —C(=O)N($C_1$-$C_6$ alkyl)$_2$; and p is an integer selected independently from 1, 2, 3, and 4.

15. The method according to claim 14, wherein X is —O—.

16. The method according to claim 14, wherein $R^5$ is selected from —H, —($C_1$-$C_7$) hydrocarbyl, and halogen.

17. The method according to claim 14, wherein one of $Q^1$, $Q^2$, $Q^3$, $Q^4$, $Q^5$, $Q^6$ and $Q^7$ is N, and the remainder of $Q^1$, $Q^2$, $Q^3$, $Q^4$, $Q^5$, $Q^6$ and $Q^7$ are C—$R^{12}$.

18. The method according to claim 17, wherein one of $Q^2$ and $Q^6$ is N; the other of $Q^2$ and $Q^6$ is C—$R^{12}$; and $Q^1$, $Q^3$, $Q^4$, $Q^5$ and $Q^7$ are C—$R^{12}$.

19. The method according to claim 14, wherein the compound according to Formula V(a) is selected from:
isoxazolidin-2-yl-[4-(4-quinolin-3-yl-phenoxy)-piperidin-1-yl]-methanone;
[4-(4-isoquinolin-3-yl-phenoxy)-piperidin-1-yl]-isoxazolidin-2-yl-methanone; isoxazolidin-2-yl-{4-[4-(8-methylquinolin-7-yl)-phenoxy]-piperidin-1-yl}-methanone;
{4-[4-(4-chloroquinolin-3-yl)-phenoxy]-piperidin-1-yl}-isoxazolidin-2-yl-methanone;
{4-[4-(8-chloroquinolin-7-yl)-phenoxy]-piperidin-1-yl}-isoxazolidin-2-yl-methanone;
isoxazolidin-2-yl-{4-[4-(4-methylquinolin-3-yl)-phenoxy]-piperidin-1-yl}-methanone;
isoxazolidin-2-yl-{4-[4-(8-methoxyquinolin-7-yl)-phenoxy]-piperidin-1-yl}-methanone;
isoxazolidin-2-yl-{4-[4-(7-methylquinolin-3-yl)-phenoxy]-piperidin-1-yl}-methanone;
isoxazolidin-2-yl-[4-(4-quinoxalin-2-yl-phenoxy)-piperidin-1-yl]-methanone;
4-[4-(4-methylquinolin-3-yl)-phenoxy]-piperidine-1-carboxylic acid methoxyamide;
4-[4-(4-methylquinolin-3-yl)-phenoxy]-piperidine-1-carboxylic acid methoxymethylamide;
4-[4-(4-methylquinolin-3-yl)-phenoxy]-piperidine-1-carboxylic acid ethylamide;
4-[4-(8-methoxyquinolin-7-yl)-phenoxy]-piperidine-1-carboxylic acid methylamide;
4-[4-(8-methoxyquinolin-7-yl)-phenoxy]-piperidine-1-carboxylic acid ethylamide;
4-[4-(4-methylquinolin-3-yl)-phenoxy]-piperidine-1-carboxylic acid hydroxyamide;
N-ethyl-4-[4-(8-methyl-7-quinolyl)phenoxy]piperidine-1-carboxamide;
N,N-dimethyl-4-[4-(8-methyl-7-quinolyl)phenoxy]piperidine-1-carboxamide;
N-methoxy-4-[4-(8-methyl-7-quinolyl)phenoxy]piperidine-1-carboxamide;
N-isopropyl-4-[4-(8-methyl-7-quinolyl)phenoxy]piperidine-1-carboxamide;
N-ethoxy-4-[4-(8-methyl-7-quinolyl)phenoxy]piperidine-1-carboxamide;
[4-[4-(8-methyl-7-quinolyl)phenoxy]-1-piperidyl]-pyrrolidin-1-yl-methanone;
N-methyl-4-[4-(8-methyl-7-quinolyl)phenoxy]piperidine-1-carboxamide;
4-[4-(8-methyl-7-quinolyl)phenoxy]-N-propyl-piperidine-1-carboxamide;
4-[4-(8-methyl-7-quinolyl)phenoxy]piperidine-1-carboxamide;
[4-[4-(8-methyl-7-quinolyl)phenoxy]-1-piperidyl]-(1-piperidyl)methanone;
[4-[4-(8-methyl-7-quinolyl)phenoxy]-1-piperidyl]-morpholinomethanone;
N-methoxy-4-[4-(8-methoxy-7-quinolyl)phenoxy]piperidine-1-carboxamide;
3-[4-(4-quinolin-3-yl-phenoxy)-piperidine-1-carbonyl]-oxazolidin-2-one;
1-[4-(4-quinolin-3-yl-phenoxy)-piperidine-1-carbonyl]-pyrrolidin-2-one;
N-ethyl-4-[4-(2-hydroxy-8-methyl-7-quinolyl)phenoxy]piperidine-1-carboxamide;
4-[4-(8-methyl-7-quinolyl)phenoxy]-N-(2-pyrrolidin-1-ylethyl)piperidine-1-carboxamide; 4-[4-(8-methyl-7-quinolyl)phenoxy]-N-(2-morpholinoethyl)piperidine-1-carboxamide;
(4-isopropylpiperazin-1-yl)-[4-[4-(8-methyl-7-quinolyl)phenoxy]-1-piperidyl]methanone; (4-methylpiperazin-1-yl)-[4-[4-(8-methyl-7-quinolyl)phenoxy]-1-piperidyl]methanone;
[4-[4-(8-methyl-7-quinolyl)phenoxy]-1-piperidyl]-(4-morpholino-1-piperidyl)methanone; (4-ethylpiperazin-1-yl)-[4-[4-(8-methyl-7-quinolyl)phenoxy]-1-piperidyl]methanone;
N-(cyclopropylmethyl)-4-[4-(8-methyl-7-quinolyl)phenoxy]piperidine-1-carboxamide;
N-isobutyl-4-[4-(8-methyl-7-quinolyl)phenoxy]piperidine-1-carboxamide;
N-(2-methoxyethyl)-4-[4-(8-methyl-7-quinolyl)phenoxy]piperidine-1-carboxamide;
N-isopropoxy-4-[4-(8-methyl-7-quinolyl)phenoxy]piperidine-1-carboxamide;
N-isobutoxy-4-[4-(8-methyl-7-quinolyl)phenoxy]piperidine-1-carboxamide;
N-(2-dimethylaminoethyl)-4-[4-(8-methyl-7-quinolyl)phenoxy]piperidine-1-carboxamide; N-[2-(1H-imidazol-4-yl)ethyl]-4-[4-(8-methyl-7-quinolyl)phenoxy], piperidine-1-carboxamide;
4-[4-(8-methyl-7-quinolyl)phenoxy]-N-tetrahydropyran-4-yl-piperidine-1-carboxamide; N-cyclobutyl-4-[4-(8-methyl-7-quinolyl)phenoxy]piperidine-1-carboxamide;
4-[4-(8-methyl-7-quinolyl)phenoxy]piperidine-1-carbohydroxamic acid;
[4-[4-(8-methyl-7-quinolyl)phenoxy]-1-piperidyl]-(oxazinan-2-yl)methanone;
N-(cyclobutylmethyl)-4-[4-(8-methyl-7-quinolyl)phenoxy]piperidine-1-carboxamide; azepan-1-yl-[4-[4-(8-methyl-7-quinolyl)phenoxy]-1-piperidyl]methanone;
4-[4-(8-methyl-7-quinolyl)phenoxy]-N-propoxy-piperidine-1-carboxamide;
N-ethyl-4-[4-(1-methyl-6-isoquinolyl)phenoxy]piperidine-1-carboxamide;
4-[4-(1-methyl-6-isoquinolyl)phenoxy]-N-propyl-piperidine-1-carboxamide;
N-isobutyl-4-[4-(1-methyl-6-isoquinolyl)phenoxy]piperidine-1-carboxamide;
4-[4-(1-methyl-6-isoquinolyl)phenoxy]piperidine-1-carboxamide;
N-(cyclopropylmethyl)-4-[4-(1-methyl-6-isoquinolyl)phenoxy]piperidine-1-carboxamide; N-isopropoxy-4-[4-(1-methyl-6-isoquinolyl)phenoxy]piperidine-1-carboxamide;
4-[4-(1-methyl-6-isoquinolyl)phenoxy]-N-propoxypiperidine-1-carboxamide;
4-[4-(1-methyl-6-isoquinolyl)phenoxy]piperidine-1-carbohydroxamic acid;
N-ethoxy-4-[4-(1-methyl-6-isoquinolyl)phenoxy]piperidine-1-carboxamide;
N-ethoxy-4-[4-(4-methyl-3-quinolyl)phenoxy]piperidine-1-carboxamide;
N-isopropoxy-4-[4-(4-methyl-3-quinolyl)phenoxy]piperidine-1-carboxamide;
4-[4-(4-methyl-3-quinolyl)phenoxy]-N-propoxy-piperidine-1-carboxamide;

N-isobutyl-4-[4-(4-methyl-3-quinolyl)phenoxy]piperidine-1-carboxamide;
4-[4-(4-methyl-3-quinolyl)phenoxy]-N-propyl-piperidine-1-carboxamide;
4-[4-(4-methyl-3-quinolyl)phenoxy]-N-methylsulfanyl-piperidine-1-carboxamide;
4-[4-(4-methyl-3-quinolyl)phenoxy]-N-ethylsulfanyl-piperidine-1-carboxamide,
1-[4-[4-(4-methyl-3-quinolyl)phenoxy]piperidine-1-carbonyl]pyrrolidin-2-one;
or a pharmaceutically acceptable salt thereof.

20. The method according to claim 14, wherein the compound of formula (Va) is

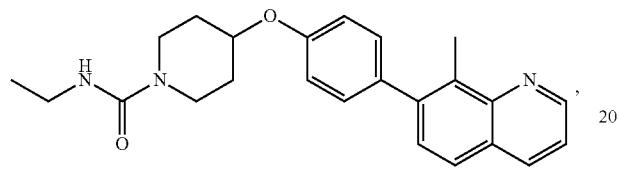

or a pharmaceutically acceptable salt thereof.

21. The method according to claim 14, wherein the compound of formula (Va) is

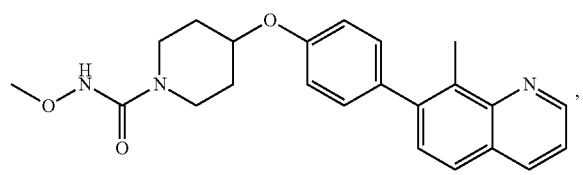 [SMILES: CONC(=O)N1CCC(Oc2ccc(-c3ccc4cccnc4c3C)cc2)CC1]

or a pharmaceutically acceptable salt thereof.

22. A method of treating a subject who is suffering from weight gain associated with drug therapy with an antipsychotic agent, said method comprising administering to the subject a therapeutically effective amount of a compound according to Formula V(a):

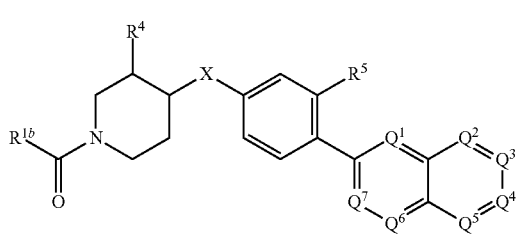

V(a)

or a pharmaceutically acceptable salt thereof, wherein:
$R^{1b}$ is selected from —$NR^7R^8$ and —$N(OR^8)R^7$;
$R^4$ is selected from —H, —($C_1$-$C_6$) alkyl, —OH, —O($C_1$-$C_6$) alkyl, halogen, and —CN;
X is selected from —O— and —S—;
$R^5$ is selected from —H, —$C_1$-$C_7$ hydrocarbyl, —$C_3$-$C_6$ heterocyclyl; halogen, —($C_1$-$C_3$) haloalkyl, —$OR^{7a}$, —CN, —$NR^{7a}R^{8a}$, —$O(CH_2)_nNR^{7a}R^{8a}$, —$O(CH_2)_nOR^{8a}$, —$NR^{8a}(CH_2)_nNR^{7a}R^{8a}$, —$NR^{8a}(CH_2)_nOR^{8a}$, —$C(=O)NR^{7a}R^{8a}$, —$C(=O)OR^{7a}$, 5-6 membered heteroaryl and substituted 5-6 membered heteroaryl;

n is an integer selected from 1, 2, 3, and 4;
$R^7$ is selected from —H, —($C_1$-$C_7$) hydrocarbyl, substituted —($C_1$-$C_7$) hydrocarbyl, —$C(=O)R^8$, and —($C_1$-$C_6$) heteroalkyl;
$R^8$ is selected from —H, and —($C_1$-$C_6$) alkyl, wherein $R^7$ can optionally be structurally connected to $R^8$ to form a 5 to 7 membered heterocyclyl ring;
$R^{7a}$ is selected from —H, —($C_1$-$C_7$) hydrocarbyl, substituted —($C_1$-$C_7$) hydrocarbyl, —$C(=O)R^8$, and —($C_1$-$C_6$) heteroalkyl;
$R^{8a}$ is selected from —H, and —($C_1$-$C_6$) alkyl, wherein $R^{7a}$ can optionally be structurally connected to $R^{8a}$ to form a 5 to 7 membered heterocyclyl ring;
$Q^1$, $Q^2$, $Q^3$, $Q^4$, $Q^5$, $Q^6$ and $Q^7$ are independently selected from N and C—$R^{12}$, provided that 1, 2 or 3 of $Q^1$, $Q^2$, $Q^3$, $Q^4$, $Q^5$, $Q^6$ and $Q^7$ are N, and the remainder of $Q^1$, $Q^2$, $Q^3$, $Q^4$, $Q^5$, $Q^6$ and $Q^7$ are C—$R^{12}$;
each $R^{12}$ is independently selected from —H, halogen, —($C_1$-$C_6$) alkyl, —($C_3$-$C_6$) cycloalkyl, 5-6 membered heterocyclyl, —OH, —O($C_1$-$C_6$) alkyl, —$O(CH_2)_p$-(5-6 membered heterocyclyl), —$O(CH_2)_p$—O($C_1$-$C_6$) alkyl, —$NH_2$, —CN, —NH($C_1$-$C_6$) alkyl, —N($C_1$-$C_6$ alkyl)$_2$, —$NH(CH_2)_p$—O($C_1$-$C_6$) alkyl, —$NH(CH_2)_p$—N($C_1$-$C_6$ alkyl)$_2$, —$C(=O)NH_2$, —$C(=O)NH(C_1$-$C_6$) alkyl, and —$C(=O)N(C_1$-$C_6$ alkyl)$_2$; and
p is an integer selected independently from 1, 2, 3, and 4.

23. The method according to claim 22, wherein X is —O—.

24. The method according to claim 22, wherein $R^5$ is selected from —H, —($C_1$-$C_7$) hydrocarbyl, and halogen.

25. The method according to claim 22, wherein one of $Q^1$, $Q^2$, $Q^3$, $Q^4$, $Q^5$, $Q^6$ and $Q^7$ is N, and the remainder of $Q^1$, $Q^2$, $Q^3$, $Q^4$, $Q^5$, $Q^6$ and $Q^7$ are C—$R^{12}$.

26. The method according to claim 25, wherein one of $Q^2$ and $Q^6$ is N; the other of $Q^2$ and $Q^6$ is C—$R^{12}$; and $Q^1$, $Q^3$, $Q^4$, $Q^5$ and $Q^7$ are C—$R^{12}$.

27. The method according to claim 22, wherein the compound according to Formula V(a) is selected from:
isoxazolidin-2-yl-[4-(4-quinolin-3-yl-phenoxy)-piperidin-1-yl]-methanone;
[4-(4-isoquinolin-3-yl-phenoxy)-piperidin-1-yl]-isoxazolidin-2-yl-methanone; isoxazolidin-2-yl-{4-[4-(8-methylquinolin-7-yl)-phenoxy]-piperidin-1-yl}-methanone;
{4-[4-(4-chloroquinolin-3-yl)-phenoxy]-piperidin-1-yl}-isoxazolidin-2-yl-methanone;
{4-[4-(8-chloroquinolin-7-yl)-phenoxy]-piperidin-1-yl}-isoxazolidin-2-yl-methanone;
isoxazolidin-2-yl-{4-[4-(4-methylquinolin-3-yl)-phenoxy]-piperidin-1-yl}-methanone;
isoxazolidin-2-yl-{4-[4-(8-methoxyquinolin-7-yl)-phenoxy]-piperidin-1-yl}-methanone;
isoxazolidin-2-yl-{4-[4-(7-methylquinolin-3-yl)-phenoxy]-piperidin-1-yl}-methanone;
isoxazolidin-2-yl-[4-(4-quinoxalin-2-yl-phenoxy)-piperidin-1-yl]-methanone;
4-[4-(4-methylquinolin-3-yl)-phenoxy]-piperidine-1-carboxylic acid methoxyamide;
4-[4-(4-methylquinolin-3-yl)-phenoxy]-piperidine-1-carboxylic acid methoxymethylamide;
4-[4-(4-methylquinolin-3-yl)-phenoxy]-piperidine-1-carboxylic acid ethylamide;
4-[4-(8-methoxyquinolin-7-yl)-phenoxy]-piperidine-1-carboxylic acid methylamide;
4-[4-(8-methoxyquinolin-7-yl)-phenoxy]-piperidine-1-carboxylic acid ethylamide;
4-[4-(4-methylquinolin-3-yl)-phenoxy]-piperidine-1-carboxylic acid hydroxyamide;

N-ethyl-4-[4-(8-methyl-7-quinolyl)phenoxy]piperidine-1-carboxamide;
N,N-dimethyl-4-[4-(8-methyl-7-quinolyl)phenoxy]piperidine-1-carboxamide;
N-methoxy-4-[4-(8-methyl-7-quinolyl)phenoxy]piperidine-1-carboxamide;
N-isopropyl-4-[4-(8-methyl-7-quinolyl)phenoxy]piperidine-1-carboxamide;
N-ethoxy-4-[4-(8-methyl-7-quinolyl)phenoxy]piperidine-1-carboxamide;
[4-[4-(8-methyl-7-quinolyl)phenoxy]-1-piperidyl]-pyrrolidin-1-yl-methanone;
N-methyl-4-[4-(8-methyl-7-quinolyl)phenoxy]piperidine-1-carboxamide;
4-[4-(8-methyl-7-quinolyl)phenoxy]-N-propyl-piperidine-1-carboxamide;
4-[4-(8-methyl-7-quinolyl)phenoxy]piperidine-1-carboxamide;
[4-[4-(8-methyl-7-quinolyl)phenoxy]-1-piperidyl]-(1-piperidyl)methanone;
[4-[4-(8-methyl-7-quinolyl)phenoxy]-1-piperidyl]-morpholinomethanone;
N-methoxy-4-[4-(8-methoxy-7-quinolyl)phenoxy]piperidine-1-carboxamide;
3-[4-(4-quinolin-3-yl-phenoxy)-piperidine-1-carbonyl]-oxazolidin-2-one;
1-[4-(4-quinolin-3-yl-phenoxy)-piperidine-1-carbonyl]-pyrrolidin-2-one;
N-ethyl-4-[4-(2-hydroxy-8-methyl-7-quinolyl)phenoxy]piperidine-1-carboxamide;
4-[4-(8-methyl-7-quinolyl)phenoxy]-N-(2-pyrrolidin-1-ylethyl)piperidine-1-carboxamide; 4-[4-(8-methyl-7-quinolyl)phenoxy]-N-(2-morpholinoethyl)piperidine-1-carboxamide;
(4-isopropylpiperazin-1-yl)-[4-[4-(8-methyl-7-quinolyl)phenoxy]-1-piperidyl]methanone; (4-methylpiperazin-1-yl)-[4-[4-(8-methyl-7-quinolyl)phenoxy]-1-piperidyl]methanone;
[4-[4-(8-methyl-7-quinolyl)phenoxy]-1-piperidyl]-(4-morpholino-1-piperidyl)methanone; (4-ethylpiperazin-1-yl)-[4-[4-(8-methyl-7-quinolyl)phenoxy]-1-piperidyl]methanone;
N-(cyclopropylmethyl)-4-[4-(8-methyl-7-quinolyl)phenoxy]piperidine-1-carboxamide;
N-isobutyl-4-[4-(8-methyl-7-quinolyl)phenoxy]piperidine-1-carboxamide;
N-(2-methoxyethyl)-4-[4-(8-methyl-7-quinolyl)phenoxy]piperidine-1-carboxamide;
N-isopropoxy-4-[4-(8-methyl-7-quinolyl)phenoxy]piperidine-1-carboxamide;
N-isobutoxy-4-[4-(8-methyl-7-quinolyl)phenoxy]piperidine-1-carboxamide;
N-(2-dimethylaminoethyl)-4-[4-(8-methyl-7-quinolyl)phenoxy]piperidine-1-carboxamide; N-[2-(1H-imidazol-4-yl)ethyl]-4-[4-(8-methyl-7-quinolyl)phenoxy], piperidine-1-carboxamide;
4-[4-(8-methyl-7-quinolyl)phenoxy]-N-tetrahydropyran-4-yl-piperidine-1-carboxamide; N-cyclobutyl-4-[4-(8-methyl-7-quinolyl)phenoxy]piperidine-1-carboxamide;
4-[4-(8-methyl-7-quinolyl)phenoxy]piperidine-1-carbohydroxamic acid;
[4-[4-(8-methyl-7-quinolyl)phenoxy]-1-piperidyl]-(oxazinan-2-yl)methanone;
N-(cyclobutylmethyl)-4-[4-(8-methyl-7-quinolyl)phenoxy]piperidine-1-carboxamide; azepan-1-yl-[4-[4-(8-methyl-7-quinolyl)phenoxy]-1-piperidyl]methanone;
4-[4-(8-methyl-7-quinolyl)phenoxy]-N-propoxy-piperidine-1-carboxamide;
N-ethyl-4-[4-(1-methyl-6-isoquinolyl)phenoxy]piperidine-1-carboxamide;
4-[4-(1-methyl-6-isoquinolyl)phenoxy]-N-propyl-piperidine-1-carboxamide;
N-isobutyl-4-[4-(1-methyl-6-isoquinolyl)phenoxy]piperidine-1-carboxamide;
4-[4-(1-methyl-6-isoquinolyl)phenoxy]piperidine-1-carboxamide;
N-(cyclopropylmethyl)-4-[4-(1-methyl-6-isoquinolyl)phenoxy]piperidine-1-carboxamide; N-isopropoxy-4-[4-(1-methyl-6-isoquinolyl)phenoxy]piperidine-1-carboxamide;
4-[4-(1-methyl-6-isoquinolyl)phenoxy]-N-propoxypiperidine-1-carboxamide;
4-[4-(1-methyl-6-isoquinolyl)phenoxy]piperidine-1-carbohydroxamic acid;
N-ethoxy-4-[4-(1-methyl-6-isoquinolyl)phenoxy]piperidine-1-carboxamide;
N-ethoxy-4-[4-(4-methyl-3-quinolyl)phenoxy]piperidine-1-carboxamide;
N-isopropoxy-4-[4-(4-methyl-3-quinolyl)phenoxy]piperidine-1-carboxamide;
4-[4-(4-methyl-3-quinolyl)phenoxy]-N-propoxy-piperidine-1-carboxamide;
N-isobutyl-4-[4-(4-methyl-3-quinolyl)phenoxy]piperidine-1-carboxamide;
4-[4-(4-methyl-3-quinolyl)phenoxy]-N-propyl-piperidine-1-carboxamide;
4-[4-(4-methyl-3-quinolyl)phenoxy]-N-methylsulfanyl-piperidine-1-carboxamide;
4-[4-(4-methyl-3-quinolyl)phenoxy]-N-ethylsulfanyl-piperidine-1-carboxamide,
1-[4-[4-(4-methyl-3-quinolyl)phenoxy]piperidine-1-carbonyl]pyrrolidin-2-one;
or a pharmaceutically acceptable salt thereof.

28. The method according to claim 22, wherein the compound of formula (Va) is

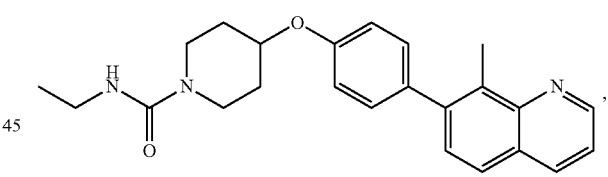

or a pharmaceutically acceptable salt thereof.

29. The method according to claim 22, wherein the compound of formula (Va) is

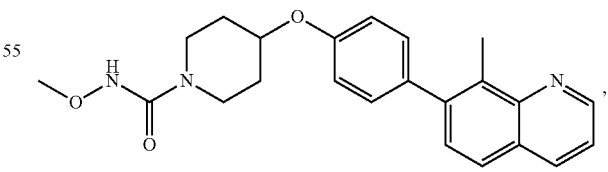

or a pharmaceutically acceptable salt thereof.

30. The method of claim 22, wherein the antipsychotic agent is selected from clozapine, risperidone, aripiprazole, olanzapine, quetiapine and ziprasidone and combinations thereof.

* * * * *